United States Patent
Farmer et al.

(10) Patent No.: US 8,841,263 B2
(45) Date of Patent: *Sep. 23, 2014

(54) MACROCYCLIC COMPOUNDS AND METHODS OF MAKING AND USING THE SAME

(75) Inventors: Jay J. Farmer, Lodi, NY (US); Ashoke Bhattacharjee, Cheshire, CT (US); Yi Chen, Chestnut Hill, MA (US); Joel A. Goldberg, Milford, CT (US); Joseph A. Ippolito, Guilford, CT (US); Zoltan F. Kanyo, North Haven, CT (US); Rongliang Lou, Cheshire, CT (US); Adegboyega K. Oyelere, Marietta, GA (US); Edward C. Sherer, Manville, NJ (US); Joyce A. Sutcliffe, West Newton, MA (US); Deping Wang, Sharon, MA (US); Yusheng Wu, New Haven, CT (US); Yanming Du, Cheshire, CT (US)

(73) Assignee: Melinta Therapeutics, Inc., New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/525,900

(22) Filed: Jun. 18, 2012

(65) Prior Publication Data
US 2012/0252747 A1     Oct. 4, 2012

Related U.S. Application Data

(63) Continuation of application No. 10/590,782, filed as application No. PCT/US2005/006082 on Feb. 25, 2005, now Pat. No. 8,202,843.

(60) Provisional application No. 60/548,280, filed on Feb. 27, 2004, provisional application No. 60/575,949, filed on Jun. 1, 2004.

(51) Int. Cl.
*A01N 43/04* (2006.01)
*A61K 31/70* (2006.01)

(52) U.S. Cl.
USPC .......................................................... 514/29

(58) Field of Classification Search
USPC .................................................. 536/7.2, 7.4
See application file for complete search history.

(56) References Cited

U.S. PATENT DOCUMENTS

| | | |
|---|---|---|
| 3,629,232 A | 12/1971 | Jones |
| 3,681,325 A | 8/1972 | Freiburg |
| 4,404,201 A | 9/1983 | Haskell et al. |
| 4,546,176 A | 10/1985 | Machida et al. |
| 5,180,719 A | 1/1993 | White et al. |
| 5,215,980 A | 6/1993 | Jones |
| 5,232,918 A | 8/1993 | Arnould et al. |
| 5,281,703 A | 1/1994 | White et al. |
| 5,336,768 A | 8/1994 | Albrecht et al. |
| 5,444,051 A | 8/1995 | Agouridas et al. |
| 5,527,780 A | 6/1996 | Agouridas et al. |
| 5,543,400 A | 8/1996 | Agouridas et al. |
| 5,658,888 A | 8/1997 | Koga et al. |
| 5,693,791 A | 12/1997 | Truett |
| 5,747,467 A | 5/1998 | Agouridas et al. |
| 5,780,605 A | 7/1998 | Or et al. |
| 5,792,765 A | 8/1998 | Riedl et al. |
| 5,866,549 A | 2/1999 | Or et al. |

(Continued)

FOREIGN PATENT DOCUMENTS

| | | |
|---|---|---|
| DE | 196 04 223 A1 | 8/1997 |
| DE | 10034627 A1 | 1/2002 |

(Continued)

OTHER PUBLICATIONS

Akritopoulou-Zanze et al., "Synthesis and antibacterial activity of novel bifunctional macrolides", *Bioorg. Med. Chem. Lett.*, pp. 1-5 (2005).
Brandt-Rauf et al., "Fluorescent assay for estimating the binding of erythromycin derivatives to ribosomes", *Antimicrob. Agents Chemother.*, 14(1):88-94 (1978).
Costa et al., "Hybrids of macrolides and nucleobases or nucleosides", *Tetrahedron Lett.*, 41:3371-3375 (2000).
Denis et al., "Novel N-demethylation of ketolide: application to the solution phase parallel synthesis of N-desosaminyl-substituted ketolides using ion exchange resins", *Tetrahedron Lett.*, 43:4171-4174 (2002).

(Continued)

*Primary Examiner* — Layla Bland
(74) *Attorney, Agent, or Firm* — Mintz Levin Cohn Ferris Glovsky and Popeo, P.C.; Ivor R. Elrifi; Heidi A. Erlacher

(57) ABSTRACT

The present invention provides macrocyclic compounds useful as therapeutic agents of the formula:

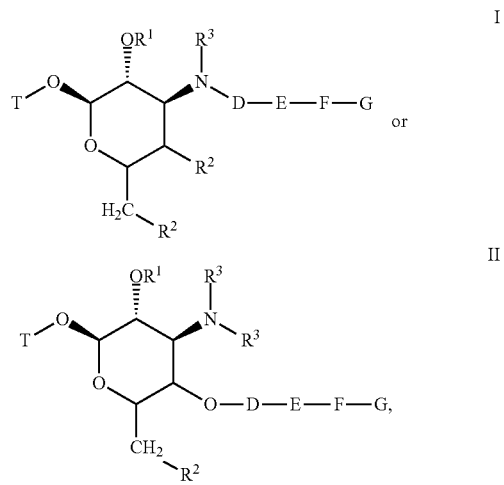

or a pharmaceutically acceptable salt, ester, N-oxide, or prodrug thereof, wherein T, $R^1$, $R^2$, $R^3$, D, E, F, and G are as defined herein. More particularly, these compounds are useful as anti-infective, antiproliferative, anti-inflammatory and prokinetic agents.

3 Claims, No Drawings

(56) References Cited

U.S. PATENT DOCUMENTS

| | | | |
|---|---|---|---|
| 5,891,643 A | 4/1999 | Fesik et al. | |
| 5,905,144 A | 5/1999 | Truett | |
| 5,955,440 A | 9/1999 | Sauer et al. | |
| 6,020,521 A | 2/2000 | Randolph et al. | |
| 6,022,965 A * | 2/2000 | Benedetti et al. | 536/125 |
| 6,034,069 A | 3/2000 | Or et al. | |
| 6,274,715 B1 | 8/2001 | Or et al. | |
| 6,288,055 B1 | 9/2001 | Natarajan et al. | |
| 6,288,234 B1 | 9/2001 | Griffin | |
| 6,355,805 B1 | 3/2002 | Choi et al. | |
| 6,355,810 B1 | 3/2002 | Griffin et al. | |
| 6,362,371 B1 | 3/2002 | Moran et al. | |
| 6,395,724 B1 | 5/2002 | Judice et al. | |
| 6,420,354 B1 | 7/2002 | Marquess et al. | |
| 6,437,119 B1 | 8/2002 | Truett | |
| 6,446,032 B1 | 9/2002 | Schimmel | |
| 6,468,979 B1 | 10/2002 | Pellacini et al. | |
| 6,479,498 B1 | 11/2002 | Marquess et al. | |
| 6,566,509 B1 | 5/2003 | Griffin et al. | |
| 6,576,615 B2 | 6/2003 | Phan et al. | |
| 6,664,240 B2 | 12/2003 | Phan et al. | |
| 6,710,034 B2 | 3/2004 | Phan et al. | |
| 6,753,415 B2 | 6/2004 | Phan et al. | |
| 6,878,691 B2 | 4/2005 | Or et al. | |
| 7,091,196 B2 | 8/2006 | Wang et al. | |
| 7,129,221 B2 | 10/2006 | Or et al. | |
| 8,278,281 B2 | 10/2012 | Bhattacharjee et al. | |
| 2002/0028943 A1 | 3/2002 | Griffin | |
| 2003/0092639 A1 | 5/2003 | Phan et al. | |
| 2003/0096764 A1 | 5/2003 | Phan et al. | |
| 2003/0158093 A1 | 8/2003 | Sun et al. | |
| 2003/0176670 A1 | 9/2003 | Griffin et al. | |
| 2003/0176848 A1 | 9/2003 | Gibson et al. | |
| 2003/0181399 A1 | 9/2003 | Wong et al. | |
| 2003/0203858 A1 | 10/2003 | Phan et al. | |
| 2003/0212010 A1 | 11/2003 | Phan et al. | |
| 2004/0014685 A1 | 1/2004 | Mercep et al. | |
| 2004/0077612 A1 | 4/2004 | Mercep et al. | |
| 2004/0097434 A1 | 5/2004 | Mercep et al. | |
| 2004/0157787 A1 | 8/2004 | Or et al. | |
| 2004/0235760 A1 | 11/2004 | Phan et al. | |
| 2005/0020823 A1 | 1/2005 | Phan et al. | |
| 2005/0197334 A1 | 9/2005 | Wang et al. | |
| 2006/0264385 A1 | 11/2006 | Wang et al. | |
| 2007/0072811 A1 | 3/2007 | Farmer et al. | |
| 2007/0149463 A1 | 6/2007 | Oyelere et al. | |

FOREIGN PATENT DOCUMENTS

| | | |
|---|---|---|
| EP | 0 213 617 A2 | 3/1987 |
| EP | 0 215 355 A2 | 3/1987 |
| EP | 0643068 A1 | 3/1995 |
| EP | 0 680 967 A1 | 11/1995 |
| EP | 0 895 999 A1 | 2/1999 |
| EP | 1 132 392 A1 | 9/2001 |
| EP | 1 201 649 A1 | 5/2002 |
| EP | 1 201 655 A2 | 5/2002 |
| WO | WO-92/17184 A2 | 10/1992 |
| WO | WO-93/07154 A1 | 4/1993 |
| WO | WO-93/24509 A1 | 12/1993 |
| WO | WO-94/10185 A1 | 5/1994 |
| WO | WO-95/07271 A1 | 3/1995 |
| WO | WO-96/18633 A1 | 6/1996 |
| WO | WO-97/35195 A1 | 9/1997 |
| WO | WO-97/48713 A1 | 12/1997 |
| WO | WO-98/56800 A1 | 12/1998 |
| WO | WO-98/56801 A1 | 12/1998 |
| WO | WO-9916779 A1 | 4/1999 |
| WO | WO-9922722 A1 | 5/1999 |
| WO | WO-99/28308 A1 | 6/1999 |
| WO | WO-9933839 A1 | 7/1999 |
| WO | WO-99/64032 A1 | 12/1999 |
| WO | WO-99/64049 A1 | 12/1999 |
| WO | WO-9963937 A2 | 12/1999 |
| WO | WO-9964416 A2 | 12/1999 |
| WO | WO-9964417 A2 | 12/1999 |
| WO | WO-0006606 A2 | 2/2000 |
| WO | WO-0021960 A1 | 4/2000 |
| WO | WO-00/42055 A2 | 7/2000 |
| WO | WO-0040589 A2 | 7/2000 |
| WO | WO-00/77016 A1 | 12/2000 |
| WO | WO-01/40238 A1 | 6/2001 |
| WO | WO-0140222 A1 | 6/2001 |
| WO | WO-0140236 A2 | 6/2001 |
| WO | WO-0142242 A1 | 6/2001 |
| WO | WO-0158885 A1 | 8/2001 |
| WO | WO-01/80863 A1 | 11/2001 |
| WO | WO-0181350 A1 | 11/2001 |
| WO | WO-02051855 | 7/2002 |
| WO | WO 02/060912 | 8/2002 |
| WO | WO-02080841 A2 | 10/2002 |
| WO | WO-02081468 A1 | 10/2002 |
| WO | WO-02081469 A1 | 10/2002 |
| WO | WO-02081470 A1 | 10/2002 |
| WO | WO-02096890 A2 | 12/2002 |
| WO | WO-02096916 A1 | 12/2002 |
| WO | WO-03011882 A1 | 2/2003 |
| WO | WO-03022824 A1 | 3/2003 |
| WO | WO-03/042228 A1 | 5/2003 |
| WO | WO-03035073 A1 | 5/2003 |
| WO | WO-03035648 A1 | 5/2003 |
| WO | WO-03/070173 A2 | 8/2003 |
| WO | WO-03/070174 A2 | 8/2003 |
| WO | WO-03/070254 A1 | 8/2003 |
| WO | WO-03072575 A1 | 9/2003 |
| WO | WO-2004/005309 A2 | 1/2004 |
| WO | WO-2004/005310 A2 | 1/2004 |
| WO | WO-2004/005313 A2 | 1/2004 |
| WO | WO-2004/013153 A2 | 2/2004 |
| WO | WO-2004/043984 A1 | 5/2004 |
| WO | WO-2004048392 A1 | 6/2004 |
| WO | WO-2004/056818 A1 | 7/2004 |
| WO | WO-2004/056819 A1 | 7/2004 |
| WO | WO-2004056817 A1 | 7/2004 |
| WO | WO-2004/078770 A1 | 9/2004 |
| WO | WO-2004/080391 A2 | 9/2004 |
| WO | WO-2004/094449 A1 | 11/2004 |
| WO | WO-2004/096221 A1 | 11/2004 |
| WO | WO-2004/108745 A2 | 12/2004 |
| WO | WO-2004/108746 A2 | 12/2004 |
| WO | WO-2005/030786 A1 | 4/2005 |
| WO | WO-2005/042554 A1 | 5/2005 |
| WO | WO-2005/049632 A1 | 6/2005 |
| WO | WO-2005/075494 A1 | 8/2005 |
| WO | WO-2005/085266 A2 | 9/2005 |
| WO | WO-2005118610 A2 | 12/2005 |
| WO | WO-2007025089 A2 | 3/2007 |
| WO | WO-2007025098 A2 | 3/2007 |
| WO | WO-2007025284 A1 | 3/2007 |

OTHER PUBLICATIONS

Faghih et al., "Synthesis of 9-deoxo-4"-deoxy-6,9-epoxyerythromycin derivatives: novel and acid-stable motilides", *J. Med. Chem.*, 41(18):3402-3408 (1998).

Gregory et al., "Antibacterials. Synthesis and structure-activity studies of 3-aryl-2-oxooxazolidines. 1. The "B" group", *J. Med. Chem.*, 32(8):1673-1681 (1989).

Hecker et al., "Application of hygromycin a structure activity relationships to the antibiotic a201a", *Bioorg. Med. Chem. Lett.*, 3(2):295-298 (1993).

Henessian et al., "Quantamycin: a computer-simulated new-generation inhibitor of bacterial ribosomal binding", *J. Am. Chem. Soc.*, 106:6114-6115 (1984).

Holmes et al., "Novel dimeric penicillin derived inhibitors of HIV-1 proteinase: interaction with the catalytic aspartates", *Bioorg. Med. Chem. Lett.*, 3(4):503-508 (1993).

Hwang et al., "1,3-dipolar cycloaddition of nitrile oxides to 1-phenylsulfonyl-1-3-butadienes:synthesis of 3-(4,5-dihydroisoxazol-5-yl)pyrroles", *Tetrahedron Let.*, 43:53-56 (2002).

Jones et al., "Chemical modifications of erythromycin antibiotics. I. 3'-De(dimethylamino)erythromycin A and B", *Chem. Modif. Erythromycin Antibiotics*, 33(2):665-670 (1968).

(56) References Cited

OTHER PUBLICATIONS

Liang et al., "Synthesis and biological activity of new 5-O-sugar modified ketolide and 2-fluoro-ketolide antibiotics", *Bioorg. Med. Chem. Lett.*, 15:1307-1310 (2005).

Mereu et al., "Design, synthesis and in vivo activity of 9-(S)-dihydroerythromycin derivatives as potent anti-inflammatory agents", *Bioorg. Med. Chem. Lett.*, 16:5801-5804 (2006).

Mutak et al., "Semisynthetic macrolide antibacterials derived from tylosin. Synthesis and structure-activity relationships of novel desmycosin analogues", *J. Med. Chem.*, 47(2):411-431 (2004).

Phan et al., "Synthesis and antibacterial activity of a novel class of 4'-substituted 16-membered ring macrolides derived from tylosin", *J. Med. Chem.*, 47(12):2965-2968 (2004).

Phillips et al., "Synthesis and antibacterial activity of 5-substituted oxazolidinones", *Bioorg. Med. Chem.*, 11:35-41 (2003).

Randolph et al., "Elimination of antibacterial activities of non-peptide luteinizing hormone-releasing hormone (LHRH) antagonists derived from erythromycin A", *Bioorg. Med. Chem. Lett.*, 14:1599-1602 (2004).

Rao et al., "Tight binding of a dimeric derivative of vancomycin with dimeric L-Lys-D-Ala-D-Ala" *J. Am. Chem. Soc.*, 119(43):10286-10290 (1997).

SciFinder Database entry for WO 93/24509, pp. 1-3 (2003).

SciFinder Database entry for WO 94/10185, pp. 1-3 (2003).

Shuker et al., "Discovering high-affinity ligands for proteins: SAR by NMR", *Science*, 274:1531-1543 (2003).

Stenmark et al., "Biomimetic synthesis of macrolide/ketolide metabolites through a selective n-Demethylation reaction", *J. Org. Chem.*, 65(12):3875-3876 (2000).

Vince et al., "Chloramphenicol binding site with analogues of chloramphenicol and puromycin", *Antimicrob. Agents Chemother.*, 8(4):439-443 (1975).

Wang et al., "Dimeric aminoglycosides: design, synthesis and RNA binding", *Bioorg. Med. Chem. Lett.*, 7(14):1951-1956 (1997).

Welch et al., "An inhibitor of ribosomal peptidyl transferase using transition-state analogy", *Biochem.*, 34(2):385-390 (1995).

Žemlička et al., "Sparsophenicol: a new synthetic hybrid antibiotic inhibiting ribosomal peptide synthesis", *J. Med. Chem.*, 25(10):1123-1125 (1982).

Žemlička et al., "Hybrid of antibiotics inhibiting protein synthesis. Synthesis and biological activity", *J. Med. Chem.*, 36(9):1239-1244 (1993).

Ban et al., "The Complete Atomic Structure of the Large Ribosomal Subunit at 2.4 Å Resolution," *Science*, 289:905-920 (2000).

Brickner, S.J., "Oxazolidinone Antibacterial Agents," *Current Pharm. Design*, 2(2):174-194 (1996).

Franceschi et al., "Structure-Based Drug Design Meets the Ribosome," *Biochem. Pharmacol.*, 71:1016-1025 (2006).

Mutak, S., "Azalides from Azithromycin to New Azalide Derivatives," *J. Antibiot.*, 60(2):85-122 (2007).

Pal, S., "A Journey Across the Sequential Development of Macrolides and Ketolides Related to Erythromycin," *Tetrahedron*, 62:3171-3200 (2006).

Sutcliffe, J.A., "The Search for New Antibiotics Targeting the 50S Ribozyme," *ASM News*, 70(11):513-519 (2004).

"Prodrugs." *Modern Pharmaceutics*. Banker, ed. New York: Marcel Dekker, Inc. Third Ed. (1996):596.

*Burger's Medicinal Chemistry and Drug Discovery. vol. 1: Principles and Practice*. Wolff, ed. San Diego, CA: ImmunoPharmaceutics, Inc. Fifth Ed. (1995):975-977.

Sano et al. "Chemical Modification of Spiramycins. V. Synthesis and Antibacterial Activity of 3'-or 4"-de-*N*-Methylspiramycin I and their *N*-Substituted Derivatives." *J. Antibiot.* 38.2(1985):186-196.

* cited by examiner

MACROCYCLIC COMPOUNDS AND METHODS OF MAKING AND USING THE SAME

RELATED APPLICATIONS

This application is a continuation application of U.S. patent application Ser. No. 10/590,782 filed Jun. 26, 2007 (now U.S. Pat. No. 8,202,843), which is a national stage application, filed under 35 U.S.C. §371, of International Application No. PCT/US2005/006082, filed on Feb. 25, 2005, which claims the benefit of and priority to U.S. Patent Application No. 60/548,280, filed Feb. 27, 2004, and to U.S. Patent Application No. 60/575,949, filed Jun. 1, 2004, the entire disclosures of each are incorporated by reference herein.

FIELD OF THE INVENTION

The present invention relates generally to the field of anti-infective, anti-proliferative, anti-inflammatory, and prokinetic agents. More particularly, the invention relates to a family of macrocyclic compounds that are useful as such agents.

BACKGROUND

Since the discovery of penicillin in the 1920s and streptomycin in the 1940s, many new compounds have been discovered or specifically designed for use as antibiotic agents. It was once believed that infectious diseases could be completely controlled or eradicated with the use of such therapeutic agents. However, such beliefs have been shaken because strains of cells or microorganisms resistant to currently effective therapeutic agents continue to evolve. In fact, virtually every antibiotic agent developed for clinical use has ultimately encountered problems with the emergence of resistant bacteria. For example, resistant strains of Gram-positive bacteria such as methicillin-resistant staphylocci, penicillin-resistant streptococci, and vancomycin-resistant enterococci have developed. These resistant bacteria can cause serious and even fatal results for patients infected with such resistant bacteria. Bacteria that are resistant to macrolide antibiotics have emerged. Also, resistant strains of Gram-negative bacteria such as *H. influenzae* and *M. catarrhalis* have been identified. See, e.g., F. D. Lowry, "Antimicrobial Resistance: The Example of *Staphylococcus aureus*," *J. Clin. Invest.*, vol. 111, no. 9, pp. 1265-1273 (2003); and Gold, H. S, and Moellering, R. C., Jr., "Antimicrobial-Drug Resistance," N. Engl. J. Med., vol. 335, pp. 1445-53 (1996).

The problem of resistance is not limited to the area of anti-infective agents, because resistance has also been encountered with anti-proliferative agents used in cancer chemotherapy.

Therefore, the need exists for new anti-infective and anti-proliferative agents that are both effective against resistant bacteria and resistant strains of cancer cells.

Despite the problem of increasing antibiotic resistance, no new major classes of antibiotics have been developed for clinical use since the approval in the United States in 2000 of the oxazolidinone ring-containing antibiotic, linezolid, which is sold under the tradename Zyvox®. See, R. C. Moellering, Jr., "Linezolid: The First Oxazolidinone Antimicrobial," *Annals of Internal Medicine*, vol. 138, no. 2, pp. 135-142 (2003). Linezolid was approved for use as an antibacterial agent active against Gram-positive organisms. However, linezolid-resistant strains of organisms are already being reported. See, Tsiodras et al., *Lancet*, vol. 358, p. 207 (2001); Gonzales et al., *Lancet*, vol 357, p. 1179 (2001); Zurenko et al., *Proceedings Of The 39th Annual Interscience Conference On Antibacterial Agents And Chemotherapy (ICAAC)*, San Francisco, Calif., USA (Sep. 26-29, 1999).

Another class of antibiotics is the macrolides, so named for their characteristic 14- to 16-membered ring. The macrolides also often have one or more 6-membered sugar-derived rings attached to the main macrolide ring. The first macrolide antibiotic to be developed was erythromycin, which was isolated from a soil sample from the Philippines in 1952. Even though erythromycin has been one of the most widely prescribed antibiotics, its disadvantages are relatively low bioavailability, gastrointestinal side effects, and a limited spectrum of activity. Another macrolide is the compound, azithromycin, which is an azolide derivative of erythromycin incorporating a methyl-substituted nitrogen in the macrolide ring. Azithromycin is sold under the tradename Zithromax®. A more recently introduced macrolide is telithromycin, which is sold under the tradename Ketek®. Telithromycin is a semisynthetic macrolide in which a hydroxyl group of the macrolide ring has been oxidized to a ketone group. See Yong-Ji Wu, Highlights of Semi-synthetic Developments from Erythromycin A, *Current Pharm. Design*, vol. 6, pp. 181-223 (2000), and Yong-Ji Wu and Wei-uo Su, Recent Developments on Ketolides and Macrolides, *Curr. Med. Chem.*, vol. 8, no. 14, pp. 1727-1758 (2001).

In the search for new therapeutic agents, researchers have tried combining or linking various portions of antibiotic molecules to create multifunctional or hybrid compounds Other researches have tried making macrolide derivatives by adding further substituents to the large macrolide ring or associated sugar rings. However, this approach for making macrolide derivatives has also met with limited success.

Notwithstanding the foregoing, there is an ongoing need for new anti-infective and anti-proliferative agents. Furthermore, because many anti-infective and anti-proliferative agents have utility as anti-inflammatory agents and prokinetic agents, there is also an ongoing need for new compounds useful as anti-inflammatory and prokinetic agents. The present invention provides compounds that meet these needs.

SUMMARY OF THE INVENTION

The invention provides compounds useful as anti-infective agents and/or anti-proliferative agents, for example, anti-biotic agents, anti-microbial agents, anti-bacterial agents, anti-fungal agents, anti-parasitic agents, anti-viral agents, and chemotherapeutic agents. The present invention also provides compounds useful as anti-inflammatory agents, and/or pro-kinetic (gastrointestinal modulatory) agents. The present invention also provides pharmaceutically acceptable salts, esters, N-oxides, or prodrugs thereof.

The present invention provides compounds having the structure of formula I or II:

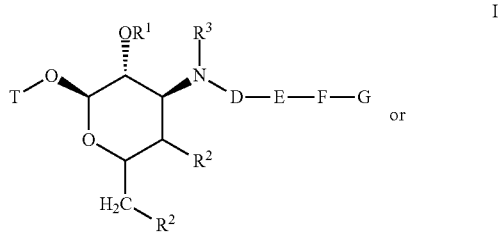

-continued

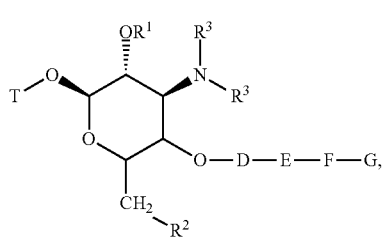
II or a stereoisomer, pharmaceutically acceptable salt, ester, N-oxide, or prodrug thereof. In the formula, variables T, D, E, F, G, R¹, R², and R³, can be selected from the respective groups of chemical moieties later defined in the detailed description.

In addition, the invention provides methods of synthesizing the foregoing compounds. Following synthesis, a therapeutically effective amount of one or more of the compounds may be formulated with a pharmaceutically acceptable carrier for administration to a mammal, particularly humans, for use as an anti-cancer, anti-biotic, anti-microbial, anti-bacterial, anti-fungal, anti-parasitic or anti-viral agent, or to treat a proliferative disease, an inflammatory disease or a gastrointestinal motility disorder, or to suspress disease states or conditions caused or mediated by nonsense or missense mutations. Accordingly, the compounds or the formulations may be administered, for example, via oral, parenteral, or topical routes, to provide an effective amount of the compound to the mammal.

The foregoing and other aspects and embodiments of the invention may be more fully understood by reference to the following detailed description and claims.

DETAILED DESCRIPTION OF THE INVENTION

The present invention provides a family of compounds that can be used as anti-proliferative agents and/or anti-infective agents. The compounds may be used without limitation, for example, as anti-cancer, anti-microbial, anti-bacterial, anti-fungal, anti-parasitic and/or anti-viral agents. Further, the present invention provides a family of compounds that can be used without limitation as anti-inflammatory agents, for example, for use in treating chronic inflammatory airway diseases, and/or as prokinetic agents, for example, for use in treating gastrointestinal motility disorders such as gastroesophageal reflux disease, gastroparesis (diabetic and post surgical), irritable bowel syndrome, and constipation. Further, the compounds can be used to treat or prevent a disease state in a mammal caused or mediated by a nonsense or missense mutation.

The compounds described herein may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C═N double bonds, and the like can also be present in the compounds described herein, and all such stable isomers are contemplated in the present invention. Cis and trans geometric isomers of the compounds of the present invention are described and may be isolated as a mixture of isomers or as separate isomeric forms. All chiral, diastereomeric, racemic, and geometric isomeric forms of a structure are intended, unless specific stereochemistry or isomeric form is specifically indicated. All processes used to prepare compounds of the present invention and intermediates made therein are considered to be part of the present invention. All tautomers of shown or described compounds are also considered to be part of the present invention.

1. Definitions

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., ═O), then 2 hydrogens on the atom are replaced. Ring double bonds, as used herein, are double bonds that are formed between two adjacent ring atoms (e.g., C═C, C═N, or N═N).

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., R³) occurs more than one time in any constituent or formula for a compound, its definition at each occurrence is independent of its definition at every other occurrence. Thus, for example, if a group is shown to be substituted with one or more R³ moieties, then the group may optionally be substituted with one, two, three, four, five, or more R³ moieties, and R³ at each occurrence is selected independently from the definition of R³. Also, combinations of substituents and/or variables are permissible, but only if such combinations result in stable compounds.

A chemical structure showing a dotted line representation for a chemical bond indicates that the bond is optionally present. For example, a dotted line drawn next to a solid single bond indicates that the bond can be either a single bond or a double bond.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible, but only if such combinations result in stable compounds.

In cases wherein there are nitrogens in the compounds of the present invention, these can be converted to N-oxides by treatment with an oxidizing agent (e.g., MCPBA and/or hydrogen peroxides) to afford other compounds of the present invention. Thus, all shown and claimed nitrogens are considered to cover both the shown nitrogen and its N-oxide (N→O) derivative.

As used herein, the term "anomeric carbon" means the acetal carbon of a glycoside.

As used herein, the term "glycoside" is a cyclic acetal.

As used herein, "alkyl" is intended to include both branched and straight-chain saturated aliphatic hydrocarbon groups having the specified number of carbon atoms. $C_{1-6}$ alkyl is intended to include $C_1$, $C_2$, $C_3$, $C_4$, $C_5$, and $C_6$ alkyl groups. $C_{1-8}$ alkyl is intended to include $C_1$, $C_2$, $C_3$, $C_4$, $C_5$, $C_6$, $C_7$, and $C_8$ alkyl groups. Examples of alkyl include, but are not limited to, methyl, ethyl, n-propyl, i-propyl, n-butyl, s-butyl, t-butyl, n-pentyl, s-pentyl, n-hexyl, n-heptyl, and n-octyl.

As used herein, "alkenyl" is intended to include hydrocarbon chains of either straight or branched configuration and one or more unsaturated carbon-carbon bonds that may occur in any stable point along the chain, such as ethenyl and propenyl. $C_{2-6}$ alkenyl is intended to include $C_2$, $C_3$, $C_4$, $C_5$, and $C_6$ alkenyl groups. $C_{2-8}$ alkenyl is intended to include $C_2$, $C_3$, $C_4$, $C_5$, $C_6$, $C_7$, and $C_8$ alkenyl groups.

As used herein, "alkynyl" is intended to include hydrocarbon chains of either straight or branched configuration and one or more triple carbon-carbon bonds that may occur in any stable point along the chain, such as ethynyl and propynyl. $C_{2-6}$ alkynyl is intended to include $C_2$, $C_3$, $C_4$, $C_5$, and $C_6$ alkynyl groups. $C_{2-8}$ alkynyl is intended to include $C_2$, $C_3$, $C_4$, $C_5$, $C_6$, $C_7$, and $C_8$ alkynyl groups.

Furthermore, "alkyl", "alkenyl", and "alkynyl" are intended to include moieties which are diradicals, i.e., having two points of attachment, an example of which in the present invention is when D is selected from these chemical groups. A nonlimiting example of such an alkyl moiety that is a diradical is —$CH_2CH_2$—, i.e., a $C_2$ alkyl group that is covalently bonded via each terminal carbon atom to the remainder of the molecule.

As used herein, the terms used to describe various carbon-containing moieties, including, for example, "alkyl," "alkenyl," "alkynyl," "phenyl," and any variations thereof, are intended to include univalent, bivalent, or multivalent species. For example, "$C_{1-6}$ alkyl-$R^3$" is intended to represent a univalent $C_{1-6}$ alkyl group substituted with a $R^3$ group, and "O—$C_{1-6}$ alkyl-$R^3$" is intended to represent a bivalent $C_{1-6}$ alkyl group, i.e., an "alkylene" group, substituted with an oxygen atom and a $R^3$ group.

As used herein, "cycloalkyl" is intended to include saturated ring groups, such as cyclopropyl, cyclobutyl, or cyclopentyl. $C_{3-8}$ cycloalkyl is intended to include $C_3$, $C_4$, $C_5$, $C_6$, $C_7$, and $C_8$ cycloalkyl groups.

As used herein, "halo" or "halogen" refers to fluoro, chloro, bromo, and iodo. "Counterion" is used to represent a small, negatively charged species such as chloride, bromide, hydroxide, acetate, and sulfate.

As used herein, "haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl.

As used herein, "alkoxy" refers to an alkyl group as defined above with the indicated number of carbon atoms attached through an oxygen bridge. $C_{1-6}$ alkoxy, is intended to include $C_1$, $C_2$, $C_3$, $C_4$, $C_5$, and $C_6$ alkoxy groups. $C_{1-8}$ alkoxy, is intended to include $C_1$, $C_2$, $C_3$, $C_4$, $C_5$, $C_6$, $C_7$, and $C_8$ alkoxy groups. Examples of alkoxy include, but are not limited to, methoxy, ethoxy, n-propoxy, i-propoxy, n-butoxy, s-butoxy, t-butoxy, n-pentoxy, s-pentoxy, n-heptoxy, and n-octoxy.

As used herein, "alkylthio" refers to an alkyl group as defined above with the indicated number of carbon atoms attached through an sulfur bridge. $C_{1-6}$ alkylthio, is intended to include $C_1$, $C_2$, $C_3$, $C_4$, $C_5$, and $C_6$ alkylthio groups. $C_{1-8}$ alkylthio, is intended to include $C_1$, $C_2$, $C_3$, $C_4$, $C_5$, $C_6$, $C_7$, and $C_8$ alkylthio groups.

As used herein, "carbocycle" or "carbocyclic ring" is intended to mean, unless otherwise specified, any stable 3, 4, 5, 6, 7, 8, 9, 10, 11, or 12-membered monocyclic, bicyclic or tricyclic ring, any of which may be saturated, unsaturated, or aromatic, recognizing that rings with certain numbers of members cannot be bicyclic or tricyclic, e.g., a 3-membered ring can only be a monocyclic ring. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl. As shown above, bridged rings are also included in the definition of carbocycle (e.g., [2.2.2] bicyclooctane). A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge. Fused (e.g., naphthyl and tetrahydronaphthyl) and spiro rings are also included.

As used herein, the term "heterocycle" means, unless otherwise stated, a stable 3, 4, 5, 6, 7, 8, 9, 10, 11, or 12-membered monocyclic, bicyclic or tricyclic ring (recognizing that rings with certain numbers of members cannot be bicyclic or tricyclic, e.g., a 3-membered ring can only be a monocyclic ring), which is saturated, unsaturated, or aromatic, and consists of carbon atoms and one or more ring heteroatoms, e.g., 1 or 1-2 or 1-3 or 1-4 or 1-5 or 1-6 heteroatoms, independently selected from the group consisting of nitrogen, oxygen, and sulfur, and including any bicyclic or tricyclic group in which any of the above-defined heterocyclic rings is fused to a second ring (e.g., a benzene ring). The nitrogen and sulfur heteroatoms may optionally be oxidized (i.e., N→O and S(O)$_p$, where p=1 or 2). When a nitrogen atom is included in the ring it is either N or NH, depending on whether or not it is attached to a double bond in the ring (i.e., a hydrogen is present if needed to maintain the tri-valency of the nitrogen atom). The nitrogen atom may be substituted or unsubstituted (i.e., N or NR wherein R is H or another substituent, as defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge. Spiro and fused rings are also included.

As used herein, the term "aromatic heterocycle" or "heteroaryl" is intended to mean a stable 5, 6, 7, 8, 9, 10, 11, or 12-membered monocyclic or bicyclic aromatic ring (recognizing that rings with certain numbers of members cannot be a bicyclic aromatic, e.g., a 5-membered ring can only be a monocyclic aromatic ring), which consists of carbon atoms and one or more heteroatoms, e.g., 1 or 1-2 or 1-3 or 1-4 or 1-5 or 1-6 heteroatoms, independently selected from the group consisting of nitrogen, oxygen, and sulfur. In the case of bicyclic heterocyclic aromatic rings, only one of the two rings needs to be aromatic (e.g., 2,3-dihydroindole), though both may be (e.g., quinoline). The second ring can also be fused or bridged as defined above for heterocycles. The nitrogen atom may be substituted or unsubstituted (i.e., N or NR wherein R is H or another substituent, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluene sulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th ed., Mack Publishing Company, Easton, Pa., USA, p. 1445 (1990).

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

As used herein, "treating" or "treatment" means the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

As used herein, "mammal" refers to human and non-human patients.

As used herein, the term "therapeutically effective amount" refers to a compound, or a combination of compounds, of the present invention present in or on a recipient in an amount sufficient to elicit biological activity, for example, anti-microbrial activity, anti-fungal activity, anti-viral activity, anti-parasitic activity, and/or anti-proliferative activity. The combination of compounds is preferably a synergistic combination. Synergy, as described, for example, by Chou and Talalay, *Adv. Enzyme Regul.* vol. 22, pp. 27-55 (1984), occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased anti-proliferative and/or anti-infective effect, or some other beneficial effect of the combination compared with the individual components.

All percentages and ratios used herein, unless otherwise indicated, are by weight.

Throughout the description, where compositions are described as having, including, or comprising specific components, or where processes are described as having, including, or comprising specific process steps, it is contemplated that compositions of the present invention also consist essentially of, or consist of, the recited components, and that the processes of the present invention also consist essentially of, or consist of, the recited processing steps. Further, it should be understood that the order of steps or order for performing certain actions are immaterial so long as the invention remains operable. Moreover, two or more steps or actions may be conducted simultaneously.

2. Compounds of the Invention

In one aspect, the invention provides a compound having the formula:

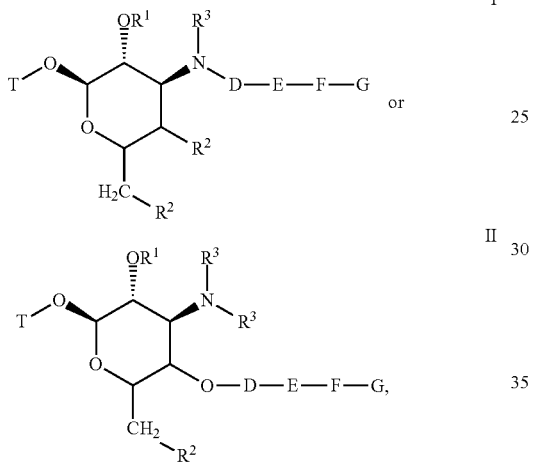

or a pharmaceutically acceptable salt, ester, N-oxide, or prodrug thereof, wherein T is a 14-, 15-, or 16-membered macrolide connected via a macrocyclic ring carbon atom;

$R^1$ and $R^3$ independently are selected from the group consisting of: (a) H, (b) a $C_{1-6}$ alkyl group, (c) a $C_{2-6}$ alkenyl group, (d) a $C_{2-6}$ alkynyl group, (e) —C(O)$R^5$, (f) —C(O)O$R^5$, (g) —C(O)—NR$^4$R$^4$R$^4$, (h) —C(S)$R^5$, (i) —C(S)O$R^5$, (j) —C(O)O$R^S$, or (k) —C(S)—NR$^4$R$^4$R$^4$; $R^2$ is hydrogen or —O$R^{12}$;

D is selected from the group consisting of:
(a) a single bond, (b) a $C_{1-6}$ alkyl group, (c) a $C_{2-6}$ alkenyl group; (d) a $C_{2-6}$ alkynyl group; (e) —C(O)—X—, (f) —C(O)O—X—, (g) —C(O)NR$^4$R$^4$—X—, (h) —C(=NR$^4$)—X—, (i) —C(=NR$^4$)O—X—, (j) —C(=NR$^4$)N—X—, (k) —SO$_2$—X—, (l) —C(NR$^4$)NR$^4$—X—, (m) —C(S)—X—, (n) —C(S)NR$^4$—X—, (o) —C(NR$^4$)S—X—, or (p) —C(O)S—X—, wherein
 i) 0-2 carbon atoms in any of (b)-(d) of D immediately above optionally is replaced by a moiety selected from the group consisting of O, S(O)$_p$, and NR$^4$,
 ii) each of the groups (b)-(d) immediately above optionally is substituted with one or more $R^5$ groups,
 iii) alternatively when $R^5$ is present as an optional substituent on (b)-(d), $R^3$ and $R^5$ can be taken together with the atoms to which they are attached to form a 3-7 membered ring, and
 iv) X is selected from the group consisting of (aa) a $C_{1-6}$ alkyl group, (bb) a $C_{2-6}$ alkenyl group, or (cc) a $C_{2-6}$ alkynyl group, wherein each of groups (aa)-(cc) optionally is substituted with one or more $R^5$ groups;

F is selected from the group consisting of:
(a) a single bond, (b) a $C_{1-6}$ alkyl group, (c) a $C_{2-6}$ alkenyl group, (d) a $C_{2-6}$ alkynyl group, wherein
 i) 0-2 carbon atoms in any of (b)-(d) of F immediately above optionally is replaced by a moiety selected from the group consisting of O, S(O)$_p$, and NR$^4$,
 ii) any of (b)-(d) of F immediately above optionally is substituted with one or more $R^5$ groups, and
 iii) any of (b)-(d) of F immediately above optionally is substituted with $C_{1-6}$ alkyl-$R^5$ groups;

E is selected from the group consisting of:
(a) a 3-10 membered saturated, unsaturated, or aromatic heterocycle containing one or more heteroatoms selected from the group consisting of nitrogen, oxygen, and sulfur,
(b) a 3-10 membered saturated, unsaturated, or aromatic carbocycle,
(c) a —W-[3-10 membered saturated, unsaturated, or aromatic heterocycle containing one or more heteroatoms selected from the group consisting of nitrogen, oxygen, and sulfur],
(d) a —W-[3-10 membered saturated, unsaturated, or aromatic carbocycle],
(e) —C(O)—, (f) —C(O)O—, (g) —C(O)NR$^4$—, (h) —C(=NR$^4$)—,
(i) —C(=NR$^4$)O—, (j) —C(=NR$^4$)NR$^4$—, (k) —OC(O)—, (l) —OC(O)O—,
(m) —OC(O)NR$^4$—, (n) —NR$^4$C(O)—, (O)—NR$^4$C(O)O—,
(p) —NR$^4$C(O)NR$^4$—, (q) —NR$^4$C(=NR$^4$)NR$^4$—, (r) —S(O)$_p$,
(s) —NR$^4$S(O)$_2$—, (t) —S(O)$_2$NR$^4$—, (u) —C(N—OR$^4$)—, (v) —CH$_2$—,
(w) —C(N—NR$^4$R$^4$)—, (x) —C(S)NR$^4$—, (y) —NR$^4$C(S)—, (z) —C(S)O—, or
(aa) —OC(S)—, wherein
 i) any of (a)-(d) immediately above optionally is substituted with one or more $R^5$ groups; and
 ii) W is selected from the group consisting of:
  (aa) —OCO—, (bb) —OC(O)O—, (cc) —OC(O)NR$^4$—,
  (dd) —NR$^4$C(O)O—, (ee) —OCNOR$^4$—,
  (ff) —NR$^4$—C(O)O—, (gg) —C(S)(NR$^4$)—, (hh) —NR$^4$—,
  (ii) —OC(S)O—, (jj) —OC(S)NR$^4$—, (kk) —NR$^4$C(S)O—, (ll) —OC(S)NOR$^4$—, (mm) —C(S)O—, (nn) -, OC(S)—, (oo) —C(O)—,
  (pp) —C(O)O—, (qq) —C(O)NR$^4$—, (rr) —C(=NR$^4$)—,
  (ss) —C(=NR$^4$)O—, (tt) —C(=NR$^4$)NR$^4$—,
  (uu) —OC(O)—, (vv) —OC(O)O—, (ww) —OC(O)NR$^4$—, (xx) —NR$^4$C(O)—, (yy) —NR$^4$C(O)O—, (zz) —NR$^4$C(O)NR$^4$—, (aaa) —NR$^4$C(=NR$^4$)NR$^4$—,
  (bbb) —S(O)$_p$, (ccc) —NR$^4$S(O)$_2$—, (ddd) —S(O)$_2$NR$^4$—, (eee) —C(N—OR$^4$)—, (fff) —C(N—NR$^4$R$^4$)—, (ggg) —C(S)NR$^4$—, or (hhh) —NR$^4$C(S)—;

G is selected from the group consisting of: (a) B' and (b) B'—Z—B", wherein
  i) each B' and B" is independently selected from the group consisting of (aa) an aryl group, (bb) a heteroaryl group, (cc) a biaryl group, (dd) a fused bicyclic or tricyclic saturated, unsaturated or aromatic ring system optionally containing one or more heteroatoms selected from the group consisting of nitrogen, oxygen, and sulfur, (ee) a 3-10 membered saturated or unsaturated heterocycle containing one or more heteroatoms selected from the group consisting of nitrogen, oxygen, and sulfur, (ff) a 3-10 membered saturated, or unsaturated carbocycle, wherein each (aa)-(ff) optionally is substituted with one or more $R^{11}$ groups; and
  ii) Z is selected from the group consisting of (aa) a single bond, (bb) a $C_{1-2}$ alkyl group, (cc) a $C_2$ alkenyl group, (dd) a $C_2$ alkynyl group, (ee) —C(O)—, (ff) —C(O)O—, (gg) —C(O)NR$^4$—, (hh) —C(=NR$^4$)—, (ii) —C(=NR$^4$)O—, (jj) —C(=NR$^4$)NR$^4$—, (kk) —S(O)$_p$, (ll) —OC(O)—, (mm) —C(S)—, (nn) —C(S)NR$^4$—, (oo) —C(NR$^4$)S—, (pp) —C(O)S—, (qq)-O—, (rr) —NR$^4$—, (ss) —NR$^4$C(O)—, (tt) —OC(NR$^4$)—, (uu) —NC(NR$^4$)—, (vv) —C(S)O—, (ww) —SC(O)—, or (xx) —OC(S);

$R^4$, at each occurrence, independently is selected from the group consisting of:
  (a) H, (b) a $C_{1-6}$ alkyl group, (c) a $C_{2-6}$ alkenyl group, (d) a $C_{2-6}$ alkynyl group, (e) a $C_{6-10}$ saturated, unsaturated, or aromatic carbocycle, (f) a 3-12 membered saturated, unsaturated, or aromatic heterocycle containing one or more heteroatoms selected from the group consisting of nitrogen, oxygen, and sulfur, (g) —C(O)—$C_{1-6}$ alkyl, (h) —C(O)—$C_{2-6}$ alkenyl, (i) —C(O)—$C_{2-6}$ alkynyl, (j) —C(O)—$C_{6-10}$ saturated, unsaturated, or aromatic carbocycle, (k) —C(±)-3-12 membered saturated, unsaturated, or aromatic heterocycle containing one or more heteroatoms selected from the group consisting of nitrogen, oxygen, and sulfur, (l) —C(O)O—$C_{1-6}$ alkyl, (m) —C(O)O—$C_{2-6}$ alkenyl, (n) —C(O)O—$C_{2-6}$ alkynyl, (o) —C(O)O—$C_{6-10}$ saturated, unsaturated, or aromatic carbocycle, p) —C(O)O-3-12 membered saturated, unsaturated, or aromatic heterocycle containing one or more heteroatoms selected from the group consisting of nitrogen, oxygen, and sulfur, and q) —C(O)NR$^6$R$^6$,
    wherein any of (b)-(p) optionally is substituted with one or more $R^5$ groups,
  alternatively, NR$^4$R$^4$ forms a 3-7 membered saturated, unsaturated or aromatic ring including the nitrogen atom to which the $R^4$ groups are bonded, wherein said ring is optionally substituted at a position other than the nitrogen atom to which the $R^4$ groups are bonded, with one or more moieties selected from the group consisting of O, S(O)$_p$, N, and NR$^8$;

$R^5$ is selected from the group consisting of:
  (a) $R^7$, (b) a $C_{1-8}$ alkyl group, (c) a $C_{2-8}$ alkenyl group, (d) a $C_{2-8}$ alkynyl group, (e) a $C_{3-12}$ saturated, unsaturated, or aromatic carbocycle, and (f) a 3-12 membered saturated, unsaturated, or aromatic heterocycle containing one or more heteroatoms selected from the group consisting of nitrogen, oxygen, and sulfur, or two $R^5$ groups, when present on the same carbon atom can be taken together with the carbon atom to which they are attached to form a Spiro 3-6 membered carbocyclic ring or heterocyclic ring containing one or more heteroatoms selected form the group consisting of nitrogen, oxygen, and sulfur;
    wherein any of (b)-(f) immediately above optionally is substituted with one or more $R^7$ groups;

$R^6$, at each occurrence, independently is selected from the group consisting of:
  (a) H, (b) a $C_{1-6}$ alkyl group, (c) a $C_{2-6}$ alkenyl group, (d) a $C_{2-6}$ alkynyl group, (e) a $C_{3-10}$ saturated, unsaturated, or aromatic carbocycle, and (f) a 3-10 membered saturated, unsaturated, or aromatic heterocycle containing one or more heteroatoms selected from the group consisting of nitrogen, oxygen, and sulfur,
    wherein any of (b)-(f) optionally is substituted with one or more moieties selected from the group consisting of:
      (aa) a carbonyl group, (bb) a formyl group, (cc) F, (dd) Cl, (ee) Br,
      (ff) I, (gg) CN, (hh) NO$_2$, (ii) —OR$^8$,
      (jj) —S(O)$_p$R$^8$, (kk) —C(O)R$^8$, (ll) —C(O)OR$^8$,
      (mm) —OC(O)R$^8$, (nn) —C(O)NR$^8$R$^8$,
      (oo) —OC(O)NR$^8$R$^8$, (pp) —C(=NR$^8$)R$^8$,
      (qq) —C(R$^8$)(R$^8$)OR$^8$, (rr) —C(R$^8$)$_2$OC(O)R$^8$,
      (ss) —C(R$^8$)(OR$^8$)(CH$_2$)$_r$NR$^8$R$^8$, (tt) —NR$^8$R$^8$,
      (uu) —NR$^8$OR$^8$, (vv) —NR$^8$C(O)R$^8$,
      (ww) —NR$^8$C(O)OR$^8$, (xx) —NR$^8$C(O)NR$^8$R$^8$,
      (yy) —NR$^8$S(O)$_r$R$^8$, (zz) —C(OR$^8$)(OR$^8$)R$^8$,
      (ab) —C(R$^8$)$_2$NR$^8$R$^8$, (ac) =NR$^8$,
      (ad) —C(S)NR$^8$R$^8$, (ae) —NR$^8$C(S)R$^8$,
      (af) —OC(S)NR$^8$R$^8$, (ag) —NR$^8$C(S)OR$^8$,
      (ah) —NR$^8$C(S)NR$^8$R$^8$, (ai) —SC(O)R$^8$,
      (aj) a $C_{1-8}$ alkyl group, (ak) a $C_{2-8}$ alkenyl group, (al) a $C_{2-8}$ alkynyl group, (am) a $C_{1-8}$ alkoxy group, (an) a $C_{1-8}$ alkylthio group, (ao) a $C_{1-8}$ acyl group, (ap) —CF$_3$,
      (aq) —SCF$_3$, (ar) a $C_{3-10}$ saturated, unsaturated, or aromatic carbocycle, and (as) a 3-10 membered saturated, unsaturated, or aromatic heterocycle containing one or more heteroatoms selected from the group consisting of nitrogen, oxygen, and sulfur,
  alternatively, NR$^6$R$^6$ forms a 3-10 membered saturated, unsaturated or aromatic ring including the nitrogen atom to which the R$^6$ groups are attached wherein said ring is optionally substituted at a position other than the nitrogen atom to which the R$^6$ groups are bonded, with one or more moieties selected from the group consisting of O, S(O)$_p$, N, and NR$^8$;
  alternatively, CR$^6$R$^6$ forms a carbonyl group;

$R^7$, at each occurrence, is selected from the group consisting of:
  (a) H, (b) =O, (c) F, (d) Cl, (e) Br, (f) I, (g) —CF$_3$, (h) —CN, (i) —N$_3$ (j) —NO$_2$, (k) —NR$^6$(CR$^6$R$^6$)$_r$R$^9$, (l) —OR$^9$, (m) —S(O)$_p$C(R$^6$R$^6$)$_r$R$^9$, (n) —C(O)(CR$^6$R$^6$)$_r$R$^9$, (o) —OC(O)(CR$^6$R$^6$)$_r$R$^9$, (p) —SC(O)(CR$^6$R$^6$)$_r$R$^9$, (q) —C(O)O(CR$^6$R$^6$)$_r$R$^9$, (r) —NR$^6$C(O)(CR$^6$R$^6$)$_r$R$^9$, (s) —C(O)NR$^6$(CR$^6$R$^6$)$_r$R$^9$, (t) —C(=NR$^6$)(CR$^6$R$^6$)$_r$R$^9$, (u) —C(=NNR$^6$)(CR$^6$R$^6$)$_r$R$^9$, (v) —C(=NNR$^6$C(O)R$^6$)(CR$^6$R$^6$)$_r$R$^9$, (w) —C(=NOR$^9$)(CR$^6$R$^6$)$_r$R$^9$, (x) —NR$^6$C(O)O(CR$^6$R$^6$)$_r$R$^9$, (y) —OC(O)NR$^6$(CR$^6$R$^6$)$_r$R$^9$, (z) —NR$^6$C(O)NR$^6$(CR$^6$R$^6$)$_r$R$^9$, (aa) —NR$^6$S(O)$_p$(CR$^6$R$^6$)$_r$R$^9$, (bb) —S(O)$_p$NR$^6$(CR$^6$R$^6$)$_r$R$^9$, (cc) —NR$^6$S(O)$_p$NR$^6$(CR$^6$R$^6$)$_r$R$^9$, (dd) —NR$^6$R$^6$, (ee) —NR$^6$(CR$^6$R$^6$), (ff) —OH, (gg) —NR$^6$R$^6$, (hh) —OCH$_3$, (ii) —S(O)$_p$R$^6$, (jj) —NC(O)R$^6$, (kk) a $C_{1-6}$ alkyl group, (ll) a $C_{2-6}$ alkenyl group, (mm) a $C_{2-6}$ alkynyl group, (nn) —$C_{3-10}$ saturated, unsaturated, or aromatic carbocycle, and (oo) 3-10 membered saturated, unsaturated, or aromatic heterocycle containing one or more heteroatoms selected from the group consisting of nitrogen, oxygen, and sulfur,
wherein any of (kk)-(oo) optionally is substituted with one or more $R^9$ groups;
alternatively, two $R^7$ groups may form —O(CH$_2$)$_u$O—;

$R^8$ is selected from the group consisting of:
(a) $R^5$, (b) H, (c) a $C_{1-6}$ alkyl group, (d) a $C_{2-6}$ alkenyl group, (e) a $C_{2-6}$ alkynyl group, (f) a $C_{3-10}$ saturated, unsaturated, or aromatic carbocycle, (g) a 3-10 membered saturated, unsaturated, or aromatic heterocycle containing one or more heteroatoms selected from the group consisting of nitrogen, oxygen, and sulfur, (h) —C(O)—C$_{1-6}$ alkyl, (i) —C(O)—C$_{1-6}$ alkenyl, (j) —C(O)—C$_{1-6}$ alkynyl, (k) —C(O)—C$_{3-10}$ saturated, unsaturated, or aromatic carbocycle, and (l) —C(O)-3-10 membered saturated, unsaturated, or aromatic heterocycle containing one or more heteroatoms selected from the group consisting of nitrogen, oxygen, and sulfur,
wherein any of (c)-(k) optionally is substituted with one or more moieties selected from the group consisting of: (aa) H, (bb) F, (cc) Cl, (dd) Br, (ee) I, (ff) CN, (gg) NO$_2$, (hh) OH, (ii) NH$_2$, (jj) NH(C$_{1-6}$ alkyl), (kk) N(C$_{1-6}$ alkyl)$_2$, (ll) a C$_{1-6}$ alkoxy group, (mm) an aryl group, (nn) a substituted aryl group, (oo) a heteroaryl group, (pp) a substituted heteroaryl group, and qq) a C$_{1-6}$ alkyl group optionally substituted with one or more moieties selected from the group consisting of an aryl group, a substituted aryl group, a heteroaryl group, a substituted heteroaryl group, F, Cl, Br, I, CN, NO$_2$, CF$_3$, SCF$_3$, and OH;

$R^9$, at each occurrence, independently is selected from the group consisting of:
(a) $R^{10}$, (b) a C$_{1-6}$ alkyl group, (c) a C$_{2-6}$ alkenyl group, (d) a C$_{2-6}$ alkynyl group, e) a C$_{3-10}$ saturated, unsaturated, or aromatic carbocycle, and f) a 340 membered saturated, unsaturated, or aromatic heterocycle containing one or more heteroatoms selected from the group consisting of nitrogen, oxygen, and sulfur,
wherein any of (b)-(f) optionally is substituted with one or more $R^{10}$ groups;

$R^{10}$, at each occurrence, independently is selected from the group consisting of:
(a) H, (b) =O, (c) F, (d) Cl, (e) Br, (f) I, (g) —CF$_3$, (h) —CN, (i) —NO$_2$, (j) —NR$^6$R$^6$, (k) —OR$^6$, (l) —S(O)$_p$R$^6$, (m) —C(O)R$^6$, (n) —C(O)OR$^6$, (o) —OC(O)R$^6$, (p) NR$^6$C(O)R$^6$, (q) —C(O)NR$^6$R$^6$, (r) —C(=NR$^6$)R$^6$, (s) —NR$^6$C(O)NR$^6$R$^6$, (t) —NR$^6$S(O)$_p$R$^6$, (u) —S(O)$_p$NR$^6$R$^6$, (v) —NR$^6$S(O)$_p$NR$^6$R$^6$, (w) a C$_{1-6}$ alkyl group, (x) a C$_{2-6}$ alkenyl group, (y) a C$_{2-6}$ alkynyl group, (z) a C$_{3-10}$ saturated, unsaturated, or aromatic carbocycle, and (aa) a 3-10 membered saturated, unsaturated, or aromatic heterocycle containing one or more heteroatoms selected from the group consisting of nitrogen, oxygen, and sulfur,
wherein any of (w)-(aa) optionally is substituted with one or more moieties selected from the group consisting of R$^6$, F, Cl, Br, I, CN, NO$_2$, —OR$^6$, —NH$_2$, —NH(C$_{1-6}$ alkyl), —N(C$_{1-6}$ alkyl)$_2$, a C$_{1-6}$ alkoxy group, a C$_{1-6}$ alkylthio group, and a C$_{1-6}$ acyl group;

$R^{11}$ each occurrence, independently is selected from the group consisting of:
(a) a carbonyl group, (b) a formyl group, (c) F, (d) Cl, (e) Br, (f) I, (g) CN, (h) NO$_2$, (i) OR$^8$, (j) —S(O)$_p$R$^8$, (k) —C(O)R$^8$, (l) —C(O)OR$^8$, (m) —OC(O)R$^8$, (n) —C(O)NR$^8$R$^8$, (o) —OC(O)NR$^8$R$^8$, (p) —C(=NR$^8$)R$^8$, (q) —C(R$^8$)(R$^8$)OR$^8$, (r) —C(R$^8$)$_2$ OC(O)R$^8$, (s) —C(R$^8$)(OR$^8$)(CH$_2$)$_r$NR$^8$R$^8$, (t) —NR$^8$R$^8$, (u) —NR$^8$OR$^8$, (v) —NR$^8$C(O)R$^8$, (w) —NR$^8$C(O)OR$^8$, (x) —NR$^8$C(O)NR$^8$R$^8$, (y) —NR$^8$S(O)$_r$R$^8$, (z) —C(OR$^8$)(OR$^8$)R$^8$, (aa) —C(R$^8$)$_2$NR$^8$R$^8$, (bb) =NR$^8$, (cc) —C(S)NR$^8$R$^8$, (dd) —NR$^8$C(S)R$^8$, (ee) —OC(S)NR$^8$R$^8$, (ff) —NR$^8$C(S)OR$^8$, (gg) —NR$^8$C(S)NR$^8$R$^8$, (hh) —SC(O)R$^8$, (ii) a C$_{1-8}$ alkyl group, (jj) a C$_{2-8}$ alkenyl group, (kk) a C$_{2-8}$ alkynyl group, (ll) a C$_{1-8}$ alkoxy group, (mm) a C$_{1-8}$ alkylthio group, (nn) a C$_{1-8}$ acyl group, (oo) a C$_{3-10}$ saturated, unsaturated, or aromatic carbocycle, and (pp) a 3-10 membered saturated, unsaturated, or aromatic heterocycle containing one or more heteroatoms selected from the group consisting of nitrogen, oxygen, and sulfur, wherein (ii)-(kk) optionally are substituted with one or more $R^5$ groups;

$R^{12}$ is selected from the group consisting of:
(a) H, (b) a C$_{1-6}$ alkyl group, (c) a C$_{2-6}$ alkenyl group, (d) a C$_{2-6}$ alkynyl group, (e) —C(O)R$^5$, (f) —C(O)OR$^5$, (g) —C(O)—NR$^4$R$^{4-4}$, (h) —C(S)R$^5$, (i) —C(S) OR$^5$, (j) —C(O)OR$^5$, (k) —C(S)—NR$^4$R$^4$R$^4$, (l) a C$_{3-10}$ saturated, unsaturated, or aromatic carbocycle, or (m) a 3-10 membered saturated, unsaturated, or aromatic heterocycle containing one or more heteroatoms selected from the group consisting of nitrogen, oxygen, and sulfur, (n) a —(C$_{1-6}$ alkyl)—C$_{3-10}$ saturated, unsaturated, or aromatic carbocycle, or (O) a —(C$_{1-6}$ alkyl)-3-10 membered saturated, unsaturated, or aromatic heterocycle containing one or more heteroatoms selected from the group consisting of nitrogen, oxygen, and sulfur,
wherein (a)-(d) and (l)-(o) optionally are substituted with one or more $R^5$ groups;

p at each occurrence is 0, 1, or 2;
r at each occurrence is 0, 1, or 2;
t at each occurrence is 0, 1, or 2;
u at each occurrence is 1, 2, 3, or 4;

provided that
i) when T is a 14 or 15 membered macrolide D-E is not

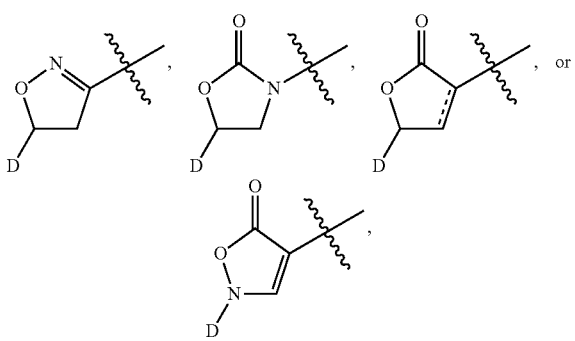

ii) when T is a 14 or 15 membered macrolide F—B' is not

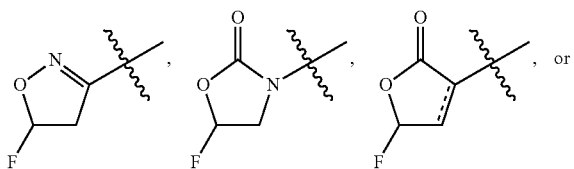

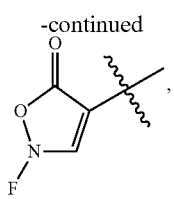

iii) when T is a 14 or 15 membered macrolide B'—Z—B" is not

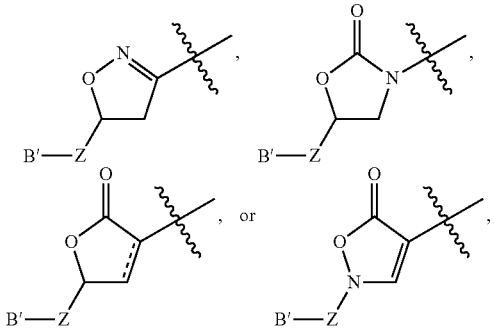

iv) when T is a 14 or 15 membered macrolide $R^{11}$ is not

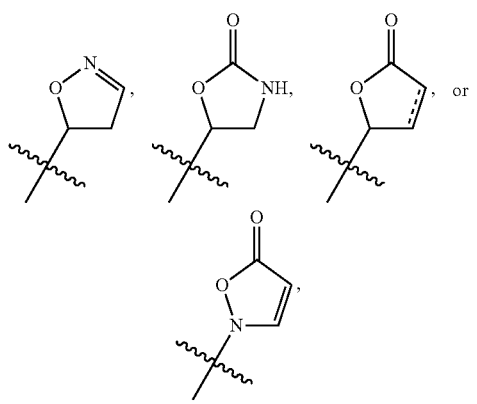

v) when the compound has formula I and T is

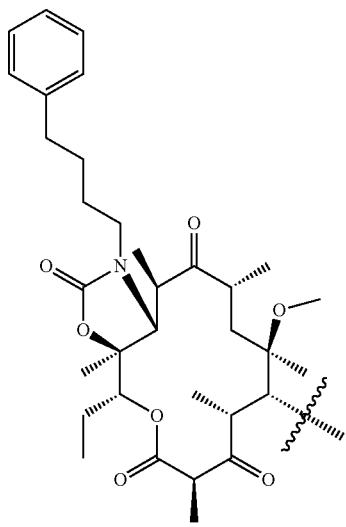 [SMILES: CC[C@H]1OC(=O)[C@H](C)C(=O)[C@H](C)[C@@H](C)[C@](C)(OC)C[C@@H](C)C(=O)[C@H](C)[C@H]2N(CCCCc3ccccc3)C(=O)O[C@]12C]

D is not a single bond or a —CH$_2$—, vi) when the compound has formula I and T is a 14 or 15 membered macrolide -D-E-F— is not a —CH$_2$—, vii) when the compound has formula I and T is a 14 or 15 membered macrolide -D-E-F-G- is not a chemical moiety selected from the chemical moieties listed in Table A,

TABLE A

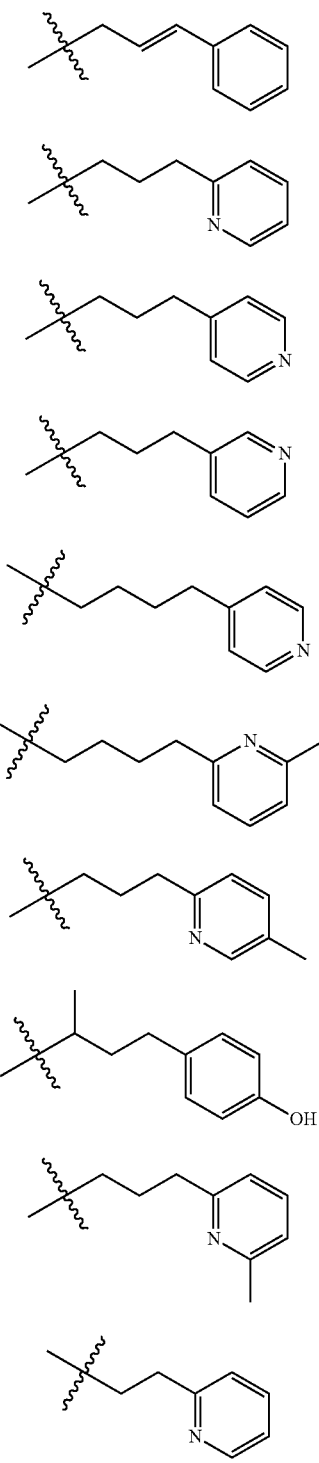

TABLE A-continued

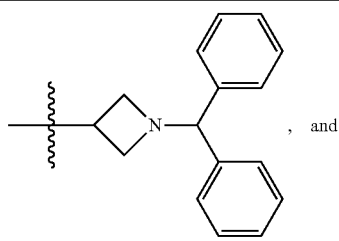
, and viii) when the compound has formula II and T is a 16 membered macrolide
  i. -D-E- is not a glycoside attached via its anomeric carbon,
  ii. -D-E-F-G is not a $C_{1-4}$ (alkyl), $C_{2-4}$(alkenyl), or $C_{2-4}$(alkynyl) chain bonded to a 5-10 membered monocyclic or bicyclic carbocyle or heterocycle or bonded to a 5 or 6 membered carbocycle or heterocycle bonded to a 5 or 6 membered carbocycle or heterocycle, further, any of said carbocycles or heterocycles being optionally substituted with one or more groups selected from the group consisting of (aa) —OH, (bb) —F, (cc) —Cl, (dd) —I, and (ee) —$NO_2$, and
  iii. -D-E-F-G- is not a chemical moiety selected from the chemical moieties listed in Table B.

TABLE B

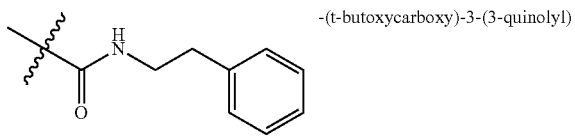
-(t-butoxycarboxy)-3-(3-quinolyl)

In certain embodiments, the invention provides a compound having the formula:

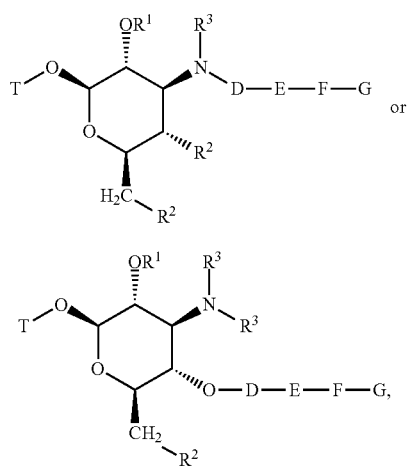

or a pharmaceutically acceptable salt, ester, N-oxide, or prodrug thereof, wherein T, D, E, F, G, $R^1$, $R^2$, and $R^3$ are as defined hereinabove.

Other embodiments of the foregoing compounds include those compounds having the formula:

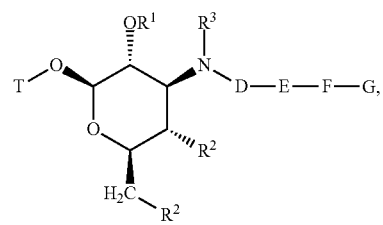

or a pharmaceutically acceptable salt, ester, N-oxide, or prodrug thereof, wherein T, D, E, F, G, $R^1$, $R^2$, and $R^3$ are as defined hereinabove.

Other embodiments of the foregoing compounds include those having the formula:

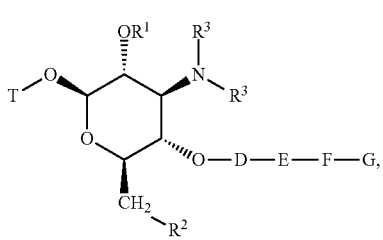

or a pharmaceutically acceptable salt, ester, N-oxide, or prodrug thereof, wherein T, D, E, F, G, $R^1$, $R^2$, and $R^3$ are as defined hereinabove.

Other embodiments of the foregoing compounds include those where T is a 14- or 15-membered macrolide (i.e., not a 16 membered macrolide) connected via a macrocyclic ring carbon atom. In other embodiments, T is a 16 membered macrolide (i.e., not a 14 or 15 membered macrolide) connected via a macrocyclic ring carbon atom.

In certain other embodiments when T is a 14-, 15-, or 16-membered macrolide
  i) D-E is not

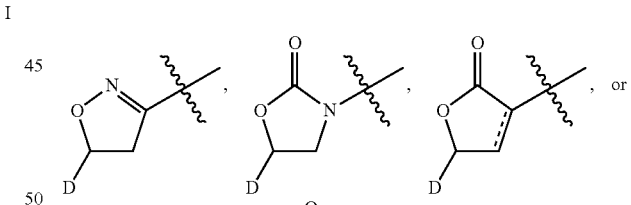

ii) F—B' is not

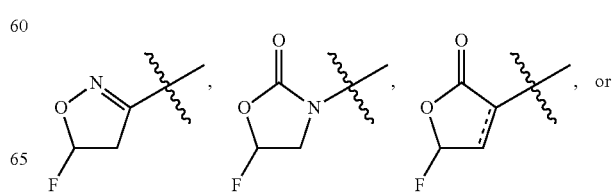

-continued

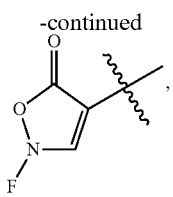

iii) B'—Z—B" is not

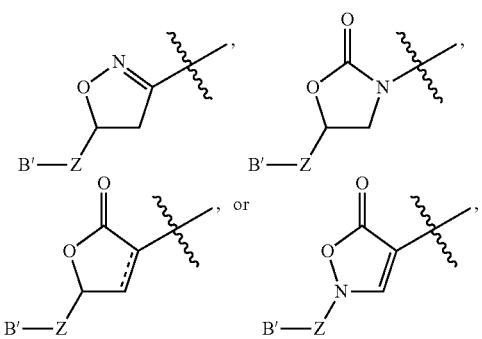

and
iv) R[11] is not

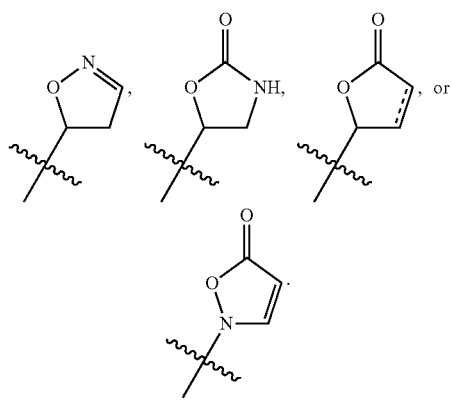

Other embodiments of the foregoing compounds include those where G is B'. Other embodiments of the foregoing compounds include those where B' is selected from the group consisting of: (a) an aryl group, (b) a heteroaryl group, (c) a biaryl group, and (d) a fused bicyclic or tricyclic unsaturated or aromatic ring system optionally containing one or more carbonyl groups and one or more heteroatoms selected from the group consisting of nitrogen, oxygen, and sulfur, wherein each (a)-(d) optionally is substituted with one or more R[11] groups.

Other embodiments of the foregoing compounds include those where E is
(a) a 3-10 membered saturated, unsaturated, or aromatic heterocycle containing one or more heteroatoms selected from the group consisting of nitrogen, oxygen, and sulfur,
(b) a 3-10 membered saturated, unsaturated, or aromatic carbocycle,
(c) a —W-[3-10 membered saturated, unsaturated, or aromatic heterocycle containing one or more heteroatoms selected from the group consisting of nitrogen, oxygen, and sulfur],
(d) a —W-[3-10 membered saturated, unsaturated, or aromatic carbocycle],
(e) —C(O)—, (f) —C(O)O—, (g) —C(O)NR[4]—, (h) —C(=NR[4])—,
(i) —C(=NR[4])O—, (j) —C(=NR[4])NR[4]—, (k) —OC(O)—, (l) —OC(O)O—,
(m) —OC(O)NR[4]—, (n) —NR[4]C(O)—, (o) —NR[4]C(O)O—,
(p) —NR[4]C(O)NR[4]—, (q) —NR[4]C(=NR[4])NR[4]—, (r) —S(O)$_p$—,
(s) —NR[4]S(O)$_2$—, (t) —S(O)$_2$NR[4]—, (u) —C(N—OR[4])—, (v) —C(N—NR[4]R[4])—,
(w) —C(S)NR[4]—, (x) —NR[4]C(S) (y) —C(S)O—, or (z) —OC(S)—, wherein
i) any of (a)-(d) immediately above optionally is substituted with one or more R[5] groups; and
ii) W is selected from the group consisting of:
(aa) —OCO—, (bb) —OC(O)O—, (cc) —OC(O)NR[4]—, (dd) —NR[4]C(O)O—, (ee) —OCNOR[4]—,
(ff) —NR[4]—C(O)O—, (gg) —C(S)(NR[4])—, (hh) —NR[4]—, (ii) —OC(S)O—, (jj) —OC(S)NR[4]—,
(kk) NR[4]C(S)O—, (ll) —OC(S)NOR[4]—, (mm) —C(S)O—, (nn) —OC(S)—, (oo) —C(O)—, (pp) —C(O)O—, (qq) —C(O)NR[4]—, (rr) —C(=NR[4])—, (ss) —C(=NR[4])O—, (tt) —C(=NR[4])NR[4]—, (uu) —OC(O)—, (vv) —OC(O)O—, (ww) —OC(O)NR[4]—, (xx) —NR[4]C(O)—, (yy) —NR[4]C(O)O—, (zz) —NR[4]C(O)NR[4]—, (aaa) —NR[4]C(=NR[4])NR[4]—, (bbb) —S(O)$_p$—, (ccc) —NR[4]S(O)$_2$—, (ddd) —S(O)$_2$NR[4]—, (eee) —C(N—OR[4])—, (fff) —C(N—NR[4]R[4])—, (ggg) —C(S)NR[4]—, or (hhh) —NR[4]C(S)—.

Other embodiments of the foregoing compounds include those where
D is selected from the group consisting of (a) a $C_{1-6}$ alkyl group, (b) a $C_{2-6}$ alkenyl group, and (c) a $C_{2-6}$ alkynyl group, wherein
i) 0-2 carbon atoms in any of (a)-(c) of D immediately above optionally is replaced by a moiety selected from the group consisting of O, S(O)$_p$, and NR[4],
ii) any of (a)-(c) of D immediately above optionally is substituted with one or more R[5] groups; and
F is selected from the group consisting of (a) a single bond, (b) a $C_{1-6}$ alkyl group, (c) a $C_{2-6}$ alkenyl group, and (d) a $C_{2-6}$ alkynyl group, wherein
i) 0-2 carbon atoms in any of (b)-(d) of F immediately above optionally is replaced by a moiety selected from the group consisting of O, S(O)$_p$, and NR[4];
ii) any of (b)-(d) of F immediately above optionally is substituted with one or more R[5] groups; and
iii) any of (b)-(d) of F immediately above optionally is substituted with $C_{1-6}$ alkyl-R[5].

Other embodiments of the foregoing compounds include those where E is selected from the group consisting of:
(a) a 3-10 membered saturated, unsaturated, or aromatic heterocycle containing one or more heteroatoms selected from the group consisting of nitrogen, oxygen, and sulfur,
(b) a 3-10 membered saturated, unsaturated, or aromatic carbocycle,
(c) a —W-[3-10 membered saturated, unsaturated, or aromatic heterocycle containing one or more heteroatoms selected from the group consisting of nitrogen, oxygen, and sulfur],
(d) a —W-[3-10 membered saturated, unsaturated, or aromatic carbocycle], (e) —C(O)—, (f) —C(O)O—, (g) —C(O)NR$^4$—, (h) —C(=NR$^4$)—, (i) —C(=NR$^4$)O—, (j) —C(=NR$^4$)NR$^4$—, (k) —OC(O)—, (l) —OC(O)O—, (m) —OC(O)NR$^4$—, (n) —NR$^4$C(O)—, (o) —NR$^4$C(O)O—, (p) —NR$^4$C(O)NR$^4$—, (q) —NR$^4$C(=NR$^4$)NR$^4$—, (r) —S(O)$_P$—, (s) —NR$^4$S(O)$_2$—, (t) —S(O)$_2$NR$^4$—, (u) —C(N—OR$^4$)—, (v) —CH$_2$—, (w) —C(N—NR$^4$R$^4$)—, (x) —C(S)NR$^4$, (Y) —NR$^4$C(S)—, (Z) —C(S)O—, or (aa) —OC(S)—, wherein i) any of (a)-(d) immediately above optionally is substituted with one or more R$^5$ groups; and ii) W is selected from the group consisting of:
(aa) —OCO—, (bb) —OC(O)O—, (cc) —OC(O)NR$^4$—, (dd) —NR$^4$C(O)O—, (ee) —OCNOR$^4$—, (ff) —NR$^4$—C(O)O—, (gg) —C(S)(NR$^4$)—, (hh) —NR$^4$, (ii) —OC(S)O—, (jj) —OC(S)NR$^4$—, (kk) —NR$^4$C(S)O—, (ll) —OC(S)NOR$^4$—, (mm) —C(S)O—, (nn) —OC(S), (oo) —C(O)—, (pp) —C(O)O—, (qq) —C(O)NR$^4$—, (rr) —C(=NR$^4$)—, (ss) —C(=NR$^4$)O—, (tt) —C(=NR$^4$)NR$^4$—, (uu) —OC(O)—, (vv) —OC(O)O—, (ww) —OC(O)NR$^4$—, (xx) —NR$^4$C(O)—, (yy) —NR$^4$C(O)O—, (zz) —NR$^4$C(O)NR$^4$—, (aaa) —NR$^4$C(=NR$^4$)NR$^4$—, (bbb) —S(O)$_p$—, (ccc) —NR$^4$S(O)$_2$—, (ddd) —S(O)$_2$NR$^4$—, (eee) —C(N—OR$^4$)—, (fff) —C(N—NR$^4$R$^4$)—, (ggg) —C(S)NR$^4$—, or (hhh) —NR$^4$C(S)—.

Other embodiments of the foregoing compounds include those where E is selected from the group consisting of:
(a) a 3-10 membered saturated, unsaturated, or aromatic heterocycle containing one or more heteroatoms selected from the group consisting of nitrogen, oxygen, and sulfur, and
(b) a 3-10 membered saturated, unsaturated, or aromatic carbocycle, wherein (a) and (b) immediately above optionally is substituted with one more R$^5$ groups.

Other embodiments of the foregoing compounds include those where E is selected from the group consisting of:
(a) —C(O)—, (b) —C(O)O—, (c) —C(O)NR$^4$—, (d) —C(=NR$^4$)—, (e) —C(=NR$^4$)O—, (f) —C(=NR$^4$)NR$^4$—, (g) —OC(O)—, (h) —OC(O)O—, (i) —OC(O)NR$^4$—, (j) —NR$^4$C(O)—, (k) —NR$^4$C(O)O—, (l) —NR$^4$C(O)NR$^4$—, (m) —NR$^4$C(=NR$^4$)NR$^4$—, (n) —S(O)$_p$—, (o) —NR$^4$S(O)$_2$—, (p) —S(O)$_2$NR$^4$—, (q) —C(N—OR$^4$)—, (r) —CH$_2$—, (s) —C(N—NR$^4$R$^4$)—, (t), —C(S)NR$^4$, (u) —NR$^4$C(S)—, (v) —C(S)O, and (w) —OC(S)—.

Other embodiments of the foregoing compounds include those where T is:

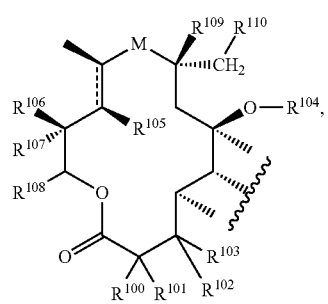

or an N-oxide, pharmaceutically acceptable salt, ester or prodrug thereof, wherein:
M is selected from the group consisting of:
(a) —C((O)—, (b) —CH(—OR$^{114}$)—, (c) —NR$^{114}$—CH$_2$—, (d) —CH$_2$—NR$^{114}$—, (e) —CH(NR$^{114}$R$^{114}$)—, (f) —C(=NNR$^{114}$R$^{114}$)—, (g) NR$^{114}$—C(O)—, (h) —C(O)NR$^{114}$, (i) —C(=NR$^{114}$)—; (j) —CR$^{115}$R$^{115}$—, (k) —C(=NOR$^{127}$)—, R$^{100}$ is selected from the group consisting of H and C$_{1-6}$ alkyl;

R$^{101}$ is selected from the group consisting of:
(a) H, (b) Cl, (c) F, (d) Br, (e) I, (f) —NR$^{114}$R$^{114}$, (g) —NR$^{114}$C(O)R$^{114}$, (h) —OR$^{114}$, (i) —OC(O)R$^{114}$, (j) —OC(O)OR$^{114}$, (k) —OC(O)NR$^{114}$R$^{114}$, (l) —O—C$_{1-6}$ alkyl, (m) —OC(O)—C$_{1-6}$ alkyl, (n) —OC(O)O—C$_{1-6}$ alkyl, (o) —OC(O)NR$^{114}$—C$_{1-6}$ alkyl, (p) C$_{1-6}$ alkyl, (q) C$_{1-6}$ alkenyl, (r) C$_{1-6}$ alkynyl, wherein any of (l)-(r) optionally is substituted with one or more R$^{115}$ groups;

R$^{102}$ is H;

R$^{103}$ is selected from the group consisting of:
(a) H, (b) —OR$^{114}$, (c) —O—C$_{1-6}$ alkyl-R$^{115}$, (d) —OC((O)R$^{114}$, (e) —OC(O)—C$_{1-6}$ alkyl-R$^{115}$, (f) —OC(O)OR$^{114}$, (g) —OC(O)O—C$_{1-6}$ alkyl-R$^{115}$, (h) —OC(O)NR$^{114}$R$^{114}$; (i) —OC(O)NR$^{114}$—C$_{1-6}$ alkyl-R$^{115}$, and (j)

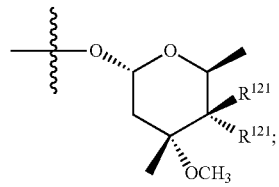

alternatively, R$^{102}$ and R$^{103}$ taken together form a carbonyl group;
alternatively, R$^{101}$ and R$^{103}$ taken together are a single bond between the respective carbons to which these two groups are attached thereby creating a double bond between the carbons to which R$^{100}$ and R$^{102}$ are attached;
alternatively, R$^{101}$ and R$^{103}$ taken together are an epoxide moiety.

R$^{104}$ is selected from the group consisting of:
(a) H, (b) R$^{114}$, (c) —C(O)R$^{114}$ (d) —C(O)OR$^{114}$ (e) —C(O)NR$^{114}$R$^{114}$, (f) —C$_{1-6}$ alkyl-K—R$^{114}$, (g) —C$_{2-6}$ alkenyl-K—R$^{114}$, and (h) —C$_{2-6}$ alkynyl-K—R$^{114}$;

alternatively R$^{103}$ and R$^{104}$, taken together with the atoms to which they are bonded, form:

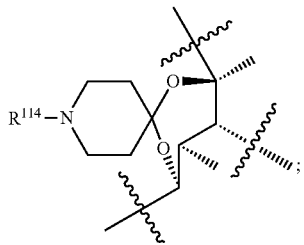

K is selected from the group consisting of:
(a) —C(O)—, (b) —C(O)O—, (c) —C(O)NR$^{114}$—, (d) —C(=NR$^{114}$)—, (e) —C(=NR$^{114}$)O—, (f) —C(=NR$^{114}$)NR$^{114}$—, (g) —OC(O)—, (h) —OC(O)O—, (i) —OC(O)NR$^{114}$—, (j) —NR$^{114}$C(O)—, (k) —NR$^{114}$C(O)O—, (l) —NR$^{114}$C(O)NR$^{114}$—, (m) —NR$^{114}$C(=NR$^{114}$)NR$^{114}$—, and (o) —S(O)$_p$—;

R$^{105}$ is selected from the group consisting of:
(a) R$^{114}$, (b) —OR$^{114}$, (c) —NR$^{114}$R$^{114}$, (d) —O—C$_{1-6}$ alkyl-R$^{115}$, (e) —C(O)—R$^{114}$, (f) —C(O)—C$_{1-6}$ alkyl-R$^{115}$, (g) —OC(O)—R$^{114}$, (h) —OC(O)—C$_{1-6}$ alkyl-R$^{115}$, (i) —OC(O)O—R$^{114}$, (j) —OC(O)O—C$_{1-6}$ alkyl-R$^{115}$, (k) —OC(O)NR$^{114}$R$^{114}$, (l) —OC(O)NR$^{114}$—C$_{1-6}$ alkyl-R$^{115}$, (m) —C(O)—C$_{2-6}$ alkenyl-R$^{115}$, and
(n) —C(O)—C$_{2-6}$ alkynyl-R$^{115}$;

alternatively, R$^{104}$ and R$^{105}$, taken together with the atoms to which they are bonded, form:

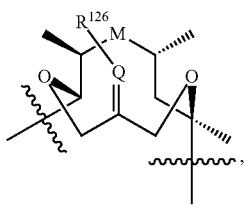

wherein
Q is CH or N, and R$^{126}$ is —OR$^{114}$, —NR$^{114}$ or R$^{114}$;
alternatively, R$^{104}$ and R$^{105}$, taken together with the atoms to which they are bonded, form:

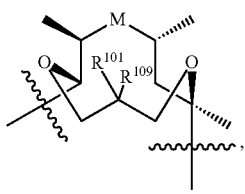

wherein
i) R$^{101}$ is as defined above;
ii) alternately, R$^{101}$ and R$^{109}$ may be taken together form a carbonyl group;
iii) alternately, R$^{101}$ and R$^{109}$ may be taken together to form the group —O(CR$^{116}$R$^{116}$)$_u$O—;
alternatively, R$^{104}$ and R$^{105}$, taken together with the atoms to which they are bonded, form:

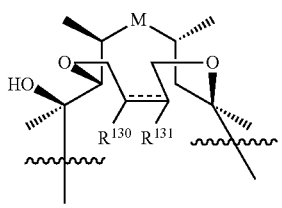

i) R$^{130}$ is —OH, =C(O), or R$^{114}$;
ii) R$^{131}$ is —OH, =C(O), or R$^{114}$;
iii) alternately, R$^{130}$ and R$^{131}$ together with the carbons to which they are attached form a 3-7 membered saturated, unsaturated or aromatic carbocyclic or heterocyclic ring which can optionally be substituted with one or more R$^{114}$ groups;

R$^{106}$ is selected from the group consisting of:
(a) —OR$^{114}$, (b) —C$_{1-6}$ alkoxy-R$^{115}$, (c) —C(O)R$^{114}$, (d) —OC(O)R$^{114}$, (e) —OC(O)OR$^{114}$, (f) —OC(O)NR$^{114}$R$^{114}$, (g) —NR$^{114}$R$^{114}$, alternatively, R$^{105}$ and R$^{106}$ taken together with the atoms to which they are attached form a 5-membered ring by attachment to each other through a chemical moiety selected from the group consisting of:
(a) —OC(R$^{115}$)$_2$O—, (b) —OC(O)O—, (c) —OC(O)NR$^{114}$—, (d) —NR$^{114}$C(O)O—, (e) —OC(O)NOR$^{114}$—, (f) —NOR$^{114}$—C(O)O—, (g) —OC(O)NNR$^{114}$R$^{114}$—, (h) —NNR$^{114}$—R$^{114}$—C(O)O—, (i) —OC(O)C(R$^{115}$)$_2$—, —C(R$^{115}$)$_2$C(O)O—, (k) —OC(S)O—, (l) —OC((S)NR$^{114}$—, (m) —NR$^{114}$C(S)O—, (n) —OC(S)NOR$^{114}$—, (o) —NOR$^{114}$—C(S)O—, (p) —OC(S)NNR$^{114}$R$^{114}$—, (q) —NNR$^{114}$R$^{114}$—C(S)O—, (r) —OC(S)C(R$^{115}$)$_2$—, and (s) —C(R$^{115}$)$_2$C(S)O—;

alternatively, M, R$^{105}$, and R$^{106}$ taken together with the atoms to which they are attached form:

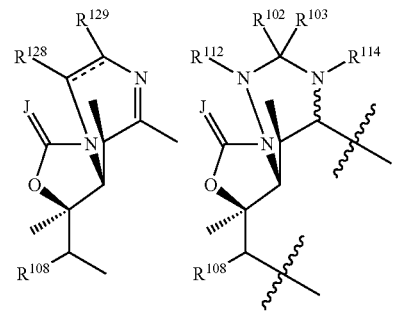

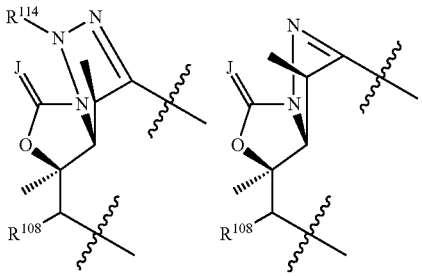

wherein J is selected from the group consisting of O, S and NR$^{114}$;

alternatively, M and R$^{104}$ taken together with the atoms to which they are attached form:

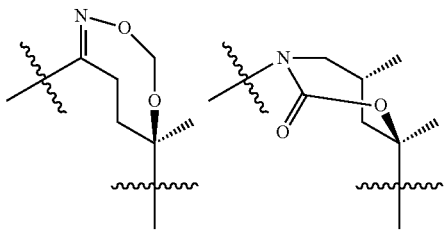

-continued

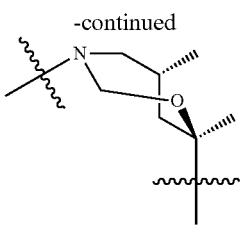

$R^{107}$ is selected from the group consisting of
(a) H, (b) —$C_{1-4}$ alkyl, (c) —$C_{2-4}$ alkenyl, which can be further substituted with $C_{1-12}$ alkyl or one or more halogens, (d) —$C_{2-4}$ alkynyl, which can be further substituted with $C_{1-12}$ alkyl or one or more halogens, (e) aryl or heteroaryl, which can be further substituted with $C_{1-12}$ alkyl or one or more halogens, (f) —C(O)H, (g) —COOH, (h) —CN, (i) —COOR$^{114}$, (j) —C(O)NR$^{114}$R$^{114}$, (k) —C(O)R$^{114}$, and (l) —C(O)SR$^{114}$, wherein (b) is further substituted with one or more substituents selected from the group consisting of (aa) —OR$^{114}$, (bb) halogen, (cc) —SR$^{114}$, (dd) $C_{1-12}$ alkyl, which can be further substituted with halogen, hydroxyl, $C_{1-6}$ alkoxy, or amino, (ee) —OR$^{114}$, (ff) —SR$^{114}$, (gg) —NR$^{114}$R$^{114}$, (hh) —CN, (ii) —NO$_2$, (jj) —NC(O)R$^{114}$, (kk) —COOR$^{114}$, (ll) —N$_3$, (mm) =N—O—R$^{114}$, (nn) =NR$^{114}$, (oo) =N—NR$^{114}$R$^{114}$, (pp) =N—NH—C(O)R$^{114}$, and (qq) =N—NH—C(O)NR$^{114}$R$^{114}$;
alternatively R$^{106}$ and R$^{107}$ are taken together with the atom to which they are attached to form an epoxide, a carbonyl, an olefin, or a substituted olefin, or a $C_3$-$C_7$ carbocyclic, carbonate, or carbamate, wherein the nitrogen of said carbamate can be further substituted with a $C_1$-$C_6$ alkyl;
$R^{108}$ is selected from the group consisting of:
(a) $C_{1-6}$ alkyl, (b) $C_{2-6}$ alkenyl, and (c) $C_{2-6}$ alkynyl, wherein any of (a)-(c) optionally is substituted with one or more R$^{114}$ groups;
$R^{111}$ is selected from the group consisting of H and —C(O)R$^{114}$;
$R^{112}$ is selected from the group consisting of H, OH, and OR$^{114}$;
$R^{113}$ selected from the group consisting of:
(a) H, (b) R$^{114}$, (c) —$C_{1-6}$ alkyl-K—R$^{114}$, (d) —$C_{2-6}$-alkenyl-K—R$^{114}$, and
(e) —$C_{2-6}$ alkynyl-K—R$^{114}$,
wherein any of (c)-(e) optionally is substituted with one or more R$^{115}$ groups;
$R^{114}$, at each occurrence, independently is selected from the group consisting of:
(a) H, (b) $C_{1-6}$ alkyl, (c) $C_{2-6}$ alkenyl, (d) $C_{2-6}$ alkynyl, (e) $C_{6-10}$ saturated, unsaturated, or aromatic carbocycle, (f) 3-12 membered saturated, unsaturated, or aromatic heterocycle containing one or more heteroatoms selected from the group consisting of nitrogen, oxygen, and sulfur, (g) —C(O)—$C_{1-6}$ alkyl, (h) —C(O)—$C_{2-6}$ alkenyl, (i) —C(O)—$C_{2-6}$ alkynyl, (j) —C(O)—$C_{6-10}$ saturated, unsaturated, or aromatic carbocycle, (k) —C(O)-3-12 membered saturated, unsaturated, or aromatic heterocycle containing one or more heteroatoms selected from the group consisting of nitrogen, oxygen, and sulfur, (l) —C(O)O—$C_{1-6}$ alkyl, (m) —C(O)O—$C_{2-6}$ alkenyl, (n) —C(O)O—$C_{2-6}$ alkynyl, (o) —C(O)O—$C_{6-10}$ saturated, unsaturated, or aromatic carbocycle, (p) —C(O)O-3-12 membered saturated, unsaturated, or aromatic heterocycle containing one or more heteroatoms selected from the group consisting of nitrogen, oxygen, and sulfur, and (q) —C(O)NR$^{116}$R$^{116}$,
wherein any of (b)-(p) optionally is substituted with one or more R$^{115}$ groups, wherein one or more non-terminal carbon moieties of any of (b)-(d) optionally is replaced with oxygen, S(O)$_p$, or —NR$^{116}$,
alternatively, NR$^{114}$R$^{114}$ forms a 3-7 membered saturated, unsaturated or aromatic ring including the nitrogen atom to which the R$^{114}$ groups are bonded and optionally one or more moieties selected from the group consisting of O, S(O)$_p$, N, and NR$^{118}$;
$R^{115}$ is selected from the group consisting of:
(a) R$^{117}$, (b) $C_{1-8}$ alkyl, (c) $C_{2-8}$ alkenyl, (d) $C_{2-8}$ alkynyl, (e) $C_{3-12}$ saturated, unsaturated, or aromatic carbocycle, (f) 3-12 membered saturated, unsaturated, or aromatic heterocycle containing one or more heteroatoms selected from the group consisting of nitrogen, oxygen, and sulfur,
wherein any of (b)-(f) optionally is substituted with one or more R$^{117}$ groups;
$R^{116}$, at each occurrence, independently is selected from the group consisting of:
(a) H, (b) $C_{1-6}$ alkyl, (c) $C_{2-6}$ alkenyl, (d) $C_{2-6}$ alkynyl, (e) $C_{3-10}$ saturated, unsaturated, or aromatic carbocycle, and (f) 3-10 membered saturated, unsaturated, or aromatic heterocycle containing one or more heteroatoms selected from the group consisting of nitrogen, oxygen, and sulfur,
wherein one or more non-terminal carbon moieties of any of (b)-(d) optionally is replaced with oxygen, S(O)$_p$, or —NR$^{114}$, wherein any of (b)-(f) optionally is substituted with one or more moieties selected from the group consisting of:
(aa) carbonyl, (bb) formyl, (cc) F, (dd) Cl, (ee) Br, (ff) I, (gg) CN, (hh) N$_3$, (ii) NO$_2$, (jj) OR$^{118}$, (kk) —S(O)$_p$R$^{118}$, (ll) —C(O)R$^{118}$, (mm) —C(O)OR$^{118}$, (nn) —OC(O)R$^{118}$, (oo) —C(O)NR$^{118}$R$^{118}$, (pp) —OC(O)NR$^{118}$R$^{118}$, (qq) —C(=NR$^{118}$)R$^{118}$, (rr) —C(R$^{118}$)(R$^{118}$)OR$^{118}$, (ss) —C(R$^{118}$)$_2$OC(O)R$^{118}$, (tt) —C(R$^{118}$)(OR$^{118}$)(CH$_2$)$_r$NR$^{118}$R$^{118}$, (uu) —NR$^{118}$R$^{118}$, (vv) —NR$^{118}$OR$^{118}$, (ww) —NR$^{118}$C(O)R$^{118}$, (xx) —NR$^{118}$C(O)OR$^{118}$, (yy) —NR$^{118}$C(O)NR$^{118}$R$^{118}$, (zz) —NR$^{118}$S(O)$_r$R$^{118}$, (ab) —C(OR$^{118}$)(0R$^{118}$)R$^{118}$, (ac) —C(R$^{118}$)$_2$NR$^{118}$R$^{118}$, (ad) =NR$^{118}$, (ae) —C(S)NR$^{118}$R$^{118}$, (af) —NR$^{118}$C(S)R$^{118}$, (ag) —OC(S)NR$^{118}$R$^{118}$, (ah) —NR$^{118}$C(S)OR$^{118}$, (ai) —NR$^{118}$C(S)NR$^{118}$R$^{118}$, (aj) —SC(O)R$^{118}$, (ak) $C_{1-8}$ alkyl, (al) $C_{2-8}$ alkenyl, (am) $C_{2-8}$ alkynyl, (an) $C_{1-8}$ alkoxy, (ao) $C_{1-8}$ alkylthio, (ap) $C_{1-8}$ acyl, (aq) saturated, unsaturated, or aromatic $C_{3-10}$ carbocycle, and (ar) saturated, unsaturated, or aromatic 3-10 membered heterocycle containing one or more heteroatoms selected from the group consisting of nitrogen, oxygen, and sulfur,
alternatively, NR$^{116}$R$^{116}$ forms a 3-10 membered saturated, unsaturated or aromatic ring including the nitrogen atom to which the R$^{116}$ groups are attached and optionally one or more moieties selected from the group consisting of O, S(O)$_p$, N, and NR$^{118}$;
alternatively, CR$^{116}$R$^{116}$ forms a carbonyl group;
$R^{117}$, at each occurrence, is selected from the group consisting of:

(a) H, (b) =O, (c) F, (d) Cl, (e) Br, (f) I, (g) $(CR^{116}R^{116})_r$CF$_3$, (h) $(CR^{116}R^{116})_r$CN, (i) $(CR^{116}R^{116})_r$NO2, (j) $(CR^{116}R^{116})_r$NR$^{116}$$(CR^{116}R^{116})_r$R$^{119}$, (k) $(CR^{116}R^{116})_r$OR$^{119}$, (l) $(CR^{116}R^{116})_r$S(O)$_p$$(CR^{116}R^{116})_r$R$^{119}$, (m) $(CR^{116}R^{116})_r$C(O)$(CR^{116}R^{116})_r$R$^{119}$, (n) $(CR^{116}R^{116})_r$OC(O)$(CR^{116}R^{116})_r$R$^{119}$, (o) $(CR^{116}R^{116})_r$SC(O)$(CR^{116}R^{116})_r$R$^{119}$, (p) $(CR^{116}R^{116})_r$C(O)O$(CR^{116}R^{116})_r$R$^{119}$, (q) $(CR^{116}R^{116})_r$NR$^{116}$C(O)$(CR^{116}R^{116})_r$R$^{119}$, (r) $(CR^{116}R^{116})_r$C(O)NR$^{116}$$(CR^{116}R^{116})_r$R$^{119}$, (s) $(CR^{116}R^{116})_r$C(=NR$^{116}$)$(CR^{116}R^{116})_r$R$^{119}$, (t) $(CR^{116}R^{116})_r$C(=NNR$^{116}$R$^{116}$)$(CR^{116}R^{116})_r$R$^{119}$, (u) $(CR^{116}R^{116})_r$C(=NNR$^{116}$R$^{116}$)$(CR^{116}R^{116})_r$R$^{119}$, (v) $(CR^{116}R^{116})_r$C(=NOR$^{119}$)$(CR^{116}R^{116})_r$R$^{119}$, (w) $(CR^{116}R^{116})_r$NR$^{116}$C(O)O$(CR^{116}R^{116})_r$R$^{119}$, (x) $(CR^{116}R^{116})_r$OC(O)NR$^{116}$$(CR^{116}R^{116})_r$R$^{119}$, (y) $(CR^{116}R^{116})_r$NR$^{116}$C(O)NR$^{116}$$(CR^{116}R^{116})_r$R$^{119}$, (z) $(CR^{116}R^{116})_r$NR$^{116}$S(O)$_p$$(CR^{116}R^{116})_r$R$^{119}$, (aa) $(CR^{116}R^{116})_r$S(O)$_p$NR$^{116}$$(CR^{116}R^{116})_r$R$^{119}$, (bb) $(CR^{116}R^{116})_r$NR$^{116}$S(O)$_p$NR$^{116}$$(CR^{116}R^{116})_r$R$^{119}$, (cc) $(CR^{116}R^{116})_r$NR$^{116}$R$^{116}$, (dd) $C_{1-6}$ alkyl, (ee) $C_{2-6}$ alkenyl, (ff) $C_{2-6}$ alkynyl, (gg) $(CR^{116}R^{116})_r$—$C_3$ saturated, unsaturated, or aromatic carbocycle, and (hh) $(CR^{116}R^{116})_r$-3-10 membered saturated, unsaturated, or aromatic heterocycle containing one or more heteroatoms selected from the group consisting of nitrogen, oxygen, and sulfur, wherein any of (dd)-(hh) optionally is substituted with one or more R$^{119}$ groups;

alternatively, two R$^{117}$ groups may form —O(CH$_2$)$_u$O—;

R$^{118}$ is selected from the group consisting of:

(a) H, (b) $C_{1-6}$ alkyl, (c) $C_{2-6}$ alkenyl, (d) $C_{2-6}$ alkynyl, (e) $C_{3-10}$ saturated, unsaturated, or aromatic carbocycle, (f) 3-10 membered saturated, unsaturated, or aromatic heterocycle containing one or more heteroatoms selected from the group consisting of nitrogen, oxygen, and sulfur, (g) —C(O)—$C_{1-6}$ alkyl, (h) —C(O)—$C_{1-6}$ alkenyl, (g) —C(O)—$C_{1-6}$ alkynyl, (i) —C(O)—$C_{3-10}$ saturated, unsaturated, or aromatic carbocycle, and (j) —C(O)-3-10 membered saturated, unsaturated, or aromatic heterocycle containing one or more heteroatoms selected from the group consisting of nitrogen, oxygen, and sulfur, wherein any of (b)-(j) optionally is substituted with one or more moieties selected from the group consisting of: (aa) H, (bb) F, (cc) Cl, (dd) Br, (ee) I, (ff) CN, (gg) NO$_2$, (hh) OH, (ii) NH$_2$, (jj) NH(C$_{1-6}$ alkyl), (kk) N(C$_{1-6}$ alkyl)$_2$, (ll) C$_{1-6}$ alkoxy, (mm) aryl, (nn) substituted aryl, (oo) heteroaryl, (pp) substituted heteroaryl, and (qq) C$_{1-6}$ alkyl, optionally substituted with one or more moieties selected from the group consisting of aryl, substituted aryl, heteroaryl, substituted heteroaryl, F, Cl, Br, I, CN, NO$_2$, and OH;

R$^{119}$, at each occurrence, independently is selected from the group consisting of:

(a) R$^{120}$, (b) C$_{1-6}$ alkyl, (c) C$_{2-6}$ alkenyl, (d) C$_{2-6}$ alkynyl, (e) C$_{3-10}$ saturated, unsaturated, or aromatic carbocycle, and (f) 3-10 membered saturated, unsaturated, or aromatic heterocycle containing one or more heteroatoms selected from the group consisting of nitrogen, oxygen, and sulfur, wherein any of (b)-(f) optionally is substituted with one or more R$^{119}$ groups;

R$^{120}$, at each occurrence, independently is selected from the group consisting of:

(a) H, (b)=O, (c) F, (d) Cl, (e) Br, (f) I, (g) $(CR^{116}R^{116})_r$CF$_3$, (h) $(CR^{116}R^{116})_r$CN, (i) $(CR^{116}R^{116})_r$NO$_2$, (j) $(CR^{116}R^{116})_r$NR$^{116}$R$^{116}$, (k) $(CR^{116}R^{116})_r$OR$^{114}$, (l) $(CR^{116}R^{116})_r$S(O)$_p$R$^{116}$, (m) $(CR^{116}R^{116})_r$C(O)OR$^{116}$, (n) $(CR^{116}R^{116})_r$C(O)OR$^{116}$, (o) $(CR^{116}R^{116})_r$OC(O)R$^{116}$, (p) $(CR^{116}R^{116})_r$NR$^{116}$C(O)R$^{116}$, (q) $(CR^{116}R^{116})_r$C(O)NR$^{116}$R$^{116}$, (r) $(CR^{116}R^{116})_r$C(=NR$^{116}$)R$^{116}$, (s) $(CR^{116}R^{116})_r$NR$^{116}$C(O)NR$^{116}$R$^{116}$, (t) $(CR^{116}R^{116})_r$NR$^{116}$S(O)$_p$R$^{116}$, (u) $(CR^{116}R^{116})_r$S(O)$_p$NR$^{116}$R$^{116}$, (v) $(CR^{116}R^{116})_r$NR$^{116}$S(O)$_p$NR$^{116}$R$^{116}$, (w) C$_{1-6}$ alkyl, (x) C$_{2-6}$ alkenyl, (y) C$_{2-6}$ alkynyl, (z) $(CR^{116}R^{116})_r$—C$_{3-10}$ saturated, unsaturated, or aromatic carbocycle, and (aa) (CR)$_r$ 3-10 membered saturated, unsaturated, or aromatic heterocycle containing one or more heteroatoms selected from the group consisting of nitrogen, oxygen, and sulfur, wherein any of (w)-(aa) optionally is substituted with one or more moieties selected from the group consisting of R$^{116}$, F, Cl, Br, I, CN, NO$_2$, —OR$^{116}$, —NH$_2$, —NH(C$_{1-6}$ alkyl), —N(C$_{1-6}$ alkyl)$_2$, C$_{1-6}$ alkoxy, C$_{1-6}$ alkylthio, and C$_{1-6}$ acyl;

R$^{121}$, at each occurrence, independently is selected from the group consisting of:

(a) H, (b) —OR$^{118}$, (c) —O—C$_{1-6}$ alkyl-OC(O)R$^{118}$, (d) —O—C$_{1-6}$ alkyl-OC(O)OR$^{118}$, (e) —O—C$_{1-6}$ alkyl-OC(O)NR$^{118}$R$^{118}$, (f) —O—C$_{1-6}$ alkyl-C(O)NR$^{118}$R$^{118}$, (g) —O—C$_{1-6}$ alkyl-NR$^{118}$C(O)R$^{118}$, (h) —O—C$_{1-6}$ alkyl-NR$^{118}$C(O)OR$^{118}$, (i) —O—C$_{1-6}$ alkyl-NR$^{118}$C(O)NR$^{118}$R$^{118}$, (j) —O—C$_{1-6}$ alkyl-NR$^{118}$C(=N(H)NR$^{118}$R$^{118}$, (k) —O—C$_{1-6}$ alkyl-S(O)$_p$R$^{118}$, (l) —O—C$_{2-6}$ alkenyl-OC(O)R$^{118}$, (m) —O—C$_{2-6}$ alkenyl-OC(O)OR$^{118}$, (n) —O—C$_{2-6}$ alkenyl-OC(O)NR$^{118}$R$^{118}$, (o) —O—C$_{2-6}$ alkenyl-C(O)NR$^{118}$R$^{118}$, (p) —O—C$_{2-6}$ alkenyl-NR$^{118}$C(O)R$^{118}$, (q) —O—C$_{2-6}$ alkenyl-NR$^{118}$C(O)OR$^{118}$, (r) —O—C$_{2-6}$ alkenyl-NR$^{118}$C(O)NR$^{118}$R$^{118}$, (s) —O—C$_{2-6}$ alkenyl-NR$^{118}$C(=N(H)NR$^{118}$R$^{118}$, (t) —O—C$_{2-6}$ alkenyl-S(O)$_p$R$^{118}$, (u) —O—C$_{2-6}$ alkynyl-OC(O)R$^{118}$, (v) —O—C$_{2-6}$ alkynyl-OC(O)OR$^{118}$, (w) —O—C$_{2-6}$ alkynyl-OC(O)NR$^{118}$R$^{118}$, (x) —O—C$_{2-6}$ alkynyl-C(O)NR$^{118}$R$^{118}$, (y) —O—C$_{2-6}$ alkynyl-NR$^{118}$C(O)R$^{118}$, (z) —O—C$_{2-6}$ alkynyl-NR$^{118}$C(O)OR$^{118}$, (aa) —O—C$_{2-6}$ alkynyl-NR$^{118}$C(O)NR$^{118}$R$^{118}$, (bb) —O—C$_{2-6}$ alkynyl-NR$^{118}$C(=N(H)NR$^{118}$R$^{118}$, (cc) —O—C$_{2-6}$ alkynyl-S(O)$_p$R$^{118}$; and (dd) —NR$^{118}$R$^{118}$;

alternatively, two R$^{121}$ groups taken together form =O, =NOR$^{118}$, or =NNR$^{118}$R$^{118}$;

R$^{122}$ is R$^{115}$;

R$^{123}$ is selected from the group consisting of:

(a) R$^{116}$, (b) F, (c) Cl, (d) Br, (e) I, (f) CN, (g) NO$_2$, and (h) —OR$^{114}$;

alternatively, R$^{122}$ and R$^{123}$ taken together are —O(CH$_2$)$_u$O—;

R$^{124}$, at each occurrence, independently is selected from the group consisting of:

(a) H, (b) F, (c) Cl, (d) Br, (e) I, (f) CN, (g) —OR$^{114}$, (h) —NO$_2$, (i) —NR$^{114}$R$^{114}$, (j) C$_{1-6}$ alkyl, (k) C$_{1-6}$ acyl, and (l) C$_{1-6}$ alkoxy;

R$^{125}$ is selected from the group consisting of:

(a) C$_{1-6}$ alkyl, (b) C$_{2-6}$ alkenyl, (c) C$_{2-6}$ alkynyl, (d) C$_{1-6}$ acyl, (e) C$_{1-6}$ alkoxy, (f) C$_{1-6}$ alkylthio, (g) saturated, unsaturated, or aromatic C$_{5-10}$ carbocycle, (h) saturated, unsaturated, or aromatic 5-10 membered heterocycle containing one or more heteroatoms selected from the group consisting of nitrogen, oxygen, and sulfur, (i) —O—$C_{1-6}$ alkyl-saturated, unsaturated, or aromatic 5-10 membered heterocycle containing one or more heteroatoms selected from the group consisting of nitrogen, oxygen, and sulfur, (j) —$NR^{114}$—$C_{1-6}$ alkyl-saturated, unsaturated, or aromatic 5-10 membered heterocycle containing one or more heteroatoms selected from the group consisting of nitrogen, oxygen, and sulfur, (k) saturated, unsaturated, or aromatic 10-membered bicyclic ring system optionally containing one or more heteroatoms selected from the group consisting of nitrogen, oxygen, and sulfur, (l) saturated, unsaturated, or aromatic 13-membered tricyclic ring system optionally containing one or more heteroatoms selected from the group consisting of nitrogen, oxygen, and sulfur, (m) —$OR^{114}$, (n) —$NR^{114}R^{114}$, (o) —$S(O)_pR^{114}$, and (p) —$R^{124}$, wherein any of (a)-(l) optionally is substituted with one or more $R^{115}$ groups;

alternatively, $R^{125}$ and one $R^{124}$ group, taken together with the atoms to which they are bonded, form a 5-7 membered saturated or unsaturated carbocycle, optionally substituted with one or more $R^{115}$ groups; or a 5-7 membered saturated or unsaturated heterocycle containing one or more atoms selected from the group consisting of nitrogen, oxygen, and sulfur, and optionally substituted with one or more $R^{115}$ groups;

$R^{126}$ at each occurrence, independently is selected from the group consisting of:
(a) hydrogen, (b) an electron-withdrawing group, (c) aryl, (d) substituted aryl, (e) heteroaryl, (f) substituted heteroaryl, and (g) $C_{1-6}$ alkyl, optionally substituted with one or more $R^{115}$ groups;

alternatively, any $R^{126}$ and any $R^{123}$, taken together with the atoms to which they are bonded, form a 5-7 membered saturated or unsaturated carbocycle, optionally substituted with one or more $R^{115}$ groups; or a 5-7 membered saturated or unsaturated heterocycle containing one or more atoms selected from the group consisting of nitrogen, oxygen, and sulfur, and optionally substituted with one or more $R^{115}$ groups;

$R^{109}$ is H or F;
$R^{127}$ is $R^{114}$, a monosaccharide or disaccharide (including amino sugars and halo sugar(s), —$(CH_2)_n$—(O—$CH_2CH_2$—$)_m$—$O(CH_2)_pCH_3$ or —$(CH_2)_n$—(O—$CH_2CH_2$—$)_m$—OH
$R^{128}$ is $R^{114}$
$R^{129}$ is $R^{114}$
$R^{110}$ is $R^{114}$ Alternatively, $R^{109}$ and $R^{110}$ taken together with the carbons to which they are attached form:

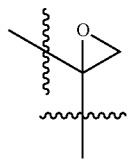

Alternately, $R^{128}$ and $R^{129}$ together with the carbons to which they are attached form a 3-6 membered saturated, unsaturated or aromatic carbocyclic or heterocyclic ring which may optionally be substituted with one or more $R^{114}$ groups;

m, at each occurrence is 0, 1, 2, 3, 4, or 5;
n, at each occurrence is 1, 2, or 3.

Other embodiments of the foregoing compounds include those where T is a macrolide selected from the group consisting of:

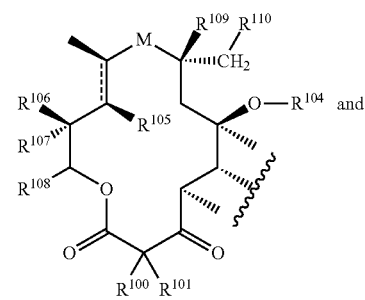

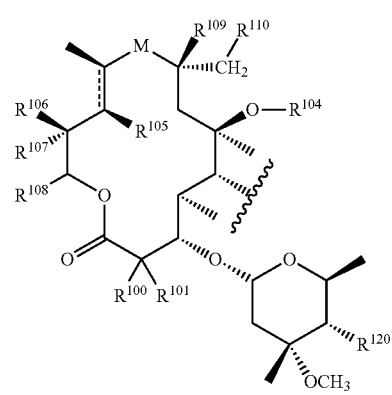

or an N-oxide pharmaceutically acceptable salt, ester, or prodrug thereof, wherein M, $R^{100}$, $R^{101}$, $R^{104}$, $R^{105}$, $R^{106}$, $R^{107}$, $R^{108}$, $R^{109}$, $R^{110}$, and $R^{120}$ are as defined hereinabove.

Other embodiments of the foregoing compounds include those where T is a macrolide selected from the group consisting of:

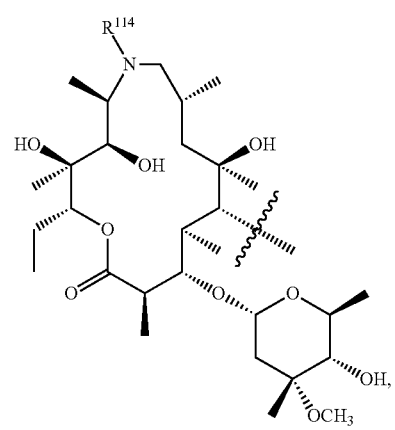

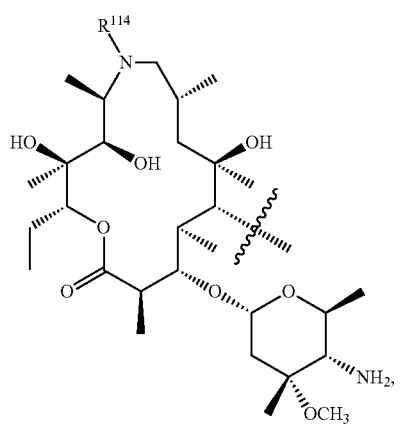
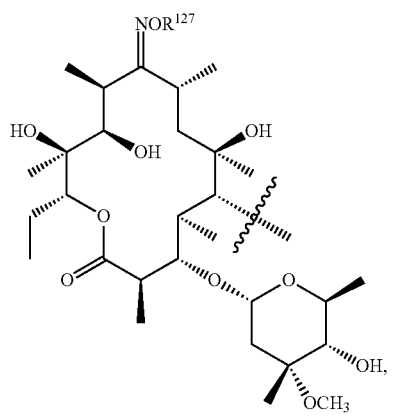
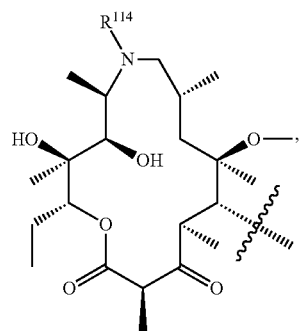
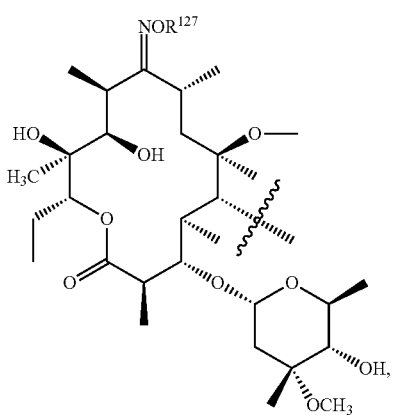
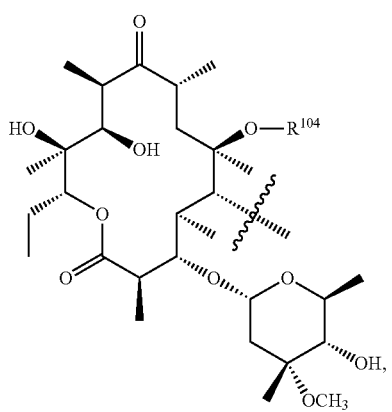
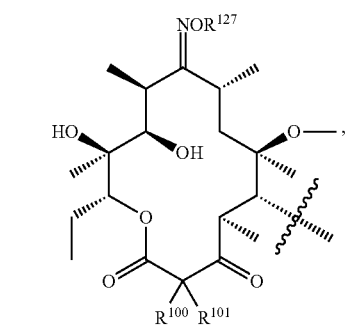
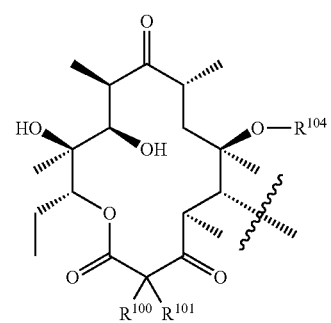
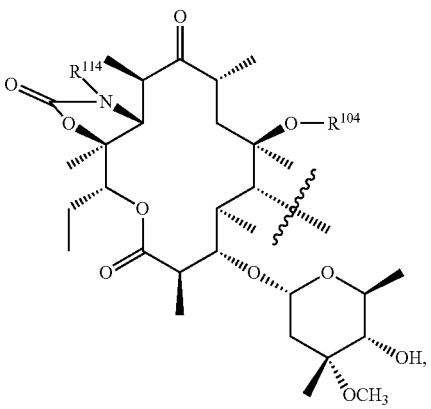

33
-continued
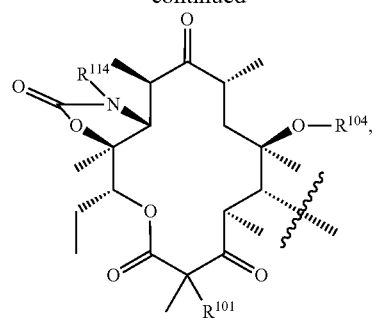
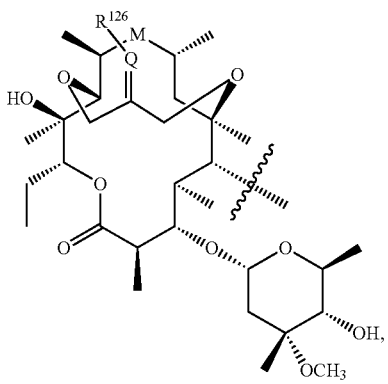
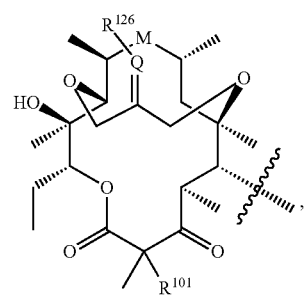
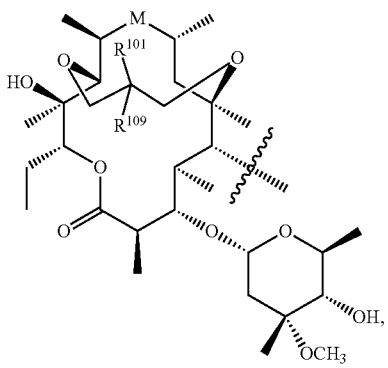
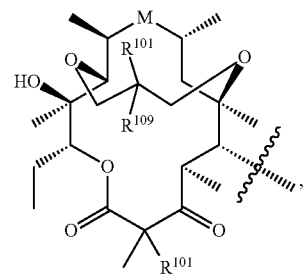
34
-continued
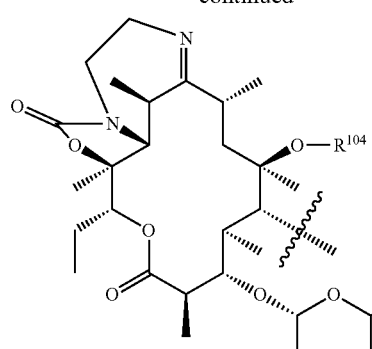
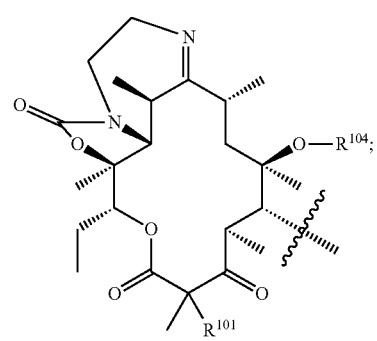
or an N-oxide pharmaceutically acceptable salt, ester, or prodrug thereof, wherein M, $R^{100}$, $R^{101}$, $R^{102}$, $R^{104}$, $R^{109}$, $R^{114}$, $R^{126}$ and $R^{127}$ are as defined hereinabove.
Other embodiments of the foregoing compounds include those where T is a macrolide selected from the group consisting of:
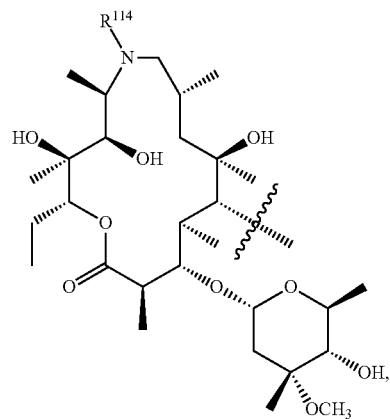
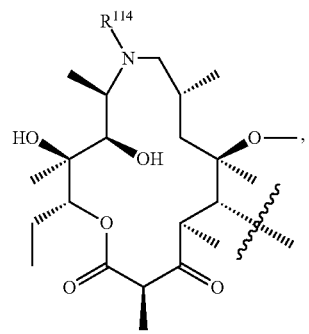

-continued
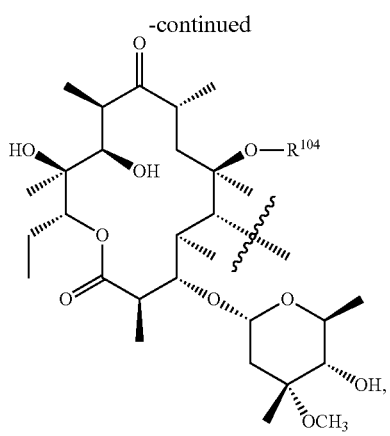
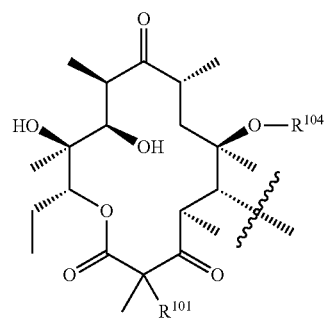
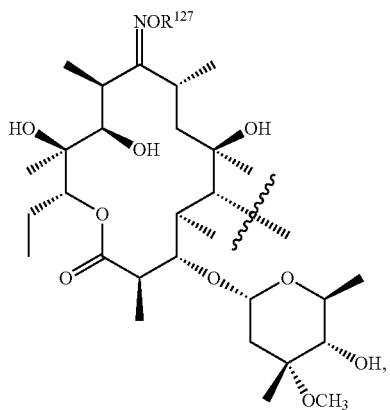
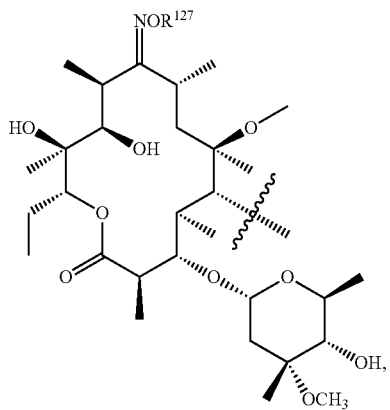
-continued
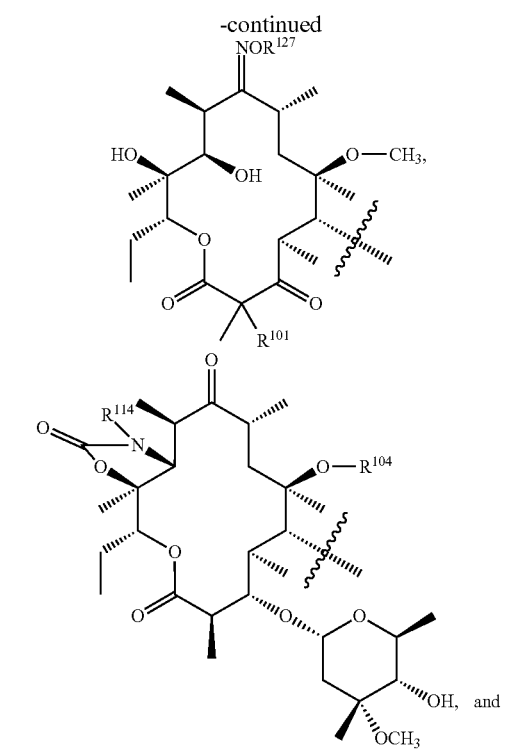
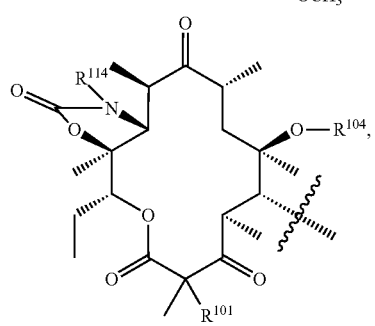
or an N-oxide pharmaceutically acceptable salt, ester, or prodrug thereof, wherein M, $R^1$, $R^2$, $R^{104}$, $R^{114}$, $R^{109}$ and $R^{127}$ are as described hereinabove.
Other embodiments of the foregoing compounds include those where T is a macrolide selected from the group consisting of T1 through T33:
T1
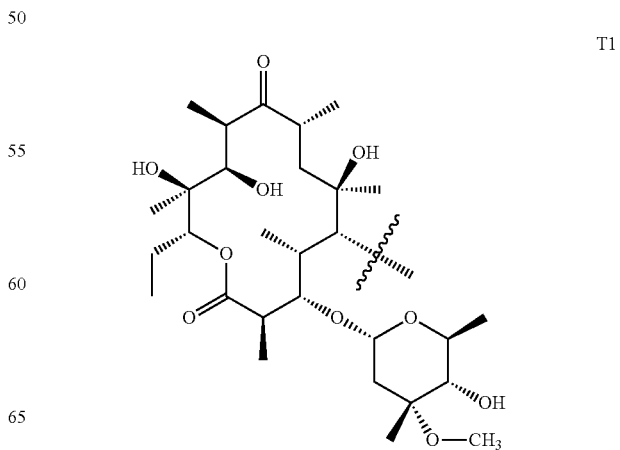

T2
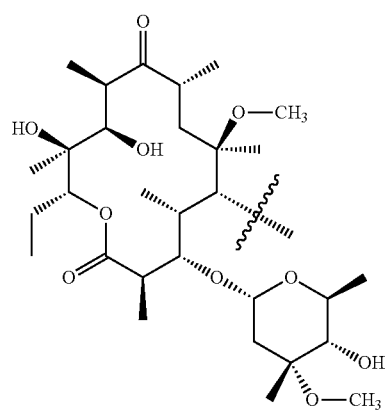
T3
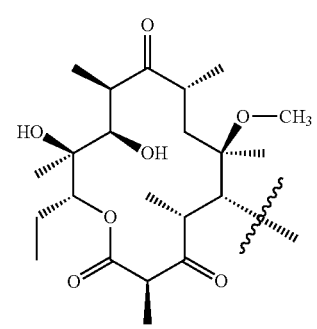
T4
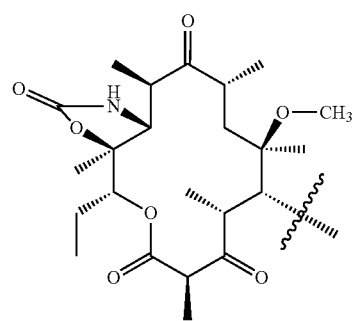
T5
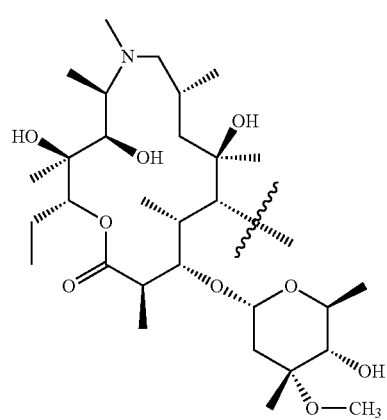
T6
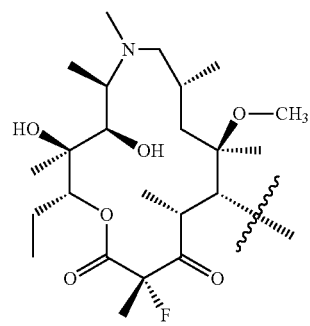
T7
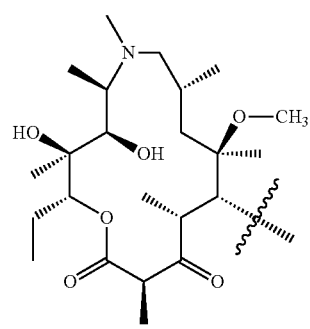
T8
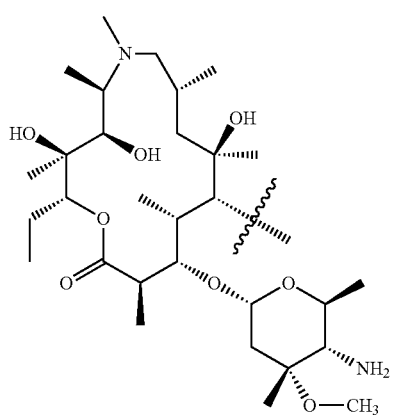
T9
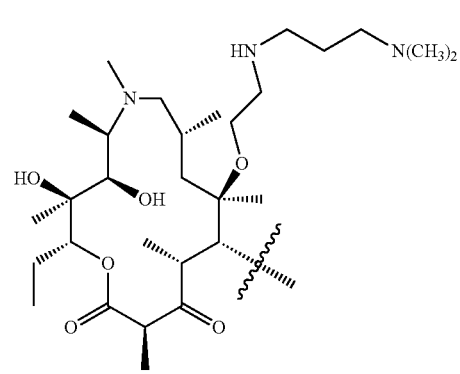

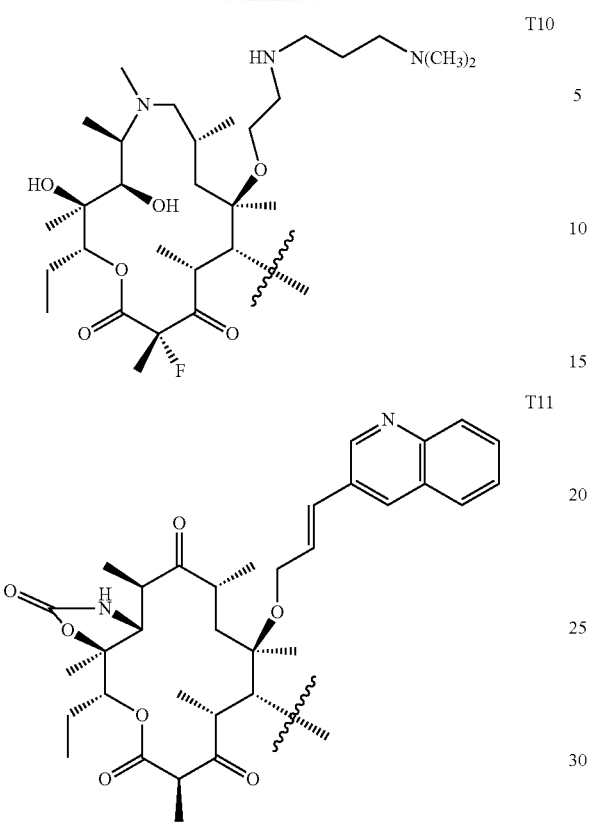
T10
T11
T12
T13
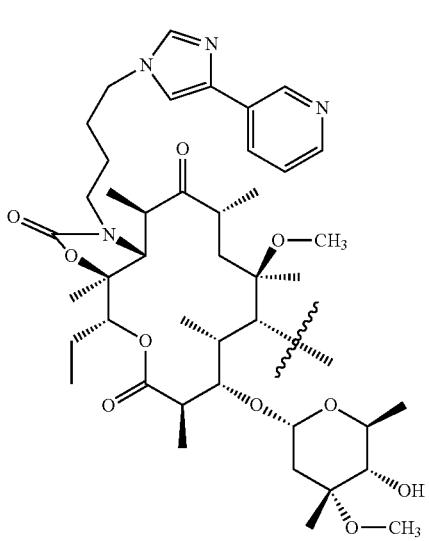
T14
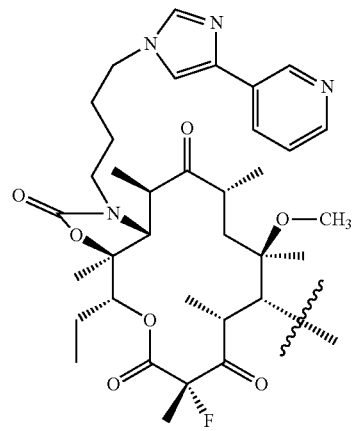
T15
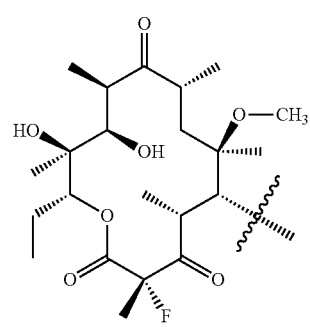
T16

41
-continued
T17
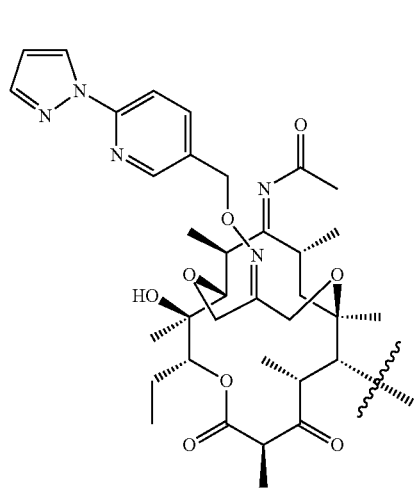
T18
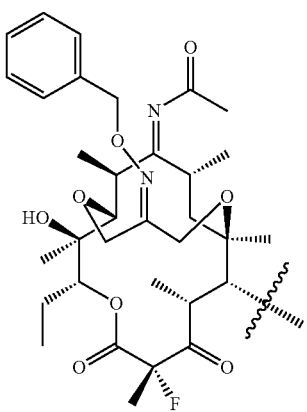
T19
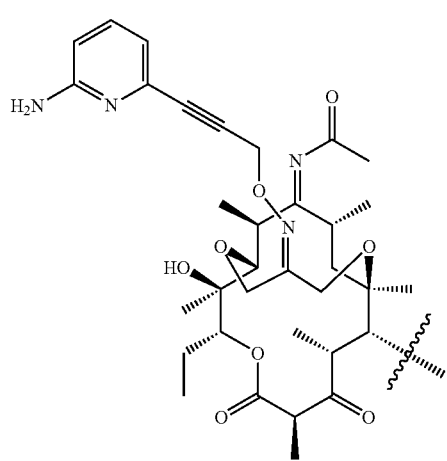
42
-continued
T20
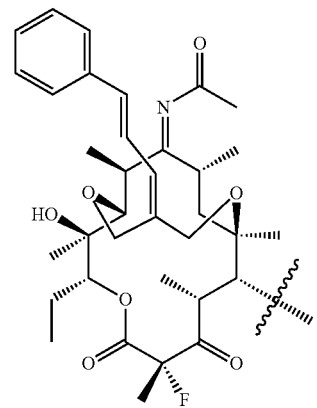
T21
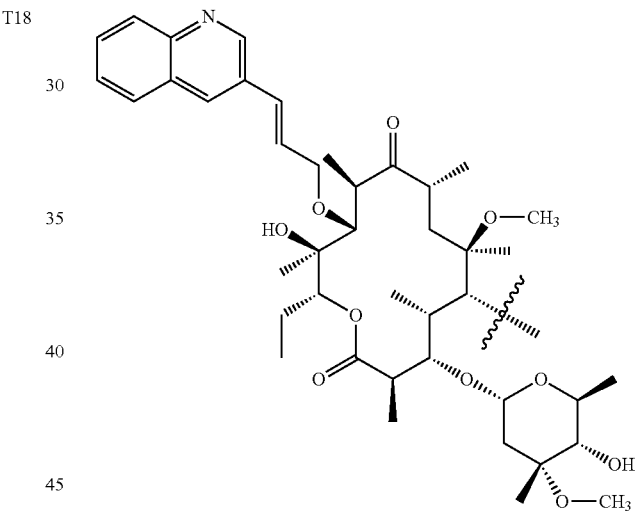
T22
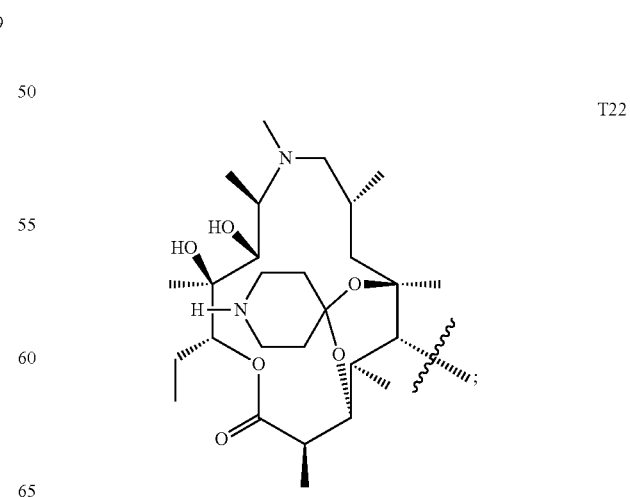

T23
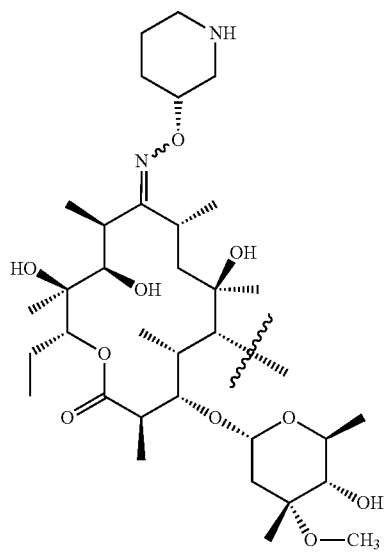
T24
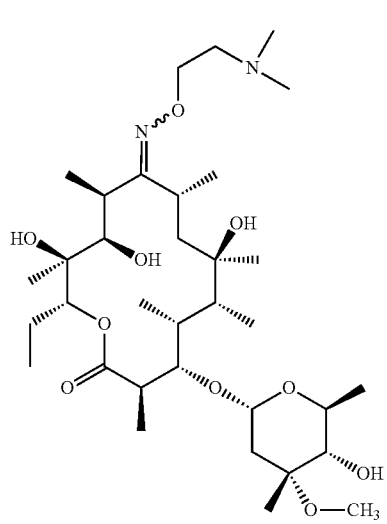
T25
T26
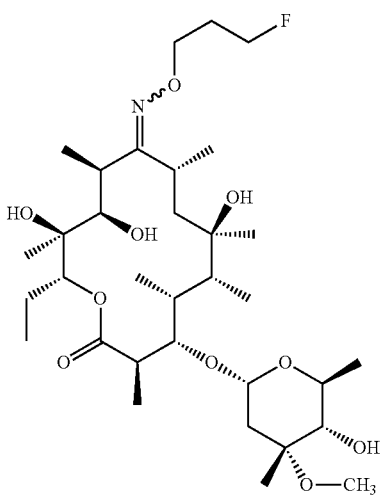
T27
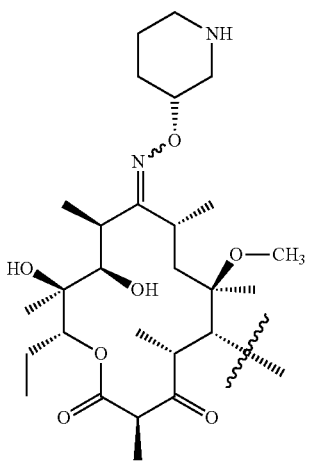
T28
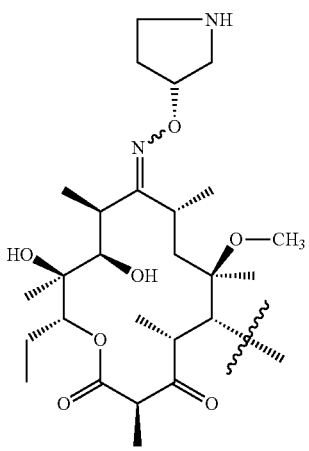

T29

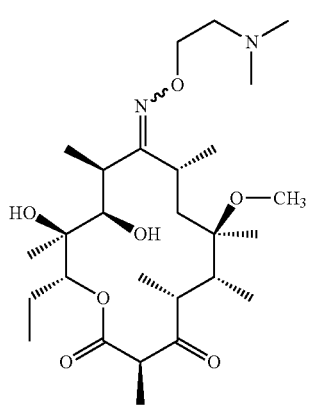

T30

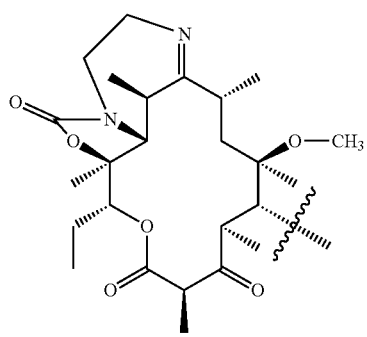

T31

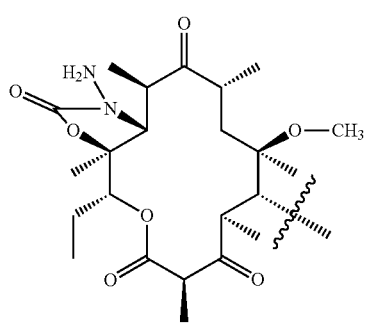

T32

T33

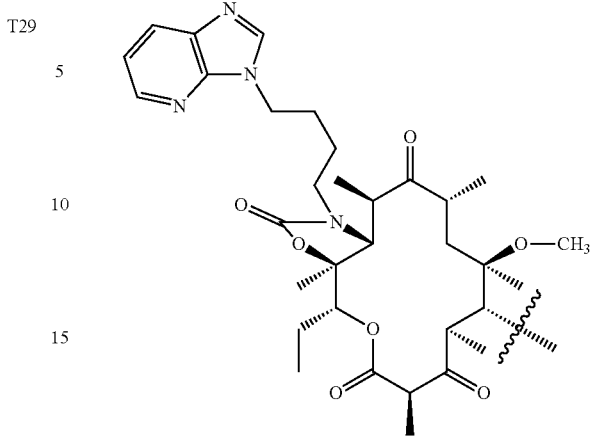

In another aspect, the invention provides a pharmaceutical composition comprising a therapeutically effective amount of one or more of the foregoing compounds and a pharmaceutically acceptable carrier. In yet another aspect, the invention provides a method for treating a microbial infection, a bacterial infection, a fungal infection, a parasitic disease, a proliferative disease, a viral infection, an inflammatory disease, or a gastrointestinal motility disorder in a mammal by administering effective amounts of the compounds of the invention or pharmaceutical compounds of the invention. In embodiments of this aspect, the compounds are administered orally, parentally, or topically. In still another aspect, the invention provides a medical device, for example, a medical stent, which contains or is coated with one or more of the foregoing compounds.

3. Synthesis of the Compounds of the Invention

The invention provides methods for making the compounds of the invention. The following schemes depict exemplary chemistries available for synthesizing the compounds of the invention.

The compound numbers, e.g., 1, 2, 3, etc. used in this section 3 of the present application and entitled "3. Synthesis of the Compounds of the Invention", are for reference within this section 3 only do not refer to and are not to be confused with any similarly numbered compounds in section 6 of the present application and entitled "6. Examples".

Scheme 1 illustrates the synthesis of triazole compounds of type 5 and 6. Erythromycin can be N-demethylated as described in the art (U.S. Pat. No. 3,725,385; Flynn et al. (1954) J. AM. CHEM. SOC. 76: 3121; Ku et al. (1997) BIOORG. MED. CHEM. LETT. 7: 1203; Stenmark et al. (2000) J. ORG. CHEM. 65: 3875) to afford secondary amine 1. Alkylation of 1 with electrophiles of type 2 yields alkynes of type 3 containing an alkyl chain of appropriate length, generally between one and about four carbon atoms between the nitrogen atom and the alkyne group. Cycloaddition of azides of type 4 with alkynes 3 generates two regioisomeric triazole products. The reaction can be thermally catalyzed, or a number of catalysts could be added to facilitate the reaction (such as, but not limited to, copper (I) iodide: see Tornoe, C. W. et al. (2002) J. ORG. CHEM. 67: 3057). The major isomer (for steric reasons) is the "anti" isomer 5, a 1,4 disubstituted triazole. The minor component is the "syn" isomer 6, a 1,5 disubstituted triazole.

Scheme 1

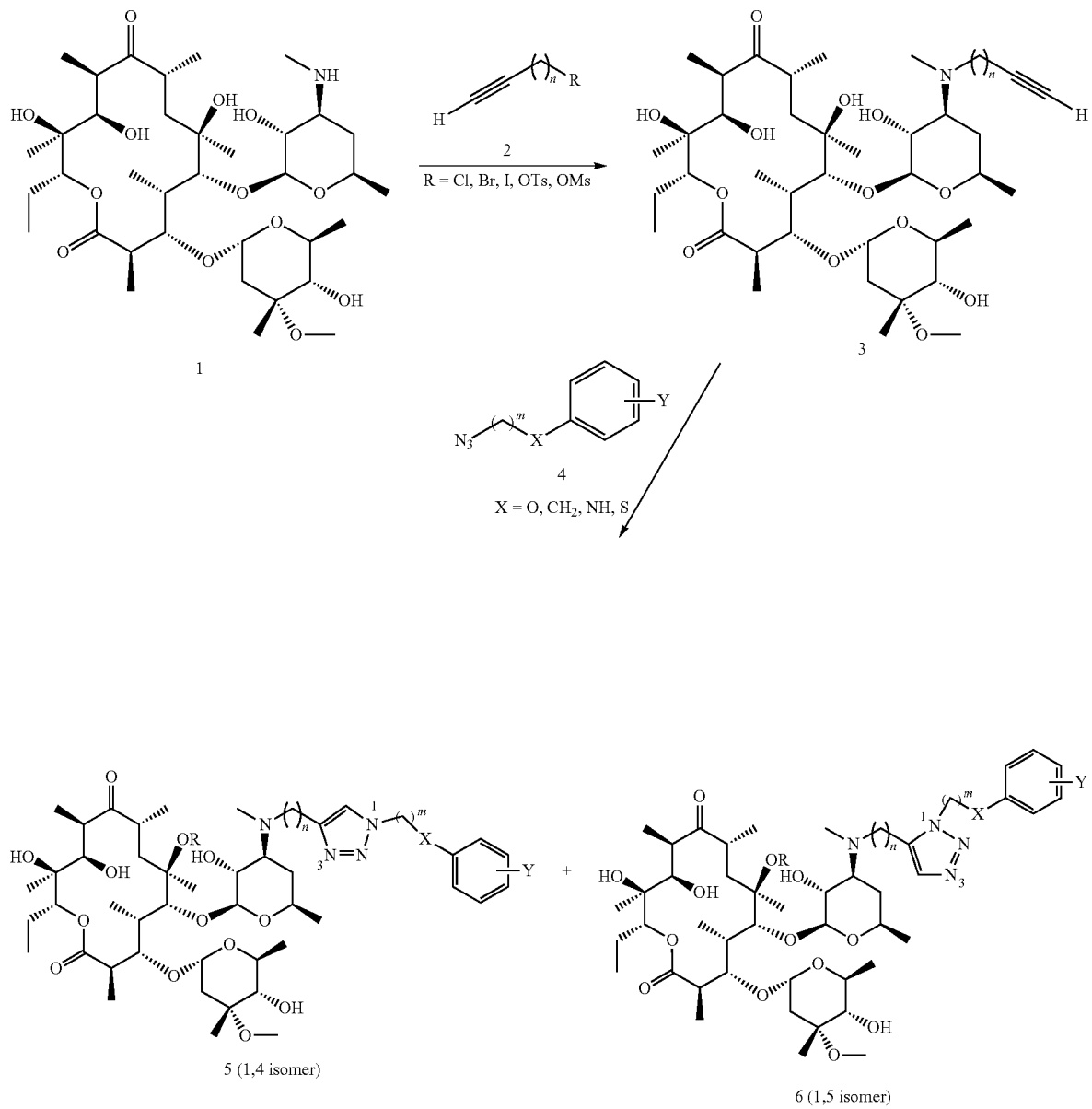

It is to be understood that other macrolide compounds such as, but not limited to, azithromycin and clarithromycin, could be N-demethylated and serve as starting materials for the chemistry exemplified in Scheme 1. Target compounds derived from such alternate macrolide precursors are to be considered within the scope of the present invention.

Scheme 2 illustrates the synthesis of exemplary tetrazole derivatives of the present invention. Amine 1 (or alternate macrolide amines) can be alkylated with nitrile-containing electrophiles of type 7 to afford macrolide nitrile intermediates of type 8. Cycloaddition reactions of nitriles 8 with azides of type 4 may lead to two regioisomeric tetrazoles; the 2,4-disubstituted tetrazoles of type 9 (the expected major product), and the 1,5 isomers of type 10.

Scheme 2
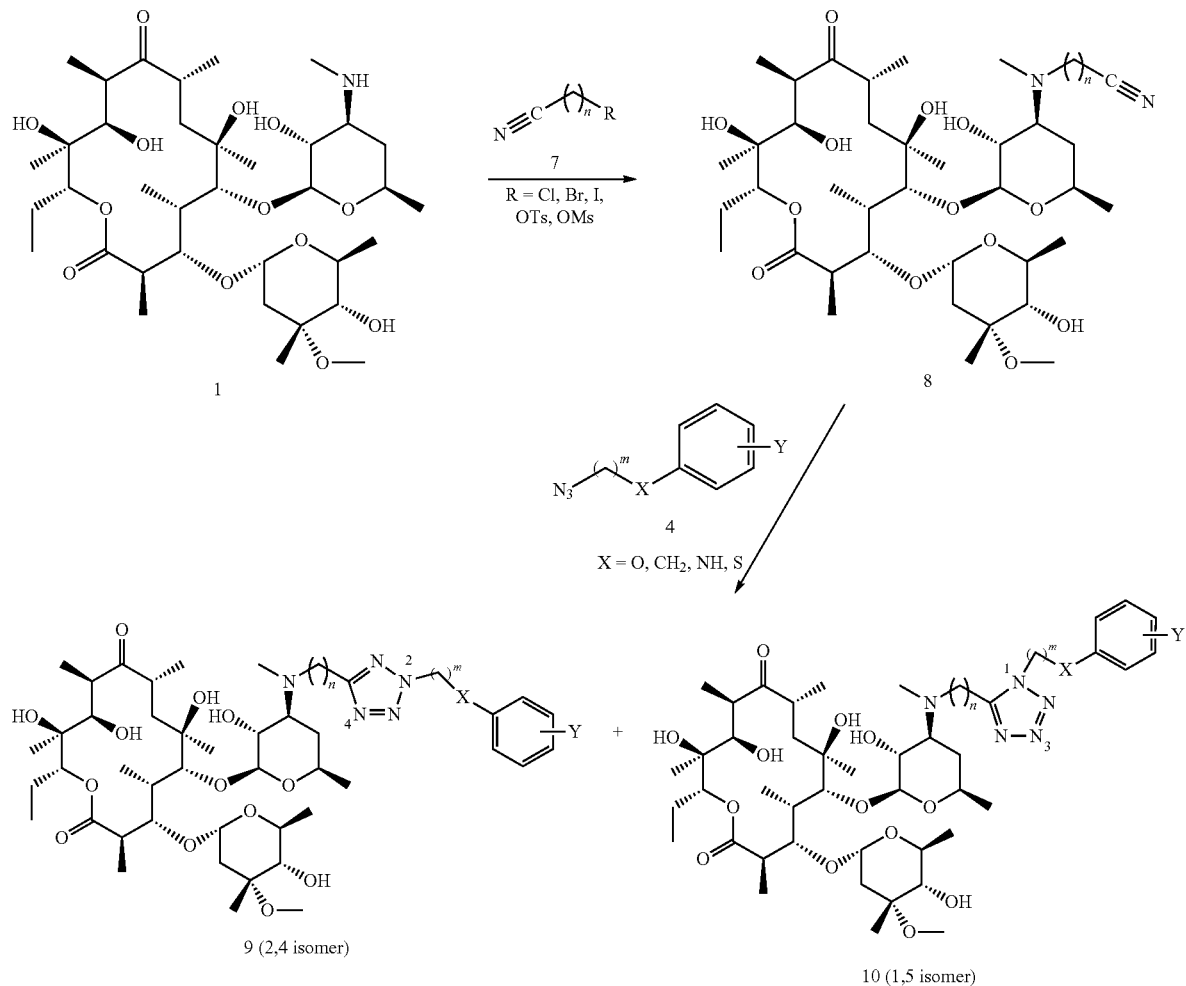
Scheme 3 depicts the synthesis of isoxazole derivatives of the present invention. Alkynes 3 can be treated with nitrile oxides of type 11 to afford regioisomeric cycloadducts 12 and 13. The major isomer should again be the "anti" derivative 12 based on steric factors.
Scheme 3
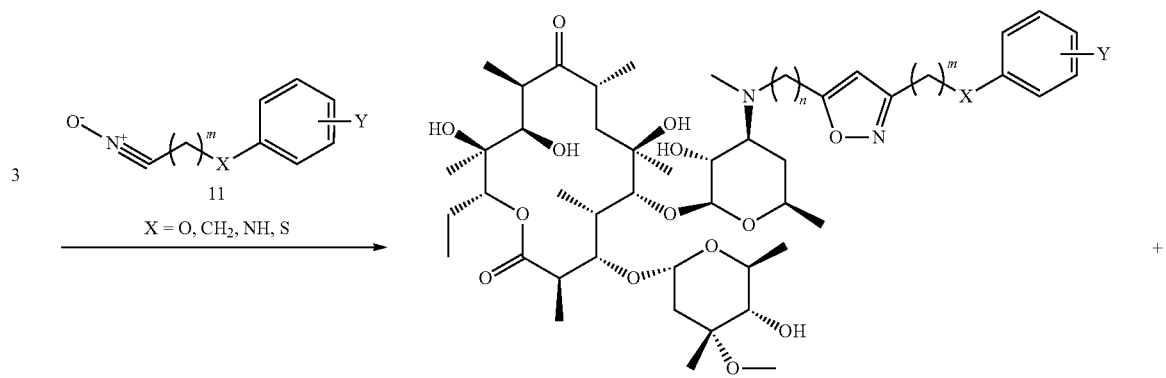

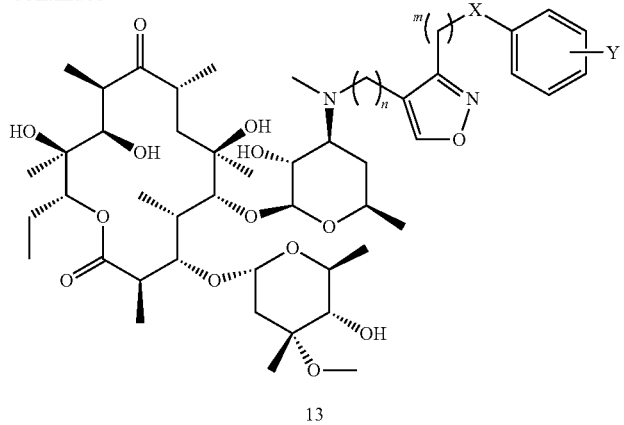

13

An alternate approach to derivatives of type 5, 6, 9, 10, 12, and 13 is illustrated by Scheme 4. Acetylenic alcohols of type 14 can be treated with azides 4 to yield intermediate alcohol 15 (along with a minor amount of the regioisomeric triazole). Tosylation of 15 will provide tosylates 16 which can serve as alkylating agents for macrolide amines of type 1 to afford targets 5 (and its isomer 6). (It will be appreciated that other sulfonate derivatives or halides could be formed from intermediate alcohol 15, and these would be useful as electrophiles for the alkylation of macrolide amines such as 1 to afford compounds of the invention.) Hydroxyalkyl nitriles of type 17 (where n is not equal to 1) can undergo cycloaddition with azides 4 to afford tetrazole intermediate 18 (along with a minor amount of the regioisomeric tetrazole). Tosylation of 18 to give 19 can again be followed by alkylation with amines of type 1 to yield derivative 9 (and its isomer 10). In an analogous fashion, acetylenes 14 can be converted to isoxazoles 20 (and its isomer). An appropriate electrophile derived from 20 can then alkylate amines 1 to afford target 12 (and its isomer 13).

Scheme 4

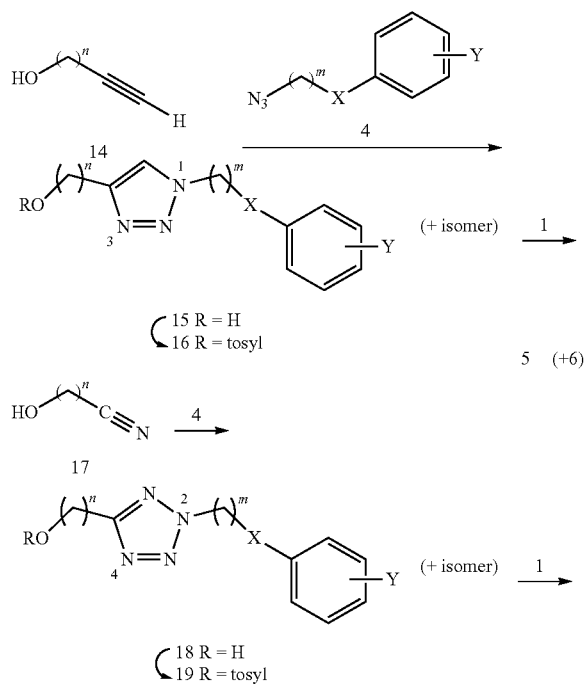

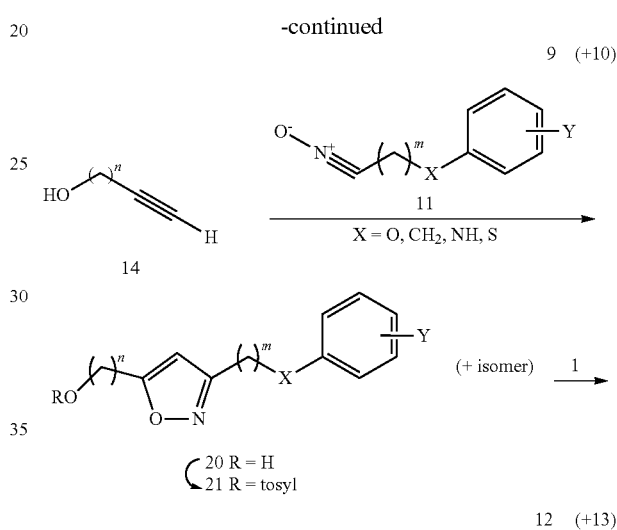

Other starting materials for the synthesis of compounds of the present invention are readily synthesizable. For example, des-methyl macrolide amines 22 and 23 can be prepared from azithromycin and clarithromycin respectively, using the same procedure for the synthesis of 1 from erythromycin. Ketolide derivatives (C-3 keto compounds synthesized from macrolides) of the present invention can be prepared by chemistry such as that shown in Scheme 5. Clarithromycin-derived amine 23 is alkylated with tosylate 24 to afford alkyne 25. The cladinose sugar at C-3 is hydrolyzed to afford the $C_{1-3}$ hydroxy intermediate 26, which is then selectively acetylated on the hydroxyl of the aminosaccharide group to yield 27. Oxidation of 27 yields C-3 keto derivative 28 which is then deacylated to provide alkyne 29. Alkyne 29 can be exposed to the chemistry of Schemes 1 and 3 above to deliver triazole and isoxazole compounds of the present invention that have C-3 keto clarithromycin-derived structures. It will be understood that alkylation of 23 with electrophiles of type 7, and then exposure of the product nitriles to the chemistry shown in Schemes 5 and 2, will yield tetrazoles that have C-3 keto clarithromycin-derived structures. Additionally, C-3 keto azithromycin and erythromycin intermediates could be prepared from 1 and 22 using the chemistry of Scheme 5, and subsequently serve as starting materials for compounds of the present invention.

22

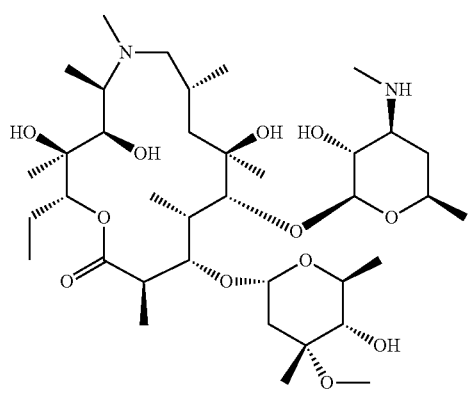

23

Scheme 5

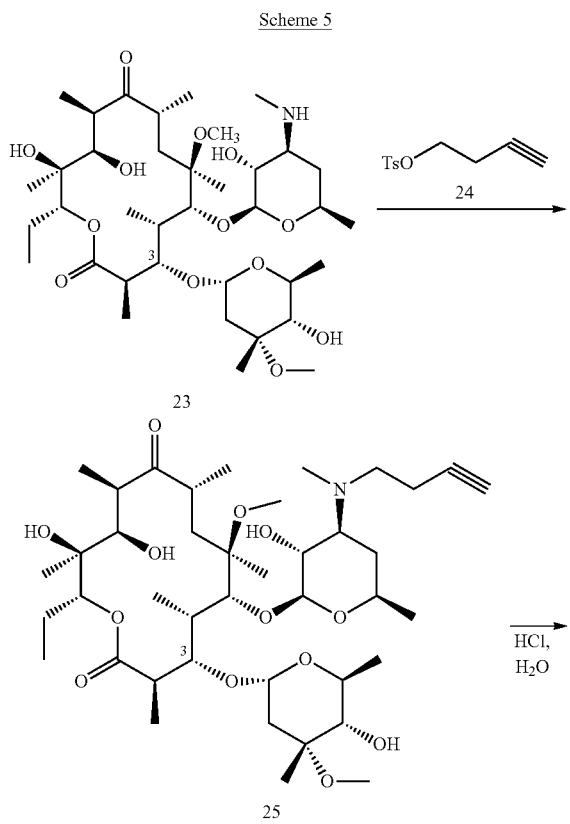

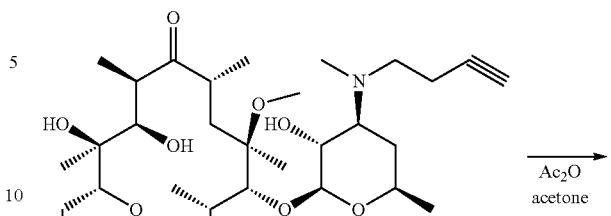

26

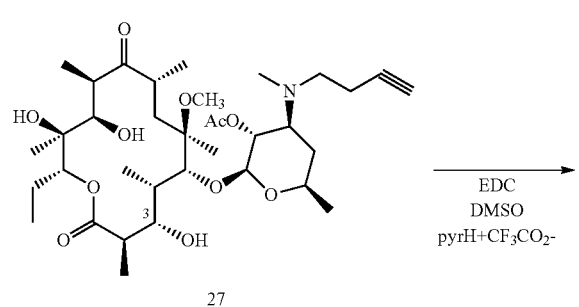

27

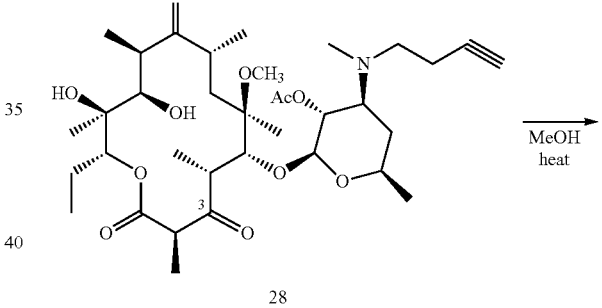

28

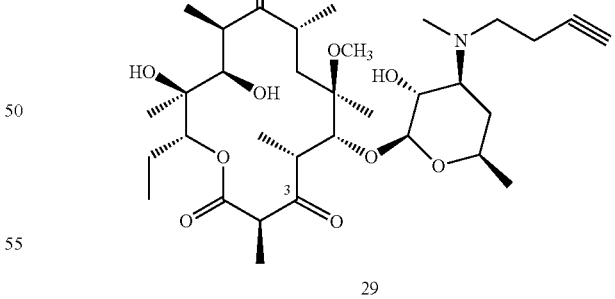

29

Acetylenes of type 2, used to synthesize the variable length ally chains in the compounds, can be derived from commercially available haloalkyl acetylenes such as propargyl bromide, or they can be readily synthesized from available hydroxyalkyl acetylenes using chemistry well known in the art. Scheme 6 illustrates how they can be synthesized from available hydroxyalkyl acetylenes of type 14 using simple chemistry well known in the art.

Scheme 6

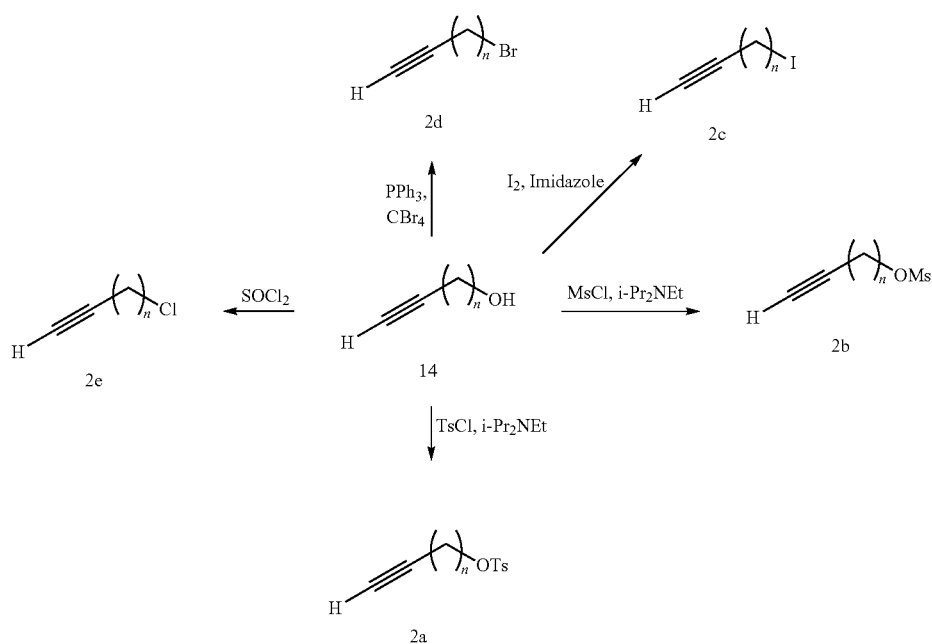

Intermediate azides of type 4 used to make compounds of the present invention can be synthesized using the methods exemplified in Schemes 7 and 8. Phenols, anilines, and thiophenols of type 30 can undergo Mitsunobu etherification processes with am-halo alcohols (such as, but not limited to, 2-bromoethanol) to generate halides of type 31. Displacement of the halogen with sodium azide yields azides 4a. Alternatively, direct alkylation of intermediates 30 with α,ω-halo alcohols yields alcohols of type 32, which can be converted to halides 31 or converted to a sulfonate derivative such as 33, for subsequent azide displacement to afford azides 4a. Arylpropanols of type 34, and pyridylpropanols of type 35, can be converted to azides 4b and 4c via sulfonates such as 36 and 37. It will be appreciated that pyridyl derivatives with alternate substitution patterns (ortho and para), and alternate chain-lengths between the aryl moiety and the azide group can also be made using chemistry known in the art. It is intended that all such isomers and homologues are within the scope of the present invention.

Scheme 7

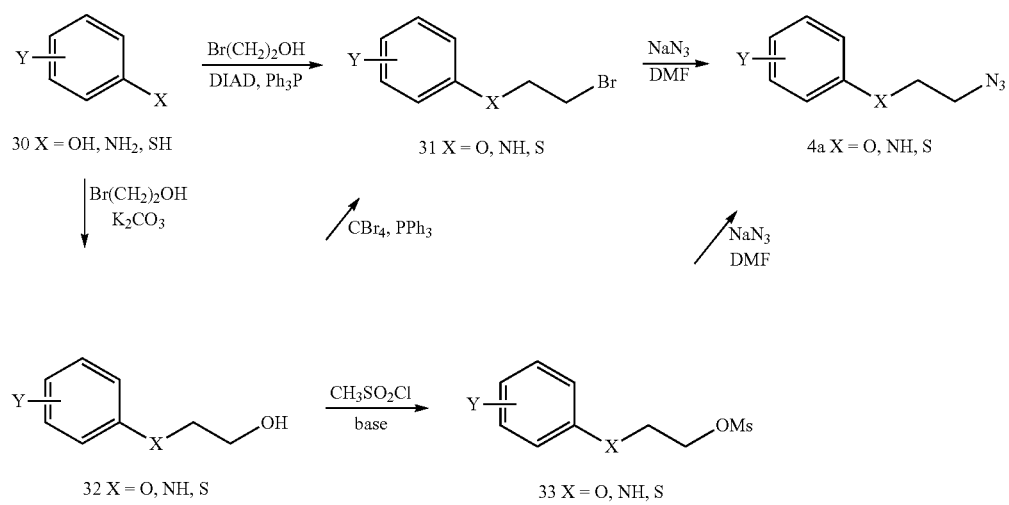

Scheme 8

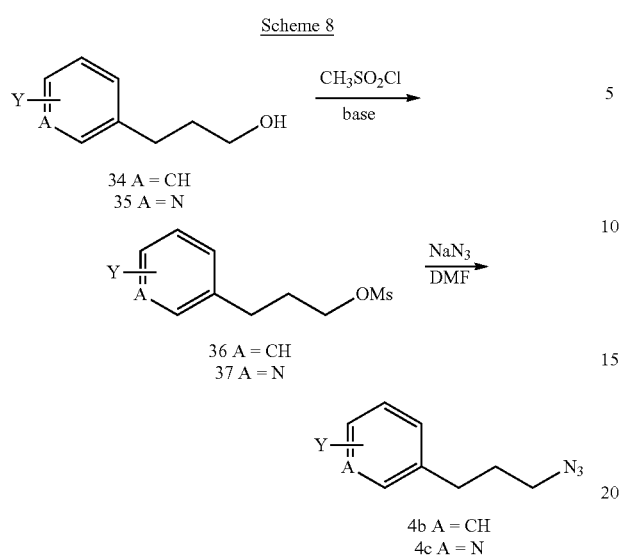

34 A = CH
35 A = N

36 A = CH
37 A = N

4b A = CH
4c A = N

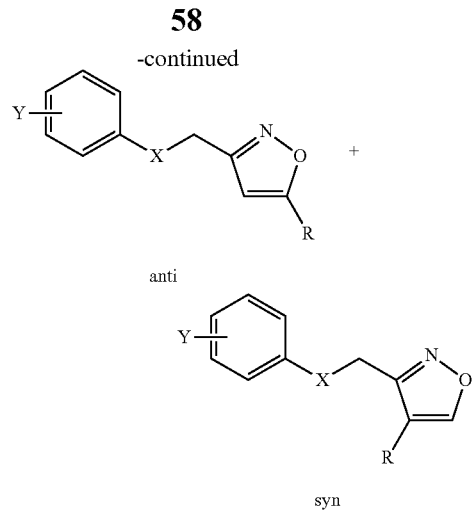

anti syn

Nitrile oxides of type 11 used to make compounds of the present invention can be synthesized using the method exemplified in Scheme 9. Substituted arylalkanols of type 32 (or pyridylalkanols) of various chain length between the aryl moiety and the alcohol group can be oxidized to aldehydes 38. Conversion of the aldehyde to oximes 39 can be followed by conversion to intermediate nitrile oxides 11 using chloramine T (or other reagents used in combination with organic amine bases such as N-bromosuccinimide, N-chlorosuccinimide, t-butyl hypochlorite, lead tetraacetate etc.). The reaction to form the nitrile oxide can be run in the presence of an appropriate alkyne to trap the unstable intermediates 11 directly, affording a mixture of anti and syn isoxazole products.

Scheme 9

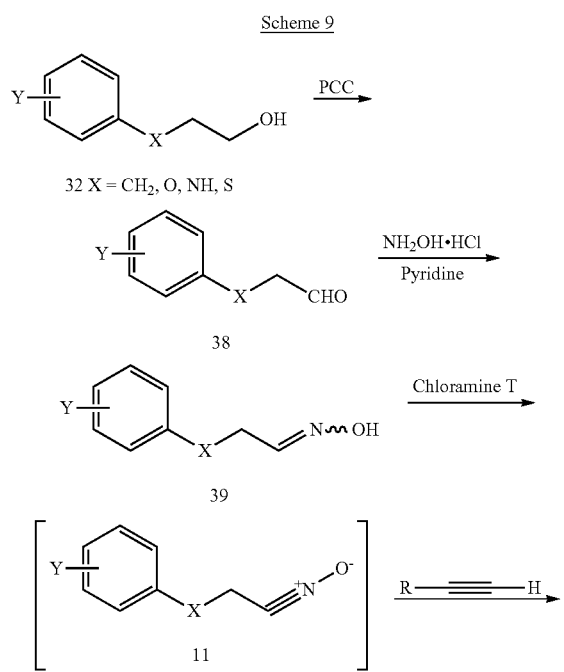

32 X = CH$_2$, O, NH, S

38

39

11

4. Characterization of Compounds of the Invention

Compounds designed, selected and/or optimized by methods described above, once produced, may be characterized using a variety of assays known to those skilled in the art to determine whether the compounds have biological activity. For example, the molecules may be characterized by conventional assays, including but not limited to those assays described below, to determine whether they have a predicted activity, binding activity and/or binding specificity.

Furthermore, high-throughput screening may be used to speed up analysis using such assays. As a result, it may be possible to rapidly screen the molecules described herein for activity, for example, as anti-cancer, anti-bacterial, anti-fungal, anti-parasitic or anti-viral agents. Also, it may be possible to assay how the compounds interact with a ribosome or ribosomal subunit and/or are effective as modulators (for example, inhibitors) of protein synthesis using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

(1) Surface Binding Studies. A variety of binding assays may be useful in screening new molecules for their binding activity. One approach includes surface plasmon resonance (SPR) that can be used to evaluate the binding properties of molecules of interest with respect to a ribosome, ribosomal subunit or a fragment thereof.

SPR methodologies measure the interaction between two or more macromolecules in real-time through the generation of a quantum-mechanical surface plasmon. One device, (BIAcore Biosensor RTM from Pharmacia Biosensor, Piscataway, N.J.) provides a focused beam of polychromatic light to the interface between a gold film (provided as a disposable biosensor "chip") and a buffer compartment that can be regulated by the user. A 100 nm thick "hydrogel" composed of carboxylated dextran that provides a matrix for the covalent immobilization of analytes of interest is attached to the gold film. When the focused light interacts with the free electron cloud of the gold film, plasmon resonance is enhanced. The resulting reflected light is spectrally depleted in wavelengths that optimally evolved the resonance. By separating the reflected polychromatic light into its component wavelengths (by means of a prism), and determining the frequencies that are depleted, the BIAcore establishes an optical interface which accurately reports the behavior of the generated surface plasmon resonance. When designed as above, the plasmon resonance (and thus the depletion spectrum) is sensitive to mass in the evanescent field (which corresponds roughly to the thickness of the hydrogel). If one component of an interacting pair is immobilized to the hydrogel, and the interacting partner is provided through the buffer compartment, the interaction between the two components can be measured in real time based on the accumulation of mass in the evanescent field and its corresponding effects of the plasmon resonance as measured by the depletion spectrum. This system permits rapid and sensitive real-time measurement of the molecular interactions without the need to label either component.

(2) Fluorescence Polarization. Fluorescence polarization (PP) is a measurement technique that can readily be applied to protein-protein, protein-ligand, or RNA-ligand interactions in order to derive $IC_{50}$s and Kds of the association reaction between two molecules. In this technique one of the molecules of interest is conjugated with a fluorophore. This is generally the smaller molecule in the system (in this case, the compound of interest). The sample mixture, containing both the ligand-probe conjugate and the ribosome, ribosomal subunit or fragment thereof, is excited with vertically polarized light. Light is absorbed by the probe fluorophores, and re-emitted a short time later. The degree of polarization of the emitted light is measured. Polarization of the emitted light is dependent on several factors, but most importantly on viscosity of the solution and on the apparent molecular weight of the fluorophore. With proper controls, changes in the degree of polarization of the emitted light depends only on changes in the apparent molecular weight of the fluorophore, which in-turn depends on whether the probe-ligand conjugate is free in solution, or is bound to a receptor. Binding assays based on FP have a number of important advantages, including the measurement of $IC_{50}$s and Kds under true homogenous equilibrium conditions, speed of analysis and amenity to automation, and ability to screen in cloudy suspensions and colored solutions.

(3) Protein Synthesis. It is contemplated that, in addition to characterization by the foregoing biochemical assays, the compound of interest may also be characterized as a modulator (for example, an inhibitor of protein synthesis) of the functional activity of the ribosome or ribosomal subunit.

Furthermore, more specific protein synthesis inhibition assays may be performed by administering the compound to a whole organism, tissue, organ, organelle, cell, a cellular or subcellular extract, or a purified ribosome preparation and observing its pharmacological and inhibitory properties by determining, for example, its inhibition constant ($IC_{50}$) for inhibiting protein synthesis. Incorporation of $^3H$ leucine or $^{35}S$ methionine, or similar experiments can be performed to investigate protein synthesis activity. A change in the amount or the rate of protein synthesis in the cell in the presence of a molecule of interest indicates that the molecule is a modulator of protein synthesis. A decrease in the rate or the amount of protein synthesis indicates that the molecule is a inhibitor of protein synthesis.

Furthermore, the compounds may be assayed for antiproliferative or anti-infective properties on a cellular level. For example, where the target organism is a microorganism, the activity of compounds of interest may be assayed by growing the microorganisms of interest in media either containing or lacking the compound. Growth inhibition may be indicative that the molecule may be acting as a protein synthesis inhibitor. More specifically, the activity of the compounds of interest against bacterial pathogens may be demonstrated by the ability of the compound to inhibit growth of defined strains of human pathogens. For this purpose, a panel of bacterial strains can be assembled to include a variety of target pathogenic species, some containing resistance mechanisms that have been characterized. Use of such a panel of organisms permits the determination of structure-activity relationships not only in regards to potency and spectrum, but also with a view to obviating resistance mechanisms. The assays may be performed in microtiter trays according to conventional methodologies as published by The National Committee for Clinical Laboratory Standards (NCCLS) guidelines (NCCLS. M7-A5-Methods for Dilution Antimicrobial Susceptibility Tests for Bacteria That Grow Aerobically; Approved Standard-Fifth Edition. NCCLS Document M100-S12/M7 (ISBN 1-56238-394-9)).

5. Formulation and Administration

The compounds of the invention may be useful in the prevention or treatment of a variety of human or other animal, including mammalian and non mammalian, disorders, including for example, bacterial infection, fungal infections, viral infections, parasitic diseases, and cancer. It is contemplated that, once identified, the active molecules of the invention may be incorporated into any suitable carrier prior to use. The dose of active molecule, mode of administration and use of suitable carrier will depend upon the intended recipient and target organism. The formulations, both for veterinary and for human medical use, of compounds according to the present invention typically include such compounds in association with a pharmaceutically acceptable carrier.

The carrier(s) should be "acceptable" in the sense of being compatible with the other ingredients of the formulations and not deleterious to the recipient. Pharmaceutically acceptable carriers, in this regard, are intended to include any and all solvents, dispersion media, coatings, anti-bacterial and anti-fungal agents, isotonic and absorption delaying agents, and the like, compatible with pharmaceutical administration. The use of such media and agents for pharmaceutically active substances is known in the art. Except insofar as any conventional media or agent is incompatible with the active compound, use thereof in the compositions is contemplated. Supplementary active compounds (identified or designed according to the invention and/or known in the art) also can be incorporated into the compositions. The formulations may conveniently be presented in dosage unit form and may be prepared by any of the methods well known in the art of pharmacy/microbiology. In general, some formulations are prepared by bringing the compound into association with a liquid carrier or a finely divided solid carrier or both, and then, if necessary, shaping the product into the desired formulation.

A pharmaceutical composition of the invention should be formulated to be compatible with its intended route of administration. Examples of routes of administration include oral or parenteral, for example, intravenous, intradermal, inhalation, transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

Useful solutions for oral or parenteral administration can be prepared by any of the methods well known in the pharmaceutical art, described, for example, in Remington's *Pharmaceutical Sciences*, (Gennaro, A., ed.), Mack Pub., (1990). Formulations for parenteral administration can also include glycocholate for buccal administration, methoxysalicylate for rectal administration, or citric acid for vaginal administration. The parenteral preparation can be enclosed in ampoules, disposable syringes or multiple dose vials made of glass or plastic. Suppositories for rectal administration also can be prepared by mixing the drug with a non-irritating excipient such as cocoa butter, other glycerides, or other compositions which are solid at room temperature and liquid at body temperatures. Formulations also can include, for example, polyalkylene glycols such as polyethylene glycol, oils of vegetable origin, and hydrogenated naphthalenes. Formulations for direct administration can include glycerol and other compositions of high viscosity. Other potentially useful parenteral carriers for these drugs include ethylene-vinyl acetate copolymer particles, osmotic pumps, implantable infusion systems, and liposomes. Formulations for inhalation administration can contain as excipients, for example, lactose, or can be aqueous solutions containing, for example, polyoxyethylene-9-lauryl ether, glycocholate and deoxycholate, or oily solutions for administration in the form of nasal drops, or as a gel to be applied intranasally. Retention enemas also can be used for rectal delivery.

Formulations of the present invention suitable for oral administration may be in the form of: discrete units such as capsules, gelatin capsules, sachets, tablets, troches, or lozenges, each containing a predetermined amount of the drug; a powder or granular composition; a solution or a suspension in an aqueous liquid or non-aqueous liquid; or an oil-in-water emulsion or a water-in-oil emulsion. The drug may also be administered in the form of a bolus, electuary or paste. A tablet may be made by compressing or moulding the drug optionally with one or more accessory ingredients. Compressed tablets may be prepared by compressing, in a suitable machine, the drug in a free-flowing form such as a powder or granules, optionally mixed by a binder, lubricant, inert diluent, surface active or dispersing agent. Moulded tablets may be made by moulding, in a suitable machine, a mixture of the powdered drug and suitable carrier moistened with an inert liquid diluent.

Oral compositions generally include an inert diluent or an edible carrier. For the purpose of oral therapeutic administration, the active compound can be incorporated with excipients. Oral compositions prepared using a fluid carrier for use as a mouthwash include the compound in the fluid carrier and are applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration may be in the form of a sterile aqueous preparation of the drug that may be in microcrystalline form, for example, in the form of an aqueous microcrystalline suspension. Liposomal formulations or biodegradable polymer systems may also be used to present the drug for both intra-articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops. Formulations for topical administration to the skin surface can be prepared by dispersing the drug with a dermatologically acceptable carrier such as a lotion, cream, ointment or soap. Particularly useful are carriers capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used.

For inhalation treatments, inhalation of powder (self-propelling or spray formulations) dispensed with a spray can, a nebulizer, or an atomizer can be used. Such formulations can be in the form of a fine powder for pulmonary administration from a powder inhalation device or self-propelling powder-dispensing formulations. In the case of self-propelling solution and spray formulations, the effect may be achieved either by choice of a valve having the desired spray characteristics (i.e., being capable of producing a spray having the desired particle size) or by incorporating the active ingredient as a suspended powder in controlled particle size. For administration by inhalation, the compounds also can be delivered in the form of an aerosol spray from pressured container or dispenser which contains a suitable propellant, e.g., a gas such as carbon dioxide, or a nebulizer.

Systemic administration also can be by transmucosal or transdermal means. For transmucosal or transdermal administration, penetrants appropriate to the barrier to be permeated are used in the formulation. Such penetrants generally are known in the art, and include, for example, for transmucosal administration, detergents and bile salts. Transmucosal administration can be accomplished through the use of nasal sprays or suppositories. For transdermal administration, the active compounds typically are formulated into ointments, salves, gels, or creams as generally known in the art.

The active compounds may be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

Oral or parenteral compositions can be formulated in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals. Furthermore, administration can be by periodic injections of a bolus, or can be made more continuous by intravenous, intramuscular or intraperitoneal administration from an external reservoir (e.g., an intravenous bag).

Where adhesion to a tissue surface is desired the composition can include the drug dispersed in a fibrinogen-thrombin composition or other bioadhesive. The compound then can be painted, sprayed or otherwise applied to the desired tissue surface. Alternatively, the drugs can be formulated for parenteral or oral administration to humans or other mammals, for example, in therapeutically effective amounts, e.g., amounts that provide appropriate concentrations of the drug to target tissue for a time sufficient to induce the desired effect.

Where the active compound is to be used as part of a transplant procedure, it can be provided to the living tissue or organ to be transplanted prior to removal of tissue or organ from the donor. The compound can be provided to the donor host. Alternatively or, in addition, once removed from the donor, the organ or living tissue can be placed in a preservation solution containing the active compound. In all cases, the active compound can be administered directly to the desired tissue, as by injection to the tissue, or it can be provided systemically, either by oral or parenteral administration, using any of the methods and formulations described herein and/or known in the art. Where the drug comprises part of a tissue or organ preservation solution, any commercially available preservation solution can be used to advantage. For example, useful solutions known in the art include Collins solution, Wisconsin solution, Belzer solution, Eurocollins solution and lactated Ringer's solution.

The compounds of the present invention can be administered directly to a tissue locus by applying the compound to a medical device that is placed in contact with the tissue. An example of a medical device is a stent, which contains or is coated with one or more of the compounds of the present invention.

For example, an active compound may be applied to a stent at the site of vascular injury. Stents can be prepared by any of the methods well known in the pharmaceutical art. See, e.g., Fattori, R. and Piva, T., "Drug Eluting Stents in Vascular Intervention," Lancet, 2003, 361, 247-249; Morice, M. C., "A New Era in the Treatment of Coronary Disease?" European Heart Journal, 2003, 24, 209-211; and Toutouzas, K. et al., "Sirolimus-Eluting Stents: A Review of Experimental and Clinical Findings," Z. Kardiol., 2002, 91(3), 49-57. The stent may be fabricated from stainless steel or another bio-compatible metal, or it may be made of a bio-compatible polymer. The active compound may be linked to the stent surface, embedded and released from polymer materials coated on the stent, or surrounded by and released through a carrier which coats or spans the stent. The stent may be used to administer single or multiple active compounds to tissues adjacent to the stent.

Active compound as identified or designed by the methods described herein can be administered to individuals to treat disorders (prophylactically or therapeutically). In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a drug as well as tailoring the dosage and/or therapeutic regimen of treatment with the drug.

In therapeutic use for treating, or combating, bacterial infections in mammals, the compounds or pharmaceutical compositions thereof will be administered orally, parenterally and/or topically at a dosage to obtain and maintain a concentration, that is, an amount, or blood-level or tissue level of active component in the animal undergoing treatment which will be anti-microbially effective. Generally, an effective amount of dosage of active component will be in the range of from about 0.1 to about 100, more preferably from about 1.0 to about 50 mg/kg of body weight/day. The amount administered will also likely depend on such variables as the type and extent of disease or indication to be treated, the overall health status of the particular patient, the relative biological efficacy of the compound delivered, the formulation of the drug, the presence and types of excipients in the formulation, and the route of administration. Also, it is to be understood that the initial dosage administered may be increased beyond the above upper level in order to rapidly achieve the desired blood-level or tissue level, or the initial dosage may be smaller than the optimum and the daily dosage may be progressively increased during the course of treatment depending on the particular situation. If desired, the daily dose may also be divided into multiple doses for administration, for example, two to four times per day.

Various disease states or conditions in humans and other mammals are found to be caused by or mediated by nonsense or missense mutations. These mutations cause or mediate the disease state or condition by adversely affecting, for example, protein synthesis, folding, trafficking and/or function. Examples of disease states or conditions in which an appreciable percentage of the disease or condition is believed to result from nonsense or missense mutations include hemophilia (factor VIII gene), neurofibromatosis (NF1 and NF2 genes), retinitis pigmentosa (human USH2A gene), bullous skin diseases like Epidermolysis bullosa pruriginosa (COL7A1 gene), cystic fibrosis (cystic fibrosis transmembrane regulator gene), breast and ovarian cancer (BRCA1 and BRCA2 genes), Duchenne muscular dystrophy (dystrophin gene), colon cancer (mismatch repair genes, predominantly in MILH1 and MSH2), and lysosomal storage disorders such as Neimann-Pick disease (acid sphingomyelinase gene). See Sanders C R, Myers J K. Disease-related misassembly of membrane proteins. Annu Rev Biophys Biomol Struct. 2004; 33:25-51; National Center for Biotechnology Information (U.S.) *Genes and disease* Bethesda, Md.: NCBI, NLM 1D: 101138560 [Book]; and Raskó, István; Downes, C S *Genes in medicine: molecular biology and human genetic disorders* 1st ed. London; New York: Chapman & Hall, 1995. NLM ID: 9502404 [Book]. The compounds of the present invention can be used to treat or prevent a disease state in a mammal caused or mediated by such nonsense or missense mutations by administering to a mammal in need thereof an effective amount of the present invention to suppress the nonsense or missense mutation involved in the disease state.

6. EXAMPLES

Nuclear magnetic resonance (NMR) spectra were obtained on a Bruker Avance 300 or Avance 500 spectrometer, or in some cases a GE-Nicolet 300 spectrometer. Common reaction solvents were either high performance liquid chromatography (HPLC) grade or American Chemical Society (ACS) grade, and anhydrous as obtained from the manufacturer unless otherwise noted. "Chromatography" or "purified by silica gel" refers to flash column chromatography using silica gel (EM Merck, Silica Gel 60, 230-400 mesh) unless otherwise noted.

The compound numbers, e.g., 1, 2, 3, etc. used in this section 6 of the present application and entitled "6. Examples", are for reference within this section 6 only and do not refer to and are not to be confused with any similarly numbered compounds in section 3 of the present application and entitled "3. Synthesis of the Compounds of the Invention".

Compounds synthesized in accordance with the invention are listed in Table 1.

TABLE 1

| Compound Number | Structure |
|---|---|
| 101 | 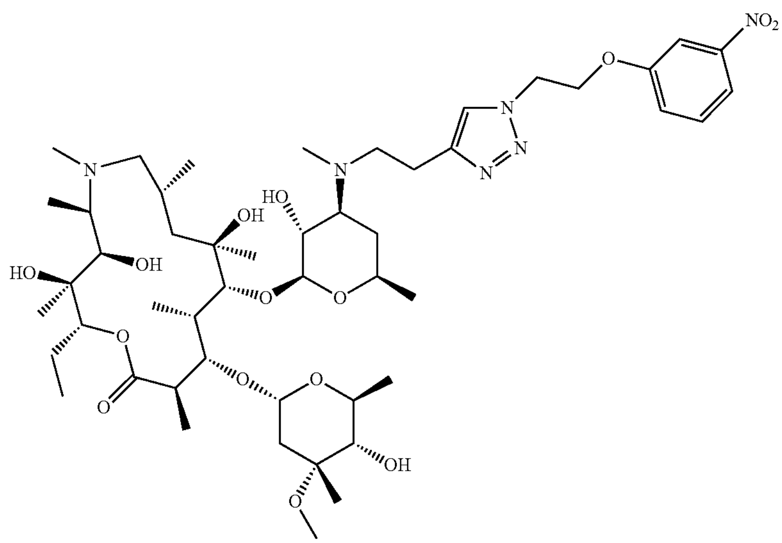 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCOc4cccc([N+](=O)[O-])c4)nn3)[C@H]2O)[C@](C)(O)C[C@@H](C)CN(C)[C@H](C)[C@@H](O)[C@]1(C)O] |
| 102 | 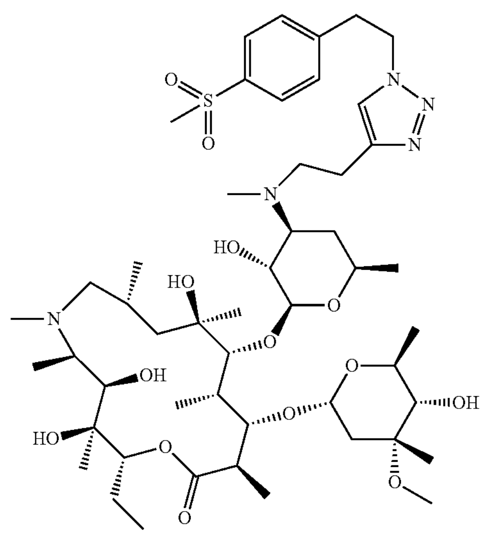 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc(S(C)(=O)=O)cc4)nn3)[C@H]2O)[C@](C)(O)C[C@@H](C)CN(C)[C@H](C)[C@@H](O)[C@]1(C)O] |

TABLE 1-continued

| Compound Number | Structure |
|---|---|
| 103 | 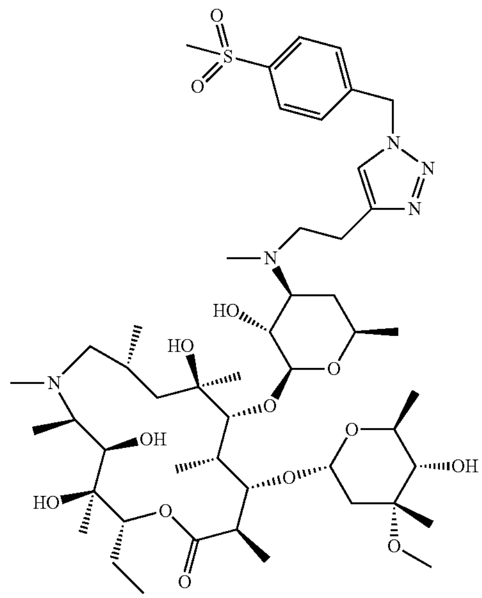 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc(S(C)(=O)=O)cc4)nn3)[C@H]2O)[C@](C)(O)C[C@@H](C)CN(C)[C@H](C)[C@@H](O)[C@]1(C)O] |
| 104 | 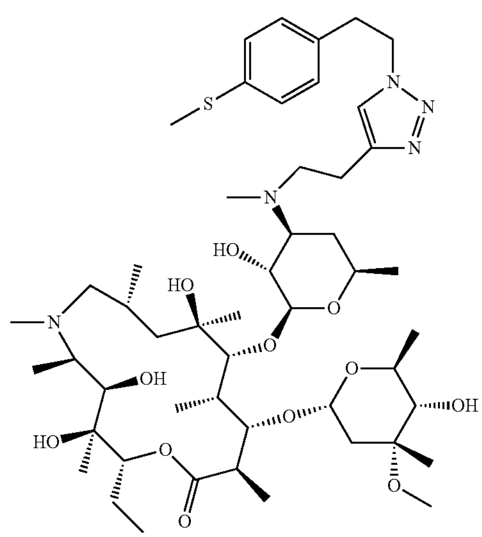 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc(SC)cc4)nn3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 105 | 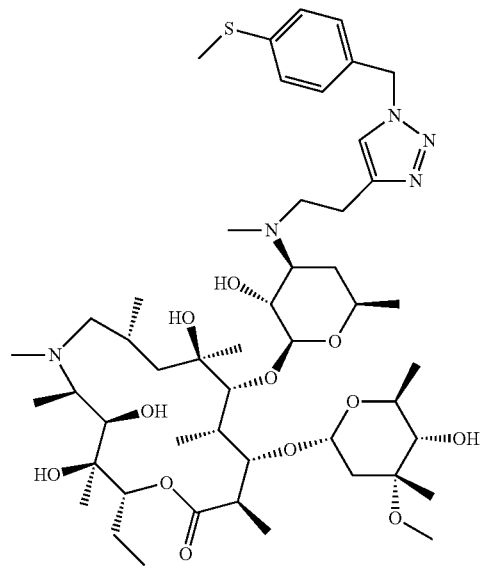 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc(SC)cc4)nn3)[C@H]2O)[C@](C)(O)C[C@@H](C)CN(C)[C@H](C)[C@@H](O)[C@]1(C)O] |
| 106 | 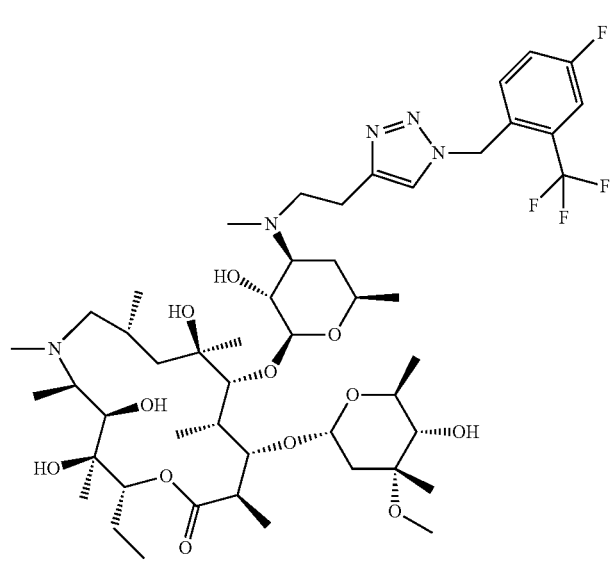 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc(F)cc4C(F)(F)F)nn3)[C@H]2O)[C@](C)(O)C[C@@H](C)CN(C)[C@H](C)[C@@H](O)[C@]1(C)O] |

った
| Compound Number | Structure |
|---|---|
| 107 | 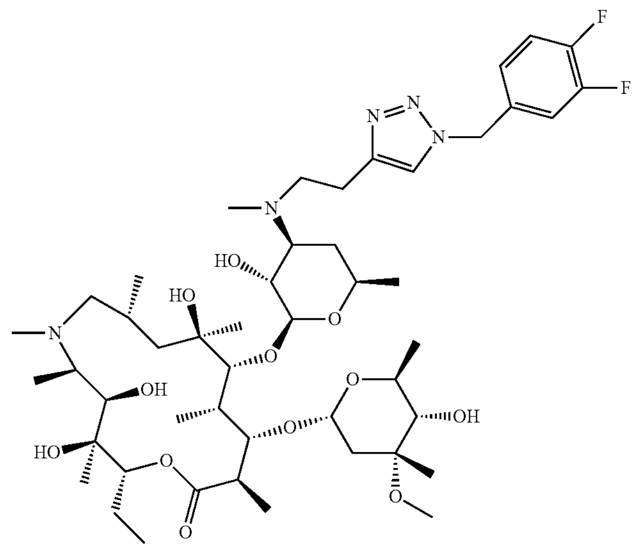 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc(F)c(F)c4)nn3)[C@H]2O)[C@](C)(O)C[C@@H](C)CN(C)[C@H](C)[C@@H](O)[C@]1(C)O] |
| 108 | 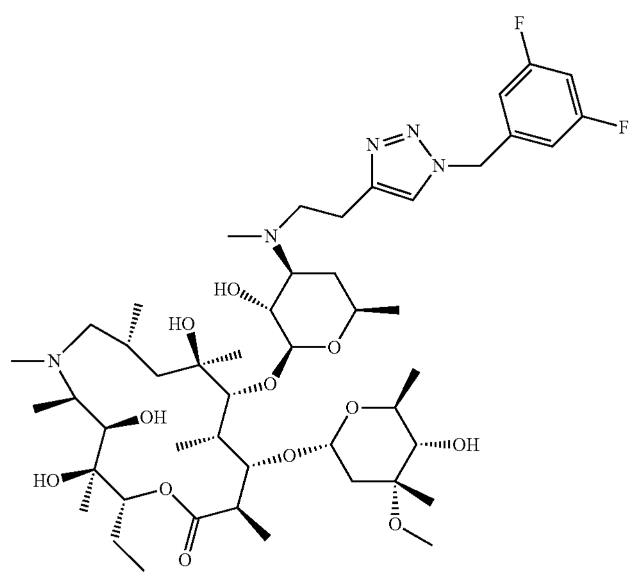 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4cc(F)cc(F)c4)nn3)[C@H]2O)[C@](C)(O)C[C@@H](C)CN(C)[C@H](C)[C@@H](O)[C@]1(C)O] |

TABLE 1-continued

| Compound Number | Structure |
|---|---|
| 109 | (2,6-difluorobenzyl triazole macrolide structure) |
| 110 | (2,3-difluorobenzyl triazole macrolide structure) |
| 111 | (2,5-difluorobenzyl triazole macrolide structure) |

TABLE 1-continued

| Compound Number | Structure |
|---|---|
| 112 | 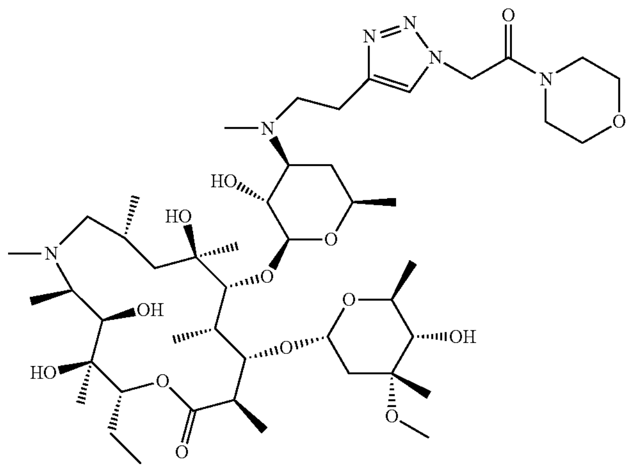 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CC(=O)N4CCOCC4)nn3)[C@H]2O)[C@](C)(O)C[C@@H](C)CN(C)[C@H](C)[C@@H](O)[C@]1(C)O] |
| 113 | 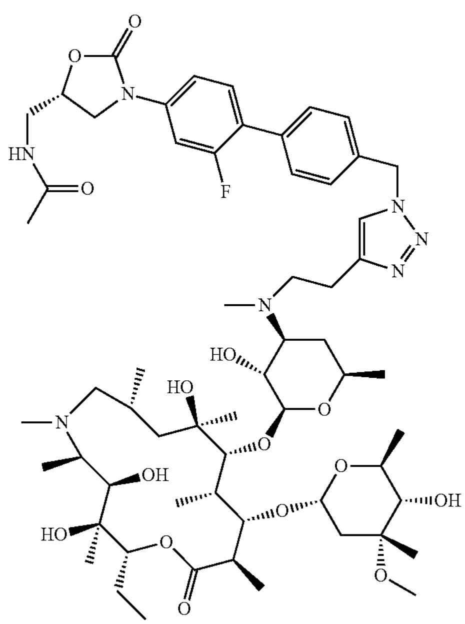 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc(-c5ccc(N6C[C@H](CNC(C)=O)OC6=O)cc5F)cc4)nn3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 114 | 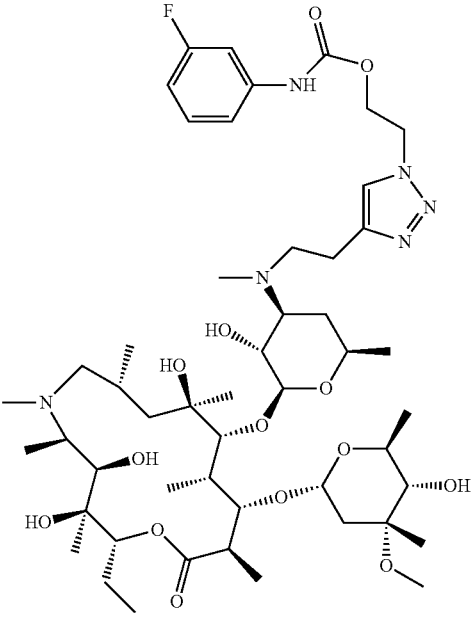 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCOC(=O)Nc4cccc(F)c4)nn3)[C@H]2O)[C@](C)(O)C[C@@H](C)CN(C)[C@H](C)[C@@H](O)[C@]1(C)O] |
| 115 | 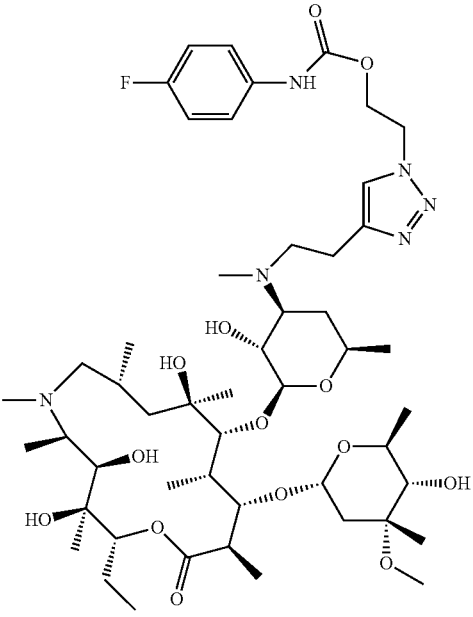 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCOC(=O)Nc4ccc(F)cc4)nn3)[C@H]2O)[C@](C)(O)C[C@@H](C)CN(C)[C@H](C)[C@@H](O)[C@]1(C)O] |

US 8,841,263 B2
TABLE 1-continued
| Compound Number | Structure |
|---|---|
| 116 | 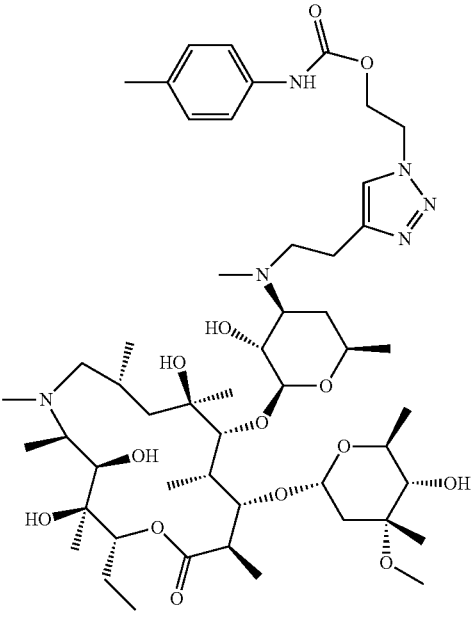 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCOC(=O)Nc4ccc(C)cc4)nn3)[C@H]2O)[C@](C)(O)C[C@@H](C)CN(C)[C@H](C)[C@@H](O)[C@]1(C)O] |
| 117 | 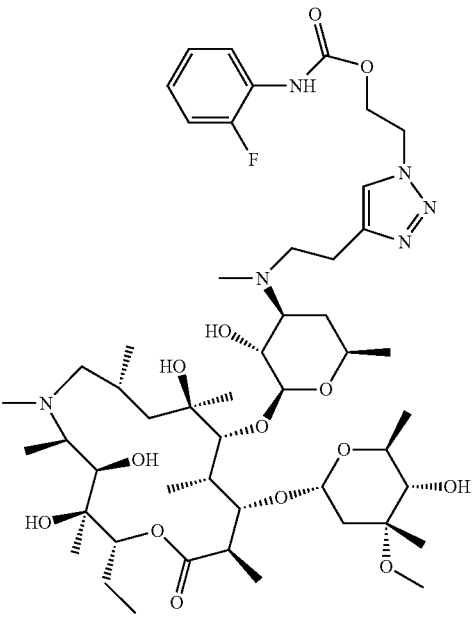 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCOC(=O)Nc4ccccc4F)nn3)[C@H]2O)[C@](C)(O)C[C@@H](C)CN(C)[C@H](C)[C@@H](O)[C@]1(C)O] |

… TABLE 1-continued
| Compound Number | Structure |
|---|---|
| 118 | 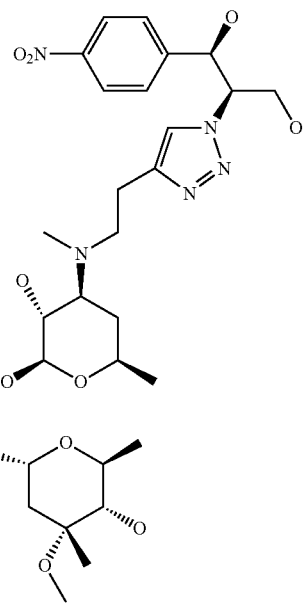 |
| 120 | 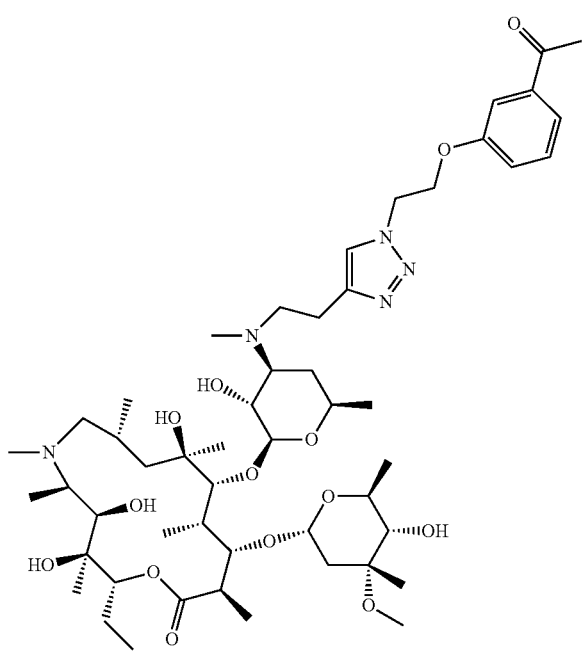 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCOc4cccc(C(C)=O)c4)nn3)[C@H]2O)[C@](C)(O)C[C@@H](C)CN(C)[C@H](C)[C@@H](O)[C@]1(C)O] |

TABLE 1-continued

| Compound Number | Structure |
| --- | --- |
| 121 | 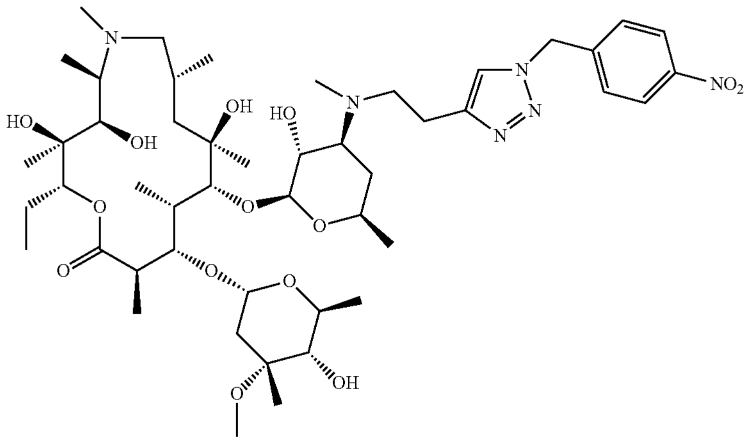 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc([N+](=O)[O-])cc4)nn3)[C@H]2O)[C@](C)(O)C[C@@H](C)CN(C)[C@H](C)[C@@H](O)[C@]1(C)O] |
| 122 | 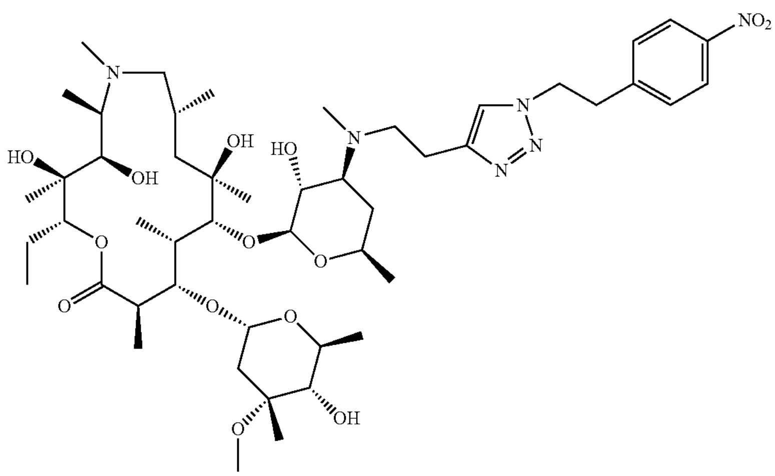 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc([N+](=O)[O-])cc4)nn3)[C@H]2O)[C@](C)(O)C[C@@H](C)CN(C)[C@H](C)[C@@H](O)[C@]1(C)O] |
| 123 | 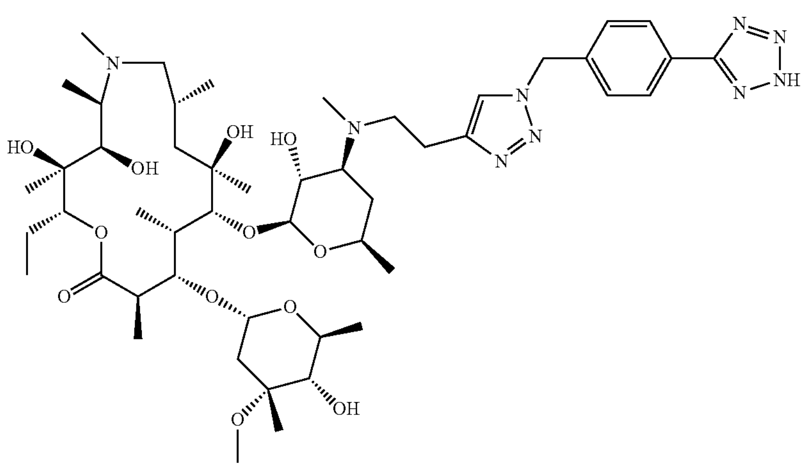 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc(-c5nn[nH]n5)cc4)nn3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 124 | 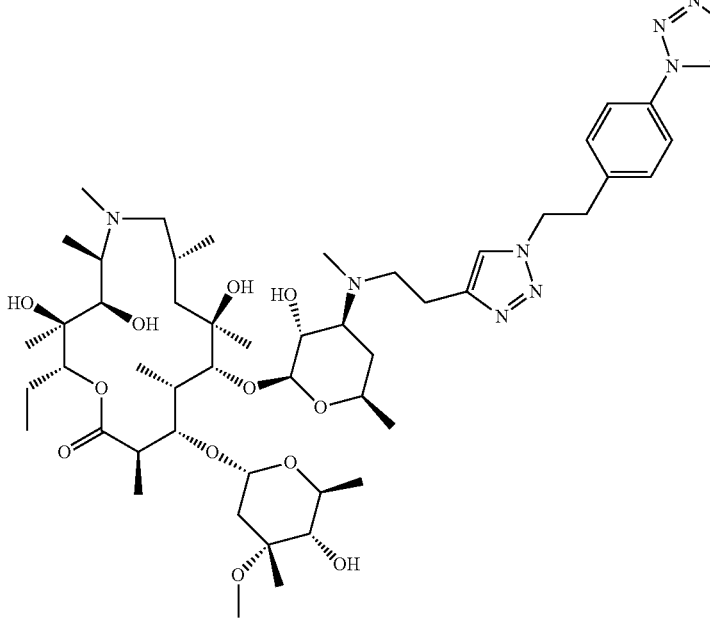 |
| 142 | 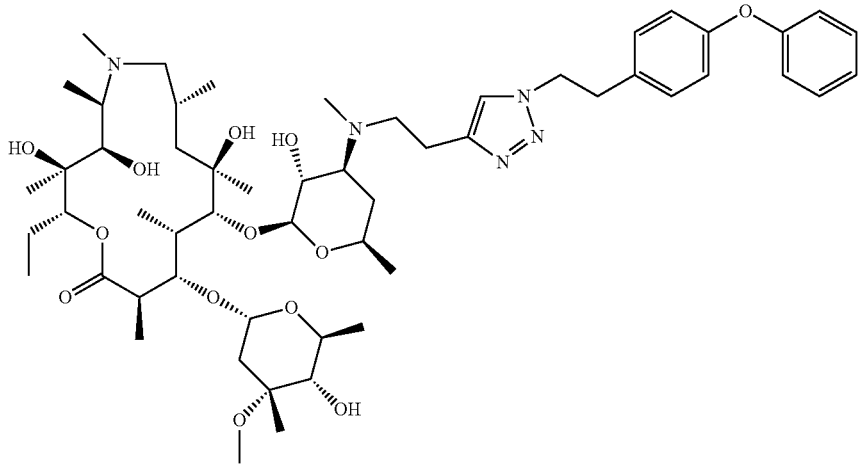 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc(Oc5ccccc5)cc4)nn3)[C@H]2O)[C@](C)(O)C[C@@H](C)CN(C)[C@H](C)[C@@H](O)[C@]1(C)O] |
| 125 | 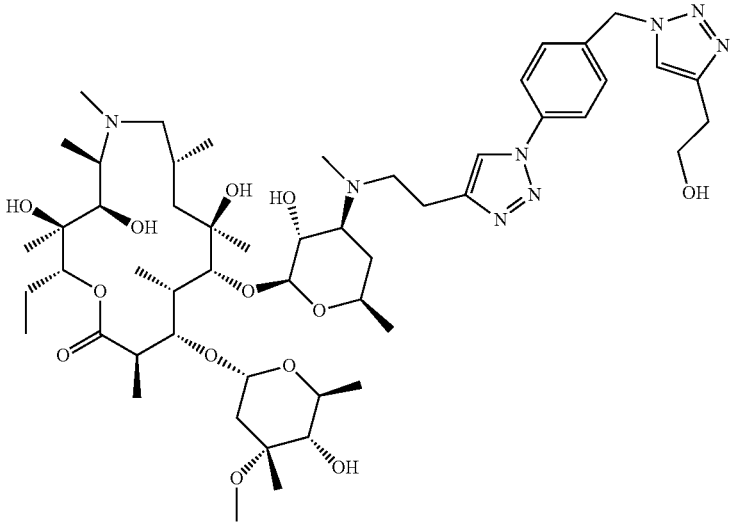 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(-c4ccc(Cn5cc(CCO)nn5)cc4)nn3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 126 | 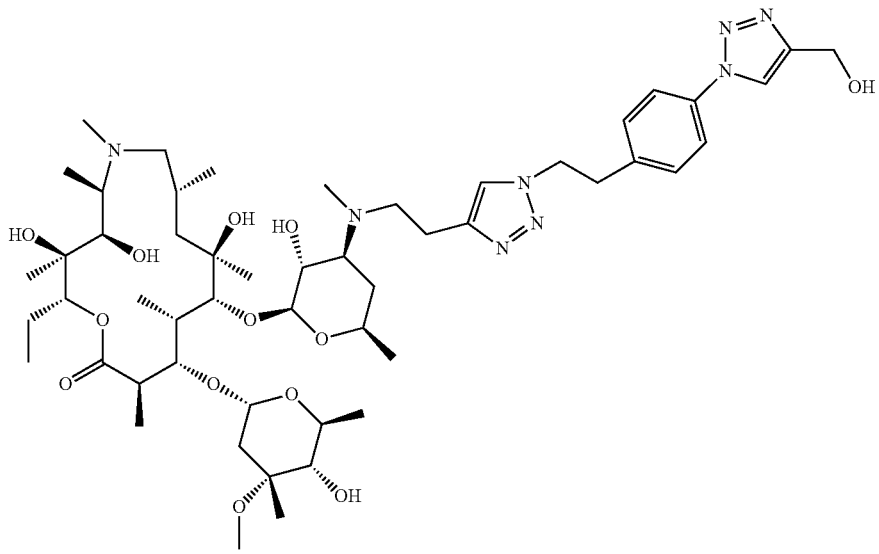 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc(-n5cc(CO)nn5)cc4)nn3)[C@H]2O)[C@](C)(O)C[C@@H](C)CN(C)[C@H](C)[C@@H](O)[C@]1(C)O] |
| 129 | 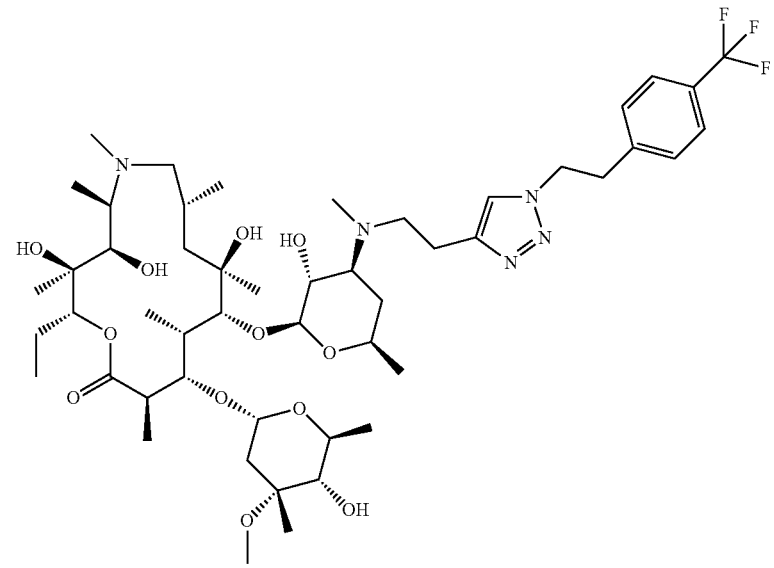 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc(C(F)(F)F)cc4)nn3)[C@H]2O)[C@](C)(O)C[C@@H](C)CN(C)[C@H](C)[C@@H](O)[C@]1(C)O] |
| 130 | 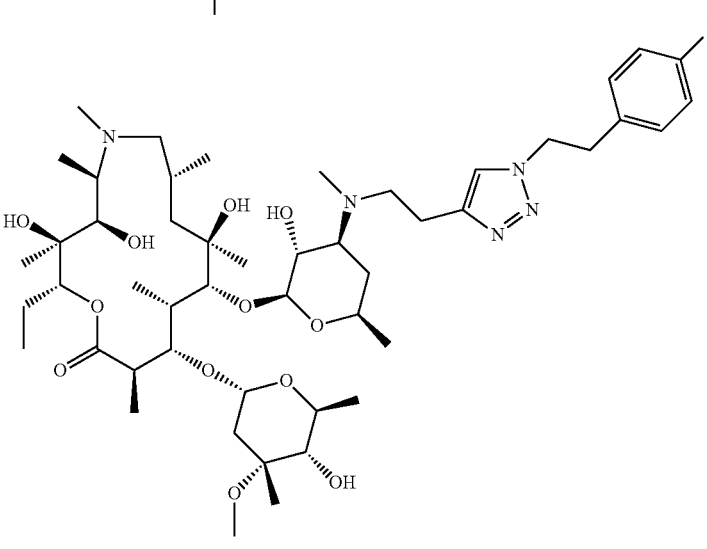 |

TABLE 1-continued
| Compound Number | Structure |
|---|---|
| 131 | 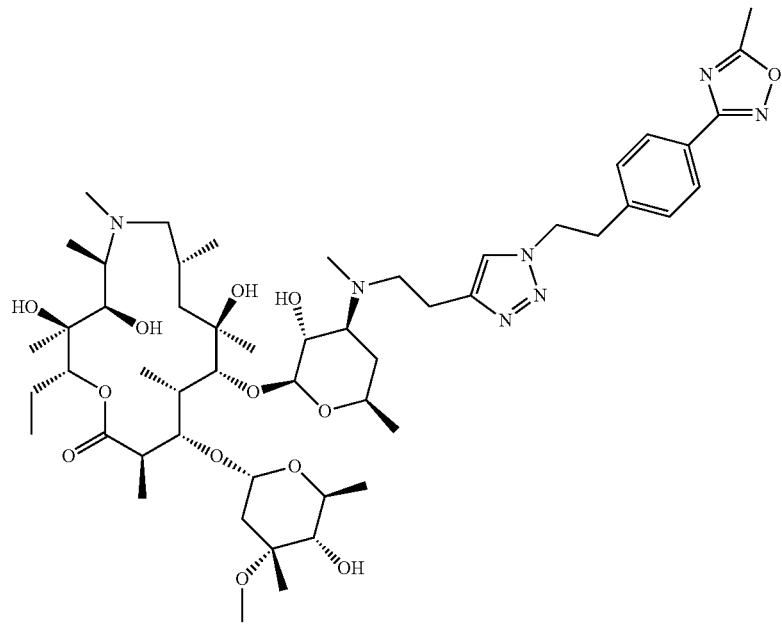 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc(-c5noc(C)n5)cc4)nn3)[C@H]2O)[C@](C)(O)C[C@@H](C)CN(C)[C@H](C)[C@@H](O)[C@]1(C)O] |
| 132 | 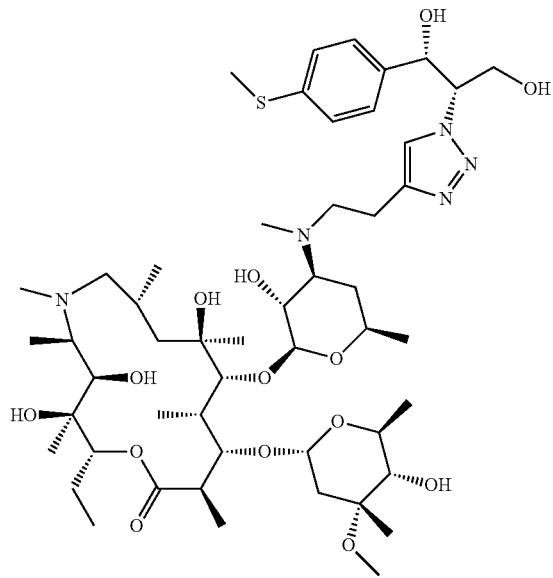 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@@H](CO)[C@@H](O)c4ccc(SC)cc4)nn3)[C@H]2O)[C@](C)(O)C[C@@H](C)CN(C)[C@H](C)[C@@H](O)[C@]1(C)O] |

| Compound Number | Structure |
|---|---|
| 133 | 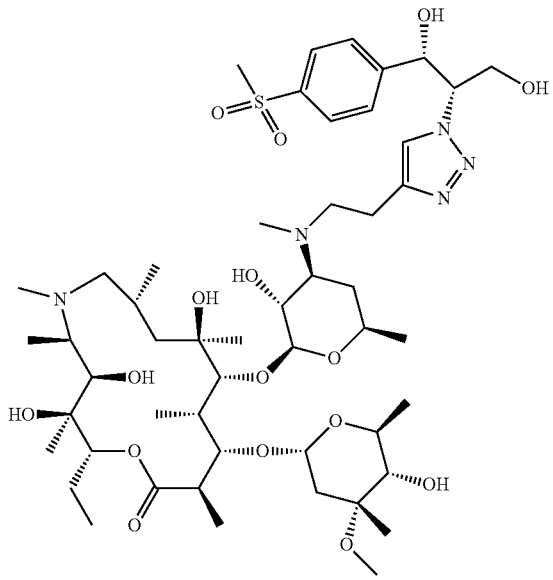 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@@H](CO)[C@@H](O)c4ccc(S(C)(=O)=O)cc4)nn3)[C@H]2O)[C@](C)(O)C[C@@H](C)CN(C)[C@H](C)[C@@H](O)[C@]1(C)O] |
| 134 | 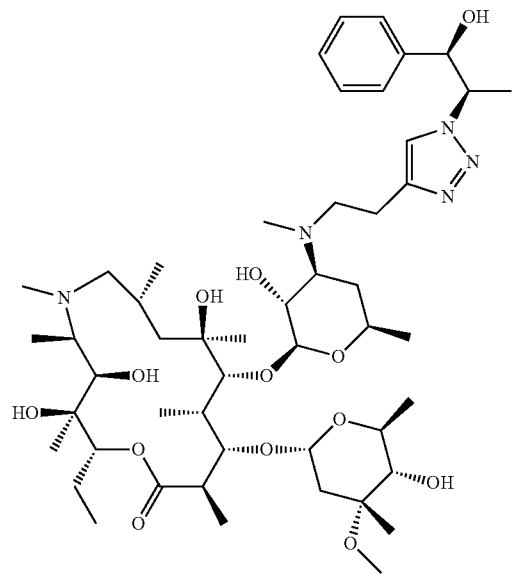 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](C)[C@H](O)c4ccccc4)nn3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 135 | 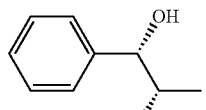 |
| 136 | 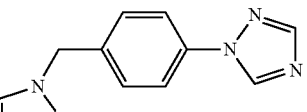 |

TABLE 1-continued

| Compound Number | Structure |
| --- | --- |
| 137 | 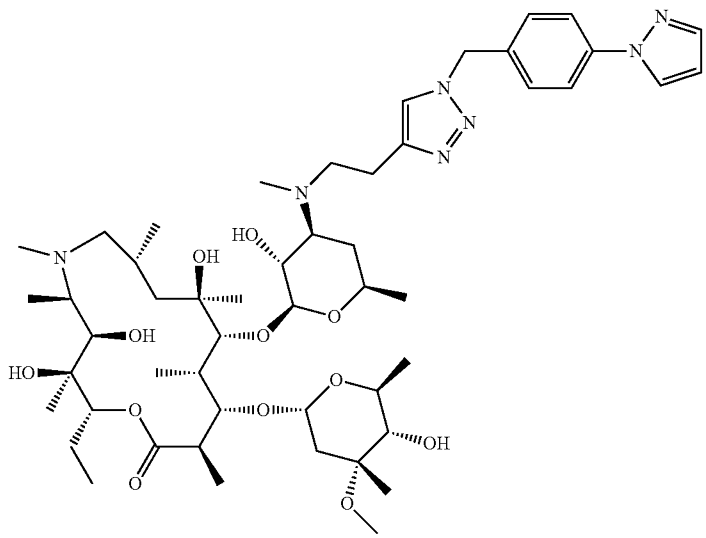 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc(-n5cccn5)cc4)nn3)[C@H]2O)[C@](C)(O)C[C@@H](C)CN(C)[C@H](C)[C@@H](O)[C@]1(C)O] |
| 138 | 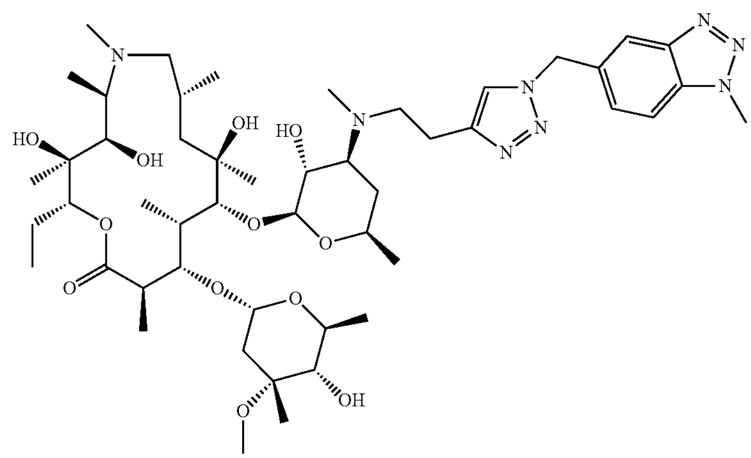 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc5c(c4)nnn5C)nn3)[C@H]2O)[C@](C)(O)C[C@@H](C)CN(C)[C@H](C)[C@@H](O)[C@]1(C)O] |
| 139 | 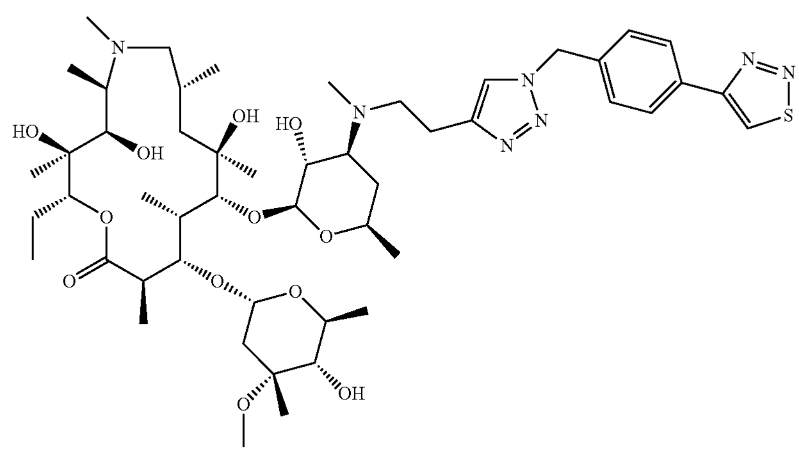 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc(-c5csnn5)cc4)nn3)[C@H]2O)[C@](C)(O)C[C@@H](C)CN(C)[C@H](C)[C@@H](O)[C@]1(C)O] |

TABLE 1-continued

| Compound Number | Structure |
| --- | --- |
| 140 | 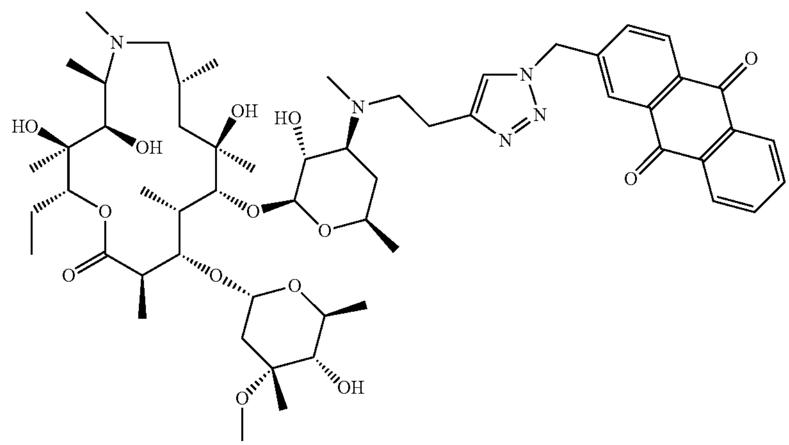 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc5c(c4)C(=O)c4ccccc4C5=O)nn3)[C@H]2O)[C@](C)(O)C[C@@H](C)CN(C)[C@H](C)[C@@H](O)[C@]1(C)O] |
| 141 | 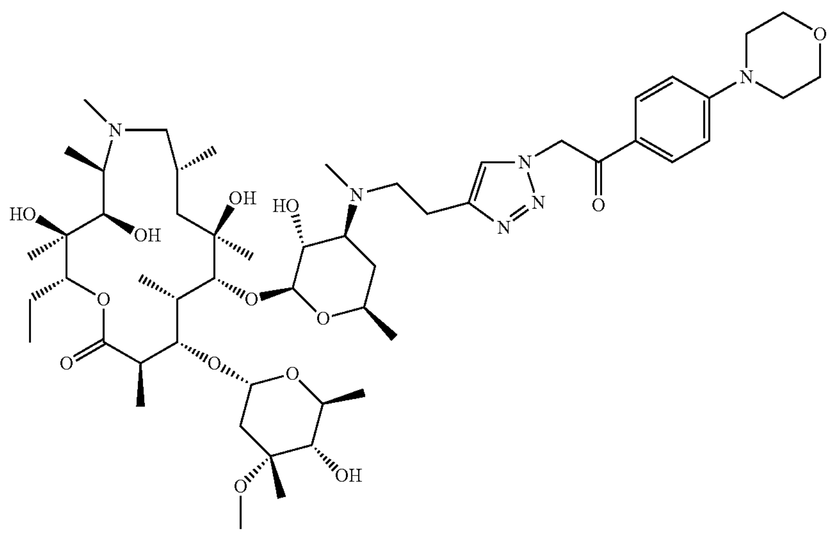 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CC(=O)c4ccc(N5CCOCC5)cc4)nn3)[C@H]2O)[C@](C)(O)C[C@@H](C)CN(C)[C@H](C)[C@@H](O)[C@]1(C)O] |
| 143 | 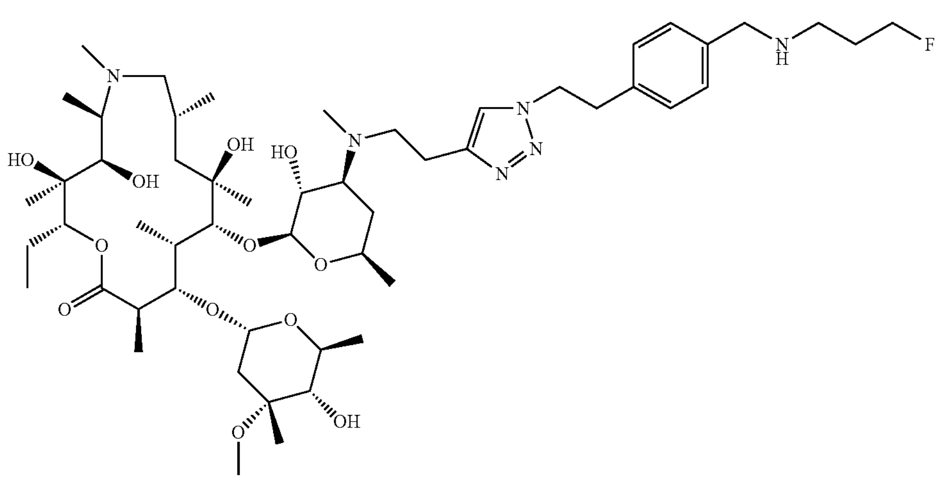 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc(CNCCCF)cc4)nn3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 144 | 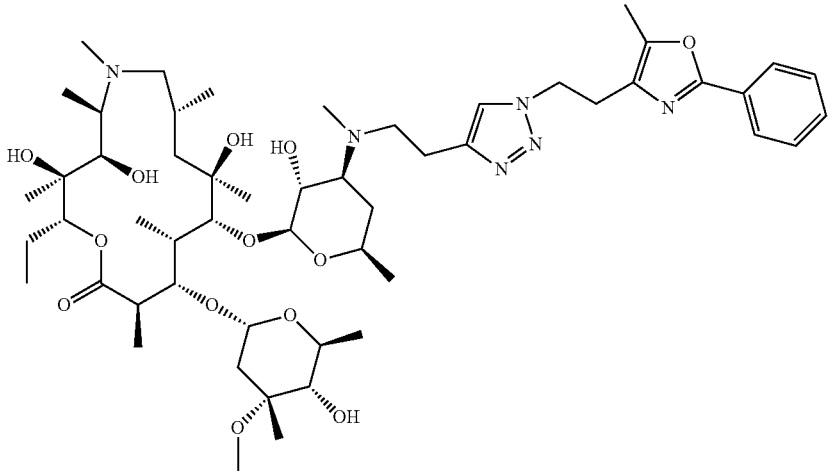 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4nc(-c5ccccc5)oc4C)nn3)[C@H]2O)[C@](C)(O)C[C@@H](C)CN(C)[C@H](C)[C@@H](O)[C@]1(C)O] |
| 145 | 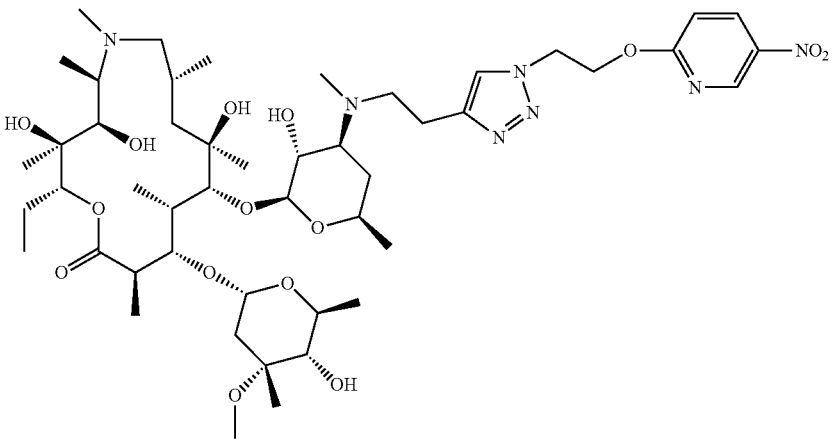 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCOc4ccc([N+](=O)[O-])cn4)nn3)[C@H]2O)[C@](C)(O)C[C@@H](C)CN(C)[C@H](C)[C@@H](O)[C@]1(C)O] |
| 146 | 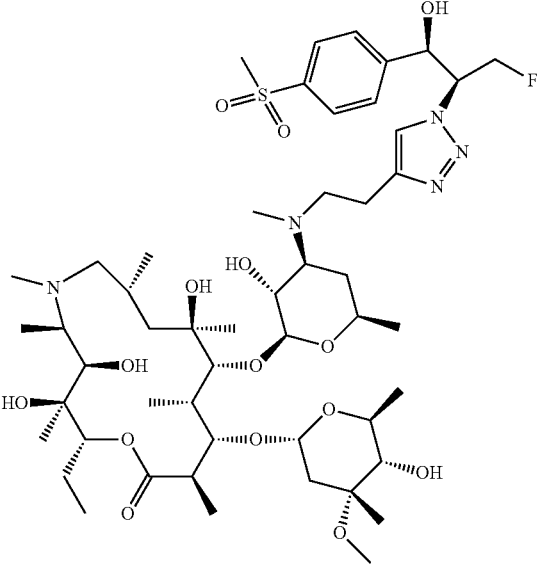 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CF)[C@H](O)c4ccc(S(C)(=O)=O)cc4)nn3)[C@H]2O)[C@](C)(O)C[C@@H](C)CN(C)[C@H](C)[C@@H](O)[C@]1(C)O] |

US 8,841,263 B2
103                                                                                  104
TABLE 1-continued
| Compound Number | Structure |
|---|---|
| 147 | 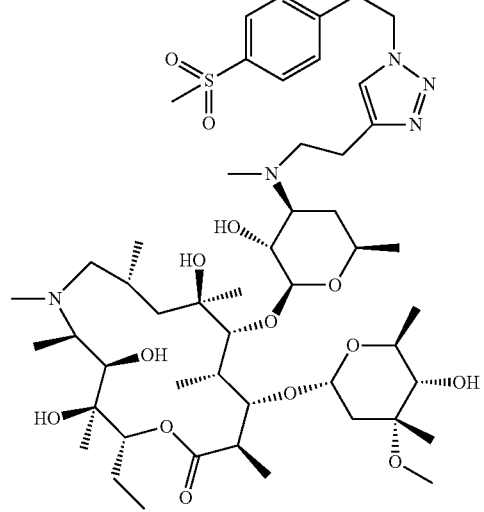 |
| 148 | 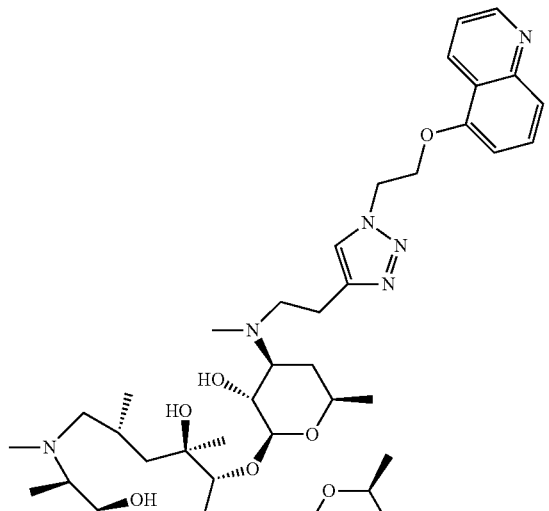 |

TABLE 1-continued
| Compound Number | Structure |
|---|---|
| 149 | 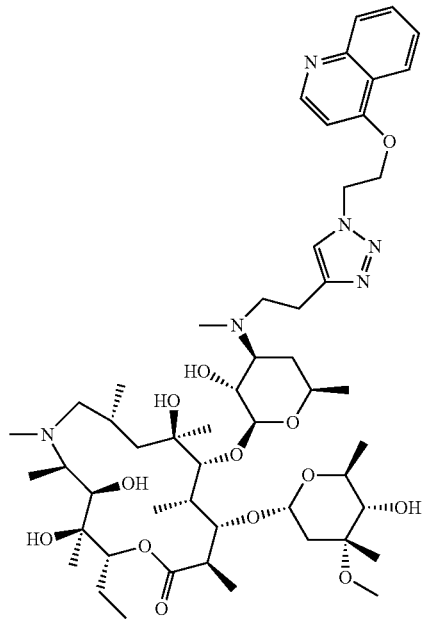 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCOc4ccnc5ccccc45)nn3)[C@H]2O)[C@](C)(O)C[C@@H](C)CN(C)[C@H](C)[C@@H](O)[C@]1(C)O] |
| 150 | 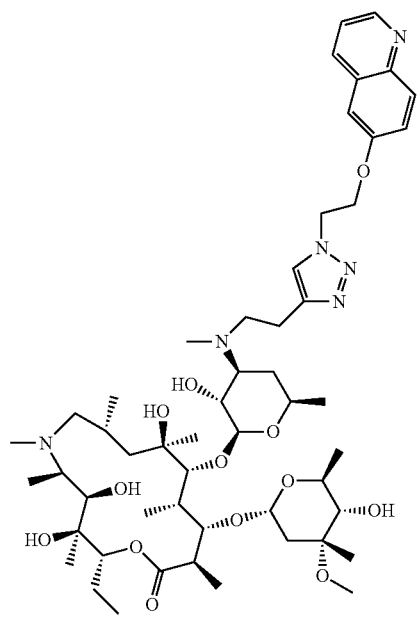 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCOc4ccc5ncccc5c4)nn3)[C@H]2O)[C@](C)(O)C[C@@H](C)CN(C)[C@H](C)[C@@H](O)[C@]1(C)O] |

TABLE 1-continued

| Compound Number | Structure |
|---|---|
| 151 | 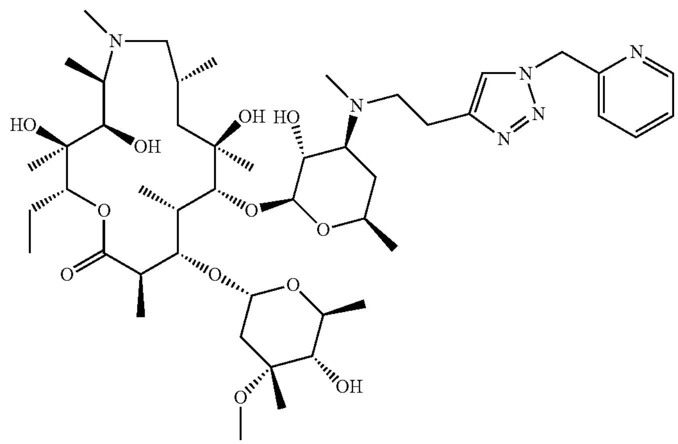 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccccn4)nn3)[C@H]2O)[C@](C)(O)C[C@@H](C)CN(C)[C@H](C)[C@@H](O)[C@]1(C)O] |
| 152 | 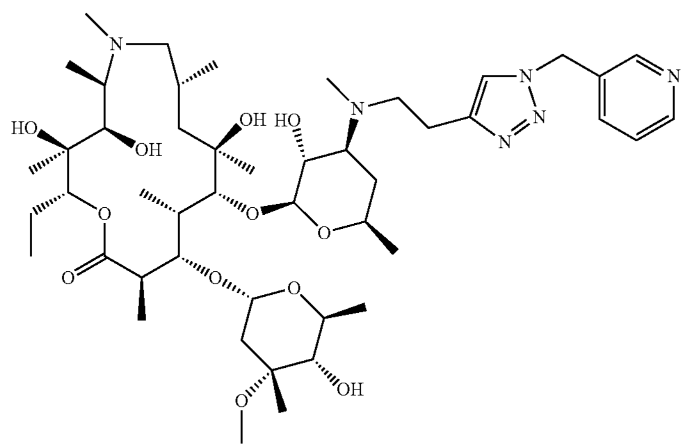 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4cccnc4)nn3)[C@H]2O)[C@](C)(O)C[C@@H](C)CN(C)[C@H](C)[C@@H](O)[C@]1(C)O] |
| 153 | 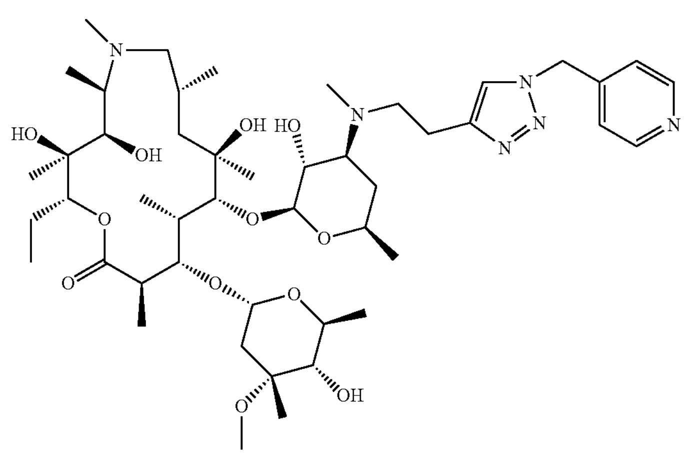 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccncc4)nn3)[C@H]2O)[C@](C)(O)C[C@@H](C)CN(C)[C@H](C)[C@@H](O)[C@]1(C)O] |

TABLE 1-continued

| Compound Number | Structure |
|---|---|
| 154 | 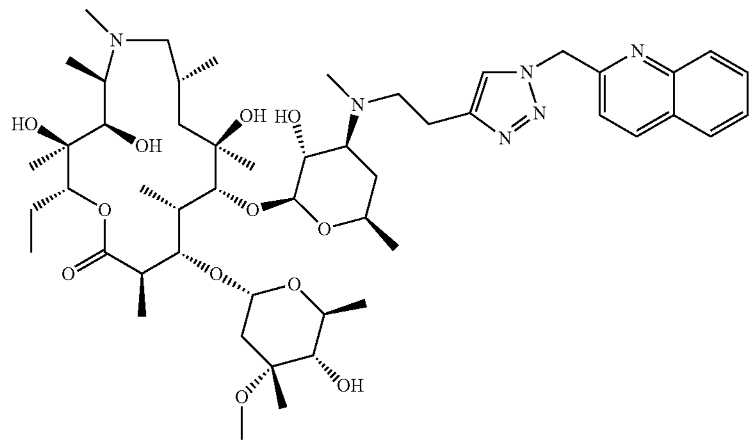 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc5ccccc5n4)nn3)[C@H]2O)[C@](C)(O)C[C@@H](C)CN(C)[C@H](C)[C@@H](O)[C@]1(C)O] |
| 155 | 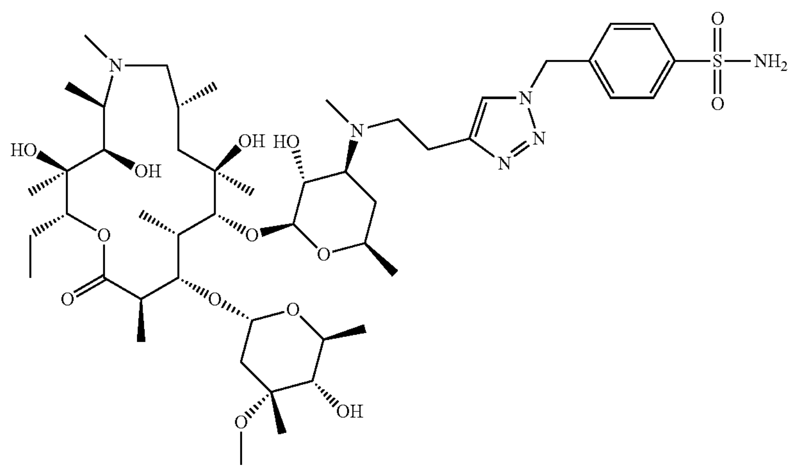 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc(S(N)(=O)=O)cc4)nn3)[C@H]2O)[C@](C)(O)C[C@@H](C)CN(C)[C@H](C)[C@@H](O)[C@]1(C)O] |
| 156 | 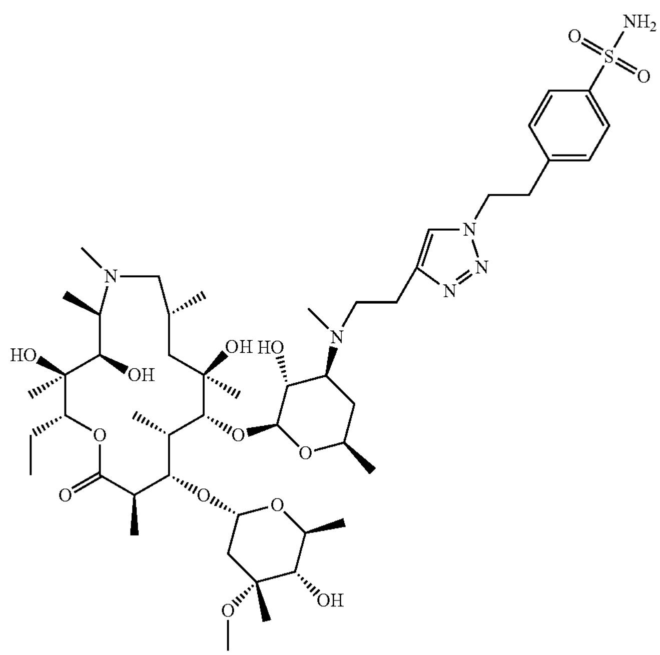 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc(S(N)(=O)=O)cc4)nn3)[C@H]2O)[C@](C)(O)C[C@@H](C)CN(C)[C@H](C)[C@@H](O)[C@]1(C)O] |

TABLE 1-continued
| Compound Number | Structure |
| --- | --- |
| 157 | 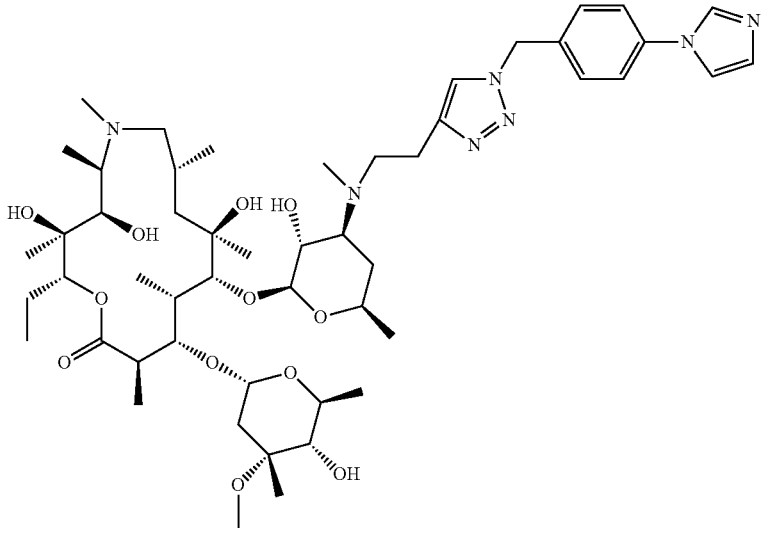 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc(-n5ccnc5)cc4)nn3)[C@H]2O)[C@](C)(O)C[C@@H](C)CN(C)[C@H](C)[C@@H](O)[C@]1(C)O] |
| 158 | 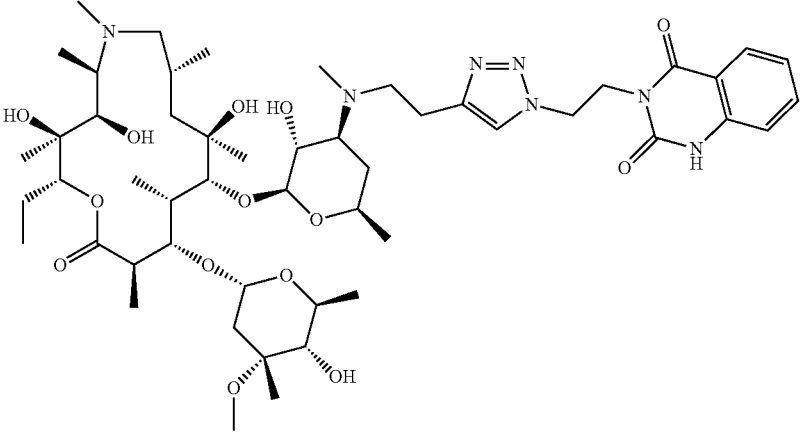 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCn4c(=O)[nH]c5ccccc5c4=O)nn3)[C@H]2O)[C@](C)(O)C[C@@H](C)CN(C)[C@H](C)[C@@H](O)[C@]1(C)O] |
| 159 | 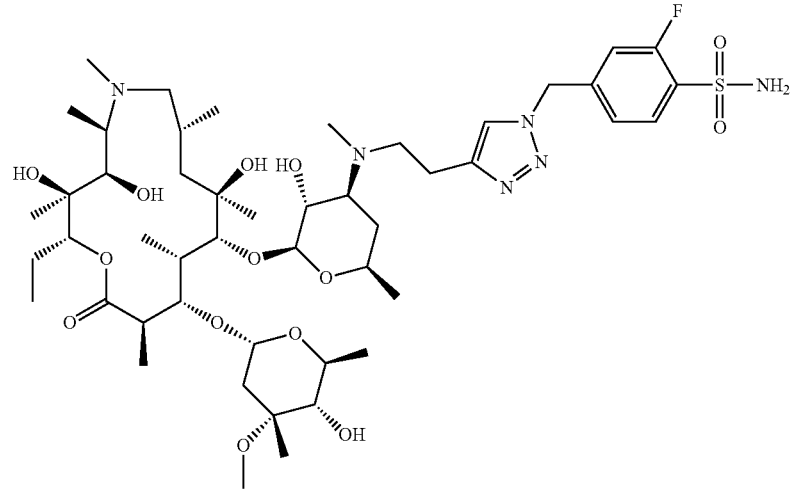 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc(S(N)(=O)=O)c(F)c4)nn3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 160 | 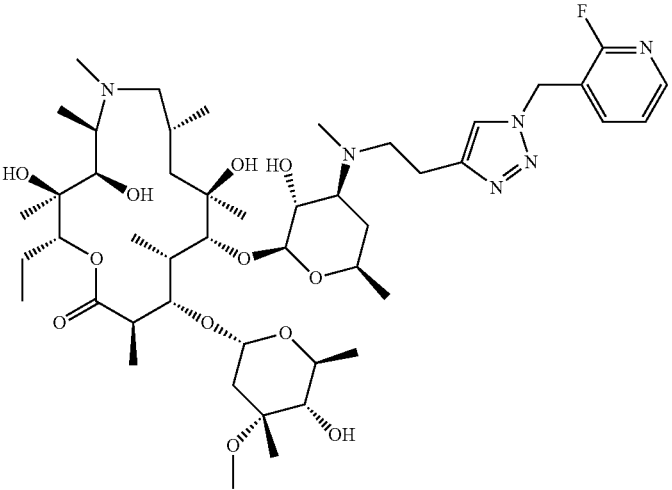 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4cccnc4F)nn3)[C@H]2O)[C@](C)(O)C[C@@H](C)CN(C)[C@H](C)[C@@H](O)[C@]1(C)O] |
| 161 | 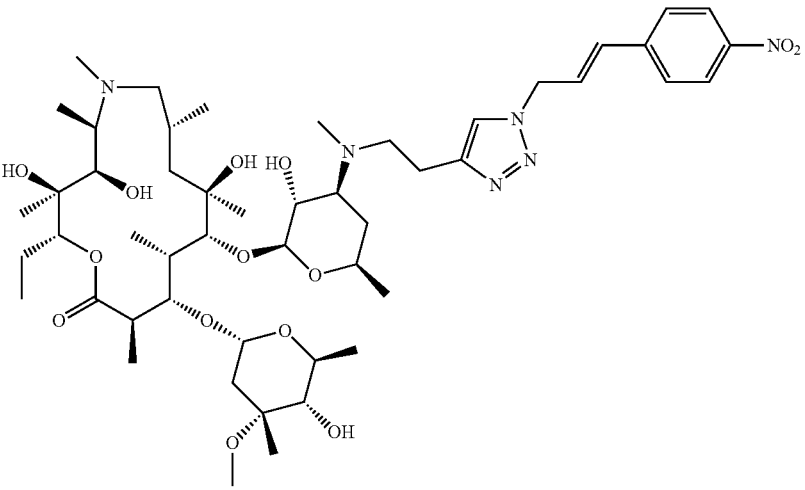 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(C/C=C/c4ccc([N+](=O)[O-])cc4)nn3)[C@H]2O)[C@](C)(O)C[C@@H](C)CN(C)[C@H](C)[C@@H](O)[C@]1(C)O] |
| 162 | 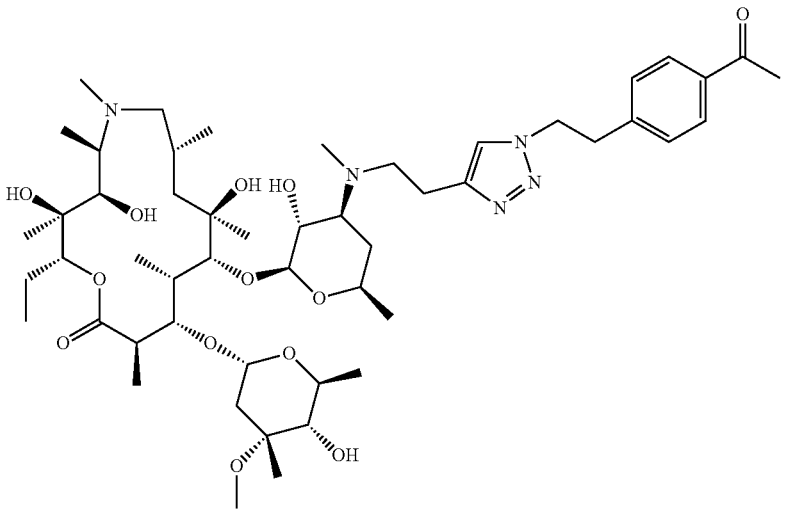 |

TABLE 1-continued
| Compound Number | Structure |
| --- | --- |
| 163 | 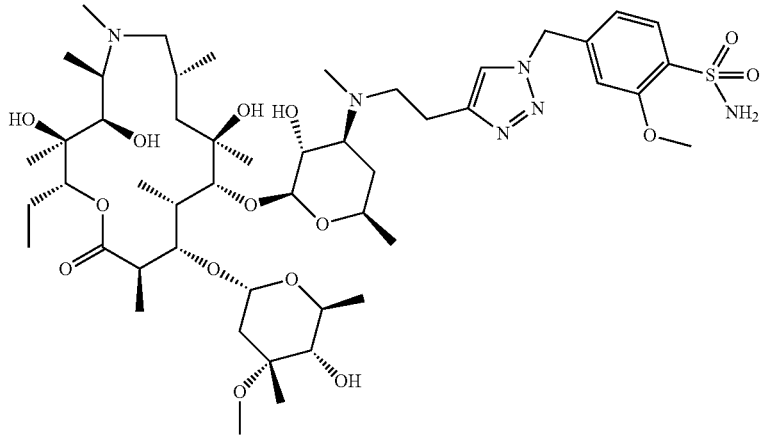 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc(S(N)(=O)=O)c(OC)c4)nn3)[C@H]2O)[C@](C)(O)C[C@@H](C)CN(C)[C@H](C)[C@@H](O)[C@]1(C)O] |
| 164 | 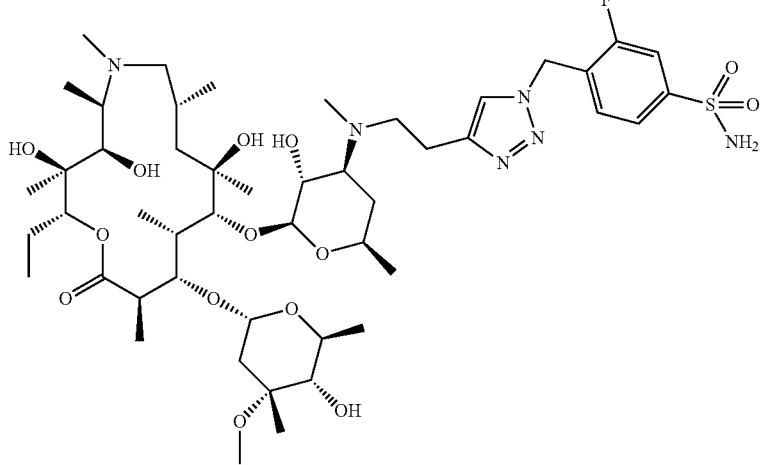 |
| 165 | 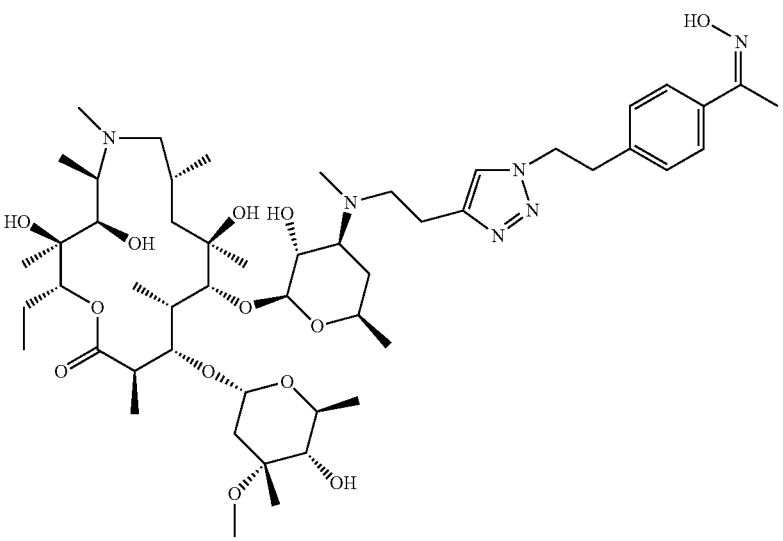 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc(/C(C)=N\O)cc4)nn3)[C@H]2O)[C@](C)(O)C[C@@H](C)CN(C)[C@H](C)[C@@H](O)[C@]1(C)O] |

TABLE 1-continued
| Compound Number | Structure |
| --- | --- |
| 166 | 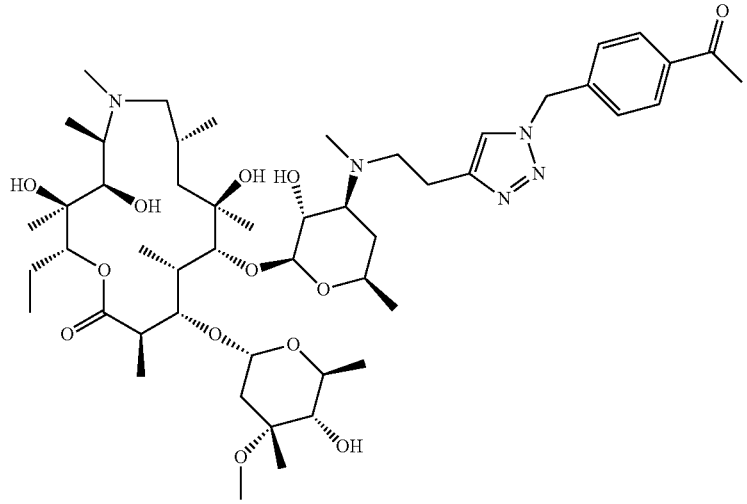 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc(C(C)=O)cc4)nn3)[C@H]2O)[C@](C)(O)C[C@@H](C)CN(C)[C@H](C)[C@@H](O)[C@]1(C)O] |
| 167 | 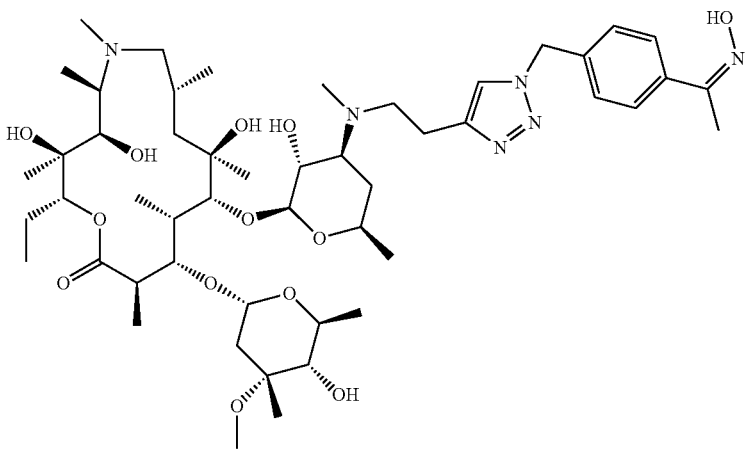 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc(/C(C)=N\O)cc4)nn3)[C@H]2O)[C@](C)(O)C[C@@H](C)CN(C)[C@H](C)[C@@H](O)[C@]1(C)O] |
| 168 | 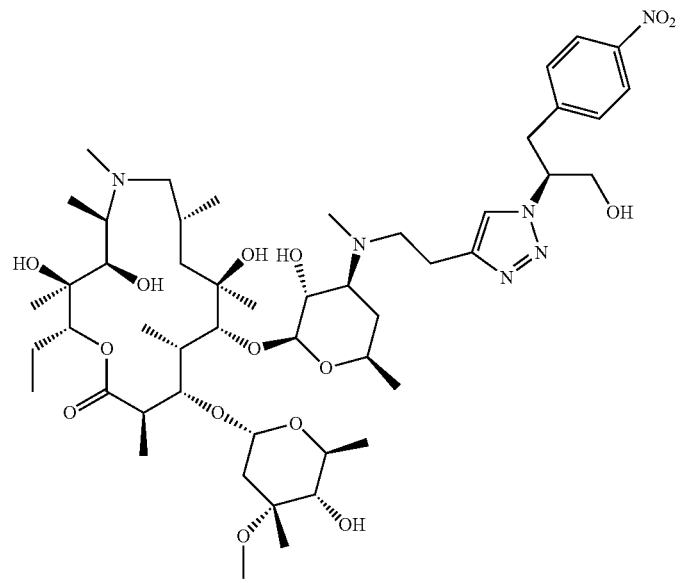 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CO)Cc4ccc([N+](=O)[O-])cc4)nn3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 169 | 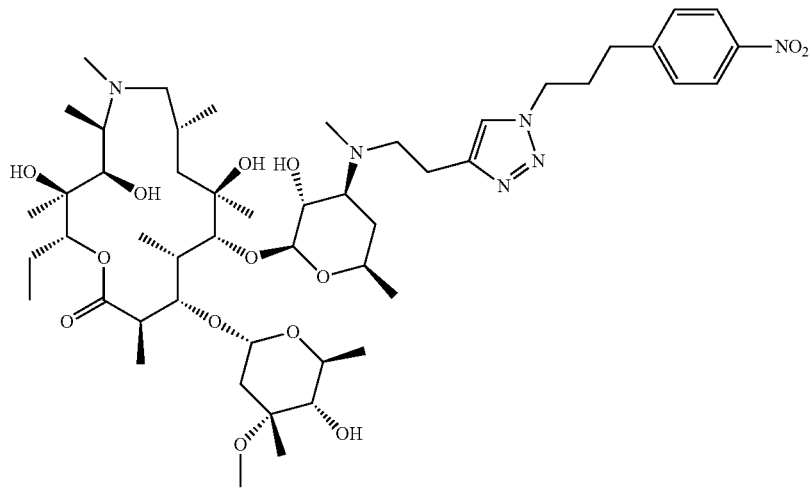 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCc4ccc([N+](=O)[O-])cc4)nn3)[C@H]2O)[C@](C)(O)C[C@@H](C)CN(C)[C@H](C)[C@@H](O)[C@]1(C)O] |
| 170 | 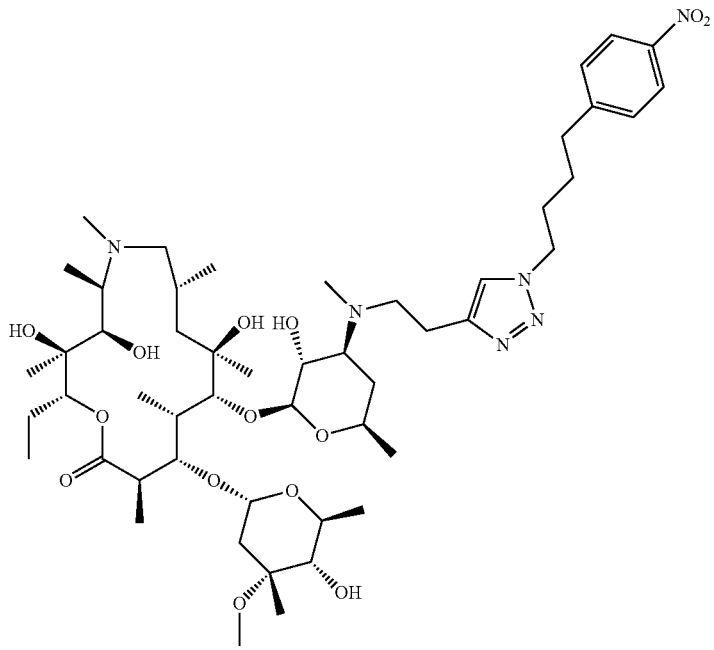 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc([N+](=O)[O-])cc4)nn3)[C@H]2O)[C@](C)(O)C[C@@H](C)CN(C)[C@H](C)[C@@H](O)[C@]1(C)O] |

TABLE 1-continued

| Compound Number | Structure |
|---|---|
| 171 | 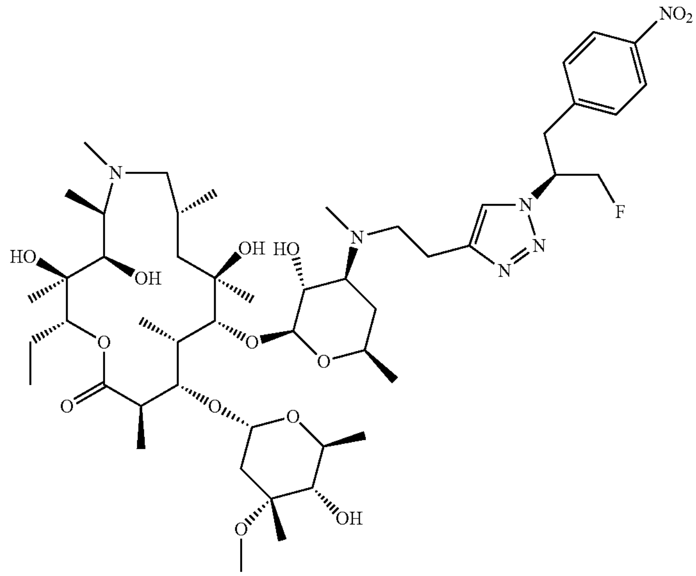 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CF)Cc4ccc([N+](=O)[O-])cc4)nn3)[C@H]2O)[C@](C)(O)C[C@@H](C)CN(C)[C@H](C)[C@@H](O)[C@]1(C)O] |
| 172 | 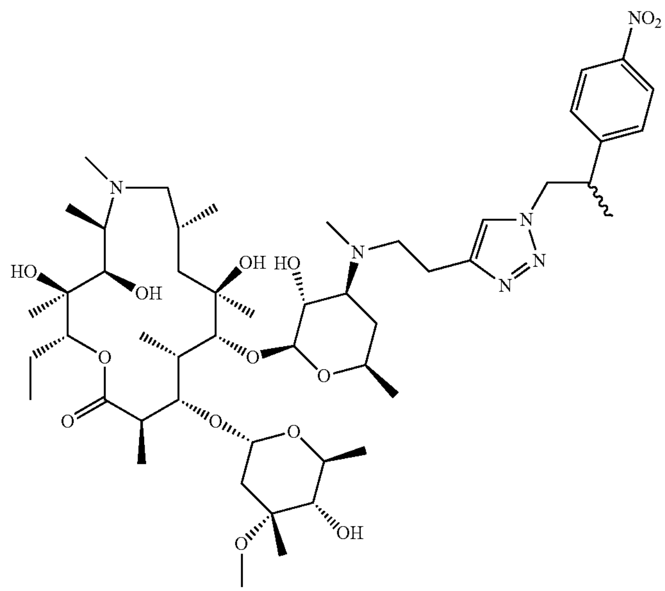 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CC(C)c4ccc([N+](=O)[O-])cc4)nn3)[C@H]2O)[C@](C)(O)C[C@@H](C)CN(C)[C@H](C)[C@@H](O)[C@]1(C)O] |
| 173 | 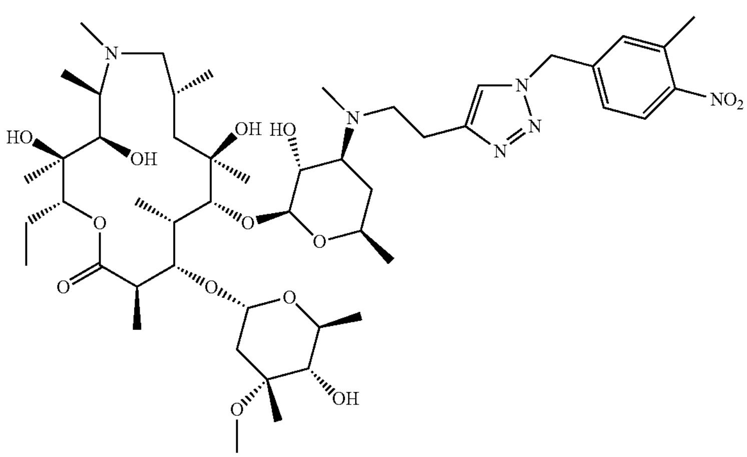 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc([N+](=O)[O-])c(C)c4)nn3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 174 | 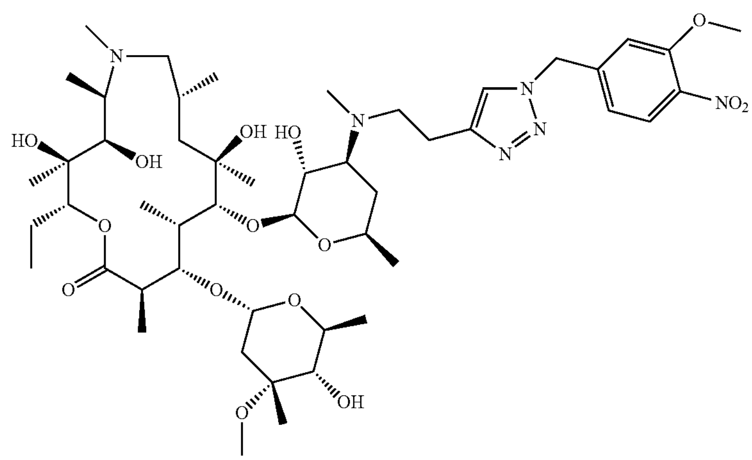 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc([N+](=O)[O-])c(OC)c4)nn3)[C@H]2O)[C@](C)(O)C[C@@H](C)CN(C)[C@H](C)[C@@H](O)[C@]1(C)O] |
| 175 | 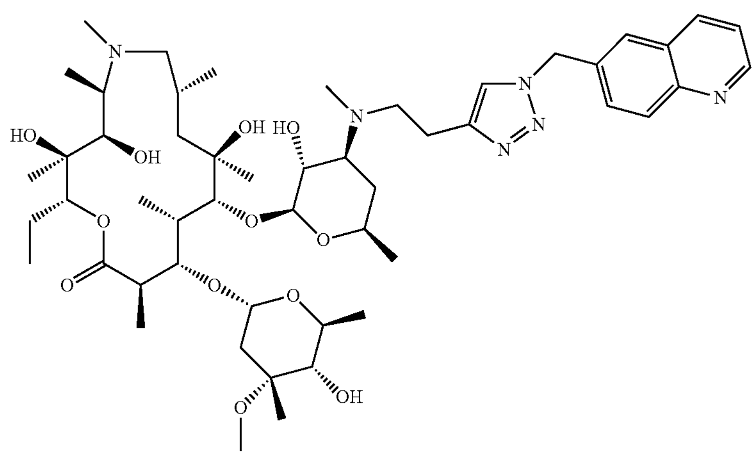 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc5ncccc5c4)nn3)[C@H]2O)[C@](C)(O)C[C@@H](C)CN(C)[C@H](C)[C@@H](O)[C@]1(C)O] |
| 176 | 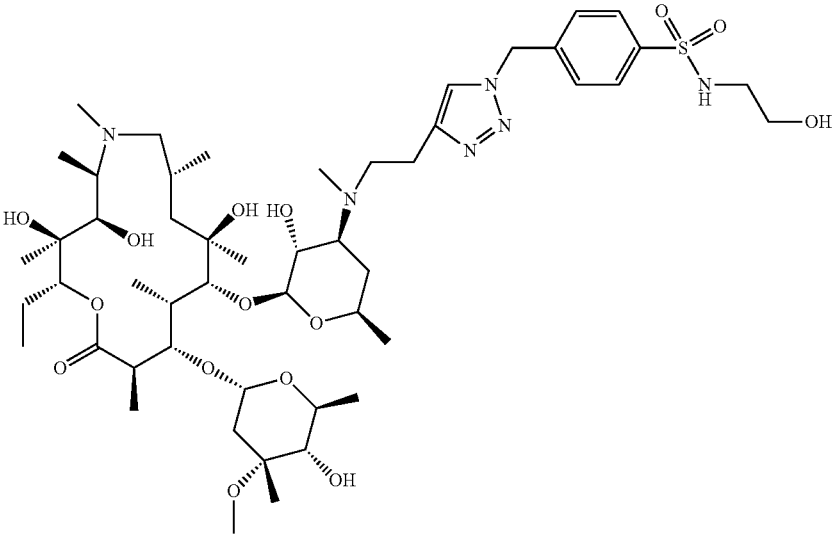 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc(S(=O)(=O)NCCO)cc4)nn3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 177 | 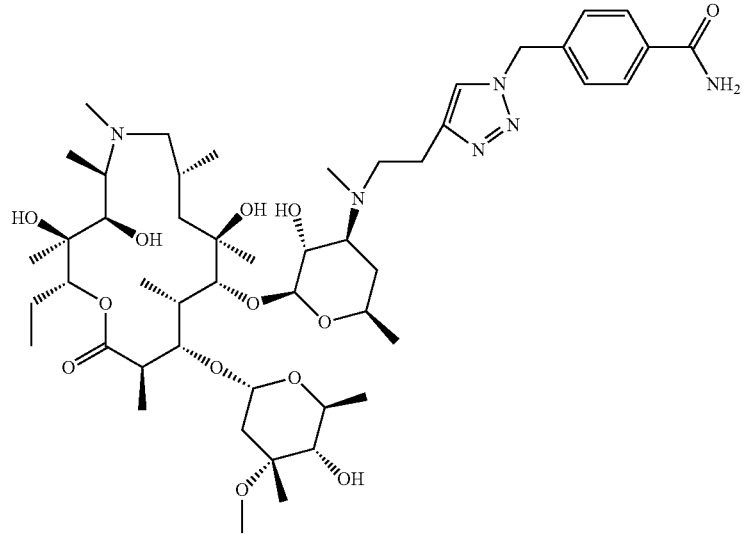 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc(C(N)=O)cc4)nn3)[C@H]2O)[C@](C)(O)C[C@@H](C)CN(C)[C@H](C)[C@@H](O)[C@]1(C)O] |
| 178 | 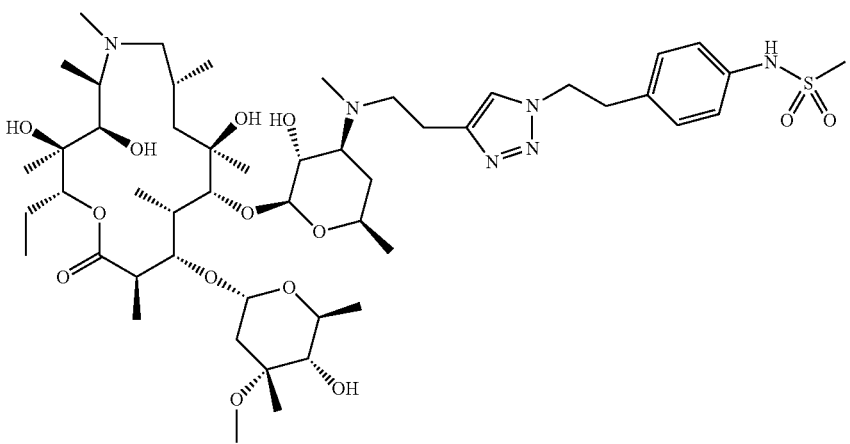 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc(NS(C)(=O)=O)cc4)nn3)[C@H]2O)[C@](C)(O)C[C@@H](C)CN(C)[C@H](C)[C@@H](O)[C@]1(C)O] |
| 179 | 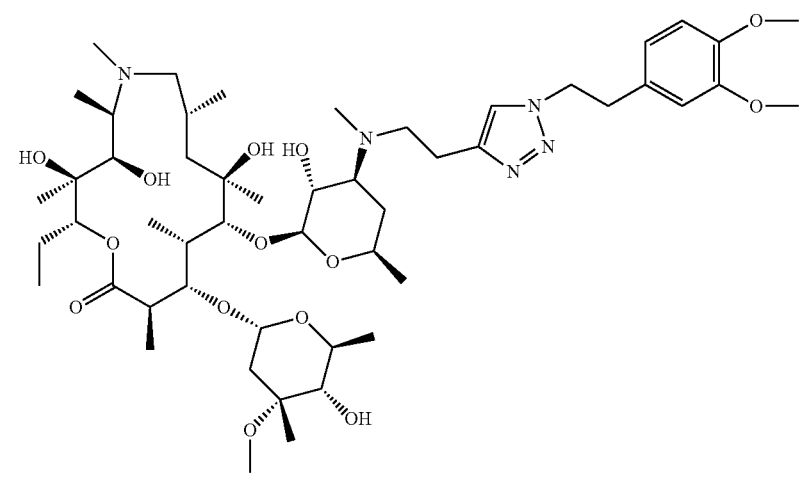 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc(OC)c(OC)c4)nn3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 180 | 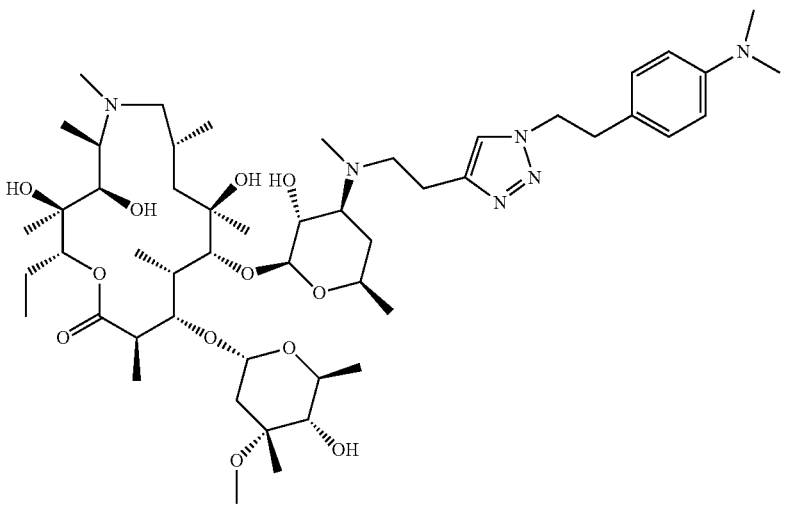 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc(N(C)C)cc4)nn3)[C@H]2O)[C@](C)(O)C[C@@H](C)CN(C)[C@H](C)[C@@H](O)[C@]1(C)O] |
| 181 | 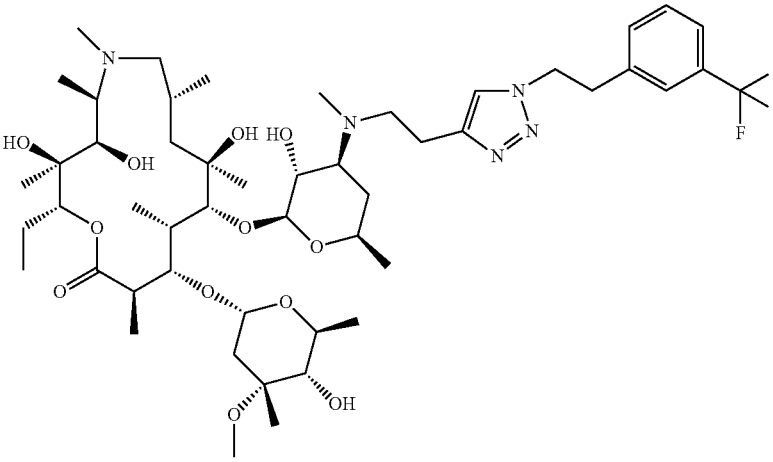 |
| 182 | 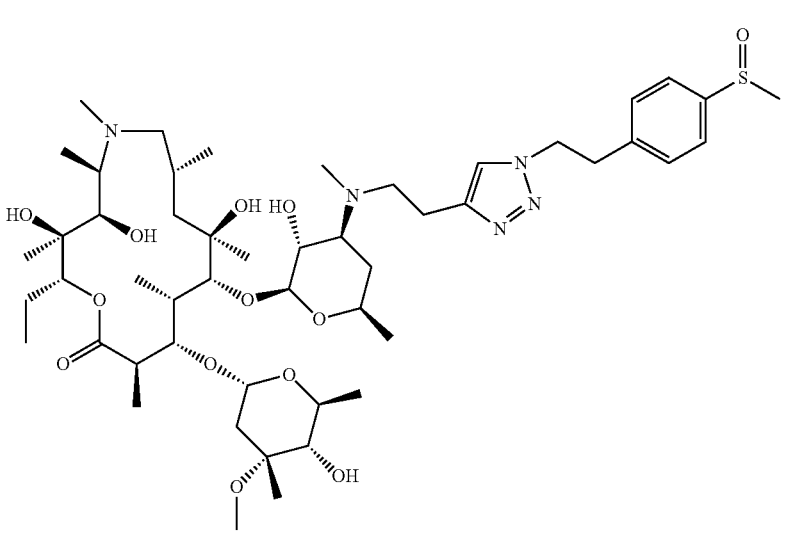 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc(S(C)=O)cc4)nn3)[C@H]2O)[C@](C)(O)C[C@@H](C)CN(C)[C@H](C)[C@@H](O)[C@]1(C)O] |

TABLE 1-continued

| Compound Number | Structure |
| --- | --- |
| 183 | 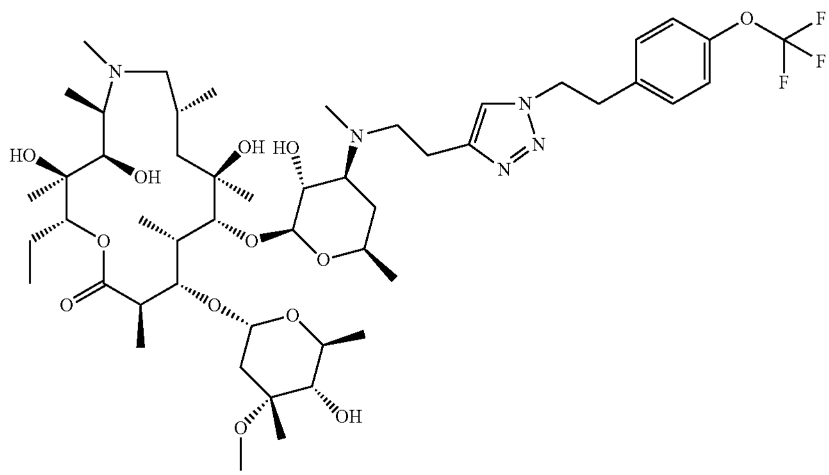 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc(OC(F)(F)F)cc4)nn3)[C@H]2O)[C@](C)(O)C[C@@H](C)CN(C)[C@H](C)[C@@H](O)[C@]1(C)O] |
| 184 | 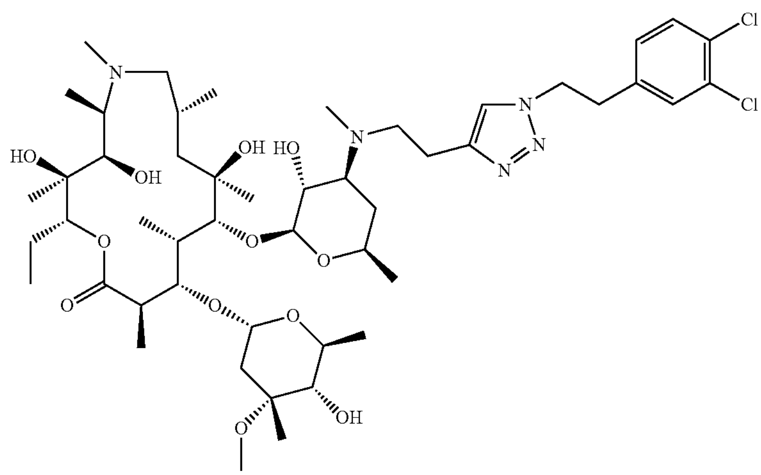 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc(Cl)c(Cl)c4)nn3)[C@H]2O)[C@](C)(O)C[C@@H](C)CN(C)[C@H](C)[C@@H](O)[C@]1(C)O] |
| 185 | 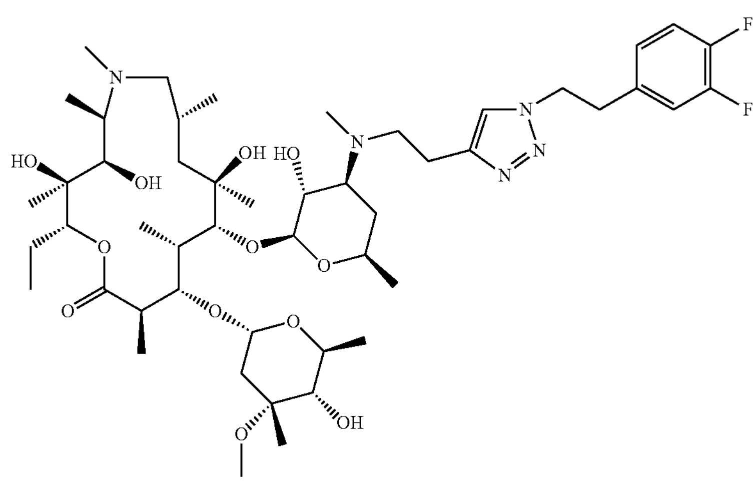 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc(F)c(F)c4)nn3)[C@H]2O)[C@](C)(O)C[C@@H](C)CN(C)[C@H](C)[C@@H](O)[C@]1(C)O] |

| Compound Number | Structure |
|---|---|
| 186 | 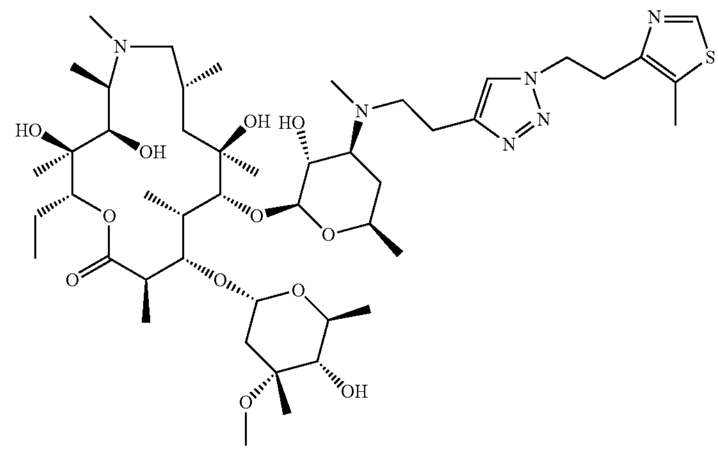 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ncsc4C)nn3)[C@H]2O)[C@](C)(O)C[C@@H](C)CN(C)[C@H](C)[C@@H](O)[C@]1(C)O] |
| 187 | 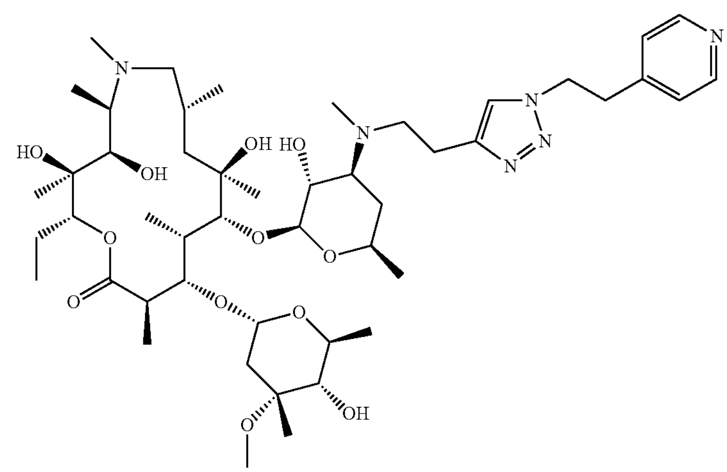 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccncc4)nn3)[C@H]2O)[C@](C)(O)C[C@@H](C)CN(C)[C@H](C)[C@@H](O)[C@]1(C)O] |
| 188 | 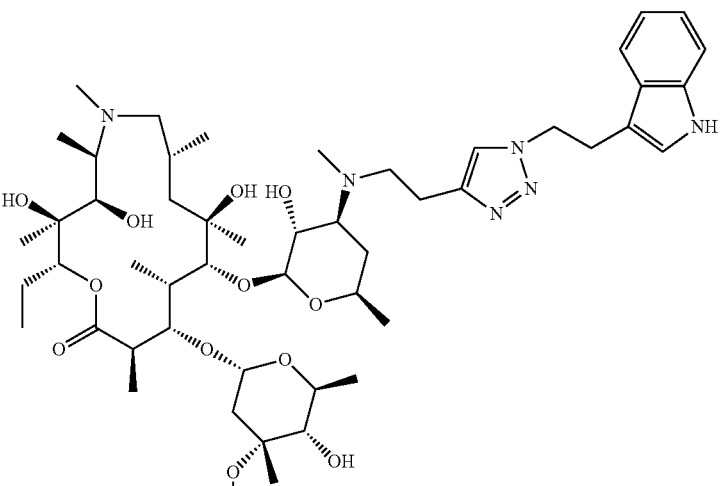 |

TABLE 1-continued

| Compound Number | Structure |
| --- | --- |
| 189 | 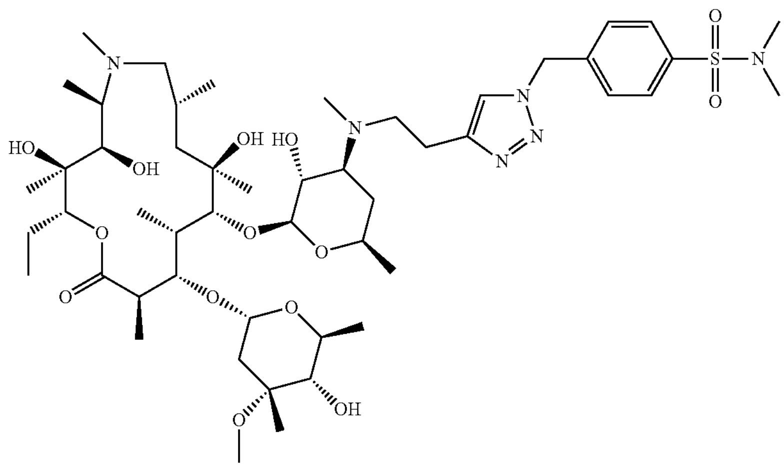 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc(S(=O)(=O)N(C)C)cc4)nn3)[C@H]2O)[C@](C)(O)C[C@@H](C)CN(C)[C@H](C)[C@@H](O)[C@]1(C)O] |
| 190 | 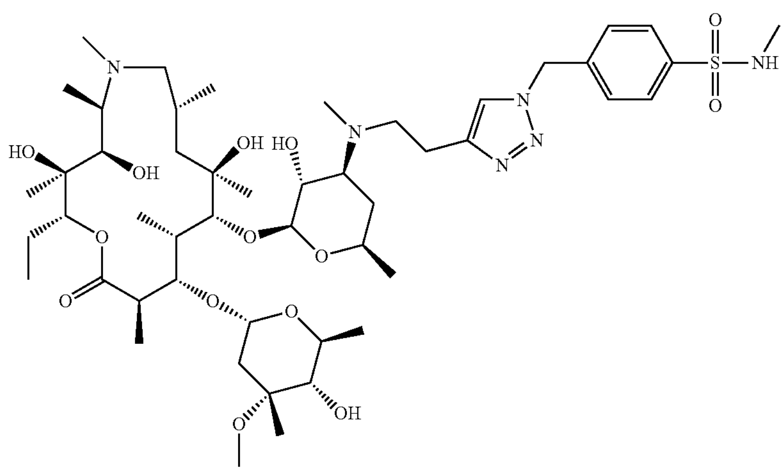 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc(S(=O)(=O)NC)cc4)nn3)[C@H]2O)[C@](C)(O)C[C@@H](C)CN(C)[C@H](C)[C@@H](O)[C@]1(C)O] |
| 191 | 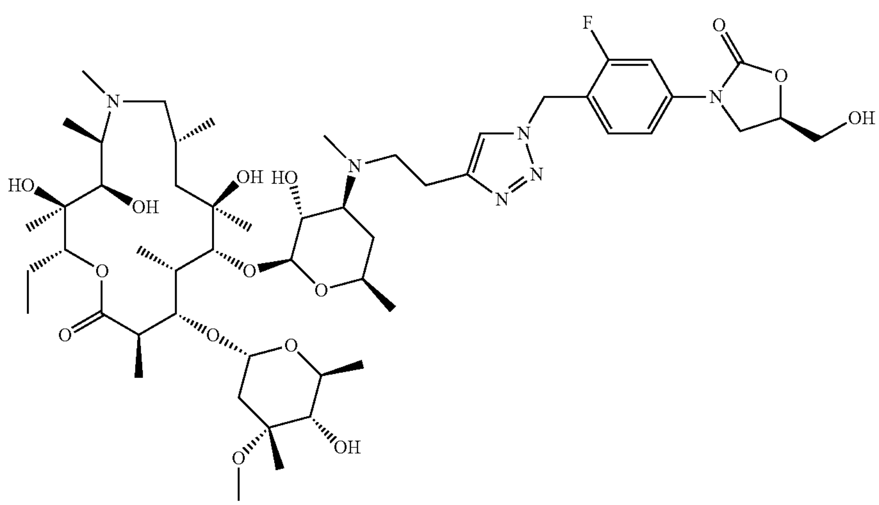 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc(N5C[C@H](CO)OC5=O)cc4F)nn3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 192 | 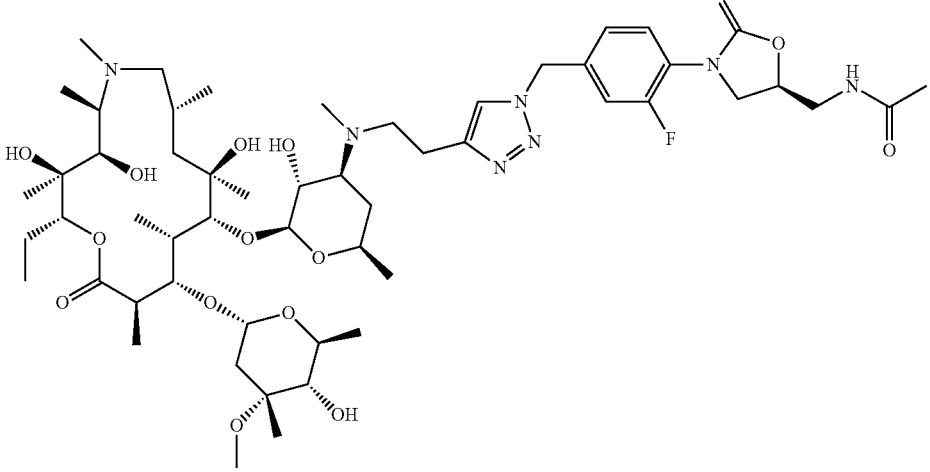 |
| 193 | 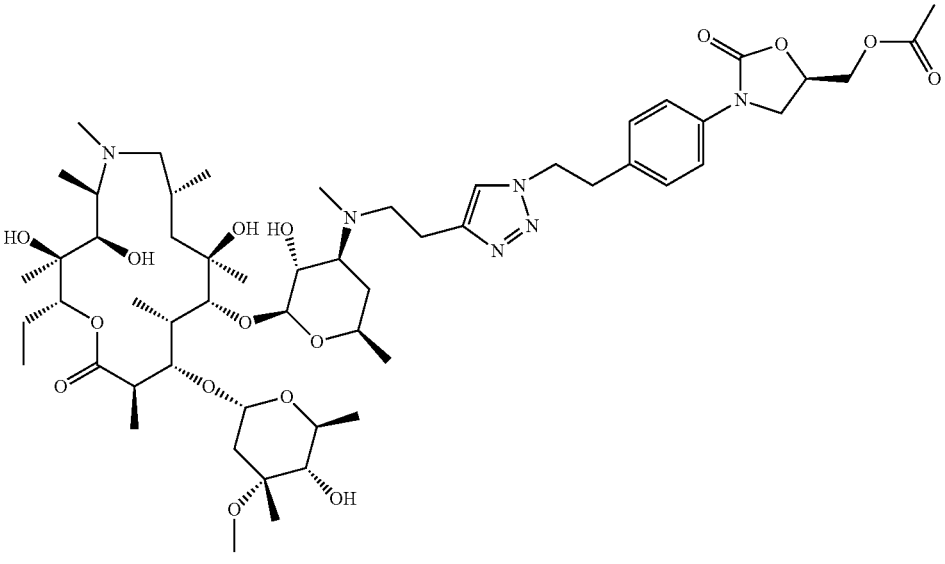 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc(N5C[C@H](COC(C)=O)OC5=O)cc4)nn3)[C@H]2O)[C@](C)(O)C[C@@H](C)CN(C)[C@H](C)[C@@H](O)[C@]1(C)O] |
| 194 | 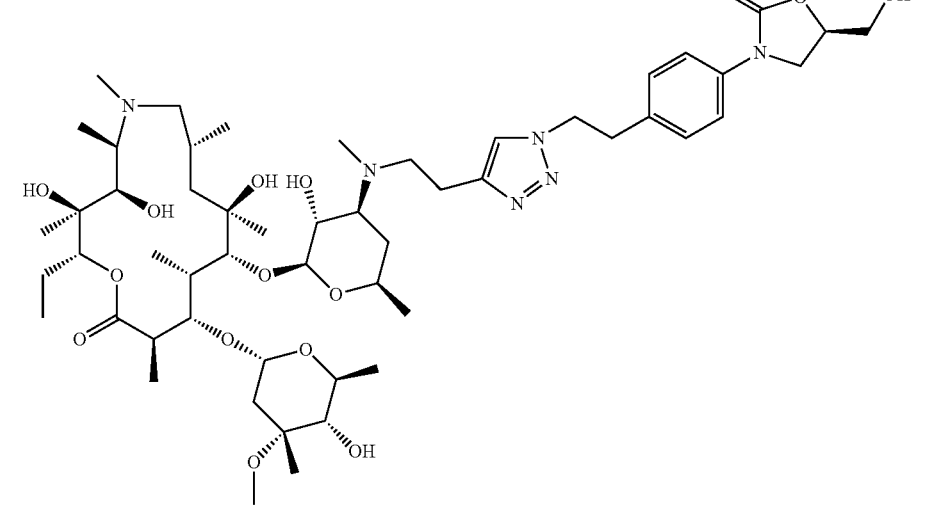 |

TABLE 1-continued

| Compound Number | Structure |
| --- | --- |
| 195 | 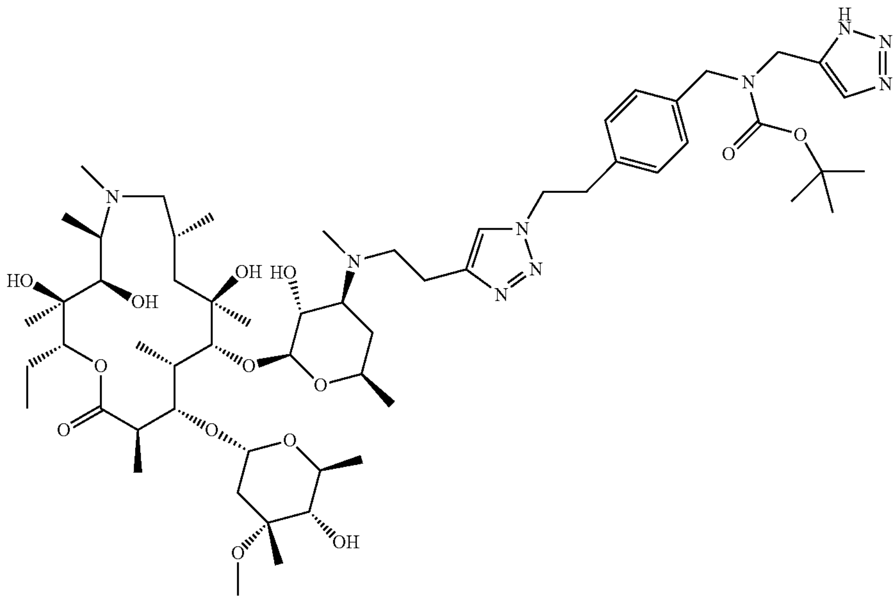 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc(CN(Cc5cnn[nH]5)C(=O)OC(C)(C)C)cc4)nn3)[C@H]2O)[C@](C)(O)C[C@@H](C)CN(C)[C@H](C)[C@@H](O)[C@]1(C)O] |
| 196 | 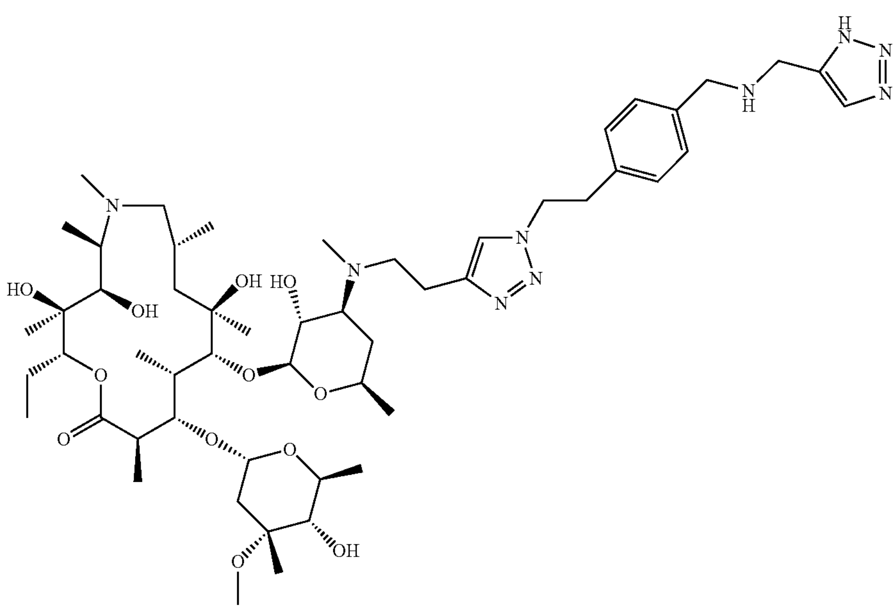 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc(CNCc5cnn[nH]5)cc4)nn3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 197 | 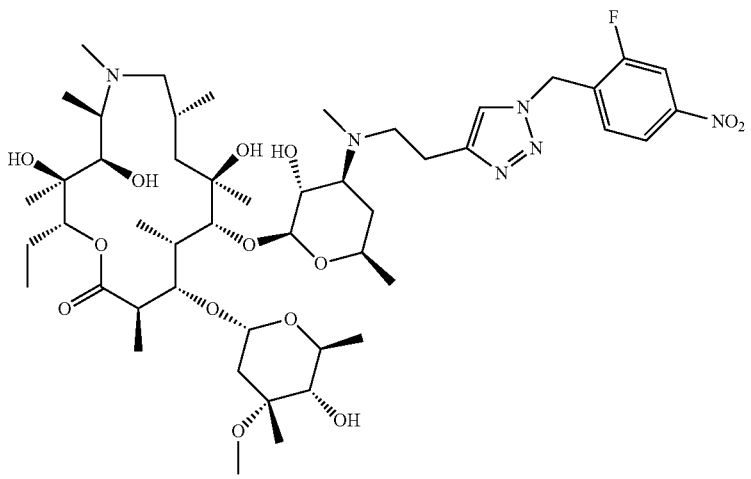 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc([N+](=O)[O-])cc4F)nn3)[C@H]2O)[C@](C)(O)C[C@@H](C)CN(C)[C@H](C)[C@@H](O)[C@]1(C)O] |
| 198 | 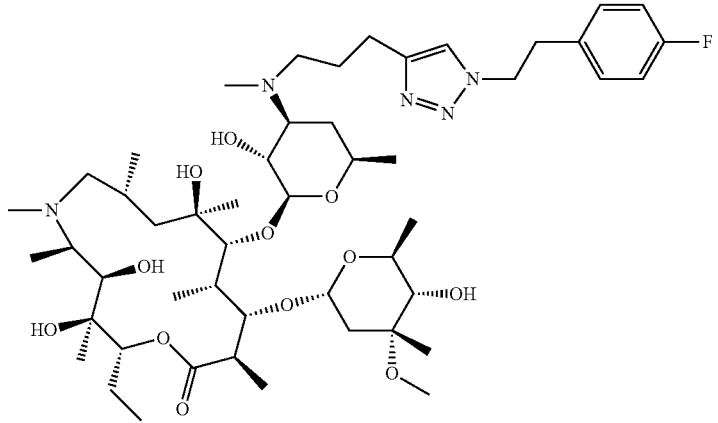 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCc3cn(CCc4ccc(F)cc4)nn3)[C@H]2O)[C@](C)(O)C[C@@H](C)CN(C)[C@H](C)[C@@H](O)[C@]1(C)O] |
| 199 | 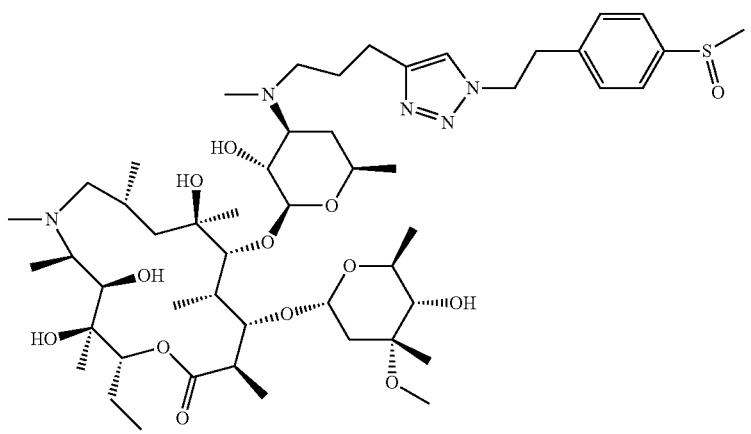 |

TABLE 1-continued

| Compound Number | Structure |
|---|---|
| 200 | 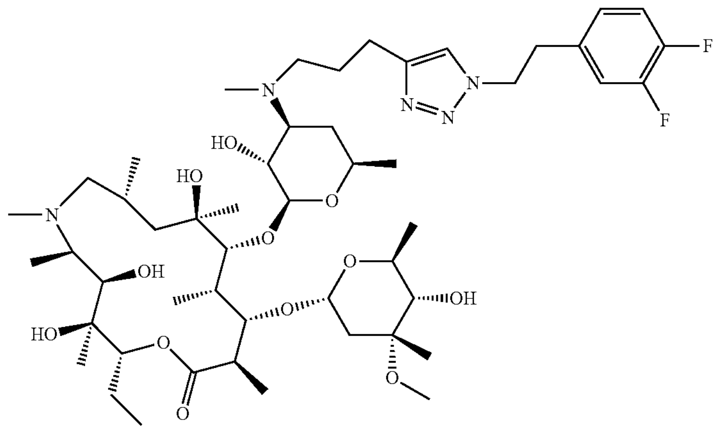 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCc3cn(CCc4ccc(F)c(F)c4)nn3)[C@H]2O)[C@](C)(O)C[C@@H](C)CN(C)[C@H](C)[C@@H](O)[C@]1(C)O] |
| 201 | 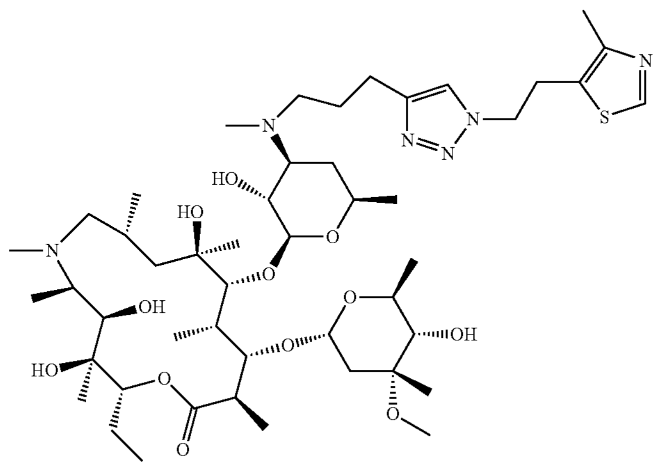 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCc3cn(CCc4scnc4C)nn3)[C@H]2O)[C@](C)(O)C[C@@H](C)CN(C)[C@H](C)[C@@H](O)[C@]1(C)O] |
| 202 | 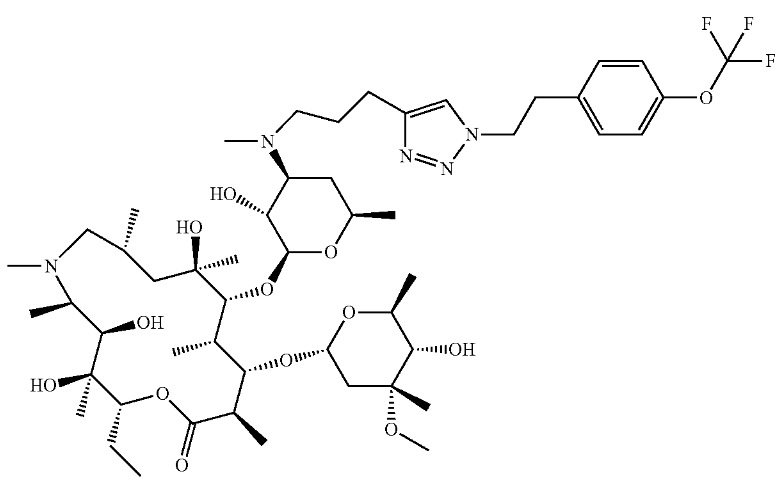 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCc3cn(CCc4ccc(OC(F)(F)F)cc4)nn3)[C@H]2O)[C@](C)(O)C[C@@H](C)CN(C)[C@H](C)[C@@H](O)[C@]1(C)O] |

TABLE 1-continued

| Compound Number | Structure |
|---|---|
| 203 | 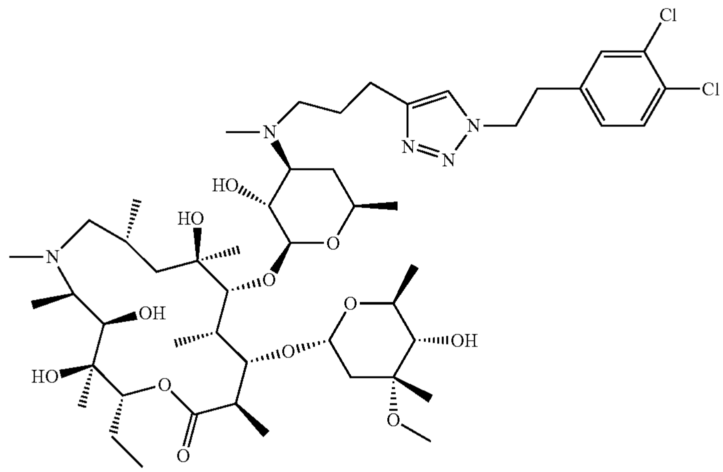 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCc3cn(CCc4ccc(Cl)c(Cl)c4)nn3)[C@H]2O)[C@](C)(O)C[C@@H](C)CN(C)[C@H](C)[C@@H](O)[C@]1(C)O] |
| 204 | 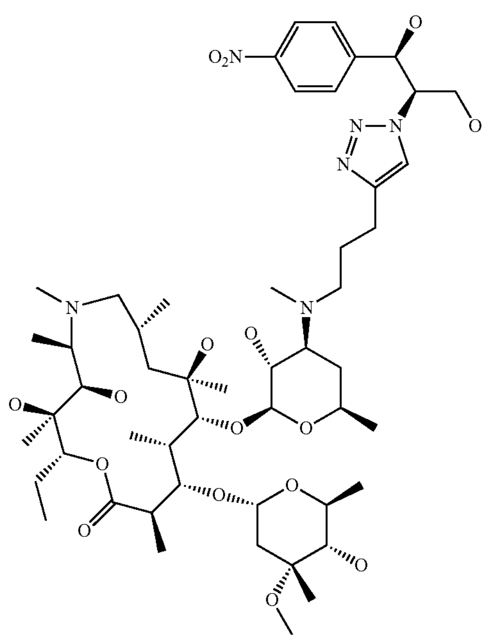 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCc3cn([C@H](CO)[C@H](O)c4ccc([N+](=O)[O-])cc4)nn3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 205 | 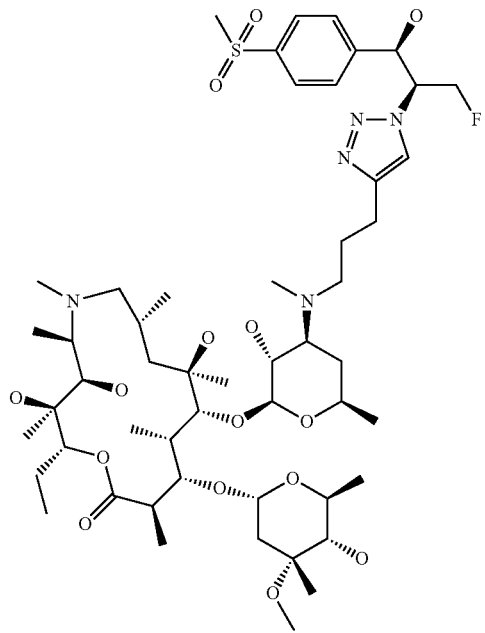 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCc3cn([C@H](CF)[C@H](O)c4ccc(S(C)(=O)=O)cc4)nn3)[C@H]2O)[C@](C)(O)C[C@@H](C)CN(C)[C@H](C)[C@@H](O)[C@]1(C)O] |
| 206 | 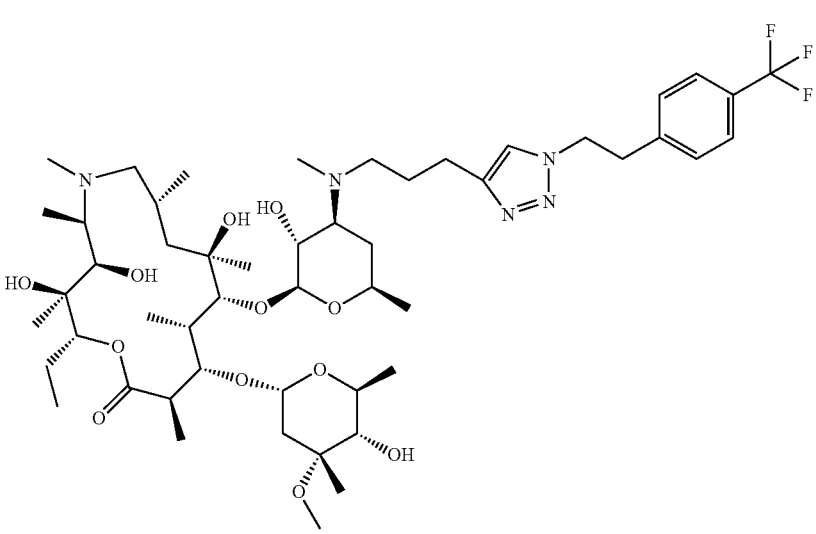 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCc3cn(CCc4ccc(C(F)(F)F)cc4)nn3)[C@H]2O)[C@](C)(O)C[C@@H](C)CN(C)[C@H](C)[C@@H](O)[C@]1(C)O] |

TABLE 1-continued

| Compound Number | Structure |
| --- | --- |
| 207 | 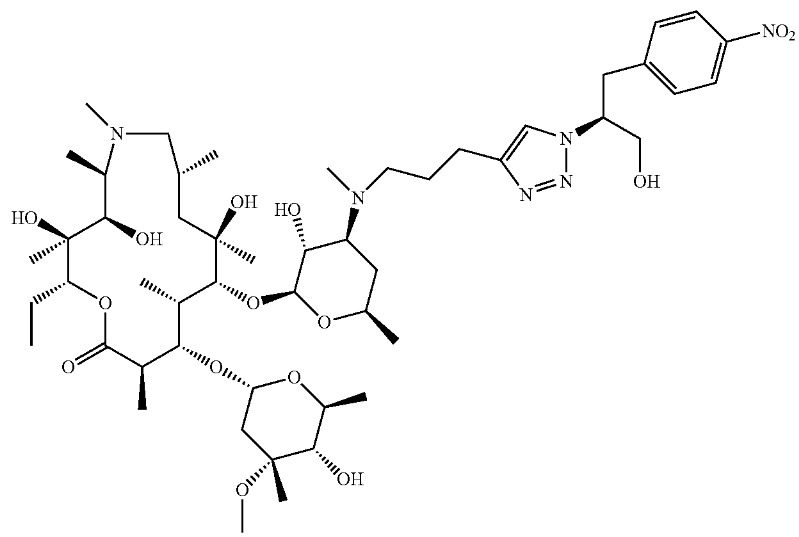 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCc3cn([C@H](CO)Cc4ccc([N+](=O)[O-])cc4)nn3)[C@H]2O)[C@](C)(O)C[C@@H](C)CN(C)[C@H](C)[C@@H](O)[C@]1(C)O] |
| 208 | 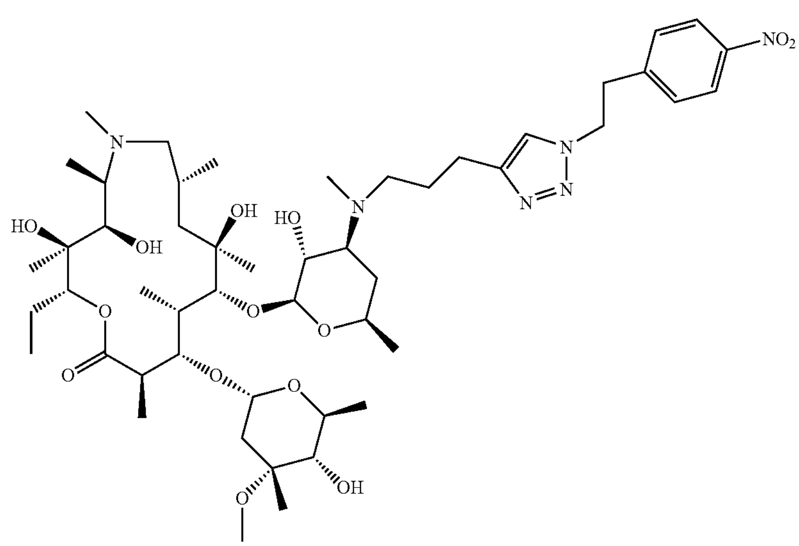 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCc3cn(CCc4ccc([N+](=O)[O-])cc4)nn3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 209 | 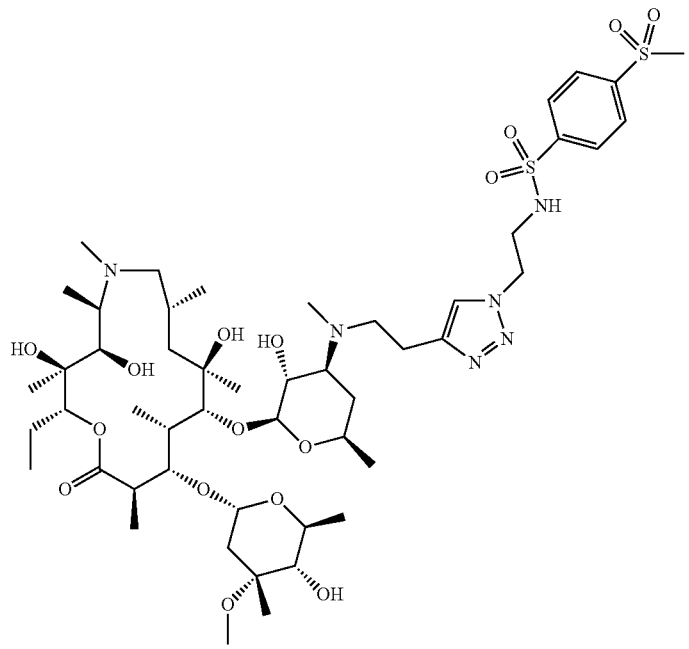 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCNS(=O)(=O)c4ccc(S(C)(=O)=O)cc4)nn3)[C@H]2O)[C@](C)(O)C[C@@H](C)CN(C)[C@H](C)[C@@H](O)[C@]1(C)O] |
| 210 | 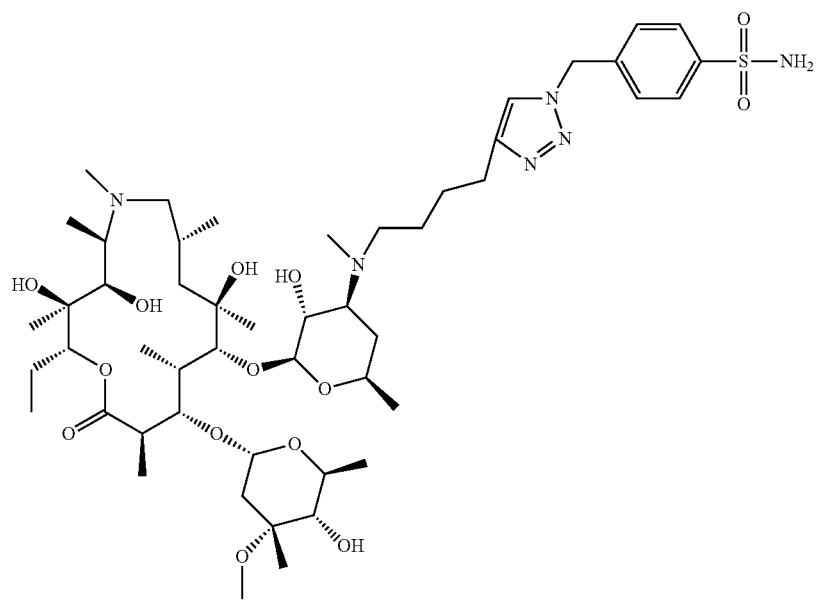 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCCc3cn(Cc4ccc(S(N)(=O)=O)cc4)nn3)[C@H]2O)[C@](C)(O)C[C@@H](C)CN(C)[C@H](C)[C@@H](O)[C@]1(C)O] |

TABLE 1-continued

| Compound Number | Structure |
|---|---|
| 211 | 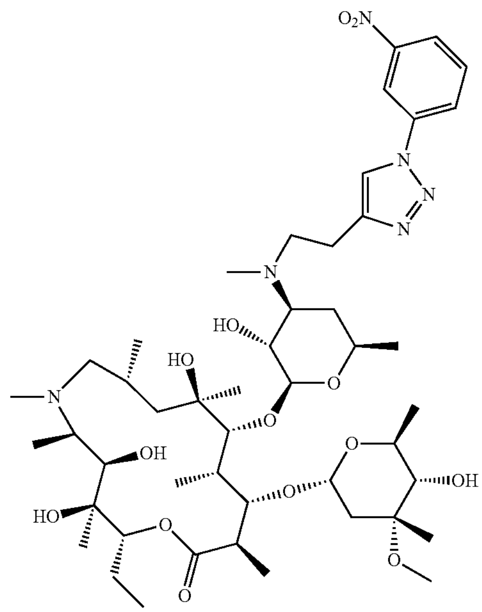 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(-c4cccc([N+](=O)[O-])c4)nn3)[C@H]2O)[C@](C)(O)C[C@@H](C)CN(C)[C@H](C)[C@@H](O)[C@]1(C)O] |
| 212 | 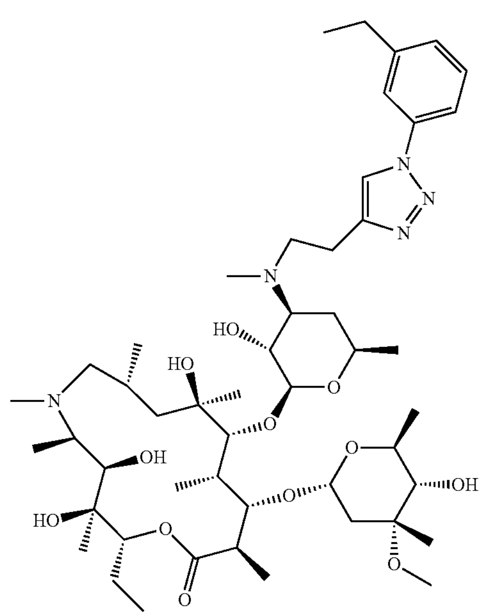 [SMILES: CCc1cccc(-n2cc(CCN(C)[C@H]3C[C@@H](C)O[C@@H](O[C@@H]4[C@@H](C)[C@H](O[C@H]5C[C@@](C)(OC)[C@@H](O)[C@H](C)O5)[C@@H](C)C(=O)O[C@H](CC)[C@@](C)(O)[C@H](O)[C@@H](C)N(C)C[C@H](C)C[C@@]4(C)O)[C@@H]3O)nn2)c1] |

TABLE 1-continued

| Compound Number | Structure |
|---|---|
| 213 | 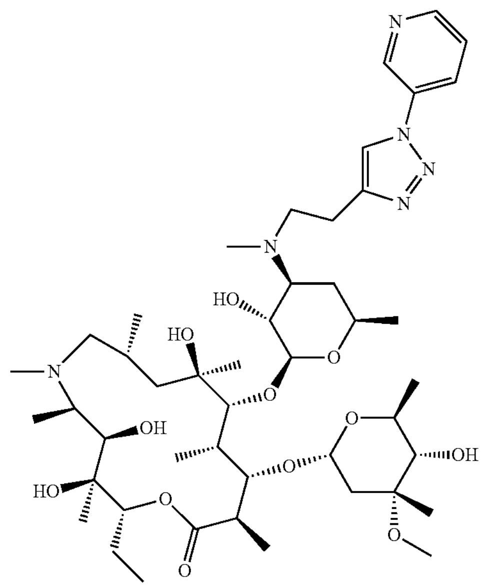 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(-c4cccnc4)nn3)[C@H]2O)[C@](C)(O)C[C@@H](C)CN(C)[C@H](C)[C@@H](O)[C@]1(C)O] |
| 214 | 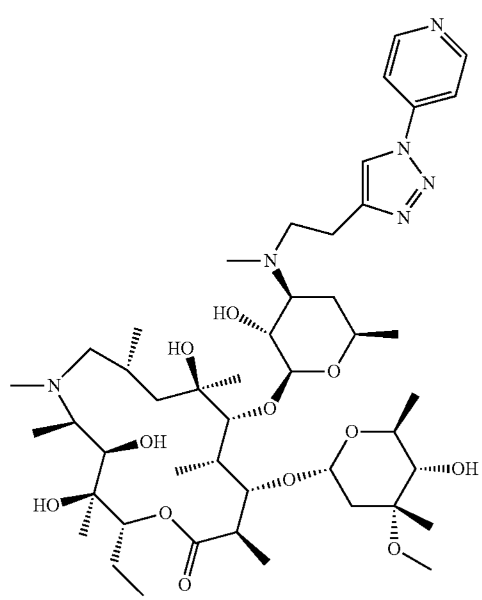 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(-c4ccncc4)nn3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 215 | 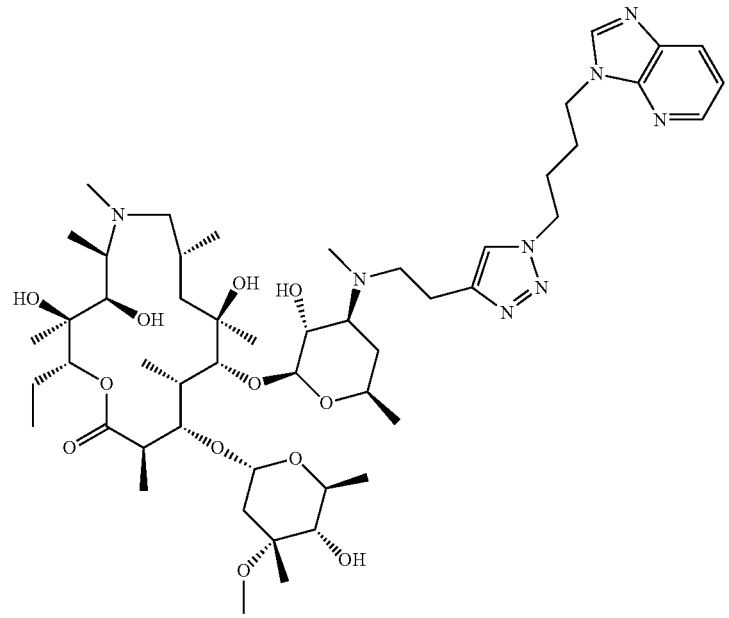 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCn4cnc5cccnc54)nn3)[C@H]2O)[C@](C)(O)C[C@@H](C)CN(C)[C@H](C)[C@@H](O)[C@]1(C)O] |
| 216 | 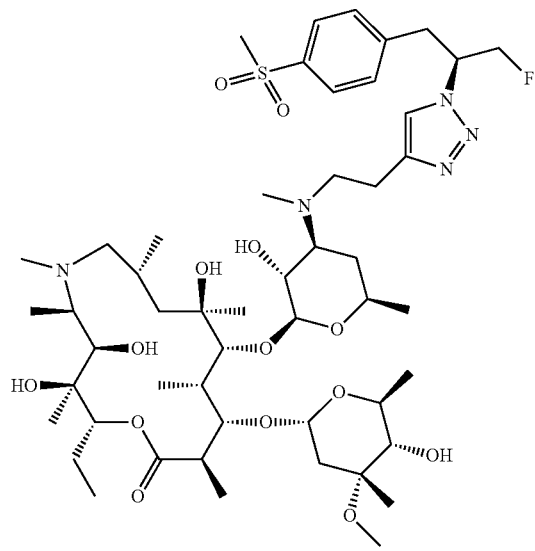 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CF)Cc4ccc(S(C)(=O)=O)cc4)nn3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 217 | 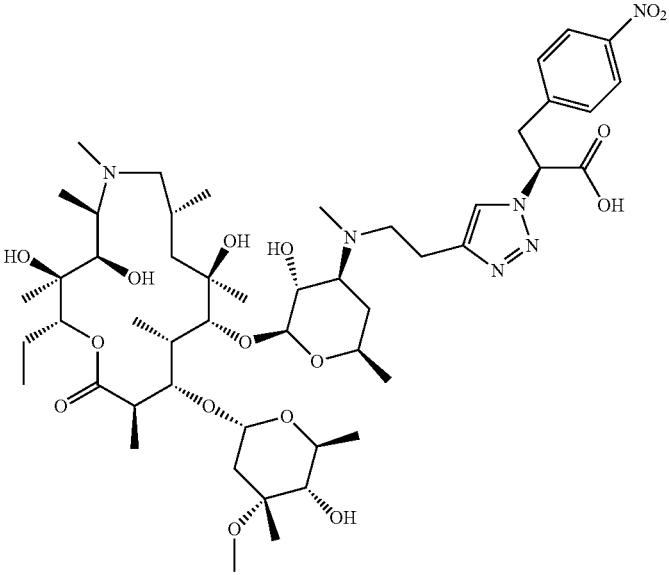 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@@H](Cc4ccc([N+](=O)[O-])cc4)C(=O)O)nn3)[C@H]2O)[C@](C)(O)C[C@@H](C)CN(C)[C@H](C)[C@@H](O)[C@]1(C)O] |
| 218 | 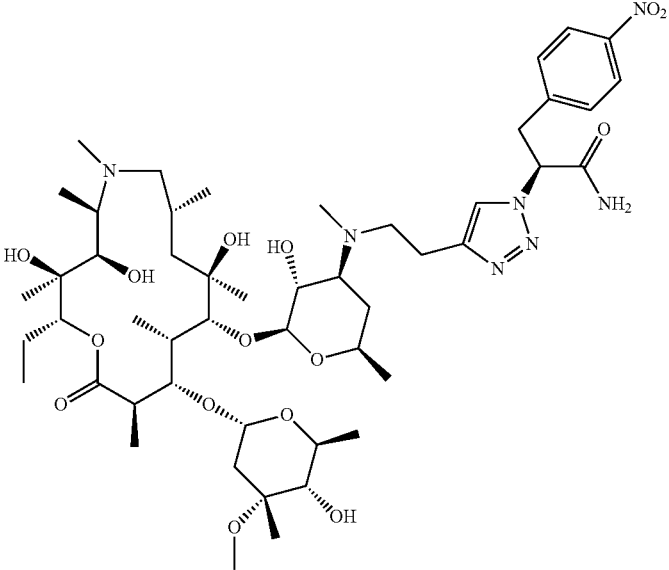 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@@H](Cc4ccc([N+](=O)[O-])cc4)C(N)=O)nn3)[C@H]2O)[C@](C)(O)C[C@@H](C)CN(C)[C@H](C)[C@@H](O)[C@]1(C)O] |

US 8,841,263 B2
TABLE 1-continued
| Compound Number | Structure |
|---|---|
| 219 | 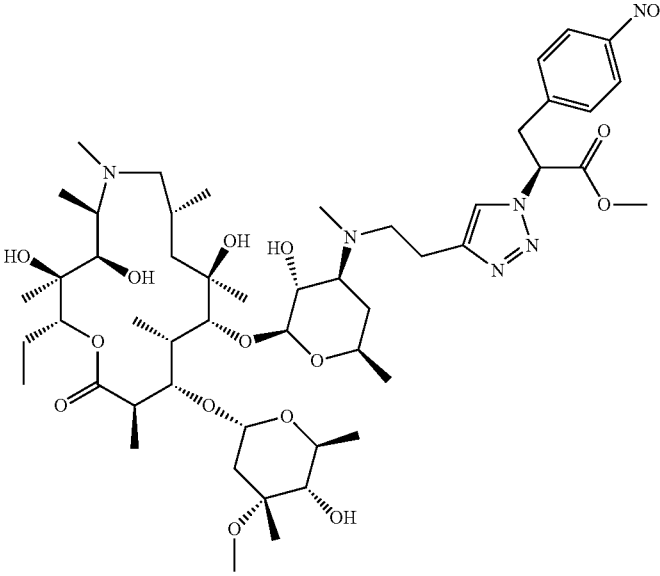 |
| 220 | 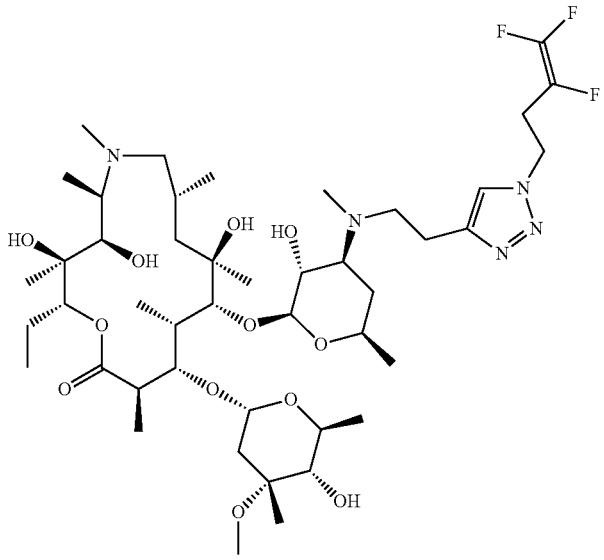 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCC(F)=C(F)F)nn3)[C@H]2O)[C@](C)(O)C[C@@H](C)CN(C)[C@H](C)[C@@H](O)[C@]1(C)O] |
| 221 | 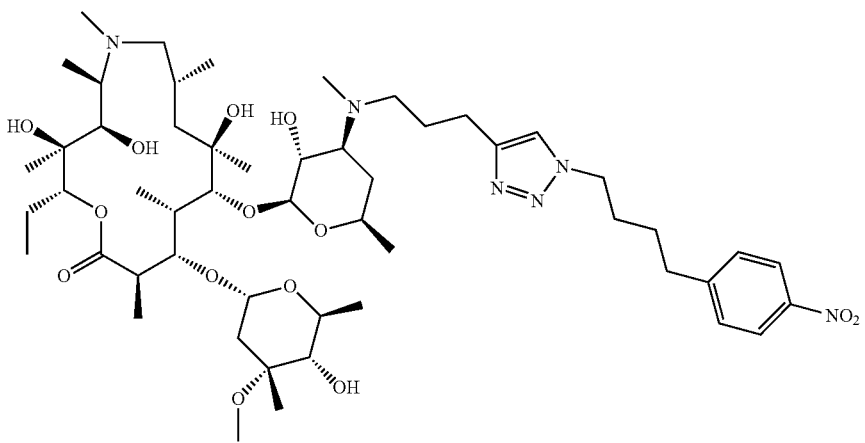 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCc3cn(CCCCc4ccc([N+](=O)[O-])cc4)nn3)[C@H]2O)[C@](C)(O)C[C@@H](C)CN(C)[C@H](C)[C@@H](O)[C@]1(C)O] |

US 8,841,263 B2
161                                                                                          162
TABLE 1-continued
| Compound Number | Structure |
|---|---|
| 222 | 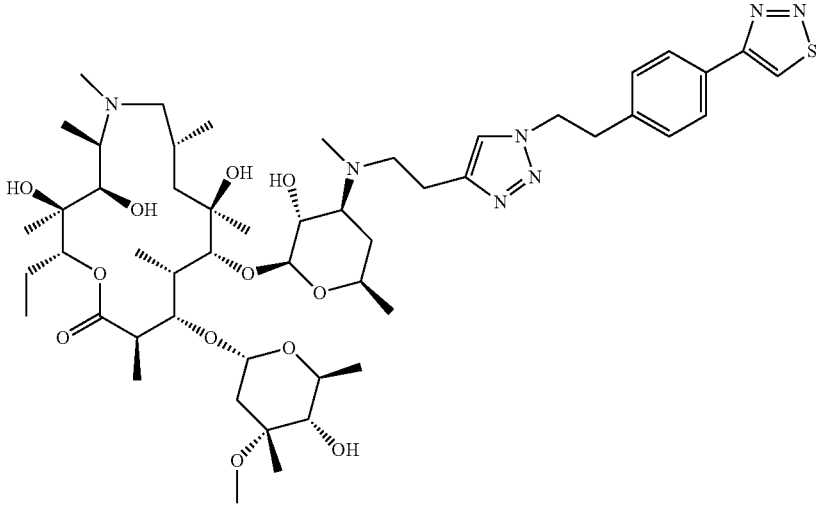 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc(-c5csnn5)cc4)nn3)[C@H]2O)[C@](C)(O)C[C@@H](C)CN(C)[C@H](C)[C@@H](O)[C@]1(C)O] |
| 223 | 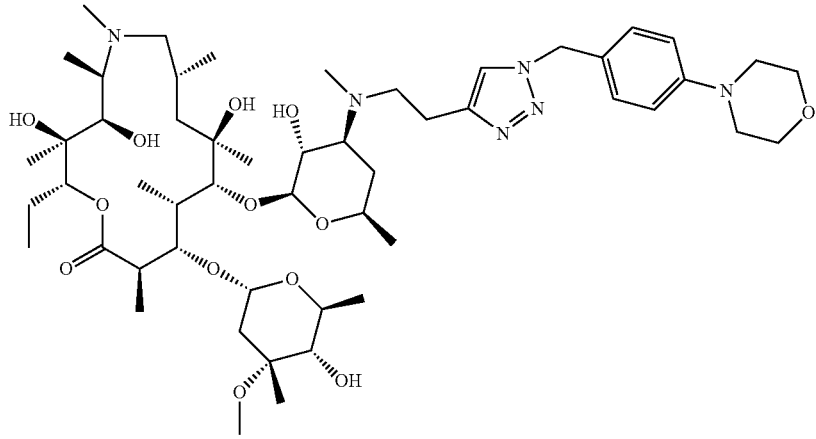 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc(N5CCOCC5)cc4)nn3)[C@H]2O)[C@](C)(O)C[C@@H](C)CN(C)[C@H](C)[C@@H](O)[C@]1(C)O] |
| 224 | 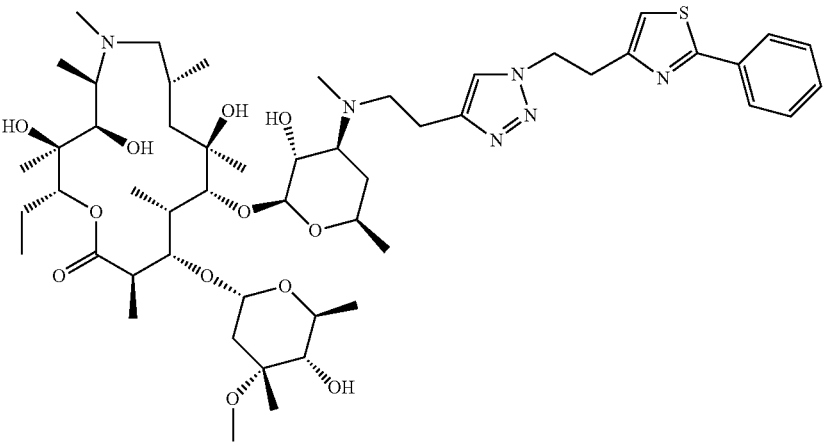 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4csc(-c5ccccc5)n4)nn3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 225 | 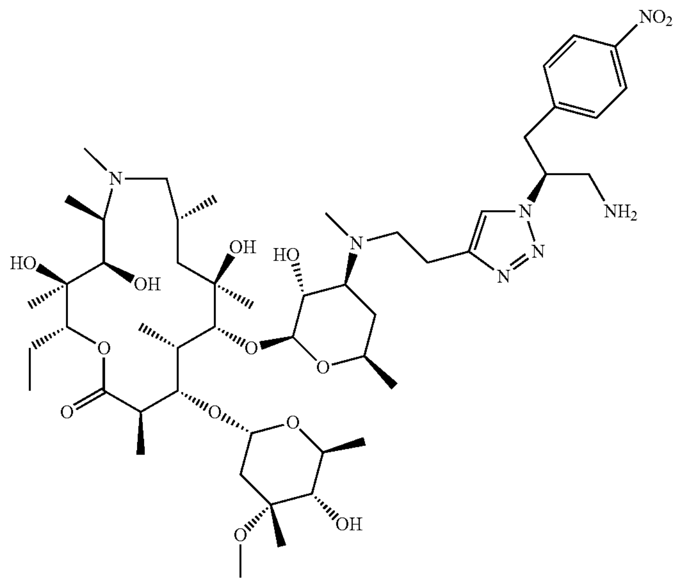 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CN)Cc4ccc([N+](=O)[O-])cc4)nn3)[C@H]2O)[C@](C)(O)C[C@@H](C)CN(C)[C@H](C)[C@@H](O)[C@]1(C)O] |
| 226 | 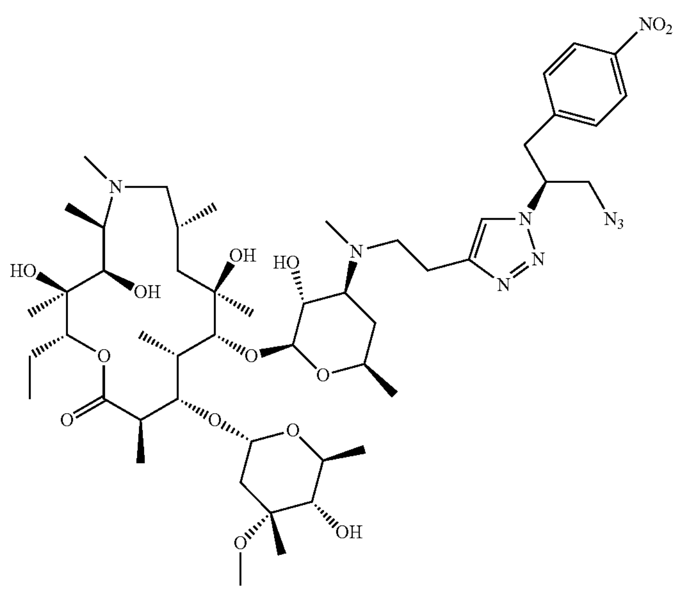 |

TABLE 1-continued
| Compound Number | Structure |
|---|---|
| 227 | 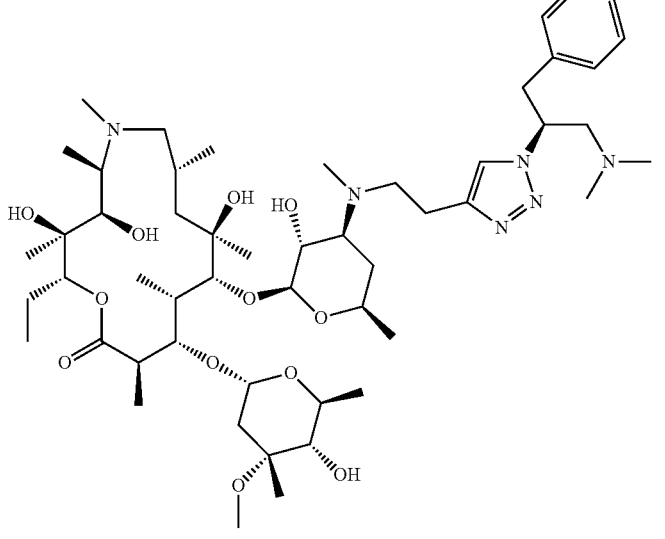 |
| 228 | 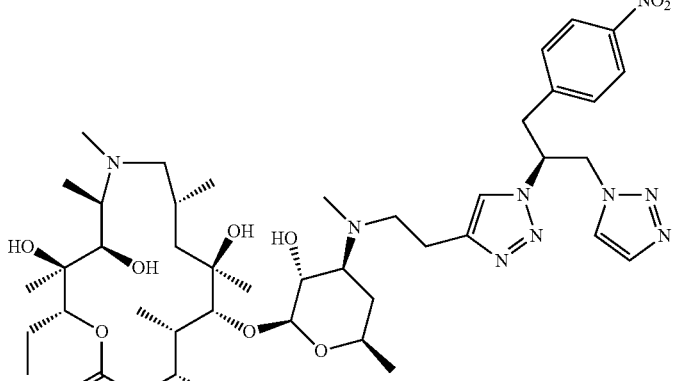 |

TABLE 1-continued
| Compound Number | Structure |
|---|---|
| 229 | 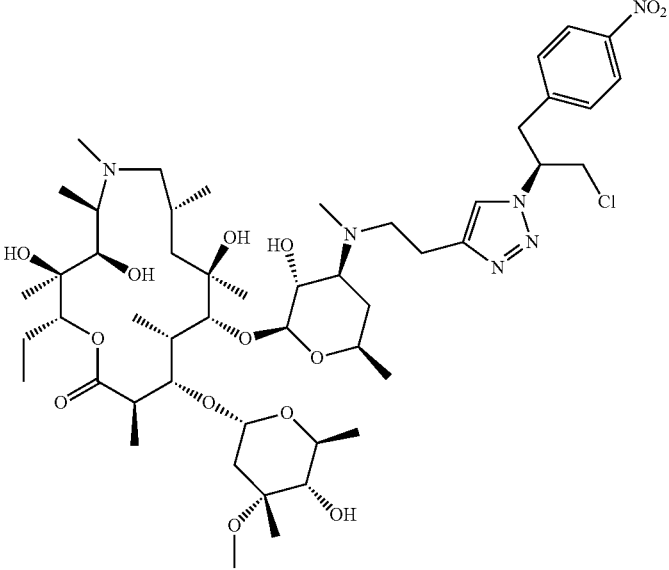 |
| 230 | 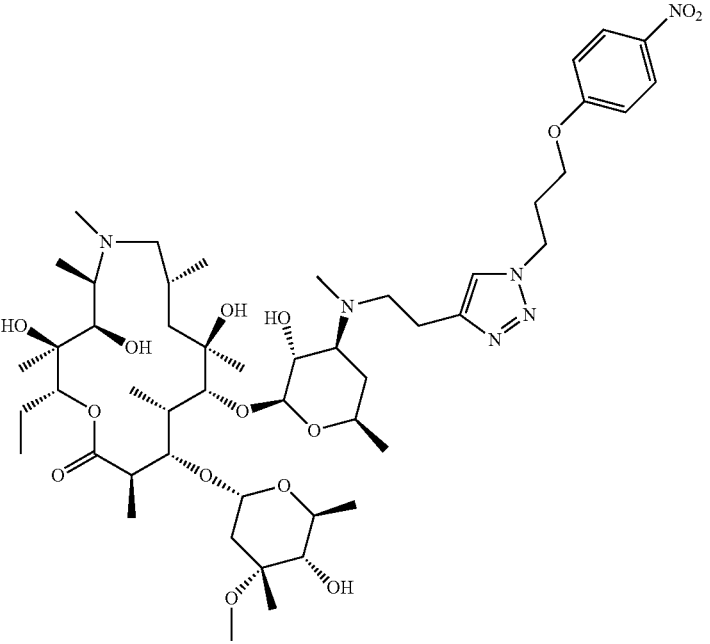 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc([N+](=O)[O-])cc4)nn3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 231 | 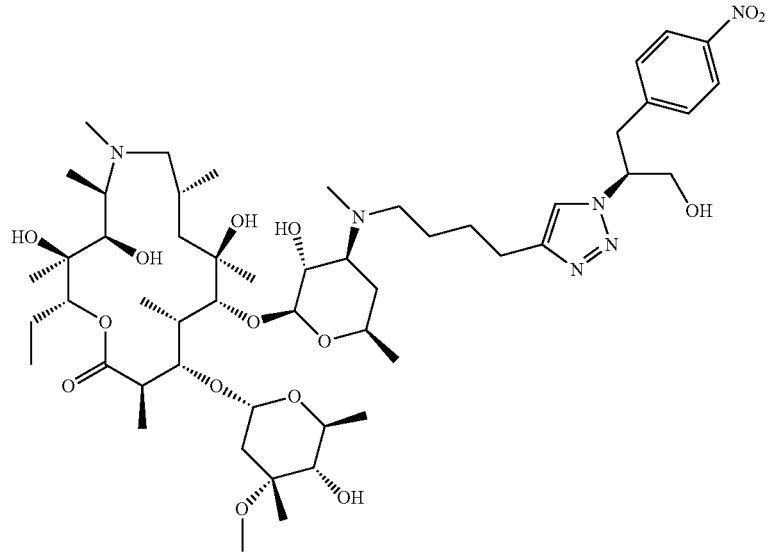 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCCc3cn([C@H](CO)Cc4ccc([N+](=O)[O-])cc4)nn3)[C@H]2O)[C@](C)(O)C[C@@H](C)CN(C)[C@H](C)[C@@H](O)[C@]1(C)O] |
| 232 | 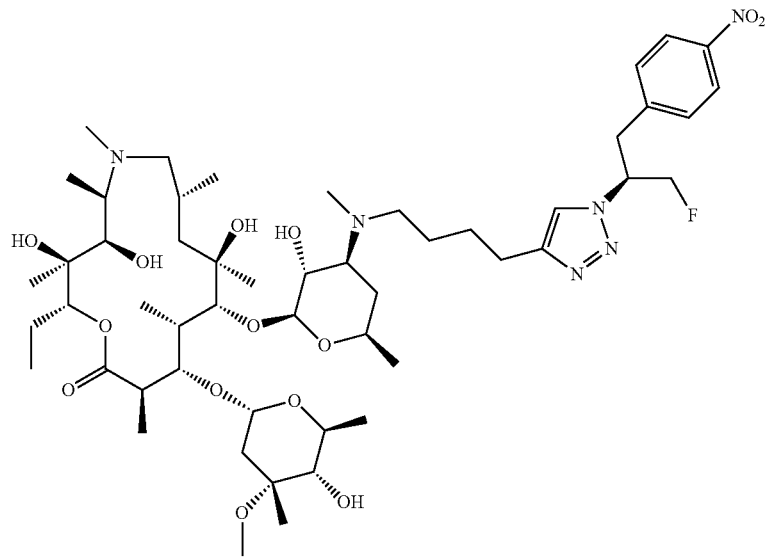 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCCc3cn([C@H](CF)Cc4ccc([N+](=O)[O-])cc4)nn3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 233 | 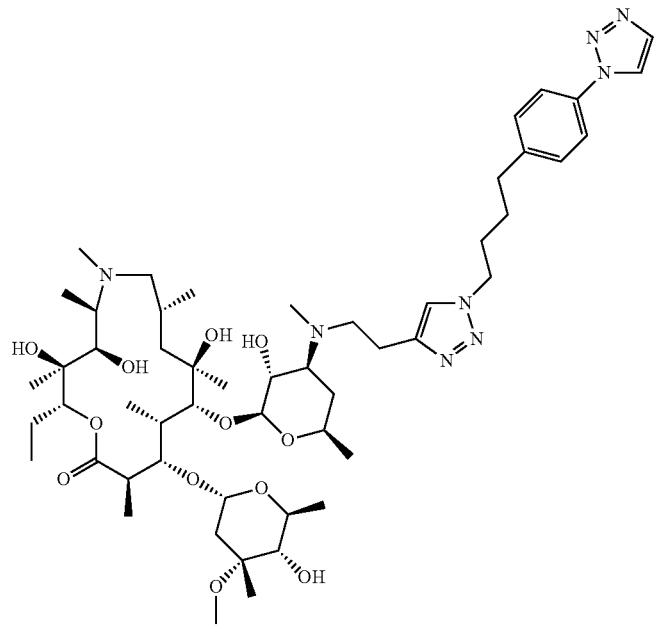 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-n5ccnn5)cc4)nn3)[C@H]2O)[C@](C)(O)C[C@@H](C)CN(C)[C@H](C)[C@@H](O)[C@]1(C)O] |
| 234 | 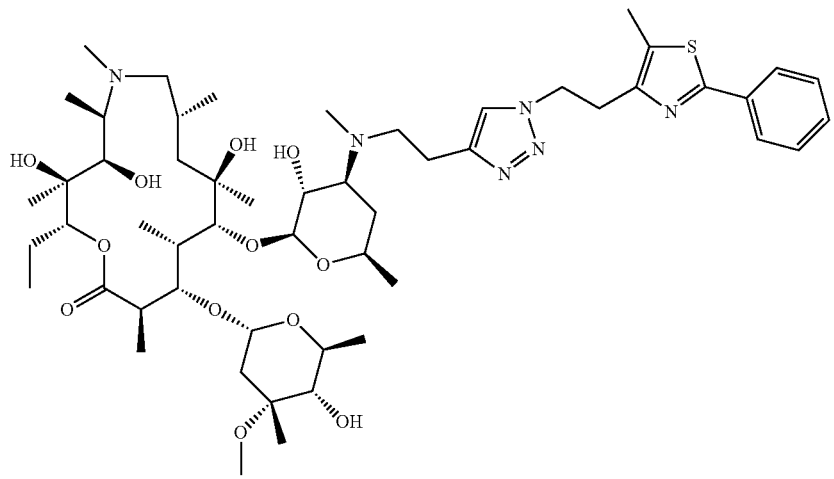 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4nc(-c5ccccc5)sc4C)nn3)[C@H]2O)[C@](C)(O)C[C@@H](C)CN(C)[C@H](C)[C@@H](O)[C@]1(C)O] |

US 8,841,263 B2
173 174
TABLE 1-continued
| Compound Number | Structure |
|---|---|
| 235 | 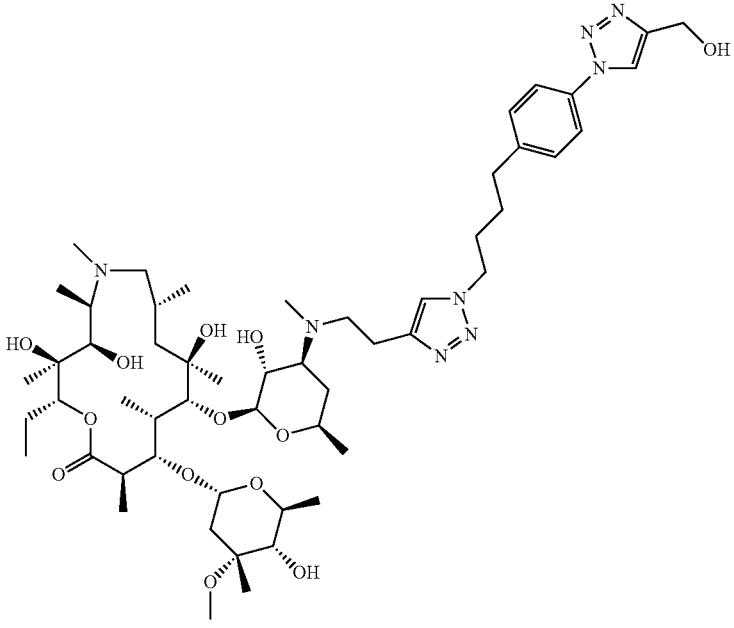 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCCc4ccc(-n5cc(CO)nn5)cc4)nn3)[C@H]2O)[C@](C)(O)C[C@@H](C)CN(C)[C@H](C)[C@@H](O)[C@]1(C)O] |
| 236 | 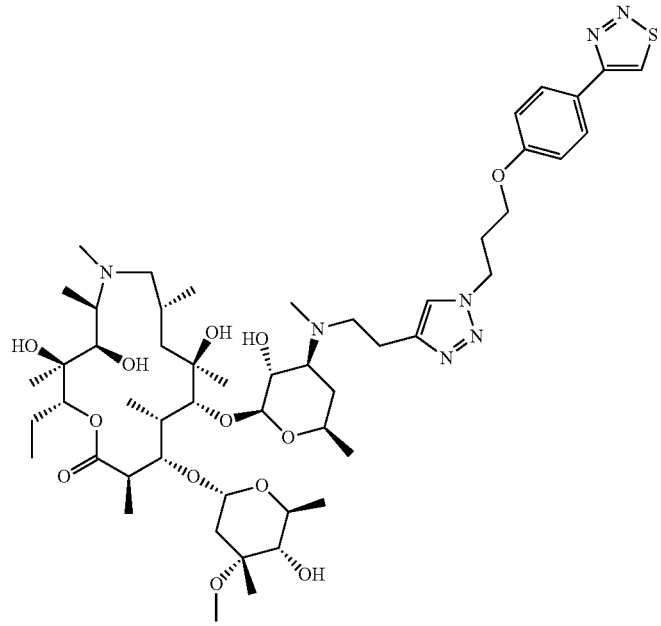 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(-c5csnn5)cc4)nn3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 237 | 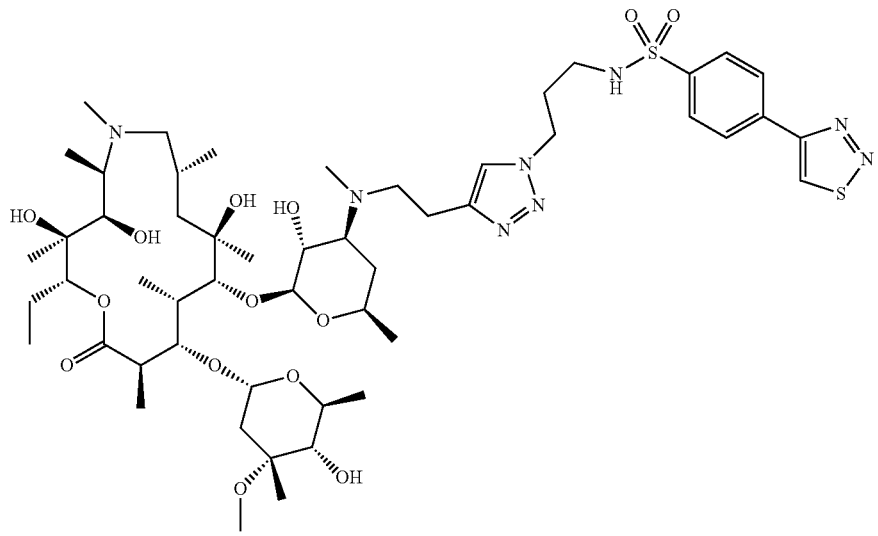 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCNS(=O)(=O)c4ccc(-c5csnn5)cc4)nn3)[C@H]2O)[C@](C)(O)C[C@@H](C)CN(C)[C@H](C)[C@@H](O)[C@]1(C)O] |
| 238 | 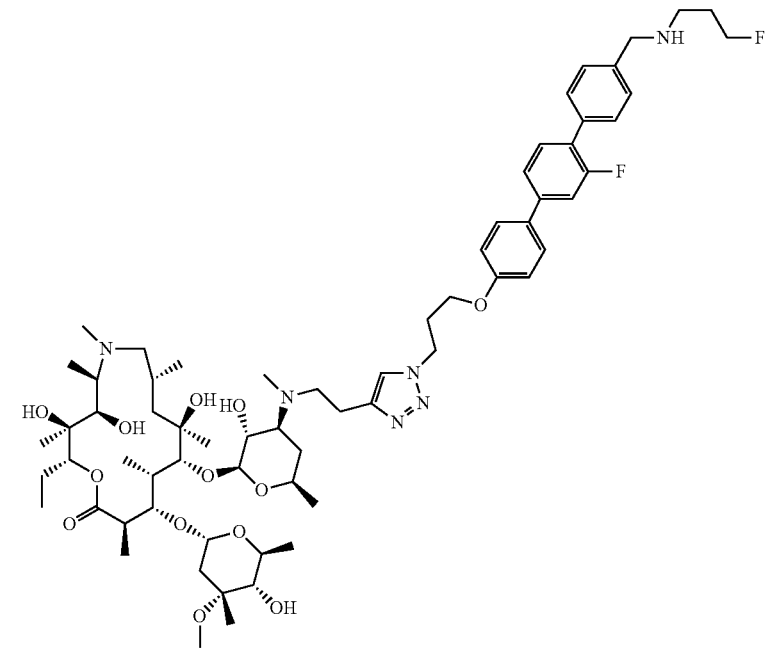 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(-c5ccc(-c6ccc(CNCCCF)cc6)c(F)c5)cc4)nn3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 239 | 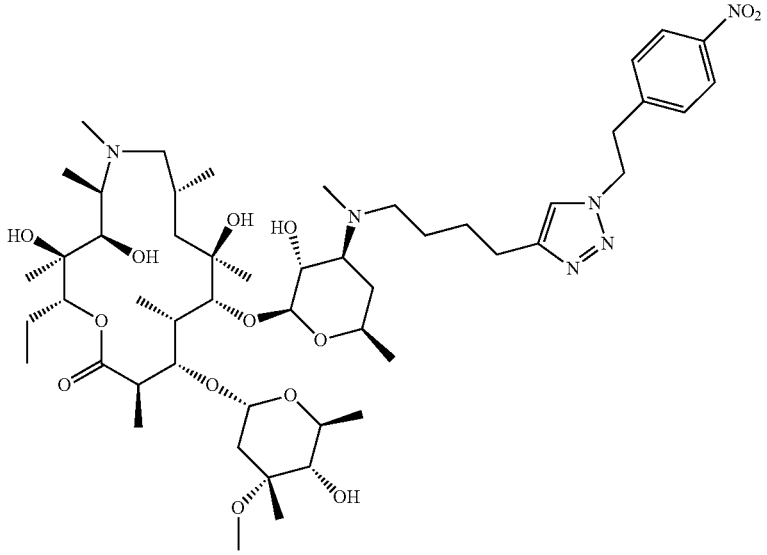 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCCc3cn(CCc4ccc([N+](=O)[O-])cc4)nn3)[C@H]2O)[C@](C)(O)C[C@@H](C)CN(C)[C@H](C)[C@@H](O)[C@]1(C)O] |
| 240 | 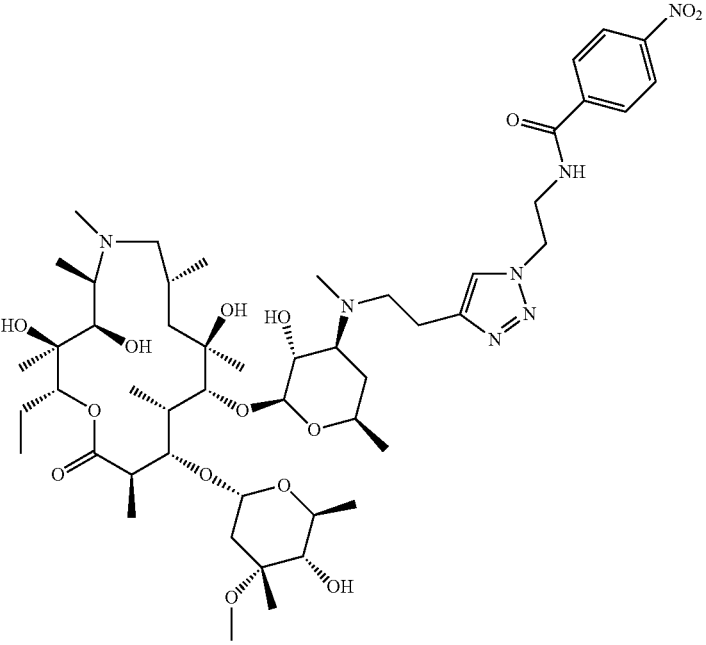 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCNC(=O)c4ccc([N+](=O)[O-])cc4)nn3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 241 | 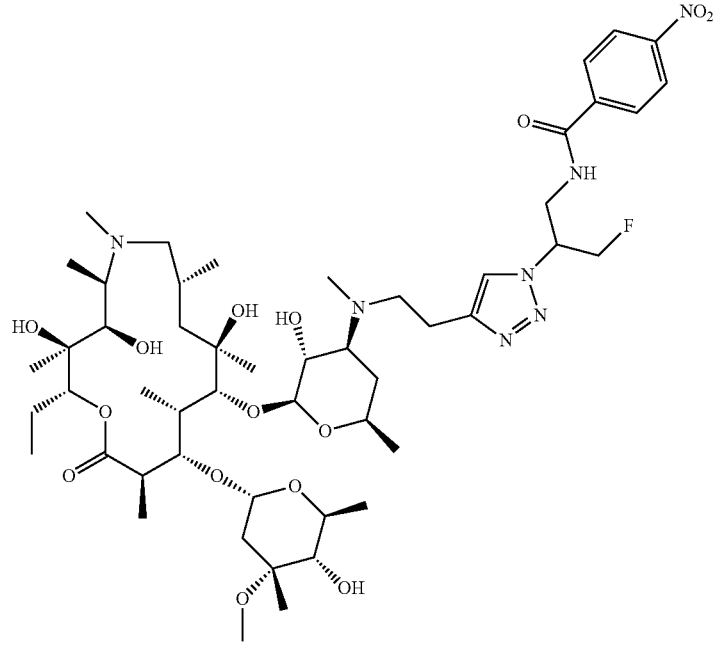 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(C(CF)CNC(=O)c4ccc([N+](=O)[O-])cc4)nn3)[C@H]2O)[C@](C)(O)C[C@@H](C)CN(C)[C@H](C)[C@@H](O)[C@]1(C)O] |
| 242 | 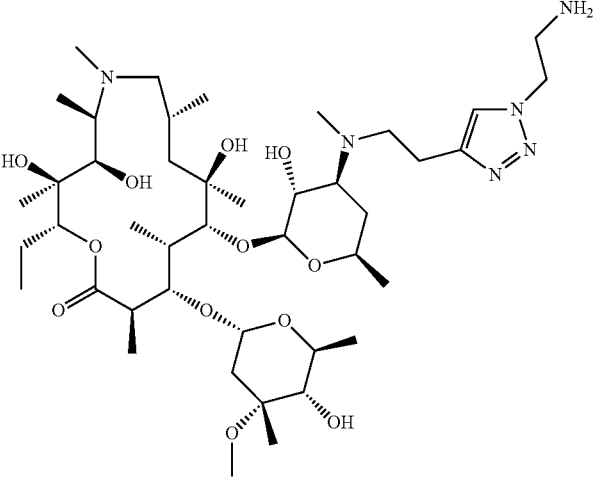 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCN)nn3)[C@H]2O)[C@](C)(O)C[C@@H](C)CN(C)[C@H](C)[C@@H](O)[C@]1(C)O] |
| 243 | 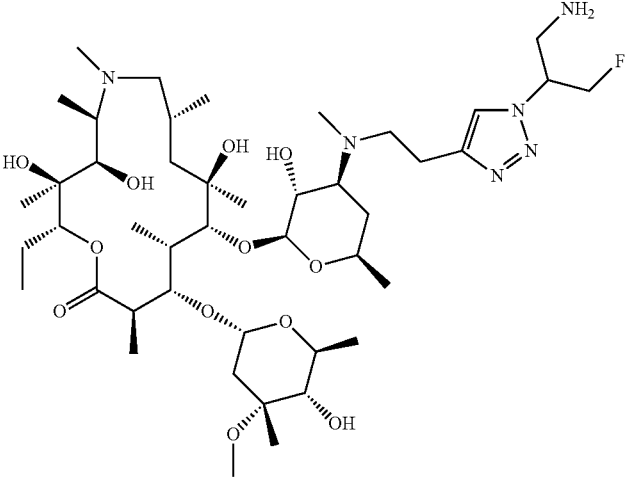 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(C(CN)CF)nn3)[C@H]2O)[C@](C)(O)C[C@@H](C)CN(C)[C@H](C)[C@@H](O)[C@]1(C)O] |

US 8,841,263 B2
181                                                                   182
TABLE 1-continued
| Compound Number | Structure |
|---|---|
| 244 | 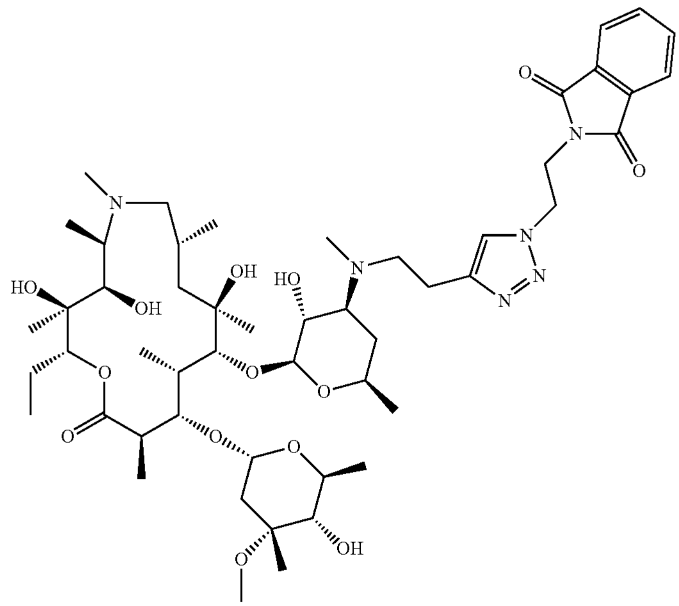 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCN4C(=O)c5ccccc5C4=O)nn3)[C@H]2O)[C@](C)(O)C[C@@H](C)CN(C)[C@H](C)[C@@H](O)[C@]1(C)O] |
| 245 | 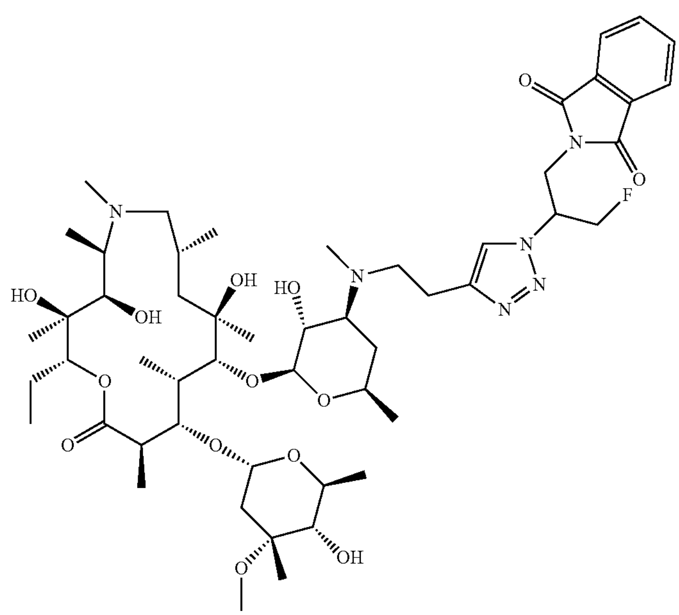 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(C(CF)CN4C(=O)c5ccccc5C4=O)nn3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 246 | 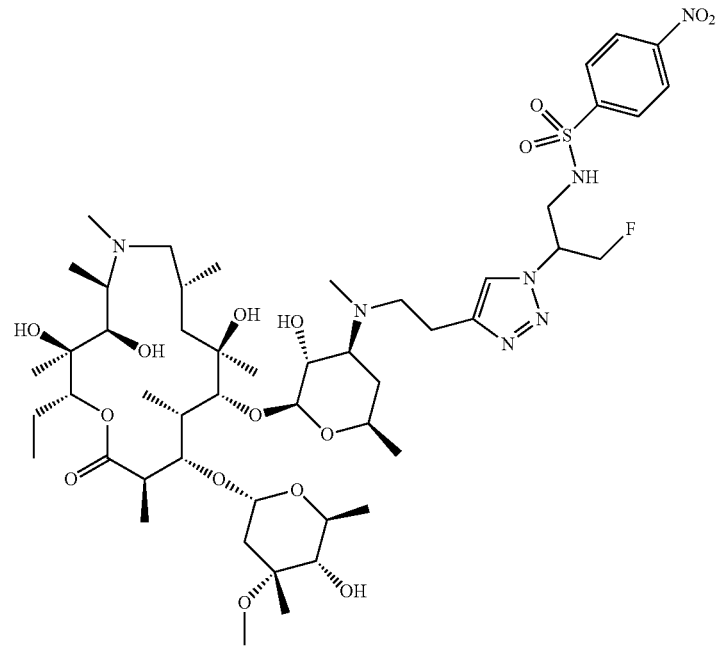 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(C(CF)CNS(=O)(=O)c4ccc([N+](=O)[O-])cc4)nn3)[C@H]2O)[C@](C)(O)C[C@@H](C)CN(C)[C@H](C)[C@@H](O)[C@]1(C)O] |
| 247 | 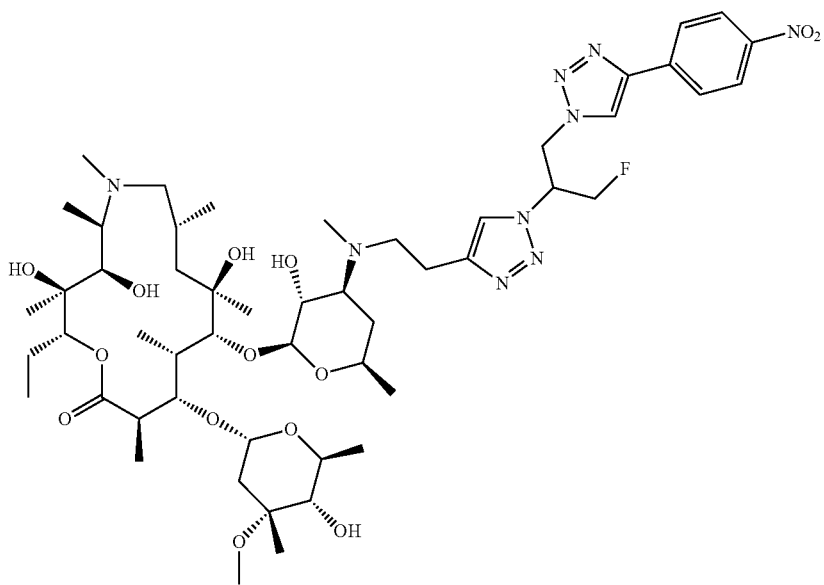 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(C(CF)Cn4cc(-c5ccc([N+](=O)[O-])cc5)nn4)nn3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 248 | 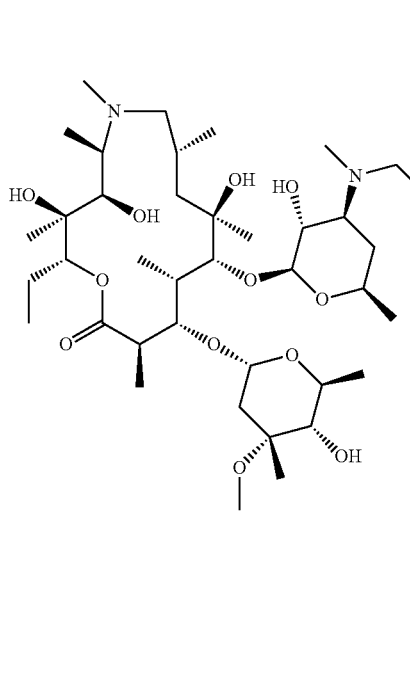 |
| 249 | 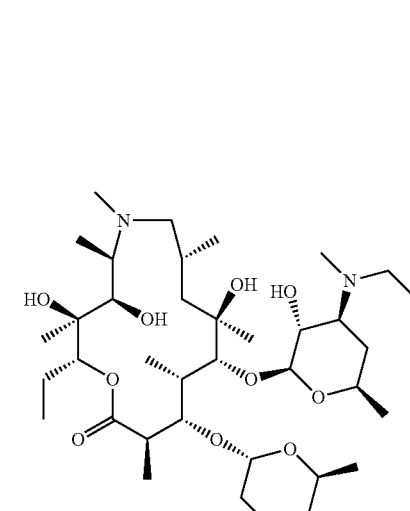 |

US 8,841,263 B2
187                                                                                             188
TABLE 1-continued
| Compound Number | Structure |
|---|---|
| 250 | 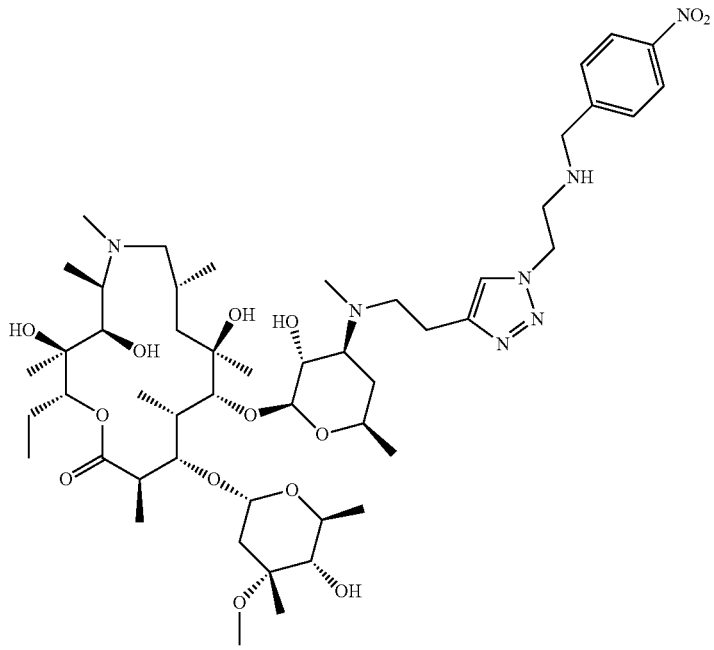 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCNCc4ccc([N+](=O)[O-])cc4)nn3)[C@H]2O)[C@](C)(O)C[C@@H](C)CN(C)[C@H](C)[C@@H](O)[C@]1(C)O] |
| 251 | 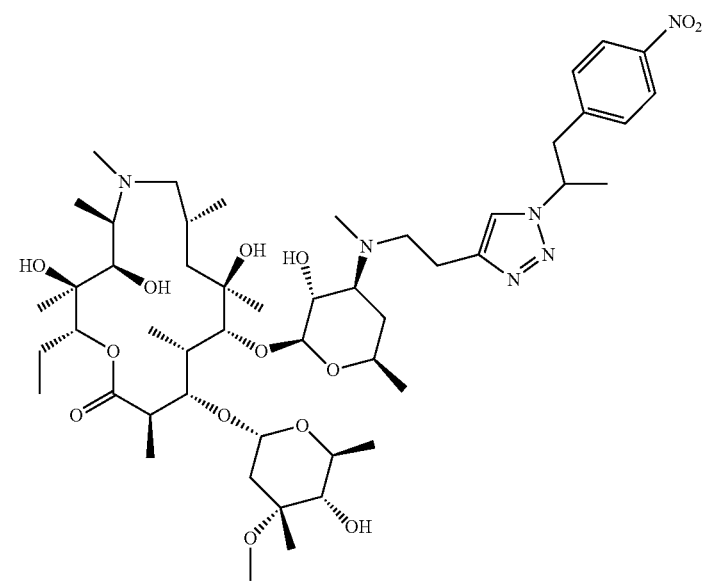 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(C(C)Cc4ccc([N+](=O)[O-])cc4)nn3)[C@H]2O)[C@](C)(O)C[C@@H](C)CN(C)[C@H](C)[C@@H](O)[C@]1(C)O] |

TABLE 1-continued
| Compound Number | Structure |
| --- | --- |
| 252 | 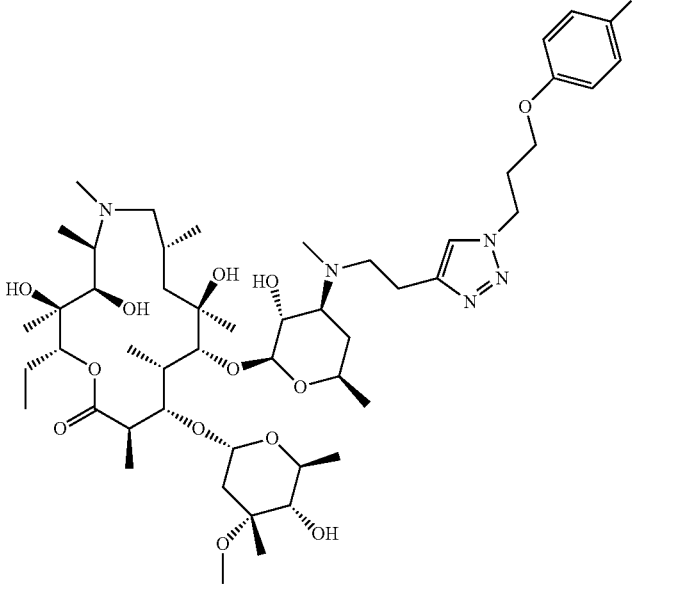 |
| 254 | 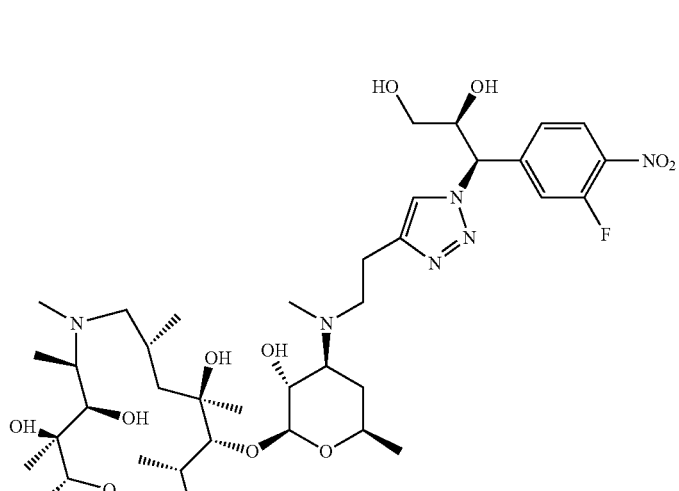 |

US 8,841,263 B2
191 192
TABLE 1-continued
| Compound Number | Structure |
|---|---|
| 255 | 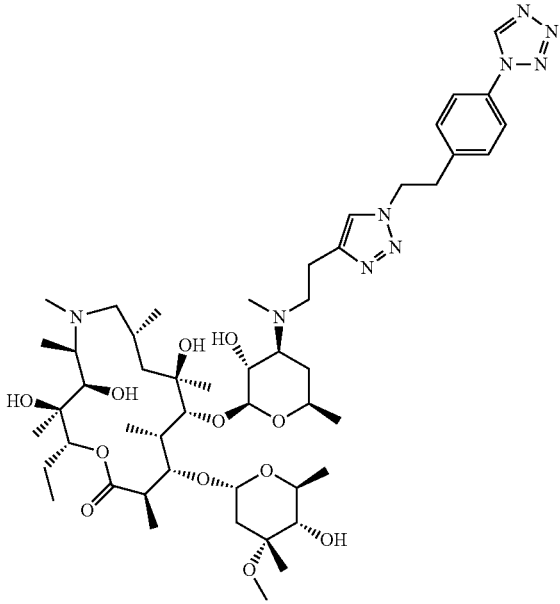 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc(-n5cnnn5)cc4)nn3)[C@H]2O)[C@](C)(O)C[C@@H](C)CN(C)[C@H](C)[C@@H](O)[C@]1(C)O] |
| 256 | 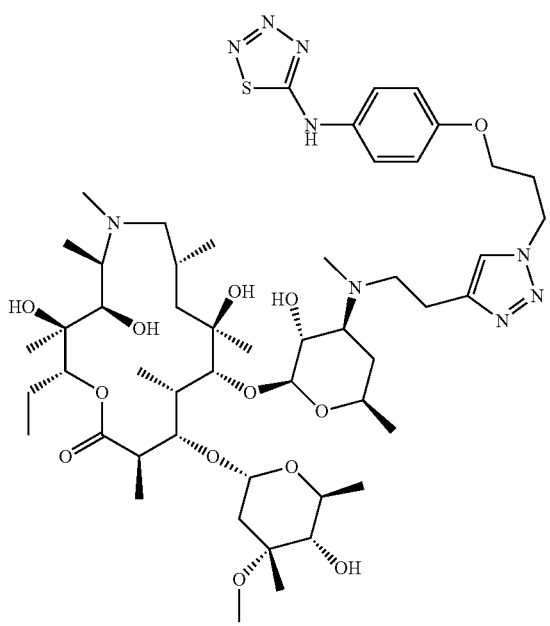 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(Nc5nnns5)cc4)nn3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 257 | 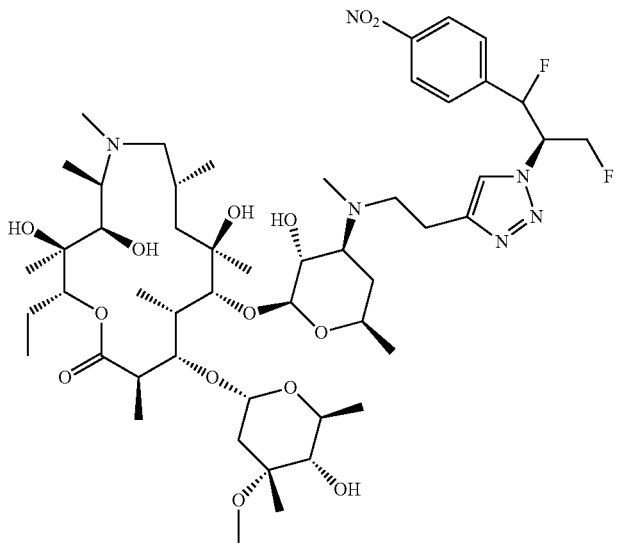 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CF)C(F)c4ccc([N+](=O)[O-])cc4)nn3)[C@H]2O)[C@](C)(O)C[C@@H](C)CN(C)[C@H](C)[C@@H](O)[C@]1(C)O] |
| 258 | 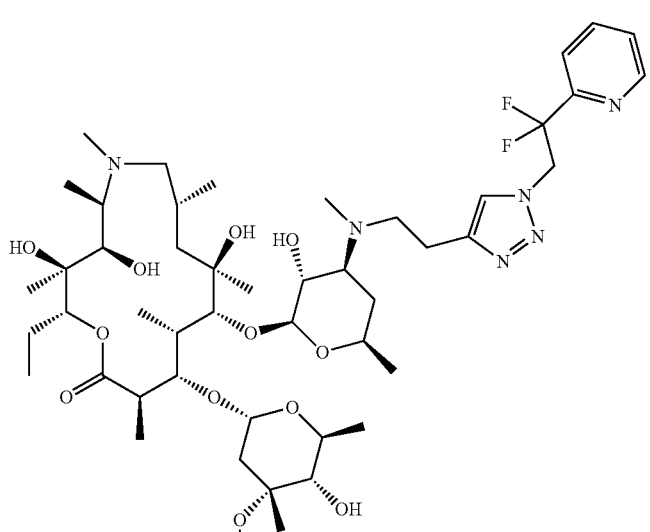 |

TABLE 1-continued

| Compound Number | Structure |
|---|---|
| 259 | 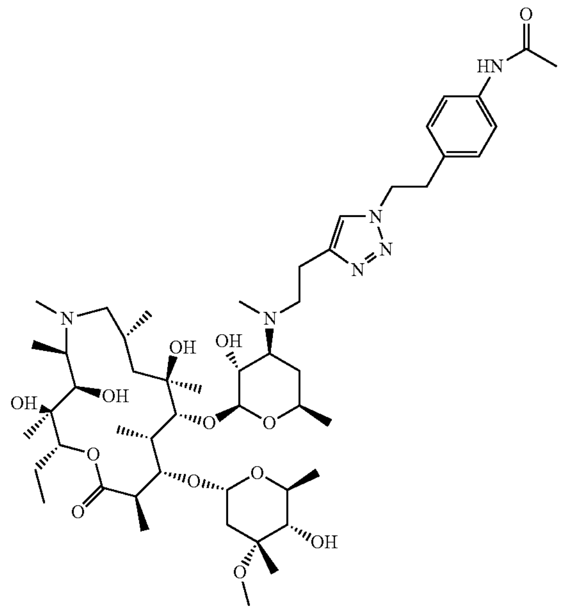 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc(NC(C)=O)cc4)nn3)[C@H]2O)[C@](C)(O)C[C@@H](C)CN(C)[C@H](C)[C@@H](O)[C@]1(C)O] |
| 260 | 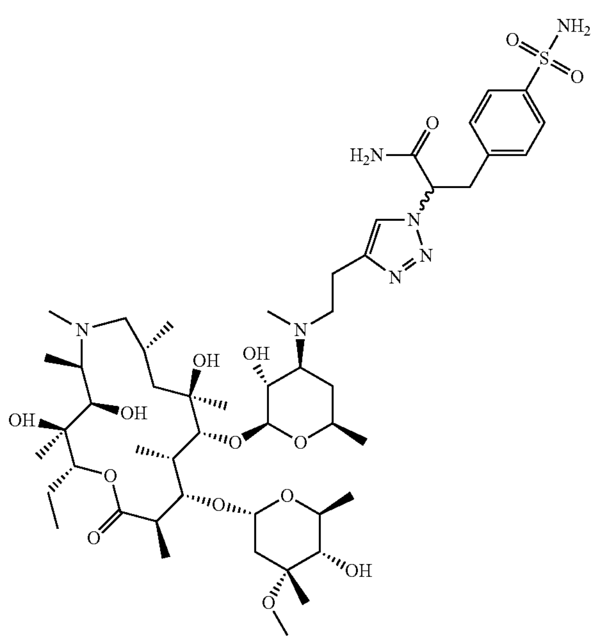 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(C(Cc4ccc(S(N)(=O)=O)cc4)C(N)=O)nn3)[C@H]2O)[C@](C)(O)C[C@@H](C)CN(C)[C@H](C)[C@@H](O)[C@]1(C)O] |

US 8,841,263 B2
197 198
TABLE 1-continued
| Compound Number | Structure |
|---|---|
| 261 | 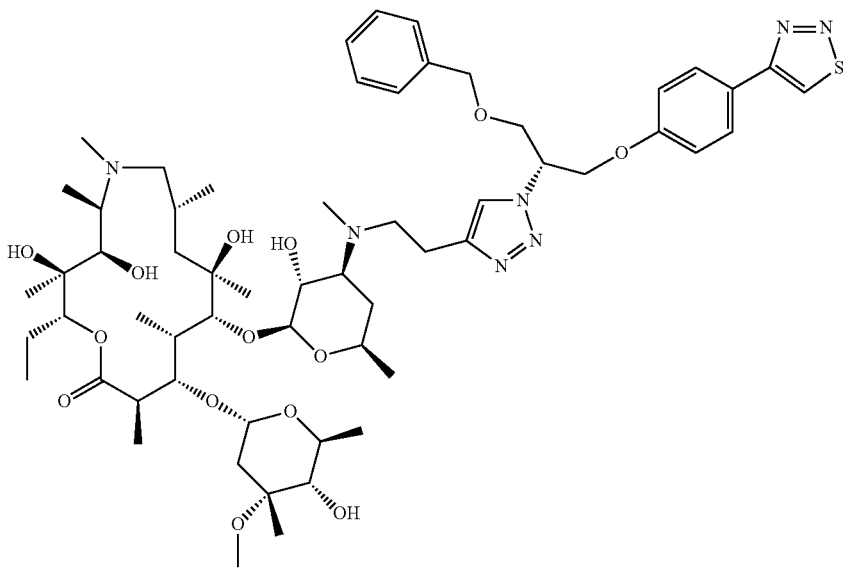 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](COCc4ccccc4)COc4ccc(-c5csnn5)cc4)nn3)[C@H]2O)[C@](C)(O)C[C@@H](C)CN(C)[C@H](C)[C@@H](O)[C@]1(C)O] |
| 262 | 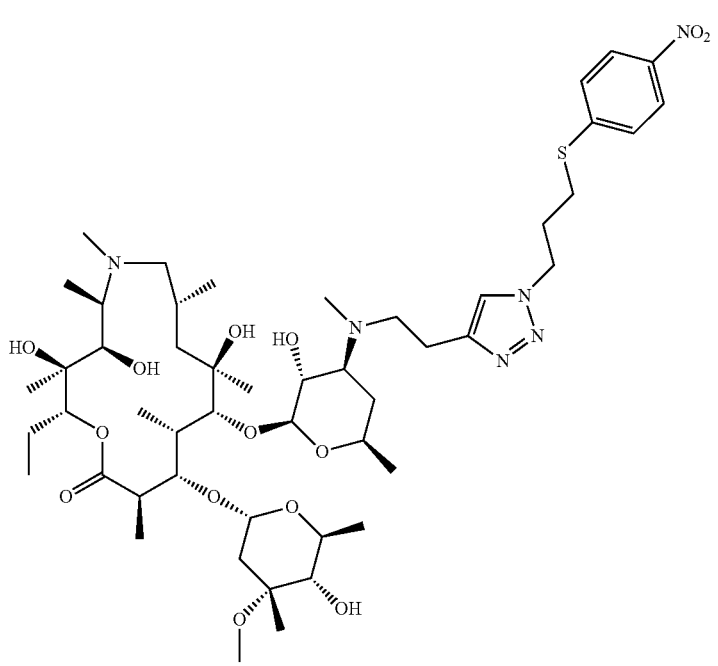 |

TABLE 1-continued
| Compound Number | Structure |
| --- | --- |
| 263 | 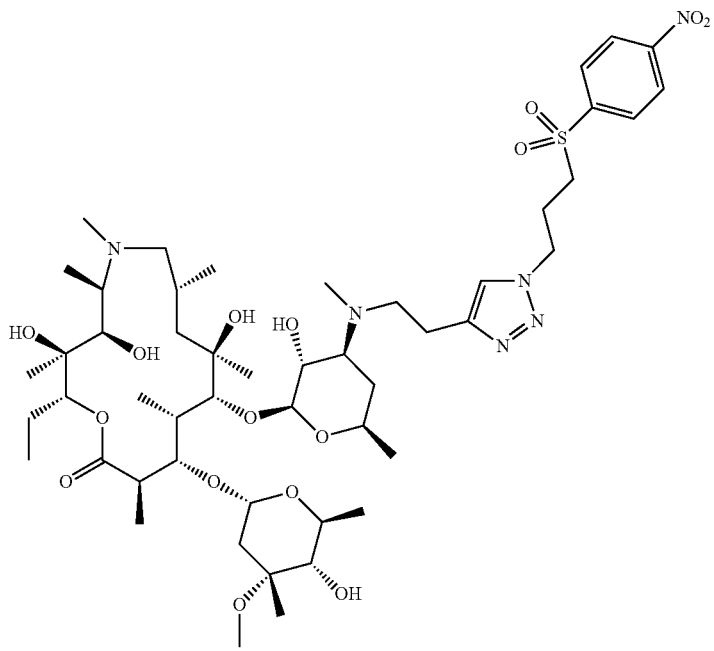 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCS(=O)(=O)c4ccc([N+](=O)[O-])cc4)nn3)[C@H]2O)[C@](C)(O)C[C@@H](C)CN(C)[C@H](C)[C@@H](O)[C@]1(C)O] |
| 264 | 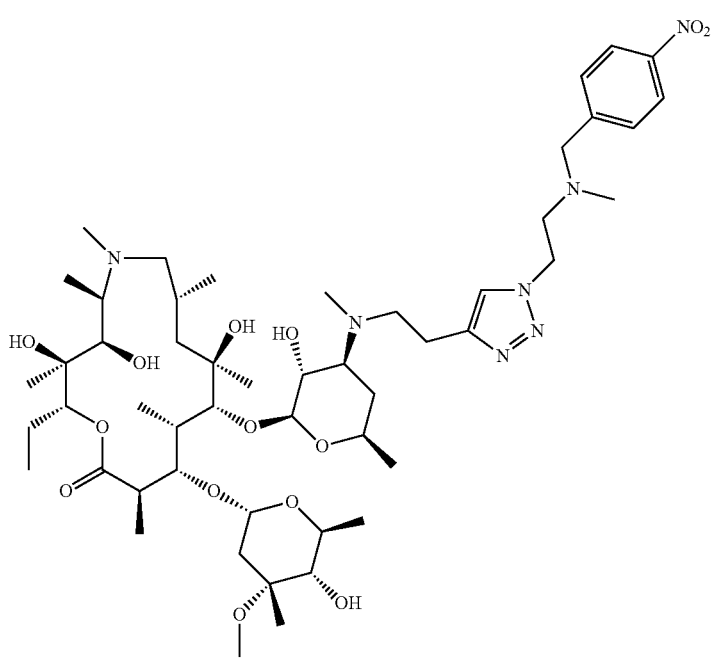 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCN(C)Cc4ccc([N+](=O)[O-])cc4)nn3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 265 | 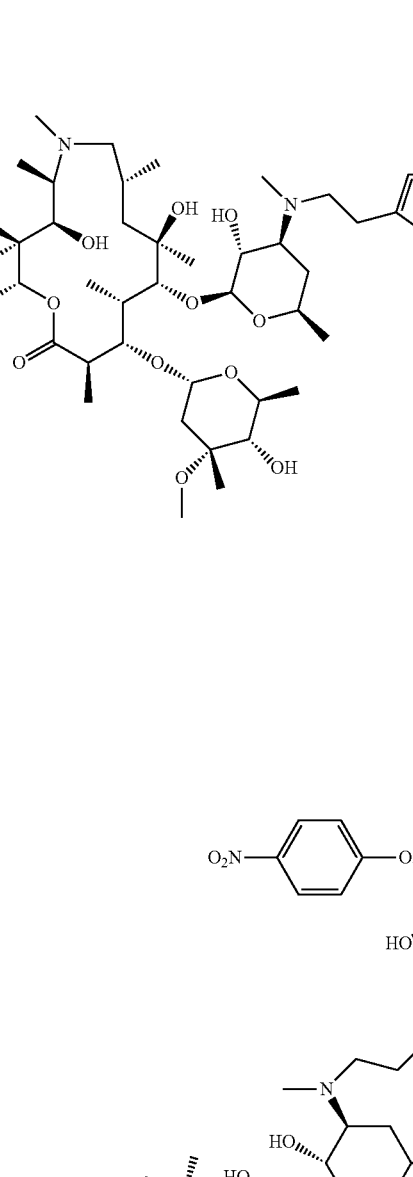 |
| 266 | 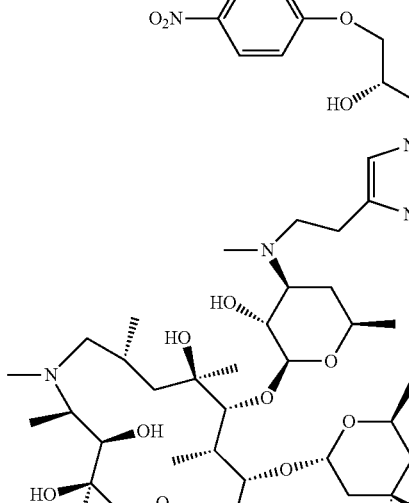 |

TABLE 1-continued
| Compound Number | Structure |
|---|---|
| 267 | 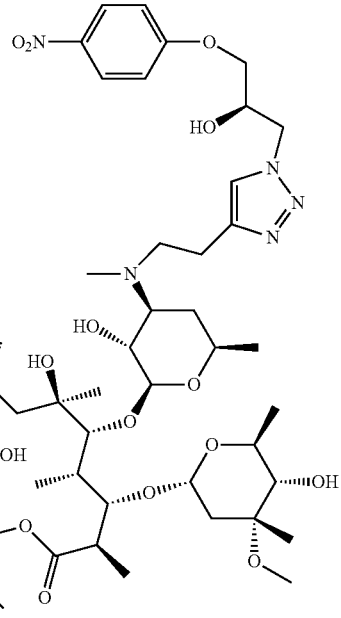 |
| 268 | 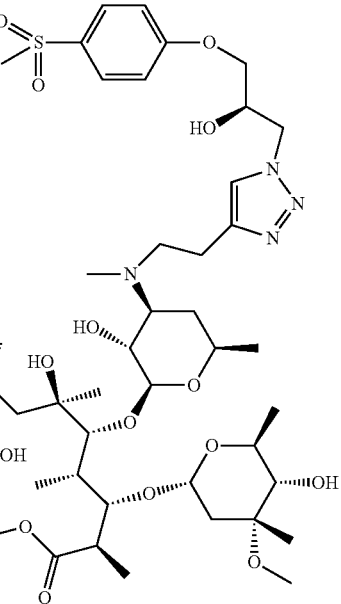 |

TABLE 1-continued
| Compound Number | Structure |
|---|---|
| 269 | 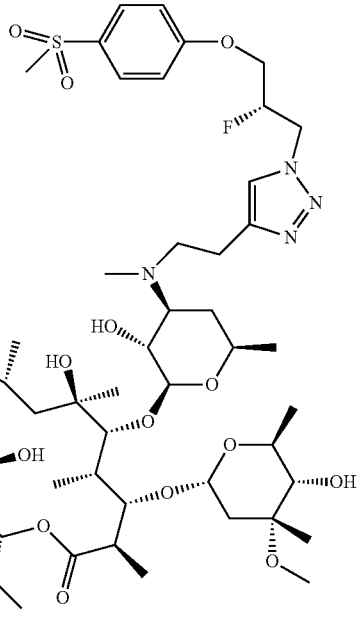 |
| 270 | 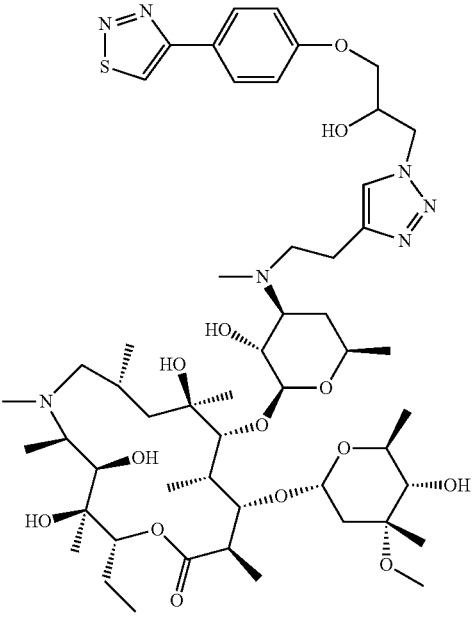 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CC(O)COc4ccc(-c5csnn5)cc4)nn3)[C@H]2O)[C@](C)(O)C[C@@H](C)CN(C)[C@H](C)[C@@H](O)[C@]1(C)O] |

TABLE 1-continued

| Compound Number | Structure |
| --- | --- |
| 271 | 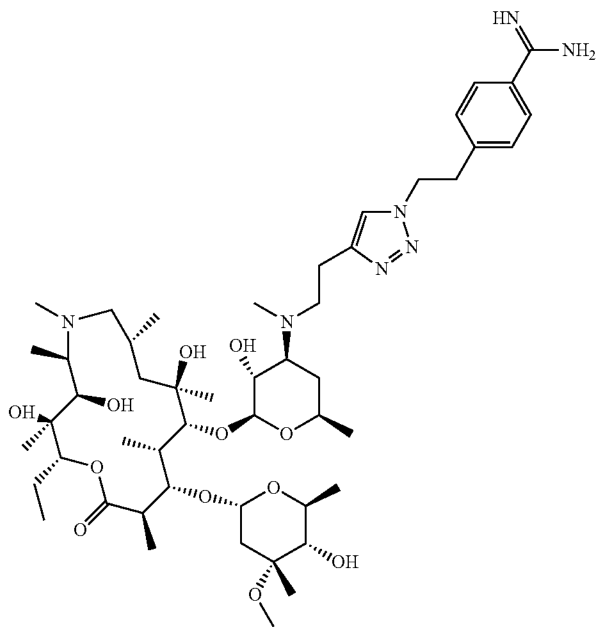 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc(C(=N)N)cc4)nn3)[C@H]2O)[C@](C)(O)C[C@@H](C)CN(C)[C@H](C)[C@@H](O)[C@]1(C)O] |
| 272 | 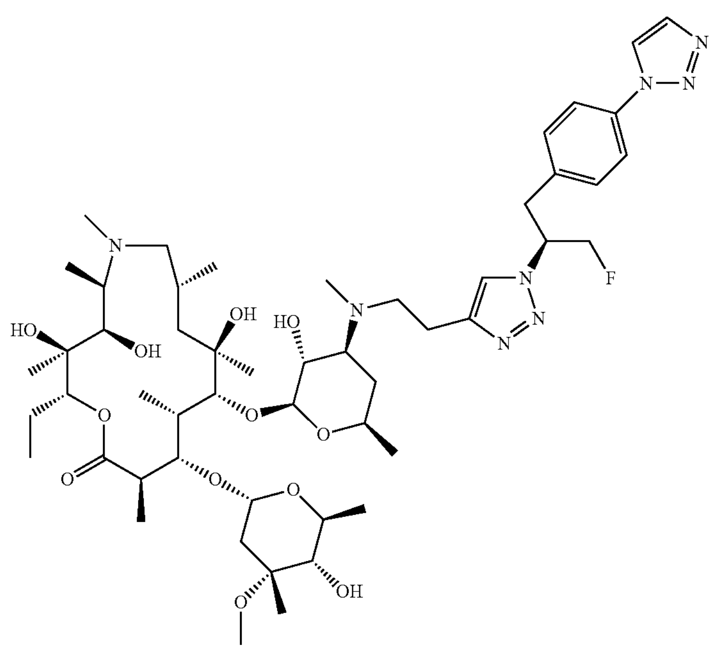 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CF)Cc4ccc(-n5ccnn5)cc4)nn3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 273 | 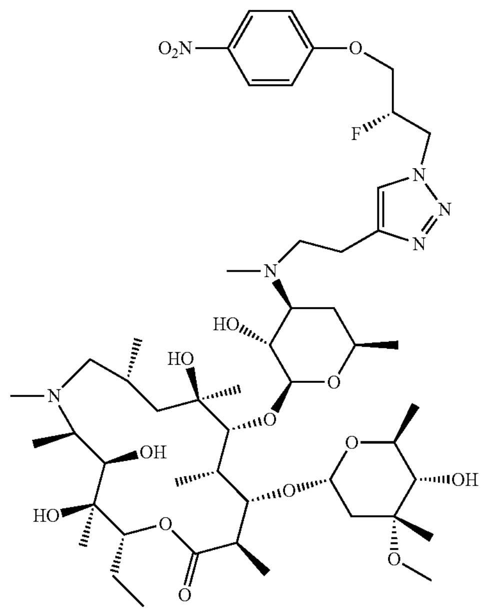 |
| 274 | 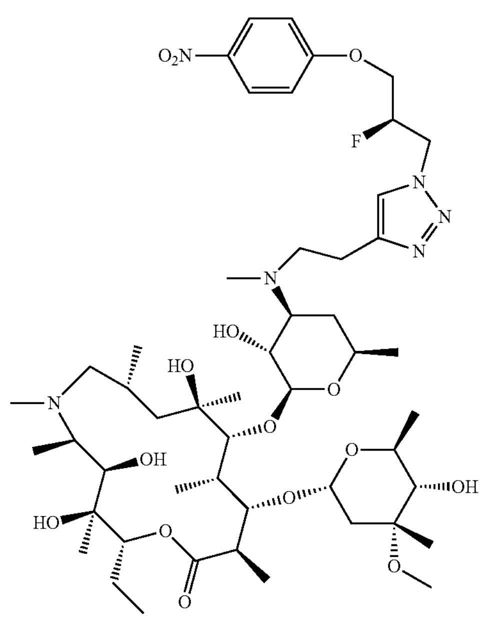 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(C[C@@H](F)COc4ccc([N+](=O)[O-])cc4)nn3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 275 | 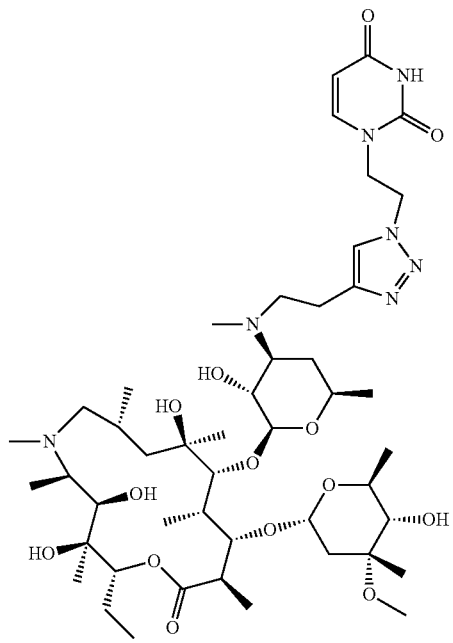 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCn4ccc(=O)[nH]c4=O)nn3)[C@H]2O)[C@](C)(O)C[C@@H](C)CN(C)[C@H](C)[C@@H](O)[C@]1(C)O] |
| 276 | 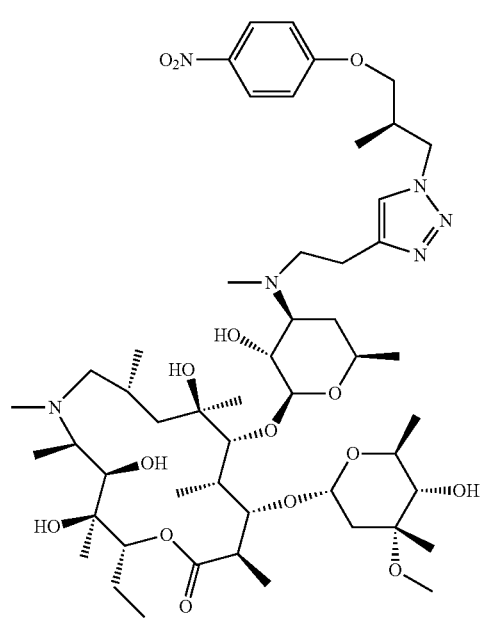 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(C[C@@H](C)COc4ccc([N+](=O)[O-])cc4)nn3)[C@H]2O)[C@](C)(O)C[C@@H](C)CN(C)[C@H](C)[C@@H](O)[C@]1(C)O] |

US 8,841,263 B2
213　　　　　　　　　　　　　　　　　　　　　　　214
TABLE 1-continued
| Compound Number | Structure |
|---|---|
| 277 | 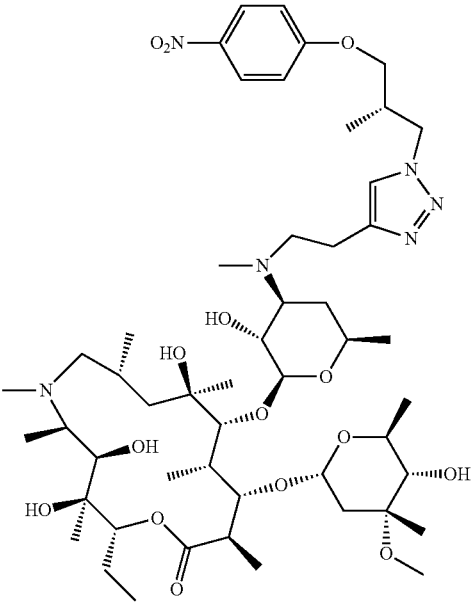 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(C[C@H](C)COc4ccc([N+](=O)[O-])cc4)nn3)[C@H]2O)[C@](C)(O)C[C@@H](C)CN(C)[C@H](C)[C@@H](O)[C@]1(C)O] |
| 278 | 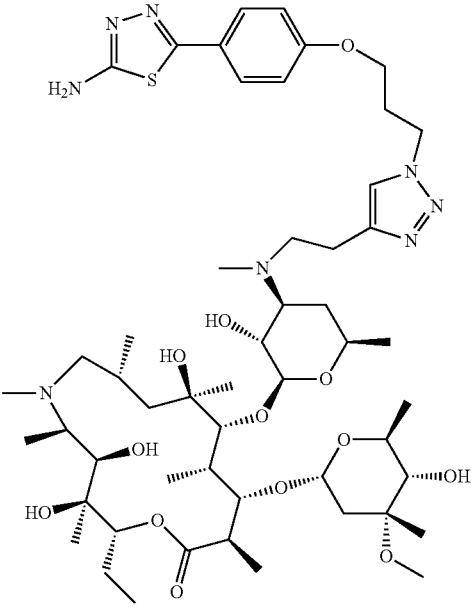 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(-c5nnc(N)s5)cc4)nn3)[C@H]2O)[C@](C)(O)C[C@@H](C)CN(C)[C@H](C)[C@@H](O)[C@]1(C)O] |

TABLE 1-continued

| Compound Number | Structure |
|---|---|
| 279 | 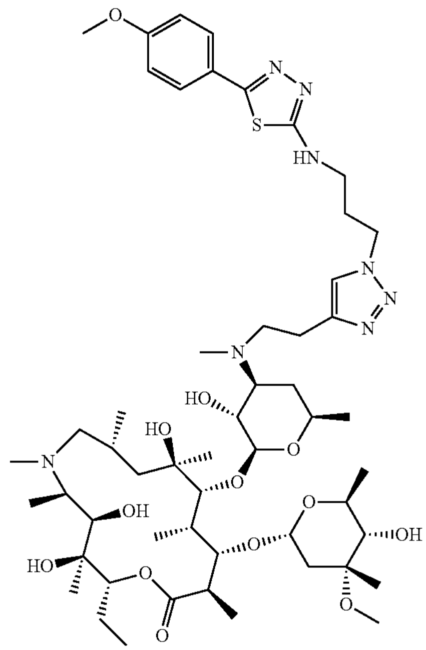 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCNc4nnc(-c5ccc(OC)cc5)s4)nn3)[C@H]2O)[C@](C)(O)C[C@@H](C)CN(C)[C@H](C)[C@@H](O)[C@]1(C)O] |
| 280 | 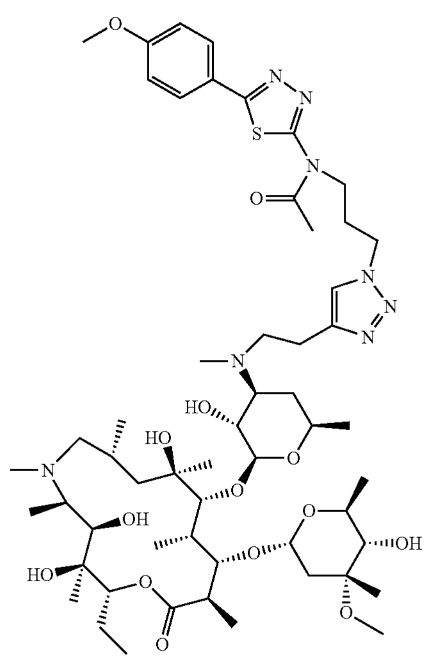 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCN(C(C)=O)c4nnc(-c5ccc(OC)cc5)s4)nn3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 290 | 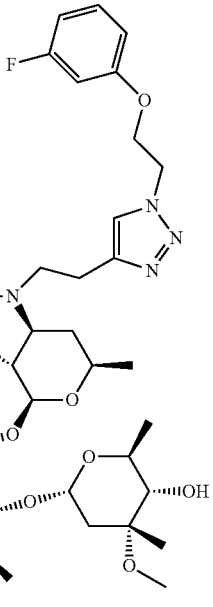 |
| 301 | 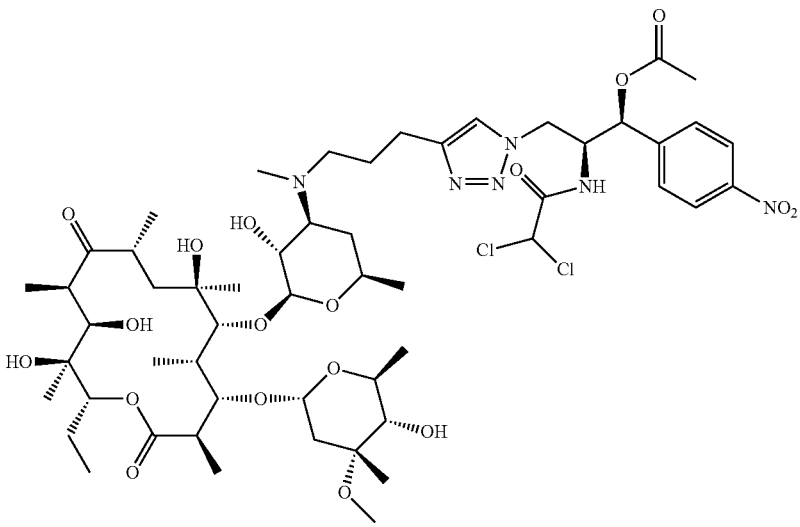 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCc3cn(C[C@H](NC(=O)C(Cl)Cl)[C@@H](OC(C)=O)c4ccc([N+](=O)[O-])cc4)nn3)[C@H]2O)[C@](C)(O)C[C@@H](C)C(=O)[C@H](C)[C@@H](O)[C@]1(C)O] |

TABLE 1-continued

| Compound Number | Structure |
|---|---|
| 302 | 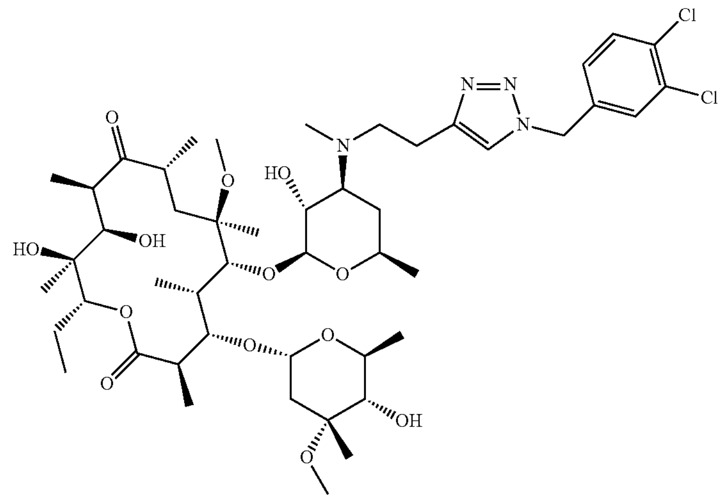 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc(Cl)c(Cl)c4)nn3)[C@H]2O)[C@](C)(OC)C[C@@H](C)C(=O)[C@H](C)[C@@H](O)[C@]1(C)O] |
| 303 | 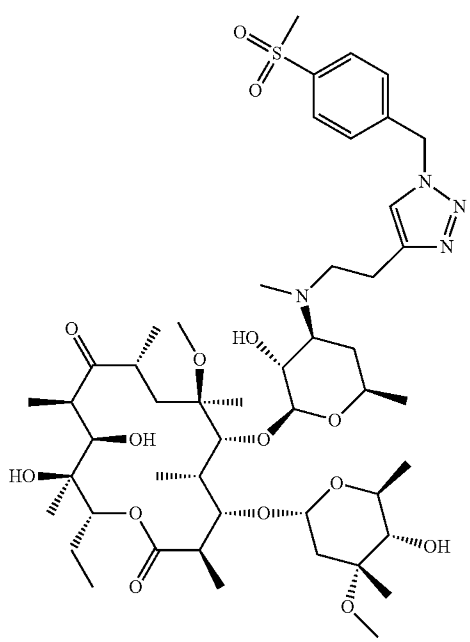 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc(S(C)(=O)=O)cc4)nn3)[C@H]2O)[C@](C)(OC)C[C@@H](C)C(=O)[C@H](C)[C@@H](O)[C@]1(C)O] |

TABLE 1-continued
| Compound Number | Structure |
|---|---|
| 304 | 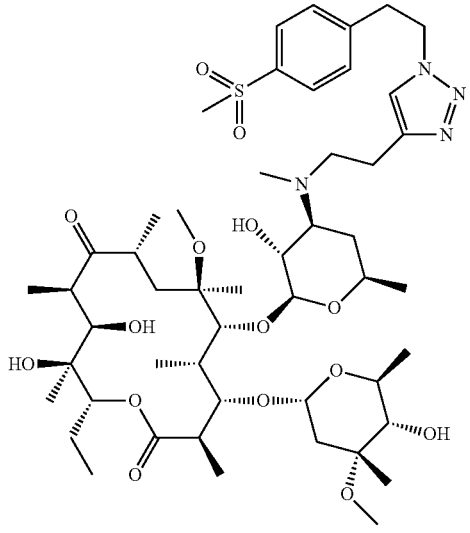 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc(S(C)(=O)=O)cc4)nn3)[C@H]2O)[C@](C)(OC)C[C@@H](C)C(=O)[C@H](C)[C@@H](O)[C@]1(C)O] |
| 305 | 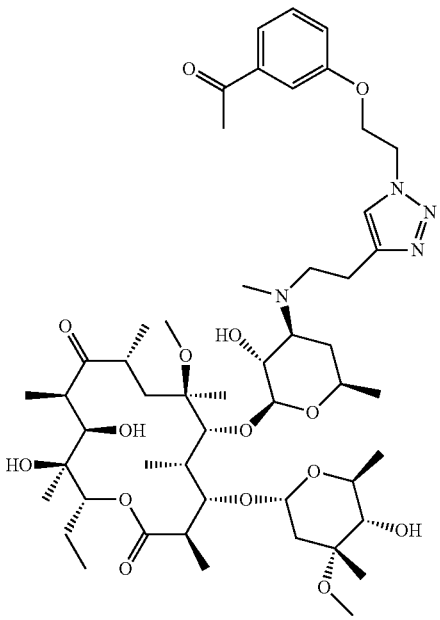 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCOc4cccc(C(C)=O)c4)nn3)[C@H]2O)[C@](C)(OC)C[C@@H](C)C(=O)[C@H](C)[C@@H](O)[C@]1(C)O] |

TABLE 1-continued

| Compound Number | Structure |
|---|---|
| 306 | 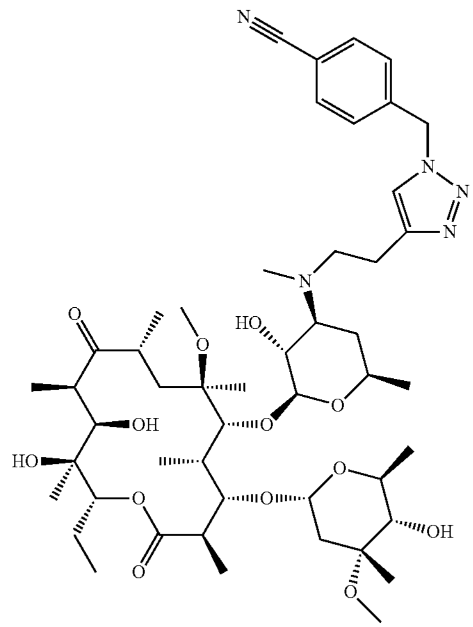 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc(C#N)cc4)nn3)[C@H]2O)[C@](C)(OC)C[C@@H](C)C(=O)[C@H](C)[C@@H](O)[C@]1(C)O] |
| 307 | 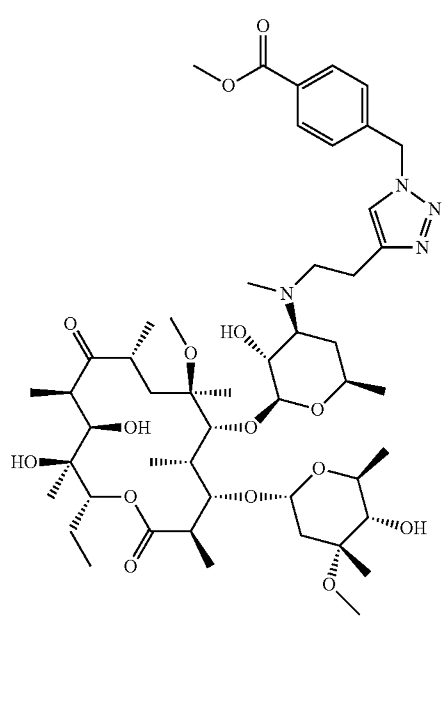 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc(C(=O)OC)cc4)nn3)[C@H]2O)[C@](C)(OC)C[C@@H](C)C(=O)[C@H](C)[C@@H](O)[C@]1(C)O] |

TABLE 1-continued

| Compound Number | Structure |
|---|---|
| 308 | 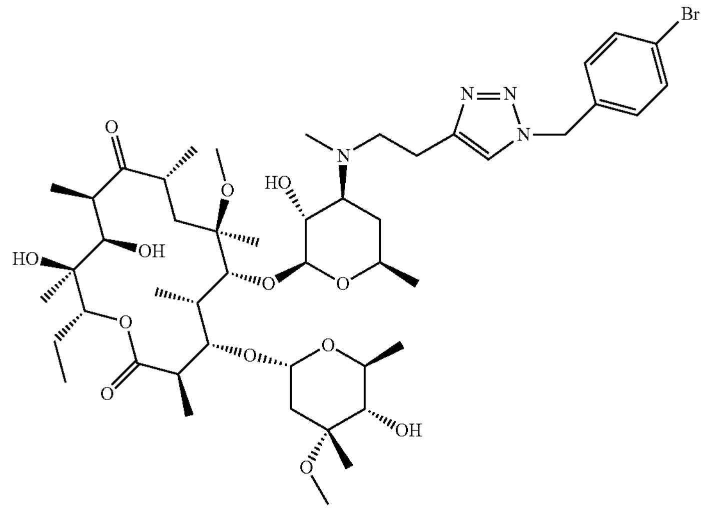 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc(Br)cc4)nn3)[C@H]2O)[C@](C)(OC)C[C@@H](C)C(=O)[C@H](C)[C@@H](O)[C@]1(C)O] |
| 309 | 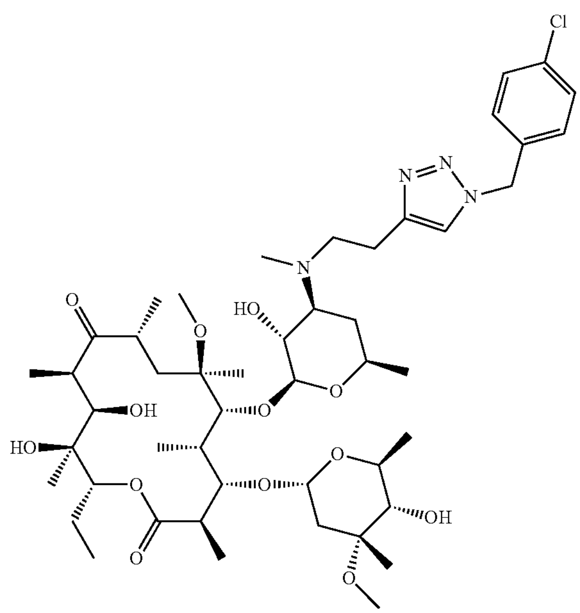 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc(Cl)cc4)nn3)[C@H]2O)[C@](C)(OC)C[C@@H](C)C(=O)[C@H](C)[C@@H](O)[C@]1(C)O] |

TABLE 1-continued

| Compound Number | Structure |
| --- | --- |
| 310 | 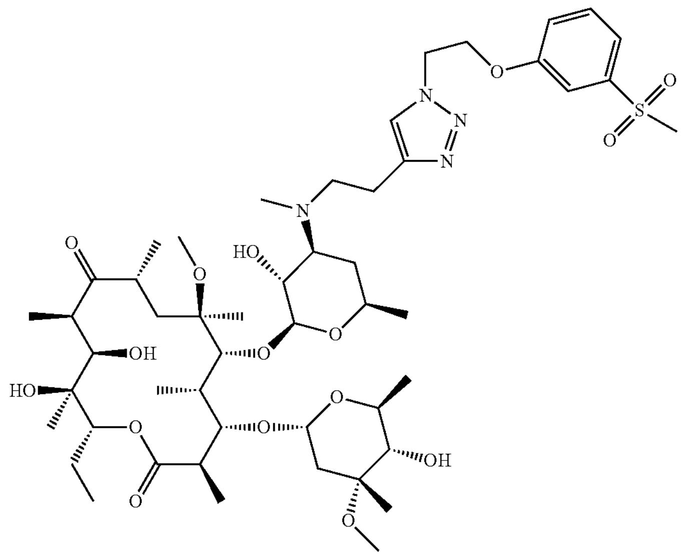 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCOc4cccc(S(C)(=O)=O)c4)nn3)[C@H]2O)[C@](C)(OC)C[C@@H](C)C(=O)[C@H](C)[C@@H](O)[C@]1(C)O] |
| 311 | 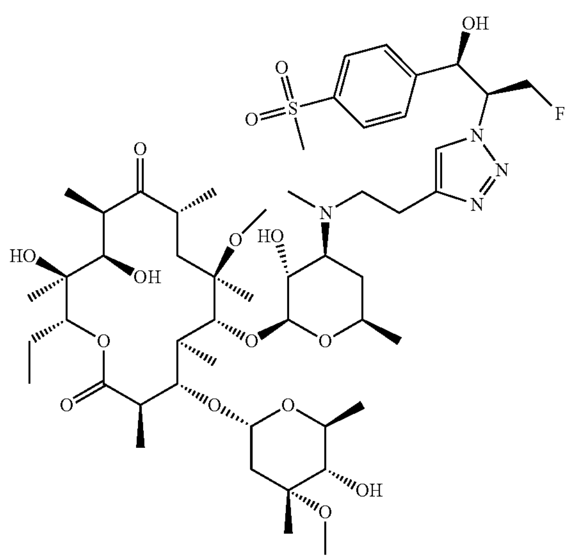 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CF)[C@H](O)c4ccc(S(C)(=O)=O)cc4)nn3)[C@H]2O)[C@](C)(OC)C[C@@H](C)C(=O)[C@H](C)[C@@H](O)[C@]1(C)O] |

TABLE 1-continued
| Compound Number | Structure |
|---|---|
| 312 | 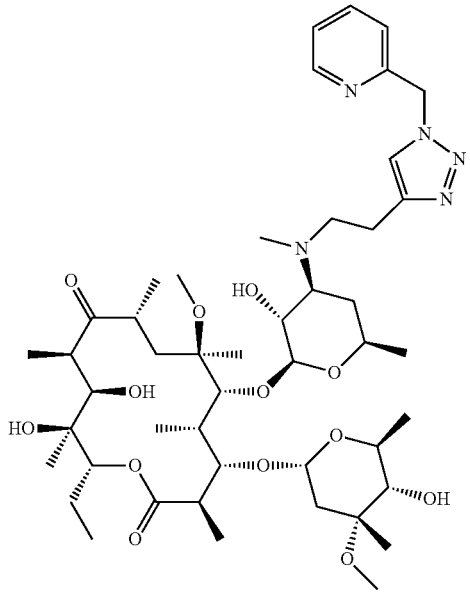 |
| 313 | 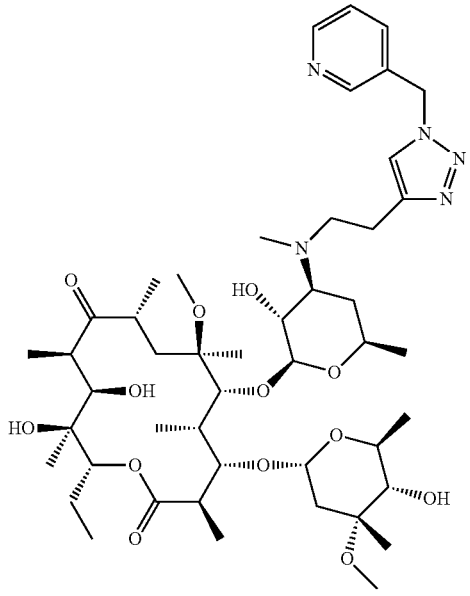 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4cccnc4)nn3)[C@H]2O)[C@](C)(OC)C[C@@H](C)C(=O)[C@H](C)[C@@H](O)[C@]1(C)O] |

TABLE 1-continued

| Compound Number | Structure |
|---|---|
| 314 | 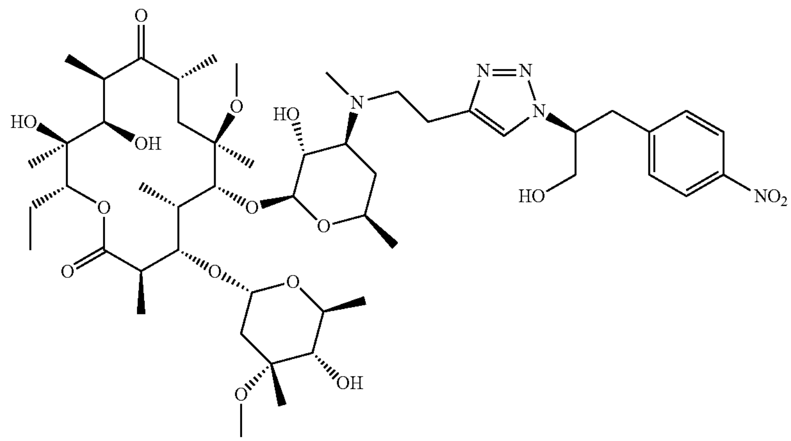 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CO)Cc4ccc([N+](=O)[O-])cc4)nn3)[C@H]2O)[C@](C)(OC)C[C@@H](C)C(=O)[C@H](C)[C@@H](O)[C@]1(C)O] |
| 315 | 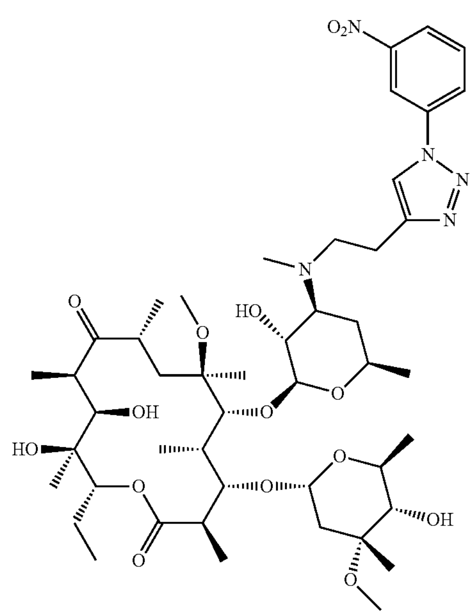 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(-c4cccc([N+](=O)[O-])c4)nn3)[C@H]2O)[C@](C)(OC)C[C@@H](C)C(=O)[C@H](C)[C@@H](O)[C@]1(C)O] |

TABLE 1-continued
| Compound Number | Structure |
|---|---|
| 316 | 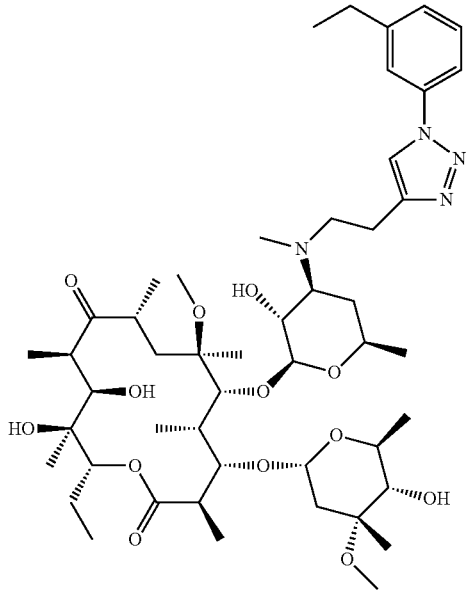 [SMILES: CCc1cccc(-n2cc(CCN(C)[C@H]3C[C@@H](C)O[C@@H](O[C@@H]4[C@@H](C)[C@H](O[C@H]5C[C@@](C)(OC)[C@@H](O)[C@H](C)O5)[C@@H](C)C(=O)O[C@H](CC)[C@@](C)(O)[C@H](O)[C@@H](C)C(=O)[C@H](C)C[C@@]4(C)OC)[C@@H]3O)nn2)c1] |
| 317 | 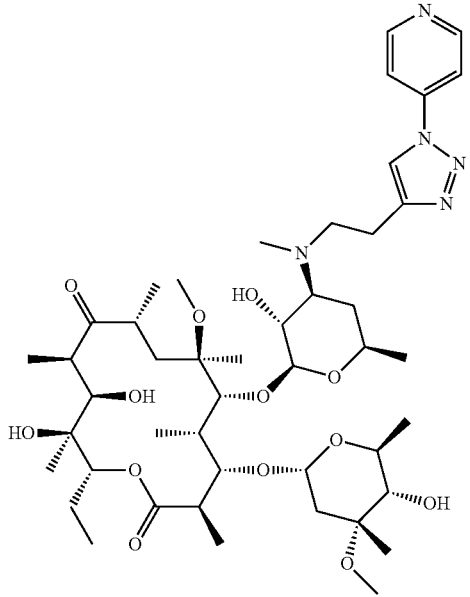 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(-c4ccncc4)nn3)[C@H]2O)[C@](C)(OC)C[C@@H](C)C(=O)[C@H](C)[C@@H](O)[C@]1(C)O] |

TABLE 1-continued
| Compound Number | Structure |
|---|---|
| 318 | 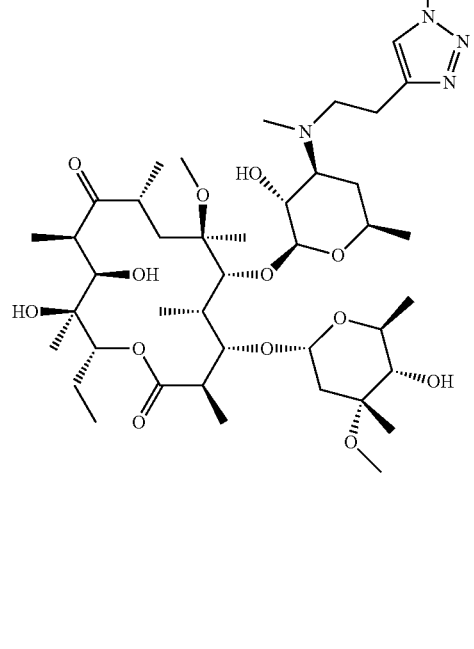 |
| 319 | 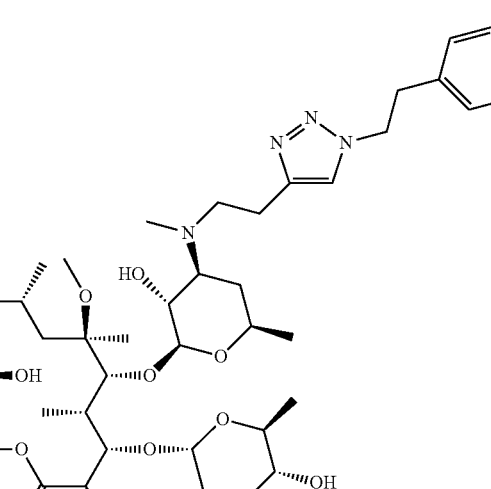 |

TABLE 1-continued

| Compound Number | Structure |
| --- | --- |
| 320 | 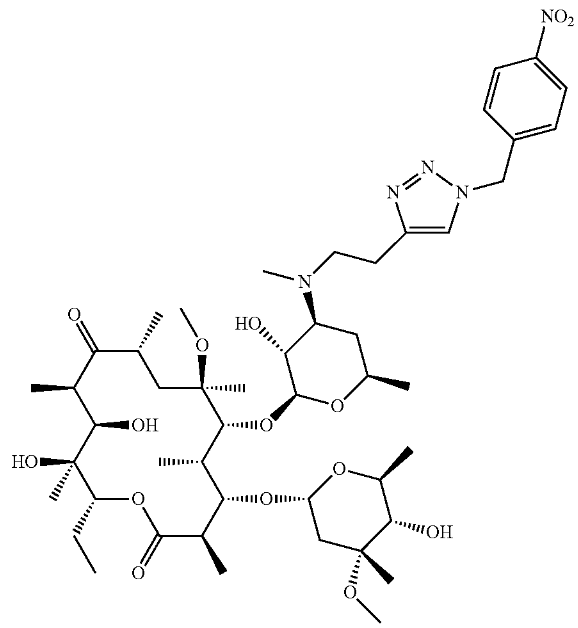 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc([N+](=O)[O-])cc4)nn3)[C@H]2O)[C@](C)(OC)C[C@@H](C)C(=O)[C@H](C)[C@@H](O)[C@]1(C)O] |
| 321 | 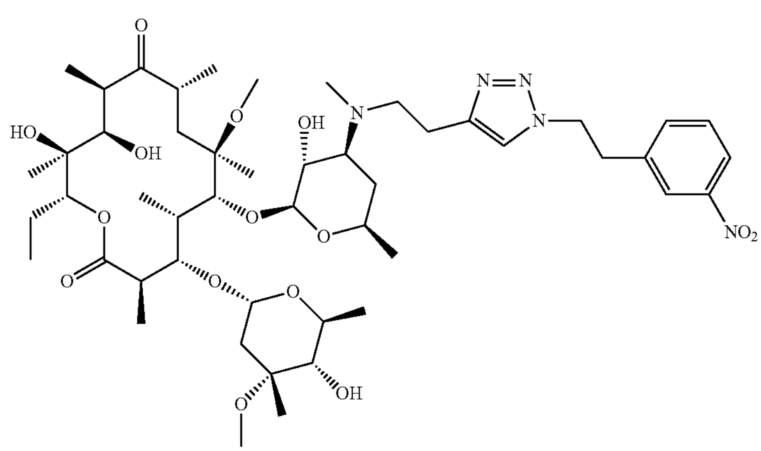 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4cccc([N+](=O)[O-])c4)nn3)[C@H]2O)[C@](C)(OC)C[C@@H](C)C(=O)[C@H](C)[C@@H](O)[C@]1(C)O] |

TABLE 1-continued

| Compound Number | Structure |
|---|---|
| 322 | (chemical structure) |
| 323 | (chemical structure) |

TABLE 1-continued

| Compound Number | Structure |
|---|---|
| 324 | 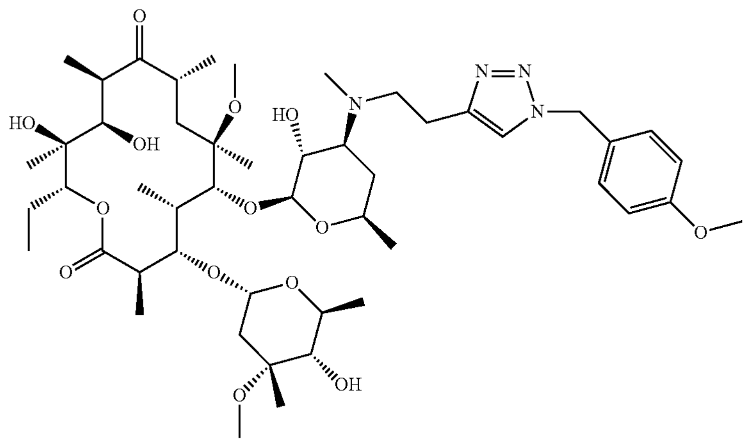 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc(OC)cc4)nn3)[C@H]2O)[C@](C)(OC)C[C@@H](C)C(=O)[C@H](C)[C@@H](O)[C@]1(C)O] |
| 325 | 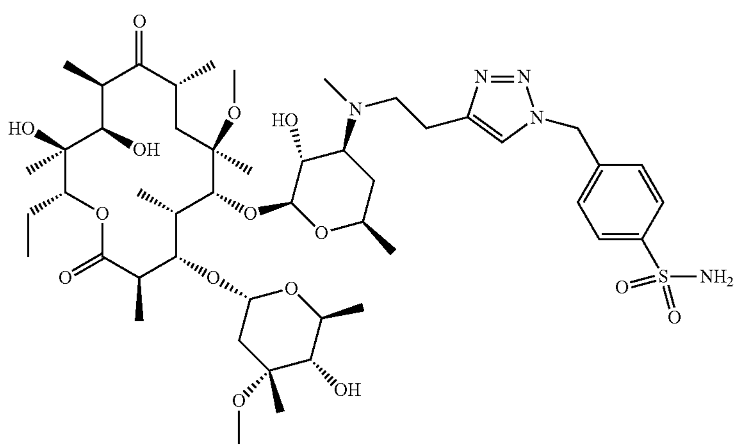 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc(S(N)(=O)=O)cc4)nn3)[C@H]2O)[C@](C)(OC)C[C@@H](C)C(=O)[C@H](C)[C@@H](O)[C@]1(C)O] |
| 326 | 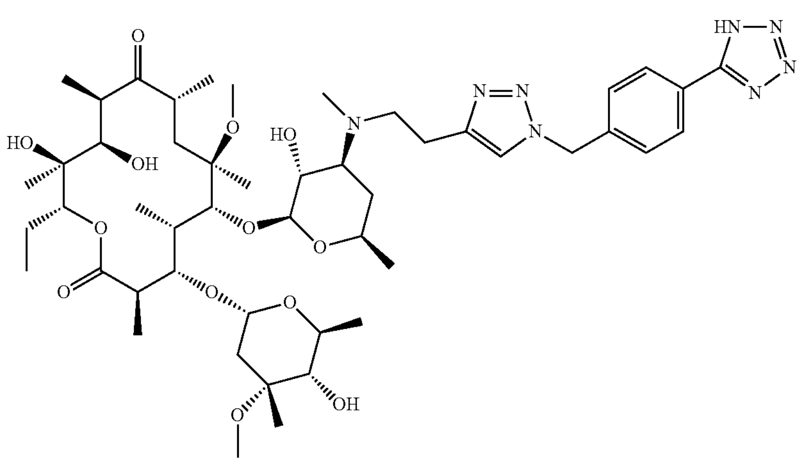 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc(-c5nnn[nH]5)cc4)nn3)[C@H]2O)[C@](C)(OC)C[C@@H](C)C(=O)[C@H](C)[C@@H](O)[C@]1(C)O] |

TABLE 1-continued

| Compound Number | Structure |
|---|---|
| 327 | 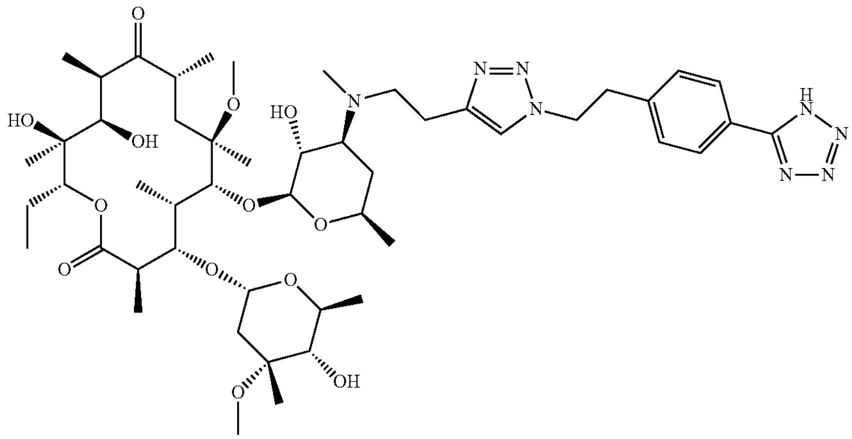 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc(-c5nnn[nH]5)cc4)nn3)[C@H]2O)[C@](C)(OC)C[C@@H](C)C(=O)[C@H](C)[C@@H](O)[C@]1(C)O] |
| 328 | 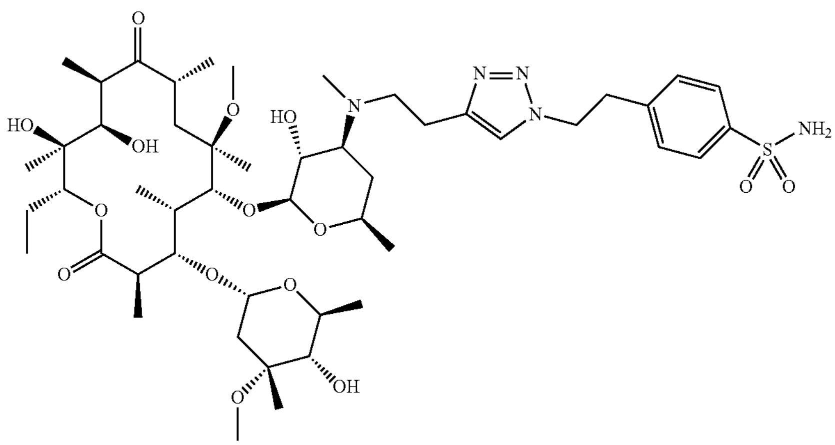 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc(S(N)(=O)=O)cc4)nn3)[C@H]2O)[C@](C)(OC)C[C@@H](C)C(=O)[C@H](C)[C@@H](O)[C@]1(C)O] |
| 329 | 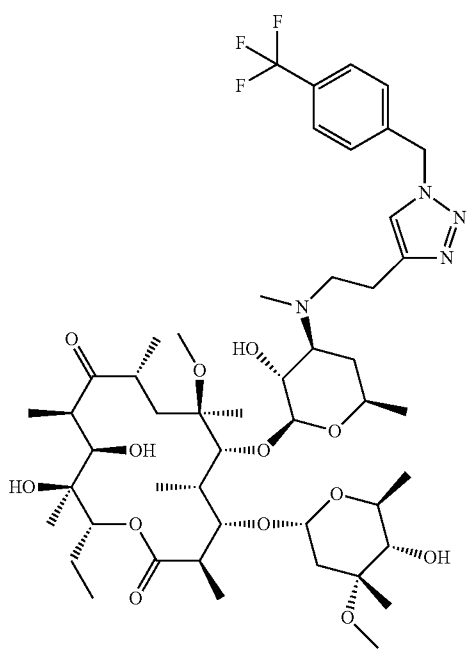 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc(C(F)(F)F)cc4)nn3)[C@H]2O)[C@](C)(OC)C[C@@H](C)C(=O)[C@H](C)[C@@H](O)[C@]1(C)O] |

TABLE 1-continued

| Compound Number | Structure |
| --- | --- |
| 330 | (chemical structure: macrolide with N-methyl-propyl-triazole-CH2-C6H4-NO2 substituent) |
| 331 | (chemical structure: macrolide with N-methyl-propyl-triazole-CH2-C6H4-F substituent) |
| 332 | (chemical structure: macrolide with N-methyl-propyl-triazole-CH2-C6H4-SO2NH2 substituent) |

TABLE 1-continued
| Compound Number | Structure |
|---|---|
| 333 | 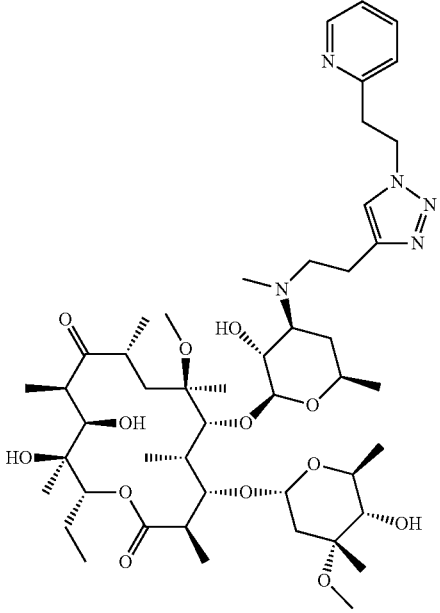 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccccn4)nn3)[C@H]2O)[C@](C)(OC)C[C@@H](C)C(=O)[C@H](C)[C@@H](O)[C@]1(C)O] |
| 334 | 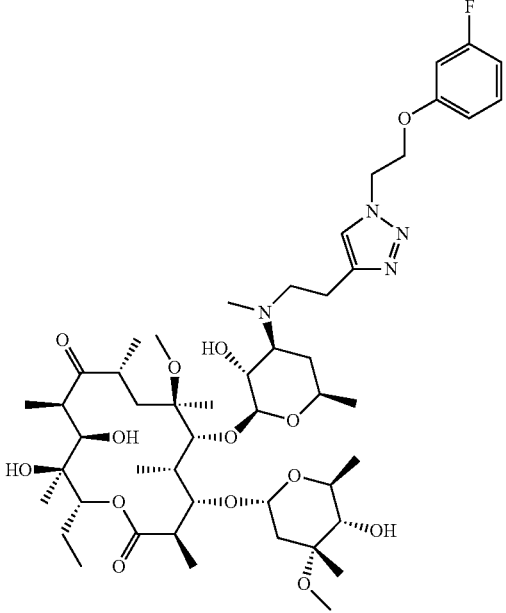 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCOc4cccc(F)c4)nn3)[C@H]2O)[C@](C)(OC)C[C@@H](C)C(=O)[C@H](C)[C@@H](O)[C@]1(C)O] |

TABLE 1-continued

| Compound Number | Structure |
|---|---|
| 335 | 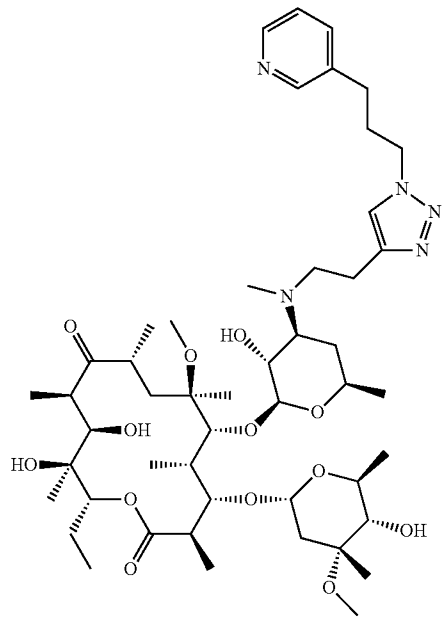 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCc4cccnc4)nn3)[C@H]2O)[C@](C)(OC)C[C@@H](C)C(=O)[C@H](C)[C@@H](O)[C@]1(C)O] |
| 336 | 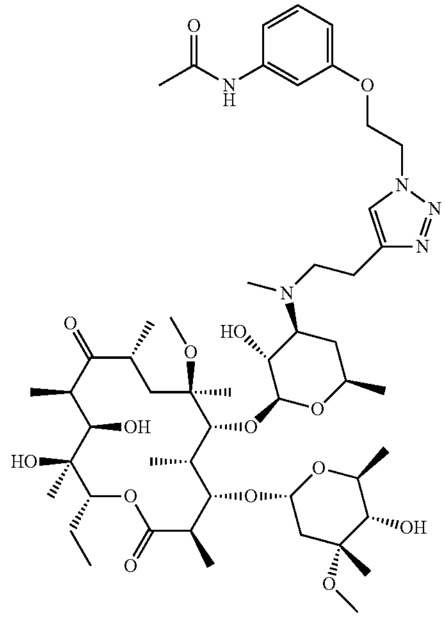 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCOc4cccc(NC(C)=O)c4)nn3)[C@H]2O)[C@](C)(OC)C[C@@H](C)C(=O)[C@H](C)[C@@H](O)[C@]1(C)O] |

TABLE 1-continued

| Compound Number | Structure |
|---|---|
| 337 | 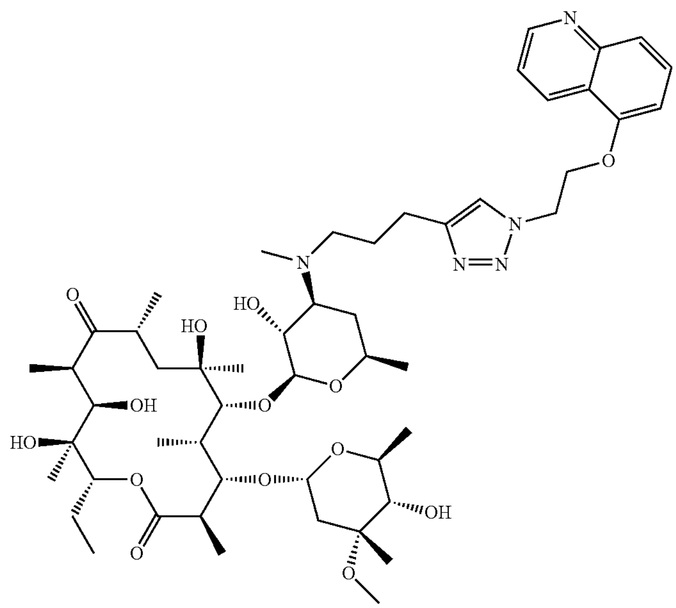 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCc3cn(CCOc4cccc5ncccc45)nn3)[C@H]2O)[C@](C)(O)C[C@@H](C)C(=O)[C@H](C)[C@@H](O)[C@]1(C)O] |
| 338 | 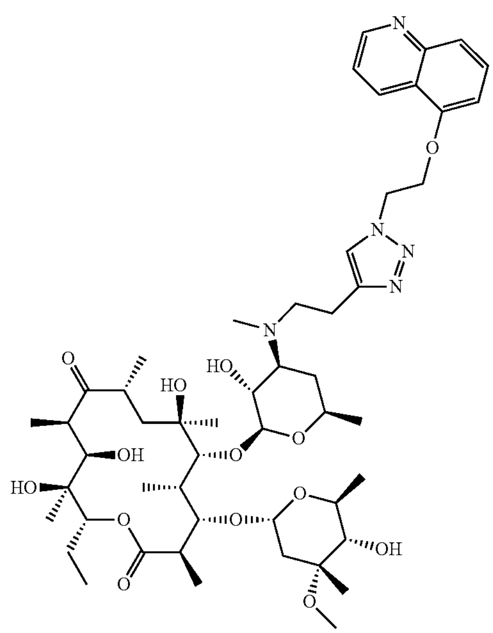 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCOc4cccc5ncccc45)nn3)[C@H]2O)[C@](C)(O)C[C@@H](C)C(=O)[C@H](C)[C@@H](O)[C@]1(C)O] |

TABLE 1-continued
| Compound Number | Structure |
|---|---|
| 339 | 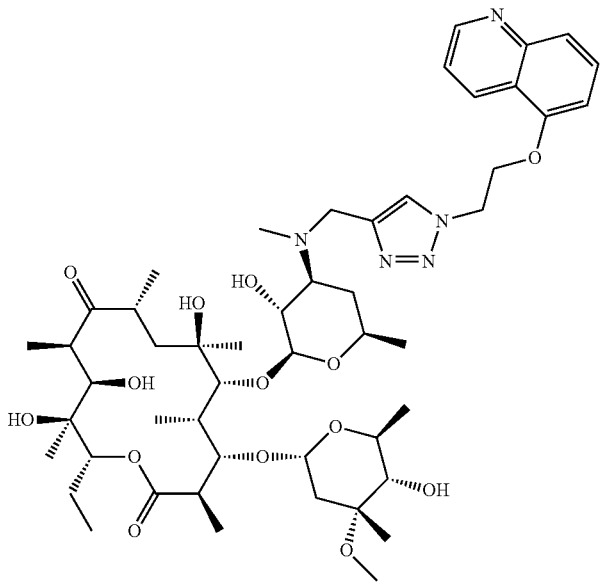 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)Cc3cn(CCOc4cccc5ncccc45)nn3)[C@H]2O)[C@](C)(O)C[C@@H](C)C(=O)[C@H](C)[C@@H](O)[C@]1(C)O] |
| 340 | 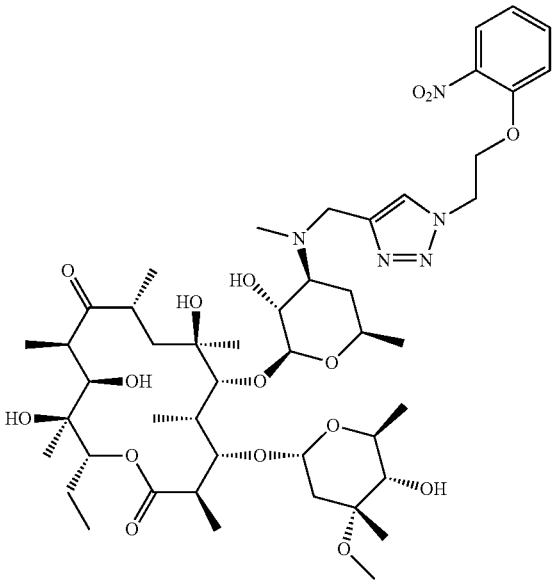 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)Cc3cn(CCOc4ccccc4[N+](=O)[O-])nn3)[C@H]2O)[C@](C)(O)C[C@@H](C)C(=O)[C@H](C)[C@@H](O)[C@]1(C)O] |

TABLE 1-continued
| Compound Number | Structure |
|---|---|
| 341 | 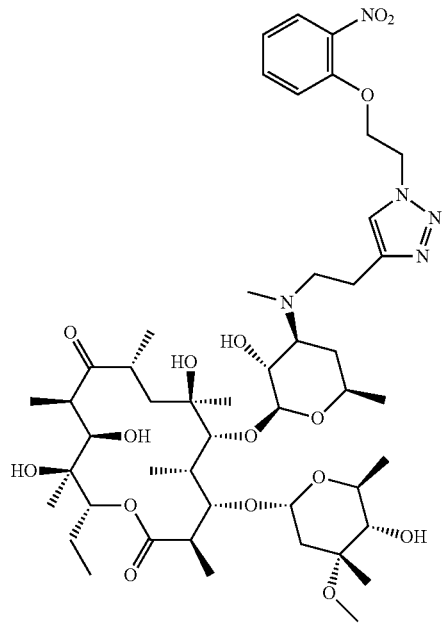 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCOc4ccccc4[N+](=O)[O-])nn3)[C@H]2O)[C@](C)(O)C[C@@H](C)C(=O)[C@H](C)[C@@H](O)[C@]1(C)O] |
| 342 | 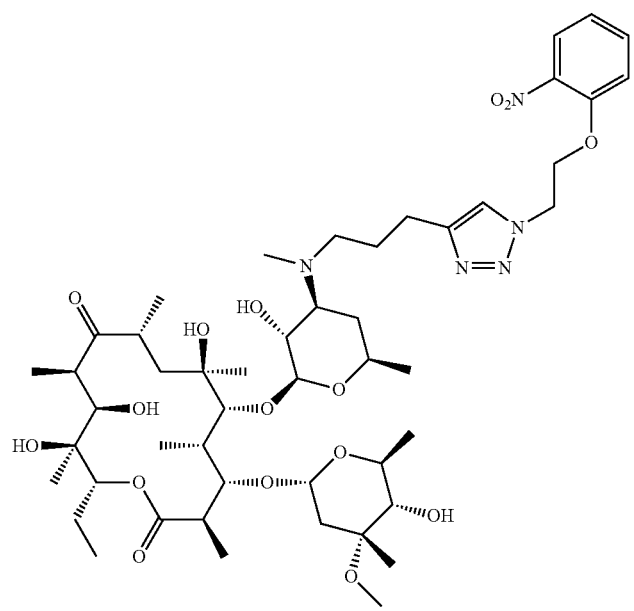 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCc3cn(CCOc4ccccc4[N+](=O)[O-])nn3)[C@H]2O)[C@](C)(O)C[C@@H](C)C(=O)[C@H](C)[C@@H](O)[C@]1(C)O] |

TABLE 1-continued
| Compound Number | Structure |
| --- | --- |
| 343 | 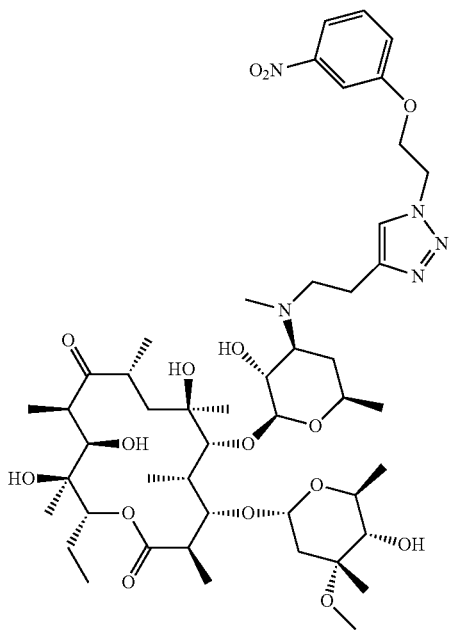 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCOc4cccc([N+](=O)[O-])c4)nn3)[C@H]2O)[C@](C)(O)C[C@@H](C)C(=O)[C@H](C)[C@@H](O)[C@]1(C)O] |
| 344 | 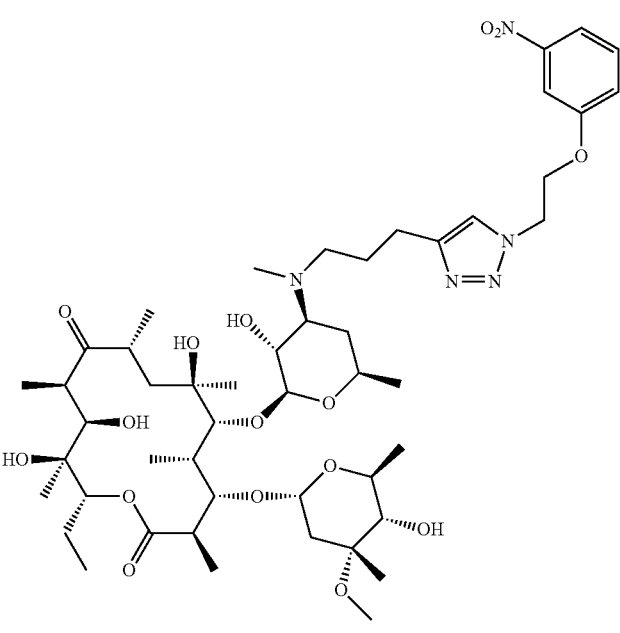 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCc3cn(CCOc4cccc([N+](=O)[O-])c4)nn3)[C@H]2O)[C@](C)(O)C[C@@H](C)C(=O)[C@H](C)[C@@H](O)[C@]1(C)O] |

TABLE 1-continued
| Compound Number | Structure |
|---|---|
| 345 | 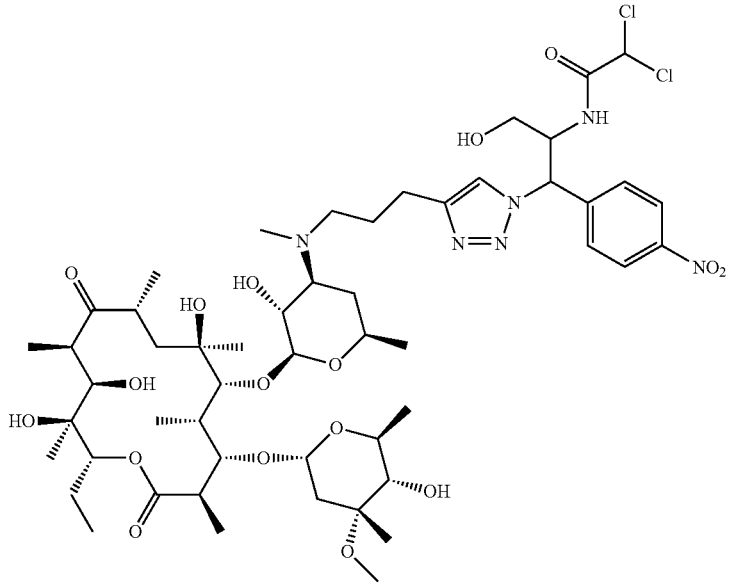 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCc3cn(C(c4ccc([N+](=O)[O-])cc4)C(CO)NC(=O)C(Cl)Cl)nn3)[C@H]2O)[C@](C)(O)C[C@@H](C)C(=O)[C@H](C)[C@@H](O)[C@]1(C)O] |
| 346 | 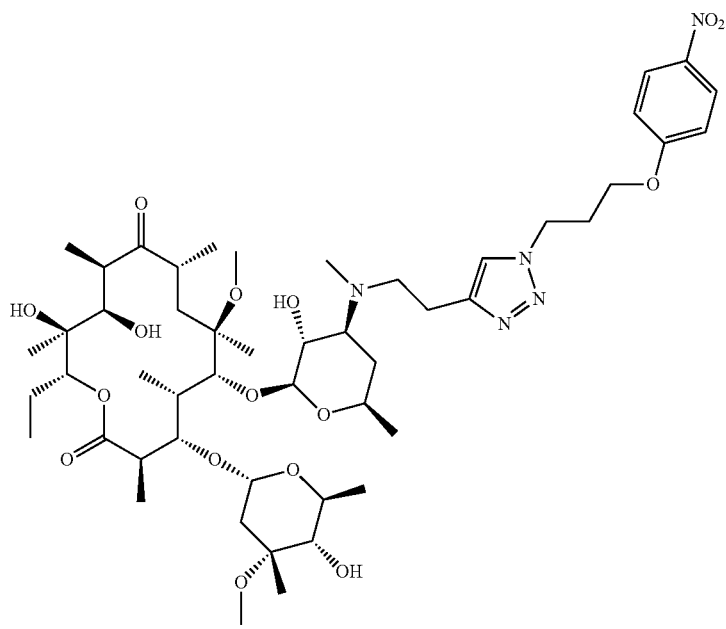 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc([N+](=O)[O-])cc4)nn3)[C@H]2O)[C@](C)(OC)C[C@@H](C)C(=O)[C@H](C)[C@@H](O)[C@]1(C)O] |

TABLE 1-continued
| Compound Number | Structure |
|---|---|
| 347 | 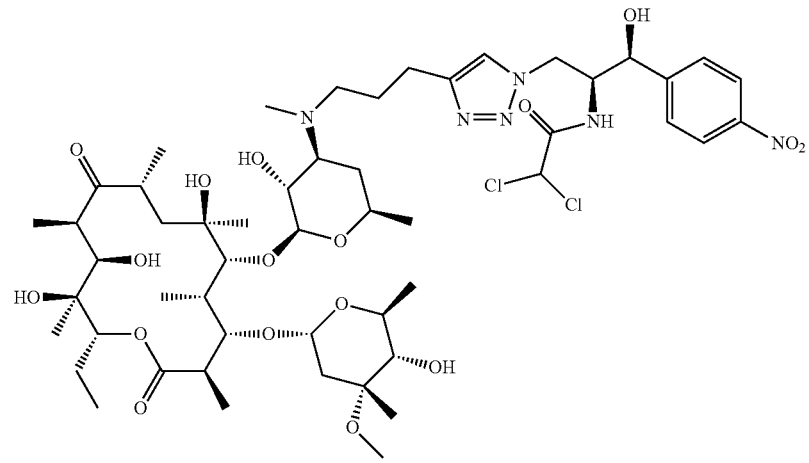 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCc3cn(C[C@H](NC(=O)C(Cl)Cl)[C@@H](O)c4ccc([N+](=O)[O-])cc4)nn3)[C@H]2O)[C@](C)(O)C[C@@H](C)C(=O)[C@H](C)[C@@H](O)[C@]1(C)O] |
| 348 | 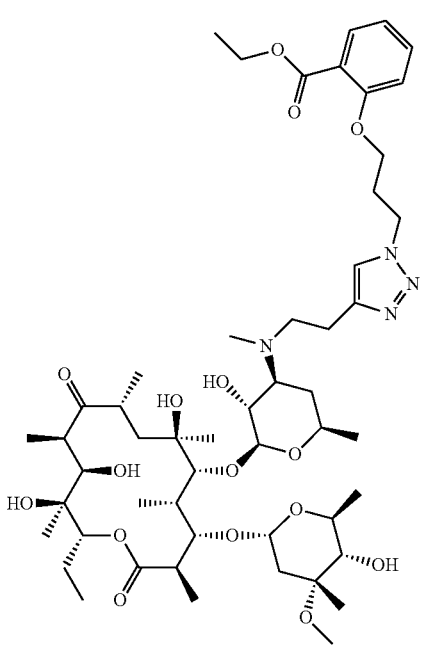 [SMILES: CCOC(=O)c1ccccc1OCCCn1cc(CCN(C)[C@H]2C[C@@H](C)O[C@@H](O[C@@H]3[C@@H](C)[C@H](O[C@H]4C[C@@](C)(OC)[C@@H](O)[C@H](C)O4)[C@@H](C)C(=O)O[C@H](CC)[C@@](C)(O)[C@H](O)[C@@H](C)C(=O)[C@H](C)C[C@@]3(C)O)[C@@H]2O)nn1] |

TABLE 1-continued
| Compound Number | Structure |
|---|---|
| 349 | 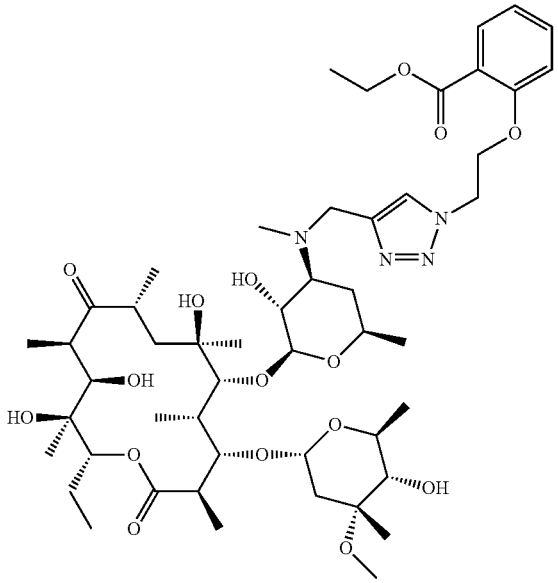 [SMILES: CCOC(=O)c1ccccc1OCCn1cc(CN(C)[C@H]2C[C@@H](C)O[C@@H](O[C@@H]3[C@@H](C)[C@H](O[C@H]4C[C@@](C)(OC)[C@@H](O)[C@H](C)O4)[C@@H](C)C(=O)O[C@H](CC)[C@@](C)(O)[C@H](O)[C@@H](C)C(=O)[C@H](C)C[C@@]3(C)O)[C@@H]2O)nn1] |
| 350 | 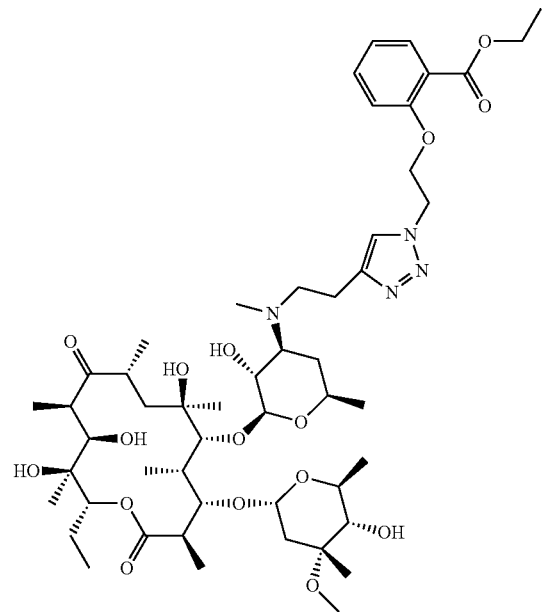 [SMILES: CCOC(=O)c1ccccc1OCCn1cc(CCN(C)[C@H]2C[C@@H](C)O[C@@H](O[C@@H]3[C@@H](C)[C@H](O[C@H]4C[C@@](C)(OC)[C@@H](O)[C@H](C)O4)[C@@H](C)C(=O)O[C@H](CC)[C@@](C)(O)[C@H](O)[C@@H](C)C(=O)[C@H](C)C[C@@]3(C)O)[C@@H]2O)nn1] |

TABLE 1-continued
| Compound Number | Structure |
|---|---|
| 351 | 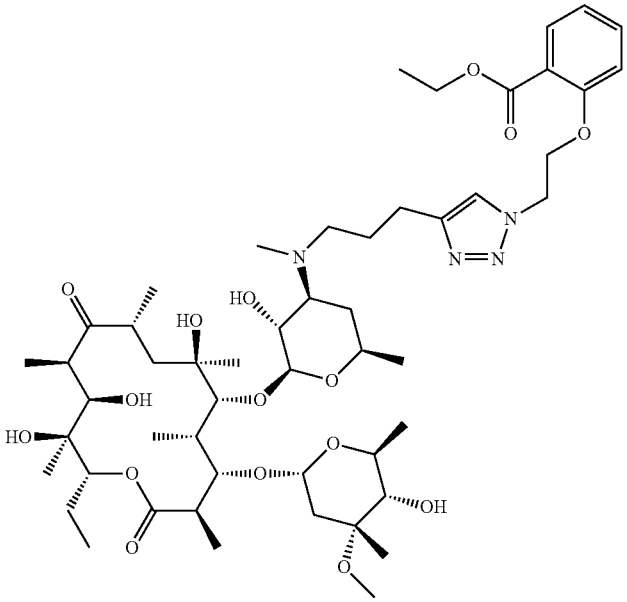 [SMILES: CCOC(=O)c1ccccc1OCCn1cc(CCCN(C)[C@H]2C[C@@H](C)O[C@@H](O[C@@H]3[C@@H](C)[C@H](O[C@H]4C[C@@](C)(OC)[C@@H](O)[C@H](C)O4)[C@@H](C)C(=O)O[C@H](CC)[C@@](C)(O)[C@H](O)[C@@H](C)C(=O)[C@H](C)C[C@@]3(C)O)[C@@H]2O)nn1] |
| 352 | 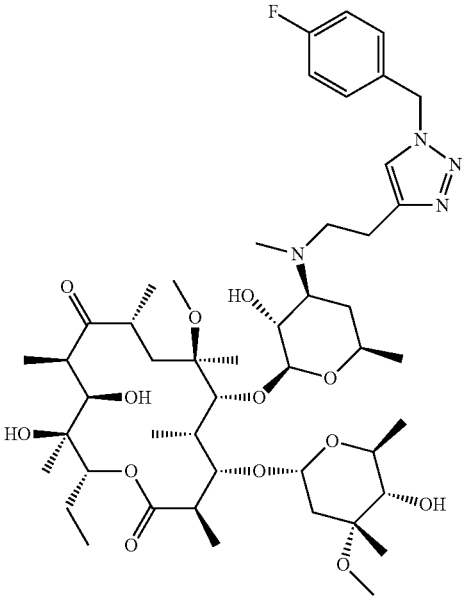 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc(F)cc4)nn3)[C@H]2O)[C@](C)(OC)C[C@@H](C)C(=O)[C@H](C)[C@@H](O)[C@]1(C)O] |

TABLE 1-continued

| Compound Number | Structure |
|---|---|
| 353 | 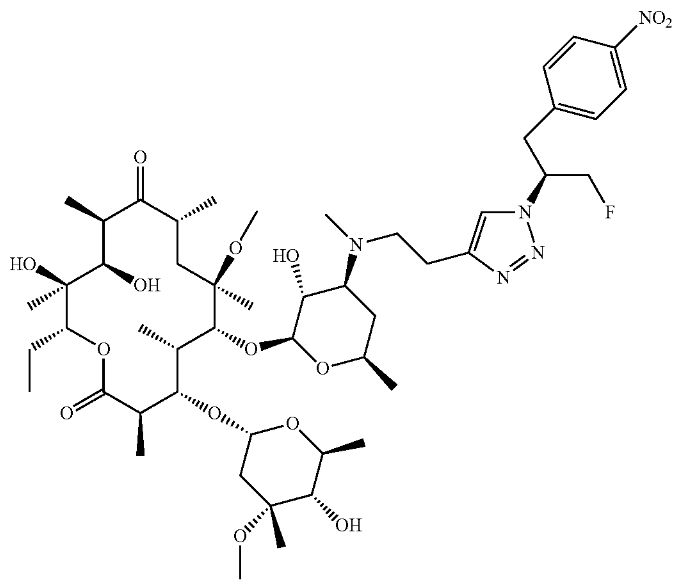 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CF)Cc4ccc([N+](=O)[O-])cc4)nn3)[C@H]2O)[C@](C)(OC)C[C@@H](C)C(=O)[C@H](C)[C@@H](O)[C@]1(C)O] |
| 354 | 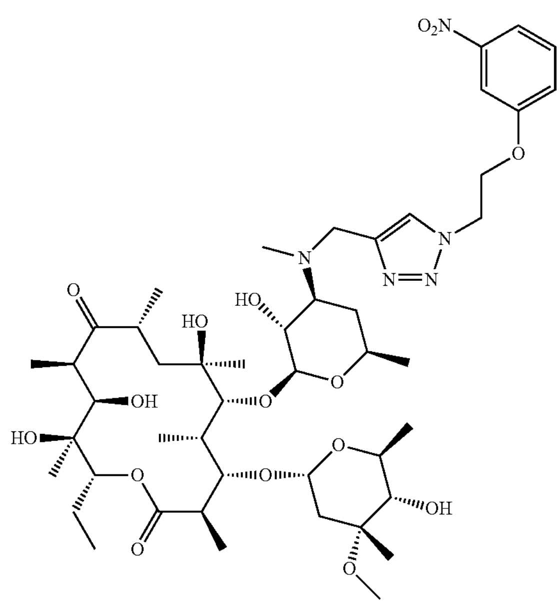 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)Cc3cn(CCOc4cccc([N+](=O)[O-])c4)nn3)[C@H]2O)[C@](C)(O)C[C@@H](C)C(=O)[C@H](C)[C@@H](O)[C@]1(C)O] |

TABLE 1-continued

| Compound Number | Structure |
|---|---|
| 355 | 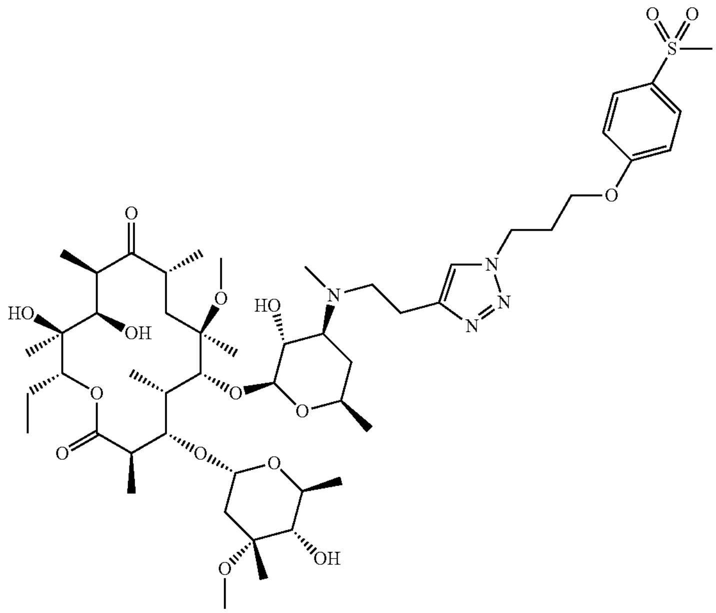 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(S(C)(=O)=O)cc4)nn3)[C@H]2O)[C@](C)(OC)C[C@@H](C)C(=O)[C@H](C)[C@@H](O)[C@]1(C)O] |
| 356 | 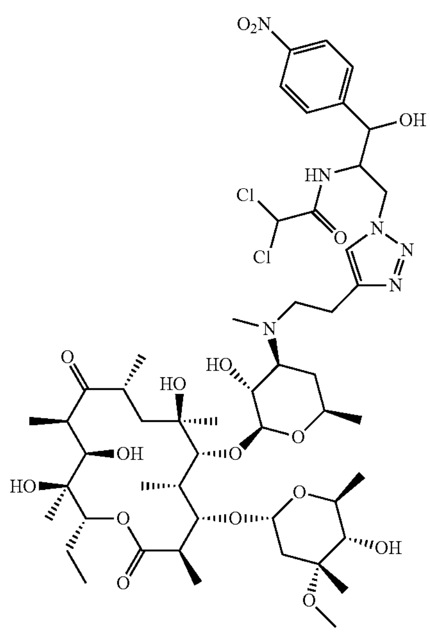 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CC(NC(=O)C(Cl)Cl)C(O)c4ccc([N+](=O)[O-])cc4)nn3)[C@H]2O)[C@](C)(O)C[C@@H](C)C(=O)[C@H](C)[C@@H](O)[C@]1(C)O] |

TABLE 1-continued

| Compound Number | Structure |
|---|---|
| 401 | 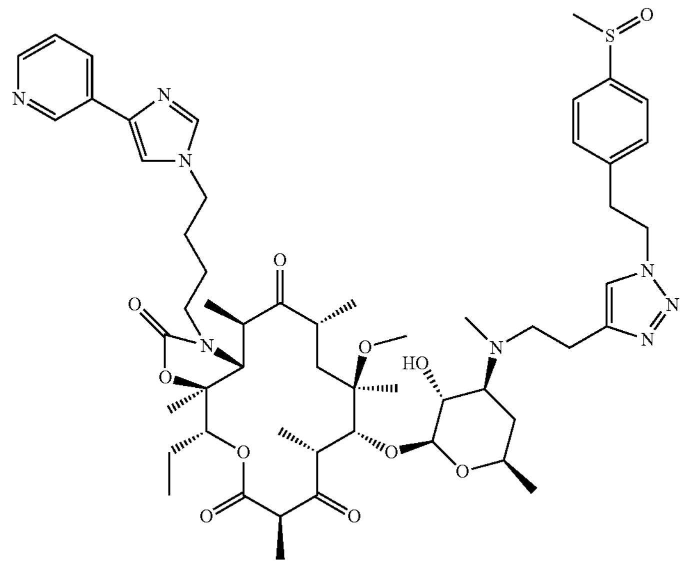 [SMILES: CC[C@H]1OC(=O)[C@H](C)C(=O)[C@H](C)[C@@H](O[C@@H]2O[C@H](C)C[C@H](N(C)CCc3cn(CCc4ccc(S(C)=O)cc4)nn3)[C@H]2O)[C@](C)(OC)C[C@@H](C)C(=O)[C@H](C)[C@H]2N(CCCCn3cnc(-c4cccnc4)c3)C(=O)O[C@]12C] |
| 402 | 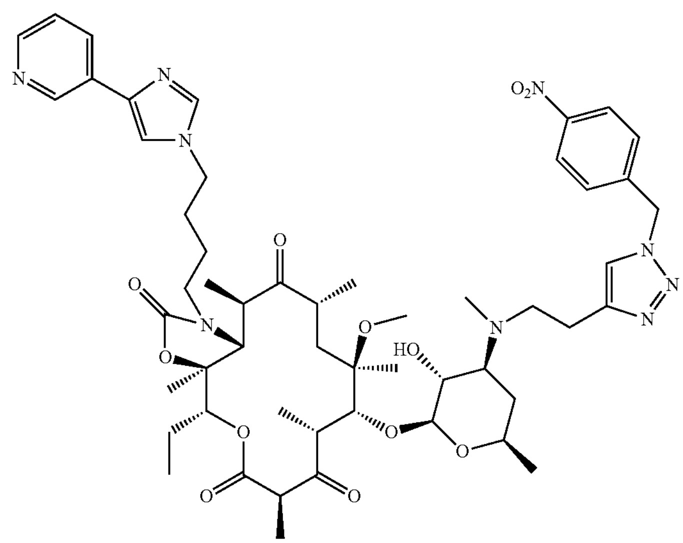 [SMILES: CC[C@H]1OC(=O)[C@H](C)C(=O)[C@H](C)[C@@H](O[C@@H]2O[C@H](C)C[C@H](N(C)CCc3cn(Cc4ccc([N+](=O)[O-])cc4)nn3)[C@H]2O)[C@](C)(OC)C[C@@H](C)C(=O)[C@H](C)[C@H]2N(CCCCn3cnc(-c4cccnc4)c3)C(=O)O[C@]12C] |

TABLE 1-continued
| Compound Number | Structure |
|---|---|
| 403 | 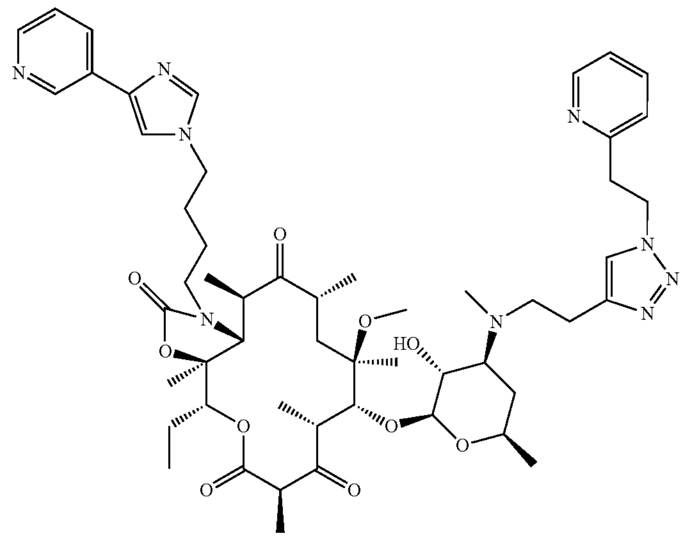 [SMILES: CC[C@H]1OC(=O)[C@H](C)C(=O)[C@H](C)[C@@H](O[C@@H]2O[C@H](C)C[C@H](N(C)CCc3cn(CCc4ccccn4)nn3)[C@H]2O)[C@](C)(OC)C[C@@H](C)C(=O)[C@H](C)[C@H]2N(CCCCn3cnc(-c4cccnc4)c3)C(=O)O[C@]12C] |
| 404 | 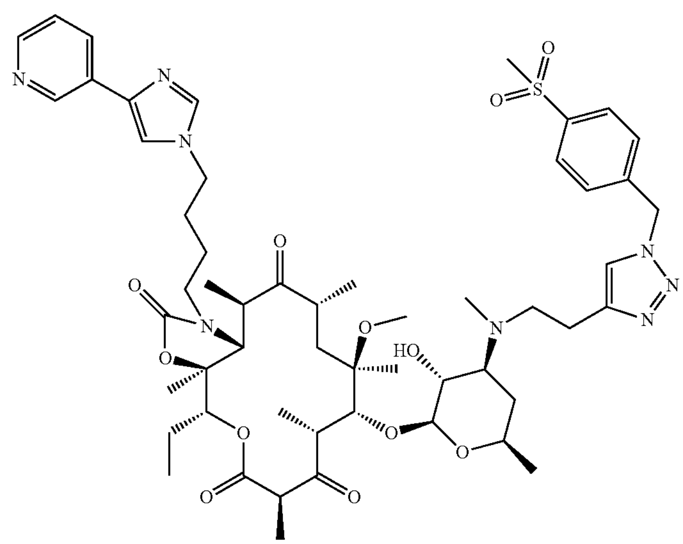 [SMILES: CC[C@H]1OC(=O)[C@H](C)C(=O)[C@H](C)[C@@H](O[C@@H]2O[C@H](C)C[C@H](N(C)CCc3cn(Cc4ccc(S(C)(=O)=O)cc4)nn3)[C@H]2O)[C@](C)(OC)C[C@@H](C)C(=O)[C@H](C)[C@H]2N(CCCCn3cnc(-c4cccnc4)c3)C(=O)O[C@]12C] |

TABLE 1-continued
| Compound Number | Structure |
|---|---|
| 405 | 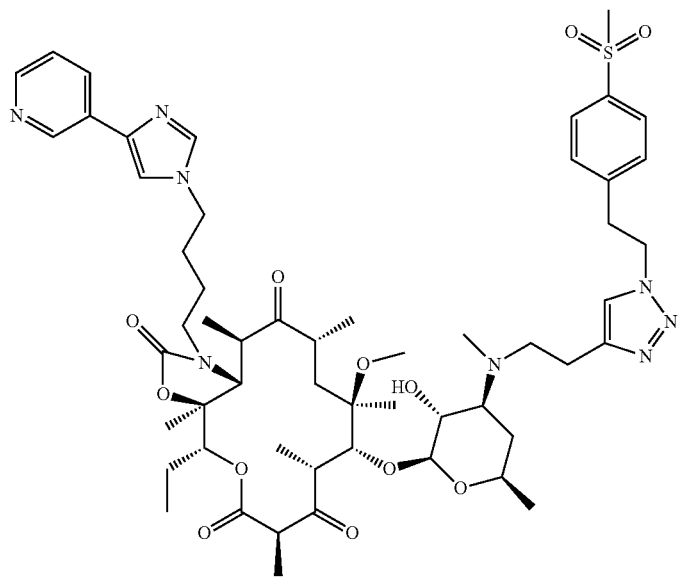 [SMILES: CC[C@H]1OC(=O)[C@H](C)C(=O)[C@H](C)[C@@H](O[C@@H]2O[C@H](C)C[C@H](N(C)CCc3cn(CCc4ccc(S(C)(=O)=O)cc4)nn3)[C@H]2O)[C@](C)(OC)C[C@@H](C)C(=O)[C@H](C)[C@H]2N(CCCCn3cnc(-c4cccnc4)c3)C(=O)O[C@]12C] |
| 406 | 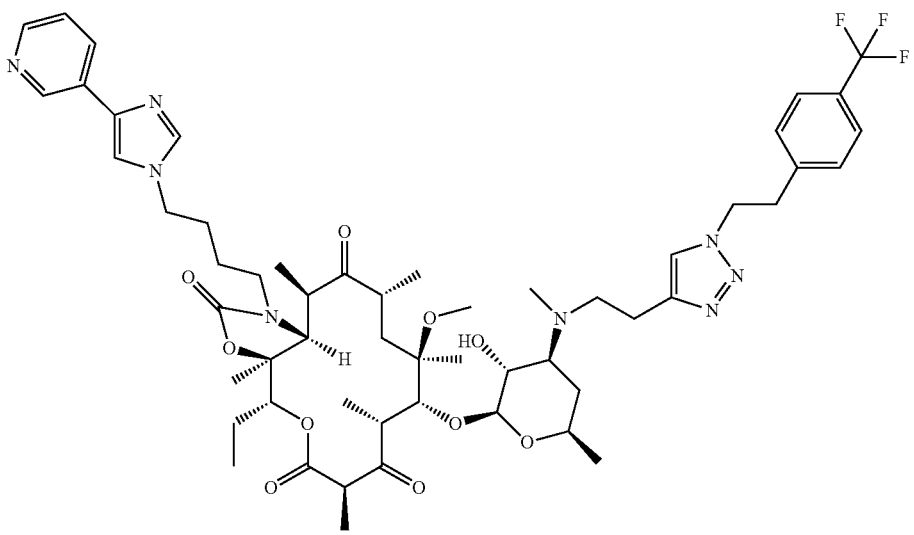 |

TABLE 1-continued
| Compound Number | Structure |
|---|---|
| 407 | 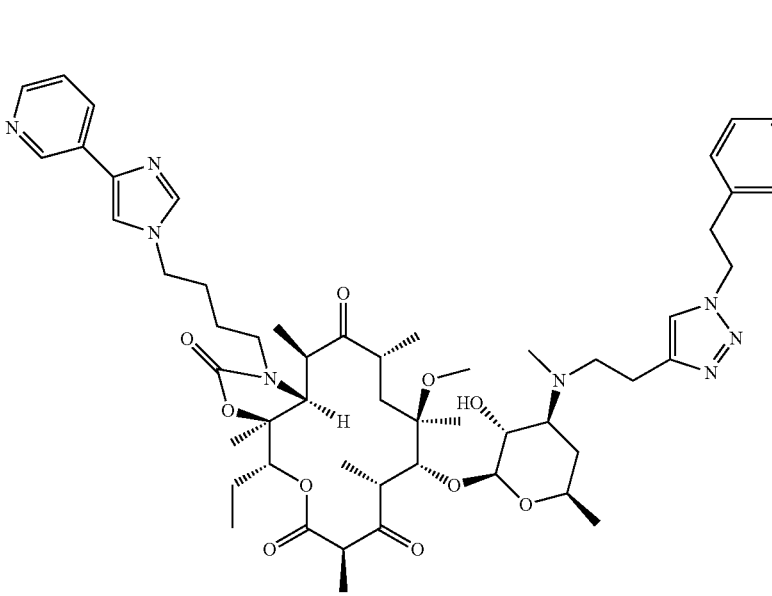 |
| 408 | 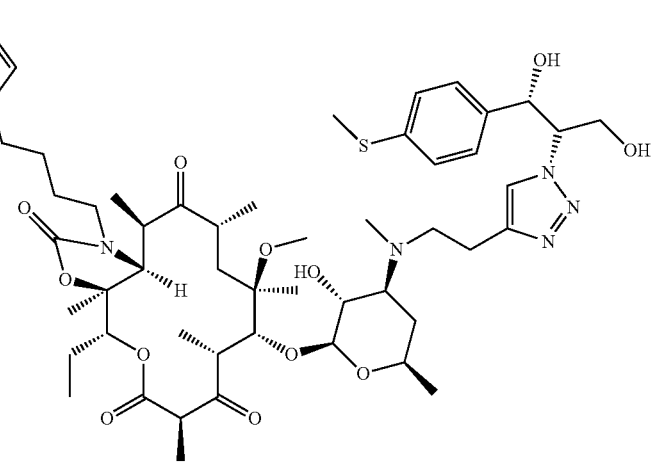 |

TABLE 1-continued

| Compound Number | Structure |
|---|---|
| 409 | 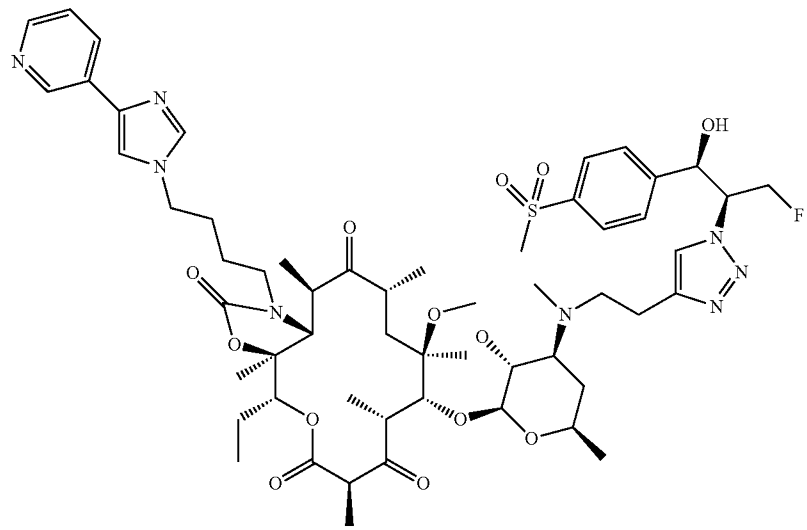 [SMILES: CC[C@H]1OC(=O)[C@H](C)C(=O)[C@H](C)[C@@H](O[C@@H]2O[C@H](C)C[C@H](N(C)CCc3cn([C@H](CF)[C@H](O)c4ccc(S(C)(=O)=O)cc4)nn3)[C@H]2O)[C@](C)(OC)C[C@@H](C)C(=O)[C@H](C)[C@H]2N(CCCCn3cnc(-c4cccnc4)c3)C(=O)O[C@]12C] |
| 410 | 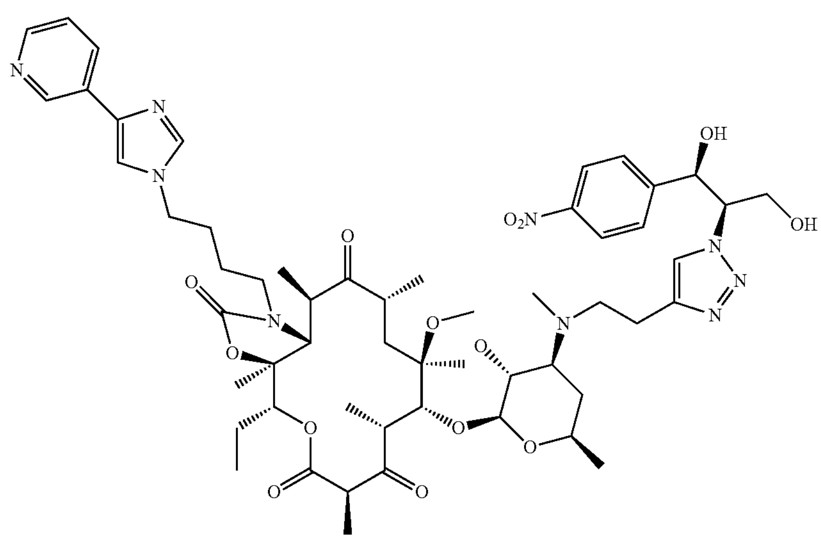 [SMILES: CC[C@H]1OC(=O)[C@H](C)C(=O)[C@H](C)[C@@H](O[C@@H]2O[C@H](C)C[C@H](N(C)CCc3cn([C@H](CO)[C@H](O)c4ccc([N+](=O)[O-])cc4)nn3)[C@H]2O)[C@](C)(OC)C[C@@H](C)C(=O)[C@H](C)[C@H]2N(CCCCn3cnc(-c4cccnc4)c3)C(=O)O[C@]12C] |

TABLE 1-continued
| Compound Number | Structure |
|---|---|
| 411 | 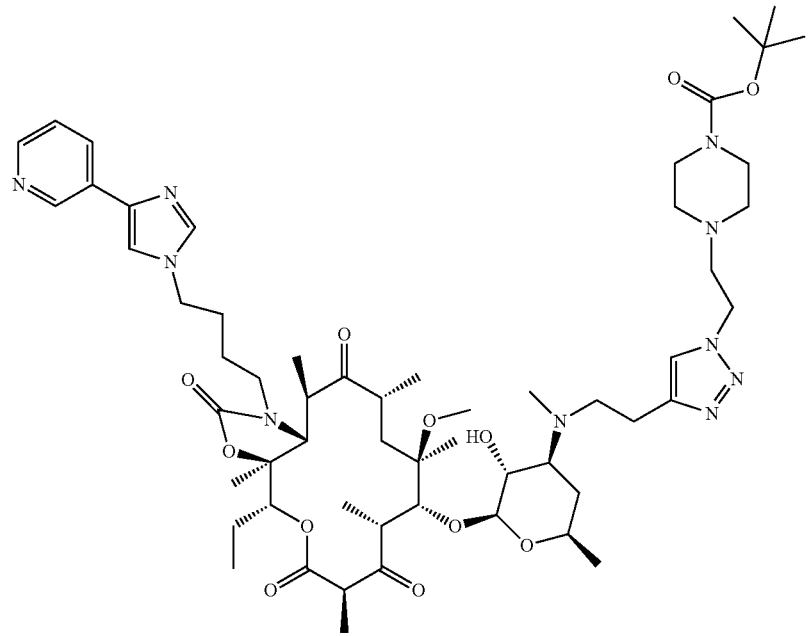 [SMILES: CC[C@H]1OC(=O)[C@H](C)C(=O)[C@H](C)[C@@H](O[C@@H]2O[C@H](C)C[C@H](N(C)CCc3cn(CCN4CCN(C(=O)OC(C)(C)C)CC4)nn3)[C@H]2O)[C@](C)(OC)C[C@@H](C)C(=O)[C@H](C)[C@H]2N(CCCCn3cnc(-c4cccnc4)c3)C(=O)O[C@]12C] |
| 412 | 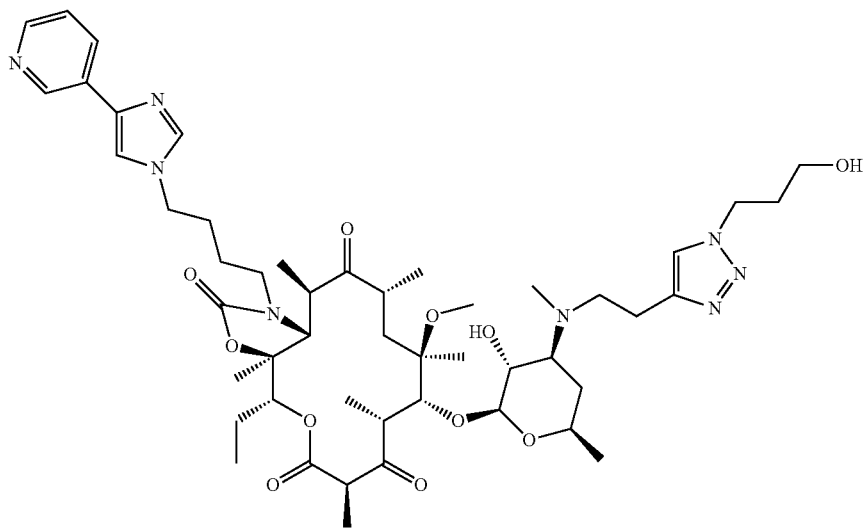 [SMILES: CC[C@H]1OC(=O)[C@H](C)C(=O)[C@H](C)[C@@H](O[C@@H]2O[C@H](C)C[C@H](N(C)CCc3cn(CCCO)nn3)[C@H]2O)[C@](C)(OC)C[C@@H](C)C(=O)[C@H](C)[C@H]2N(CCCCn3cnc(-c4cccnc4)c3)C(=O)O[C@]12C] |

TABLE 1-continued

| Compound Number | Structure |
|---|---|
| 413 | 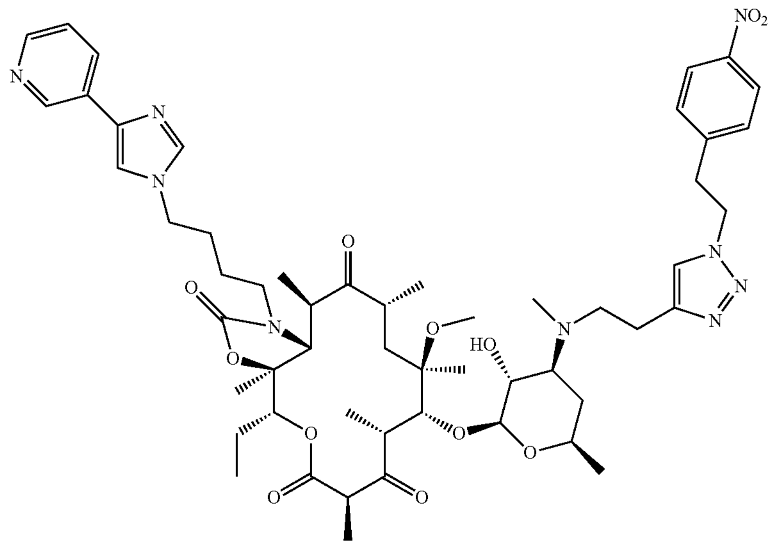 [SMILES: CC[C@H]1OC(=O)[C@H](C)C(=O)[C@H](C)[C@@H](O[C@@H]2O[C@H](C)C[C@H](N(C)CCc3cn(CCc4ccc([N+](=O)[O-])cc4)nn3)[C@H]2O)[C@](C)(OC)C[C@@H](C)C(=O)[C@H](C)[C@H]2N(CCCCn3cnc(-c4cccnc4)c3)C(=O)O[C@]12C] |
| 414 | 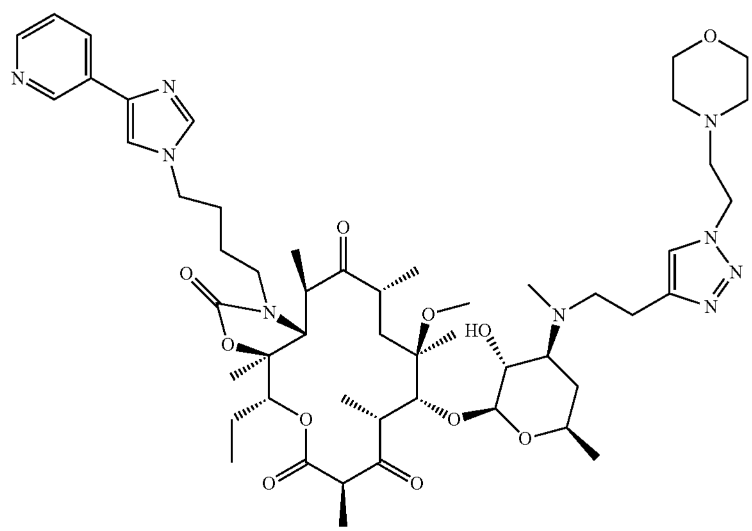 [SMILES: CC[C@H]1OC(=O)[C@H](C)C(=O)[C@H](C)[C@@H](O[C@@H]2O[C@H](C)C[C@H](N(C)CCc3cn(CCN4CCOCC4)nn3)[C@H]2O)[C@](C)(OC)C[C@@H](C)C(=O)[C@H](C)[C@H]2N(CCCCn3cnc(-c4cccnc4)c3)C(=O)O[C@]12C] |
| 415 | 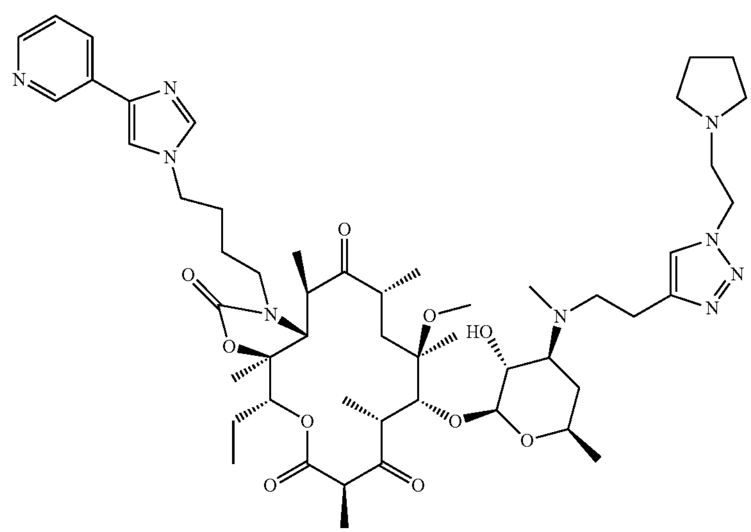 [SMILES: CC[C@H]1OC(=O)[C@H](C)C(=O)[C@H](C)[C@@H](O[C@@H]2O[C@H](C)C[C@H](N(C)CCc3cn(CCN4CCCC4)nn3)[C@H]2O)[C@](C)(OC)C[C@@H](C)C(=O)[C@H](C)[C@H]2N(CCCCn3cnc(-c4cccnc4)c3)C(=O)O[C@]12C] |

TABLE 1-continued

| Compound Number | Structure |
|---|---|
| 416 | 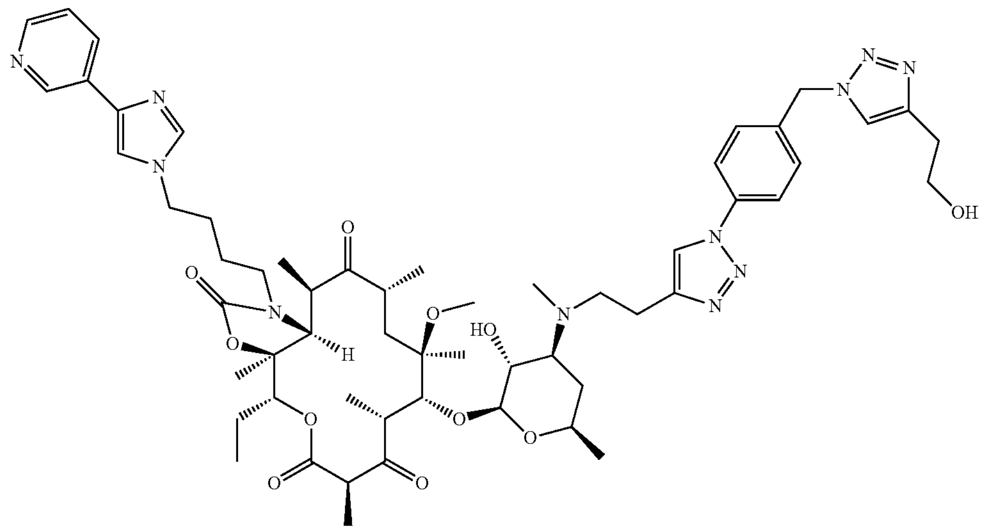 |
| 417 | 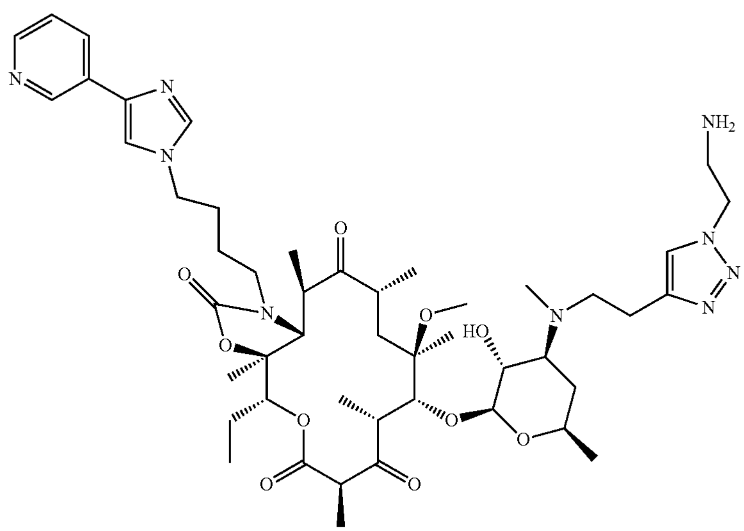 [SMILES: CC[C@H]1OC(=O)[C@H](C)C(=O)[C@H](C)[C@@H](O[C@@H]2O[C@H](C)C[C@H](N(C)CCc3cn(CCN)nn3)[C@H]2O)[C@](C)(OC)C[C@@H](C)C(=O)[C@H](C)[C@H]2N(CCCCn3cnc(-c4cccnc4)c3)C(=O)O[C@]12C] |
| 425 | 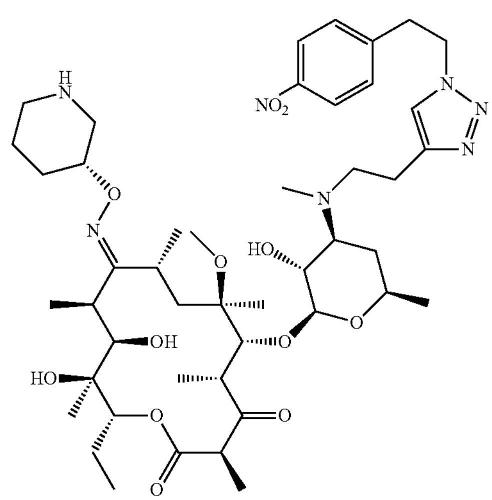 [SMILES: CC[C@H]1OC(=O)[C@H](C)C(=O)[C@H](C)[C@@H](O[C@@H]2O[C@H](C)C[C@H](N(C)CCc3cn(CCc4ccc([N+](=O)[O-])cc4)nn3)[C@H]2O)[C@](C)(OC)C[C@@H](C)/C(=N\O[C@@H]2CCCNC2)[C@H](C)[C@@H](O)[C@]1(C)O] |

US 8,841,263 B2
287                                                                                     288
TABLE 1-continued
| Compound Number | Structure |
|---|---|
| 426 | 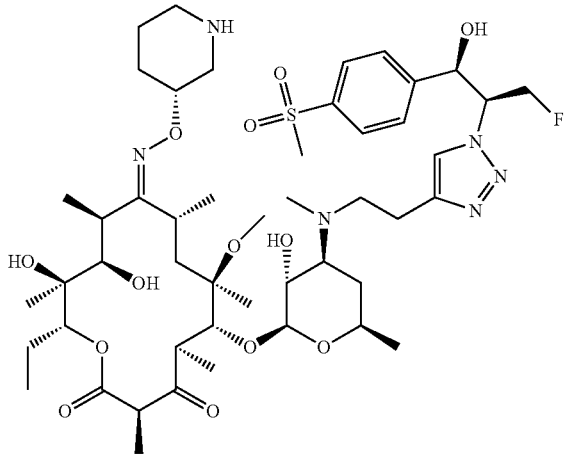 [SMILES: CC[C@H]1OC(=O)[C@H](C)C(=O)[C@H](C)[C@@H](O[C@@H]2O[C@H](C)C[C@H](N(C)CCc3cn([C@H](CF)[C@H](O)c4ccc(S(C)(=O)=O)cc4)nn3)[C@H]2O)[C@](C)(OC)C[C@@H](C)/C(=N\O[C@@H]2CCCNC2)[C@H](C)[C@@H](O)[C@]1(C)O] |
| 427 | 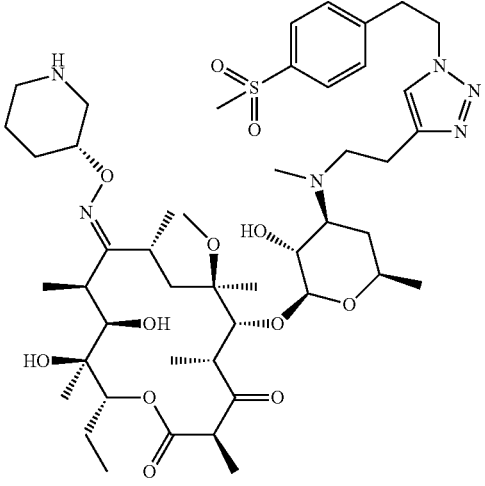 [SMILES: CC[C@H]1OC(=O)[C@H](C)C(=O)[C@H](C)[C@@H](O[C@@H]2O[C@H](C)C[C@H](N(C)CCc3cn(CCc4ccc(S(C)(=O)=O)cc4)nn3)[C@H]2O)[C@](C)(OC)C[C@@H](C)/C(=N\O[C@@H]2CCCNC2)[C@H](C)[C@@H](O)[C@]1(C)O] |
| 428 | 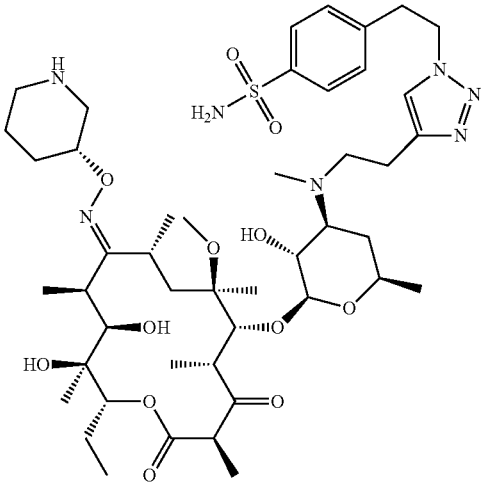 [SMILES: CC[C@H]1OC(=O)[C@H](C)C(=O)[C@H](C)[C@@H](O[C@@H]2O[C@H](C)C[C@H](N(C)CCc3cn(CCc4ccc(S(N)(=O)=O)cc4)nn3)[C@H]2O)[C@](C)(OC)C[C@@H](C)/C(=N\O[C@@H]2CCCNC2)[C@H](C)[C@@H](O)[C@]1(C)O] |

TABLE 1-continued

| Compound Number | Structure |
|---|---|
| 429 | 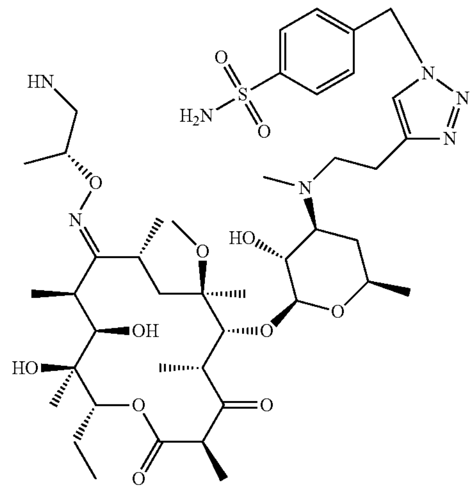 [SMILES: CC[C@H]1OC(=O)[C@H](C)C(=O)[C@H](C)[C@@H](O[C@@H]2O[C@H](C)C[C@H](N(C)CCc3cn(Cc4ccc(S(N)(=O)=O)cc4)nn3)[C@H]2O)[C@](C)(OC)C[C@@H](C)/C(=N\O[C@H](C)CN)[C@H](C)[C@@H](O)[C@]1(C)O] |
| 430 | 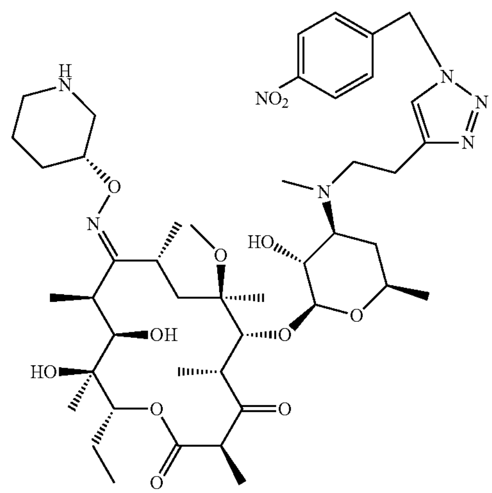 [SMILES: CC[C@H]1OC(=O)[C@H](C)C(=O)[C@H](C)[C@@H](O[C@@H]2O[C@H](C)C[C@H](N(C)CCc3cn(Cc4ccc([N+](=O)[O-])cc4)nn3)[C@H]2O)[C@](C)(OC)C[C@@H](C)/C(=N\O[C@@H]2CCCNC2)[C@H](C)[C@@H](O)[C@]1(C)O] |
| 431 | 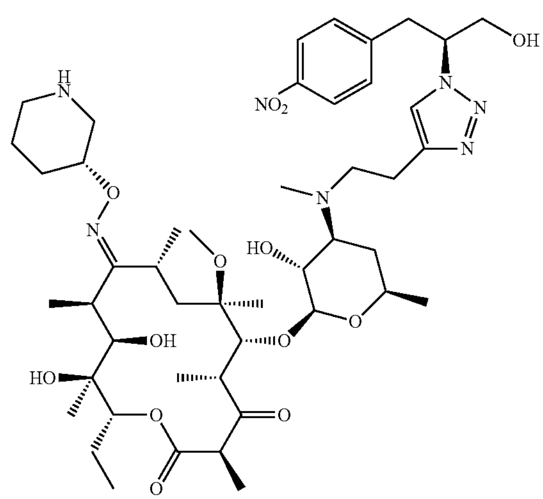 [SMILES: CC[C@H]1OC(=O)[C@H](C)C(=O)[C@H](C)[C@@H](O[C@@H]2O[C@H](C)C[C@H](N(C)CCc3cn([C@H](CO)Cc4ccc([N+](=O)[O-])cc4)nn3)[C@H]2O)[C@](C)(OC)C[C@@H](C)/C(=N\O[C@@H]2CCCNC2)[C@H](C)[C@@H](O)[C@]1(C)O] |

TABLE 1-continued

| Compound Number | Structure |
|---|---|
| 432 | 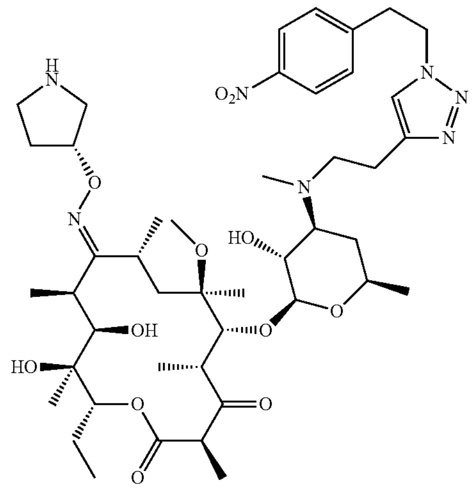 [SMILES: CC[C@H]1OC(=O)[C@H](C)C(=O)[C@H](C)[C@@H](O[C@@H]2O[C@H](C)C[C@H](N(C)CCc3cn(CCc4ccc([N+](=O)[O-])cc4)nn3)[C@H]2O)[C@](C)(OC)C[C@@H](C)/C(=N\O[C@@H]2CCNC2)[C@H](C)[C@@H](O)[C@]1(C)O] |
| 433 | 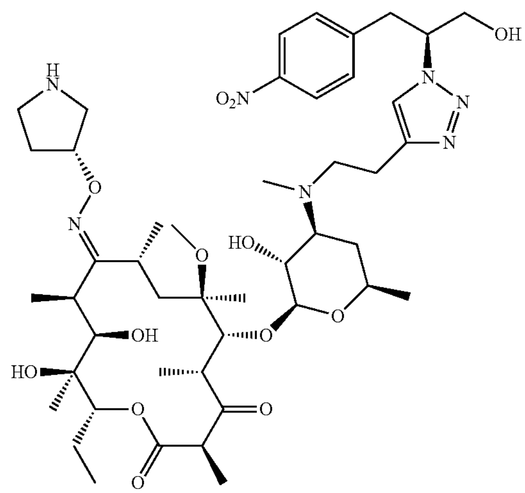 [SMILES: CC[C@H]1OC(=O)[C@H](C)C(=O)[C@H](C)[C@@H](O[C@@H]2O[C@H](C)C[C@H](N(C)CCc3cn([C@H](CO)Cc4ccc([N+](=O)[O-])cc4)nn3)[C@H]2O)[C@](C)(OC)C[C@@H](C)/C(=N\O[C@@H]2CCNC2)[C@H](C)[C@@H](O)[C@]1(C)O] |
| 434 | 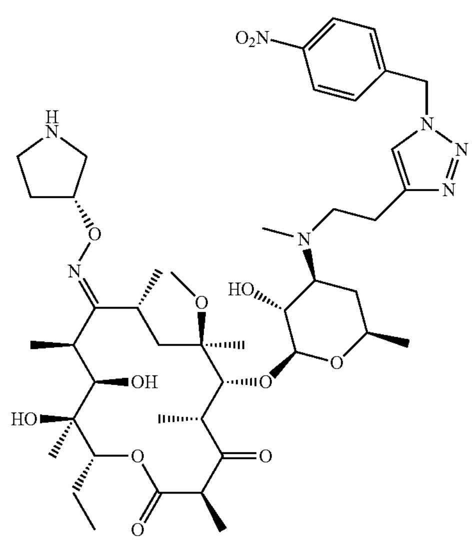 [SMILES: CC[C@H]1OC(=O)[C@H](C)C(=O)[C@H](C)[C@@H](O[C@@H]2O[C@H](C)C[C@H](N(C)CCc3cn(Cc4ccc([N+](=O)[O-])cc4)nn3)[C@H]2O)[C@](C)(OC)C[C@@H](C)/C(=N\O[C@@H]2CCNC2)[C@H](C)[C@@H](O)[C@]1(C)O] |

TABLE 1-continued

| Compound Number | Structure |
| --- | --- |
| 435 | 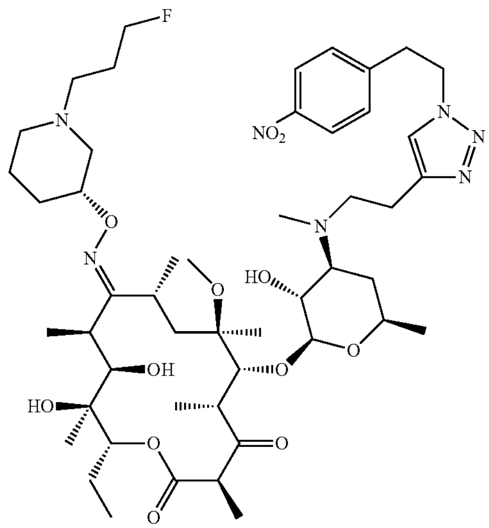 [SMILES: CC[C@H]1OC(=O)[C@H](C)C(=O)[C@H](C)[C@@H](O[C@@H]2O[C@H](C)C[C@H](N(C)CCc3cn(CCc4ccc([N+](=O)[O-])cc4)nn3)[C@H]2O)[C@](C)(OC)C[C@@H](C)/C(=N\O[C@@H]2CCCN(CCCF)C2)[C@H](C)[C@@H](O)[C@]1(C)O] |
| 436 | 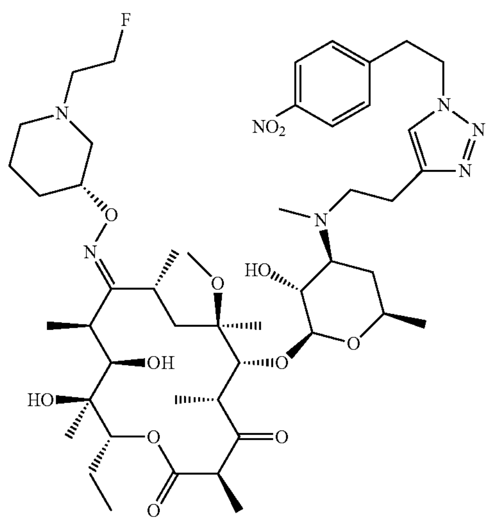 [SMILES: CC[C@H]1OC(=O)[C@H](C)C(=O)[C@H](C)[C@@H](O[C@@H]2O[C@H](C)C[C@H](N(C)CCc3cn(CCc4ccc([N+](=O)[O-])cc4)nn3)[C@H]2O)[C@](C)(OC)C[C@@H](C)/C(=N\O[C@@H]2CCCN(CCF)C2)[C@H](C)[C@@H](O)[C@]1(C)O] |
| 437 | 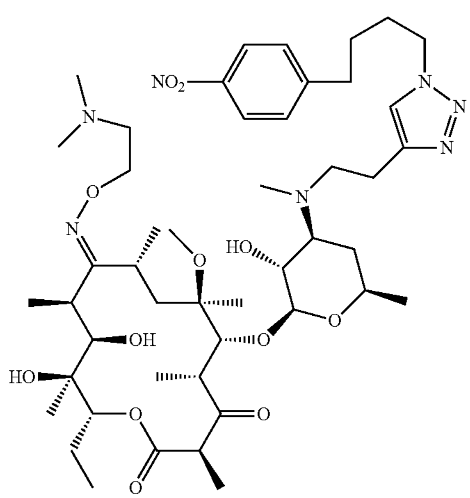 [SMILES: CC[C@H]1OC(=O)[C@H](C)C(=O)[C@H](C)[C@@H](O[C@@H]2O[C@H](C)C[C@H](N(C)CCc3cn(CCCCc4ccc([N+](=O)[O-])cc4)nn3)[C@H]2O)[C@](C)(OC)C[C@@H](C)/C(=N\OCCN(C)C)[C@H](C)[C@@H](O)[C@]1(C)O] |

TABLE 1-continued
| Compound Number | Structure |
|---|---|
| 438 | 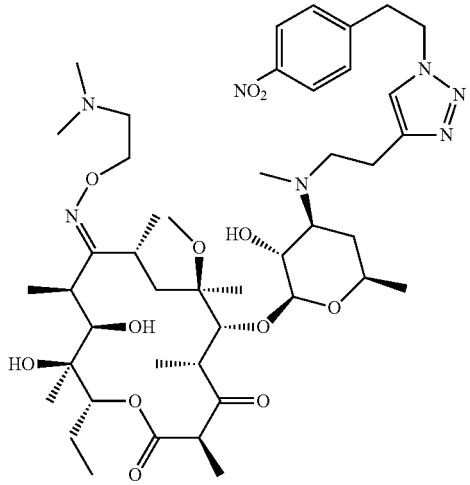 [SMILES: CC[C@H]1OC(=O)[C@H](C)C(=O)[C@H](C)[C@@H](O[C@@H]2O[C@H](C)C[C@H](N(C)CCc3cn(CCc4ccc([N+](=O)[O-])cc4)nn3)[C@H]2O)[C@](C)(OC)C[C@@H](C)/C(=N\OCCN(C)C)[C@H](C)[C@@H](O)[C@]1(C)O] |
| 439 | 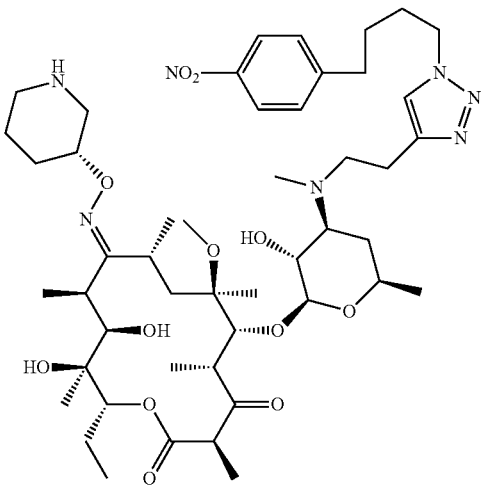 [SMILES: CC[C@H]1OC(=O)[C@H](C)C(=O)[C@H](C)[C@@H](O[C@@H]2O[C@H](C)C[C@H](N(C)CCc3cn(CCCCc4ccc([N+](=O)[O-])cc4)nn3)[C@H]2O)[C@](C)(OC)C[C@@H](C)/C(=N\O[C@@H]2CCCNC2)[C@H](C)[C@@H](O)[C@]1(C)O] |
| 440 | 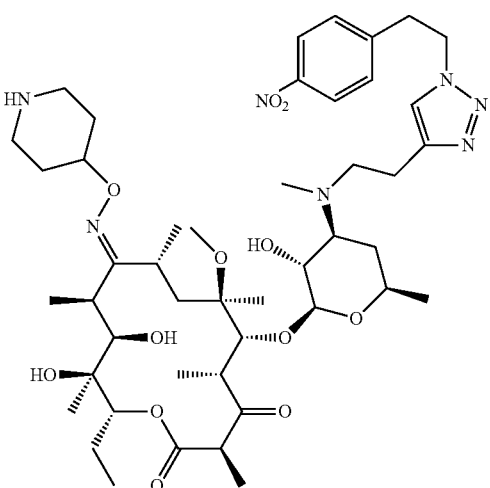 [SMILES: CC[C@H]1OC(=O)[C@H](C)C(=O)[C@H](C)[C@@H](O[C@@H]2O[C@H](C)C[C@H](N(C)CCc3cn(CCc4ccc([N+](=O)[O-])cc4)nn3)[C@H]2O)[C@](C)(OC)C[C@@H](C)/C(=N\OC2CCNCC2)[C@H](C)[C@@H](O)[C@]1(C)O] |

US 8,841,263 B2
297                                                                                                          298
TABLE 1-continued
| Compound Number | Structure |
|---|---|
| 441 | 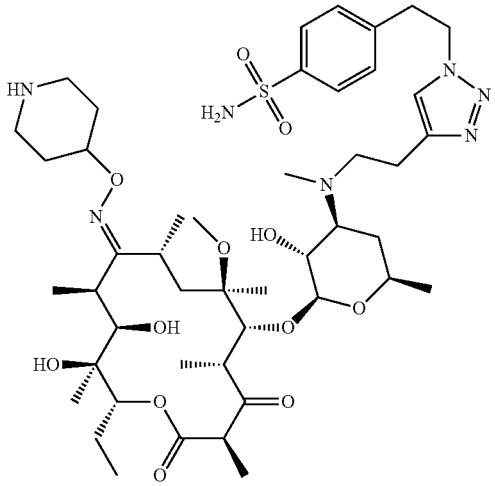 [SMILES: CC[C@H]1OC(=O)[C@H](C)C(=O)[C@H](C)[C@@H](O[C@@H]2O[C@H](C)C[C@H](N(C)CCc3cn(CCc4ccc(S(N)(=O)=O)cc4)nn3)[C@H]2O)[C@](C)(OC)C[C@@H](C)/C(=N\OC2CCNCC2)[C@H](C)[C@@H](O)[C@]1(C)O] |
| 442 | 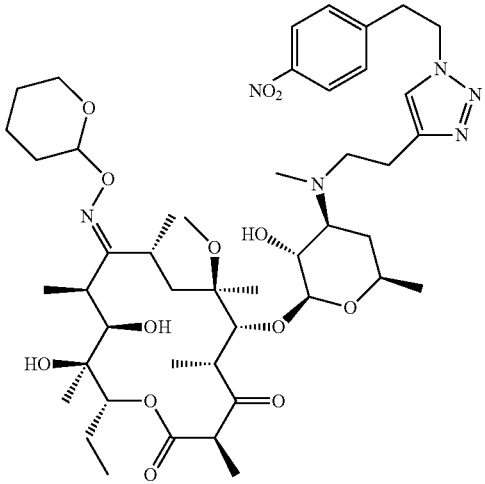 [SMILES: CC[C@H]1OC(=O)[C@H](C)C(=O)[C@H](C)[C@@H](O[C@@H]2O[C@H](C)C[C@H](N(C)CCc3cn(CCc4ccc([N+](=O)[O-])cc4)nn3)[C@H]2O)[C@](C)(OC)C[C@@H](C)/C(=N\OC2CCCCO2)[C@H](C)[C@@H](O)[C@]1(C)O] |
| 443 | 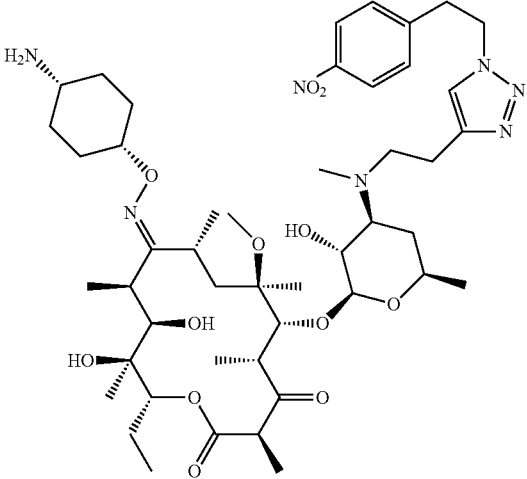 [SMILES: CC[C@H]1OC(=O)[C@H](C)C(=O)[C@H](C)[C@@H](O[C@@H]2O[C@H](C)C[C@H](N(C)CCc3cn(CCc4ccc([N+](=O)[O-])cc4)nn3)[C@H]2O)[C@](C)(OC)C[C@@H](C)/C(=N\O[C@H]2CC[C@@H](N)CC2)[C@H](C)[C@@H](O)[C@]1(C)O] |

TABLE 1-continued

| Compound Number | Structure |
|---|---|
| 444 | 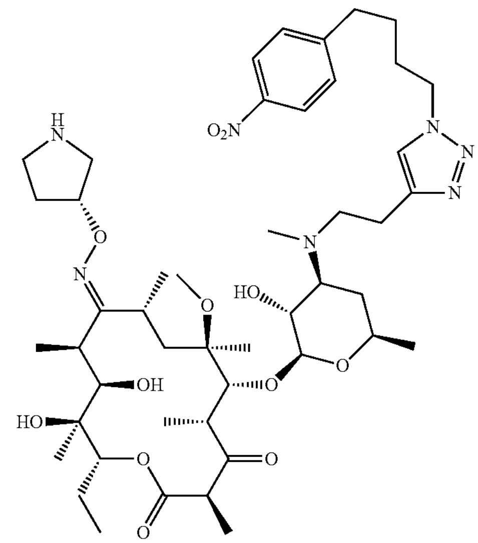 [SMILES: CC[C@H]1OC(=O)[C@H](C)C(=O)[C@H](C)[C@@H](O[C@@H]2O[C@H](C)C[C@H](N(C)CCc3cn(CCCCc4ccc([N+](=O)[O-])cc4)nn3)[C@H]2O)[C@](C)(OC)C[C@@H](C)/C(=N\O[C@@H]2CCNC2)[C@H](C)[C@@H](O)[C@]1(C)O] |
| 445 | 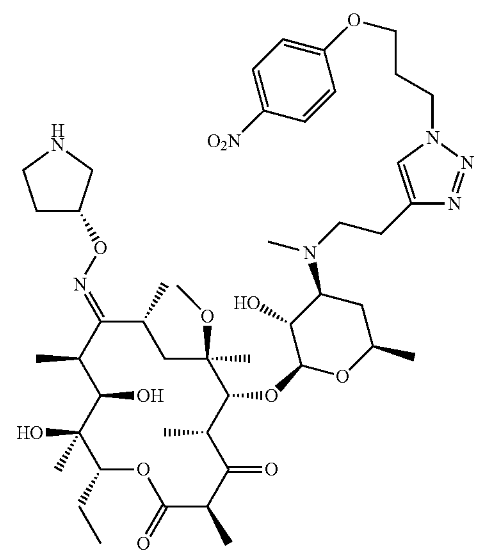 [SMILES: CC[C@H]1OC(=O)[C@H](C)C(=O)[C@H](C)[C@@H](O[C@@H]2O[C@H](C)C[C@H](N(C)CCc3cn(CCCOc4ccc([N+](=O)[O-])cc4)nn3)[C@H]2O)[C@](C)(OC)C[C@@H](C)/C(=N\O[C@@H]2CCNC2)[C@H](C)[C@@H](O)[C@]1(C)O] |
| 446 | 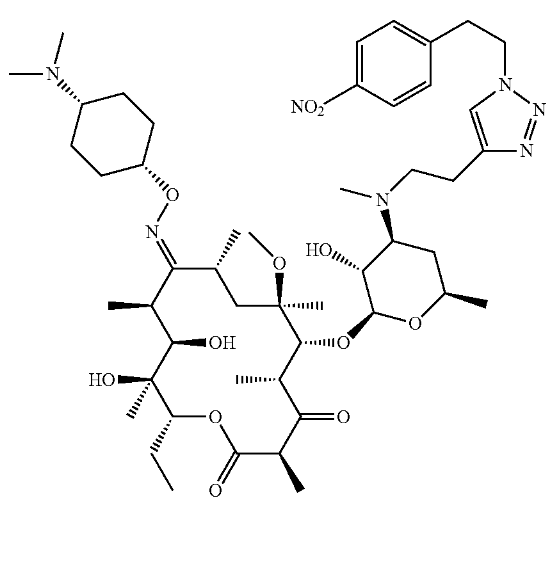 [SMILES: CC[C@H]1OC(=O)[C@H](C)C(=O)[C@H](C)[C@@H](O[C@@H]2O[C@H](C)C[C@H](N(C)CCc3cn(CCc4ccc([N+](=O)[O-])cc4)nn3)[C@H]2O)[C@](C)(OC)C[C@@H](C)/C(=N\O[C@H]2CC[C@@H](N(C)C)CC2)[C@H](C)[C@@H](O)[C@]1(C)O] |

TABLE 1-continued

| Compound Number | Structure |
|---|---|
| 447 | 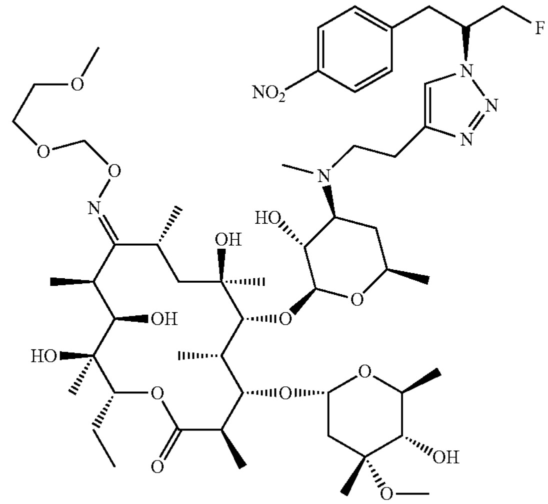 |
| 448 | 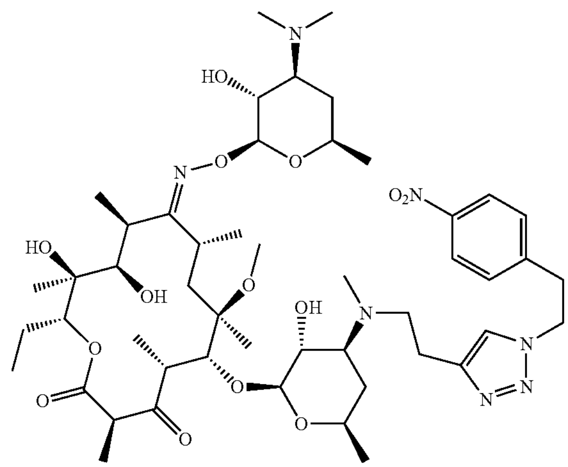 [SMILES: CC[C@H]1OC(=O)[C@H](C)C(=O)[C@H](C)[C@@H](O[C@@H]2O[C@H](C)C[C@H](N(C)CCc3cn(CCc4ccc([N+](=O)[O-])cc4)nn3)[C@H]2O)[C@](C)(OC)C[C@@H](C)/C(=N\O[C@@H]2O[C@H](C)C[C@H](N(C)C)[C@H]2O)[C@H](C)[C@@H](O)[C@]1(C)O] |
| 449 | 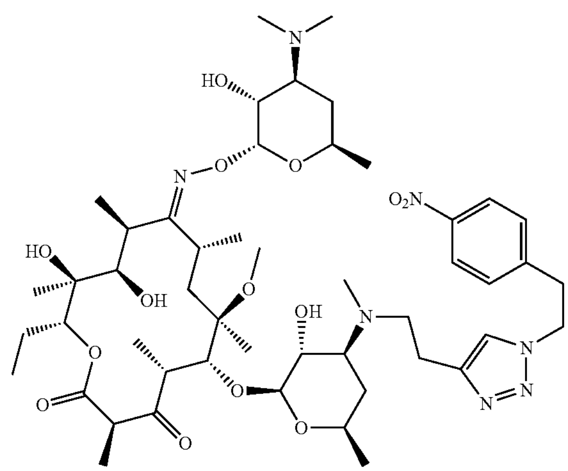 [SMILES: CC[C@H]1OC(=O)[C@H](C)C(=O)[C@H](C)[C@@H](O[C@@H]2O[C@H](C)C[C@H](N(C)CCc3cn(CCc4ccc([N+](=O)[O-])cc4)nn3)[C@H]2O)[C@](C)(OC)C[C@@H](C)/C(=N\O[C@H]2O[C@H](C)C[C@H](N(C)C)[C@H]2O)[C@H](C)[C@@H](O)[C@]1(C)O] |

TABLE 1-continued

| Compound Number | Structure |
|---|---|
| 450 | 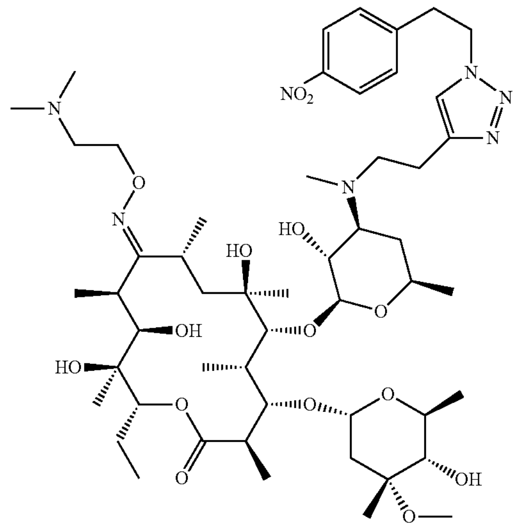 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc([N+](=O)[O-])cc4)nn3)[C@H]2O)[C@](C)(O)C[C@@H](C)/C(=N\OCCN(C)C)[C@H](C)[C@@H](O)[C@]1(C)O] |
| 451 | 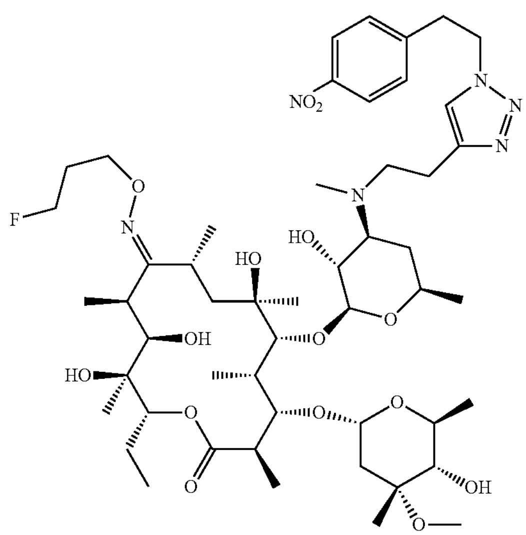 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc([N+](=O)[O-])cc4)nn3)[C@H]2O)[C@](C)(O)C[C@@H](C)/C(=N\OCCCF)[C@H](C)[C@@H](O)[C@]1(C)O] |

TABLE 1-continued
| Compound Number | Structure |
|---|---|
| 460 | 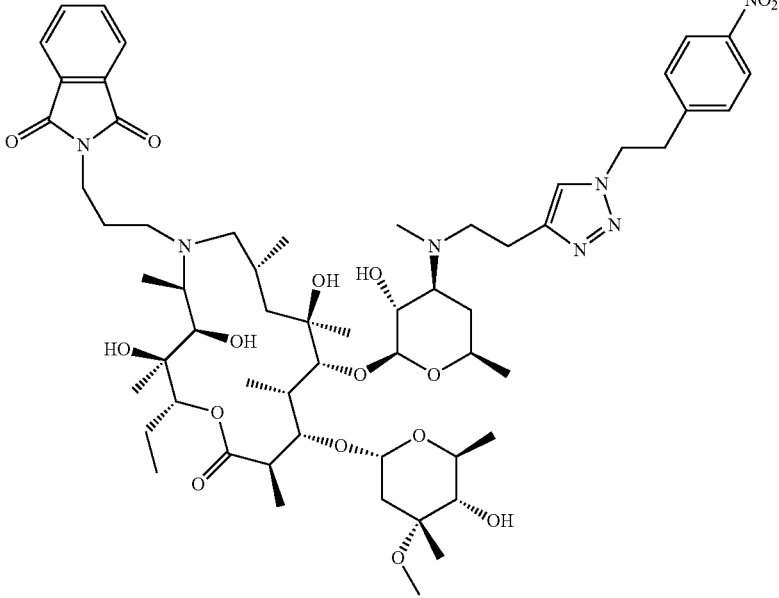 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc([N+](=O)[O-])cc4)nn3)[C@H]2O)[C@](C)(O)C[C@@H](C)CN(CCCN2C(=O)c3ccccc3C2=O)[C@H](C)[C@@H](O)[C@]1(C)O] |
| 461 | 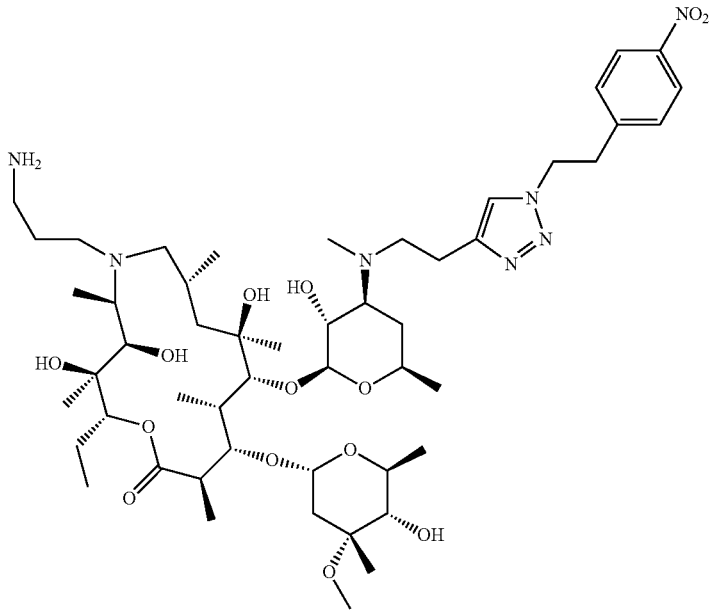 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc([N+](=O)[O-])cc4)nn3)[C@H]2O)[C@](C)(O)C[C@@H](C)CN(CCCN)[C@H](C)[C@@H](O)[C@]1(C)O] |

TABLE 1-continued
| Compound Number | Structure |
|---|---|
| 462 | 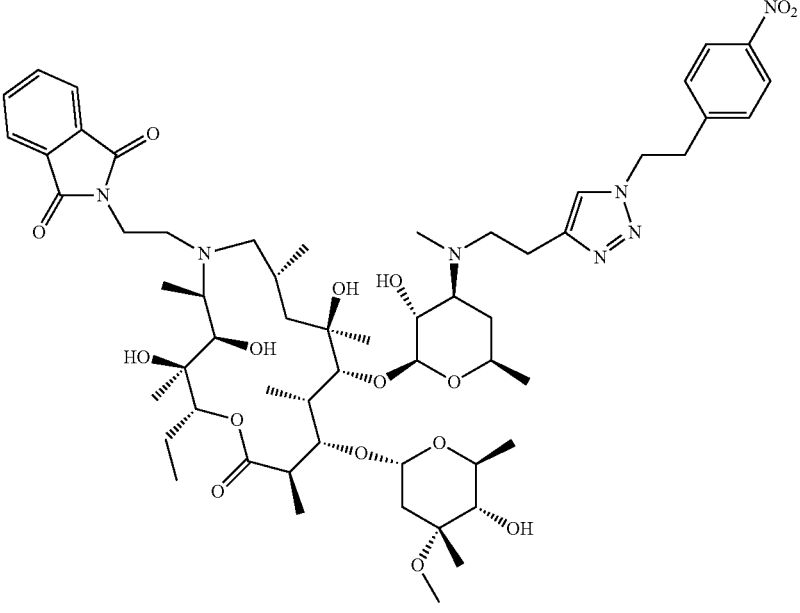 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc([N+](=O)[O-])cc4)nn3)[C@H]2O)[C@](C)(O)C[C@@H](C)CN(CCN2C(=O)c3ccccc3C2=O)[C@H](C)[C@@H](O)[C@]1(C)O] |
| 463 | 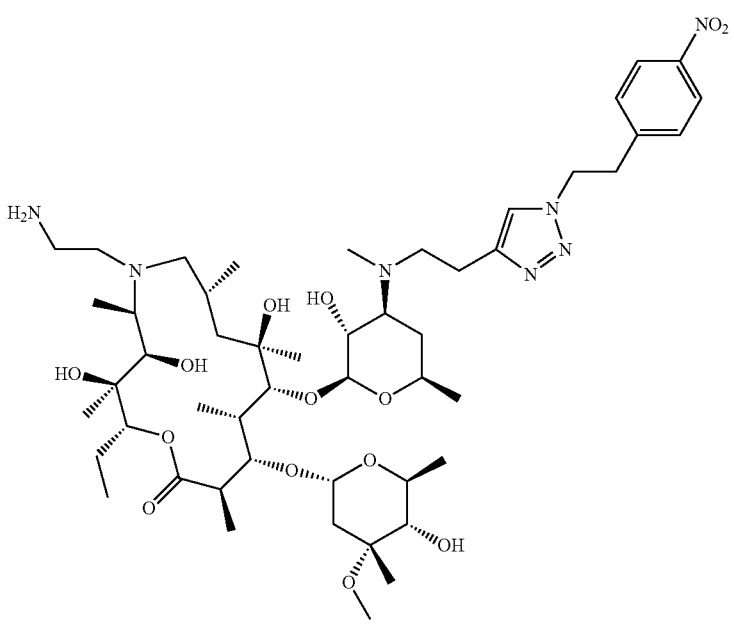 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc([N+](=O)[O-])cc4)nn3)[C@H]2O)[C@](C)(O)C[C@@H](C)CN(CCN)[C@H](C)[C@@H](O)[C@]1(C)O] |

TABLE 1-continued
| Compound Number | Structure |
|---|---|
| 464 | 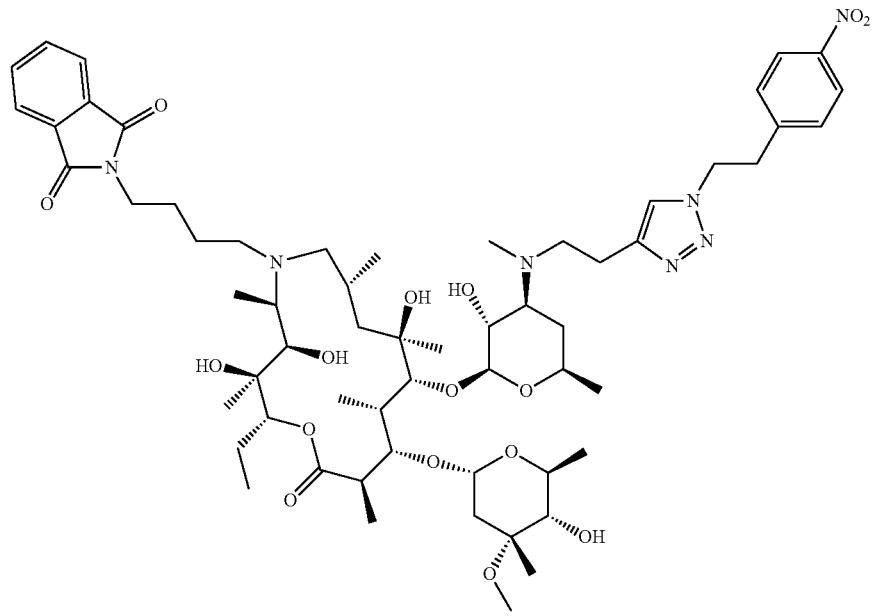 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc([N+](=O)[O-])cc4)nn3)[C@H]2O)[C@](C)(O)C[C@@H](C)CN(CCCCN2C(=O)c3ccccc3C2=O)[C@H](C)[C@@H](O)[C@]1(C)O] |
| 465 | 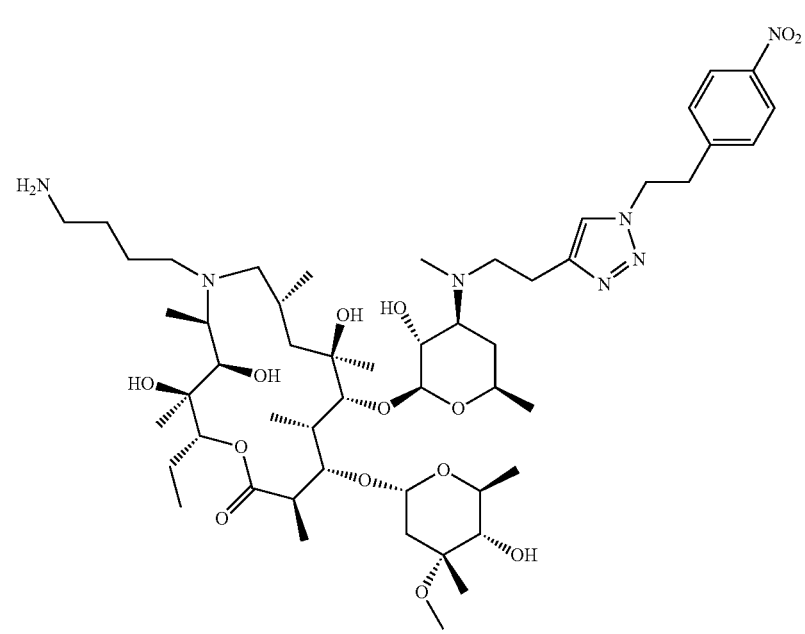 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc([N+](=O)[O-])cc4)nn3)[C@H]2O)[C@](C)(O)C[C@@H](C)CN(CCCCN)[C@H](C)[C@@H](O)[C@]1(C)O] |

TABLE 1-continued
| Compound Number | Structure |
|---|---|
| 466 | 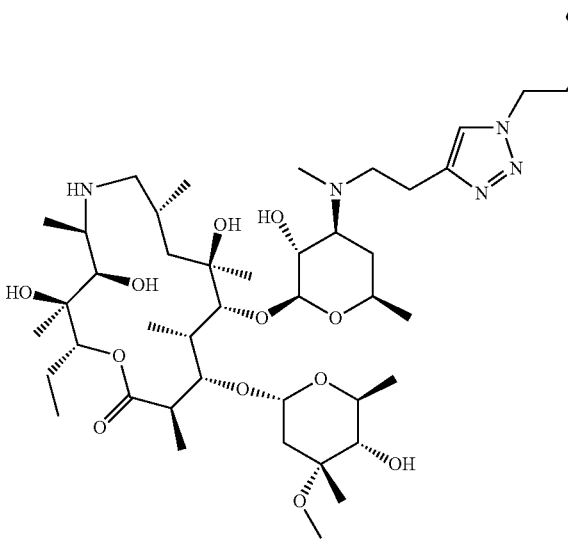 |
| 475 | 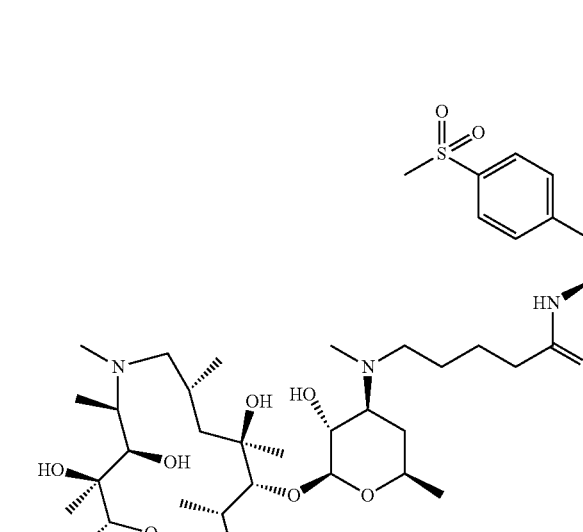 |

TABLE 1-continued
| Compound Number | Structure |
|---|---|
| 476 | 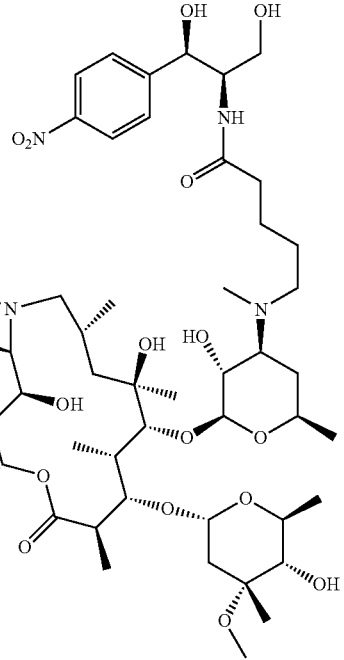 |
| 477 | 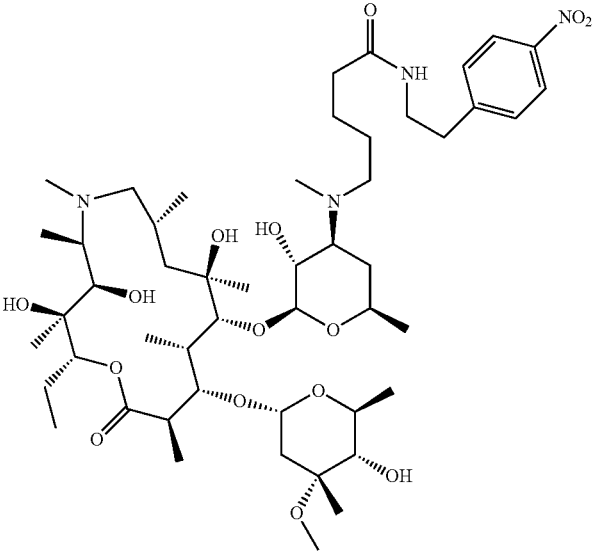 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCCC(=O)NCCc3ccc([N+](=O)[O-])cc3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 478 | 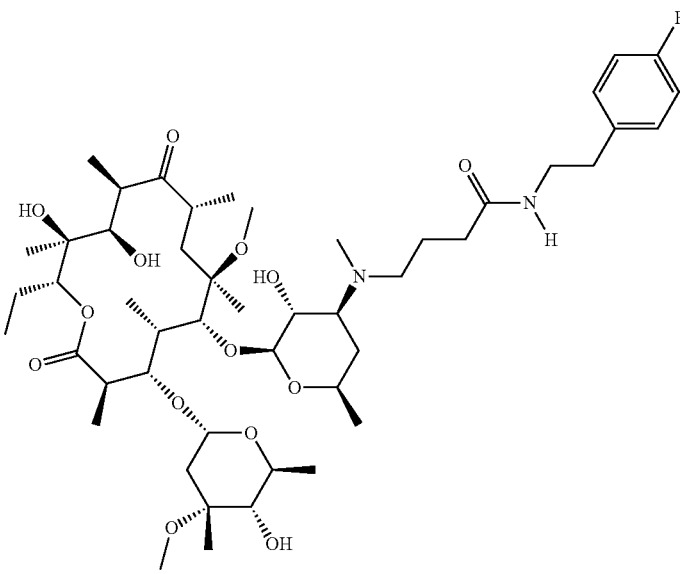 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCC(=O)NCCc3ccc(F)cc3)[C@H]2O)[C@](C)(OC)C[C@@H](C)C(=O)[C@H](C)[C@@H](O)[C@]1(C)O] |
| 479 | 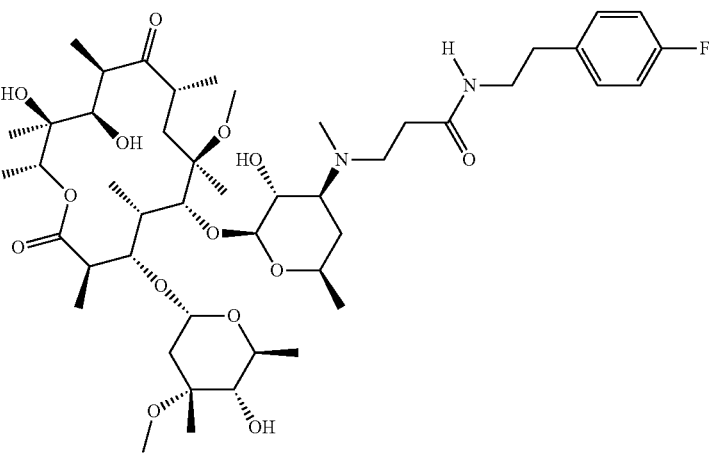 |
| 480 | 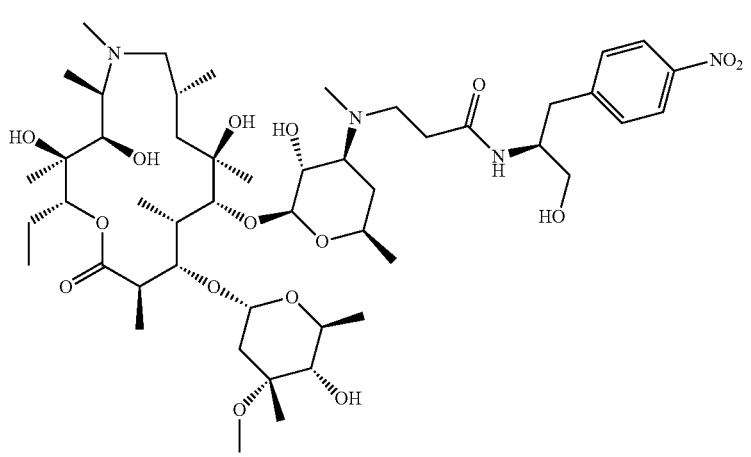 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCC(=O)N[C@H](CO)Cc3ccc([N+](=O)[O-])cc3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 501 | 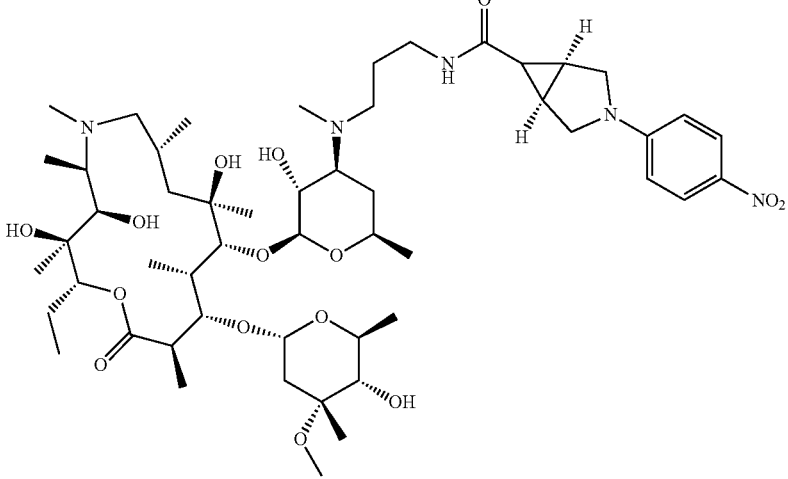 |
| 502 | 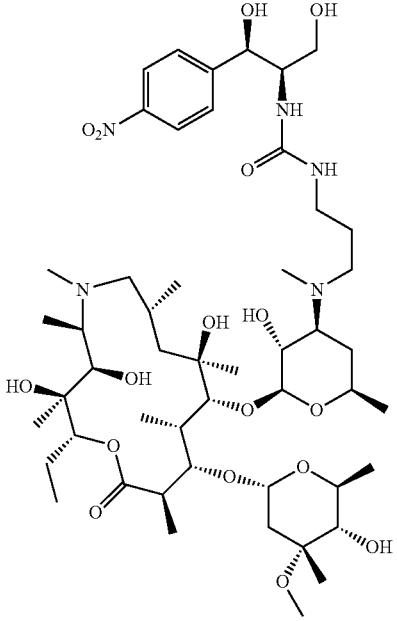 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCNC(=O)N[C@H](CO)[C@H](O)c3ccc([N+](=O)[O-])cc3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 503 | 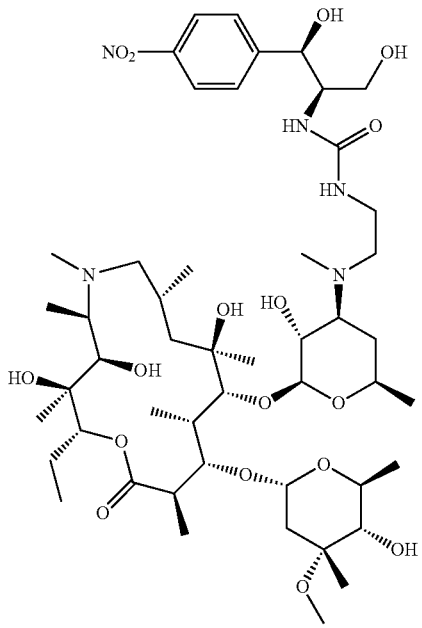 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCNC(=O)N[C@H](CO)[C@H](O)c3ccc([N+](=O)[O-])cc3)[C@H]2O)[C@](C)(O)C[C@@H](C)CN(C)[C@H](C)[C@@H](O)[C@]1(C)O] |
| 504 | 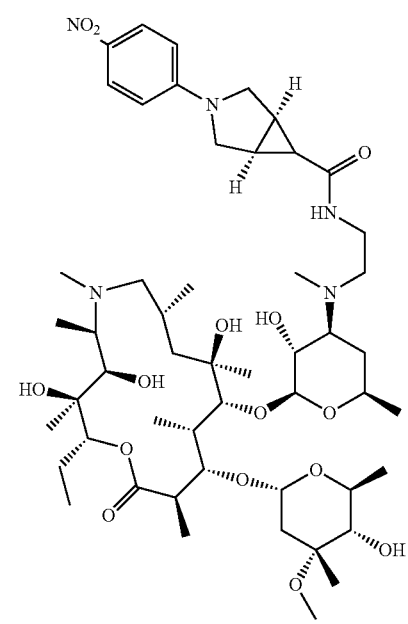 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCNC(=O)C3[C@H]4CN(c5ccc([N+](=O)[O-])cc5)C[C@@H]34)[C@H]2O)[C@](C)(O)C[C@@H](C)CN(C)[C@H](C)[C@@H](O)[C@]1(C)O] |

TABLE 1-continued

| Compound Number | Structure |
| --- | --- |
| 505 | 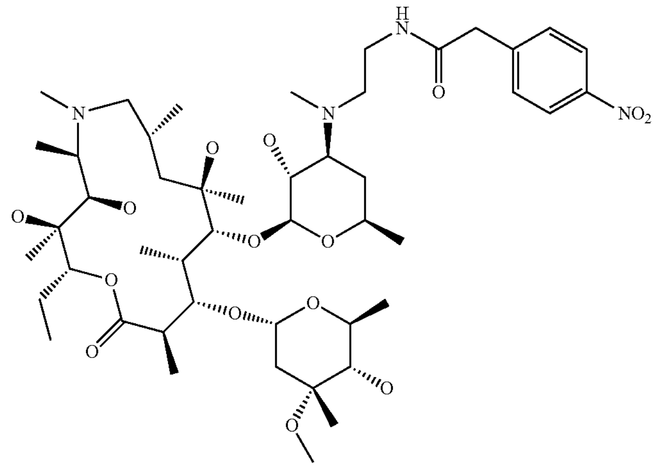 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCNC(=O)Cc3ccc([N+](=O)[O-])cc3)[C@H]2O)[C@](C)(O)C[C@@H](C)CN(C)[C@H](C)[C@@H](O)[C@]1(C)O] |
| 506 | 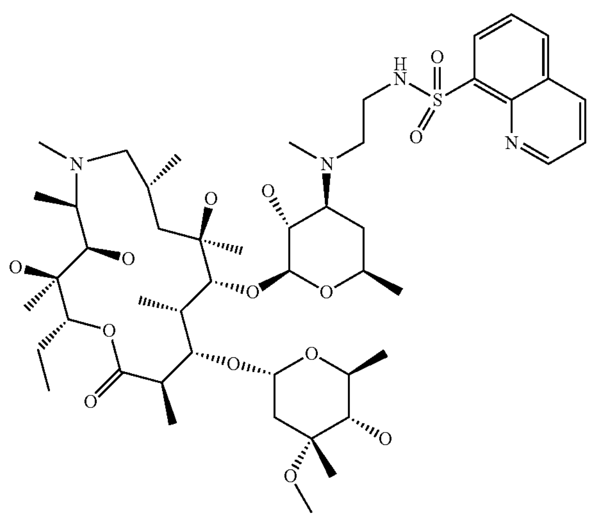 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCNS(=O)(=O)c3cccc4cccnc34)[C@H]2O)[C@](C)(O)C[C@@H](C)CN(C)[C@H](C)[C@@H](O)[C@]1(C)O] |
| 507 | 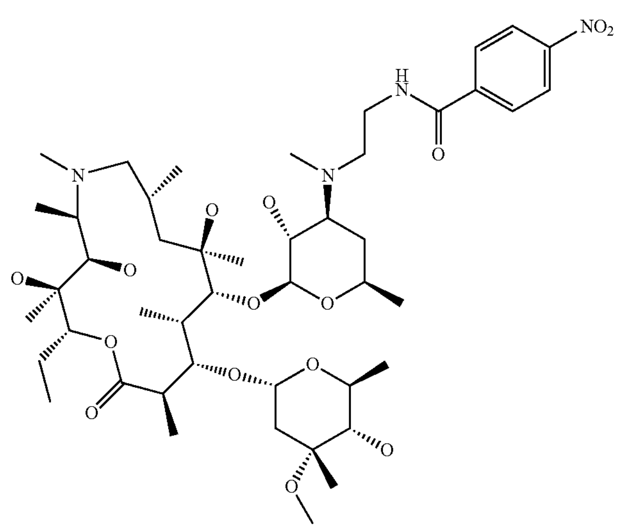 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCNC(=O)c3ccc([N+](=O)[O-])cc3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 508 | 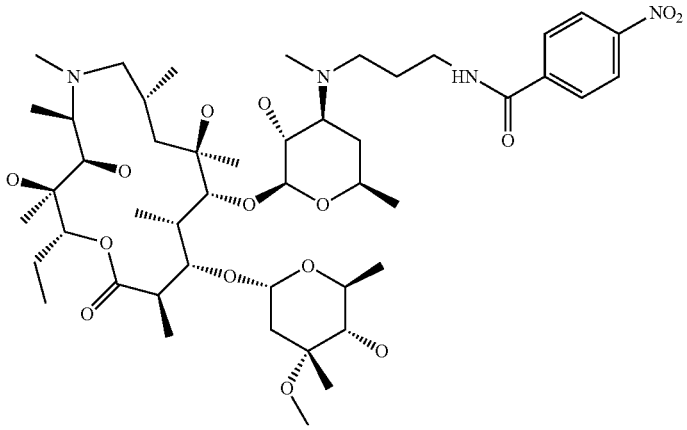 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCNC(=O)c3ccc([N+](=O)[O-])cc3)[C@H]2O)[C@](C)(O)C[C@@H](C)CN(C)[C@H](C)[C@@H](O)[C@]1(C)O] |
| 509 | 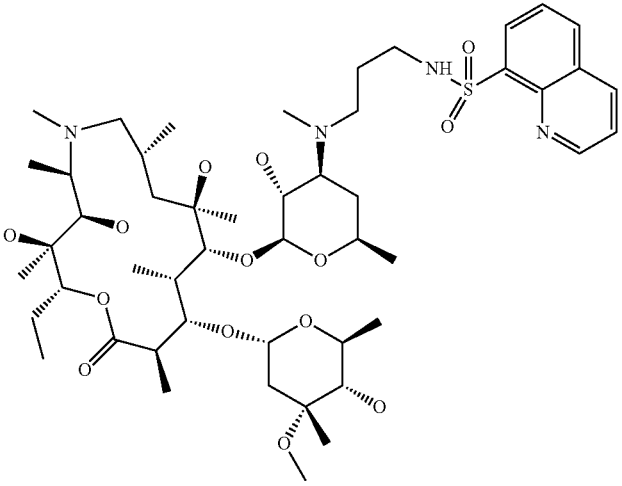 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCNS(=O)(=O)c3cccc4cccnc34)[C@H]2O)[C@](C)(O)C[C@@H](C)CN(C)[C@H](C)[C@@H](O)[C@]1(C)O] |
| 510 | 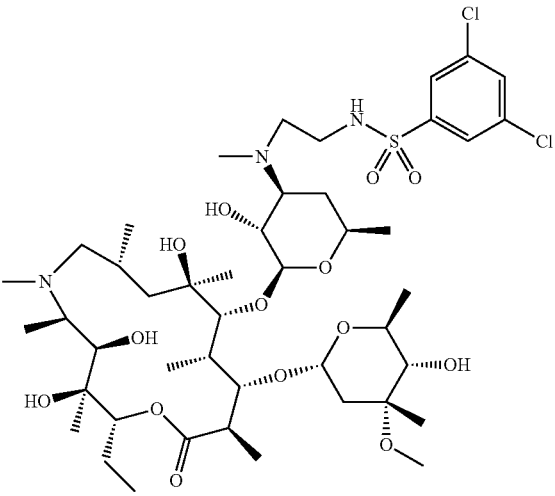 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCNS(=O)(=O)c3cc(Cl)cc(Cl)c3)[C@H]2O)[C@](C)(O)C[C@@H](C)CN(C)[C@H](C)[C@@H](O)[C@]1(C)O] |

TABLE 1-continued

| Compound Number | Structure |
|---|---|
| 511 | 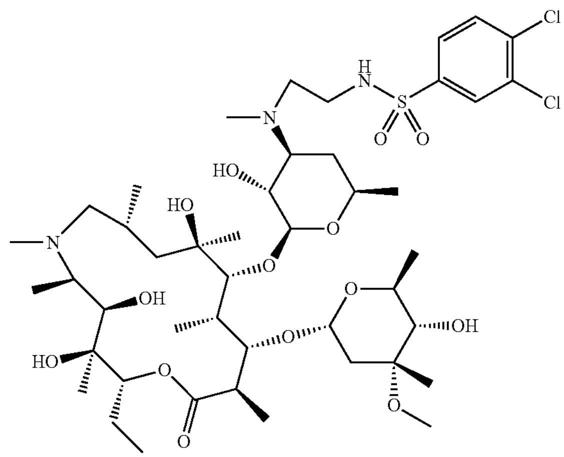 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCNS(=O)(=O)c3ccc(Cl)c(Cl)c3)[C@H]2O)[C@](C)(O)C[C@@H](C)CN(C)[C@H](C)[C@@H](O)[C@]1(C)O] |
| 512 | 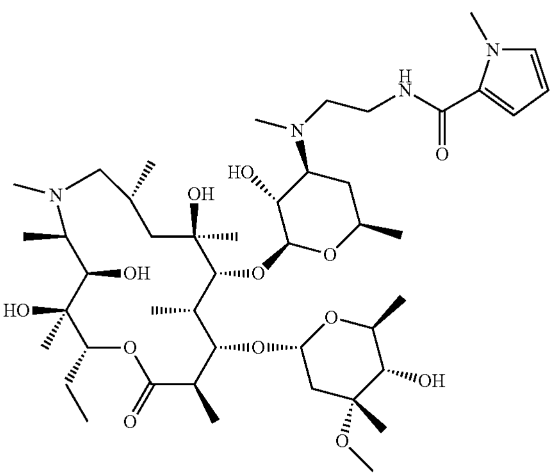 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCNC(=O)c3cccn3C)[C@H]2O)[C@](C)(O)C[C@@H](C)CN(C)[C@H](C)[C@@H](O)[C@]1(C)O] |
| 513 | 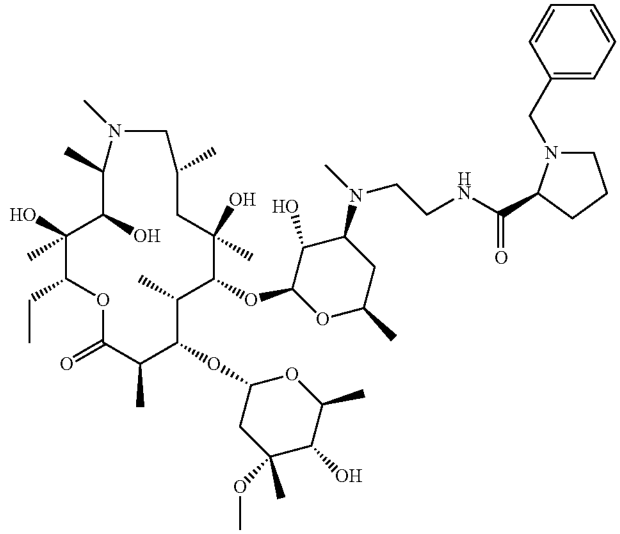 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCNC(=O)[C@@H]3CCCN3Cc3ccccc3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 514 | 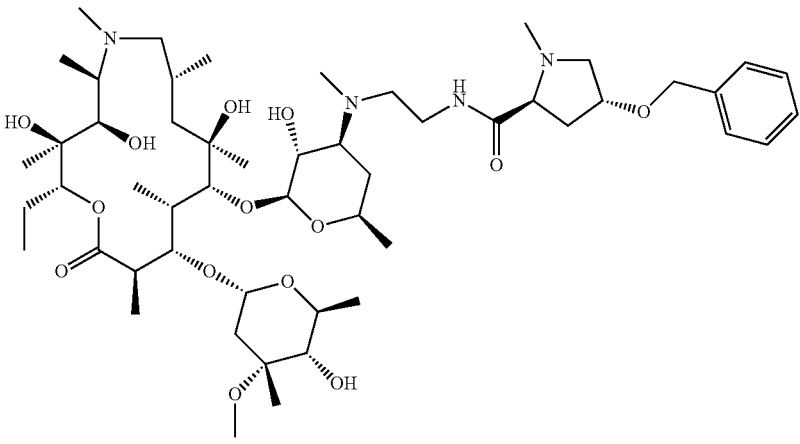 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCNC(=O)[C@@H]3C[C@@H](OCc4ccccc4)CN3C)[C@H]2O)[C@](C)(O)C[C@@H](C)CN(C)[C@H](C)[C@@H](O)[C@]1(C)O] |
| 515 | 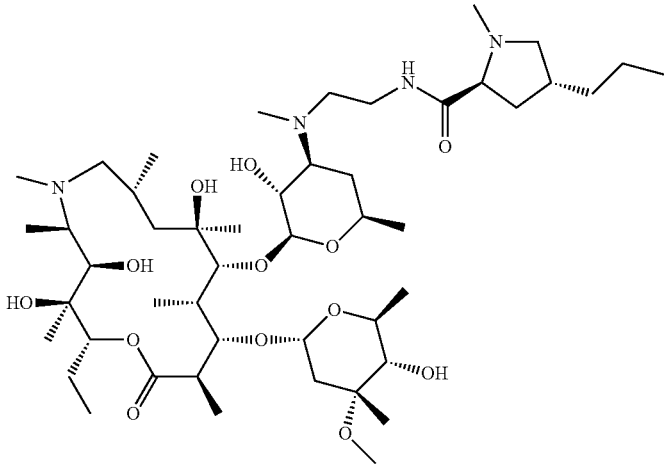 [SMILES: CCC[C@@H]1C[C@@H](C(=O)NCCN(C)[C@H]2C[C@@H](C)O[C@@H](O[C@@H]3[C@@H](C)[C@H](O[C@H]4C[C@@](C)(OC)[C@@H](O)[C@H](C)O4)[C@@H](C)C(=O)O[C@H](CC)[C@@](C)(O)[C@H](O)[C@@H](C)N(C)C[C@H](C)C[C@@]3(C)O)[C@@H]2O)N(C)C1] |
| 525 | 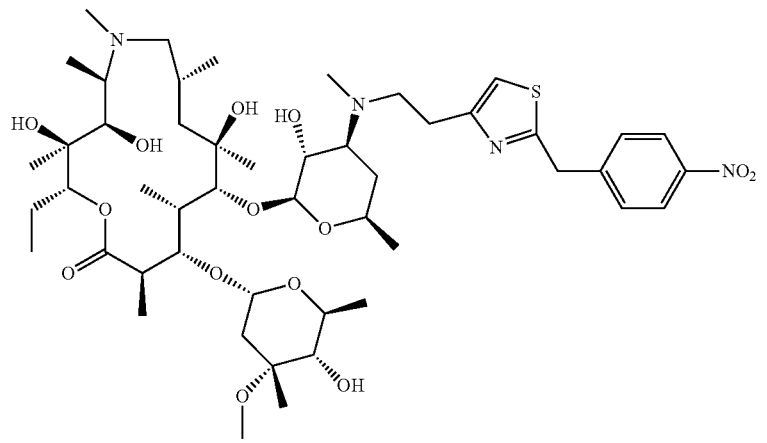 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3csc(Cc4ccc([N+](=O)[O-])cc4)n3)[C@H]2O)[C@](C)(O)C[C@@H](C)CN(C)[C@H](C)[C@@H](O)[C@]1(C)O] |

TABLE 1-continued

| Compound Number | Structure |
| --- | --- |
| 526 | 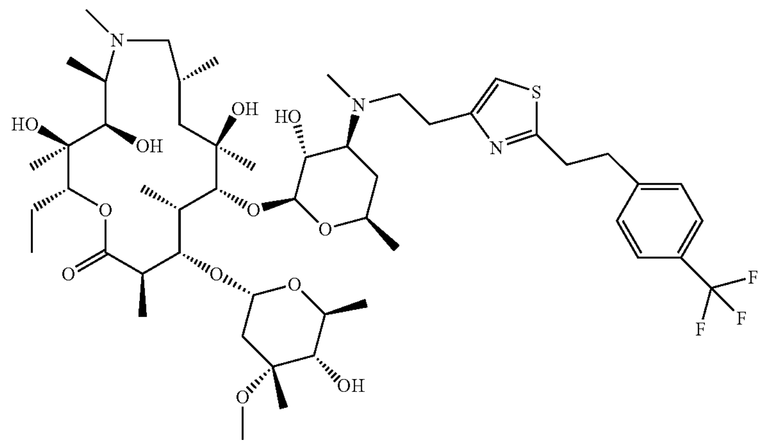 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3csc(CCc4ccc(C(F)(F)F)cc4)n3)[C@H]2O)[C@](C)(O)C[C@@H](C)CN(C)[C@H](C)[C@@H](O)[C@]1(C)O] |
| 527 | 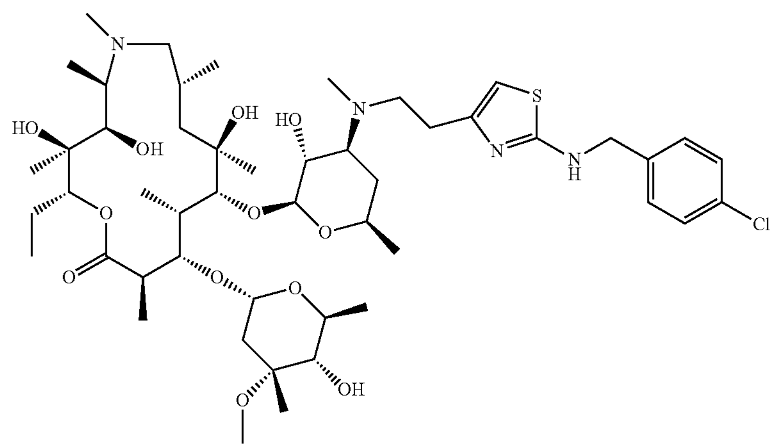 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3csc(NCc4ccc(Cl)cc4)n3)[C@H]2O)[C@](C)(O)C[C@@H](C)CN(C)[C@H](C)[C@@H](O)[C@]1(C)O] |
| 528 | 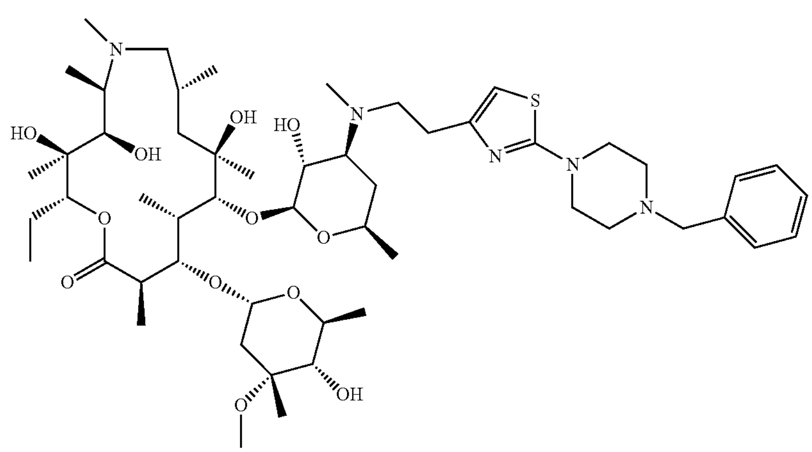 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3csc(N4CCN(Cc5ccccc5)CC4)n3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 529 | 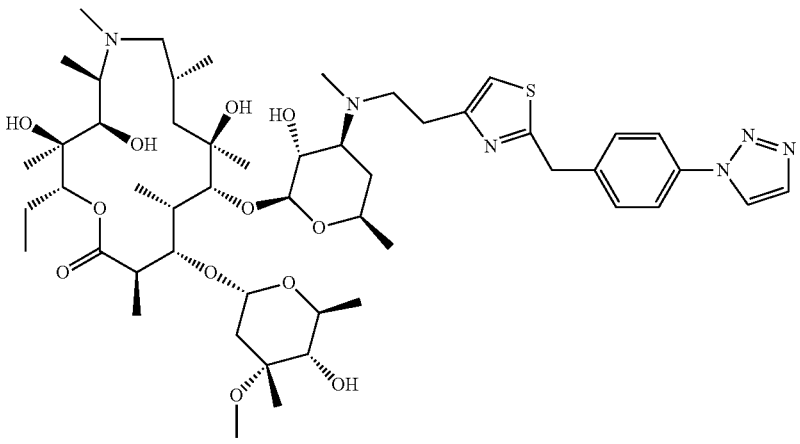 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3csc(Cc4ccc(-n5ccnn5)cc4)n3)[C@H]2O)[C@](C)(O)C[C@@H](C)CN(C)[C@H](C)[C@@H](O)[C@]1(C)O] |
| 550 | 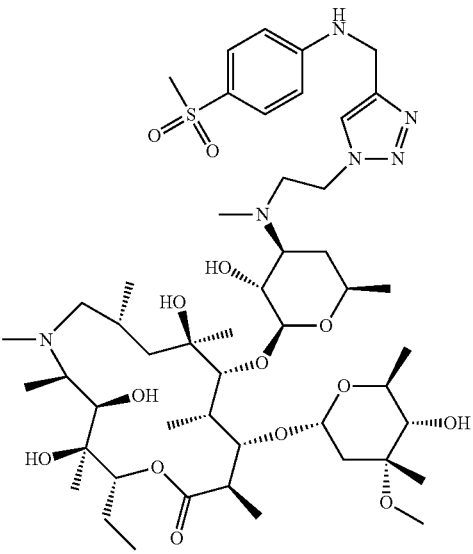 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCn3cc(CNc4ccc(S(C)(=O)=O)cc4)nn3)[C@H]2O)[C@](C)(O)C[C@@H](C)CN(C)[C@H](C)[C@@H](O)[C@]1(C)O] |
| 551 | 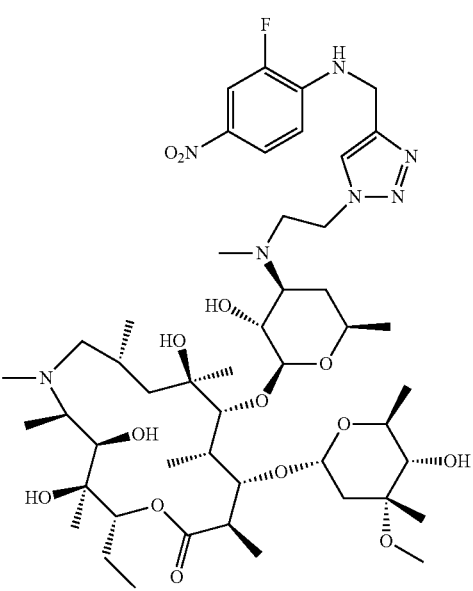 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCn3cc(CNc4ccc([N+](=O)[O-])cc4F)nn3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 552 | 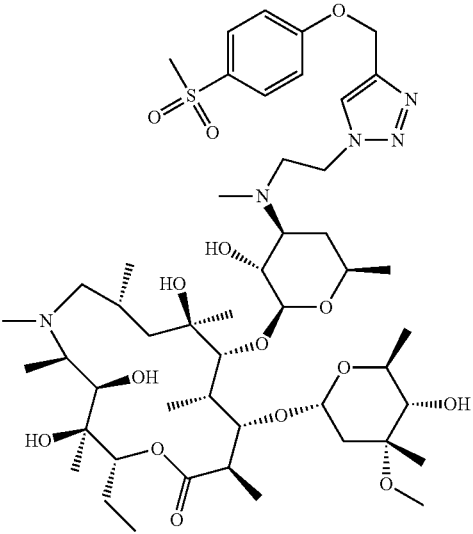 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCn3cc(COc4ccc(S(C)(=O)=O)cc4)nn3)[C@H]2O)[C@](C)(O)C[C@@H](C)CN(C)[C@H](C)[C@@H](O)[C@]1(C)O] |
| 553 | 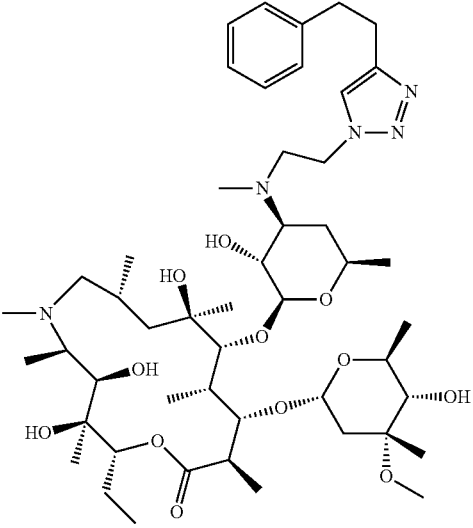 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCn3cc(CCc4ccccc4)nn3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 554 | 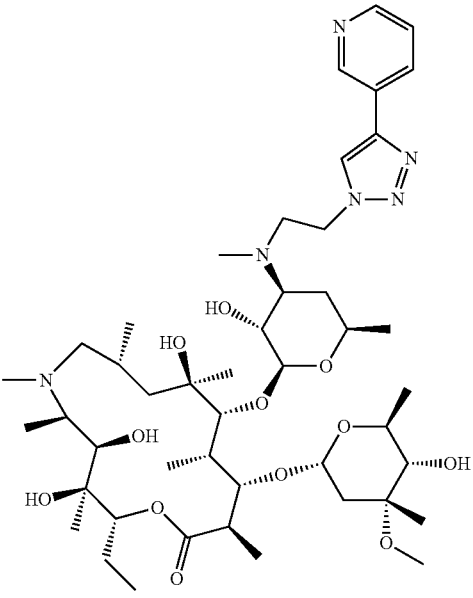 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCn3cc(-c4cccnc4)nn3)[C@H]2O)[C@](C)(O)C[C@@H](C)CN(C)[C@H](C)[C@@H](O)[C@]1(C)O] |
| 555 | 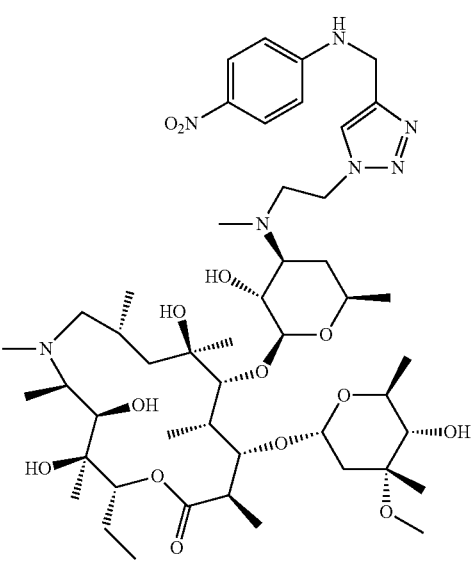 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCn3cc(CNc4ccc([N+](=O)[O-])cc4)nn3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 556 | 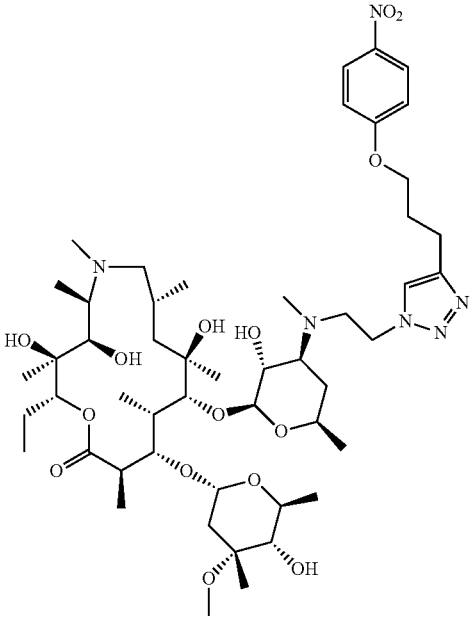 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCn3cc(CCCOc4ccc([N+](=O)[O-])cc4)nn3)[C@H]2O)[C@](C)(O)C[C@@H](C)CN(C)[C@H](C)[C@@H](O)[C@]1(C)O] |
| 601 | 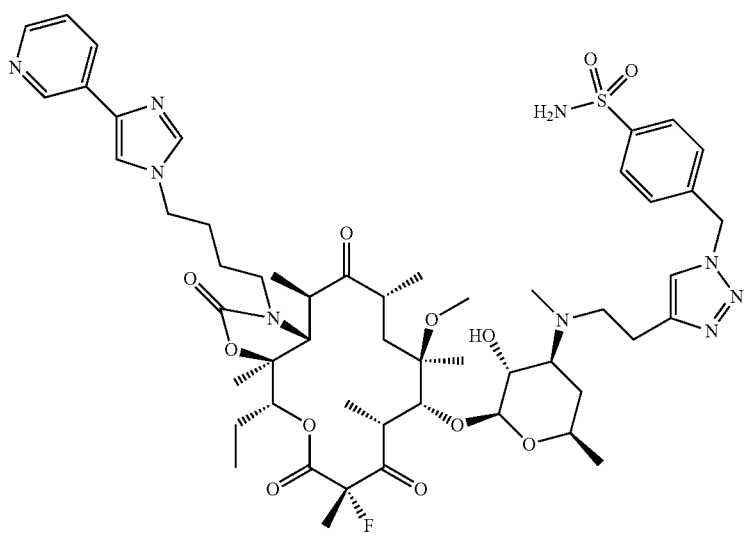 [SMILES: CC[C@H]1OC(=O)[C@@](C)(F)C(=O)[C@H](C)[C@@H](O[C@@H]2O[C@H](C)C[C@H](N(C)CCc3cn(Cc4ccc(S(N)(=O)=O)cc4)nn3)[C@H]2O)[C@](C)(OC)C[C@@H](C)C(=O)[C@H](C)[C@H]2N(CCCCn3cnc(-c4cccnc4)c3)C(=O)O[C@]12C] |

TABLE 1-continued

| Compound Number | Structure |
|---|---|
| 602 | 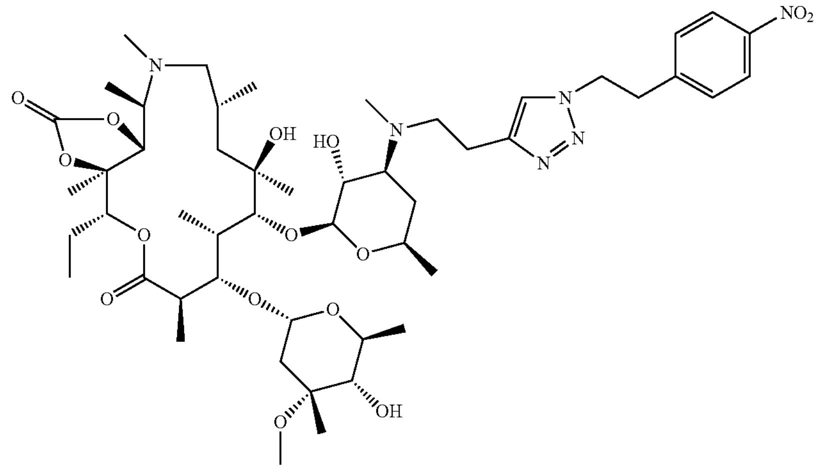 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc([N+](=O)[O-])cc4)nn3)[C@H]2O)[C@](C)(O)C[C@@H](C)CN(C)[C@H](C)[C@H]2OC(=O)O[C@@]21C] |
| 603 | 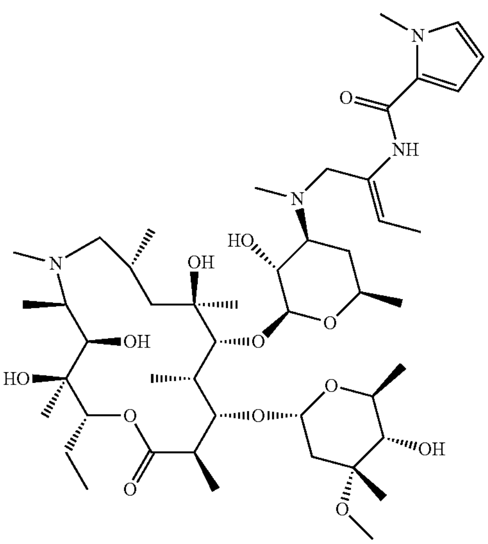 [SMILES: C/C=C(/CN(C)[C@H]1C[C@@H](C)O[C@@H](O[C@@H]2[C@@H](C)[C@H](O[C@H]3C[C@@](C)(OC)[C@@H](O)[C@H](C)O3)[C@@H](C)C(=O)O[C@H](CC)[C@@](C)(O)[C@H](O)[C@@H](C)N(C)C[C@H](C)C[C@@]2(C)O)[C@@H]1O)NC(=O)c1cccn1C] |
| 604 | 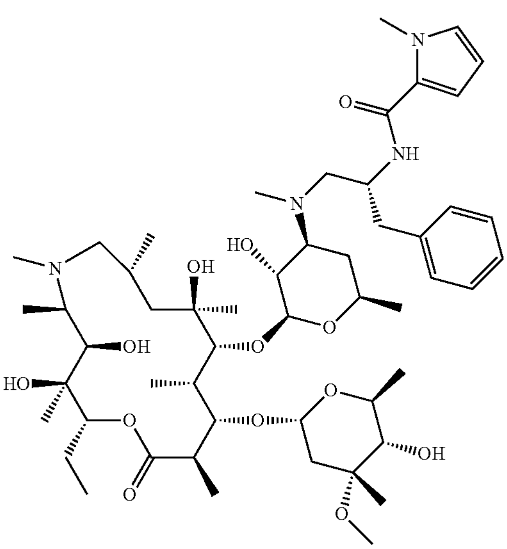 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)C[C@@H](Cc3ccccc3)NC(=O)c3cccn3C)[C@H]2O)[C@](C)(O)C[C@@H](C)CN(C)[C@H](C)[C@@H](O)[C@]1(C)O] |

TABLE 1-continued
| Compound Number | Structure |
|---|---|
| 605 | 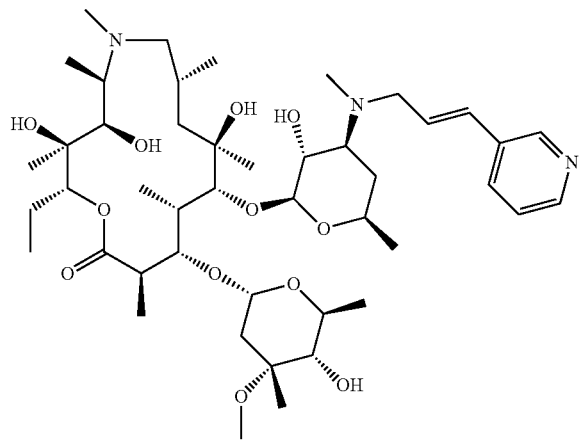 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)C/C=C/c3cccnc3)[C@H]2O)[C@](C)(O)C[C@@H](C)CN(C)[C@H](C)[C@@H](O)[C@]1(C)O] |
| 606 | 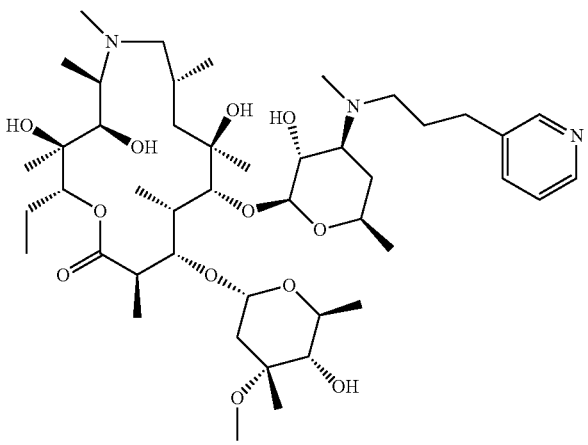 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCc3cccnc3)[C@H]2O)[C@](C)(O)C[C@@H](C)CN(C)[C@H](C)[C@@H](O)[C@]1(C)O] |
| 607 | 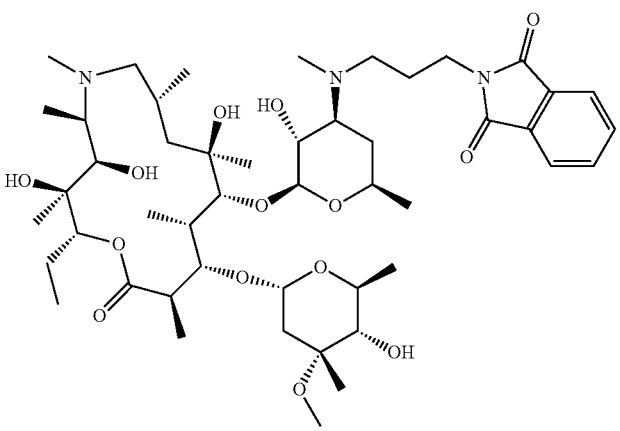 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCN3C(=O)c4ccccc4C3=O)[C@H]2O)[C@](C)(O)C[C@@H](C)CN(C)[C@H](C)[C@@H](O)[C@]1(C)O] |

TABLE 1-continued
| Compound Number | Structure |
|---|---|
| 608 | 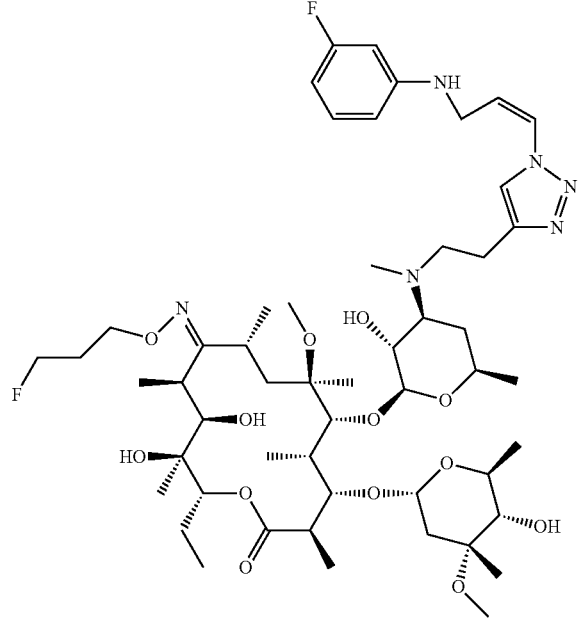 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(/C=C\CNc4cccc(F)c4)nn3)[C@H]2O)[C@](C)(OC)C[C@@H](C)/C(=N/OCCCF)[C@H](C)[C@@H](O)[C@]1(C)O] |
| 609 | 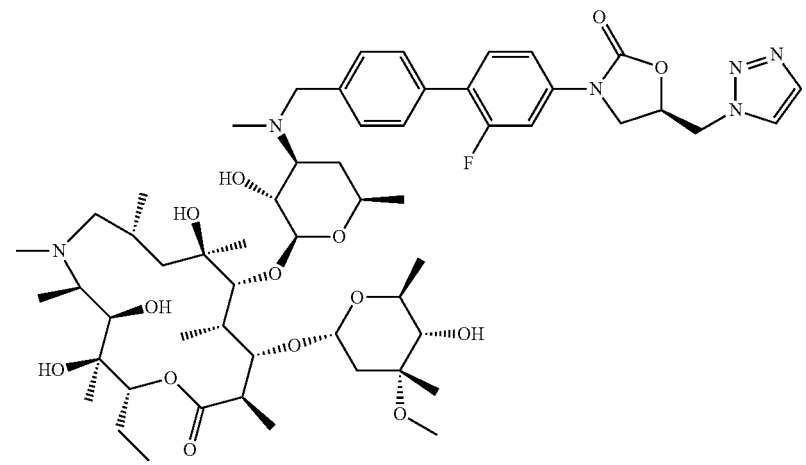 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)Cc3ccc(-c4ccc(N5C[C@H](Cn6ccnn6)OC5=O)cc4F)cc3)[C@H]2O)[C@](C)(O)C[C@@H](C)CN(C)[C@H](C)[C@@H](O)[C@]1(C)O] |
| 610 | 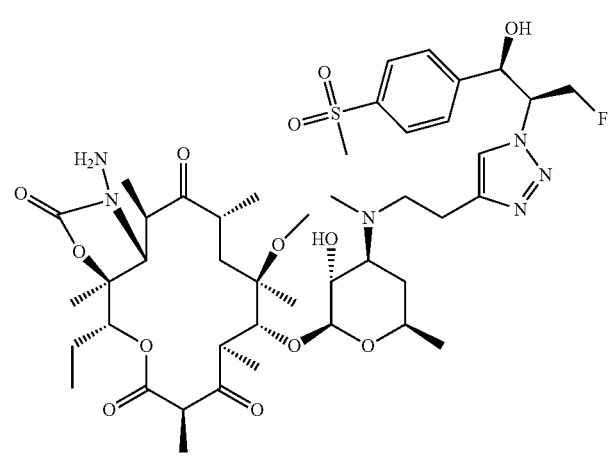 [SMILES: CC[C@H]1OC(=O)[C@H](C)C(=O)[C@H](C)[C@@H](O[C@@H]2O[C@H](C)C[C@H](N(C)CCc3cn([C@H](CF)[C@H](O)c4ccc(S(C)(=O)=O)cc4)nn3)[C@H]2O)[C@](C)(OC)C[C@@H](C)C(=O)[C@H](C)[C@H]2N(N)C(=O)O[C@]12C] |

TABLE 1-continued
| Compound Number | Structure |
|---|---|
| 611 | 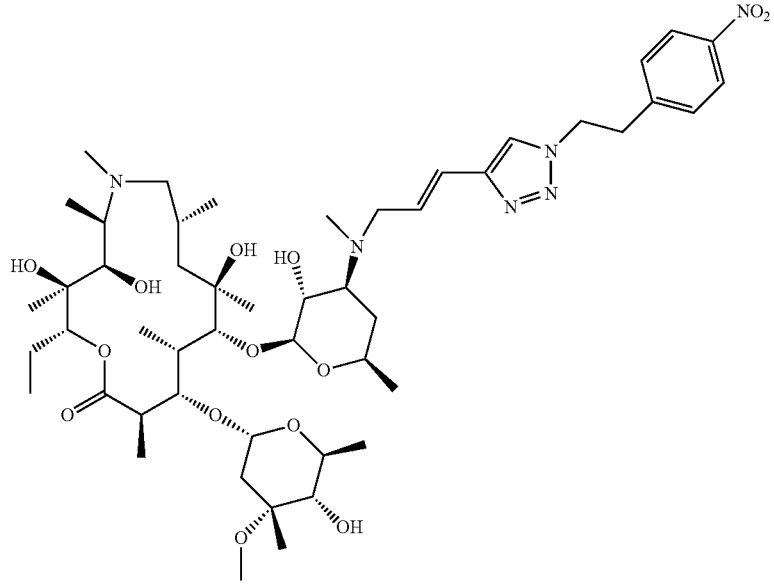 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)C/C=C/c3cn(CCc4ccc([N+](=O)[O-])cc4)nn3)[C@H]2O)[C@](C)(O)C[C@@H](C)CN(C)[C@H](C)[C@@H](O)[C@]1(C)O] |
| 612 | 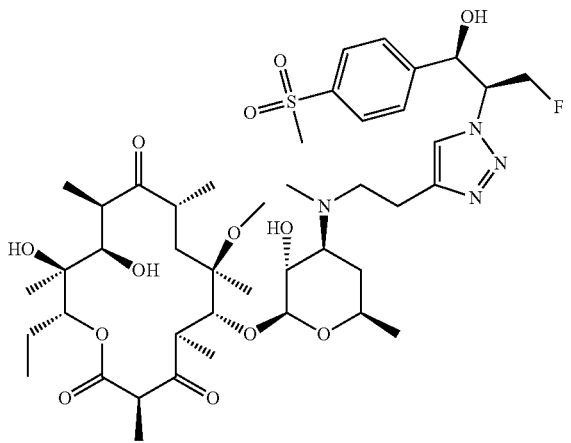 [SMILES: CC[C@H]1OC(=O)[C@H](C)C(=O)[C@H](C)[C@@H](O[C@@H]2O[C@H](C)C[C@H](N(C)CCc3cn([C@H](CF)[C@H](O)c4ccc(S(C)(=O)=O)cc4)nn3)[C@H]2O)[C@](C)(OC)C[C@@H](C)C(=O)[C@H](C)[C@@H](O)[C@]1(C)O] |
| 613 | 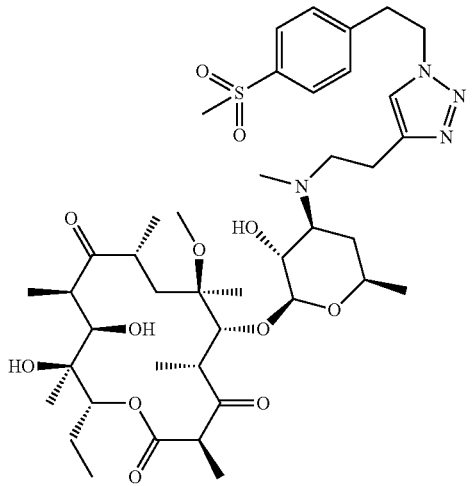 [SMILES: CC[C@H]1OC(=O)[C@H](C)C(=O)[C@H](C)[C@@H](O[C@@H]2O[C@H](C)C[C@H](N(C)CCc3cn(CCc4ccc(S(C)(=O)=O)cc4)nn3)[C@H]2O)[C@](C)(OC)C[C@@H](C)C(=O)[C@H](C)[C@@H](O)[C@]1(C)O] |

TABLE 1-continued

| Compound Number | Structure |
| --- | --- |
| 614 | 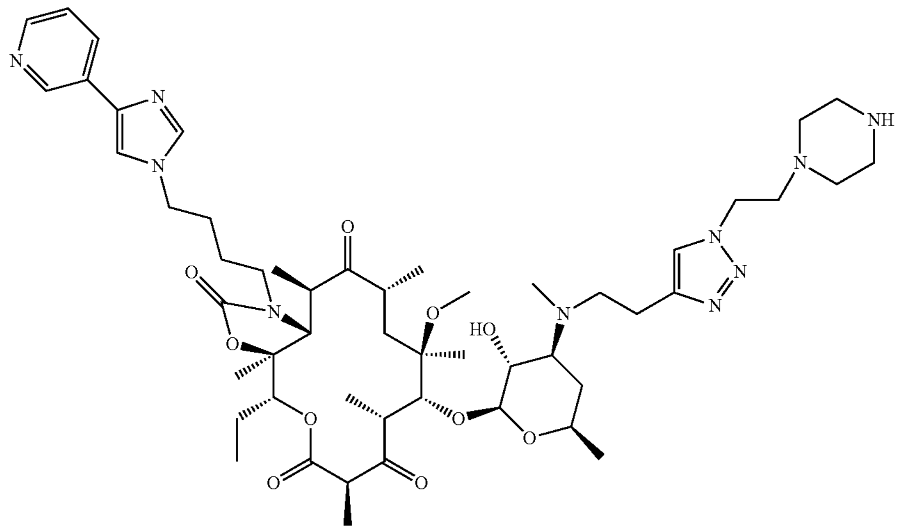 [SMILES: CC[C@H]1OC(=O)[C@H](C)C(=O)[C@H](C)[C@@H](O[C@@H]2O[C@H](C)C[C@H](N(C)CCc3cn(CCN4CCNCC4)nn3)[C@H]2O)[C@](C)(OC)C[C@@H](C)C(=O)[C@H](C)[C@H]2N(CCCCn3cnc(-c4cccnc4)c3)C(=O)O[C@]12C] |
| 615 | 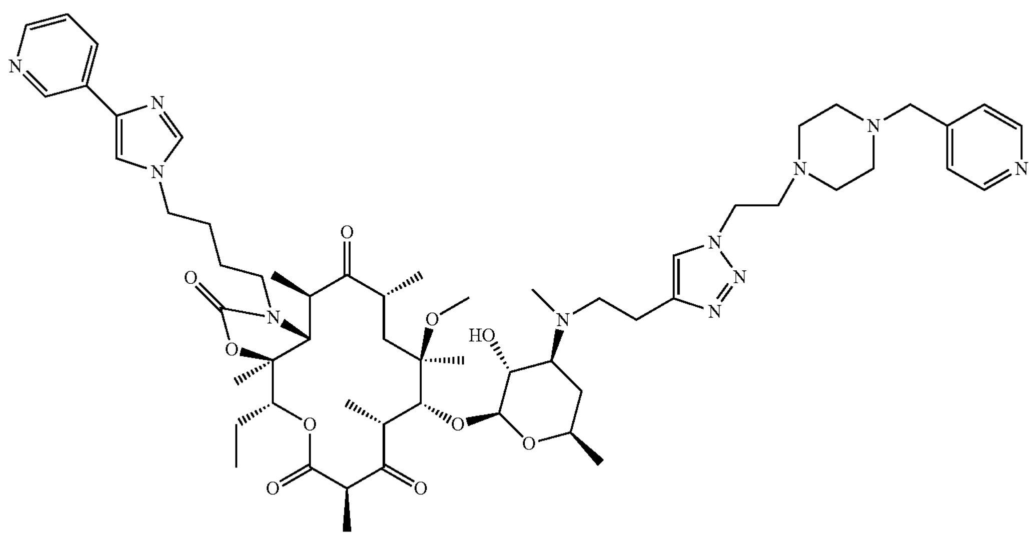 [SMILES: CC[C@H]1OC(=O)[C@H](C)C(=O)[C@H](C)[C@@H](O[C@@H]2O[C@H](C)C[C@H](N(C)CCc3cn(CCN4CCN(Cc5ccncc5)CC4)nn3)[C@H]2O)[C@](C)(OC)C[C@@H](C)C(=O)[C@H](C)[C@H]2N(CCCCn3cnc(-c4cccnc4)c3)C(=O)O[C@]12C] |
| 616 | 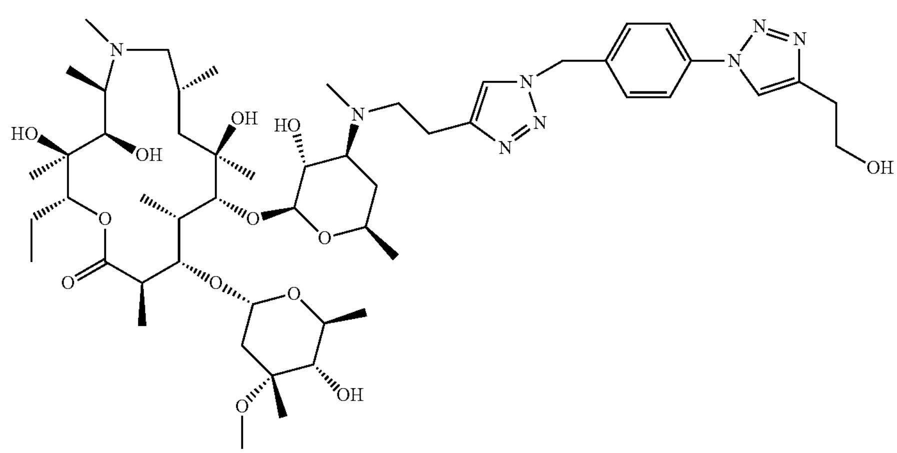 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc(-n5cc(CCO)nn5)cc4)nn3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 617 | 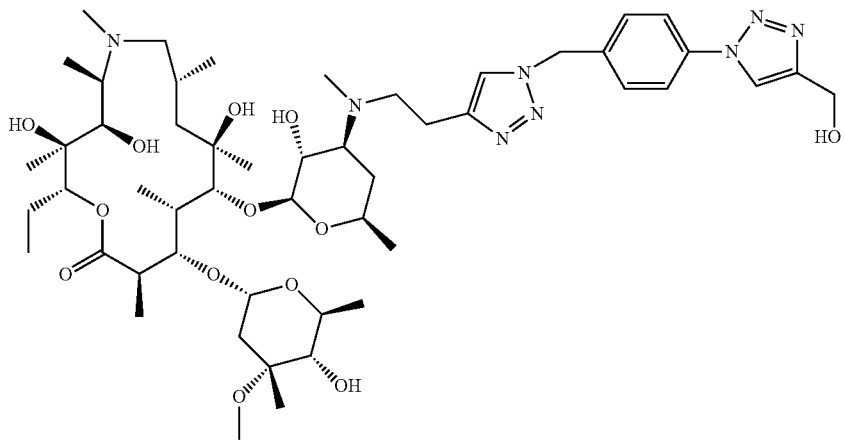 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc(-n5cc(CO)nn5)cc4)nn3)[C@H]2O)[C@](C)(O)C[C@@H](C)CN(C)[C@H](C)[C@@H](O)[C@]1(C)O] |
| 618 | 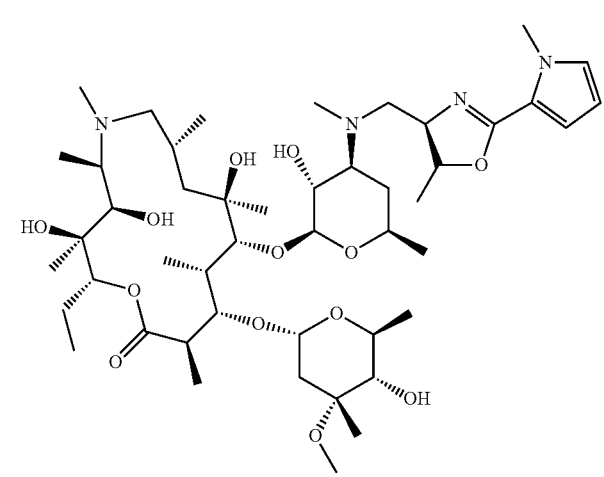 |
| 619 | 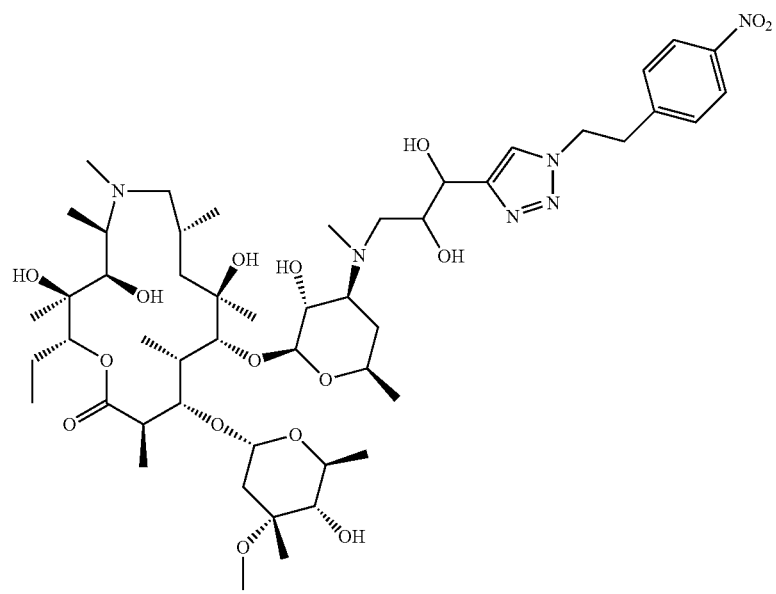 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CC(O)C(O)c3cn(CCc4ccc([N+](=O)[O-])cc4)nn3)[C@H]2O)[C@](C)(O)C[C@@H](C)CN(C)[C@H](C)[C@@H](O)[C@]1(C)O] |

TABLE 1-continued
| Compound Number | Structure |
|---|---|
| 620 | 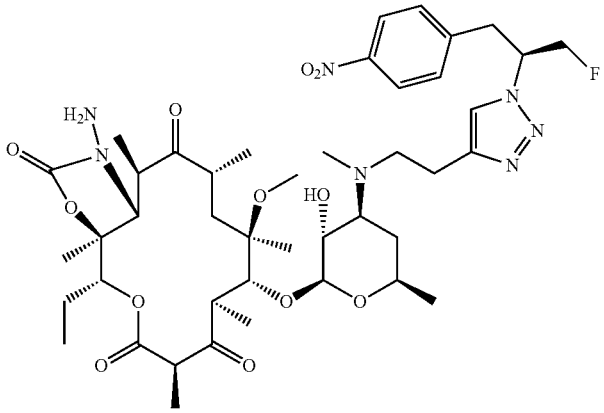 [SMILES: CC[C@H]1OC(=O)[C@H](C)C(=O)[C@H](C)[C@@H](O[C@@H]2O[C@H](C)C[C@H](N(C)CCc3cn([C@H](CF)Cc4ccc([N+](=O)[O-])cc4)nn3)[C@H]2O)[C@](C)(OC)C[C@@H](C)C(=O)[C@H](C)[C@H]2N(N)C(=O)O[C@]12C] |
| 621 | 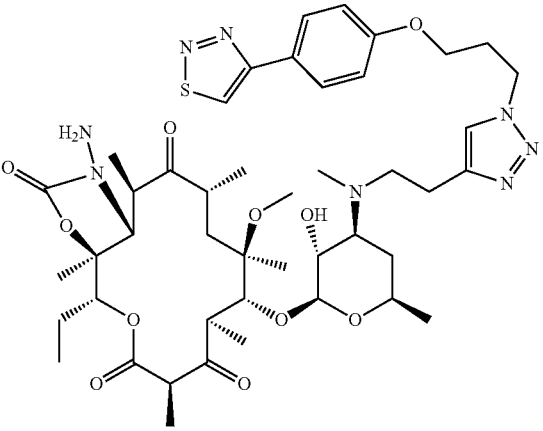 [SMILES: CC[C@H]1OC(=O)[C@H](C)C(=O)[C@H](C)[C@@H](O[C@@H]2O[C@H](C)C[C@H](N(C)CCc3cn(CCCOc4ccc(-c5csnn5)cc4)nn3)[C@H]2O)[C@](C)(OC)C[C@@H](C)C(=O)[C@H](C)[C@H]2N(N)C(=O)O[C@]12C] |
| 622 | 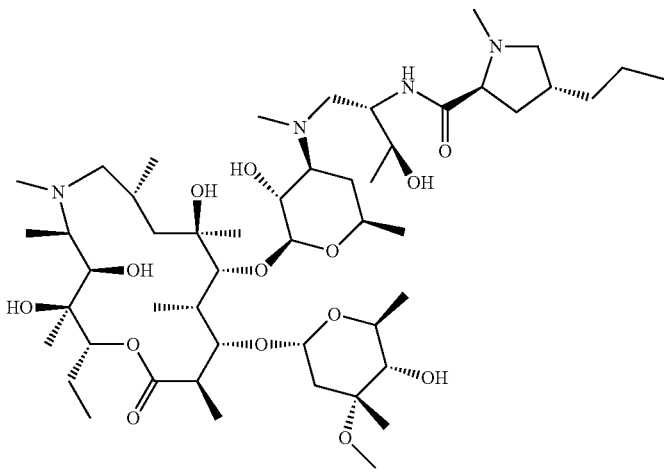 [SMILES: CCC[C@@H]1C[C@@H](C(=O)N[C@@H](CN(C)[C@H]2C[C@@H](C)O[C@@H](O[C@@H]3[C@@H](C)[C@H](O[C@H]4C[C@@](C)(OC)[C@@H](O)[C@H](C)O4)[C@@H](C)C(=O)O[C@H](CC)[C@@](C)(O)[C@H](O)[C@@H](C)N(C)C[C@H](C)C[C@@]3(C)O)[C@@H]2O)[C@H](C)O)N(C)C1] |

TABLE 1-continued
| Compound Number | Structure |
|---|---|
| 623 | 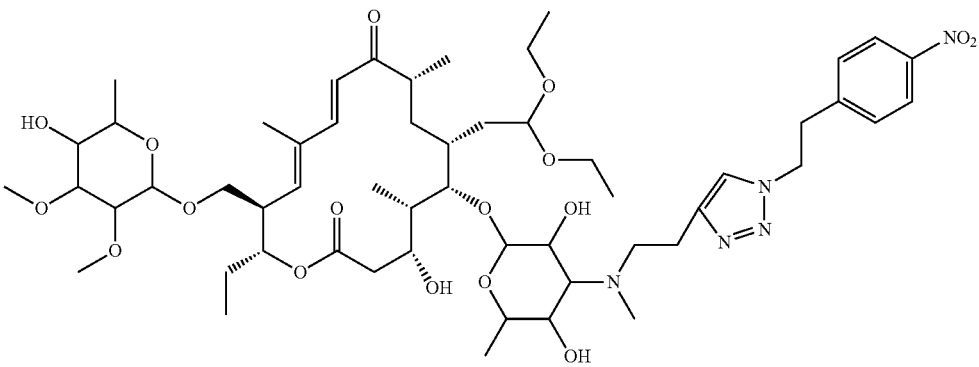 [SMILES: CCOC(C[C@H]1C[C@@H](C)C(=O)/C=C/C(C)=C/[C@H](COC2OC(C)C(O)C(OC)C2OC)[C@@H](CC)OC(=O)C[C@@H](O)[C@H](C)[C@H]1OC1OC(C)C(O)C(N(C)CCc2cn(CCc3ccc([N+](=O)[O-])cc3)nn2)C1O)OCC] |
| 624 | 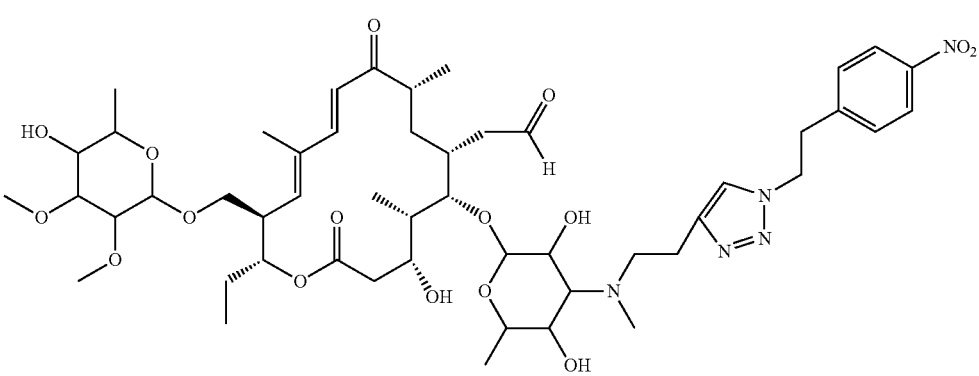 [SMILES: CC[C@H]1OC(=O)C[C@@H](O)[C@H](C)[C@@H](OC2OC(C)C(O)C(N(C)CCc3cn(CCc4ccc([N+](=O)[O-])cc4)nn3)C2O)[C@@H](CC=O)C[C@@H](C)C(=O)/C=C/C(C)=C/[C@@H]1COC1OC(C)C(O)C(OC)C1OC] |
| 625 | 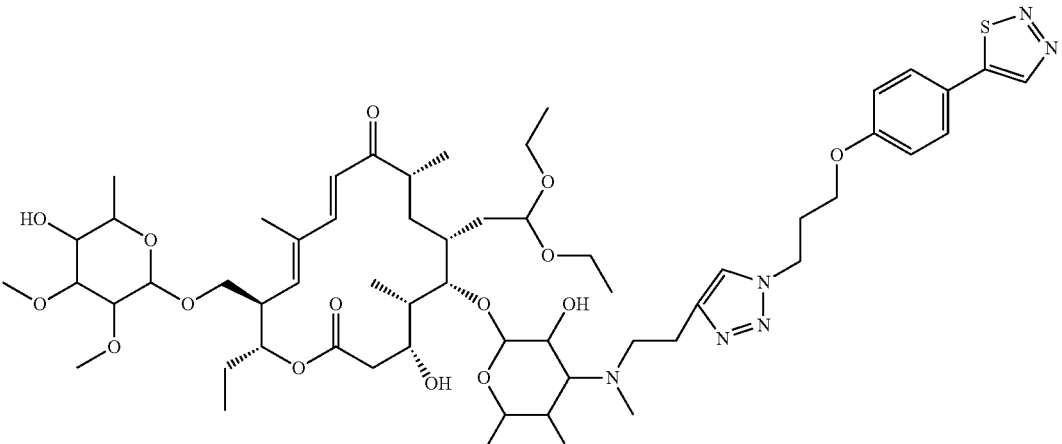 |

TABLE 1-continued

| Compound Number | Structure |
|---|---|
| 626 | |
| 627 | |
| 628 | |

TABLE 1-continued

| Compound Number | Structure |
|---|---|
| 629 | 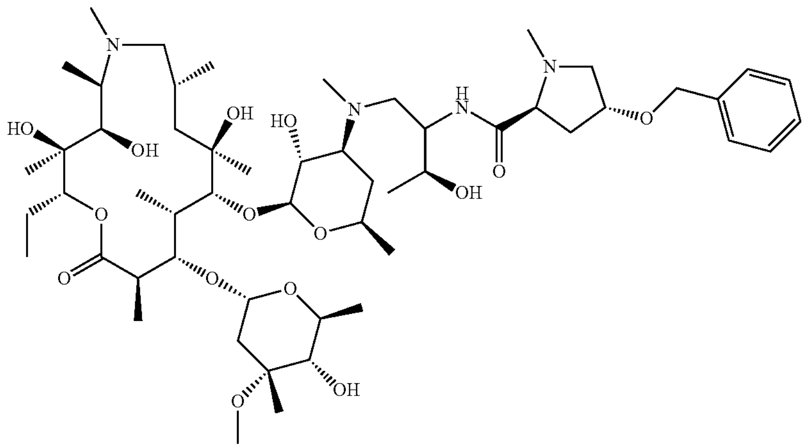 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CC(NC(=O)[C@@H]3C[C@@H](OCc4ccccc4)CN3C)[C@H](C)O)[C@H]2O)[C@](C)(O)C[C@@H](C)CN(C)[C@H](C)[C@@H](O)[C@]1(C)O] |
| 630 | 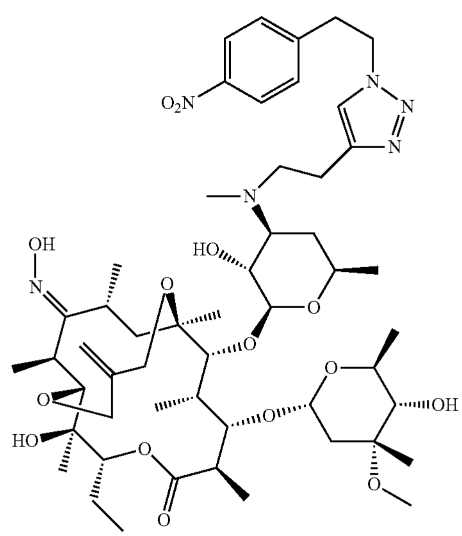 [SMILES: C=C1CO[C@@H]2[C@@H](C)/C(=N/O)[C@H](C)C[C@@](C)(OC1)[C@H](O[C@@H]1O[C@H](C)C[C@H](N(C)CCc3cn(CCc4ccc([N+](=O)[O-])cc4)nn3)[C@H]1O)[C@@H](C)[C@H](O[C@H]1C[C@@](C)(OC)[C@@H](O)[C@H](C)O1)[C@@H](C)C(=O)O[C@H](CC)[C@@]2(C)O] |

Example 1

Synthesis of Compounds 101-280

Schemes 100 and 101 below depict the synthesis of compounds 101-280. Demethylation of azithromycin 1 selectively produced 3'-N-desmethylazithromycin 2. Amine 2 was selectively alkylated with tosylates 11, 12 and 13 to produce alkynes 3, 4 and 5, respectively. As shown in Scheme 101 alkynes 3, 4, or 5 are reacted with azides 14a-14gm in the presence of copper(I) iodide to selectively afford the triazoles 101-280.

Scheme 100: Synthesis of alkynes 3, 4 and 5.

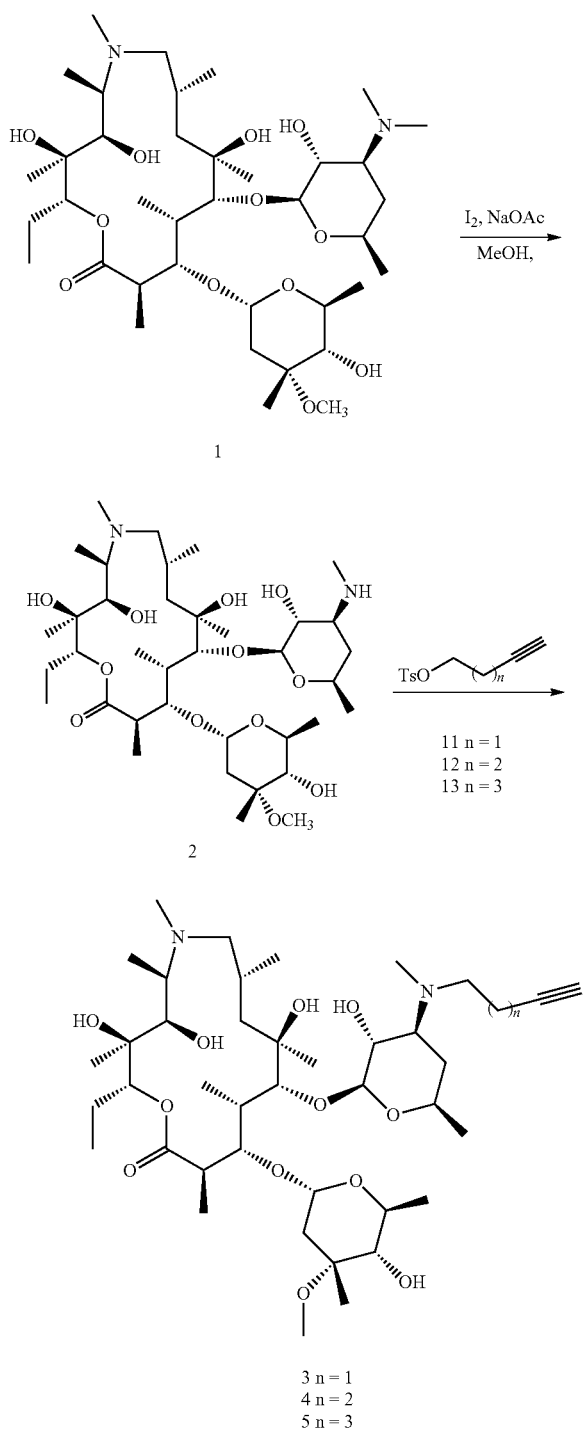

Synthesis of 3'-N-desmethylazithromycin 2

Azithromycin 1 (0.80 grams (g), 1.02 millimoles (mmol)) and sodium acetate (NaOAc) (0.712 g, 8.06 mmol) were dissolved in 80% aqueous methanol (MeOH) (25 mL). The solution was heated to 50° C. followed by addition of iodine ($I_2$) (0.272 g, 1.07 mmol) in three batches within 3 minutes. The reaction was maintained at a pH between 8-9 by adding 1N sodium hydroxide (NaOH) (1 mL) at 10 min and 45 minute intervals. The solution turned colorless within 45 minutes (min), however, stirring was continued for 2 hours (hr). TLC methylene chloride($CH_2Cl_2$)/MeOH/ammonium chloride ($NH_4OH$) 10:1:0.05) after 2 hours showed a single major product (Rf=0.66). The reaction was cooled to room temperature (rt), poured into $H_2O$ (75 mL) containing $NH_4OH$ (1.5 mL) and extracted with chloroform ($CHCl_3$) (3×30 mL). The combined organic layers were washed with $H_2O$ (30 mL) containing $NH_4OH$ (1.5 mL), dried over $Na_2SO_4$ and the solvent evaporated to give a white residue. The crude was purified on a silica gel column eluting with $CH_2Cl_2$/MeOH/$NH_4OH$ 18:1:0.05 to 10:1:0.05 to provide amine 2 (0.41 g, 55%).

Synthesis of Alkyne 5

A mixture of 3'-N-desmethylazithromycin 2 (0.5 g, 0.7 mmol) and tosylate 13 (0.20 g, 0.82 mmol) in N,N-diisopropylethylamine (Hunig's base) (3 mL) was stirred at 80° C. for 4 hours. The reaction mixture was diluted to 50 mL with ethylacetate (EtOAc) and washed with $NaHCO_3$(aq) and with brine (1×30 mL). The organic layer was dried over $K_2CO_3$ and the solvent was evaporated to give 0.65 g of a yellow foam. The crude product was purified on silica gel column eluting with $CH_2Cl_2$/MeOH 40:1 to give 5 as a white solid (0.42 g, 74%).

Synthesis of Alkyne 4

Alkyne 3 was made from 3'-N-desmethylazithromycin 2 and tosylate 12 using the same procedure described for the synthesis of compound 5.

Synthesis of Alkyne 3

Alkyne 3 was made from 3'-N-desmethylazithromycin 2 and tosylate 11 using the same procedure described for the synthesis of compound 5.

TABLE 2

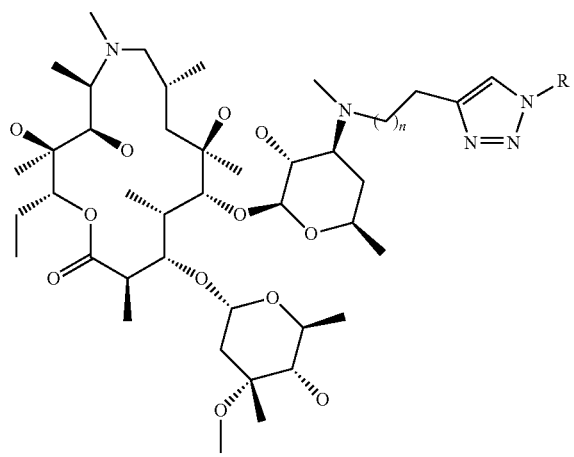

| Compound | R | Azide | n | Alkyne | Yield | LCMS (M/Z) |
|---|---|---|---|---|---|---|
| 101 | 3-nitrophenoxy-neopentyl | 14a | 1 | 3 | 55% | ND |
| 102 | 4-(methylsulfonyl)phenyl-neopentyl | 14b | 1 | 3 | 62% | 507.0 $(M + 2H)^{2+}$<br>1012.9 $(M + H)^+$ |
| 103 | 4-(methylsulfonyl)phenyl-neopentyl | 14c | 1 | 3 | 57% | 500.1 $(M + 2H)^{2+}$<br>998.9 $(M + H)^+$<br>1020.9 $(M + Na)^+$ |
| 104 | 4-(methylthio)phenyl-neopentyl | 14d | 1 | 3 | 67% | 491.1 $(M + 2H)^{2+}$<br>980.9 $(M + H)^+$<br>1002.9 $(M + Na)^+$ |
| 105 | 4-(methylthio)phenyl-neopentyl | 14e | 1 | 3 | 76% | 484.1 $(M + 2H)^{2+}$<br>966.9 $(M + H)^+$ |
| 106 | 2-(trifluoromethyl)-4-fluorophenyl-neopentyl | 14f | 1 | 3 | 95% | 504.0 $(M + 2H)^{2+}$<br>1008.9 $(M + H)^+$ |

TABLE 2-continued
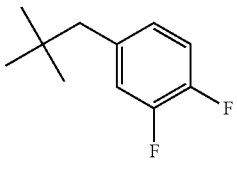
| Compound | R | Azide | n | Alkyne | Yield | LCMS (M/Z) |
|---|---|---|---|---|---|---|
| 107 | 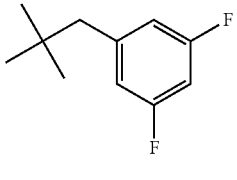 | 14g | 1 | 3 | 79% | 479.2 $(M + 2H)^{2+}$<br>798.6 $(M - C_8H_{15}O_3 + H)^+$<br>956.9 (M |
| 108 | 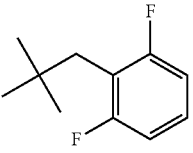 | 14h | 1 | 3 | 93% | 479.2 $(M + 2H)^{2+}$<br>798.6 $(M - C_8H_{15}O_3 + H)^+$<br>956.8 (M |
| 109 | 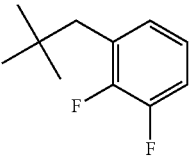 | 14i | 1 | 3 | 79% | 479.1 $(M + 2H)^{2+}$<br>798.5 $(M - C_8H_{15}O_3 + H)^+$<br>956.7 (M |
| 110 | 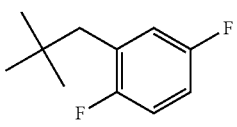 | 14k | 1 | 3 | 97% | 479.2 $(M + 2H)^{2+}$<br>798.6 $(M - C_8H_{15}O_3 + H)^+$<br>956.8 (M |
| 111 | 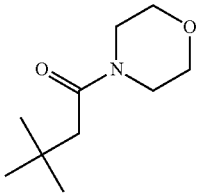 | 14l | 1 | 3 | 97% | 479.0 $(M + 2H)^{2+}$<br>956.7 $(M + H)^+$ |
| 112 |  | 14m | 1 | 3 | 49% | 479.5 $(M + 2H)^{2+}$<br>957.9 $(M + H)^+$ |

TABLE 2-continued
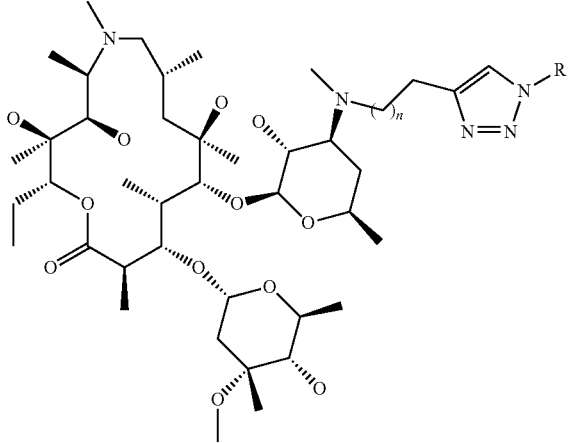
| Compound | R | Azide | n | Alkyne | Yield | LCMS (M/Z) |
|---|---|---|---|---|---|---|
| 113 | 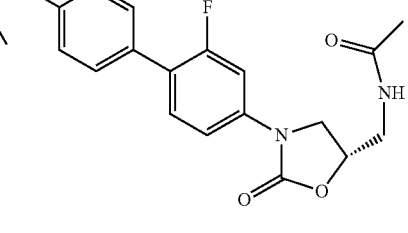 | 14n | 1 | 3 | 30% | 586.1 (M + 2H)$^{2+}$<br>1171.1 (M + H)$^+$ |
| 114 | 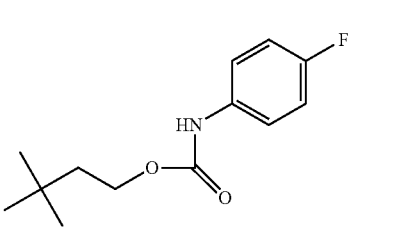 | 14o | 1 | 3 | 70% | 506.6 (M + 2H)$^{2+}$ |
| 115 | 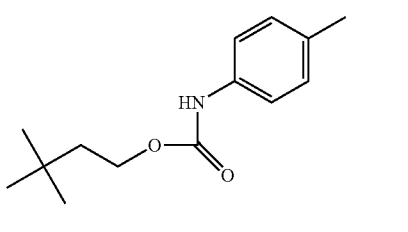 | 14p | 1 | 3 | 88% | 506.6 (M + 2H)$^{2+}$ |
| 116 | 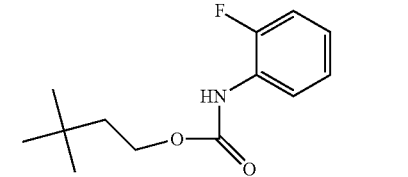 | 14q | 1 | 3 | 62% | 504.6 (M + 2H)$^{2+}$ |
| 117 |  | 14r | 1 | 3 | 78% | 506.6 (M + 2H)$^{2+}$ |

TABLE 2-continued
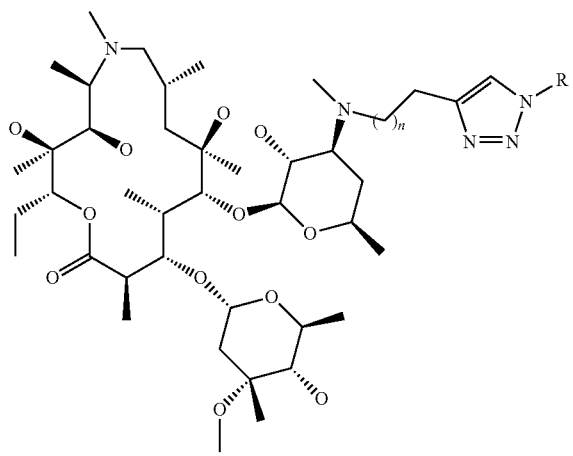
| Compound | R | Azide | n | Alkyne | Yield | LCMS (M/Z) |
|---|---|---|---|---|---|---|
| 118 | (structure with OH, nitrophenyl ketone) | 14s | 1 | 3 | 43% | 513.6 (M + 2H)$^{2+}$ |
| 119 | (neopentyloxy-3-fluorophenyl) | 14t | 1 | 3 | 51% | 585.6 (M + 2H)$^{2+}$ |
| 120 | (neopentyloxy-3-acetylphenyl) | 14u | 1 | 3 | 74% | 497.3 (M + 2H)$^{2+}$ |
| 121 | (neopentyl-4-nitrobenzyl) | 14v | 1 | 3 | 47% | 965.2 (M + H)$^+$<br>987.1 (M + Na)$^+$ |
| 122 | (4-nitrophenethyl neopentyl) | 14w | 1 | 3 | 96% | 979.5 (M + H)$^+$<br>1001.4 (M + Na)$^+$ |
| 123 | (4-tetrazolylphenyl neopentyl) | 14x | 1 | 3 | 61% | 988.4 (M + H)$^+$ |

TABLE 2-continued

| Compound | R | Azide | n | Alkyne | Yield | LCMS (M/Z) |
|---|---|---|---|---|---|---|
| 124 | (4-neopentyl-phenyl triazole) | 14y | 1 | 3 | 28% | 1004.1 (M + H)+ <br> 1023.3 (M + Na)+ |
| 125 | (4-tert-butylbenzyl triazole-ethanol) | 14z | 1 | 3 | 70% | 1031.4 (M + H)+ |
| 126 | (4-neopentylphenyl triazole-methanol) | 14aa | 1 | 3 | 51% | 1031.9 (M + H)+ |
| 129 | (4-trifluoromethyl-neopentylphenyl) | 14ad | 1 | 3 | 69% | 1002.7 (M + H)+ <br> 1024.6 (M + Na)+ |
| 130 | (4-fluoro-neopentylphenyl) | 14ae | 1 | 3 | 73% | 952.7 (M + H)+ <br> 974.7 (M + Na)+ |
| 131 | (4-neopentylphenyl-methyl-oxadiazole) | 14af | 1 | 3 | 85% | 1016.9 (M + H)+ <br> 1038.9 (M + Na)+ |

TABLE 2-continued

| Compound | R | Azide | n | Alkyne | Yield | LCMS (M/Z) |
| --- | --- | --- | --- | --- | --- | --- |
| 132 | | 14ag | 1 | 3 | 92% | 514.1 (M + 2H)$^{2+}$ |
| 133 | | 14ah | 1 | 3 | 38% | 530.1 (M + 2H)$^{2+}$ |
| 134 | | 14ai | 1 | 3 | 39% | 483.2 (M + 2H)$^{2+}$ |
| 135 | | 14aj | 1 | 3 | 37% | 483.1 (M + 2H)$^{2+}$ |
| 136 | | 14ak | 1 | 3 | 60% | 494.6 (M + 2H)$^{2+}$ |
| 137 | | 14al | 1 | 3 | 67% | 494.1 (M + 2H)$^{2+}$ |

TABLE 2-continued
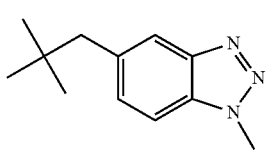
| Compound | R | Azide | n | Alkyne | Yield | LCMS (M/Z) |
|---|---|---|---|---|---|---|
| 138 | 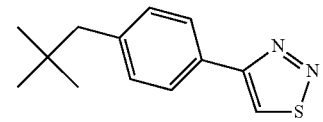 | 14am | 1 | 3 | 81% | 488.6 (M + 2H)$^{2+}$<br>975.8 (M + H)$^+$ |
| 139 | 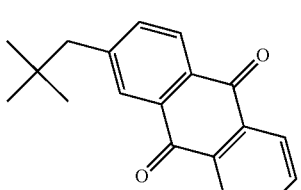 | 14an | 1 | 3 | 67% | 503.1 (M + 2H)$^{2+}$ |
| 140 | 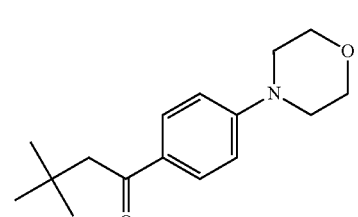 | 14ao | 1 | 3 | 74% | 526.1 (M + 2H)$^{2+}$ |
| 141 | 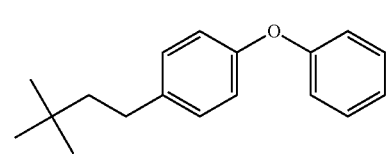 | 14ap | 1 | 3 | 46% | 517.7 (M + 2H)$^{2+}$<br>1034.0 (M + H)$^+$ |
| 142 | 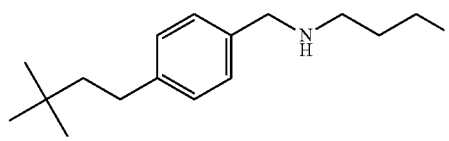 | 14aq | 1 | 3 | 79% | 514.1 (M + 2H)$^{2+}$ |
| 143 | | 14ar | 1 | 3 | 59% | 512.6 (M + 2H)$^{2+}$ |

TABLE 2-continued

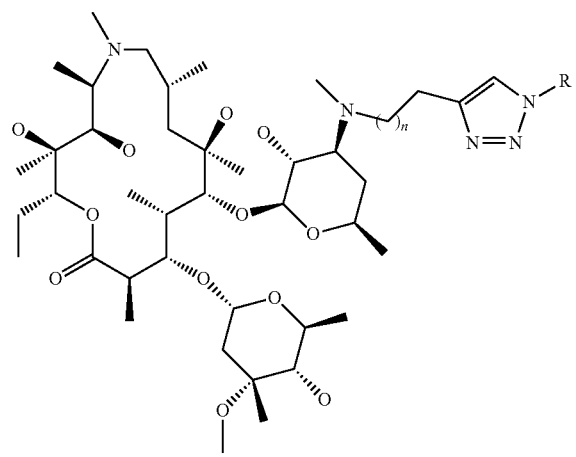

| Compound | R | Azide | n | Alkyne | Yield | LCMS (M/Z) |
|---|---|---|---|---|---|---|
| 144 | (5-methyl-2-phenyloxazol-4-yl)propyl with gem-dimethyl | 14as | 1 | 3 | 94% | 508.6 (M + 2H)²⁺<br>1015.9 (M + H)⁺ |
| 145 | (5-nitropyridin-2-yloxy)propyl with gem-dimethyl | 14at | 1 | 3 | 80% | 499.0 (M + 2H)²⁺ |
| 146 | 2-(fluoromethyl)-3-hydroxy-3-(4-(methylsulfonyl)phenyl)-tert-butyl derivative | 14au | 1 | 3 | 35% | 531.2 (M + 2H)²⁺ |
| 147 | 1-(4-(methylsulfonyl)phenyl)-4,4-dimethylpentan-1-one derivative | 14av | 1 | 3 | 32% | 514.3 (M + 2H)²⁺ |
| 148 | (quinolin-5-yloxy)propyl with gem-dimethyl | 14aw | 1 | 3 | 69% | 501.2 (M + 2H)²⁺ |
| 149 | (quinolin-4-yloxy)propyl with gem-dimethyl | 14ax | 1 | 3 | 87% | 501.1 (M + 2H)²⁺ |

TABLE 2-continued
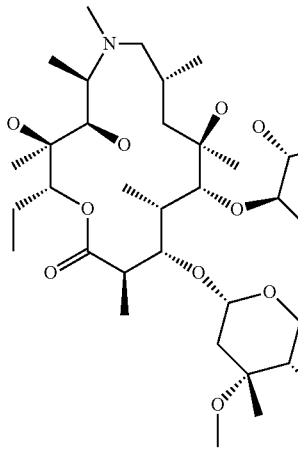
| Compound | R | Azide | n | Alkyne | Yield | LCMS (M/Z) |
|---|---|---|---|---|---|---|
| 150 | 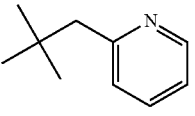 | 14ay | 1 | 3 | 50% | 501.4 (M + 2H)$^{2+}$ |
| 151 | 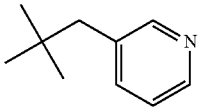 | 14az | 1 | 3 | 62% | 461.4 (M + 2H)$^{2+}$ |
| 152 | 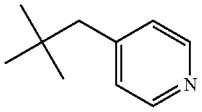 | 14ba | 1 | 3 | 42% | 461.2 (M + 2H)$^{2+}$ |
| 153 | 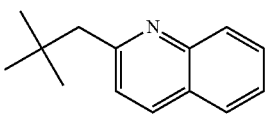 | 14bb | 1 | 3 | 45% | 461.0 (M + 2H)$^{2+}$ |
| 154 | 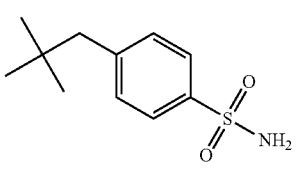 | 14bc | 1 | 3 | 66% | 486.4 (M + 2H)$^{2+}$ |
| 155 | 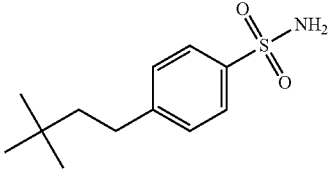 | 14bd | 1 | 3 | 93% | 500.5 (M + 2H)$^{2+}$ |
| 156 |  | 14be | 1 | 3 | 88% | 507.4 (M + 2H)$^{2+}$ |

TABLE 2-continued
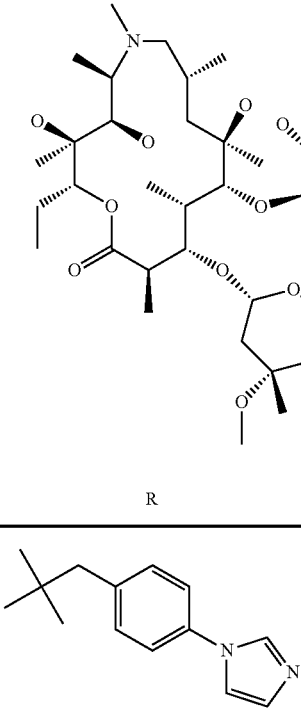
| Compound | R | Azide | n | Alkyne | Yield | LCMS (M/Z) |
|---|---|---|---|---|---|---|
| 157 | 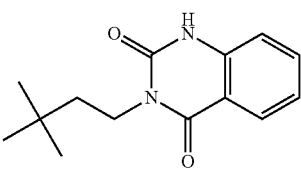 | 14bf | 1 | 3 | 62% | 493.7 $(M + 2H)^{2+}$<br>987.2 $(M + H)^+$ |
| 158 | 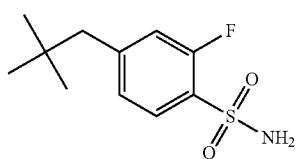 | 14bg | 1 | 3 | 70% | 509.9 $(M + 2H)^{2+}$<br>1018.3 $(M + H)^+$ |
| 159 | 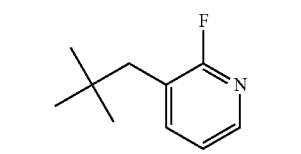 | 14bh | 1 | 3 | 37% | 509.7 $(M + 2H)^{2+}$<br>1017.9 $(M + H)^+$ |
| 160 | 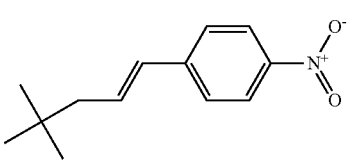 | 14bi | 1 | 3 | 75% | 470.6 $(M + 2H)^{2+}$ |
| 161 | 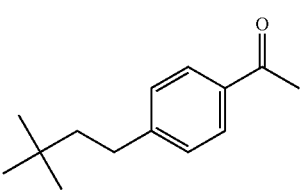 | 14bj | 1 | 3 | 82% | 496.6 $(M + 2H)^{2+}$<br>991.9 $(M + H)^+$ |
| 162 |  | 14bk | 1 | 3 | 69% | 489.1 $(M + 2H)^{2+}$ |

TABLE 2-continued
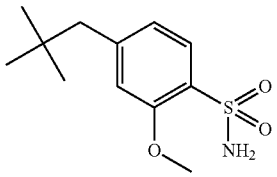 [SMILES: COc1cc(CC(C)(C)C)ccc1S(N)(=O)=O]
| Compound | R | Azide | n | Alkyne | Yield | LCMS (M/Z) |
|---|---|---|---|---|---|---|
| 163 | 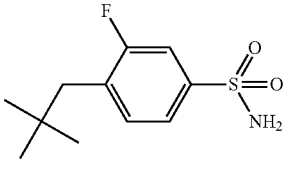 | 14bl | 1 | 3 | 57% | 515.5 (M + 2H)$^{2+}$<br>1029.9 (M + H)$^+$ |
| 164 | 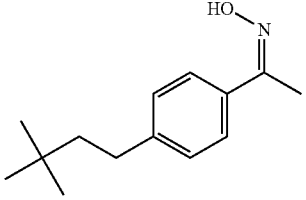 | 14bm | 1 | 3 | 57% | 509.6 (M + 2H)$^{2+}$<br>1017.8 (M + H)$^+$ |
| 165 | 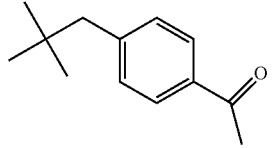 | 14bn | 1 | 3 | 63% | 496.7 (M + 2H)$^{2+}$ |
| 166 | 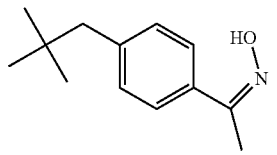 | 14bo | 1 | 3 | 89% | 482.1 (M + 2H)$^{2+}$ |
| 167 | 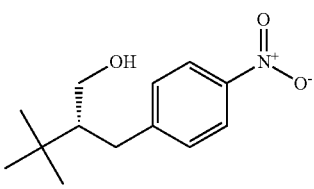 | 14bp | 1 | 3 | 90% | 489.5 (M + 2H)$^{2+}$<br>977.9 (M + H)$^+$ |
| 168 |  | 14bq | 1 | 3 | 83% | 505.6 (M + 2H)$^{2+}$<br>1009.9 (M + H)$^+$<br>1031.9 (M + Na)$^+$ |

TABLE 2-continued
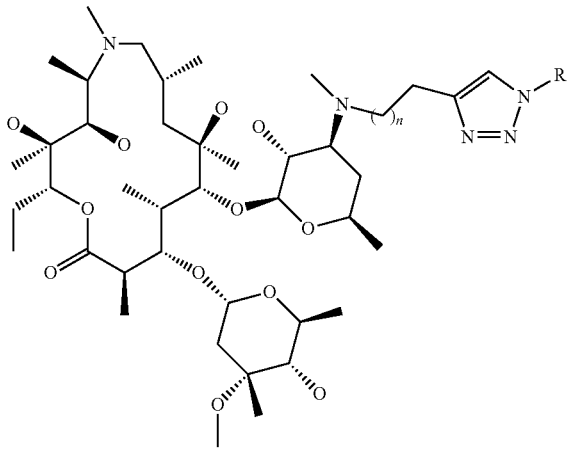
| Compound | R | Azide | n | Alkyne | Yield | LCMS (M/Z) |
|---|---|---|---|---|---|---|
| 169 | 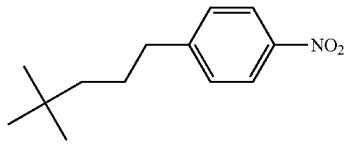 | 14br | 1 | 3 | 89% | 497.6 (M + 2H)$^{2+}$ |
| 170 | 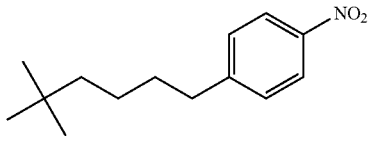 | 14bs | 1 | 3 | 81% | 504.5 (M + 2H)$^{2+}$ |
| 171 | 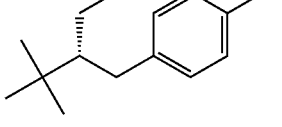 | 14bt | 1 | 3 | 84% | 506.6 (M + 2H)$^{2+}$ |
| 172 | 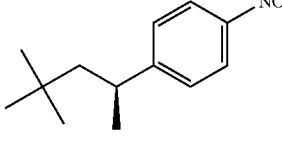 | 14bu | 1 | 3 | 91% | 497.6 (M + 2H)$^{2+}$ |
| 173 | 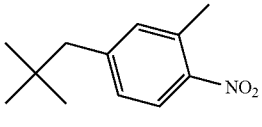 | 14bv | 1 | 3 | 93% | 490.6 (M + 2H)$^{2+}$<br>979.9 (M + H)$^+$ |
| 174 | 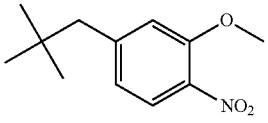 | 14bw | 1 | 3 | 96% | 505.6 (M + 2H)$^{2+}$<br>995.99 (M + H)$^+$<br>1017.9 (M + Na)$^+$ |
| 175 | 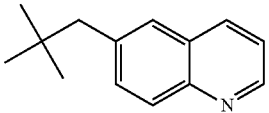 | 14bx | 1 | 3 | 97% | 486.5 (M + 2H)$^{2+}$<br>972.0 (M + H)$^+$ |

TABLE 2-continued

| Compound | R | Azide | n | Alkyne | Yield | LCMS (M/Z) |
|---|---|---|---|---|---|---|
| 176 | (4-neopentylphenyl)sulfonamido-ethanol group | 14bz | 1 | 3 | 70% | 522.4 (M + 2H)$^{2+}$<br>1043.4 (M + H)$^{+}$ |
| 177 | 4-neopentylbenzamide | 14ca | 1 | 3 | 55% | 482.2 (M + 2H)$^{2+}$<br>963.5 (M + H)$^{+}$ |
| 178 | N-(4-neopentylphenyl)methanesulfonamide | 14cb | 1 | 3 | 88% | 514.3 (M + 2H)$^{2+}$<br>1027.5 (M + H)$^{+}$ |
| 179 | 4-neopentyl-1,2-dimethoxybenzene | 14cc | 1 | 3 | 94% | 498.0 (M + 2H)$^{2+}$<br>1016.7 (M + Na)$^{+}$ |
| 180 | 4-neopentyl-N,N-dimethylaniline | 14cd | 1 | 3 | 82% | 489.5 (M + 2H)$^{2+}$<br>977.6 (M + H)$^{+}$ |
| 181 | 3-(trifluoromethyl)-neopentylbenzene | 14ce | 1 | 3 | 83% | 501.9 (M + 2H)$^{2+}$<br>1002.7 (M + H)$^{+}$ |
| 182 | 4-neopentylphenyl methyl sulfoxide | 14cf | 1 | 3 | 90% | 499.1 (M + 2H)$^{2+}$<br>996.7 (M + H)$^{+}$ |

TABLE 2-continued

| Compound | R | Azide | n | Alkyne | Yield | LCMS (M/Z) |
| --- | --- | --- | --- | --- | --- | --- |
| 183 | 4-(OCF3)-phenyl-neopentyl | 14cg | 1 | 3 | 79% | 510.0 (M + 2H)$^{2+}$<br>1018.8 (M + H)$^+$<br>1040.8 (M + Na)$^+$ |
| 184 | 3,4-dichlorophenyl-neopentyl | 14ch | 1 | 3 | 93% | 502.7 (M + 2H)$^{2+}$<br>1002.7 (M + H)$^+$<br>1024.7 (M + Na)$^+$ |
| 185 | 3,4-difluorophenyl-neopentyl | 14ci | 1 | 3 | 54% | 486.0 (M + 2H)$^{2+}$<br>970.8 (M + H)$^+$<br>992.8 (M + Na)$^+$ |
| 186 | 5-methylthiazol-4-yl-neopentyl | 14cj | 1 | 3 | 91% | 478.5 (M + 2H)$^{2+}$<br>955.7 (M + H)$^+$ |
| 187 | pyridin-4-yl-neopentyl | 14ck | 1 | 3 | 40% | 468.3 (M + 2H)$^{2+}$<br>935.9 (M + H)$^+$ |
| 188 | indol-3-yl-neopentyl | 14cl | 1 | 3 | 72% | 487.5 (M + 2H)$^{2+}$<br>973.9 (M + H)$^+$ |
| 189 | 4-(N,N-dimethylsulfamoyl)phenyl-neopentyl | 14cm | 1 | 3 | 75% | 514.6 (M + 2H)$^{2+}$<br>1027.8 (M + H)$^+$ |

TABLE 2-continued

| Compound | R | Azide | n | Alkyne | Yield | LCMS (M/Z) |
|---|---|---|---|---|---|---|
| 190 | (neopentyl-phenyl-SO2NHMe) | 14cn | 1 | 3 | 98% | 507.4 (M + 2H)$^{2+}$<br>1013.8 (M + H)$^+$ |
| 191 | (neopentyl-fluorophenyl-oxazolidinone-CH2OH) | 14co | 1 | 3 | 89% | 527.6 (M + 2H)$^{2+}$<br>1053.8 (M + H)$^+$<br>1075.9 (M + Na)$^+$ |
| 192 | (neopentyl-fluorophenyl-oxazolidinone-CH2NHAc) | 14cp | 1 | 3 | 85% | 548.1 (M + 2H)$^{2+}$<br>1094.1 (M + H)$^+$ |
| 193 | (neohexyl-phenyl-oxazolidinone-CH2OAc) | 14cq | 1 | 3 | 92% | 546.9 (M + 2H)$^{2+}$<br>1092.0 (M + H)$^+$ |
| 194 | (neohexyl-phenyl-oxazolidinone-CH2OH) | 14cr | 1 | 3 | 88% | 525.8 (M + 2H)$^{2+}$<br>1049.9 (M + H)$^+$ |

TABLE 2-continued
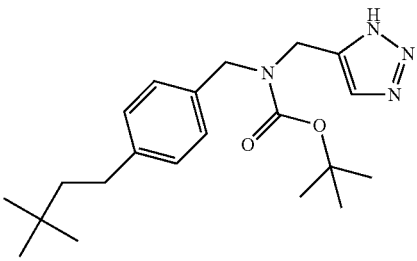 [SMILES: CC(C)(C)CCc1ccc(CN(Cc2cnn[nH]2)C(=O)OC(C)(C)C)cc1]
| Compound | R | Azide | n | Alkyne | Yield | LCMS (M/Z) |
|---|---|---|---|---|---|---|
| 195 | 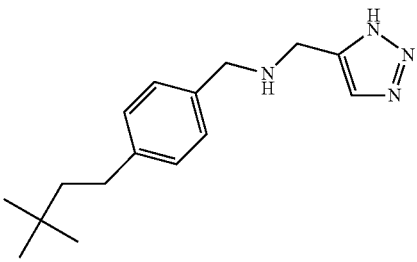 | 14cs | 1 | 3 | 87% | 573.3 (M + 2H)$^{2+}$ |
| 196 | 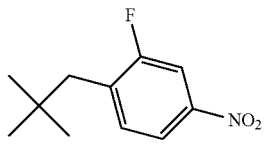 | 14ct | 1 | 3 | 58% | 523.2 (M + 2H)$^{2+}$ |
| 197 | 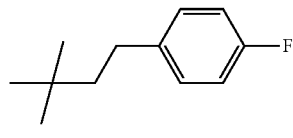 | 14cu | 1 | 3 | 75% | 492.6 (M + 2H)$^{2+}$ |
| 198 | 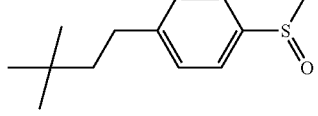 | 14ae | 2 | 4 | 83% | 484.0 (M + 2H)$^{2+}$<br>966.6 (M + H)$^+$ |
| 199 | 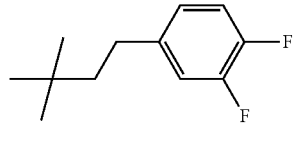 | 14cf | 2 | 4 | 79% | 506.1 (M + 2H)$^{2+}$<br>1010.7 (M + H)$^+$ |
| 200 |  | 14ci | 2 | 4 | 87% | 493.0 (M + 2H)$^{2+}$ |

TABLE 2-continued

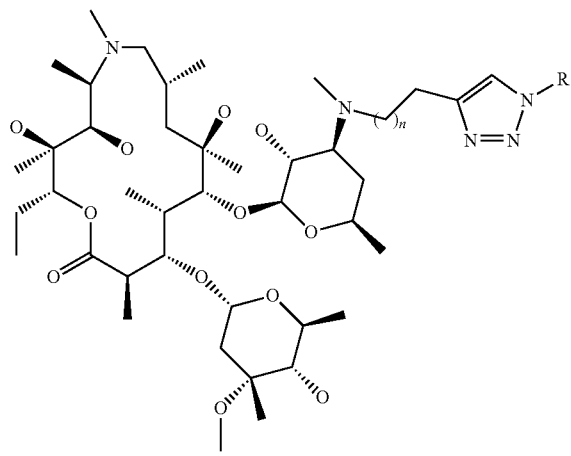

| Compound | R | Azide | n | Alkyne | Yield | LCMS (M/Z) |
|---|---|---|---|---|---|---|
| 201 | 4-methylthiazole with neopentyl linker | 14cj | 2 | 4 | 83% | 485.5 $(M + 2H)^{2+}$<br>969.6 $(M + H)^+$ |
| 202 | 4-(trifluoromethoxy)phenyl with neopentyl linker | 14cg | 2 | 4 | 83% | 516.7 $(M + 2H)^{2+}$<br>1032.8 $(M + H)^+$ |
| 203 | 3,4-dichlorophenyl with neopentyl linker | 14ch | 2 | 4 | 87% | 509.7 $(M + 2H)^{2+}$<br>1016.7 $(M + H)^+$ |
| 204 | hydroxymethyl, 4-nitrophenyl diol with tBu | 14s | 2 | 4 | 21% | 1040.5 $(M + H)^+$ |
| 205 | fluoromethyl, 4-(methylsulfonyl)phenyl with tBu | 14cv | 2 | 4 | 63% | 1076.6 $(M + H)^+$ |
| 206 | 4-(trifluoromethyl)phenyl with neopentyl linker | 14ad | 2 | 4 | 84% | 1016.7 $(M + H)^+$<br>1038.7 $(M + Na)^+$ |
| 207 | hydroxymethyl, 4-nitrophenyl with tBu | 14bq | 2 | 4 | 93% | 512.5 $(M + 2H)^{2+}$ |

TABLE 2-continued

| Compound | R | Azide | n | Alkyne | Yield | LCMS (M/Z) |
|---|---|---|---|---|---|---|
| 208 | 4-nitrophenyl neopentyl | 14w | 2 | 4 | 93% | 497.6 (M + 2H)$^{2+}$<br>994.4 (M + H)$^+$ |
| 209 | (5R)-3-(4-tert-butyl-3-fluorophenyl)-5-(hydroxymethyl)oxazolidin-2-one, Chiral | 14cx | 3 | 5 | 88% | 534.8 (M + 2H)$^{2+}$<br>909.8 (M − C$_8$H$_{15}$O$_3$ + H)$^+$<br>1068.0 (M |
| 210 | 4-sulfamoylphenyl neopentyl | 14bd | 3 | 5 | 92% | 514.7 (M + 2H)$^{2+}$ |
| 211 | 2-(3-nitrophenyl)propan-2-yl | 14dg | 1 | 3 | 90% | 951.3 (M + H)$^+$ |
| 212 | 2-(3-ethylphenyl)propan-2-yl | 14dh | 1 | 3 | 63% | 934.4 (M + H)$^+$ |
| 213 | 2-(pyridin-3-yl)propan-2-yl | 14dj | 1 | 3 | 83% | 907.3 (M + H)$^+$ |

TABLE 2-continued

| Compound | R | Azide | n | Alkyne | Yield | LCMS (M/Z) |
| --- | --- | --- | --- | --- | --- | --- |
| 214 | 4-tert-butylpyridine group | 14di | 1 | 3 | 83% | 907.3 (M + H)$^+$ |
| 215 | imidazopyridine group | 14ec | 1 | 3 | 92% | 502.7 (M + 2H)$^{2+}$ |
| 216 | methylsulfonylphenyl group | 14ed | 1 | 3 | 97% | 1045 (M + H)$^+$ |
| 217 | nitrophenyl acyl chloride group | 14ef | 1 | 3 | 67% | 512.5 (M + 2H)$^{2+}$ |
| 218 | nitrophenyl aldehyde group | 14eg | 1 | 3 | 96% | 512.1 (M + 2H)$^{2+}$ |

TABLE 2-continued
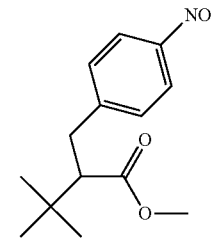
| Compound | R | Azide | n | Alkyne | Yield | LCMS (M/Z) |
|---|---|---|---|---|---|---|
| 219 | 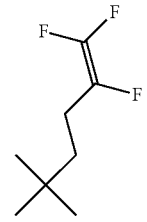 | 14eh | 1 | 3 | 91% | 519.5 (M + 2H)$^{2+}$ |
| 220 | 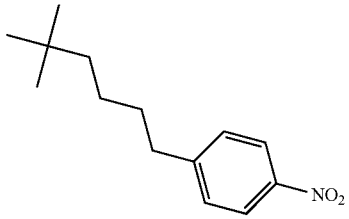 | 14ei | 1 | 3 | 80% | 470.0 (M + 2H)$^{2+}$<br>938.9 (M + H)$^{+}$ |
| 221 | 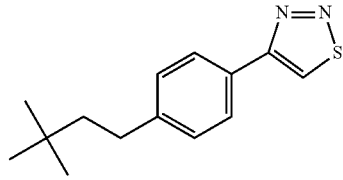 | 14ej | 2 | 4 | 90% | 511.6 (M + 2H)$^{2+}$ |
| 222 | 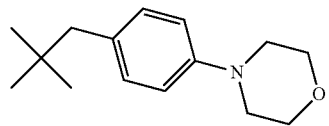 | 14el | 1 | 3 | 76% | 510.1 (M + 2H)$^{2+}$ |
| 223 |  | 14em | 1 | 3 | 62% | 1006.0 (M + H)$^{+}$ |

TABLE 2-continued

| Compound | R | Azide | n | Alkyne | Yield | LCMS (M/Z) |
|---|---|---|---|---|---|---|
| 224 | 4-(3,3-dimethylbutyl)-2-phenylthiazole | 14en | 1 | 3 | 47% | 509.6 (M + 2H)$^{2+}$ |
| 225 | 4-nitrobenzyl-neopentyl-NH$_2$ | 14eo | 1 | 3 | 69% | 505.0 (M + 2H)$^{2+}$ |
| 226 | 4-nitrobenzyl-neopentyl-CH$_3$ | N/A | 1 | 3 | 97% | 518.1 (M + 2H)$^{2+}$ |
| 227 | 4-nitrobenzyl-neopentyl-N(CH$_3$)$_2$ | 14eq | 1 | 3 | 73% | 519.2 (M + 2H)$^{2+}$ |
| 228 | 4-nitrobenzyl-neopentyl-triazole | 14er | 1 | 3 | 49% | 531.1 (M + 2H)$^{2+}$ |

TABLE 2-continued
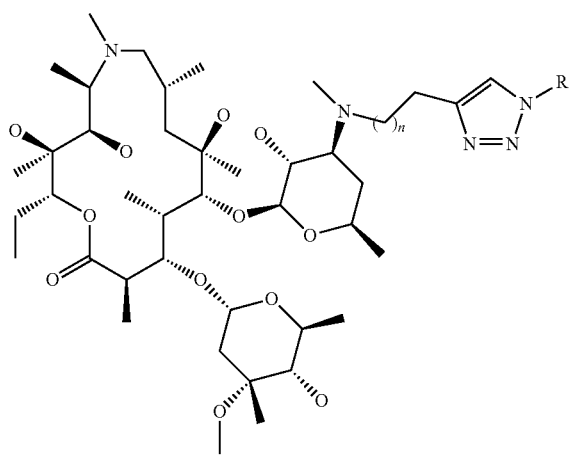
| Compound | R | Azide | n | Alkyne | Yield | LCMS (M/Z) |
|---|---|---|---|---|---|---|
| 229 | ![4-nitrobenzyl-neopentyl-CH2Cl] | 14es | 1 | 3 | 89% | 514.6 (M + 2H)$^{2+}$ |
| 230 | ![4-nitrophenoxy-propyl-tBu] | 14et | 1 | 3 | 74% | 505.6 (M + 2H)$^{2+}$ |
| 231 | ![4-nitrobenzyl-neopentyl-CH2OH] | 14eu | 3 | 5 | 65% | 519.8 (M + 2H)$^{2+}$ |
| 232 | ![4-nitrobenzyl-neopentyl-CH2F] | 14ev | 3 | 5 | 34% | 505.6 (M + 2H)$^{2+}$ |

TABLE 2-continued

| Compound | R | Azide | n | Alkyne | Yield | LCMS (M/Z) |
|---|---|---|---|---|---|---|
| 233 | (4-(5,5-dimethylhexyl)phenyl-triazole) | 14ew | 1 | 3 | 64% | 515.6 (M + 2H)$^{2+}$<br>1030.0 (M + H)$^{+}$ |
| 234 | (4-(3,3-dimethylbutyl)-5-methyl-2-phenylthiazole) | 14ex | 1 | 3 | 52% | 516.6 (M + 2H)$^{2+}$<br>1031.9 (M + H)$^{+}$ |
| 235 | (1-(4-(5,5-dimethylhexyl)phenyl)-4-(hydroxymethyl)triazole) | 14ey | 1 | 3 | 77% | 530.6 (M + 2H)$^{2+}$ |

TABLE 2-continued
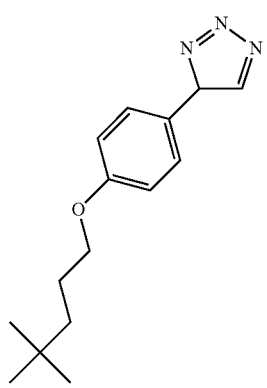 [SMILES: CC(C)(C)CCCOc1ccc(C2C=NN=N2)cc1]
| Compound | R | Azide | n | Alkyne | Yield | LCMS (M/Z) |
|---|---|---|---|---|---|---|
| 236 | 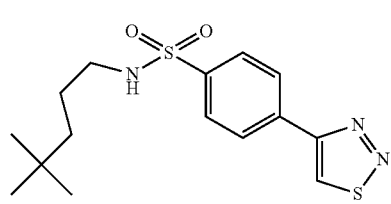 | 14ez | 1 | 3 | 62% | 525.1 (M + 2H)$^{2+}$ |
| 237 | 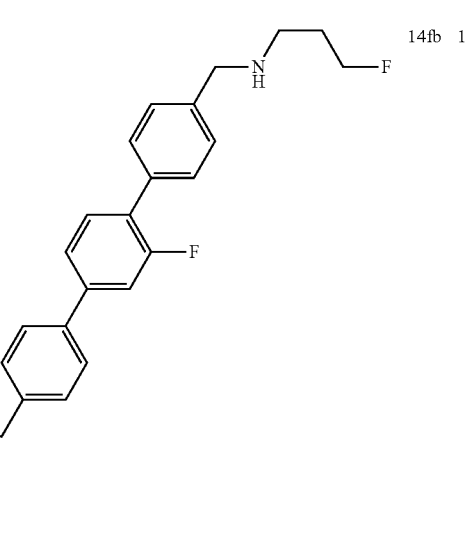 | 14fa | 1 | 3 | 66% | 556.6 (M + 2H)$^{2+}$ |
| 238 |  | 14fb | 1 | 3 | 88% | 408.8 (M + 3H)$^{3+}$ |

TABLE 2-continued
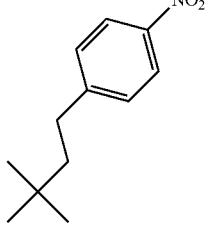
| Compound | R | Azide | n | Alkyne | Yield | LCMS (M/Z) |
|---|---|---|---|---|---|---|
| 239 | 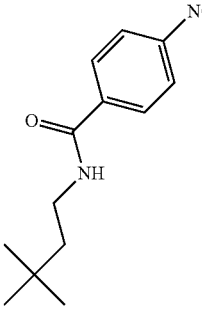 | 14w | 3 | 5 | 44% | 504.4 (M + 2H)$^{2+}$ |
| 240 | 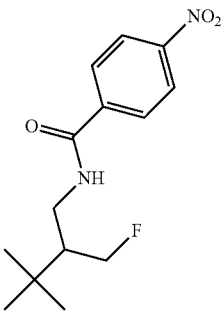 | 14fd | 1 | 3 | 83% | 512.0 (M + 2H)$^{2+}$ |
| 241 | 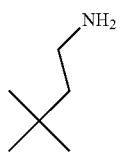 | 14fe | 1 | 3 | 61% | 528.1 (M + 2H)$^{2+}$ |
| 242 |  | 14ff | 1 | 3 | 89% | 437.5 (M + 2H)$^{2+}$ |

TABLE 2-continued
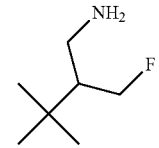
| Compound | R | Azide | n | Alkyne | Yield | LCMS (M/Z) |
|---|---|---|---|---|---|---|
| 243 | 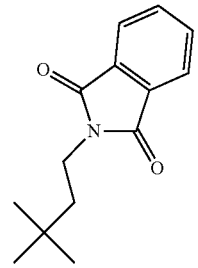 | 14fg | 1 | 3 | 90% | 453.3 $(M + 2H)^{2+}$ |
| 244 | 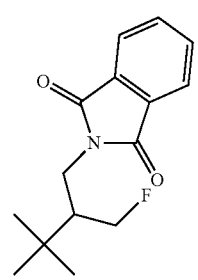 | 14fh | 1 | 3 | 92% | 502.6 $(M + 2H)^{2+}$<br>1003.9 $(M + H)^+$ |
| 245 | 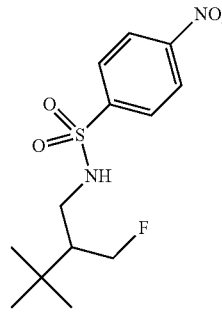 | 14fi | 1 | 3 | 83% | 518.5 $(M + 2H)^{2+}$ |
| 246 |  | 14fj | 1 | 3 | 36% | 546.1 $(M + 2H)^{2+}$ |

TABLE 2-continued
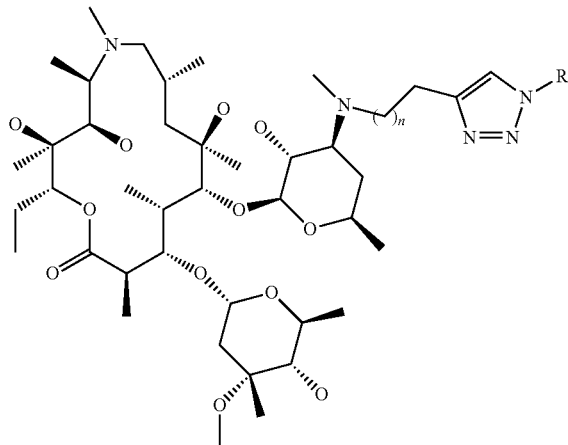
| Compound | R | Azide | n | Alkyne | Yield | LCMS (M/Z) |
|---|---|---|---|---|---|---|
| 247 | (triazole-phenyl-NO2 with N-CH2-C(CH3)2-CH2F substituent) | 14fk | 1 | 3 | 56% | 540.1 $(M + 2H)^{2+}$ |
| 248 | (4-nitrophenylsulfonamide with neopentyl group) | 14fl | 1 | 3 | 80% | 530.1 $(M + 2H)^{2+}$ |
| 249 | (4-methylsulfonylphenylsulfonamide with neopentyl group) | 14fm | 1 | 3 | 66% | 546.6 $(M + 2H)^{2+}$ |

TABLE 2-continued

| Compound | R | Azide | n | Alkyne | Yield | LCMS (M/Z) |
|---|---|---|---|---|---|---|
| 250 | *4-nitrobenzyl-NH-CH2CH2-C(CH3)3* | 14fn | 1 | 3 | 24% | 505.0 (M + 2H)$^{2+}$ |
| 251 | *4-nitrobenzyl-CH(CH3)-C(CH3)3* | 14fo | 1 | 3 | 96% | 497.6 (M + 2H)$^{2+}$ 993.7 (M + H)$^+$ |
| 252 | *4-(methylsulfonyl)phenyl-O-(CH2)3-C(CH3)3* | 14fp | 1 | 3 | 95% | 522.1 (M + 2H)$^{2+}$ |
| 254 | *HO-CH2-CH(OH)-CH(C(CH3)3)-(3-F-4-NO2-phenyl)* | 14fr | 1 | 3 | 30% | 522.6 (M + 2H)$^{2+}$ |

TABLE 2-continued
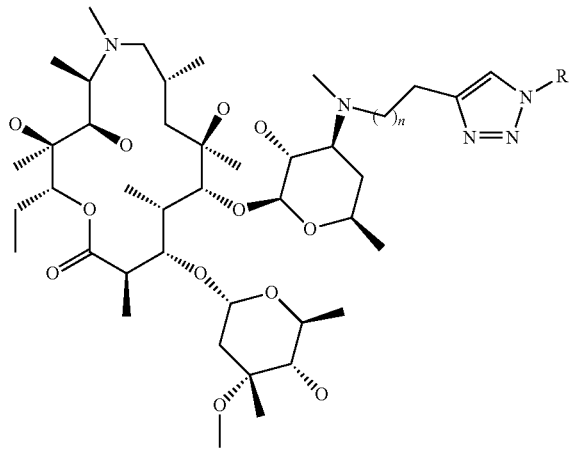
| Compound | R | Azide | n | Alkyne | Yield | LCMS (M/Z) |
|---|---|---|---|---|---|---|
| 255 | (1-tetrazolyl phenyl with neopentyl group) | 14fs | 1 | 3 | 29% | 1003.7 (M + H)$^+$ |
| 256 | (thiatriazole-NH-phenyl-O-alkyl) | 14ft | 1 | 3 | 27% | 533.1 (M + 2H)$^{2+}$ |
| 257 | (NO$_2$-phenyl with CHF, CH$_2$F, t-Bu) | 14fu | 1 | 3 | 89% | 1002.8 (M + H)$^+$ |
| 258 | (pyridyl-CF$_2$-neopentyl) | 14fv | 1 | 3 | 91% | 515.5 (M + 2H)$^{2+}$<br>1029.8 (M + H)$^+$ |

TABLE 2-continued

| Compound | R | Azide | n | Alkyne | Yield | LCMS (M/Z) |
|---|---|---|---|---|---|---|
| 259 | | 14fw | 1 | 3 | 20% | 991.8 (M + H$^{2+}$) |
| 260 | | 14fx | 1 | 3 | 50% | 1056.8 (M + H)$^+$ |
| 261 | | 14fy | 1 | 3 | 60% | 578.1 (M + 2H)$^{2+}$<br>1154.9 (M + H)$^+$ |
| 262 | | 14fz | 1 | 3 | 92% | 533.1 (M + 2H)$^{2+}$ |

TABLE 2-continued
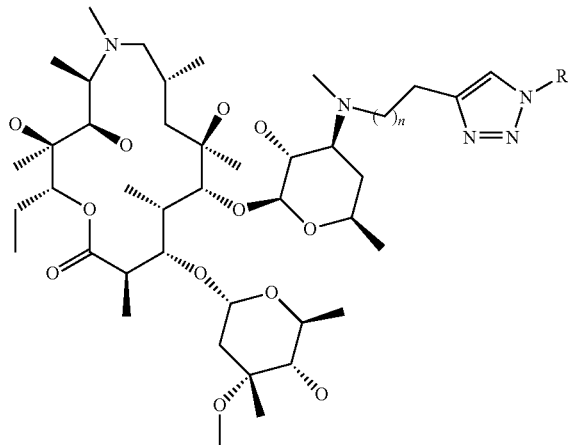
| Compound | R | Azide | n | Alkyne | Yield | LCMS (M/Z) |
|---|---|---|---|---|---|---|
| 263 | 4-((3,3-dimethylbutyl)sulfonyl)phenyl with NO$_2$ | 14ga | 1 | 3 | 90% | 529.5 (M + 2H)$^{2+}$ |
| 264 | N-methyl-N-(3,3-dimethylbutyl)-4-nitrobenzylamine | 14gb | 1 | 3 | 87% | 511.9 (M + 2H)$^{2+}$ |
| 265 | N-(3,3-dimethylbutyl)-4-(methylsulfonyl)benzylamine | 14gc | 1 | 3 | 45% | 521.5 (M + 2H)$^{2+}$ |

TABLE 2-continued

| Compound | R | Azide | n | Alkyne | Yield | LCMS (M/Z) |
|---|---|---|---|---|---|---|
| 266 | 4-nitrophenoxy-CH₂-CH(OH)-CH₂-C(CH₃)₃ | 14gd | 1 | 3 | 94% | 513.6 (M + 2H)²⁺ |
| 267 | 4-nitrophenoxy-CH₂-CH(OH)-CH₂-C(CH₃)₃ | 14ge | 1 | 3 | 79% | 513.6 (M + 2H)²⁺ |
| 268 | 4-(methylsulfonyl)phenoxy-CH₂-CH(OH)-CH₂-C(CH₃)₃ | 14gf | 1 | 3 | 75% | 530 (M + 2H)²⁺ |
| 269 | 4-(methylsulfonyl)phenoxy-CH₂-CH(F)-CH₂-C(CH₃)₃ | 14gg | 1 | 3 | 78% | 531 (M + 2H)²⁺<br>1060.7 (M + H)⁺ |
| 270 | 4-(1,2,3-thiadiazol-4-yl)phenoxy-CH₂-CH(OH)-CH₂-C(CH₃)₃ | 14gh | 1 | 3 | 88% | 533.1 (M + 2H)²⁺<br>1064.8 (M + H)⁺ |

TABLE 2-continued
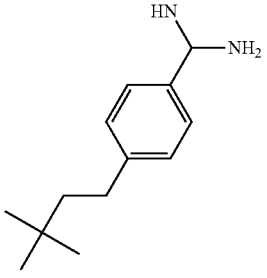
| Compound | R | Azide | n | Alkyne | Yield | LCMS (M/Z) |
|---|---|---|---|---|---|---|
| 271 | 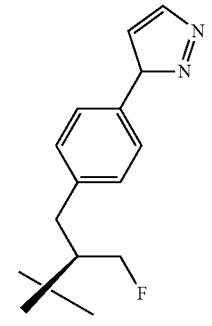 | 14gi | 1 | 3 | 14% | 976.7 (M + H)$^+$ |
| 272 | 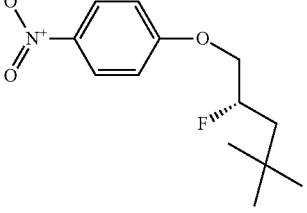 | 14gj | 1 | 3 | 76% | 530 (M + 2H)$^{2+}$ |
| 273 | 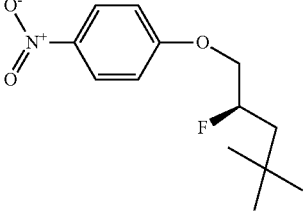 | 14gk | 1 | 3 | 56% | 514.6 (M + 2H)$^{2+}$<br>1064.8 (M + H)$^+$ |
| 274 |  | 14gl | 1 | 3 | 61% | 514.6 (M + 2H)$^{2+}$<br>1064.8 (M + H)$^+$ |

TABLE 2-continued
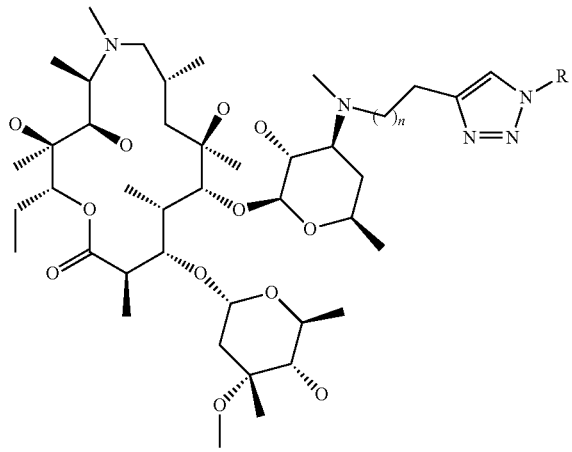
| Compound | R | Azide | n | Alkyne | Yield | LCMS (M/Z) |
|---|---|---|---|---|---|---|
| 275 | (1-(3,3-dimethylbutyl)uracil group) | 14gm | 1 | 3 | 55% | 485.1 (M + 2H)$^{2+}$ |
| 276 | (4-nitrophenoxy-(2S)-methyl-4,4-dimethylpentyl group) | 14gn | 1 | 3 | 85% | 512.6 (M + 2H)$^{2+}$<br>1024 (M + H)$^{+}$ |
| 277 | (4-nitrophenoxy-(2R)-methyl-4,4-dimethylpentyl group) | 14go | 1 | 3 | 88% | 512.6 (M + 2H)$^{2+}$<br>1024 (M + H)$^{+}$ |

TABLE 2-continued
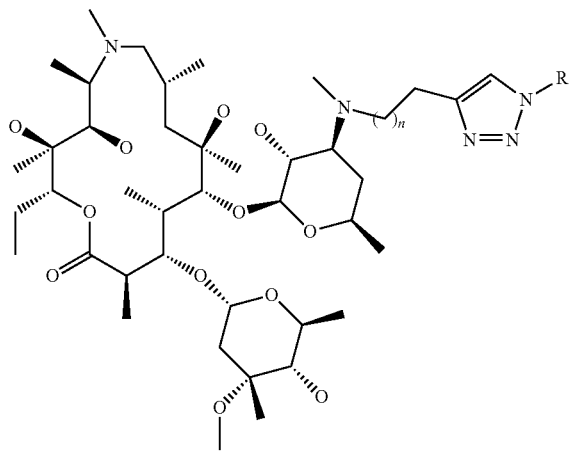
| Compound | R | Azide | n | Alkyne | Yield | LCMS (M/Z) |
|---|---|---|---|---|---|---|
| 278 | ![structure: 5-amino-1,3,4-thiadiazole linked to phenyl-O-CH2CH2CH2-C(CH3)3] | 14fq | 1 | 3 | 46% | 532.4 (M + 2H)$^{2+}$ |
| 279 | ![structure: 4-methoxyphenyl-1,3,4-thiadiazole-NH-CH2CH2CH2-C(CH3)3] | 14ab | 1 | 3 | 23% | 539.5 (M + 2H)$^{2+}$ |
| 280 | ![structure: 4-methoxyphenyl-1,3,4-thiadiazole-N(COCH3)-CH2CH2CH2-C(CH3)3] | 14ac | 1 | 3 | 42% | 560.6 (M + 2H)$^{2+}$ |

Scheme 101: Synthesis of compounds of Table 2

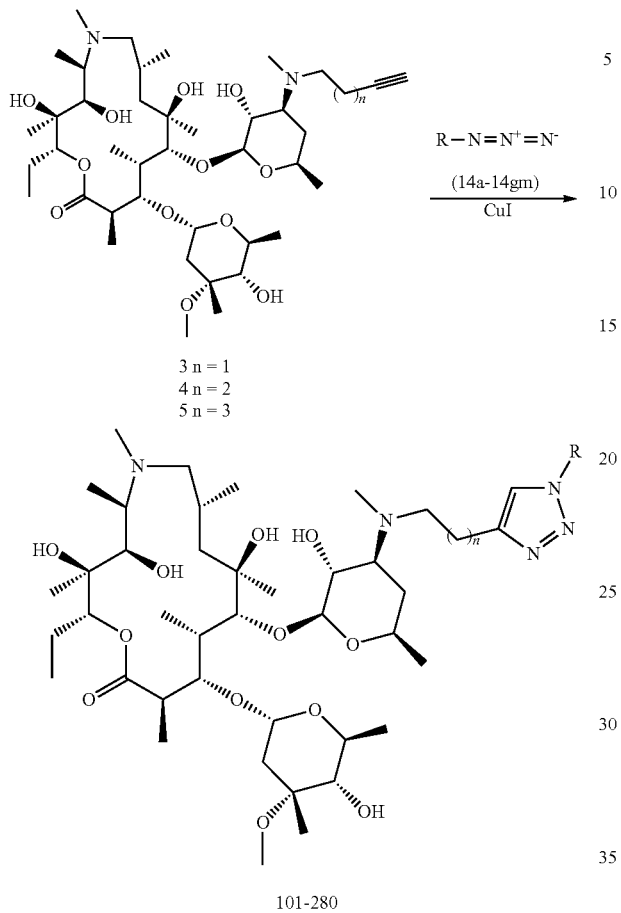

3 n = 1
4 n = 2
5 n = 3

101-280

Triazoles 101-280 were produced from alkynes 3, 4, and 5 using azides 14a-14gm under one of several similar reaction conditions as exemplified by Conditions A, B, C, and D below for compounds 151, 155, 159, and 158 respectively. Use of Conditions A and C, which do not include the step of degassing the reaction mixture, resulted in the formation of significant amounts of iodinated side-products in addition to the desired product and thereby generally produced lower isolated yields. Additionally, reduction of the amount of copper iodide used in the reaction to 0.5 molar equivalents or less as in conditions B and D also resulted in reduced formation of iodinated by-products. As demonstrated in Condition D, the presence of Hunig's base was not essential for the success of the triazole formation step; however, it was found preferable that the base be included since it often resulted in a higher rate of reaction and allowed correspondingly shorter reaction times to be used.

Condition A

Synthesis of Triazole 151

To a stirred solution of alkyne 3 (30 mg, 0.04 mmol), azide 14az (10 mg, 0.07 mmol) and Hunig's base (10 μL) in 0.5 mL tetrahydrofuran (THF) was added CuI (5 mg, 0.03 mmol). The mixture was stirred at ambient temperature for 16 h then diluted with $CH_2Cl_2$ (10 mL) and washed with a 3:1 mixture of saturated aqueous $NH_4Cl$ and 28% aqueous $NH_4OH$ (10 mL) and with brine (10 mL) the aqueous washes were back-extracted with $CH_2Cl_2$ (2×10 mL). The combined organic extracts were dried over $K_2CO_3$, filtered, and concentrated to afford 52 mg of crude product which was purified by chromatography on silica gel (elution with 40:1 2M $NH_3$ in MeOH and $CH_2Cl_2$) to give the title compound as a white solid (22 mg, 63%). (943.4 [M+Na]$^+$, 921.3 [M+H], 461.3 [M+2H]$^{2+}$.

Condition B

Synthesis of Triazole 155

A solution of alkyne 3 (80 mg, 0.10 mmol) and azide 14bd (21 mg, 0.12 mmol) and Hunig's base in 0.4 mL THF was thoroughly degassed by alternately evacuating the reaction vessel and purging with dry argon. CuI was then added (2 mg, 0.01 mmol) and the mixture was further degassed. The mixture was stirred under argon for 6 h then diluted with $CH_2Cl_2$ (20 mL) and washed with a 3:1 mixture of saturated aqueous $NH_4Cl$ and 28% aqueous $NH_4OH$ (10 mL) and with brine (10 mL) the aqueous washes were back-extracted with $CH_2Cl_2$ (2×15 mL). The combined organic extracts were dried over $K_2CO_3$, filtered, and concentrated to afford 115 mg of crude product which was purified by chromatography on silica gel (eluted with 2M $NH_3$ in MeOH (2.5%) and $CH_2Cl_2$ (97.5%). To give the title compound as a white solid (94 mg, 0.094 mmol). MS (ESI) m/e 999.3 [M+H]$^+$, 500.4 [M+2H]$^{2+}$.

Condition C

Synthesis of Triazole 159

To a stirred solution of alkyne 3 (79 mg, 0.10 mmol) and Hunig's base (0.2 mL) in 3 mL THF was added azide 14bh (115 mg, 0.50 mmol) and CuI (20 mg, 0.10 mmol). The reaction mixture was stirred under argon for 60 h then poured into saturated aqueous $NH_4Cl$ and extracted with $CH_2Cl_2$. The organic extracts were dried over $Na_2SO_4$, filtered, and concentrated to afford a crude residue which was purified by silica gel chromatography (eluted with 25:1:0.1 $CH_2Cl_2$: MeOH:$NH_4OH$) and then by preparative TLC (elution with 25:1:0.1 $CH_2Cl_2$:MeOH:$NH_4OH$) to afford the title compound as a white solid (38 mg, 0.037 mmol). MS (ESI) m/e 1017.9 [M+H]$^+$, 509.7 [M+2H]$^{2+}$.

Condition D

Synthesis of Triazole 158

A solution of alkyne 3 (120 mg, 0.15 mmol) and azide 14bg (60 mg, 0.25 mmol) in 2.7 mL THF was thoroughly degassed by alternately evacuating the reaction vessel and purging with dry argon. CuI was then added (10 mg, 0.05 mmol) and the mixture was further degassed. The mixture was stirred under argon for 4 h then concentrated in vacuo, dissolved in $CH_2Cl_2$ (1 mL), and placed directly on a silica gel column. Elution with 2 molar (M) $NH_3$ in MeOH (3%) and $CH_2Cl_2$ (97%) gave the title compound as a white solid (80 mg, 0.08 mmol). MS (ESI) m/e 1019.6 [M+H]$^+$, 510.6 [M+2H]$^{2+}$.

The remainder of the compounds in Table 2 were synthesized from alkynes 3, 4, or 5 and the appropriate azides 14a-14gm as indicated in table 2 using conditions closely analogous to one of the four procedures above. The time required for each reaction to proceed to completion was variable and was dependent upon several factors including: the specific substrates; the amount of Cu(I) salt used; the presence or absence of Hunig's base; and the concentration of the reactants. Reactions were monitored for the disappearance of the starting materials by TLC and/or LCMS and were typically allowed to run for between about 2 h to about 72 h. Reactions were stopped when analysis demonstrated that the starting alkyne substrate had been substantially consumed. The workup and purification protocols exemplified in conditions A-D are typical of those used for all reactions. Slight modifications to the described workup procedures may have been used (such modifications include the use of different aqueous wash solutions, different organic solvents for extraction, the use of other anhydrous salts for the drying of organic extracts, and the employment of different solvent mixtures for the chromatographic purification of the compounds). In all cases, the methods used for the workup of the reaction mixtures, the extraction of products, the drying of organic extracts, and for the isolation and purification of the title compounds were typical of procedures familiar to those trained in the art of organic synthesis. There were no specific or unusual protocols employed in the isolation and purification of the reaction products that were found to be critical in these processes. The isolated chemical yields for the synthesis of compounds 101-280 were variable and are indicated in the penultimate column of Table 2.

Example 2

Synthesis of Compounds 301-357

Schemes 103 and 104 below depict the synthesis of compounds 301-357. Demethylation of erythromycin A selectively produced 3'-N-desmethyl-erythromycin A 20. Similarly, demethylation of clarithromycin yielded 3'-N-desmethyl-clarithromycin 21. Amines 20 and 21 were selectively N-alkylated with propargyl bromide or with tosylates 11 or 12 to produce alkynes 23, 24, 25, 26, 27, or 28. As shown in Scheme 2 alkynes 23-28 are reacted with azides 14a-14eb in the presence of copper (I) iodide to selectively afford the triazoles 301-357.

Scheme 103: Synthesis of alkynes 23-28.

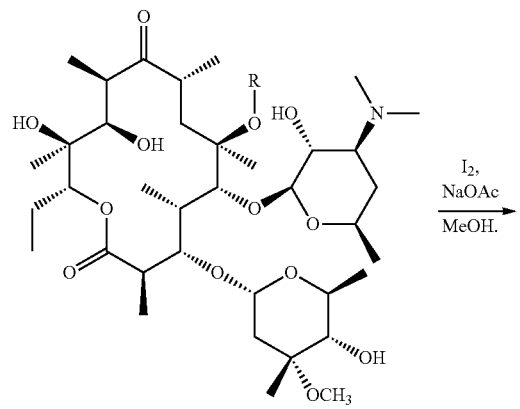

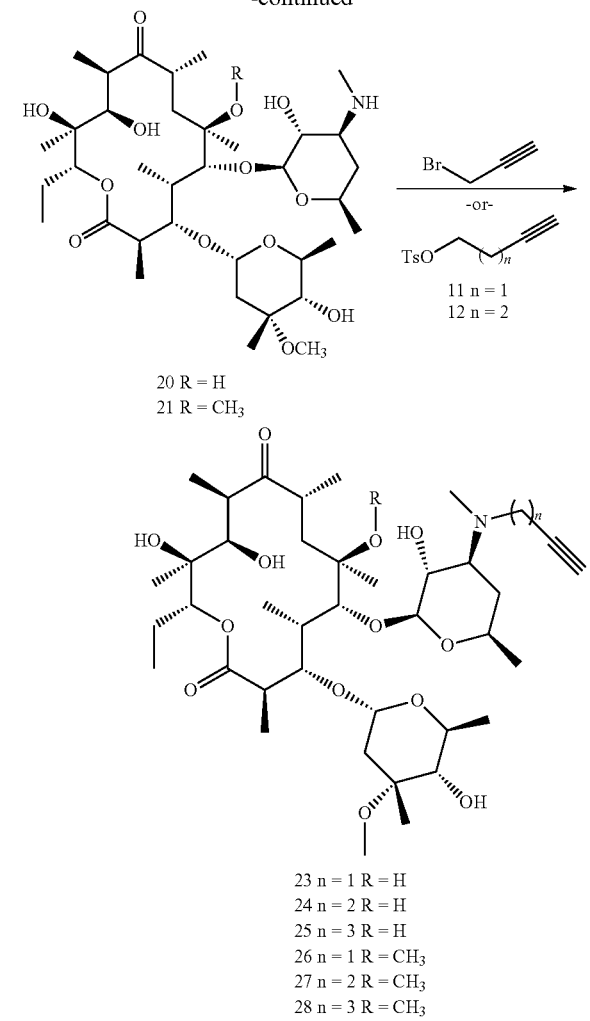

Synthesis of 3'-N-desmethyl-erythromycin A 20

Compound 20 was made from erythromycin A employing the procedure described in U.S. Pat. No. 3,725,385.

Synthesis of 3'-N-desmethyl-clarithromycin 21

To a mixture of clarithromycin (1.00 g, 1.3 mmol) and NaOAc.3H$_2$O (0.885 g, 6.5 mmol) was added MeOH—H$_2$O (20 mL, 4:1), and the mixture heated to 55-60° C. Iodine (0.330 g, 1.3 mmol) was added portion-wise and the reaction stirred at 55-60° C. for 3 h. The reaction mixture was poured into 50 mL chloroform (CHCl$_3$) containing 1 mL ammonium hydroxide. It was extracted with CHCl$_3$ (4×50 mL), washed with water (70 mL) containing 5 mL ammonium hydroxide, dried (anhydrous Na$_2$SO$_4$), concentrated, and purified by flash chromatography (silica gel, CHCl$_3$:MeOH:NH$_4$OH 100:10:0.1) to afford 21. Yield: 0.9 g (92%).

Synthesis of Alkyne 24

A mixture of 3'-N-desmethyl-erythromycin A 20 (1.0 g, 1.4 mmol) and tosylate 11 (1.25 g, 5.6 mmol) in anhydrous THF (15 mL) and Hunig's base (2.2 mL, 11.9 mmol) was kept stirring at 55° C. for 48 hours. The reaction was poured into CH$_2$Cl$_2$ (50 mL), extracted with 2% aqueous NH$_4$OH (3×30 mL) and saturated brine (1×30 mL). The organic layer was dried over Na$_2$SO$_4$ and the solvent was evaporated away. The crude was purified on a silica gel column eluting with CH$_2$Cl$_2$/MeOH 10:1 to give 24 (0.35 g, 32%).

Synthesis of Alkyne 23

Alkyne 23 was made from 3'-N-desmethyl-erythromycin A 20 and propargyl bromide using the same procedure described for the synthesis of compound 24.

Synthesis of Alkyne 25

Alkyne 25 was made from 3'-N-desmethyl-erythromycin A 20 and tosylate 12 using the same procedure described for the synthesis of compound 24.

Synthesis of Alkyne 26

Alkyne 26 was made from 3'-N-desmethyl-clarithromycin 21 and propargyl bromide using the same procedure described for the synthesis of compound 24.

Synthesis of Alkyne 27

Alkyne 27 was made from 3'-N-desmethyl-clarithromycin 21 and tosylate 11 using the same procedure described for the synthesis of compound 24.

Synthesis of Alkyne 28

Alkyne 28 was made from 3'-N-desmethyl-clarithromycin 21 and tosylate 12 using the same procedure described for the synthesis of compound 24.

TABLE 3

| Compound | R | n | X | Azide | Alkyne | Yield | LCMS (M/Z) |
|---|---|---|---|---|---|---|---|
| 301 | (ethyl)CH(NHCOCHCl$_2$)-CH(OAc)-(4-NO$_2$-C$_6$H$_4$) | 3 | H | 14cy | 8 | 77% | 1175.3 (M + H)$^+$ |
| 302 | ethyl-(3,4-dichlorophenyl) | 2 | CH$_3$ | 14da | 9 | 30% | 987.8 (M + H)$^+$ ; 1009.8 (M + Na)$^+$ |
| 303 | ethyl-(4-methylsulfonylphenyl) | 2 | CH$_3$ | 14c | 9 | 21% | 997.8 (M + H)$^+$ ; 1009.8 (M + Na)$^+$ |
| 304 | propyl-(4-methylsulfonylphenyl) | 2 | CH$_3$ | 14b | 9 | 57% | 1011.8 (M + H)$^+$ ; 1033.8 (M + Na)$^+$ |

TABLE 3-continued

| Compound | R | n | X | Azide | Alkyne | Yield | LCMS (M/Z) |
|---|---|---|---|---|---|---|---|
| 305 | (3-acetylphenyl propoxy) | 2 | CH₃ | 14u | 9 | 82% | 991.5 (M + H)⁺ |
| 306 | (4-cyanophenyl ethyl) | 2 | CH₃ | 14db | 9 | 68% | 945.5 (M + H)⁺<br>966.3 (M + Na)⁺ |
| 307 | (4-methoxycarbonylphenyl ethyl) | 2 | CH₃ | 14dc | 9 | 83% | 978.4 (M + H)⁺<br>999.3 (M + Na)⁺ |
| 308 | (4-bromophenyl ethyl) | 2 | CH₃ | 14dd | 9 | 77% | 997.2 (M + H)⁺<br>1021.6 (M + Na)⁺ |
| 309 | (4-chlorophenyl ethyl) | 2 | CH₃ | 14de | 9 | 92% | 953.4 (M + H)⁺<br>975.4 (M + Na)⁺ |
| 310 | (3-methylsulfonylphenyl propoxy) | 2 | CH₃ | 14df | 9 | 92% | 1028.3 (M + H)⁺<br>1049.2 (M + Na)⁺ |
| 311 | (fluoromethyl hydroxy methylsulfonylphenyl) | 2 | CH₃ | 14au | 9 | 59% | 1059.9 (M + H)⁺<br>1081.8 (M + Na)⁺ |

TABLE 3-continued
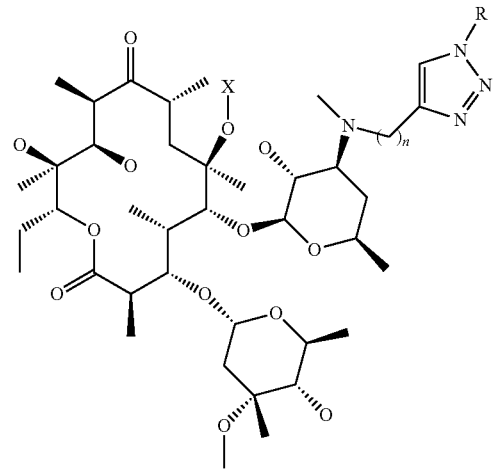
| Compound | R | n | X | Azide | Alkyne | Yield | LCMS (M/Z) |
|---|---|---|---|---|---|---|---|
| 312 | 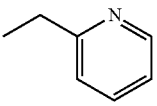 | 2 | CH₃ | 14az | 9 | 66% | 921.2 (M + H)⁺<br>943.3 (M + Na)⁺ |
| 313 | 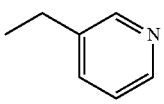 | 2 | CH₃ | 14ba | 9 | 80% | 921.1 (M + H)⁺<br>943.3 (M + Na)⁺ |
| 314 | 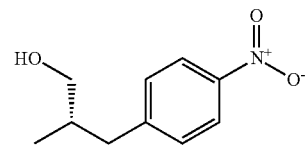 | 2 | CH₃ | 14bq | 9 | 79% | 1008.9 (M + H)⁺<br>1030.9 (M + Na)⁺ |
| 315 | 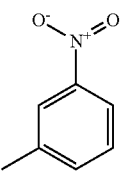 | 2 | CH₃ | 14dg | 9 | 95% | 951.4 (M + H)⁺ |
| 316 | 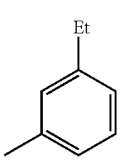 | 2 | CH₃ | 14dh | 9 | 88% | 933.5 (M + H)⁺ |
| 317 | 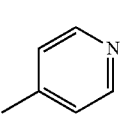 | 2 | CH₃ | 14di | 9 | 66% | 906.7 (M + H)⁺ |
| 318 | 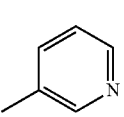 | 2 | CH₃ | 14dj | 9 | 90% | 906.6 (M + H)⁺ |
| 319 | 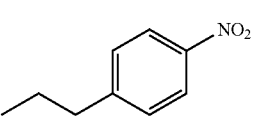 | 2 | CH₃ | 14w | 9 | 91% | 979.3 (M + H)⁺ |

TABLE 3-continued

| Compound | R | n | X | Azide | Alkyne | Yield | LCMS (M/Z) |
|---|---|---|---|---|---|---|---|
| 320 | 4-nitrophenethyl | 2 | CH$_3$ | 14v | 9 | 93% | 964.4 (M + H)$^+$ |
| 321 | 3-nitro-propylphenyl | 2 | CH$_3$ | 14dk | 9 | 91% | 979.2 (M + H)$^+$ |
| 322 | 4-(hydroxymethyl)phenethyl | 2 | CH$_3$ | 14dm | 9 | 89% | 949.4 (M + H)$^+$ |
| 323 | 4-nitrotolyl | 2 | CH$_3$ | 14dn | 9 | 92% | 950.4 (M + H)$^+$ |
| 324 | 4-methoxyphenethyl | 2 | CH$_3$ | 14do | 9 | 84% | 950.2 (M + H)$^+$ |
| 325 | 4-sulfamoylphenethyl | 2 | CH$_3$ | 14bd | 9 | 84% | 999.3 (M + H)$^+$ |
| 326 | 4-(1H-tetrazol-5-yl)phenethyl | 2 | CH$_3$ | 14x | 9 | 68% | 987.3 (M + H)$^+$ |

TABLE 3-continued
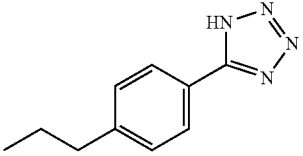
| Compound | R | n | X | Azide | Alkyne | Yield | LCMS (M/Z) |
|---|---|---|---|---|---|---|---|
| 327 | 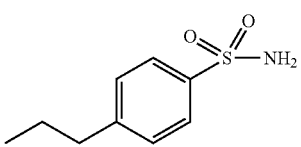 | 2 | $CH_3$ | 14dp | 9 | 66% | 1001.3 $(M + H)^+$ |
| 328 | 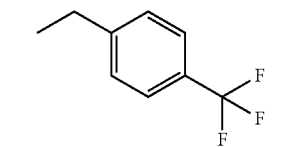 | 2 | $CH_3$ | 14be | 9 | 68% | 1012.2 $(M + H)^+$ |
| 329 | 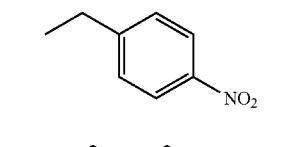 | 2 | $CH_3$ | 14dq | 9 | 84% | 987.3 $(M + H)^+$ |
| 330 | 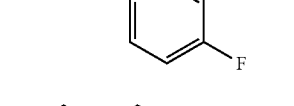 | 3 | $CH_3$ | 14v | 10 | 94% | 978.43 $(M + H)^+$ |
| 331 | 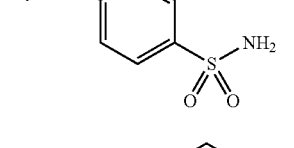 | 3 | $CH_3$ | 14dr | 10 | 86% | 951.2 $(M + H)^+$ |
| 332 | 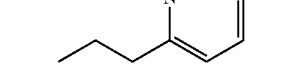 | 3 | $CH_3$ | 14bd | 10 | 86% | 1012.3 $(M + H)^+$ |
| 333 | 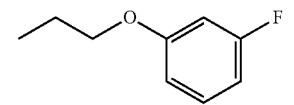 | 2 | $CH_3$ | 14dx | 9 | 73% | 935 $(M + H)^+$ |
| 334 |  | 2 | $CH_3$ | 14t | 9 | 57% | 968 $(M + H)^+$ |

TABLE 3-continued

| Compound | R | n | X | Azide | Alkyne | Yield | LCMS (M/Z) |
|---|---|---|---|---|---|---|---|
| 335 | (3-pyridyl)propyl | 2 | CH₃ | 14dy | 9 | 38% | 949 (M + H)⁺ |
| 336 | 3-(propyloxy)phenyl-NHCOCH₃ | 2 | CH₃ | 14dz | 9 | 52% | 1007 (M + H)⁺ |
| 337 | 5-(propyloxy)quinolinyl | 3 | H | 14aw | 8 | 78% | 1001.4 (M + H)⁺ |
| 338 | 5-(propyloxy)quinolinyl | 2 | H | 14aw | 7 | 81% | 1001.4 (M + H)⁺ |
| 339 | 5-(propyloxy)quinolinyl | 1 | H | 14aw | 6 | 81% | 1001.4 (M + H)⁺ |
| 340 | 2-nitro-6-(propyloxy)phenyl | 1 | H | 14ds | 6 | 63% | 967 (M + H)⁺ |
| 341 | 2-nitro-6-(propyloxy)phenyl | 2 | H | 14ds | 7 | 78% | 981 (M + H)⁺ |
| 342 | 2-nitro-6-(propyloxy)phenyl | 3 | H | 14ds | 8 | 63% | 995 (M + H)⁺ |

TABLE 3-continued
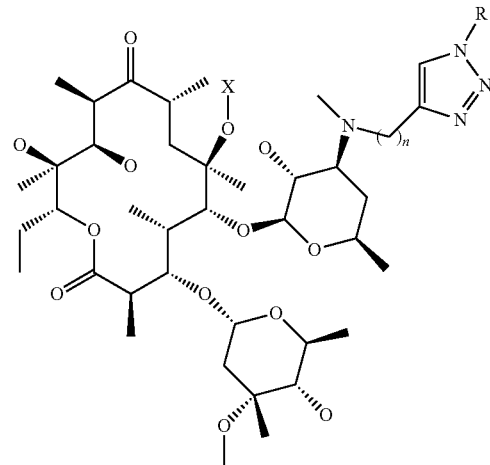
| Compound | R | n | X | Azide | Alkyne | Yield | LCMS (M/Z) |
|---|---|---|---|---|---|---|---|
| 343 | 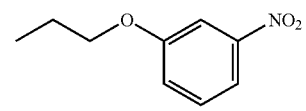 | 2 | H | 14a | 7 | 34% | 981 (M + H)$^+$ |
| 344 | 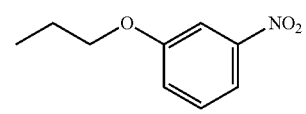 | 3 | H | 14a | 8 | 67% | 995 (M + H)$^+$ |
| 345 | 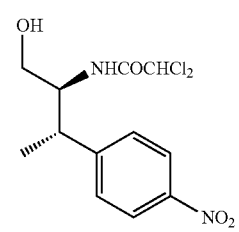 | 3 | H | 14dt | 8 | 75% | 1133.3 (M + H)$^+$ |
| 346 | 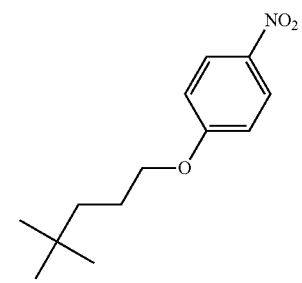 | 2 | CH$_3$ | 14et | 9 | 89% | 1008.9 (M + H)$^+$ |
| 347 |  | 3 | H | 14du | 7 | 84% | 1133.3 (M + H)$^+$ |
| 348 | 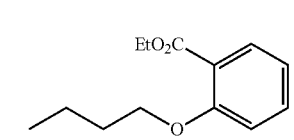 | 2 | H | 14dv | 7 | 68% | 1022 (M + H)$^+$ |

TABLE 3-continued

| Compound | R | n | X | Azide | Alkyne | Yield | LCMS (M/Z) |
|---|---|---|---|---|---|---|---|
| 349 | 2-(propoxy)-EtO2C-phenyl | 1 | H | 14dw | 6 | 69% | 994 (M + H)+ |
| 350 | 2-(propoxy)-EtO2C-phenyl | 2 | H | 14dw | 7 | 35% | 1008 (M + H)+ |
| 351 | 2-(propoxy)-EtO2C-phenyl | 3 | H | 14dw | 8 | 30% | 1022 (M + H)+ |
| 352 | 4-fluorophenethyl | 2 | CH3 | 14dr | 9 | 97% | 937.3 (M + H)+ |
| 353 | 4-nitrophenyl-CH2-C(CH3)2-CH2F | 2 | CH3 | 14bt | 9 | 85% | 1010.8 (M + H)+<br>1032.8 (M + Na)+ |
| 354 | 3-nitro-(propoxy)phenyl | 1 | H | 14a | 6 | 95% | 967 (M + H)+ |

TABLE 3-continued
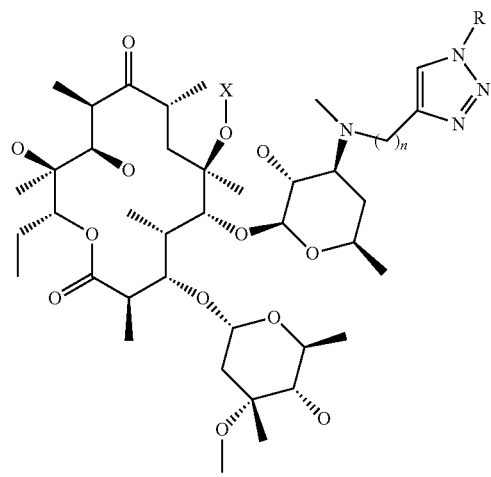
| Compound | R | n | X | Azide | Alkyne | Yield | LCMS (M/Z) |
|---|---|---|---|---|---|---|---|
| 355 | 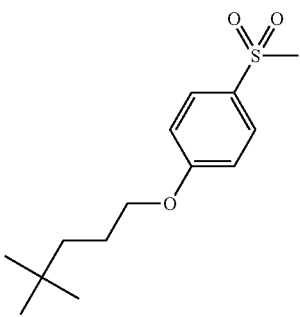 | 2 | CH$_3$ | 14fp | 9 | 95% | 1041.8 (M + H)$^+$<br>1063.7 (M + Na)$^+$ |
| 356 | 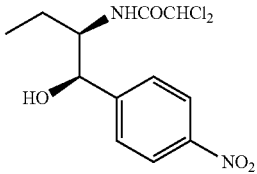 | 2 | H | 14du | 8 | 73% | 1122.4 (M + H)$^+$ |
| 357 | 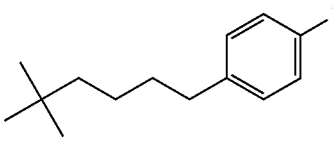 | 2 | CH$_3$ | 14ej | 9 | 89% | 1006.9 (M + H)$^+$<br>1028.9 (M + Na)$^+$ |

Scheme 104: Synthesis of compounds of Table 3

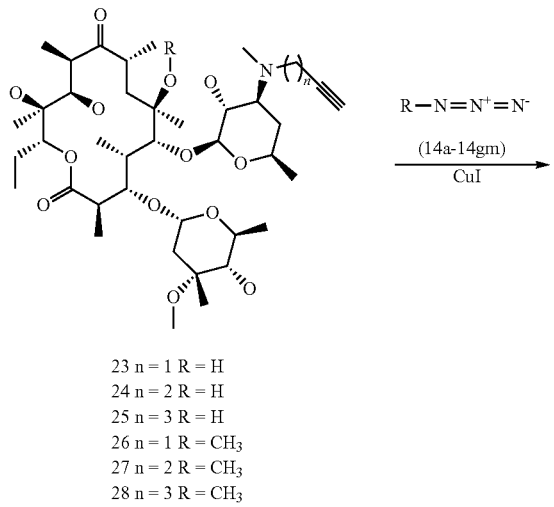

23 n = 1 R = H
24 n = 2 R = H
25 n = 3 R = H
26 n = 1 R = CH$_3$
27 n = 2 R = CH$_3$
28 n = 3 R = CH$_3$

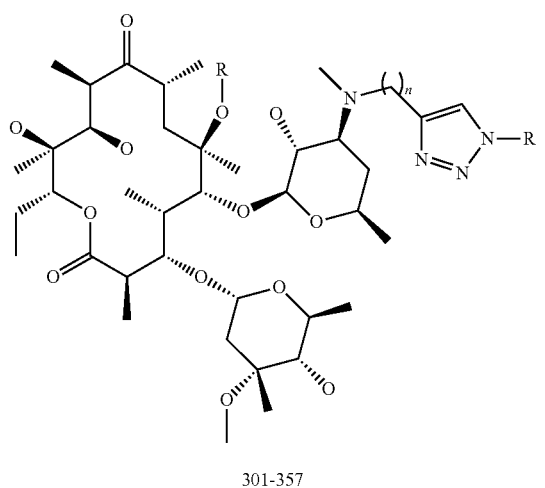

301-357

Triazoles 301-357 were produced from alkynes 23-28 using azides 14a-14gm under reaction conditions as exemplified by Conditions A, B, C, and D above for compounds 101-280 in Example 1. As above, the use of Conditions A and C, which do not include the step of degassing the reaction mixture, resulted in the formation of iodinated side-products and generally lower yields. Additionally, reduction of the amount of copper salt used in the reaction to 0.5 molar equivalents or less as in conditions B and D resulted in reduced formation of iodinated by-products.

The compounds in Table 2 were synthesized using conditions closely analogous to conditions A, B, C, and D described above. The time required for each reaction to proceed to completion was again variable and was dependent upon the several variables noted above including: the specific substrates, the amount of Copper (I) salt used, the presence or absence of Hunig's base, and the concentration of the reactants. Reactions were monitored for the disappearance of the starting materials by TLC and/or LCMS and were typically allowed to run for between about 2 h to about 72 h with the majority being about 16 h. Reactions were stopped when analysis demonstrated that the starting alkyne substrate had been substantially consumed. The workup and purification protocols exemplified in conditions A-D are typical of those used for all products in Table 2. Slight modifications to the described workup procedures may have been used as set forth above for the compounds of Table 2.

Example 3

Synthesis of Compounds 401-417

Compounds 401-417 shown in Table 4 were derived from telithromycin using methodology analogous to that described above for the compounds of Tables 2 and 3. Telithromycin was selectively N-demethylated and then alkylated with tosylate 11 as described for azithromycin, erythromycin and clarithromycin above. The resulting alkyne was elaborated to the corresponding triazoles using the same copper catalyzed [3+2] cycloaddition reaction with azides 14 discussed above.

Synthesis of 3'-N-Desmethyl telithromycin 30

To a solution of telithromycin 29 (3.0 g, 3.60 mmol) in anhydrous acetonitrile (70 mL) was added N-iodosuccinimide (NIS) (0.98 g, 4.32 mmol) in two portions within 30 min at 0° C. under argon atmosphere. The mixture was allowed to warm to rt and stirred overnight. CH$_2$Cl$_2$ (250 mL) and 5% Na$_2$S$_2$O$_3$ (80 mL) were added and the two layers separated. The organic layer was extracted with 5% Na$_2$S$_2$O$_3$ (1×80 mL), dilute NH$_4$Cl (1×80 mL) and dried over Na$_2$SO$_4$. Solvent was evaporated and the crude was purified on silica gel eluting with 0-8% methanolic ammonia (2N NH$_3$) in CH$_2$Cl$_2$ to give compound 30 as white solid (1.95 g, 68%). MS (ESI) M/E; M+H$^+$ 798.6.

Scheme 105 Synthesis of alkyne 31.
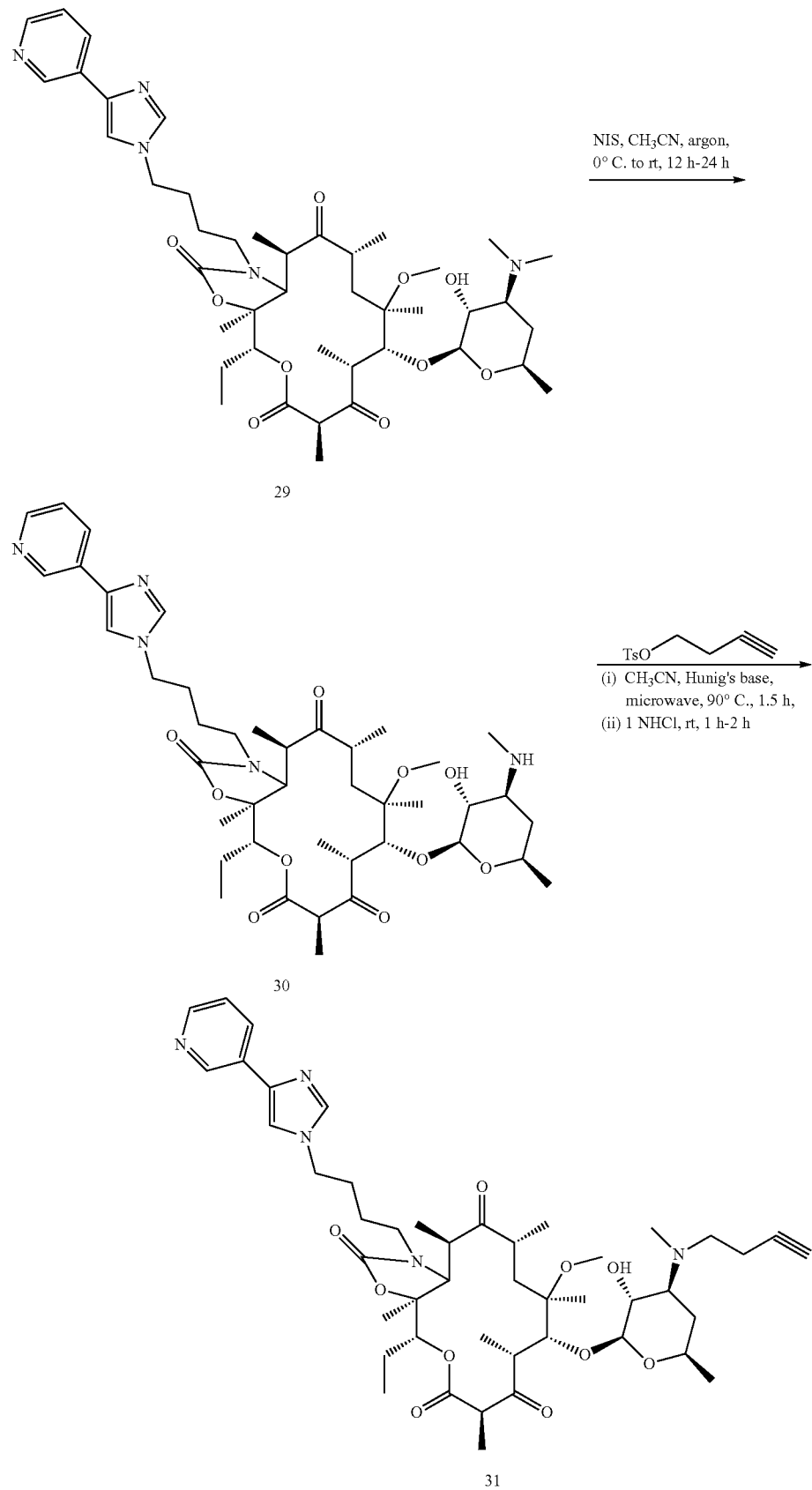

Synthesis of 3'-N-(but-3-ynyl) telithromycin 31

Protocol A: A mixture of amine 30 (0.66 g, 0.83 mmol) and tosylate 11 (0.33 g, 1.49 mmol) in THF (15 mL) and Hunig's base (3 mL) was heated at 90° C. for 5 days. The solvent was evaporated; the residue was dissolved in 1N HCl (50 mL) and kept stirring at room temperature for about 1 h. $CH_2Cl_2$ (30 mL) was added and the two layers were separated. The aqueous layer was extracted with $CH_2Cl_2$ (2×30 mL) and basified with NaOH (1N) to form a whitish-suspension. The suspension was extracted with $CH_2Cl_2$ (3×30 mL) and the organic layer was dried over $Na_2SO_4$. Solvent was evaporated and the crude was purified on silica gel eluting with 0-6% methanolic ammonia (2N $NH_3$) in $CH_2Cl_2$ to give compound 31 as white solid (0.12 g, 17%). MS (ESI) m/e 850.8 (M+H)+.

Synthesis of 3'-N-(but-3-ynyl) telithromycin 31

Protocol B: A mixture of amine 30 (0.66 g, 0.83 mmol), and tosylate 11 (0.40 g, 1.84 mmol) in acetonitrile (10 mL) and Hunig's base (0.18 mL, 1.0 mmol) was microwave heated to 90° C. within 10 min and maintained at 90° C. for 1.5 h. The reaction was vented within 15 min and solvent was evaporated. The residue was dissolved in 1N HCl (60 mL) and kept stirring at room temperature for about 2 h. $CH_2Cl_2$ (30 mL) was added and the two layers were separated. The aqueous layer was extracted with $CH_2Cl_2$ (2×30 mL) and basified with 50% KOH to form a whitish-suspension. The suspension was extracted with $CH_2Cl_2$ (3×30 mL) and the organic layer was dried over $Na_2SO_4$. The solvent was evaporated and the crude was purified by preparative TLC (2000 micron plate) eluting with $CH_2Cl_2$/methanolic ammonia (2N $NH_3$) 12:1 to give compound 31 as white solid (0.19 g, 27%). MS (ESI) m/e 850.8 (M+H)+.

TABLE 4

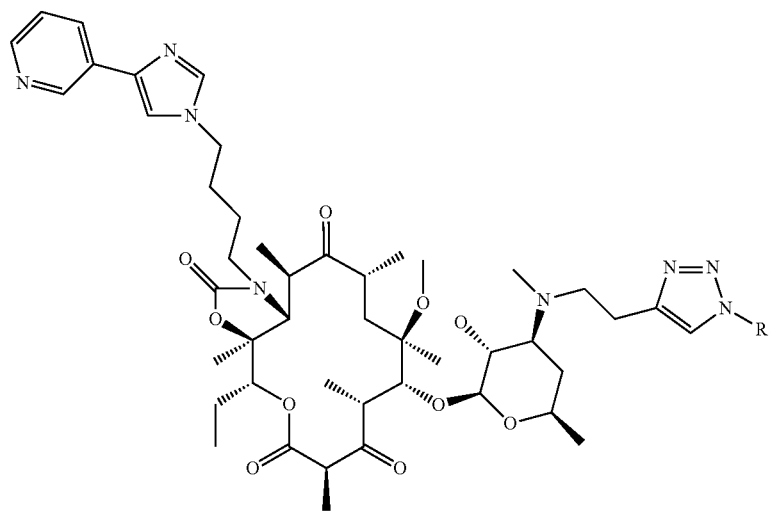

| Compound | R | Azide | Yield | LCMS M/Z |
|---|---|---|---|---|
| 401 | ![structure] | 14cf | 99% | 538.7 $(M + 2H)^{2+}$ |
| 402 | ![structure] | 14v | 67% | 515.1 $(M + 2H)^{2+}$ |
| 403 | ![structure] | 14dx | 97% | 500.1 $(M + 2H)^{2+}$ |
| 404 | ![structure] | 14b | 83% | 531.7 $(M + 2H)^{2+}$ |

TABLE 4-continued

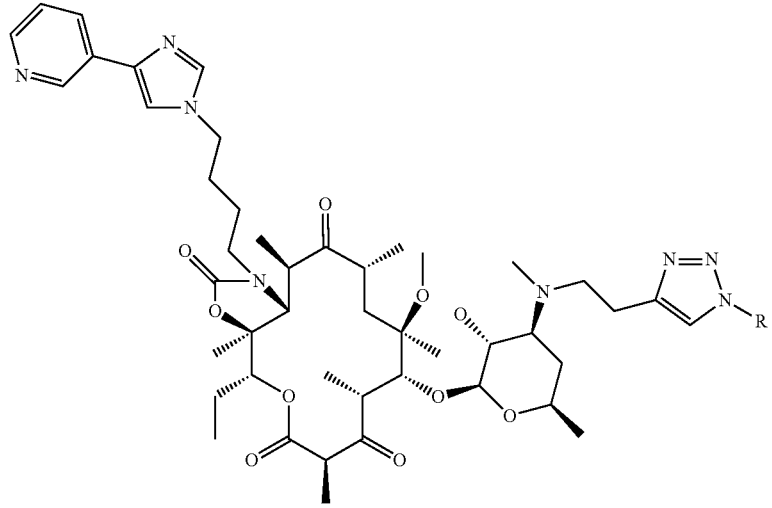

| Compound | R | Azide | Yield | LCMS M/Z |
|---|---|---|---|---|
| 405 | 4-propylphenyl methylsulfonyl | 14db | 81% | 530.7 $(M + 2H)^{2+}$<br>1059.9 $(M + H)^+$ |
| 406 | 4-propylphenyl CF$_3$ | 14ad | 34% | 533.7 $(M + 2H)^{2+}$ |
| 407 | 1-(4-propylphenyl)-4-(hydroxymethyl)triazole | 14aa | 51% | 548.5 $(M + 2H)^{2+}$<br>1116.9 $(M + Na)^+$ |
| 408 | 1-hydroxy-2-(4-methylthiophenyl)-2-hydroxypropyl | 14ag | 68% | 548.2 $(M + 2H)^{2+}$ |
| 409 | 1-fluoro-2-(4-methylsulfonylphenyl)-2-hydroxypropyl | 14au | 66% | 545.8 $(M + 2H)^{2+}$ |
| 410 | 1-hydroxy-2-(4-nitrophenyl)-2-hydroxypropyl | 14s | 38% | 562.8 $(M + 2H)^{2+}$ |

TABLE 4-continued

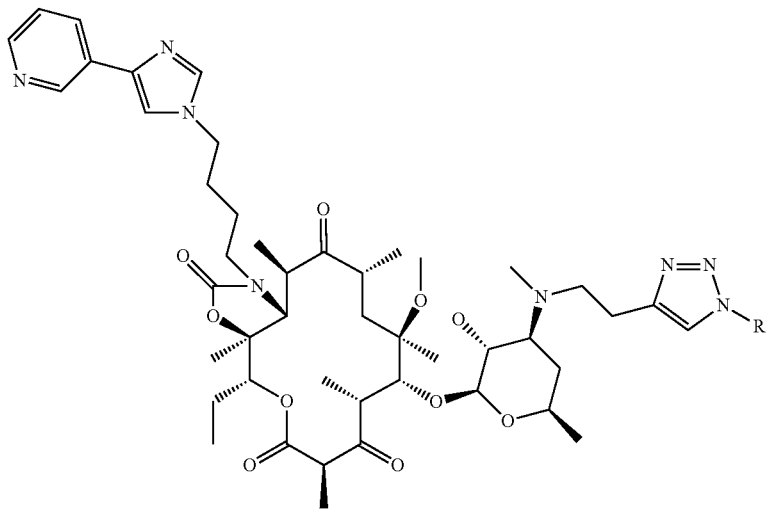

| Compound | R | Azide | Yield | LCMS M/Z |
|---|---|---|---|---|
| 411 | (tert-butyl piperazine-1-carboxylate propyl) | 14ea | 61% | 545.1 (M + 2H)$^{2+}$ |
| 412 | (butyl-OH) | 14eb | 98% | 553.7 (M + 2H)$^{2+}$<br>1127.9 (M + Na)$^+$ |
| 413 | (propyl-4-nitrophenyl) | 14w | 52% | 476.6 (M + 2H)$^{2+}$<br>973.9 (M + Na)$^+$ |
| 414 | (propyl-morpholine) | 14by | 78% | 522.1 (M + 2H)$^{2+}$ |
| 415 | (propyl-pyrrolidine) | 14j | 86% | 504.1 (M + 2H)$^{2+}$<br>1029.1 (M + Na)$^+$ |
| 416 | (4-methylbenzyl triazole ethanol) | 14z | 89% | 496.1 (M + 2H)$^{2+}$<br>991.1 (M + H)$^+$ |
| 417 | (3,3-dimethyl-butyl-NH$_2$) | 14ff | 30% | 469.0 (M + 2H)$^{2+}$<br>958.9 (M + Na)$^+$ |

Triazoles 401-417 were produced from alkyne 31 using azides 14a-14gm under reaction conditions similar to those described above for the compounds of Tables 4 and 5. As above, the use of conditions which did not include the step of degassing the reaction mixture, resulted in the formation of iodinated side-products and generally lower yields. Additionally, reduction of the amount of copper salt used in the reaction to 0.5 molar equivalents or less resulted in reduced formation of iodinated by-products.

The procedure detailed below for the synthesis of compound 406 from azide 14ad is typical of those used for all compounds in Table 4. As described in Example 1, the time required for each reaction to proceed to completion was again variable and was dependent upon the several variables noted above including: the specific substrates, the amount of Copper (I) salt used, the presence or absence of Hunig's base, and the concentration of the reactants. Reactions were monitored for the disappearance of the starting materials by TLC and/or LCMS and were typically allowed to run for between about 6 h to about 24 h and were stopped when analysis demonstrated that the starting alkyne substrate had been substantially consumed. The workup and purification protocols exemplified in conditions A-D in Example 1 are typical of those used for all products in Table 6. Slight modifications to the described workup procedures may have been used as described above in Example 1 for the synthesis of compounds of Table 4.

Scheme 106: Synthesis of compound 406

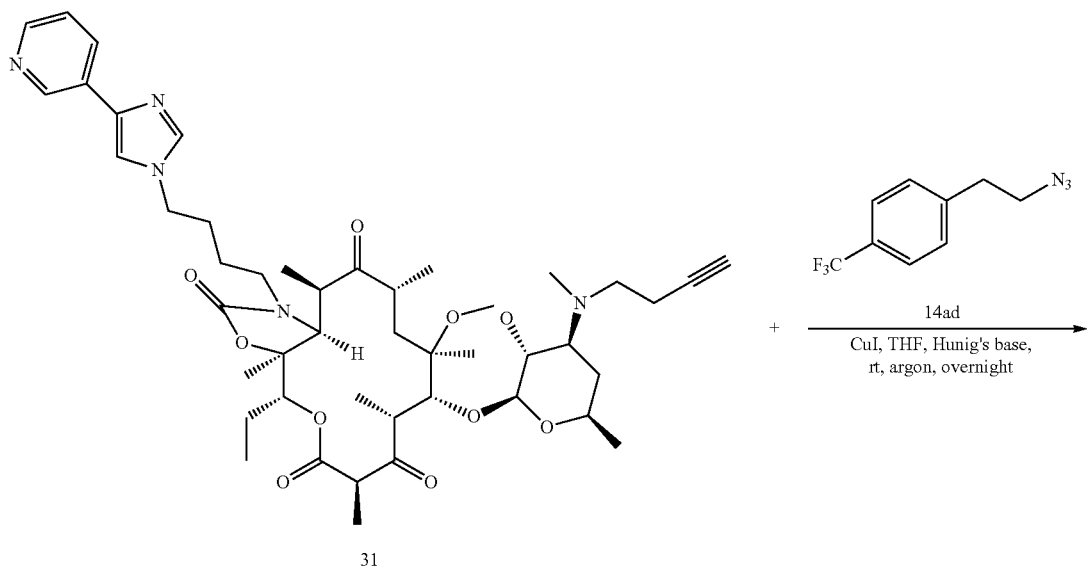

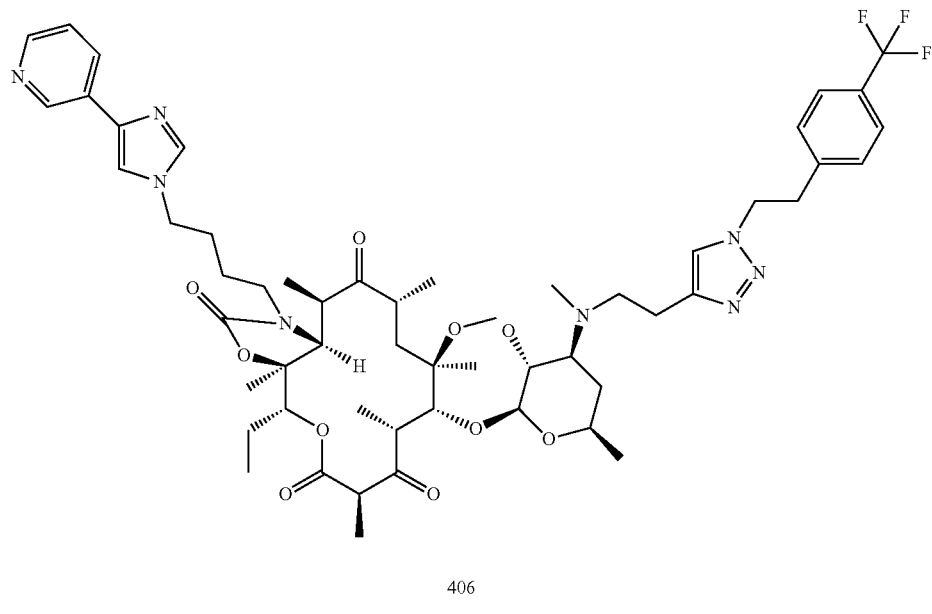

Synthesis of Compound 406

This compound was obtained from the reaction of alkyne 31 (0.06 g, 0.07 mmol) with azide 14ad (0.030 g, 0.14 mmol) under argon atmosphere in the presence of CuI (0.030 g, 0.14 mmol) in THF (5 mL) and Hunig's base (0.05 mL) mixture at room temperature overnight with workup as described before. The crude reaction was purified by preparative TLC (2000 micron plate) eluting with $CH_2Cl_2$/MeOH 12:1 to give triazole 406 as white solid (0.025 g, 34%). MS (ESI) m/e 533.7 $(M+2H)^{2+}$.

Example 4

Synthesis of Compounds 425-451

The oximes 425-433 of Table 5 were synthesized from alkynes 400a to 400i by copper(I)-promoted cycloaddition with azides 14a-14gm in a manner analogous to the procedures presented previously. Alkyne precursors 401a-401i with substituted oxime functionality at the 9-position of the macrocyclic ring were prepared from alkynes 27, 24, and as shown below.

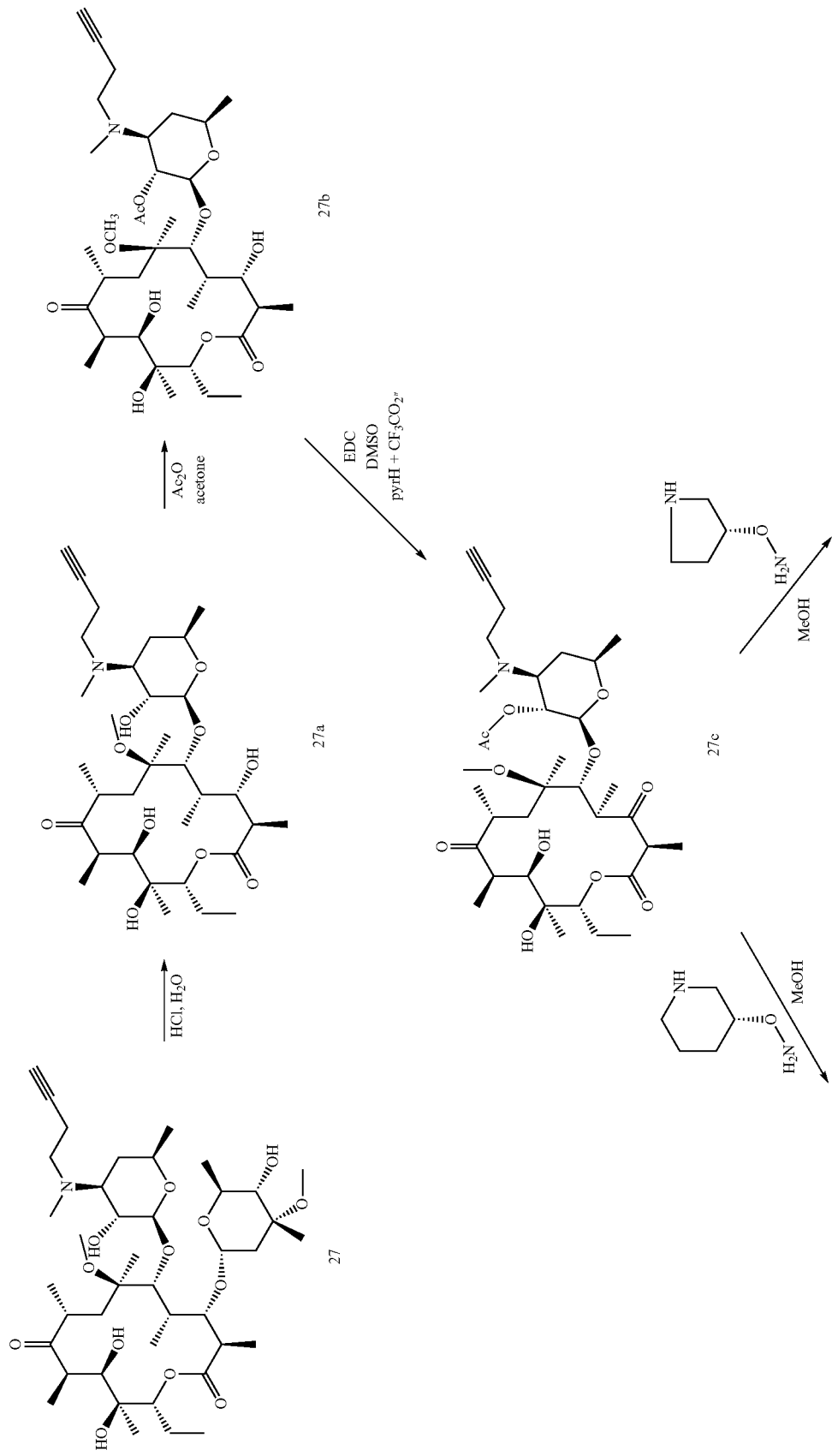

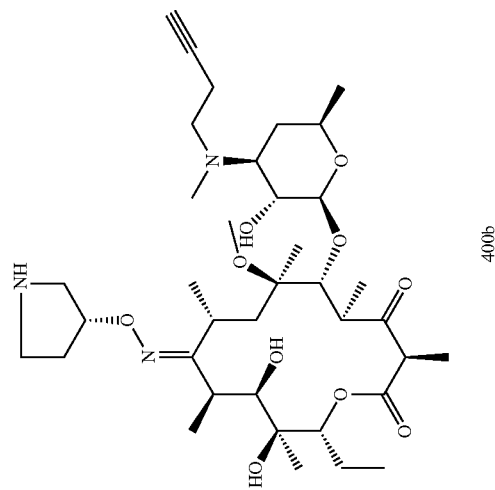
400b
-continued
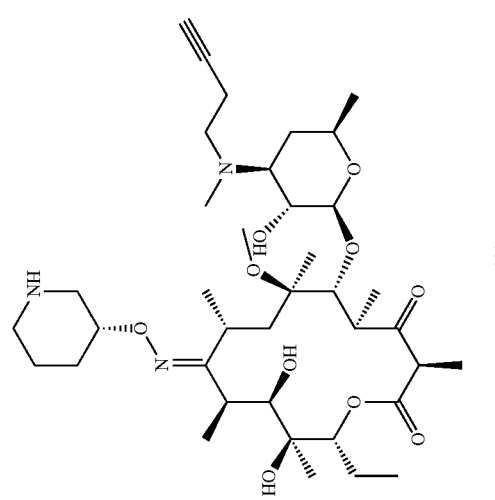
400a

Synthesis of alcohol 27a

To the alkyne 27 (0.700 g) was added 10 mL 0.9N HCl and the mixture was stirred for 4h at room temperature. The reaction mixture was saturated with sodium chloride and was adjusted to pH 8 using aqueous $NH_4OH$ solution. The solution was extracted with ethyl acetate (3×30 mL), dried (with $Na_2SO_4$), and concentrated under reduced pressure. Purification of the crude reaction mixture by flash chromatography (silica gel, 60% ethyl acetate in hexane) afforded 0.200 g (35% yield) of the descladinose derivative 27a. Data for 27a: $^1$HNMR (300 MHz, $CDCl_3$, partial): δ 0.82 (t, 3H), 2.25 (s, 3H), 3.00 (s, 3H), 3.25 (dd, 1H), 3.55 (m, 2H), 3.70 (s, 1H), 3.85 (s, 3.95 (s, 1H), 4.40 (d, 1H), 5.15 (dd, 1H).

Synthesis of Acetate 27b

To a solution of 27a (0.200 g, 0.32 mmol) in acetone (2 mL) was added acetic anhydride (0.050 mL, 0.5 mmol) and the mixture was stirred overnight at room temperature. The reaction was quenched with water and extracted with ethyl acetate (3×50 mL). The combined organic fractions were washed with saturated sodium bicarbonate (3×50 mL), dried (anhydrous $Na_2SO_4$), and concentrated under reduced pressure. The crude reaction mixture was purified by flash chromatography (silica gel, 50% ethyl acetate in hexane) to yield 0.100 g (50% yield) of acetate 27b. Data for 27b: $^1$HNMR(300 MHz, $CDCl_3$, partial): δ 0.84 (t, 3H), 2.00 (s, 3H), 2.20 (s, 3H), 2.90 (s, 3H), 3.00 (q, 1H), 3.25 (s, 1H, 3.47 (m, 2H), 3.70 (bs, 1H), 3.82 (bs, 1H), 3.97 (s, 1H), 4.60 (d, 1H), 4.77 (dd, 1H), 5.15 (dd, 1H).

Synthesis of Ketolide 27c

To a solution of acetate 27b (0.090 g, 0.134 mmol), EDC.HCl (0.172 g, 0.90 mmol), and dimethyl sulfoxide (DMSO) (0.171 mL, 2.41 mmol) in $CH_2Cl_2$ (1.5 mL) was added dropwise a solution of pyridinium trifluoroacetate (0.174 g, 0.90 mmol) in $CH_2Cl_2$ (1 mL) at 15° C. The reaction mixture was slowly warmed up to room temperature and stirred for 3 h. The reaction was quenched with water (2 mL), and allowed to stir for 30 min. The mixture was then poured into $CHCl_3$ (50 mL), and the organic layer was washed with water (2×50 mL), dried (over anhydrous $Na_2SO_4$), and concentrated under reduced pressure. The crude material was purified by flash chromatography (silica gel, 30% ethyl acetate in hexane) to yield 0.070 g (78%) of the ketolide 27c. Data for 27c: MS (ESI) m/e 668 (M+H)$^+$; $^1$HNMR (300 MHz, $CDCl_3$, partial): δ 0.86 (t, 3H), 2.00 (s, 3H), 2.24 (s, 3H), 2.70 (s, 3H), 2.95-3.10 (m, 1H), 3.15-3.05 (m, 1H), 3.45-3.65 (m, 1H), 3.80 (q, 1H), 3.90 (s, 1H), 4.28 (d, 1H), 4.40 (d, 1H), 4.76 (dd, 1H), 5.10 (dd, 1H).

Synthesis of Oxime 400a

To a solution of 27c (2.0 g, 2.9 mmol) in MeOH (10 mL) was added (R)—N-Piperidin-3-yl-hydroxylamine hydrobromide (1.26 g, 4.4 mmol). The reaction mixture was stirred at rt for 14 h. The mixture was then poured into (50 mL) and water (50 mL) the pH was adjusted to 11 by addition of $NH_4OH$ and the organic layer was separated and washed with brine (50 mL), dried (over anhydrous $Na_2SO_4$), and concentrated under reduced pressure. The crude material was purified by flash chromatography (silica gel, 12:1 $CH_2Cl_2$ and 2M methanolic ammonia) to yield 2 g (78%) of the oxime 400a as a 1:1 mixture of E/Z isomers. Data for 400a: MS (ESI) m/e 724.7 (M+H)$^+$.

Synthesis of Oxime 400b

Oxime 400b was synthesized from alkyne 27c and (R)—N-Pyrollidin-3-yl-hydroxylamine hydrobromide using the conditions described above for the synthesis of oxime 400a. Data for 400b: MS (ESI) m/e 710.6 (M+H)$^+$.

Scheme 108

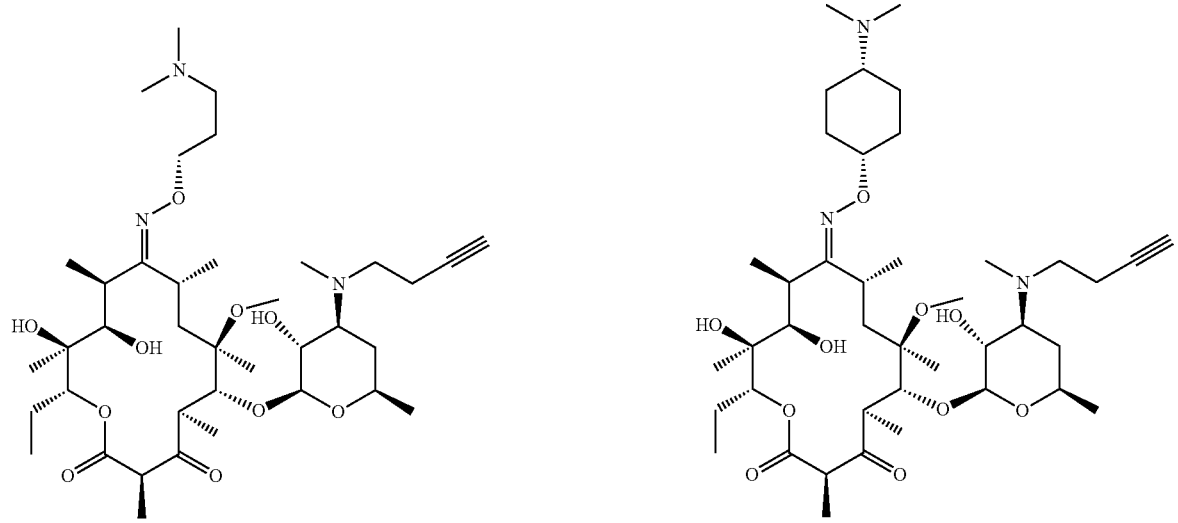

400c  400f

-continued
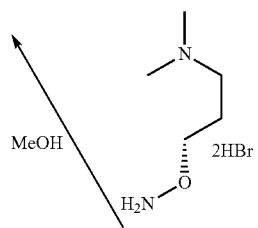
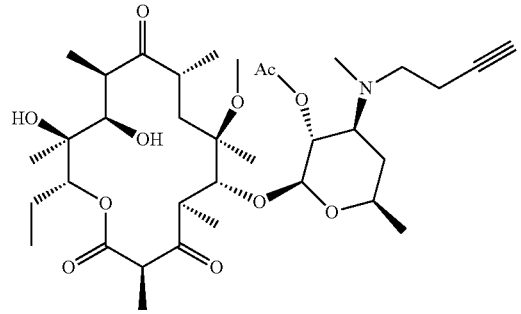
27c
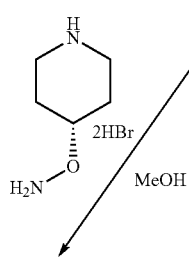
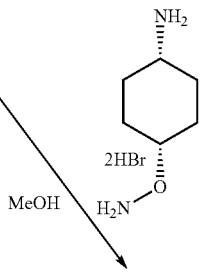
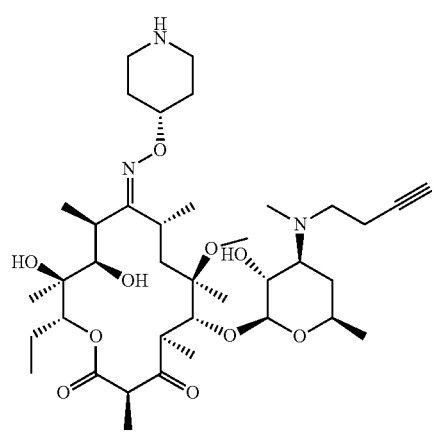
400d
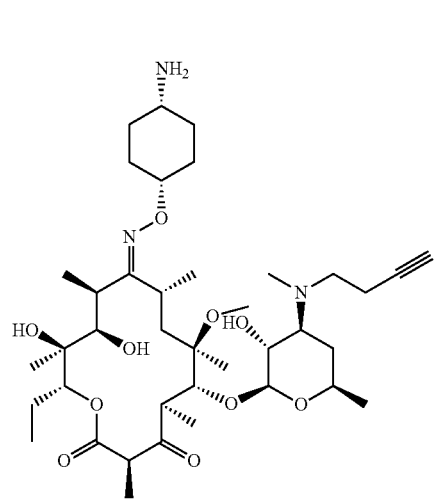
400e

Synthesis of Oxime 400c

Oxime 400c was synthesized from alkyne 27c and N-[2-dimethylaminoethyl]-hydroxylamine hydrobromide using the conditions described above for the synthesis of oxime 400a. Data for 400b: MS (ESI) m/e 726.5 (M+H)$^+$.

Synthesis of Oxime 400d

Oxime 400d was synthesized from alkyne 27c and N-Piperidin-4-yl-hydroxylamine hydrobromide using the conditions described above for the synthesis of oxime 400a. Data for 400d: MS (ESI) m/e 724.6 (M+H)$^+$.

Synthesis of Oxime 400e

Oxime 400e was synthesized from alkyne 27c and cis-4-aminocylcohexyl-hydroxylamine hydrobromide using the conditions described above for the synthesis of oxime 400a. Data for 400e: MS (ESI) m/e 738.7 (M+H)$^+$.

Synthesis of Oxime 400f

To a solution of oxime 400f (20 mg, 0.02 mmol) in CHCl$_3$ (0.2 mL) was added formaldehyde (5 mg of 37% aqueous solution, 0.06 mmol) and formic acid (6 mg, 0.12 mmol). The mixture was heated at 50° C. in a sealed tube for 12 h. The reaction mixture was partitioned between aqueous NaHCO$_3$ (10 mL) and chloroform (10 mL) the organic fraction was dried on K$_2$CO$_3$, filtered and concentrated to give alkyne 400f as a white solid (18 mg). Data for 400f: MS (ESI) m/e 766.7 (M+H)$^+$.

Synthesis of Oxime Triazoles 425-431, and 439

These triazoles were synthesized from the alkyne 400a and the azides indicated in Table 6 using the standard copper-promoted cycloaddition conditions as previously described.

Synthesis of Oxime Triazoles 432-434, and 444-445

These triazoles were synthesized from the alkyne 400b and the azides indicated in Table 6 using the standard copper-promoted cycloaddition conditions as previously described.

Synthesis of Oxime Triazoles 437 and 438

These triazoles were synthesized from the alkyne 400c and the azides indicated in Table 6 using the standard copper-promoted cycloaddition conditions as previously described.

Synthesis of Oxime Triazoles 440 and 441

These triazoles were synthesized from the alkyne 400d and the azides indicated in Table 6 using the standard copper-promoted cycloaddition conditions as previously described.

Synthesis of Oxime Triazole 443

These triazoles were synthesized from the alkyne 400e and the azide 14w using the standard copper-promoted cycloaddition conditions as previously described.

Synthesis of Oxime Triazole 448

These triazoles were synthesized from the alkyne 400f and the azide 14w using the standard copper-promoted cycloaddition conditions as previously described.

Synthesis of Compound 448 and 449

Compound 449 was synthesized from alkyne 400 g. This alkyne was derived from 27c and intermediate 39 as shown in Scheme 109 below. O-desosaminyl hydroxylamine 39 was synthesized from desosamine HCl salt in four synthetic steps proceeding by benzyl ester protection of the 2' OH group, Mitsunobu reaction with N-hydroxyphthalimide, debenzylation and reduction of the phthalimide group.

Scheme 109

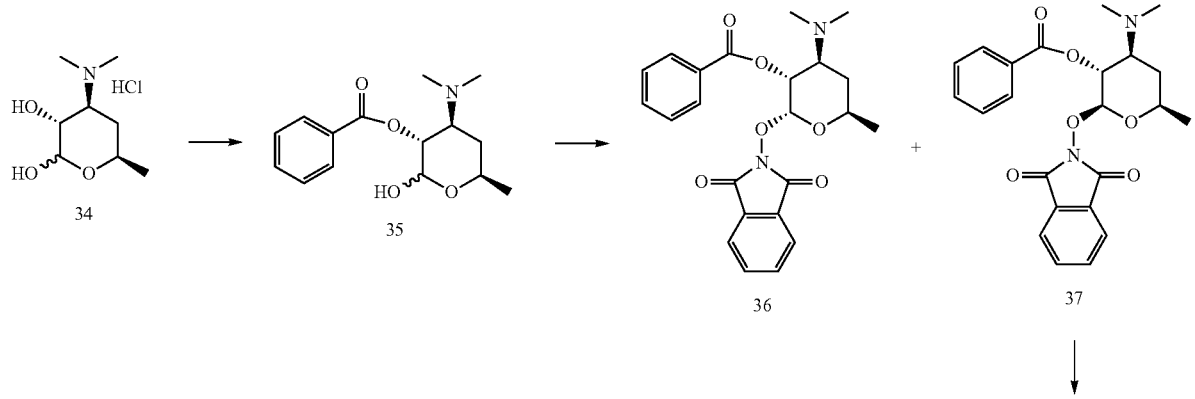

-continued

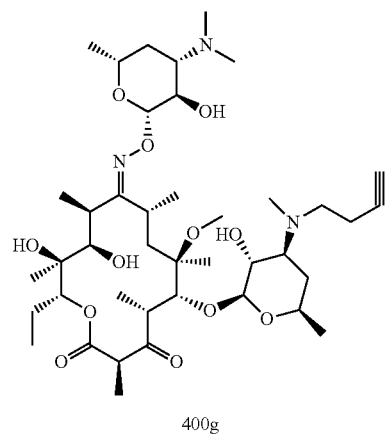

475

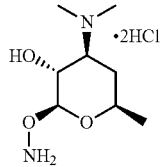

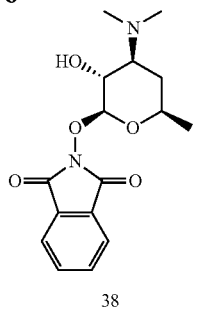

476

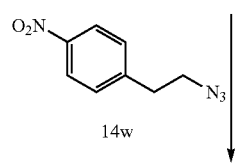

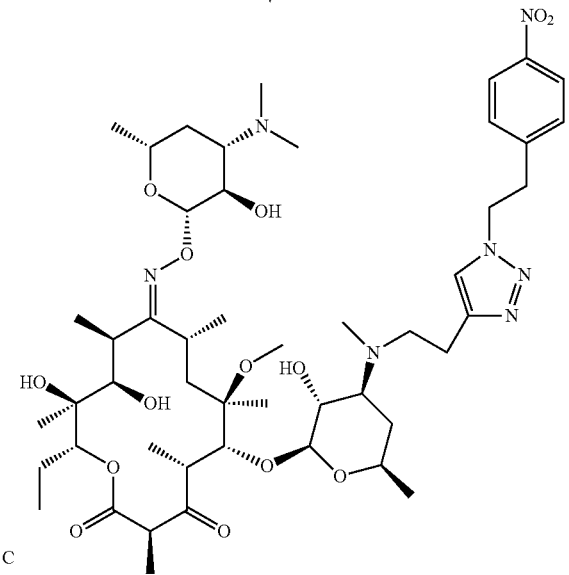

449

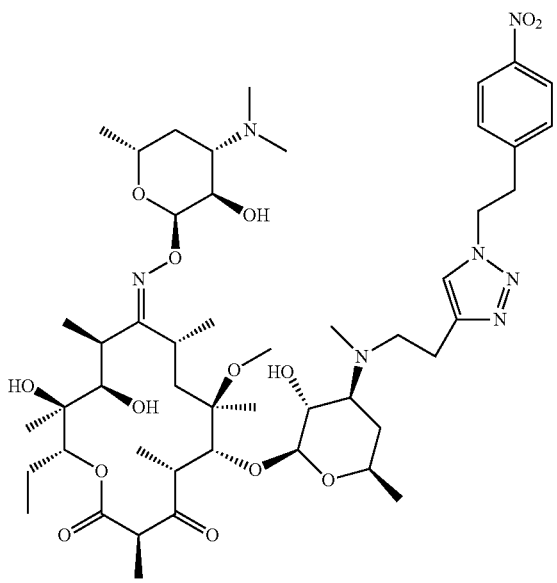

448

Synthesis of 34

Desosamine hydrochloride was prepared according to literature (*JACS*, 1954, 76, 3121-3131) procedure.

Synthesis of 35

To a suspension of 34 (3.5 g, 16.5 mmol) in acetone (100 mL) was added $K_2CO_3$ (4.6 g, 33.1 mmol) and stirred for 30 minutes. Then was added benzoic anhydride (4.5 g, 19.8 mmol) and stirred for 16 h at ambient temperature. The reaction mixture was diluted with $CH_2Cl_2$ (100 mL) and water (100 mL). Organic layer was separated and the aqueous layer was extracted with $CH_2Cl_2$ (2×100 mL). The combined organic layer was dried, concentrated and purified by flash chromatography over silica gel (50% acetone in hexane). Yield 2.8 g (61%). The compound 35 was isolated as a mixture of anomers and used for the next step without further purification. Data for 35 (mixture of anomers): $^1$H NMR (300 MHz, $CDCl_3$): δ 1.22 (d, 1.5H), 1.30 (d, 1.5H), 1.40-1.54 (m, 1H), 1.80 (m, 1H), 2.32 (s, 3H), 2.34 (s, 3H), 2.95-3.04 (m, 1H), 3.31-3.40 (m, 0.5H), 3.63-3.72 (m, 0.5H), 4.19-4.27 (m, 0.5H), 4.67 (d, 0.5H), 4.98 (dd, 0.5H), 5.16 (dd, 0.5H), 5.43 (d, 0.5H), 7.43 (t, 2H), 7.57 (t, 1H), 8.07 (t, 2H).

Synthesis of 36-37

To solution of 35 (2.7 g, 9.7 mmol), N-hydroxyphthalimide (1.7 g, 10.7 mmol) and $Ph_3P$ (2.8 g, 10.7 mmol) in THF was added DIAD (2.1 mL, 10.7 mmol) at 0° C. and stirred at ambient temperature for 12 h. The resulting solution was concentrated under reduced pressure and the crude material was redissolved in EtOAc (100 mL). This organic layer was washed with 1N NaOH (2×75 mL), water (1×75 mL) and brine (2×75 mL). It was dried (anhydrous $Na_2SO_4$), concentrated and purified by flash chromatography over silica gel (30% acetone in hexane) to gave 36 (0.9 g) and 37 (1.8 g) as anomers. Data for 4: ¹H NMR (300 MHz, CDCl₃): δ 1.33 (d, 3H), 1.69 (dd, 1H), 1.84 (ddd, 1H), 2.34 (s, 6H), 3.02 (ddd, 1H), 3.67 (dq, 1H), 5.16 (d, 1H), 5.45 (dd, 1H), 7.50 (t, 2H), 7.55 (d, 1H), 7.71 (dd, 2H), 7.81 (dd, 2H), 8.19 (d, 2H).

Synthesis of 38

A solution of 37 (1.8 g) in MeOH (50 mL) was stirred at ambient temperature for 12 h. The resulting solution was concentrated under reduced pressure and the crude material thus obtained was purified by flash chromatography over silica gel (50% acetone in hexane) to gave 0.6 g of 38.

Synthesis of 39

Hydrazine (0.514 mL, 16.4 mmol) was added to a solution of 38 (0.55 g, 1.64 mmol) in EtOH (5 mL) and heated to 60° C. for 1 h. Then the white suspension was stirred for 12 h at ambient temperature. The white material was filtered and washed with MeOH (3×20 mL). The combined filtrate was concentrated and purified by flash chromatography over silica gel (CH₂Cl₂:2% NH₃-MeOH=9:1) to gave 0.155 g of pure base which converted to hydrochloride salt 39 using 2M HCl.

Synthesis of 400 g

A solution of 39 (0.82 mmol) and macrolide alkyne 27c (0.493 g, 0.74 mmol) in EtOH (3 mL) was heated to 60° C. for 72 h. Then the solution was concentrated and purified by flash chromatography over silica gel (CH₂Cl₂:2% NH3-MeOH=10:1) to gave 400d (0.08 g) as white solid. MS (ESI) m/e 799 (M+H)⁺, 400 (M+2H)⁺.

Synthesis of 449

To a mixture of 400d (0.0275 g, 0.034 mmol), 14w (0.001 g, 0.052 mmol) and CuI (0.007 g, 0.034 mmol) was added THF (2 mL) under argon atmosphere. Then was added few drops of Hunig's base and stirred at ambient temperature for 2 h. The reaction mixture was quenched with saturated NH₄OH solution containing 20% NH₄OH (10 mL) and stirred for 30 mins at ambient temperature. The mixture was extracted with methylene chloride (3×20 mL) and the combined organic extract was washed with saturated ammonium chloride solution containing 10% ammonium hydroxide (1×50 mL). The resulting solution was dried with anhydrous Na₂SO₄, concentrated and purified by flash chromatography over silica gel (CH₂Cl₂:2% NH₃-MeOH=10:1) to gave 0.023 g of 449. MS (ESI) m/e 496 (M+2H)²⁺; ¹H NMR (300 MHz, CDCl₃, partial): δ 0.85 (t, 3H), 1.05 (d, 3H), 1.15 (d, 3H), 3.33 (t, 2H), 3.81 (d, 1H), 4.10-4.28 (m, 3H), 4.58 (d, 2H), 4.84 (d, 1H), 5.20 (d, 1H), 7.08 (s, 1H), 7.24 (d, 2H), 8.14 (d, 2H).

Synthesis of 448

The compound 448 was synthesized from intermediate 36 using the same chemical sequences as described for 449. Data for 448: MS (ESI) m/e 496 (M+2H)²⁺.

Oximes 434 and 435 were synthesized from compound 425 by alkylation of the nitrogen of the piperidinyl oxime with 3-bromo-1-fluoropropane or 2-bromofluoroethane respectively as shown in Scheme 110 below.

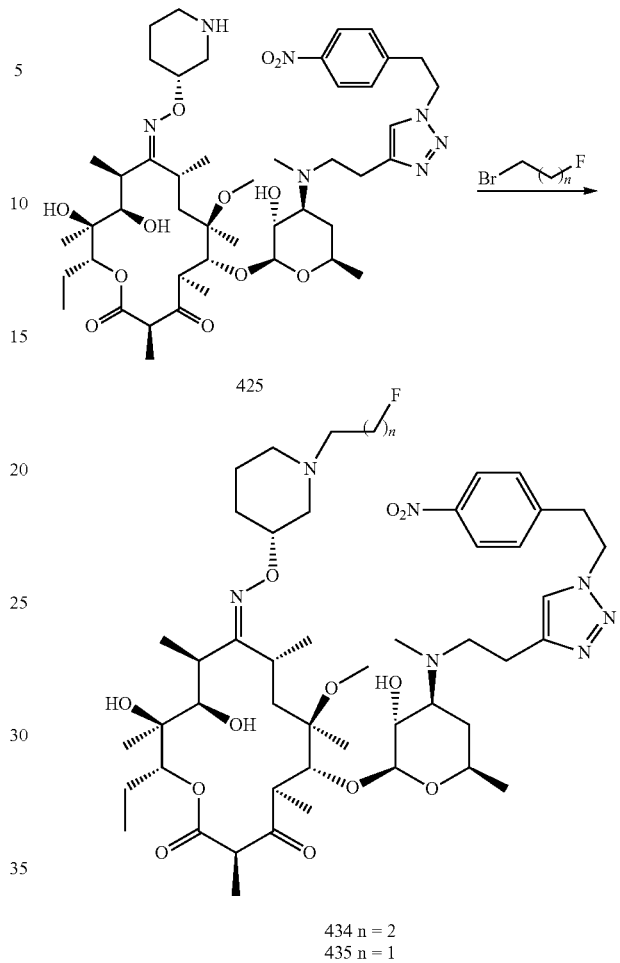

Scheme 110

Synthesis of 434

A solution of oxime 425 (0.04 g, 0.04 mmol) and 3-bromo-1-fluoropropane (0.012 mL, 0.13 mmol) in DMF (0.8 mL) was heated at 60° C. for 14 h. The reaction mixture was diluted with water (20 mL) and brine (10 mL) and extracted with CH₂Cl₂ (3×30 mL) the combined organic extracts were dried (Na₂SO₄), filtered and concentrated. The crude material was purified by flash chromatography (silica gel, 3:100:0.1 MeOH/CH₂Cl₂/NH₄OH) to yield 0.023 g of the oxime 434. Data for 434: MS (ESI) m/e 489.1 (M+2H)²⁺.

Synthesis of 435

Compound 435 was synthesized from compound 425 and 2-bromofluoroethane under the conditions described for the synthesis of compound 434. Data for 435: MS (ESI) m/e 482.1 (M+2H)²⁺.

Compound 436 was prepared via a different approach by oximation after cycloaddition as shown in Scheme 110.

Synthesis of Compound 436

Scheme 111 below depicts the synthesis of compound 436 starting from alkyne 27c. Deacylation of 27c in methanol provided alkyne 27d, which was treated with azide 14au to provide triazole 436a. This triazole was treated with 3(R)-Hydroxyamino-piperidine-1-carboxylic acid benzyl ester to give the carbobenzoxy (CBZ)-protected oxime as a mixture of E/Z isomers. The CBZ group was removed by hydrogenolysis to afford compound 436.

Scheme 111
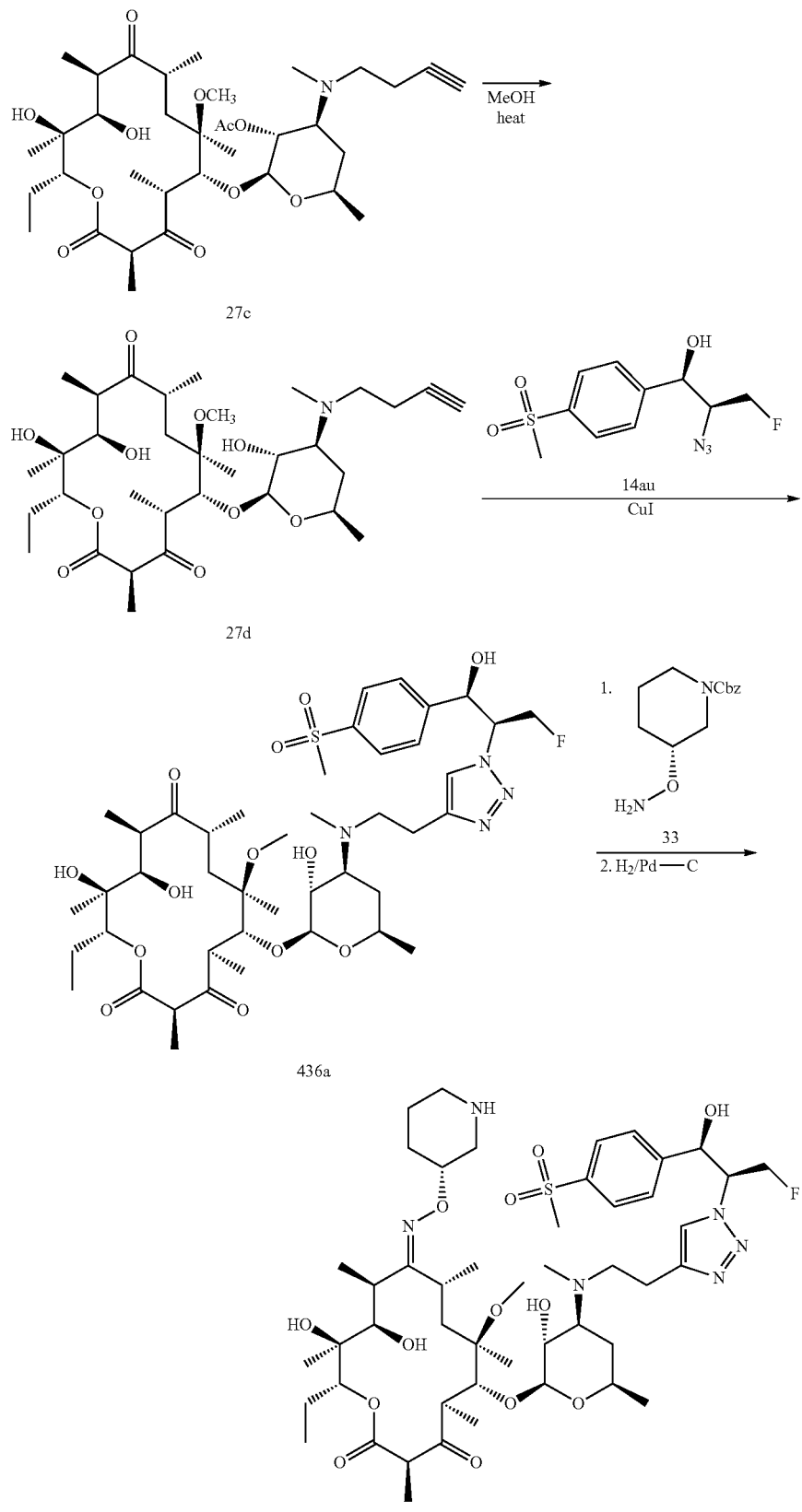

Synthesis of Alkyne 27d

A solution of ketolide 27c (0.230 g) in MeOH (10 mL) was heated at 50° C. for 48 h. The solvent was removed under reduced pressure to yield pure deacetylated product 27d (0.190 g, 88%). Data for 27d: MS (ESI) m/e 626 (M+H)$^+$; $^1$HNMR (300 MHz, CDCl$_3$, partial): ™ 0.85 (t, 3H), 2.25 (s, 3H), 2.70 (s, 3H), 2.97 (q, 1H), 3.10 (t, 1H), 3.18 (dd, 1H), 3.5 (m, 1H), 3.80-3.97 (m, 2H), 4.32 (m, 2H), 5.15 (dd, 1H).

Synthesis of 436a

Triazole 436a was synthesized from alkyne 27d and azide 14au using the copper catalyzed cycloaddition conditions disclosed for the compounds of Table 1 above.

Synthesis of 436

A solution of alkoxyamine 33 (0.13 g, 0.50 mmol) in ethyl ether (1.0 mL), was treated with 2.0 M hydrogen chloride in ethyl ether (1.5 mL, 3.0 mmol), stirred at 23° C. for 1 h, and evaporated to a white foam. A solution of this hydrochloride salt in ethanol (3.5 mL) was treated with 436a (0.15 g, 0.17 mmol) and the reaction mixture stirred at 55° C. for 16 h, and then cooled to room temperature and diluted with H$_2$O (30 mL). Ammonium hydroxide was added to adjust the pH to 10, and the reaction mixture was extracted with ethyl acetate (3×30 mL), dried (Na$_2$SO$_4$), and evaporated to a yellow oil.

A solution of the crude CBZ-protected intermediate in ethanol (10 mL) was treated with 10% Pd/C (100 mg) and the reaction mixture was stirred at 23° C. for 12 h under a balloon of hydrogen. Filtration and evaporation provided crude material which was purified by preparative thin-layer chromatography (SiO$_2$, 10% 2M NH$_3$-methanol/dichloromethane) to provide 436 (80 mg, 0.080 mmol) as a white solid: LCMS (ESI) m/e 550 (M+2H)$^{2+}$.

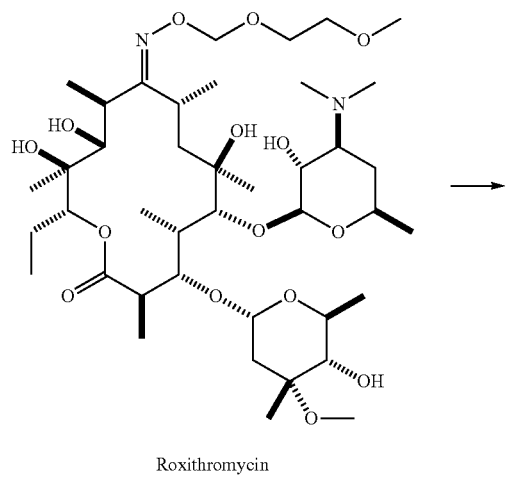

Scheme 112 Synthesis of intermediate 400h

Roxithromycin

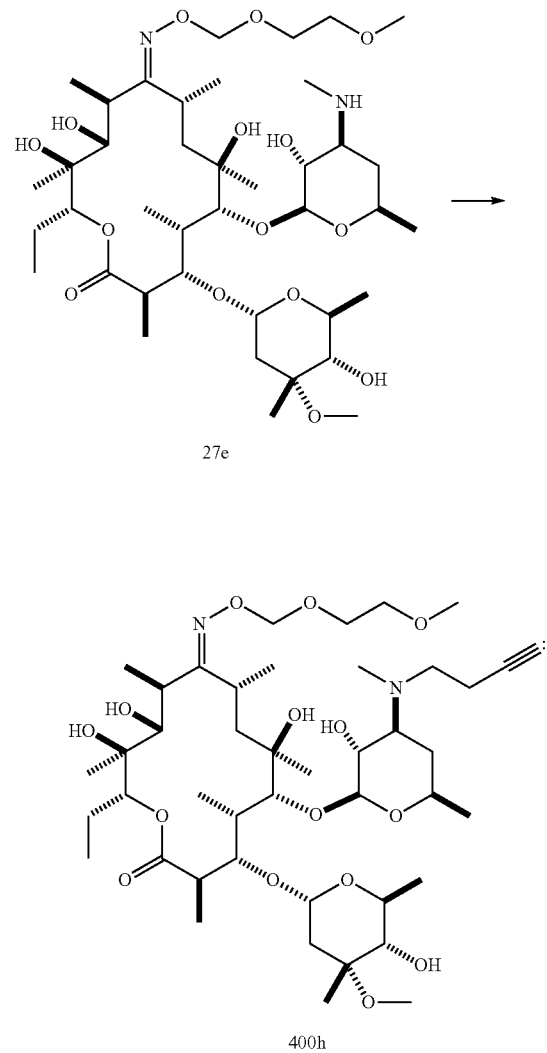

27e

400h

Synthesis of Compound 27e

To a mixture of Roxithromycin (850 mg, 0.914 mmol, 90%) and NaOAc (828 mg, 10.000 mmol) in a mixture of MeOH (6.0mL) and water (1.5 mL) at 48° C. was added I$_2$ in four portions (each portion: 63.5 mg) over 30 min, after each portion I$_2$, followed by 1N NaOH (400 μL). The reaction was continued for 30 min. The solvent was removed and EtOAc (100 mL) was added, followed by water (20 mL). The organic phase was washed with brine (40 mL×2), dried with Na$_2$SO$_4$. The residue was separated by flash chromatography (FC) (6/94/0.2 MeOH/CH$_2$Cl$_2$/NH$_4$OH), giving 600 mg compound 27e in 80% yield.

LCMS (ESI) m/e 824 (M+H)$^+$.

Synthesis of Compound 400h

A mixture of compound 27e (500 mg, 0.608 mmol) and toluene-4-sulfonic acid but-3-ynyl ester in a mixture solvents of THF (5.4 mL) and Hunig's base (1.6 mL) was refluxed for 48 hr. The reaction mixture was concentrated, then, EtOAc (100 mL) was added. The organic layer was washed with saturated NaHCO$_3$ (20 mL), and brine (50 mL). Compound 400h was isolated by FC (3/100/0.2 MeOH/CH$_2$Cl$_2$/ NH$_4$OH), gave 316 mg in 59% yield.

LCMS (ESI) m/e 876 (M+H)$^+$.

Synthesis of Compound 447

This compound was synthesized from alkyne 400h and azide 14bt using the conditions described in Example 1.

Scheme 113

NH$_2$OH·HCl →

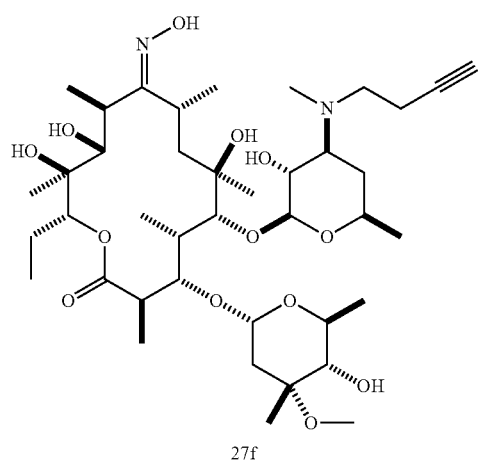

27f

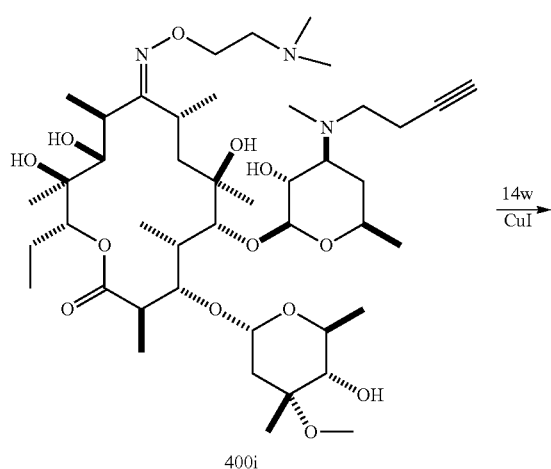

400i

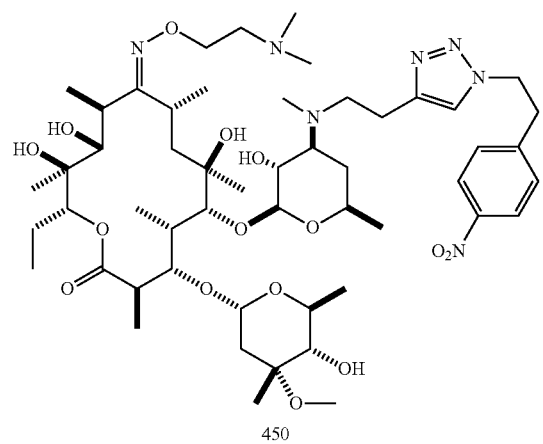

450

Synthesis of Compounds 450 and 451

A mixture of 9-oxime compound 27f (100 mg, 0.125 mmol), NaCO3 (106 mg, 0.998 mmol) and 2-chloroethyldimethylamine HCl salt (109 mg, 0.749 mmol) in acetone (1.0 mL) in seal tube was stirred at 70° C. for 5 days, then, EtOAc (30 mL) was added washed with 1N NaOH (2 mL) and water (15 mL), Compound 400h was isolated by FC (3/100/ 0.2 MeOH/CH$_2$Cl$_2$/NH$_4$OH), gave 75 mg in 70% yield.

MS (ESI) m/e 859 (M+H)$^+$.

Triazole 450 was synthesized from alkyne 400i and azide 14w using the conditions of Example 1.

Synthesis of Alkyne 400j

To a mixture of 9-oxime compound 27f (180 mg, 0.229 mmol), 3-fluoropropyl bromide (161 mg, 1.144 mmol) and Bu$_4$NBr (37 mg, 0.115 mmol) in CH$_2$Cl$_2$ (9.0 mL) was added 50% NaOH (3.0 mL). The mixture was stirred at room temperature for 45 min, then, water (20 mL) was added. The aqueous phase was extracted with CH$_2$Cl$_2$ (20 mL×2). The combined organic layers were washed with brine (50 mL). Compound 400j was isolated by FC (25/75/0.2 Acetone/Hexane/NH$_4$OH), gave 94 mg in 48% yield. MS (ESI) m/e 848 (M+H)$^+$.

Triazole 451 was synthesized from oxime alkyne 27f and alkyne 400j by alkylation with 3-fluoro-1-bromo propane followed by cycloaddition with azide 14w as described for the synthesis of compound 450.

TABLE 5

| Compound | R | R' | S | Azide | LCMS (M/Z) |
|---|---|---|---|---|---|
| 425 | 4-nitrophenyl-propyl | 3-methoxy piperidine (NH) | =O | 14w | 459.0 (M + 2H)²⁺<br>919.9 (M + H)⁺ |
| 426 | 1-(4-methylsulfonylphenyl)-3-fluoro-2-methyl-1-hydroxypropyl | 3-methoxy piperidine (NH) | =O | 14au | 459.0 (M + 2H)²⁺<br>919.9 (M + H)⁺ |
| 427 | 4-(methylsulfonyl)phenyl-propyl | 3-methoxy piperidine (NH) | =O | 14b | 476.0 (M + 2H)²⁺ |
| 428 | 4-sulfamoylphenyl-propyl | 3-methoxy piperidine (NH) | =O | 14be | 469.0 (M + 2H)²⁺<br>936.7 (M + H)⁺ |
| 429 | 4-sulfamoylphenyl-ethyl | 3-methoxy piperidine (NH) | =O | 14bd | 452.0 (M + 2H)²⁺ |
| 430 | 4-nitrophenyl-ethyl | 3-methoxy piperidine (NH) | =O | 14v | 474.1 (M + 2H)²⁺ |

Note: LCMS values use superscript notation: $(M + 2H)^{2+}$ and $(M + H)^{+}$.

TABLE 5-continued

| Compound | R | R' | S | Azide | LCMS (M/Z) |
|---|---|---|---|---|---|
| 431 | (S)-3-(4-nitrophenyl)-2-methylpropan-1-ol | (3S)-3-methoxypiperidine | =O | 14bq | 451.1 (M + 2H)²⁺ 902.7 (M + H)⁺ |
| 432 | 1-nitro-4-propylbenzene | (3S)-3-methoxypyrrolidine | =O | 14w | 467.0 (M + 2H)²⁺ 932.8 (M + H)⁺ |
| 433 | (S)-3-(4-nitrophenyl)-2-methylpropan-1-ol | (3S)-3-methoxypyrrolidine | =O | 14bq | 444.9 (M + 2H)²⁺ 888.6 (M + H)⁺ |
| 434 | 1-ethyl-4-nitrobenzene | (3S)-3-methoxypyrrolidine | =O | n/a | 489.1 (M + 2H)²⁺ |
| 435 | 1-nitro-4-propylbenzene | 1-(3-fluoropropyl)-3-methoxypiperidine | =O | n/a | 482.1 (M + 2H)²⁺ |

TABLE 5-continued
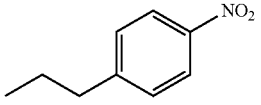
| Compound | R | R' | S | Azide | LCMS (M/Z) |
|---|---|---|---|---|---|
| 436 | 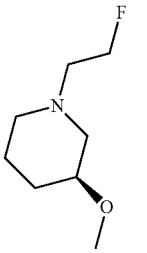 | 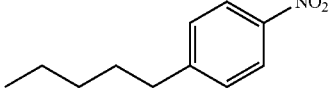 | =O | 14w | 550 (M + 2H)$^{2+}$ |
| 437 | 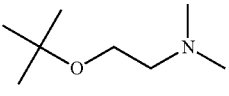 | 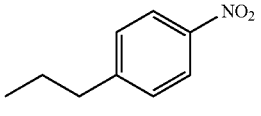 | =O | 14ej | 467 (M + 2H)$^{2+}$<br>933 (M + H)$^+$ |
| 438 | 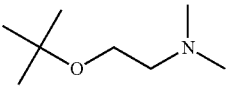 | 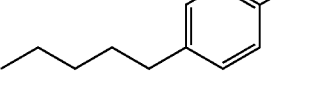 | =O | 14w | 453 (M + 2H)$^{2+}$<br>905 (M + H)$^+$ |
| 439 | 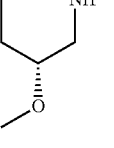 | 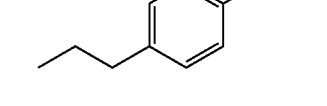 | =O | 14ej | 473 (M + 2H)$^{2+}$<br>945 (M + H)$^+$ |
| 440 | 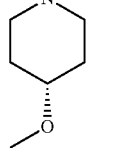 | 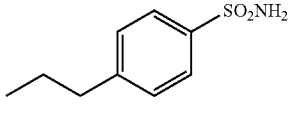 | =O | 14w | 459 (M + 2H)$^{2+}$<br>917 (M + H)$^+$ |
| 441 | 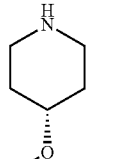 |  | =O | 14b | 476 (M + 2H)$^{2+}$<br>951 (M + H)$^+$ |

TABLE 5-continued
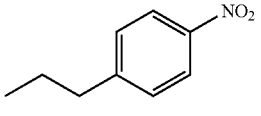
| Compound | R | R' | S | Azide | LCMS (M/Z) |
|---|---|---|---|---|---|
| 442 | 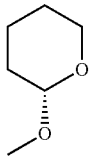 | 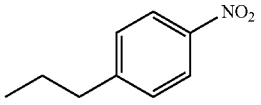 | =O | 14w | 918 (M + H)+ |
| 443 | 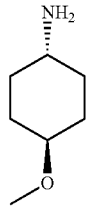 | 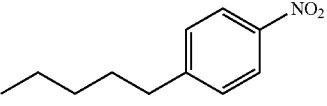 | =O | 14w | 466 (M + 2H)²⁺<br>931 (M + H)+ |
| 444 | 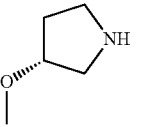 | 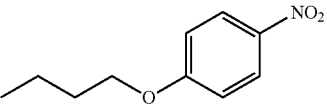 | =O | 14ej | 466 (M + 2H)²⁺<br>930.8 (M + H)+ |
| 445 | 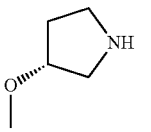 | 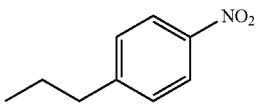 | =O | 14et | 467 (M + 2H)²⁺ |
| 446 | 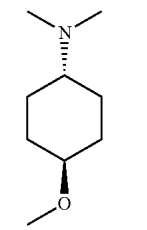 | 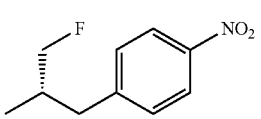 | =O | 14w | 480 (M + 2H)²⁺<br>959 (M + H)+ |
| 447 | 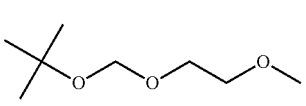 | 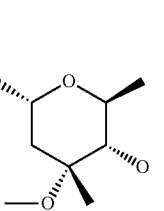 | | 14bt | 550 (M + 2H)²⁺<br>1100 (M + H)+ |

TABLE 5-continued

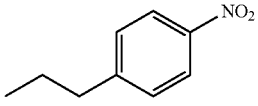

| Compound | R | R' | S | Azide | LCMS (M/Z) |
|---|---|---|---|---|---|
| 448 | 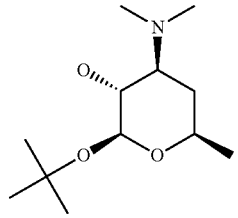 | 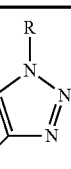 | =O | 14w | 496 (M + 2H)$^{2+}$ |
| 449 |  | 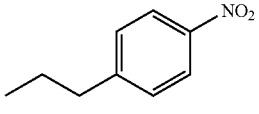 | =O | 14w | 496 (M + 2H)$^{2+}$ |
| 450 | 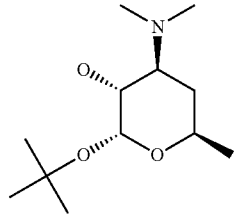 |  |  | 14w | 526 (M + 2H)$^{2+}$<br>1051 (M + H)$^+$ |
| 451 | 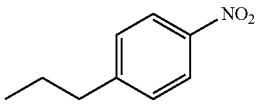 | 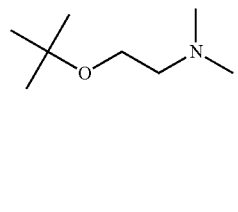 | 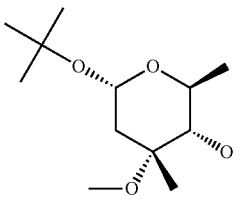 | 14w | 520 (M + 2H)$^{2+}$<br>1040 (M + H)$^+$ |

Example 5

Synthesis of Compounds 460-466

Alkyne 41 shown in Scheme 114, was derived from 9' N-desmethyl azithromycin under conditions identical to those described in Example 1 for the synthesis of Alkyne 4 above. This alkyne was the common intermediate for all of the compounds in Table 6. Compound 466 was derived directly from alkyne 41 by copper promoted [3+2] cycloaddition with azide 14w using the conditions of Example 1.

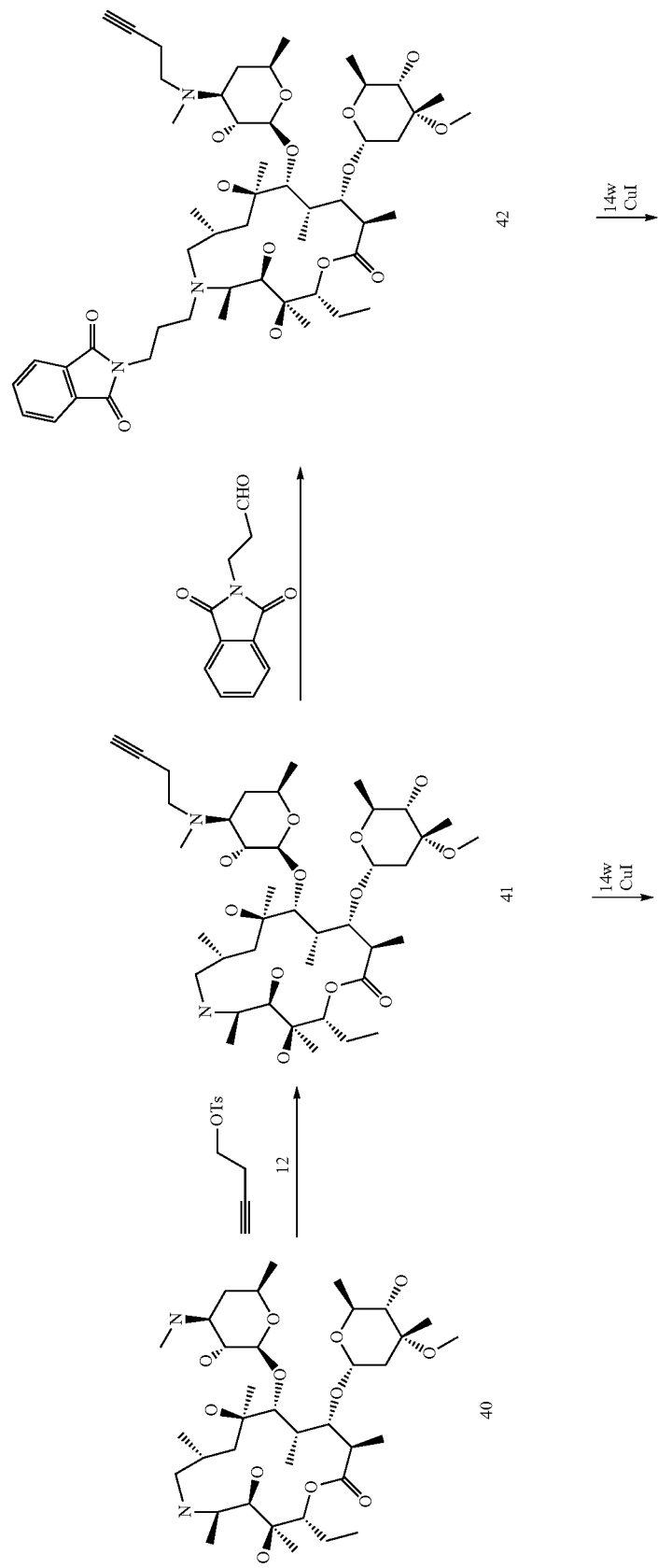

497
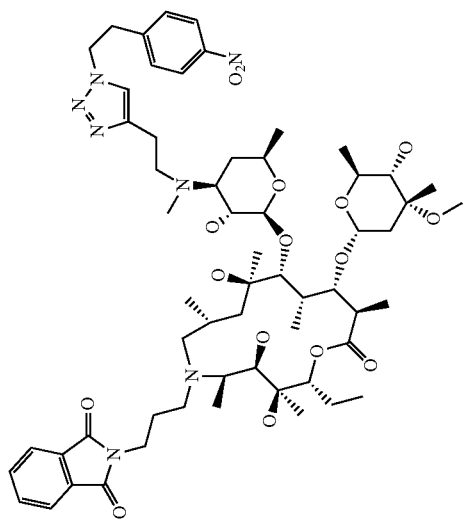
498
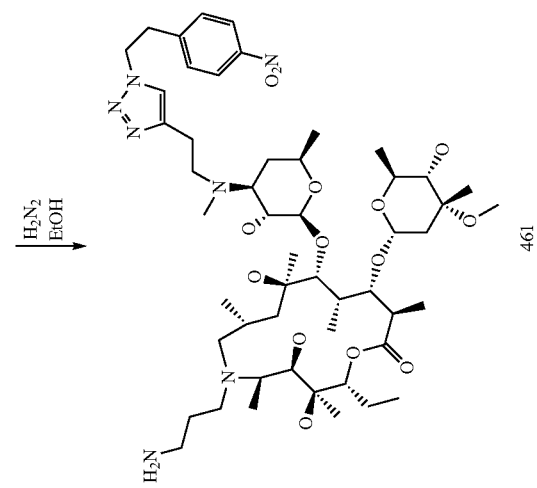
-continued
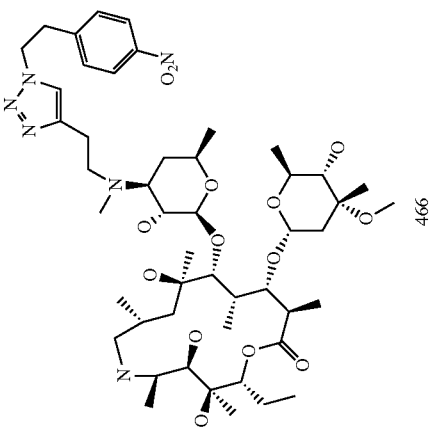

Synthesis of Alkyne 41

A solution of 5.0 g (6.93 mmol) of 3',9'-bis-N-desmethyl azithromycin 40 and 3.107 g (13.80 mmol) of tosylate 11 in 60 mL of Hunig's base and 8 mL of acetonitrile was heated to 100° C. for 24 h. After cooling, the solvents were removed by rotary evaporation, and the residue was purified through silica gel column chromatography to give 1.70 g of final product. MS (ESI) m/e 774 (M+H)$^+$.

Synthesis of Compound 42

A solution of 0.200 g (0.26 mmol) of 41, 0.262 g (1.29 mmol) of 3-(N-phthalimidyl)-propionaldehyde, and 0.110 g (0.52 mmol) of NaB(OAc)$_3$H in 1.5 mL of DMF was stirred at 25° C. for 4 h. The reaction mixture was diluted with H$_2$O, extracted with CH$_2$Cl$_2$ (50 mL×3), combined organic layers were washed with brine, dried over MgSO$_4$, concentrated, purified through silica gel column chromatography to give 0.200 g of product. MS (ESI) m/e 961 (M+H)$^+$.

Synthesis of Triazole 460

A solution of 0.200 g (0.20 mmol) of alkyne 42, 0.080 g (0.41 mmol) of azide 14w, and 0.040 g (0.20 mmol) of CuI in 15 mL of THF was degassed, then put under argon. To it was added 0.2 mL of Hunig's base. The reaction was stirred at 25° C. for 6 h. Subsequently, to the mixture was added 40 mL of 10% NH$_4$OH, stirred for 10 min, extracted with CH$_2$Cl$_2$ (50 ml×3), the combined organic layers were washed with brine, dried, concentrated, purified by preparative TLC to give 0.098 g of compound 460. MS (ESI) m/e 1153 (M+H)$^+$.

Synthesis of Triazole 461

A solution of 0.025 g (0.02 mmol) of RX-460 and 0.002 g (0.04 mmol) of hydrazine in 2.0 ml of ethanol was kept under refluxing for 6 h. After cooling down, ethanol was removed, the residue was suspended in 5.0 mL of CH$_2$Cl$_2$, filtered through a cotton-stuffed pipette, and collected organic solvent was concentrated. This process was repeated a couple of more times if necessary until MS and proton NMR gave indications that the material was pure enough to give 0.020 g of final product. MS (ESI) m/e 1023 (M+H)$^+$.

Synthesis of Compounds 462 and 463

Compound 462 was synthesized from alkyne 41 and 2-(N-phthalimidyl)-acetaldehyde using the procedure described above for compound 460.

Compound 463 was synthesized from compound 462 using the conditions described above for the synthesis of compound 461 from 460.

Synthesis of Compounds 464 and 465

Compound 464 was synthesized from alkyne 41 and 4-(N-phthalimidyl)-butyraldehyde using the procedure described above for compound 460.

Compound 465 was synthesized from compound 464 using the conditions described above for the synthesis of compound 461 from 460.

TABLE 6

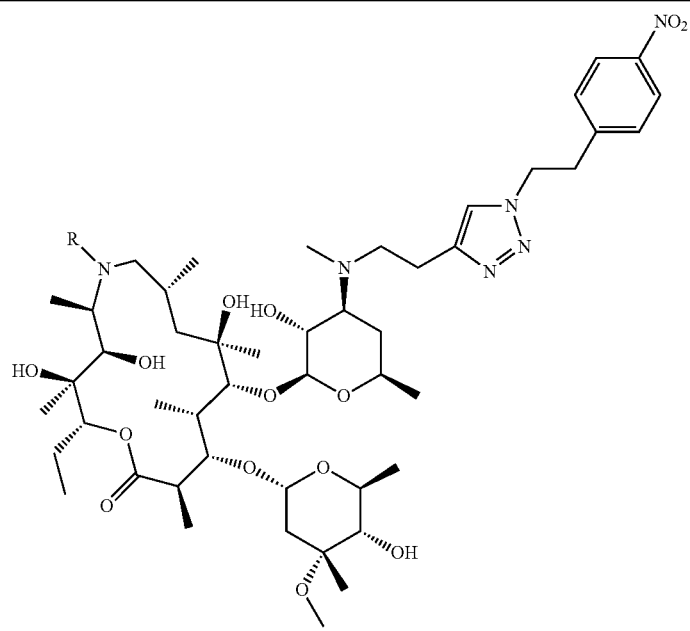

| Compound | R | LCMS (M/Z) |
|---|---|---|
| 460 | | 1153.0 (M + H)$^+$ |

TABLE 6-continued

[Structure of macrolide compound with R-N group, showing azithromycin-like core with triazole linker to 4-nitrophenethyl group]

| Compound | R | LCMS (M/Z) |
| --- | --- | --- |
| 461 | -CH2CH2CH2CH2-NH2 | 1023.0 (M + H)+ |
| 462 | -CH2CH2CH2-N(phthalimide) | 1138.0 (M + H)+ |
| 463 | H2N-CH2CH2CH2- | 1009 (M + H)+ |
| 464 | -CH2CH2CH2CH2CH2-N(phthalimide) | 1167.0 (M + H)+ |
| 465 | H2N-CH2CH2CH2CH2CH2- | 1037.0 (M + H)+ |
| 466 | H | 966.1 (M + H)+ |

Example 6

Synthesis of Compounds 475-480

TABLE 7

| Compound | R | Macrolide | n | LCMS (M/Z) |
|---|---|---|---|---|
| 475 | (4-methylsulfonylphenyl)-CH(OH)-CH(NH-tBu)-CH2F | Azithromycin | 3 | 532.1 (M + 2H)$^{2+}$ |
| 476 | (4-nitrophenyl)-CH(OH)-CH(NH-tBu)-CH2OH | Azithromycin | 3 | 516.2 (M + 2H)$^{2+}$ |
| 477 | tBu-NH-CH2-CH2-(4-nitrophenyl) | Azithromycin | 3 | 493 (M + 2H)$^{2+}$ |
| 478 | tBu-NH-CH2-CH2-(4-fluorophenyl) | Clarithromycin | 2 | 941 (M + H)$^+$ |
| 479 | tBu(NH)-CH2-CH2-(4-fluorophenyl) | Clarithromycin | 1 | 927 (M + H)$^+$ |
| 480 | tBu-NH-CH(CH2OH)-CH2-(4-nitrophenyl) | Azithromycin | 1 | 493.6 (M + 2H)$^{2+}$ |

As shown in Scheme 115 below, the precursor carboxylic acid derivatives 44 and 46 were readily synthesized from amine 2 by alkylation with appropriate omega bromoesters followed by saponification. These carboxylic acids were elaborated by amide coupling with appropriate amines to afford final compounds 475-477 and 480

Scheme 115

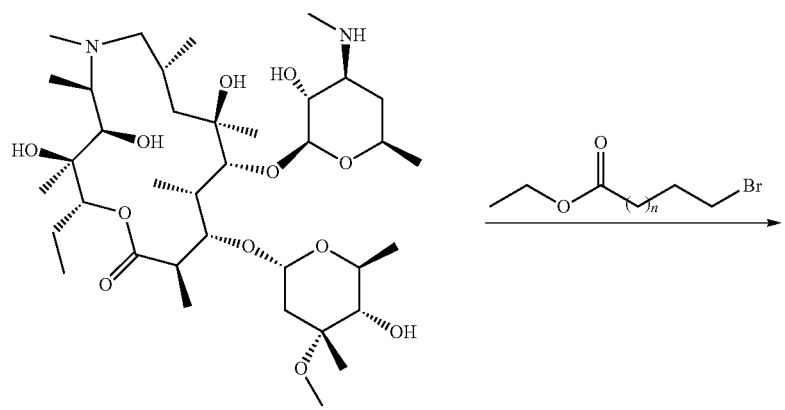

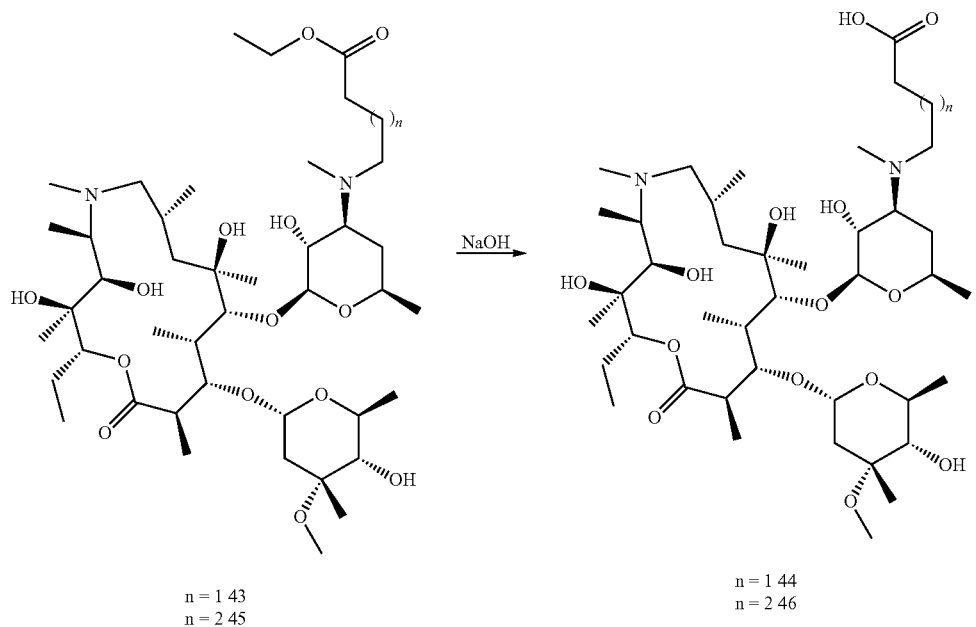

n = 1 43
n = 2 45 n = 1 44
n = 2 46

Synthesis of Compound 43

A solution of desmethylazithromycin 2 (3.7 g, 5 mmol) in diisopropylethylamine (25 mL) was treated with ethyl 5-bromobutyrate (7.2 g, 50 mmol) and stirred at 105° C. for 5 h. The reaction mixture was cooled to room temperature, decanted, and the liquid portion evaporated to a yellow oil. Flash chromatography ($SiO_2$, 6% 2M $NH_3$-methanol/dichloromethane) provided 43 (2.7 g, 3.2 mmol) as a white foamy solid: LCMS (ESI) m/e 850 (M+H)$^+$.

Synthesis of Compound 44

A solution of 43 (0.60 g, 0.70 mmol) in methanol (16 mL) and $H_2O$ (2.4 mL) was treated with 1.0 M aqueous sodium hydroxide (2.0 mL, 2.0 mmol) and stirred at 50° C. for 2.5 h. The reaction mixture was cooled to room temperature and quenched by the addition of acetic acid (0.12 mL, 2.0 mmol), and evaporated to a white powder. Flash chromatography ($SiO_2$, 10% 2M $NH_3$-methanol/dichloromethane) provided 44 (0.40 g, 0.49 mmol) as a white powder: LCMS (ESI) m/e 836 (M+Na)$^+$.

Synthesis of Compound 45

A solution of desmethylazithromycin 2 (3.7 g, 5 mmol) in diisopropylethylamine (25 mL) was treated with ethyl 5-bromovalerate (5.2 g, 25 mmol) and stirred at 105° C. for 4 h. The reaction mixture was cooled to room temperature, diluted with dichloromethane (100 mL), washed with $H_2O$ (100 mL), dried (Na$_2$SO$_4$) and evaporated. Flash chromatography (SiO$_2$, 6% 2M NH$_3$-methanol/dichloromethane) provided 45 (0.55 g, 0.64 mmol) as a colorless oil: LCMS (ESI) m/e 864 (M+H)$^+$.

Synthesis of Compound 46

A solution of 45 (0.54 g, 0.62 mmol) in methanol (10 mL) and H$_2$O (1.25 mL) was treated with 1.0 M aqueous sodium hydroxide (1.25 mL, 1.25 mmol) and stirred at 45° C. for 2.5 h. The reaction mixture was cooled to room temperature and quenched by the addition of 1.0 M hydrochloric acid (1.25 mL, 1.25 mmol), extracted with dichloromethane (3×30 mL), dried (Na$_2$SO$_4$), and evaporated to provide 46 (0.52 g, 0.62 mmol) as a white powder: LCMS (ESI) m/e 836 (M+2H)$^+$.

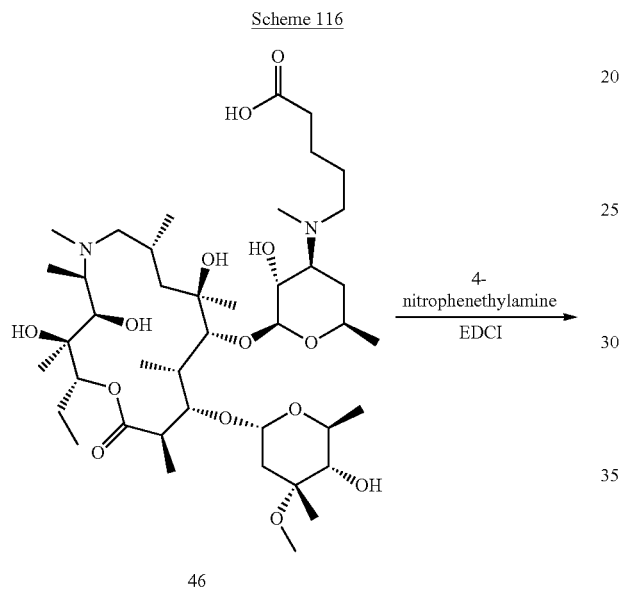

Scheme 116

46

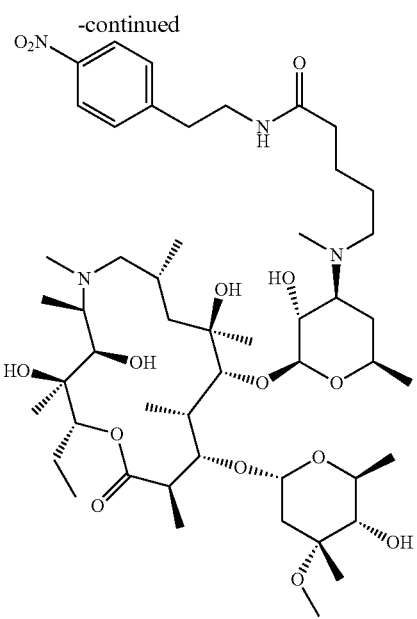

477

Synthesis of Compound 477

A solution of 46 (30 mg, 0.035 mmol) in dichloromethane (0.5 mL) was treated with 4-nitrophenethlamine hydrochloride (14 mg, 0.070 mmol), diisopropylethylamine (0.018 mL, 0.11 mmol) and 1-ethyl-3-(3-dimethylaminopropyl)carbodiimide (10 mg, 0.053 mmol), and stirred at 23° C. for 12 h. The reaction mixture was evaporated to a yellow film and purified by preparative thin-layer chromatography (SiO$_2$, 5% 2M NH$_3$-methanol/dichloromethane) to provide 477 (7.0 mg, 0.0071 mmol) as a white film: LCMS (ESI) m/e 493 (M+2H)$^{2+}$.

Scheme 117

46

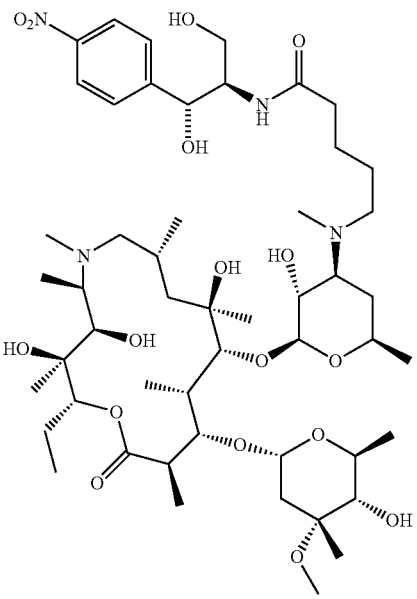

476

A solution of 46 (31 mg, 0.037 mmol) in DMF (0.4 mL) was treated with D-(−)-threo-2-amino-1-(4-nitrophenyl)-1,3-propanediol (7.9 mg, 0.037 mmol) and 1-ethyl-3-(3-dimethylaminopropyl)carbodiimide (8.5 mg, 0.037 mmol), and stirred at 23° C. for 16 h. The reaction mixture was evaporated to a yellow film and purified by preparative thin-layer chromatography (SiO$_2$, 5% 2M NH$_3$-methanol/dichloromethane) to provide 476 (10 mg, 0.0097 mmol) as a white solid: LCMS (ESI) m/e 516 (M+2H)$^{2+}$.

Scheme 118

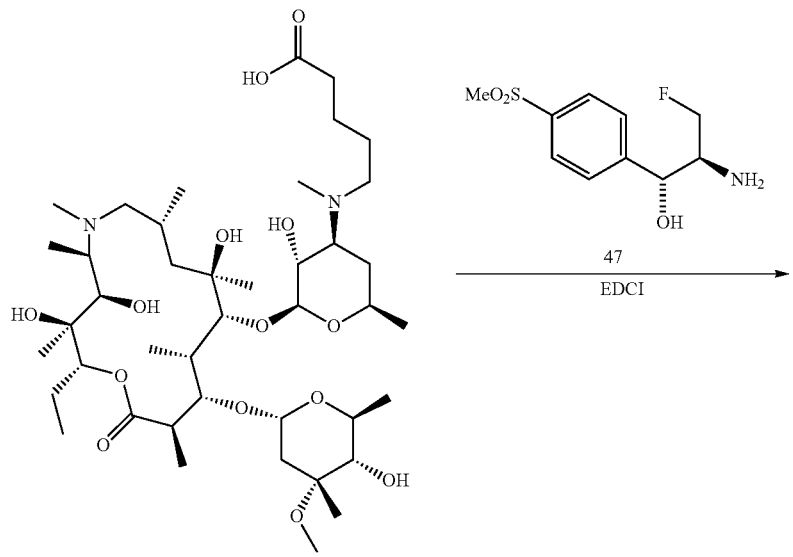

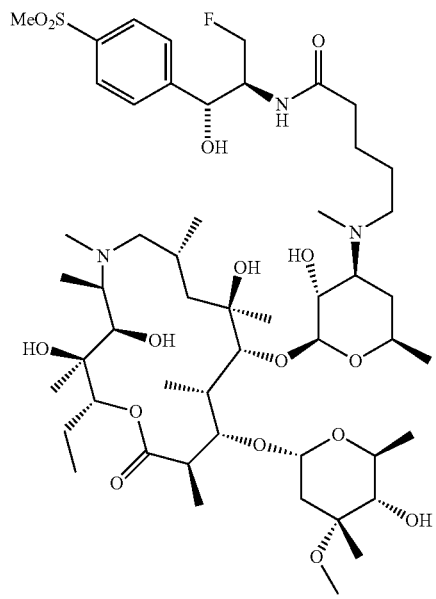

475

A solution of 46 (40 mg, 0.048 mmol) in CH$_2$Cl$_2$ (0.7 mL) was treated with Flofenicol amine 47 (12 mg, 0.048 mmol) and 1-ethyl-3-(3-dimethylaminopropyl)carbodiimide (10 mg, 0.053 mmol), and stirred at 23° C. for 16 h. The reaction mixture was evaporated to a yellow film and purified by preparative thin-layer chromatography (SiO$_2$, 5% 2M NH$_3$-methanol/dichloromethane) to provide compound 475 (8 mg, 0.008 mmol) as a white solid: LCMS (ESI) m/e 532.1 (M+2H)$^{2+}$.

Synthesis of Compounds 478 and 479

These compounds were synthesized from clarithromycin amine 21 ethyl 4-bromobutyrate or ethyl 3-bromopropionate and 4 fluorophenethyl amine using the chemistries described above for compound 477.

Synthesis of Compound 480

Compound 480 was synthesized from amine 2 and bromide 48 as shown in Scheme 117 using the alkylating conditions described for the synthesis of alkyne 3 in Example 1.

Scheme 119

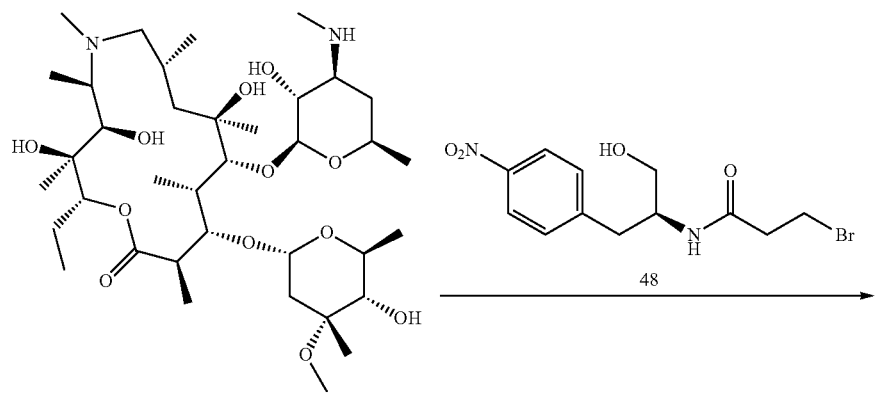

2

-continued
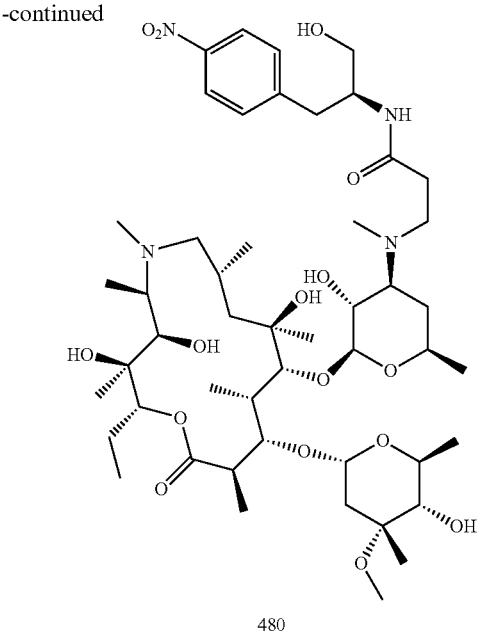
480
Example 7
Synthesis of Compounds 501-515
TABLE 8
| Compound | R | n | LCMS (M/Z) |
|---|---|---|---|
| 501 | ![4-nitrophenyl bicyclic pyrrolidine carbonyl] | 2 | 505 (M + 2H)²⁺ |
TABLE 8-continued
| Compound | R | n | LCMS (M/Z) |
|---|---|---|---|
| 502 | ![pivaloyl-NH-CH(CH2OH)-CH(OH)-4-nitrophenyl] | 2 | 516 (M + 2H)²⁺ |
| 503 | ![pivaloyl-NH-CH(CH2OH)-CH(OH)-4-nitrophenyl] | 1 | 509 (M + 2H)²⁺ |

TABLE 8-continued
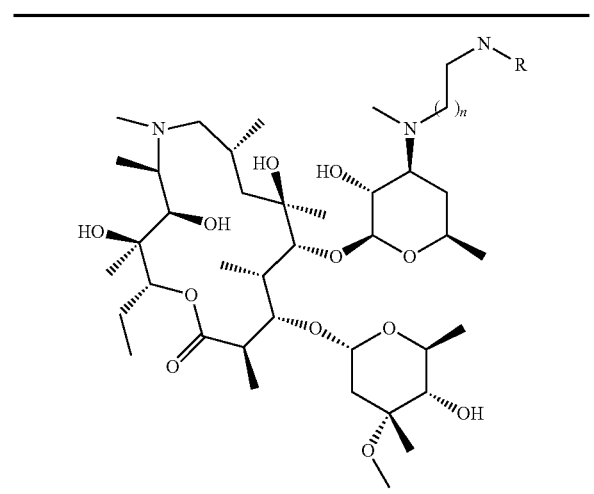
| Compound | R | n | LCMS (M/Z) |
|---|---|---|---|
| 504 | 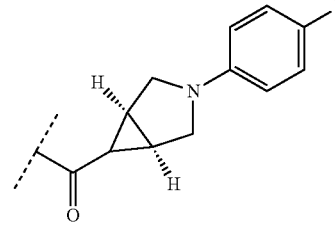 | 1 | 505 (M + 2H)²⁺ |
| 505 | 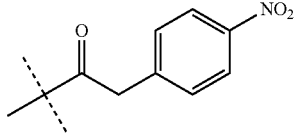 | 1 | 471.7 (M + 2H)²⁺ |
| 506 | 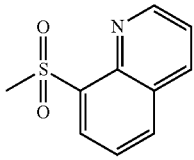 | 1 | 485.6 (M + 2H)²⁺ |
| 507 | 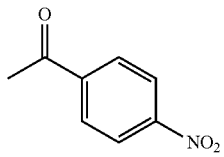 | 1 | 464.6 (M + 2H)²⁺ |
| 508 | 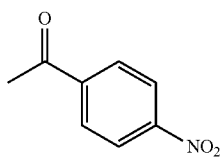 | 2 | 471.7 (M + 2H)²⁺ |
TABLE 8-continued
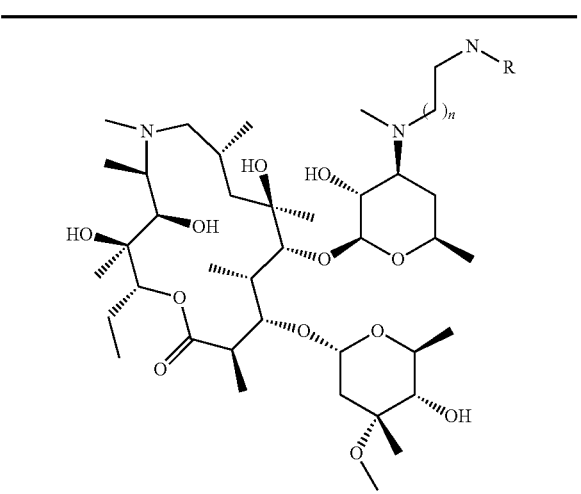
| Compound | R | n | LCMS (M/Z) |
|---|---|---|---|
| 509 | 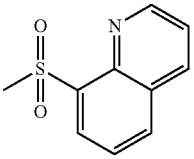 | 2 | 492.7 (M + 2H)²⁺ |
| 510 | 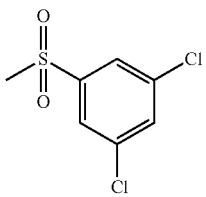 | 1 | 988.7 (M + H)⁺ |
| 511 | 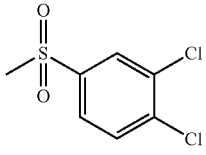 | 1 | 988.7 (M + H)⁺ |
| 512 | 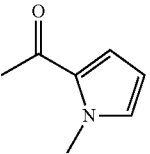 | 1 | 443.6 (M + 2H)²⁺ |
| 513 | 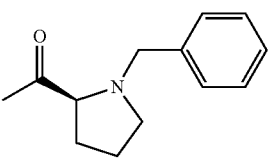 | 1 | 483.7 (M + 2H)²⁺ |

TABLE 8-continued

[Macrolide structure with N-R substituent]

| Compound | R | n | LCMS (M/Z) |
|---|---|---|---|
| 514 | [1-methyl-2-acetyl-4-benzyloxy-pyrrolidinyl] | 1 | 498.8 (M + 2H)$^{2+}$ |
| 515 | [1-methyl-2-acetyl-4-propyl-pyrrolidinyl] | 1 | 466.6 (M + 2H)$^{2+}$ |

The amide-, sulfonamide-, and urea-linked derivatives 501-515 of Table 8 were synthesized from amines 500a and 500b by addition of suitable carboxylic acids, sulfonyl chlorides, or acyl imidazoles respectively under standard conditions. The amines 500a-b were synthesized as shown in Scheme 120.

Scheme 120

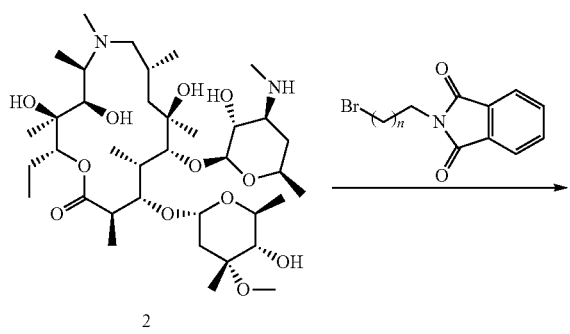

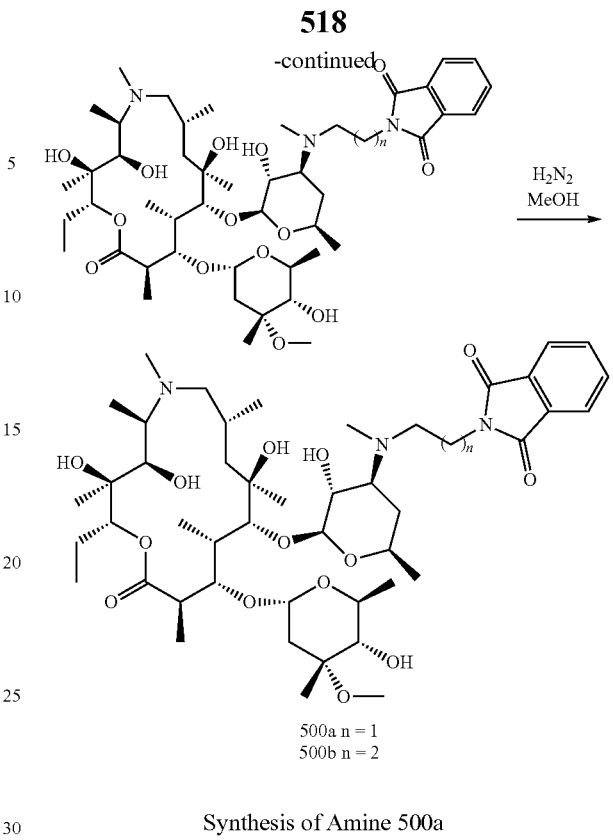

500a n = 1
500b n = 2

Synthesis of Amine 500a

To a solution of amine 2 (2.0 g, 2.7 mmol) in Hunig's base (5 mL) was added N-[2-bromoethyl]-phthalimide (0.76 g, 3 mmol). The mixture was heated to 100° C. in a sealed tube for 1.5 h. The mixture was diluted with water (100 mL) and extracted with $CH_2Cl_2$ (3×50 mL). The combined organic extracts were dried ($K_2CO_3$), filtered, and concentrated. The crude product was purified by silica gel chromatography (eluted with 1-4% methanolic ammonia (2M $NH_3$) in $CH_2Cl_2$) to give the phthalimide derivative as a white solid (1.8 g, 1.9 mmol).

To a solution of this phthalimide (1.0 g, 1.1 mmol) in EtOH (10 mL) was added hydrazine (1 mL of 80% aqueous solution). The mixture was stirred at rt for 8 h, then the solidified reaction residue was dissolved in $CH_2Cl_2$ (100 mL) and washed with water (3×50 mL). The organic layer was dried over $K_2CO_3$, filtered and concentrated to give 0.82 g of a white solid which was used without further purification.

Synthesis of Amine 500b

Compound 500b was synthesized from amine 2 N-[3-bromopropyl]-phthalimide using the conditions described above for compound 500a.

Compound 503 was synthesized from the amine 500a and the N-acyl imidazole derivative of the his silyl ether derivative of D-(−)-threo-2-amino-1-(4-nitrophenyl)-1,3-propanediol. This yielded the bis-silyl-protected precursor 503a which was desilylated with tetrabutyl ammonium fluoride to afford compound 503 as shown in Scheme 121 below.

Scheme 121

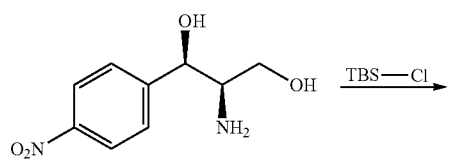

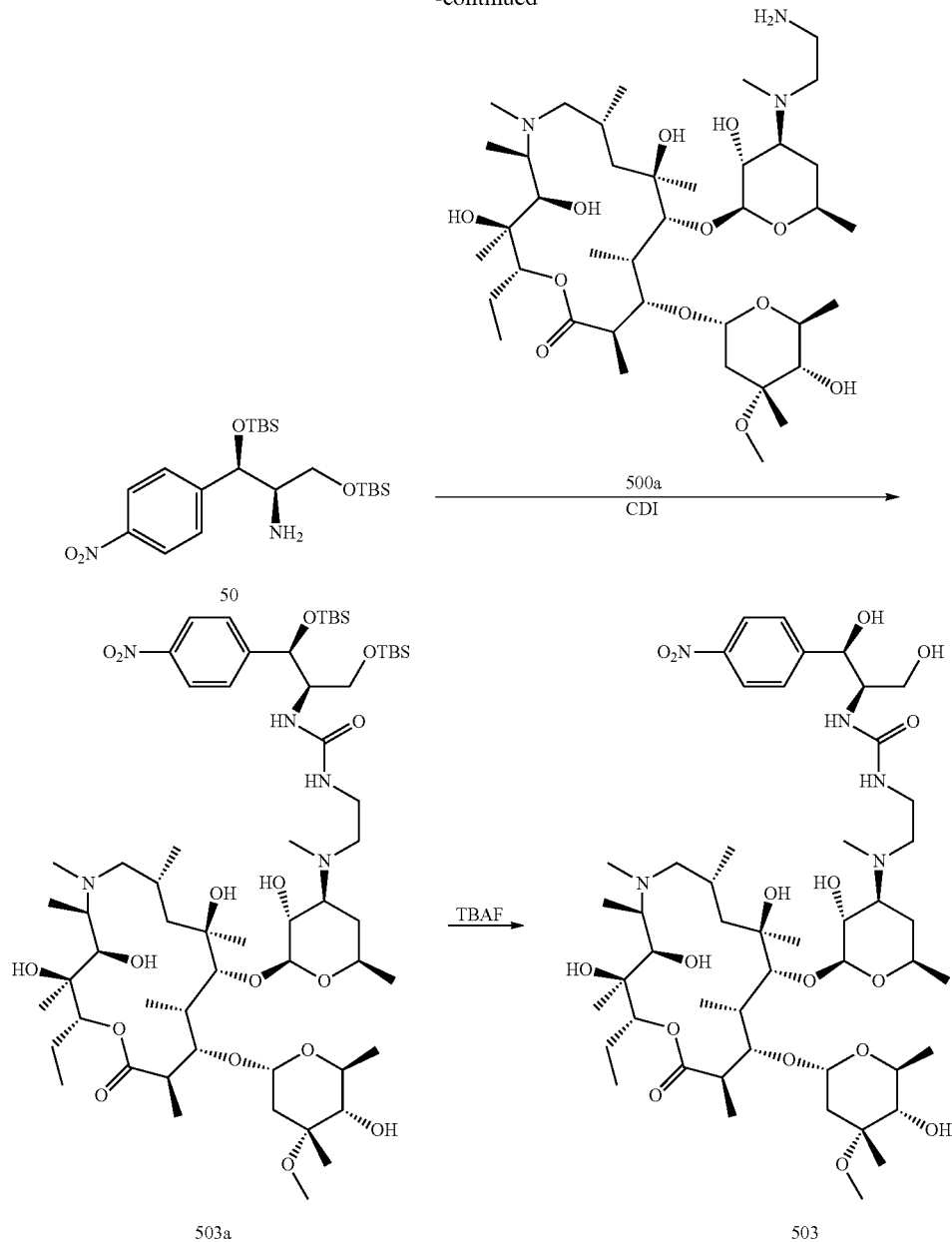

Synthesis of Compound 503

A solution of D-(−)-threo-2-amino-1-(4-nitrophenyl)-1,3-propanediol (2.1 g, 10 mmol) in dimethylformamide (200 mL) was treated with imadazole (2.0 g, 30 mmol) and tert-butyldimethylchlorosilane (3.0 g, 20 mmol), and stirred at 23° C. for 16 h. The reaction mixture was diluted with ethyl ether (300 mL), washed with $H_2O$ (3×300 mL), and dried ($Na_2SO_4$). Flash chromatography ($SiO_2$, 20% ethyl acetate/hexanes) provided the bis-silyl ether 50 (2.6 g, 5.9 mmol) as a yellow oil.

A solution of the bis-silyl ether 50 (44 mg, 0.10 mmol) in dichloromethane (1.0 mL) was treated with triethylamine (0.028 mL, 0.20 mmol) and 1,1-carbonyldiimadazole (16 mg, 0.10 mmol), and stirred at 23° C. for 3 h. Amine 500a (78 mg, 0.10 mmol) was added and the reaction mixture was stirred at 23° C. for an additional 12 h, and then evaporated to a yellow film and purified by preparative thin-layer chrmatography ($SiO_2$, 10% 2M $NH_3$-methanol/dichloromethane) to provide 503a (65 mg, 0.064 mmol) as a white film: LCMS (ESI) m/e 623 $(M+2H)^{2+}$ A solution of 503a (50 mg, 0.040 mmol) in tetrahydrofuran (0.8 mL) was treated with tetrabutylamonium fluoride (0.16 mL of a 1.0 M solution, 0.16 mmol) and acetic acid (0.005 mL, 0.08 mmol), and stirred at 23° C. for 4 h. The reaction mixture was diluted with $H_2O$ (20 mL), and extracted with dichloromethane (3×20 mL), dried ($Na_2SO_4$), evaporated, and purified by preparative thin-layer chromatography ($SiO_2$, 5% 2M $NH_3$-methanol/dichloromethane) to provide 503 (19 mg, 0.019 mmol) as a white film: LCMS (ESI) m/e 509 $(M+2H)^{2+}$.

Synthesis of Compound 502

Compound 502 was synthesized from amine 500b and D-(−)-threo-2-amino-1-(4-nitrophenyl)-1,3-propanediol as described above for compound 503.

Synthesis of Compound 501

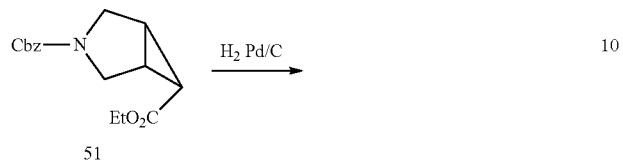

Scheme 122

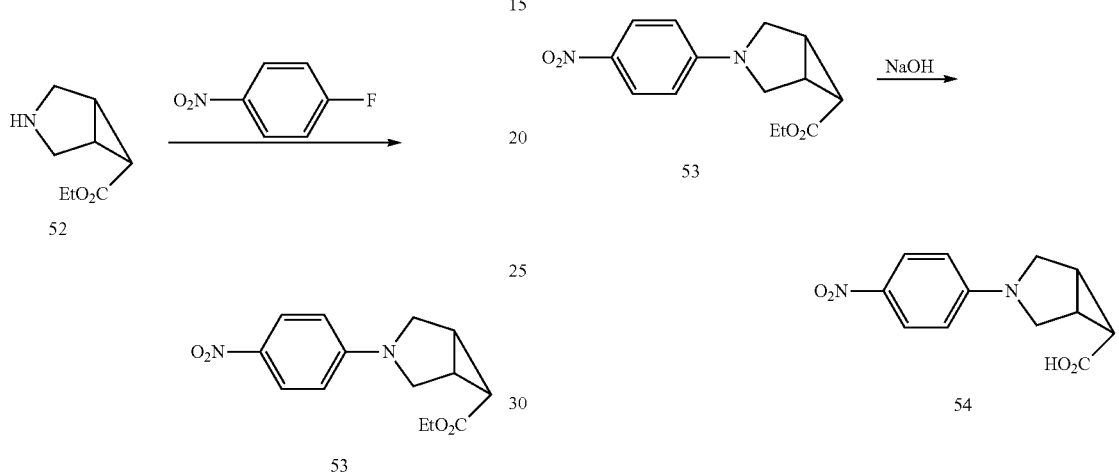

A solution of CBZ amine 51 (U.S. Pat. No. 5,164,402) (1.5 g, 5.2 mmol) in methanol (30 mL) was treated with 10% Pd/C (0.15 g) and stirred under a balloon of hydrogen at 23° C. for 2 h. The reaction mixture was filtered through a plug of silica gel and evaporated to provide the crude amine 52 as a yellow oil.

A solution of this amine 52 in acetonitrile (5.0 mL) was treated with diisopropylethylamine (2.0 mL, 12 mmol) and 4-fluoro-nitrobenzene (0.60 mL 5.7 mmol), and stirred at 70° C. for 16 h. The reaction mixture was evaporated and purified by flash chromatography (SiO$_2$, 20-50% ethyl acetate/hexanes) to provide the ethyl ester 53 (0.76 g, 2.8 mmol) as a yellow oil.

Scheme 123

A solution of ethyl ester 53 (0.43 g, 1.6 mmol) in tetrahydrofuran (12 mL) and methanol (4.0 mL) was treated with 1.0 M aqueous sodium hydroxide (3.1 mL, 3.1 mmol) and stirred at 50° C. for 6 h. The reaction mixture was cooled to room temperature and quenched by the addition of 1.0 M hydrochloric acid (3.1 mL, 3.1 mmol), extracted with dichloromethane (3×20 mL), dried (Na$_2$SO$_4$), and evaporated to provide the carboxylic acid 54 (0.32 g, 1.1 mmol) as a yellow powder.

Scheme 124

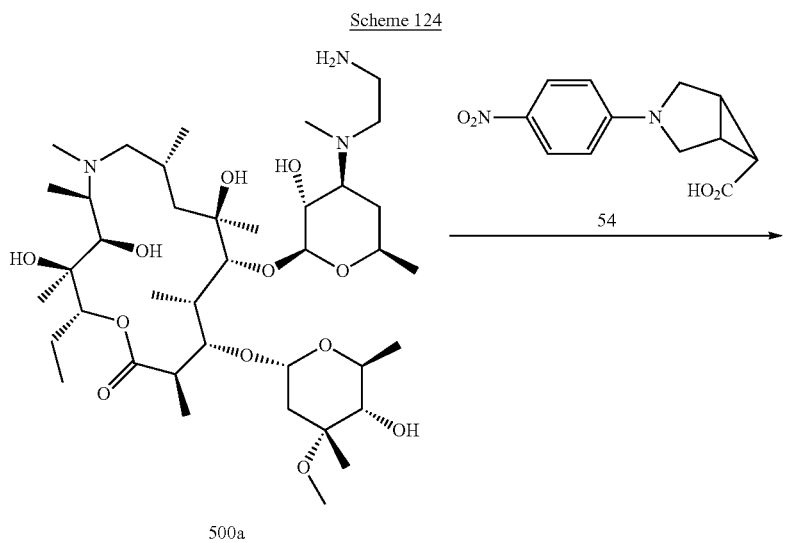

500a

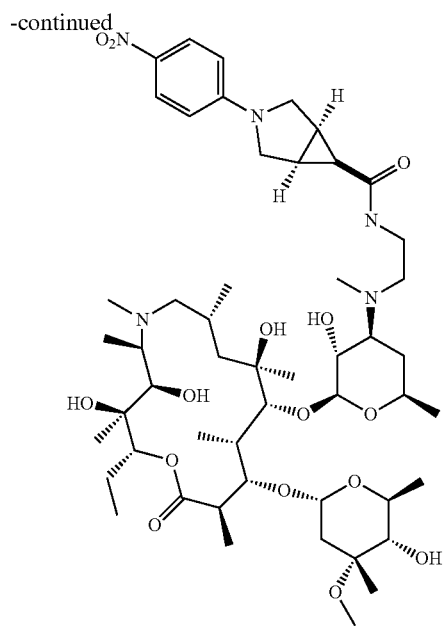

501

A solution of amine 500a (78 mg, 0.10 mmol) in dichloromethane (1.0 mL) was treated with carboxylic acid 54 (25 mg, 0.10 mmol), triethylamine (0.042 mL, 0.3 mmol) and O-(7-azabenzotriazol-1-yl)-N,N,N',N'-tetramethyluronium hexafluorophosphate (57 mg, 0.15 mmol) and stirred at 23° C. for 4 h. The reaction mixture was evaporated to a yellow film and purified by preparative thin-layer chromatography (SiO$_2$, 5% 2M NH$_3$-methanol/dichloromethane) to provide 501 (20 mg, 0.02 mmol) as a yellow film: LCMS (ESI) m/e 505 (M+2H)$^{2+}$.

Synthesis of Compounds 504, 505, 507, 508, and 512-515

These compounds were synthesized from amines 500a and 500b and the appropriate carboxylic acids using protocols analogous to the one described above for compound 501.

Synthesis of Compound 506

To a solution of 500a (50 mg, 0.056 mmol) in CH$_2$Cl$_2$ (1 mL) and Hunig's base (0.1 mL) was added 8-quinoline sulfonyl chloride (0.07 mmol). The mixture was stirred at rt for 1 h, then the entire reaction mixture was placed directly on a silica gel column and eluted with 0-3% 2M methanolic ammonia in CH$_2$Cl$_2$ to afford the 506 as a white solid (52 mg, 0.052 mmol). LCMS (ESI) m/e 535 (M+2H)$^{2+}$.

Synthesis of Compounds 509, 510 and 511

Compound 509, 510 and 511 were synthesized from amines 500a and 500b in a similar fashion to the compound 506.

Example 8

Synthesis of Compounds 525-529

TABLE 9

| Compound | R | LCMS (M/Z) |
|---|---|---|
| 525 | 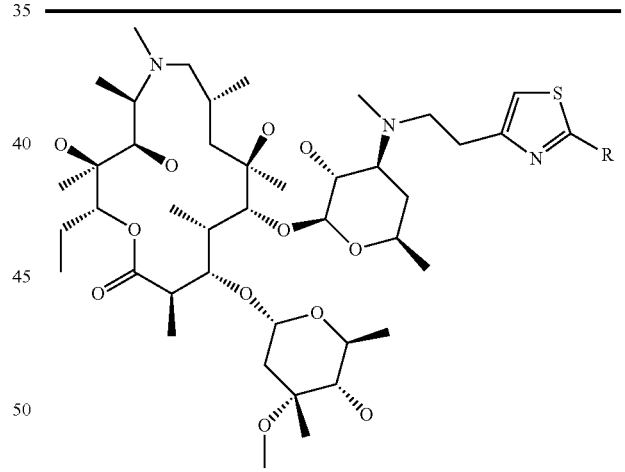 | 491.6 (M + 2H)$^{2+}$ 981.7 (M + H)$^+$ 1003.8 (M + Na)$^+$ |
| 526 | | 510.0 (M + 2H)$^{2+}$ 1018.8 (M + H)$^+$ 1040.7 (M + Na)$^+$ |

525

TABLE 9-continued

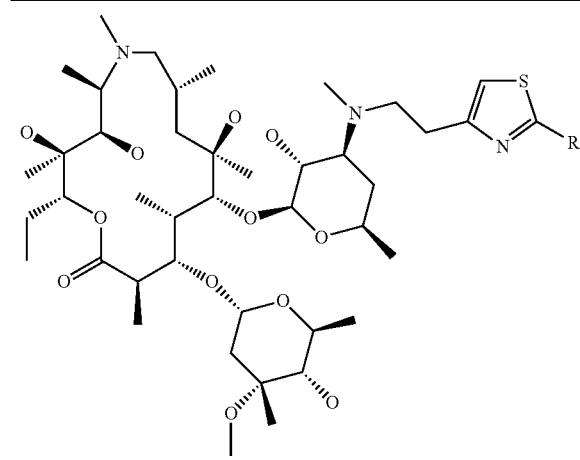

| Compound | R | LCMS (M/Z) |
|---|---|---|
| 527 | 4-chlorophenethylamino | 494.2 (M + 2H)$^{2+}$ <br> 985.8 (M + H)$^+$ |
| 528 | 4-methyl-1-benzylpiperazinyl | 511.1 (M + 2H)$^{2+}$ <br> 1020.9 (M + H)$^+$ |

526

TABLE 9-continued

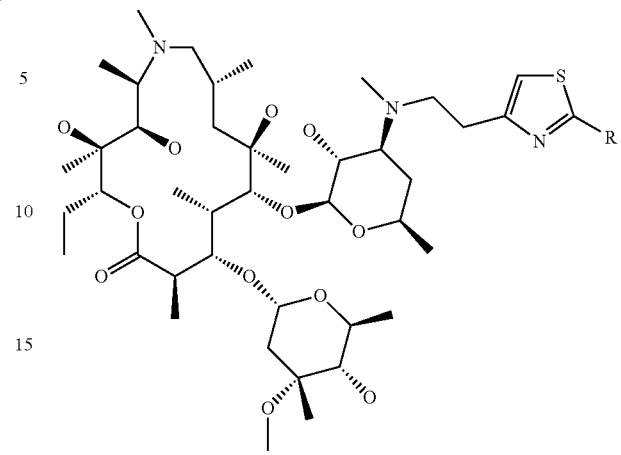

| Compound | R | LCMS (M/Z) |
|---|---|---|
| 529 | 4-ethylphenyl-1H-1,2,3-triazol-1-yl | 502.5 (M + 2H)$^{2+}$ <br> 1003.4 (M + H)$^+$ |

The thiazole linked compounds of Table 9 were synthesized by alkylation of 3'-N-desmethyl azithromycin 2 with 4-[2-bromoethyl] thiazoles as shown in Scheme 125 and as demonstrated below for the synthesis of compound 529.

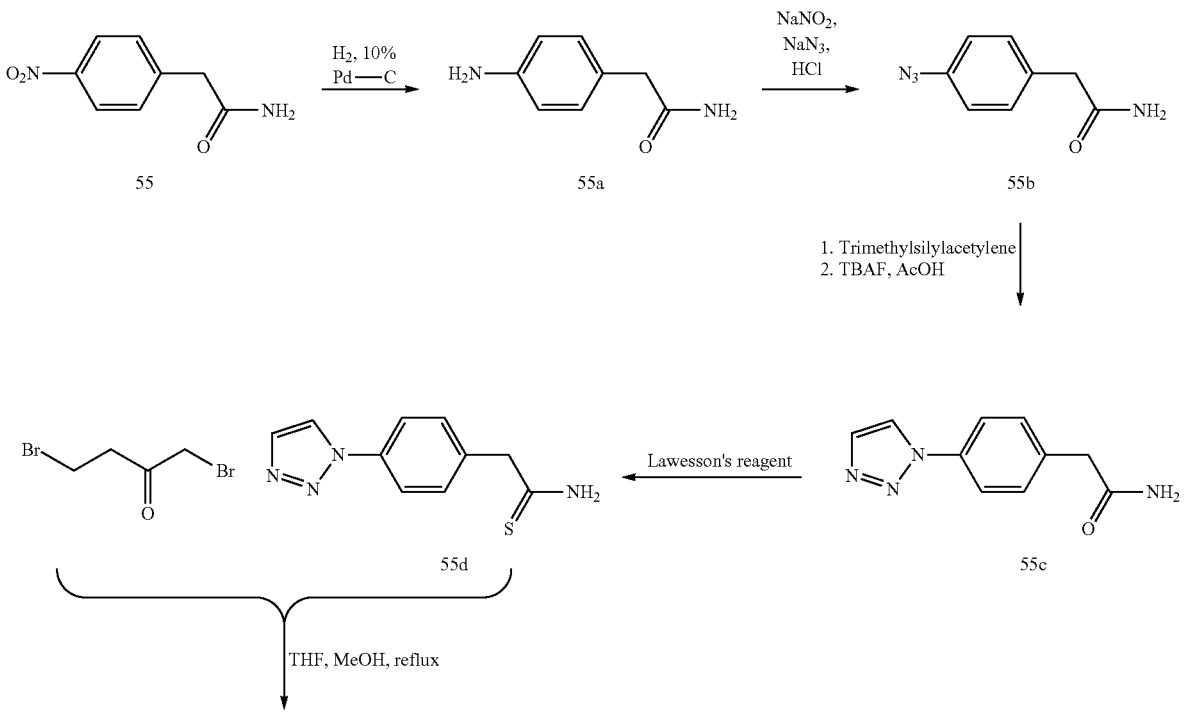

Scheme 125

-continued

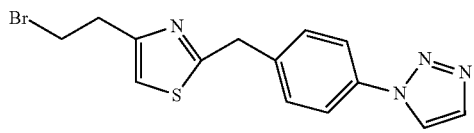

55e

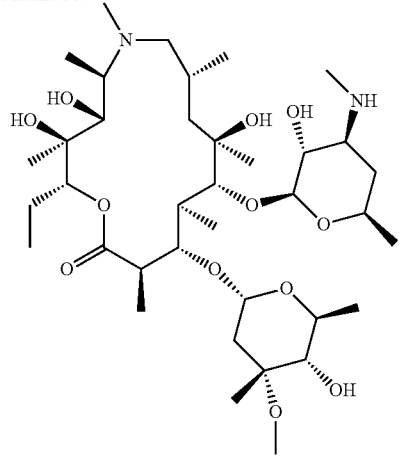

2

Hunig's base, THF, reflux

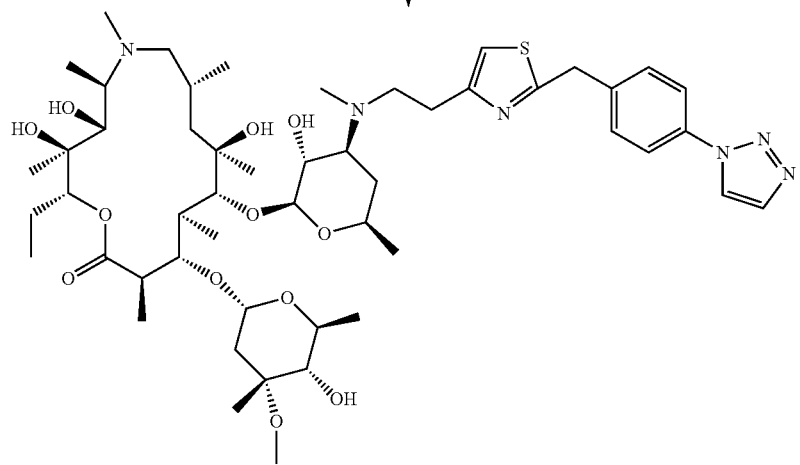

529

Synthesis of 4-aminophenylacetamide 55a

To a solution of 4-nitrophenylacetamide 55 (3.2 g, 1.78 mmol) in methanol (50 mL) was added 10% Pd—C (0.32 g) and the resulted mixture was stirred at room temperature for 24 h under 1 atm hydrogen atmosphere. Pd—C was removed by filtration on Celite. The filtered solution was evaporated to provide 55a (2.35 g, 90% yield). $^1$HNMR (300 MHz, CDCl$_3$-CD$_3$OD): δ 7.06 (d, J=8 Hz, 2H), 6.72 (d, J=8 Hz, 2H), 3.41 (s, 2H).

Synthesis of Azide 55b

Azide 55b was prepared from 55a following the procedure for the preparation of azide 14au. Yield, 44%; $^1$HNMR (300 MHz, CDCl$_3$-CD$_3$OD): δ 7.20 (d, J=6 Hz, 2H), 6.94 (d, J=6 Hz, 2H), 3.45 (s, 2H).

Synthesis of Triazole 55c

A solution of azide 55b (640 mg, 3.64 mmol) and trimethylacetylene (700 mg, 7.14 mmol) in DMF (25 mL) was heated at 90° C. for 48 h. The reaction was evaporated to dry in vacuum. The resulted residue was dissolved in THF (15 mL). A solution of TBAF (1.0 M in THF, 7.5 mL, 7.5 mmol) and acetic acid (220 mg, 3.6 mmol) was added. The reaction was stirred at RT for 24 h. THF was removed and the residue was suspended in water and stirred for 15 min. a white solid was collected by filtration to provide 55c (596 mg, 81% yield). $^1$HNMR (300 MHz, CDCl$_3$-CD$_3$OD): δ 8.01 (d, J=1 Hz, 1H), 7.69 (d, J=1 Hz, 1H), 7.57 (d, J=8 Hz, 2H), 7.33 (d, J=8 Hz, 2H), 3.45 (s, 2H).

Synthesis of Thiocarboxylic Amide 55d

The mixture of 55c (180 mg, 0.89 mmol) and Lawesson's reagent (288 mg, 0.71 mmol) in THF (3 mL) was refluxed under argon for 2 h. The reaction was diluted with CH$_2$Cl$_2$, washed with brine, dried over MgSO$_4$ and concentrated in vacuum. Chromatography (25:1:0.1/CH$_2$Cl$_2$:MeOH:NH$_3$.H$_2$O) of crude product afforded 55d (150 mg, 77% yield). $^1$HNMR (300 MHz, CDCl$_3$-CD$_3$OD): δ 8.01 (s, 1H), 7.75 (s, 1H), 7.62 (d, J=8 Hz, 2H), 7.44 (d, J=8 Hz, 2H), 3.96 (s, 2H).

Synthesis of Thiazole 55e

To a solution of 55d (165 mg, 0.72 mmol) in THF (8 mL) and MeOH (2 mL) was added 1,4 dibromobutanone (130 mg, 0.60 mmol). After refluxing for 2 h, the reaction was diluted with $CH_2Cl_2$, washed with saturated $NaHCO_3$, dried over $MgSO_4$ and concentrated. Chromatography (40:1:0.1/$CH_2Cl_2$:MeOH:$NH_3.H_2O$) of crude product provided 55e (165 mg, 79% yield); $^1$HNMR (300 MHz, $CDCl_3$-$CD_3OD$): δ 7.92 (d, J=1 Hz, 1H), 7.76 (d, J=1 Hz, 1H), 7.64 (d, J =9 Hz, 2H), 7.39 (d, J=9 Hz, 2H), 6.87 (s, 1H), 4.29 (s, 2H), 3.63 (t, J=7 Hz, 2H), 3.22 (t, J=7 Hz, 2H).

Synthesis of 529

The mixture of 55e (150 mg, 0.43 mmol), N-desmethylazithromycin 2 (276 mg, 0.36 mmol), Hunig's base (4 mL) and KI (300 mg, 1.81 mmol) in THF (10 mL) was refluxed for 8 h. THF was removed in vacuum and the residue was dissolved in $CH_2Cl_2$, the solution was washed with brine, dried over $MgSO_4$, concentrated to dry and purified by chromatography (25:1:0.1/$CH_2Cl_2$:MeOH:$NH_3.H_2O$) to provide 529 (255 mg, 71% yield); MS (ESI): 1003.4 (M+H)$^+$, 502.5 (100%). $^1$HNMR (300 MHz, $CDCl_3$, partial) δ 7.92 (s, 1H), 7.78 (s, 1H), 7.64 (d, J=8 Hz, 2H), 7.42 (d, J=8 Hz, 2H), 6.78 (s, 1H), 4.38 (d, J=7 Hz, 1H), 4.29 (s, 2H), 3.26 (s, 3H), 2.28 (s, 3H), 2.25 (s, 3H).

The remaining compounds of Table 9 were synthesized by alkylating 3'-N-desmethyl azithromycin 2 with appropriately substituted 4-[2-bromoethyl] thiazoles using procedures analogous to those presented above for compound 529.

Example 9

Synthesis of Compounds 550-556

TABLE 10

| Compound | R | LCMS (M/Z) |
|---|---|---|
| 550 | 4-(methylsulfonyl)phenyl-NH-ethyl | 507 (M + 2H)$^{2+}$ 1014 (M + H)$^+$ |
| 551 | 2-fluoro-4-nitrophenyl-NH-ethyl | 500 (M + 2H)$^{2+}$ 999 (M + H)$^+$ |
| 552 | 4-(methylsulfonyl)-2-ethoxyphenyl | 508 (M + 2H)$^{2+}$ 1015 (M + H)$^+$ |
| 553 | phenylpropyl | 468 (M + 2H)$^{2+}$ 935 (M + H)$^+$ |
| 554 | (3-methylpyridin-2-yl) | 455 (M + 2H)$^{2+}$ 908 (M + H)$^+$ |
| 555 | 4-nitrophenyl-NH-ethyl | 491 (M + 2H)$^{2+}$ 981 (M + H)$^+$ |
| 556 | 4-(4,4-dimethylpentyloxy)-nitrophenyl | 505.5 (M + 2H)$^{2+}$ 1010.4 (M + H)$^+$ |

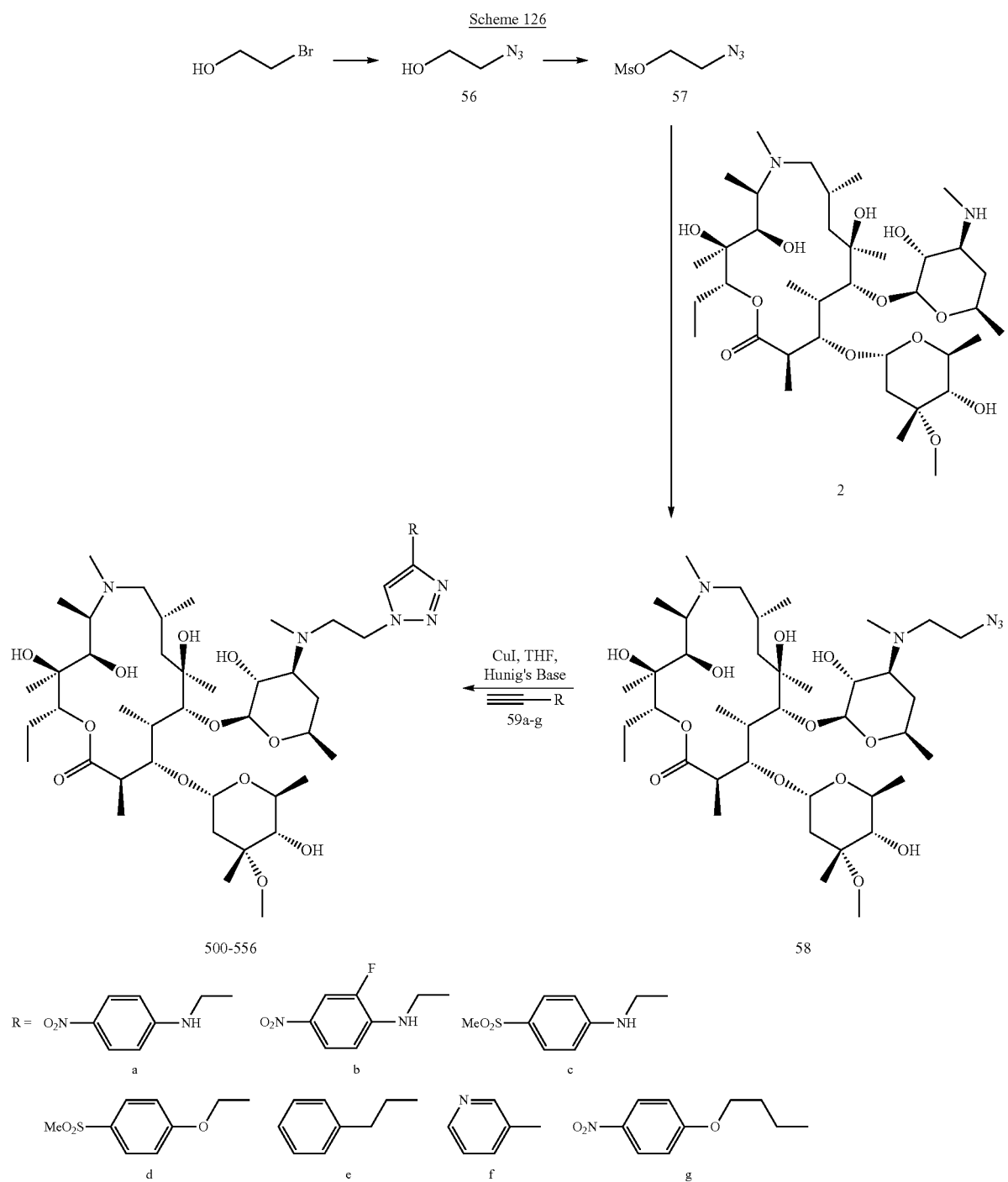

Synthesis of 2-azido ethanol (56)

A mixture of 2-bromoethanol (2 mL, 26.8 mmol) and NaN₃ (3.48 g, 53.6 mmol) was heated at 70° C. for 12 h and then poured into a mixture of ethyl ether and water (150 mL, 1:1). The organic layer was separated and the aqueous layer was extracted with ethyl ether (2×30 mL). The combined organic layer was washed with water (1×100 mL), dried and carefully reduced the volume and used for the next step without further purification.

Synthesis of 2-azido ethyl methylsulphonate (57)

Methane sulphonyl chloride (3.1 mL, 40.2 mmol) was added to a solution of 2 (26.8 mmol) and triethyl amine (5.6 mmol, 40.2 mmol) in methylene chloride (50 mL) at 0° C. and stirred at ambient temperature for 12 h. The reaction mixture was diluted with methylene chloride (50 mL) and washed with saturated sodium bicarbonate (2×100 mL) solution. The solution was dried with anhydrous Na₂SO₄, filtered and carefully concentrated to reduced volume and used for the next step without further purification.

Synthesis of 58

A solution of amine 2 (2 g, 2.7 mmol) and 57 (8.2 mmol) in a mixture of THF and Hunig's base (40 mL, 1:1) was refluxed for 24 h. The reaction mixture was concentrated and dissolved in $CH_2Cl_2$ (100 mL). The organic layer was washed with brine (2×100 mL), dried, concentrated in reduced pressure and purified by flash chromatography over silica gel ($CH_2Cl_2$: 2% $NH_3$-MeOH) to afford 1 g of 58. MS (ESI) m/e 805 (M+H)$^+$.

Synthesis of 59a-c, 59d and 59g

Alkynes 59a-c were synthesized according to the procedure described in literature (*J. Med. Chem.*, 1996, 39, 904-917).

Data for 59a: $^1$H NMR (300 MHz, $CDCl_3$): δ 2.29 (t, 1H), 4.04 (dd, 2H), 4.68 (brs, 1H), 6.65 (d, 2H), 8.14 (d, 2H).

Data for 59b: $^1$H NMR (300 MHz, $CDCl_3$): δ 2.32 (t, 1H), 4.09 (dd, 2H), 4.90 (brs, 1H), 6.79 (t, 1H), 7.93 (dd, 1H), 8.06 (dd, 1H).

Data for 59c: $^1$H NMR (300 MHz, $CDCl_3$): δ 2.27 (t, 1H), 3.02 (s, 3H), 4.01 (dd, 2H), 4.53 (brs, 1H), 6.73 (d, 2H), 7.75 (d, 2H).

Alkyne 59d was synthesized by alkylation of 4-methylsulphonyl phenol with propargyl bromide in presence of $K_2CO_3$. $^1$H NMR (300 MHz, $CDCl_3$): δ 2.58 (t, 1H), 3.04 (s, 3H), 4.78 (d, 2H), 7.11 (d, 2H), 7.89 (d, 2H).

Alkyne 59g: To a solution of 4-Nitrophenol (1 g, 7.2 mmol), 4-pentyne-1-ol (0.775 mL, 7.9 mmol) and $Ph_3P$ (2.2 g, 8.28 mmol) in THF (15 mL) was added DIAD (2 mL, 7.9 mmol) at 0° C. and stirred 2 h at ambient temperature. The solution was concentrated and the residue was redissolved in diethyl ether (75 mL). The ethereal layer was successively washed with brine (1×50 mL), 1N NaOH (1×50 mL) and $H_2O$ (1×50 mL). The resulting solution was dried (anhydrous $Na_2SO_4$), concentrated and the crude material was purified by flash chromatography over silica gel (20% EtOAc-hexane). After titration with ether, 1 g of 59g was isolated as an off-white solid. $^1$H NMR (300 MHz, $CDCl_3$): δ 1.99 (t, 1H), 2.03-2.09 (m, 2H), 2.44 (dt, 2H), 4.18 (t, 2H), 6.97 (d, 2H), 8.22 (d, 2H).

Synthesis of 550-556

General Method

To a mixture of 59a-g (0.0746 mmol), 58 (0.0622 mmol) and CuI (0.0746 mmol) was added THF (5 mL) under argon atmosphere. Then was added few drops of Hunig's base and stirred at ambient temperature for 2 h. The reaction mixture was quenched with saturated $NH_4OH$ solution containing 20% $NH_4OH$ (25 mL) and stirred for 30 mins at ambient temperature. The mixture was extracted with methylene chloride (3×50 mL) and the combined organic extract was washed with saturated ammonium chloride solution containing 10% ammonium hydroxide (2×50 mL). The resulting solution was dried with anhydrous $Na_2SO_4$, concentrated and purified by preparative TLC (first using $CH_2Cl_2$: 2% $NH_3$-MeOH=10:1 and then EtOAc: $Et_3N$=8:2) to afford pure 550-556.

Data for 555: Yield 50%. MS (ESI) m/e 981 (M+H)$^+$, 491 (M+2H)$^+$; $^1$H NMR (300 MHz, $CDCl_3$, partial): δ 0.86-0.91 (m, 6H), 0.94 (d, 2H), 3.21 (t, 1H), 3.3 (s, 3H), 4.05 (t, 1H), 4.26 (brs, 1H), 4.36 (d, 1H), 4.44 (t, 2H), 4.51 (d, 2H), 4.68 (d, 2H), 5.12 (d, 2H), 5.2 (brs, 1H), 6.61 (d, 2H), 7.67 (s, 1H), 8.14 (d, 2H).

Data for 551: Yield 60%. MS (ESI) m/e 999 (M+H)$^+$, 500 (M+2H)$^+$; $^1$H NMR (300 MHz, $CDCl_3$, partial): δ 0.86-0.90 (m, 6H), 0.91 (d, 3H), 3.29 (s, 3H), 4.57 (d, 2H), 5.15 (d, 1H), 5.30 (brs, 1H), 6.76 (t, 1H), 7.70 (s, 1H), 7.89 (dd, 1H), 7.99 (dd, 1H).

Data for 550: Yield 50%. MS (ESI) m/e 1014 (MA+H)$^+$, 507 (M+2H)$^+$; $^1$H NMR (300 MHz, $CDCl_3$, partial): δ 0.87 (d, 3H), 0.91 (d, 3H), 1.09 (d, 3H), 3.32 (s, 3H), 3.61 (d, 1H), 4.66 (d, 1H), 4.99 (t, 1H), 5.11 (d, 1H), 6.68 (d, 2H), 7.63 (s, 1H), 7.70 (d, 2H).

Data for 552: Yield 55%. MS (ESI) m/e 1015 (M+H)$^+$, 508 (M+2H)$^+$; $^1$H NMR (300 MHz, $CDCl_3$, partial): δ 0.86-0.91 (m, 6H), 0.99 (d, 3H), 3.28 (s, 3H), 3.64 (d, 1H), 3.67 (s, 1H), 4.05 (m, 1H), 4.25 (d, 1H), 4.38 (d, 1H), 4.45 (t, 1H), 4.70 (d, 1H), 5.11 (d, 1H), 5.27 (s, 2H), 7.12 (d, 2H), 7.81 (s, 1H), 7.86 (d, 2H).

Data for 553: Yield 50%. MS (ESI) m/e 935 (M+H)$^+$, 468 (M+2H)$^+$; $^1$H NMR (300 MHz, $CDCl_3$, partial): δ 0.86-0.92 (m, 6H), 0.99 (d, 3H), 3.48 (s, 3H), 3.62 (d, 1H), 3.66 (s, 1H), 4.02-4.07 (m, 1H), 4.35-4.41 (m, 3H), 4.67 (dd, 1H), 5.09 (d, 1H), 7.17-7.31 (m, 6H).

Data for 554: Yield 40%. MS (ESI) m/e 908 (M+H)$^+$, 455 (M+2H)$^+$; $^1$H NMR (300 MHz, $CDCl_3$, partial): δ 0.86-0.91 (m, 6H), 0.97 (d, 3H), 3.25 (s, 3H), 3.62 (d, 1H), 3.66 (s, 1H), 4.05 (brt, 1H), 4.23 (brs, 1H), 4.38 (d, 1H), 4.50 (t, 2H), 4.67 (d, 1H), 5.11 (d, 1H), 7.35 (dd, 1H), 8.17 (s, 1H), 8.20 (d, 1H), 8.56 (d, 1H), 8.98 (s, 1H).

Data for 556: Yield 90%. MS (ESI) m/e 1010 (M+H)$^+$, 505.5 (M+2H)$^+$; $^1$H NMR (300 MHz, $CDCl_3$, partial): δ 0.86-0.91 (m, 6H), 0.94 (d, 3H), 3.30 (s, 3H), 4.12 (t, 2H), 4.26 (t, 2H), 4.27-4.42 (m, 3H), 4.67 (dd, 1H), 5.05 (d, 1H), 6.96 (d, 2H), 7.42 (s, 1H), 8.20 (d, 2H).

Synthesis of Azides 14a-14gm

The azides 14a-14gm shown in Table 11 were used to synthesize numerous compounds of the invention including 101-280, 301-357, 401-417, 425-451, and 460-466. The azides were readily synthesized by methods known from the literature. Exemplary azide syntheses are presented below. The remaining azides of Table 11 were synthesized in analogous fashion from appropriate commercial starting materials.

TABLE 11

| Structure | Compound |
|---|---|
| 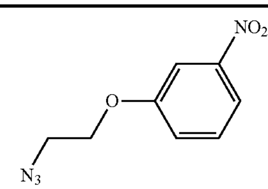 | 14a |
| 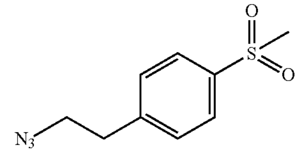 | 14b |
| 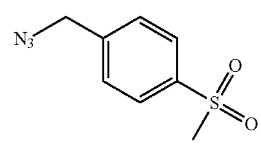 | 14c |

TABLE 11-continued
| Structure | Compound |
|---|---|
| 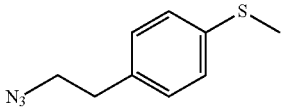 | 14d |
| 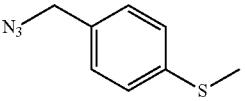 | 14e |
| 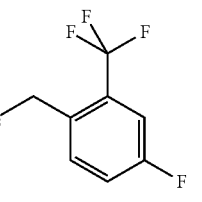 | 14f |
| 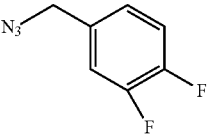 [SMILES: [N-]=[N+]=NCc1ccc(F)c(F)c1] | 14g |
| 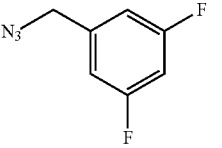 [SMILES: [N-]=[N+]=NCc1cc(F)cc(F)c1] | 14h |
| 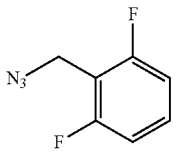 [SMILES: [N-]=[N+]=NCc1c(F)cccc1F] | 14i |
| 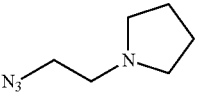 | 14j |
| 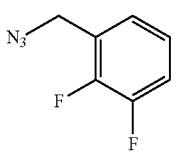 | 14k |
| 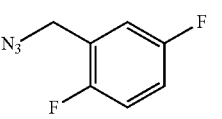 [SMILES: [N-]=[N+]=NCc1cc(F)ccc1F] | 14l |
| 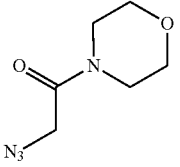 | 14m |
| 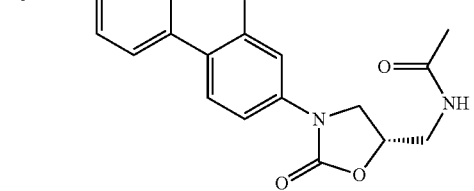 | 14n |
| 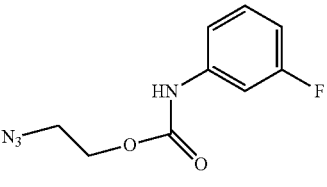 [SMILES: [N-]=[N+]=NCCOC(=O)Nc1cccc(F)c1] | 14o |
| 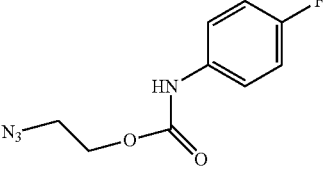 | 14p |
| 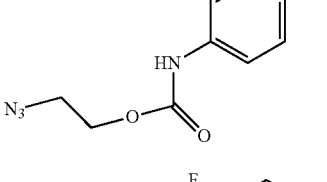 | 14q |
| 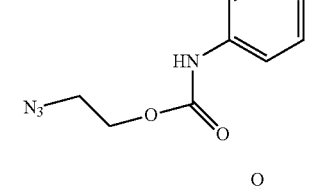 | 14r |
| 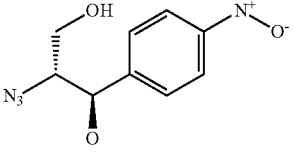 | 14s |
| 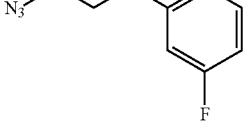 | 14t |
| 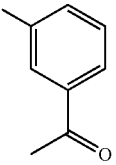 | 14u |

TABLE 11-continued

| Structure | Compound |
|---|---|
| (4-nitrobenzyl azide) | 14v |
| (2-(4-nitrophenyl)ethyl azide) | 14w |
| (4-(2H-tetrazol-5-yl)benzyl azide) | 14x |
| (2-(4-(1H-1,2,3-triazol-1-yl)phenyl)ethyl azide) | 14y |
| (1-(4-azidobenzyl)-1H-1,2,3-triazole-4-ethanol derivative) | 14z |
| (1-(4-(2-azidoethyl)phenyl)-1H-1,2,3-triazol-4-yl)methanol | 14aa |
| (5-(4-methoxyphenyl)-N-(3-azidopropyl)-1,3,4-thiadiazol-2-amine) | 14ab |
| (N-acetyl derivative with 3-azidopropyl) | 14ac |

TABLE 11-continued

| Structure | Compound |
|---|---|
| (2-(4-(trifluoromethyl)phenyl)ethyl azide) | 14ad |
| (2-(4-fluorophenyl)ethyl azide) | 14ae |
| (2-(4-(5-methyl-1,2,4-oxadiazol-3-yl)phenyl)ethyl azide) | 14af |
| (2-azido-1-(4-(methylthio)phenyl)propane-1,3-diol) | 14ag |
| (2-azido-1-(4-(methylsulfonyl)phenyl)propane-1,3-diol) | 14ah |
| (2-azido-1-phenylpropan-1-ol) | 14ai |
| (2-azido-1-phenylpropan-1-ol stereoisomer) | 14aj |
| (4-(1H-1,2,4-triazol-1-yl)benzyl azide) | 14ak |
| (4-(1H-pyrazol-1-yl)benzyl azide) | 14al |

TABLE 11-continued

| Structure | Compound |
|---|---|
| (5-azidomethyl-1-methyl-1H-benzotriazole) | 14am |
| (4-(azidomethyl)phenyl-1,2,3-thiadiazole) | 14an |
| (2-(azidomethyl)anthracene-9,10-dione) | 14ao |
| (2-azido-1-(4-morpholinophenyl)ethanone) | 14ap |
| (1-(2-azidoethyl)-4-phenoxybenzene) | 14aq |
| (N-(4-(2-azidoethyl)benzyl)-3-fluoropropan-1-amine) | 14ar |
| (4-(2-azidoethyl)-5-methyl-2-phenyloxazole) | 14as |
| (2-(2-azidoethoxy)-5-nitropyridine) | 14at |
| (2-azido-3-fluoro-1-(4-(methylsulfonyl)phenyl)propan-1-ol) | 14au |

TABLE 11-continued

| Structure | Compound |
|---|---|
| (2-azido-1-(4-(methylsulfonyl)phenyl)ethanone) | 14av |
| (5-(2-azidoethoxy)quinoline) | 14aw |
| (4-(2-azidoethoxy)quinoline) | 14ax |
| (6-(2-azidoethoxy)quinoline) | 14ay |
| (2-(azidomethyl)pyridine) | 14az |
| (3-(azidomethyl)pyridine) | 14ba |
| (4-(azidomethyl)pyridine) | 14bb |
| (2-(azidomethyl)quinoline) | 14bc |
| (4-(azidomethyl)benzenesulfonamide) | 14bd |
| (4-(2-azidoethyl)benzenesulfonamide) | 14be |
| (1-(4-(azidomethyl)phenyl)-1H-pyrrole) | 14bf |

TABLE 11-continued

| Structure | Compound |
|---|---|
| (structure) | 14bg |
| (structure) | 14bh |
| (structure) | 14bi |
| (structure) | 14bj |
| (structure) | 14bk |
| (structure) | 14bl |
| (structure) | 14bm |
| (structure) | 14bn |
| (structure) | 14bo |
| (structure) | 14bp |
| (structure) | 14bq |
| (structure) | 14br |
| (structure) | 14bs |
| (structure) | 14bt |
| (structure) | 14bu |
| (structure) | 14bv |
| (structure) | 14bw |
| (structure) | 14bx |
| (structure) | 14by |
| (structure) | 14bz |

TABLE 11-continued
| Structure | Compound |
|---|---|
| 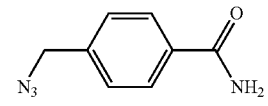 | 14ca |
| 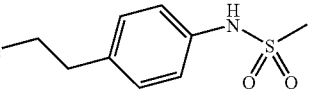 | 14cb |
| 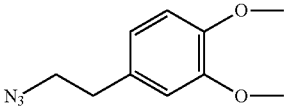 | 14cc |
| 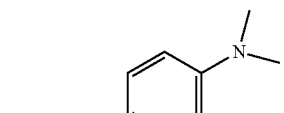 | 14cd |
| 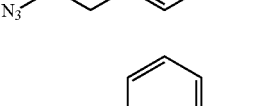 | 14ce |
| 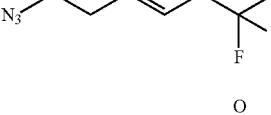 | 14cf |
| 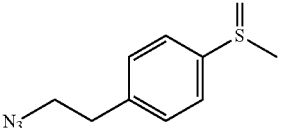 | 14cg |
| 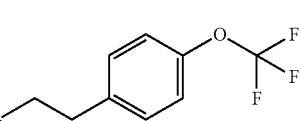 | 14ch |
| 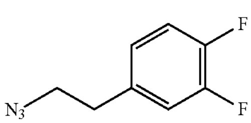 | 14ci |
| 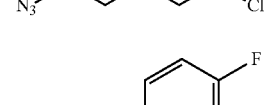 | 14cj |
| 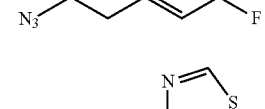 | 14ck |
TABLE 11-continued
| Structure | Compound |
|---|---|
| 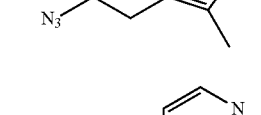 | 14cl |
| 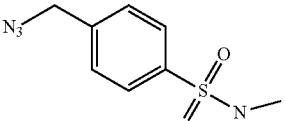 | 14cm |
| 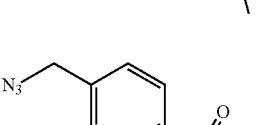 | 14cn |
| 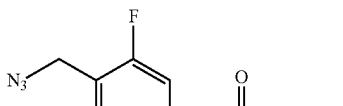 | 14co |
| 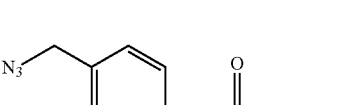 | 14cp |
| 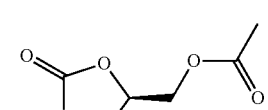 | 14cq |
| 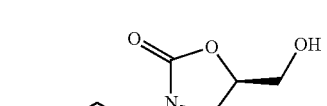 | 14cr |

TABLE 11-continued

| Structure | Compound |
|---|---|
| (structure) | 14cs |
| (structure) | 14ct |
| (structure) | 14cu |
| (structure) | 14cv |
| (structure) | 14cx Chiral |
| (structure) | 14cy |
| (structure) | 14da |
| (structure) | 14db |
| (structure) | 14dc |
| (structure) | 14dd |
| (structure) | 14de |
| (structure) | 14df |
| (structure) | 14dg |
| (structure) | 14dh |
| (structure) | 14di |
| (structure) | 14dj |
| (structure) | 14dk |
| (structure) | 14dl |
| (structure) | 14dm |
| (structure) | 14dn |

TABLE 11-continued

| Structure | Compound |
|---|---|
| 4-methoxybenzyl azide | 14do |
| 2-(4-(1H-tetrazol-5-yl)phenyl)ethyl azide | 14dp |
| 4-(trifluoromethyl)benzyl azide | 14dq |
| 4-fluorobenzyl azide | 14dr |
| 1-(2-azidoethoxy)-2-nitrobenzene | 14ds |
| TBS-protected azido-nitrophenyl chloroacetamide | 14dt |
| azido-hydroxy-nitrophenyl chloroacetamide | 14du |
| ethyl 2-(3-azidopropoxy)benzoate | 14dv |
| ethyl 2-(2-azidoethoxy)benzoate | 14dw |
| 2-(2-azidoethyl)pyridine | 14dx |
| 3-(3-azidopropyl)pyridine | 14dy |
| N-(3-(2-azidoethoxy)phenyl)acetamide | 14dz |
| tert-butyl 4-(2-azidoethyl)piperazine-1-carboxylate | 14ea |
| 3-azidopropan-1-ol | 14eb |
| 1-(4-azidobutyl)-1H-imidazo[4,5-b]pyridine | 14ec |
| (S)-1-azido-3-(4-(methylsulfonyl)phenyl)-2-fluoropropane | 14ed |
| (S)-2-azido-3-(4-nitrophenyl)propanoate ester | 14ef |
| (S)-2-azido-3-(4-nitrophenyl)propanamide | 14eg |

TABLE 11-continued

| Structure | Compound |
|---|---|
| (4-nitrobenzyl with azido and methyl ester) | 14eh |
| (1,1,2-trifluorobutene with azido group) | 14ei |
| (4-(4-azidobutyl)nitrobenzene) | 14ej |
| (4-(1,2,3-thiadiazol-4-yl)phenyl ethyl azide) | 14el |
| (4-(azidomethyl)phenyl morpholine) | 14em |
| (2-phenyl-4-(2-azidoethyl)thiazole) | 14en |
| (4-nitrobenzyl with azido and aminomethyl) | 14eo |
| (4-nitrophenoxy with (S)-2-methyl-3-azidopropyl) | 14ep |

TABLE 11-continued

| Structure | Compound |
|---|---|
| (4-nitrobenzyl with azido and dimethylamino) | 14eq |
| (4-nitrobenzyl with azido and 1,2,3-triazolylmethyl) | 14er |
| (4-nitrobenzyl with azido and chloromethyl) | 14es |
| (4-nitrophenoxy propyl azide) | 14et |
| (4-nitrobenzyl with azido and hydroxymethyl) | 14eu |
| (4-nitrobenzyl with azido and fluoromethyl) | 14ev |

TABLE 11-continued
| Structure | Compound |
|---|---|
| 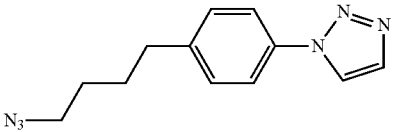 [SMILES: [N-]=[N+]=NCCCCc1ccc(-n2ccnn2)cc1] | 14ew |
| 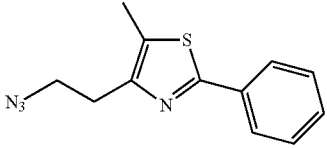 [SMILES: Cc1sc(-c2ccccc2)nc1CCN=[N+]=[N-]] | 14ex |
| 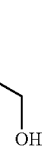 | 14ey |
| 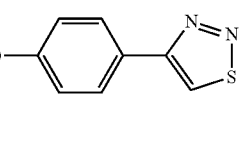 | 14ez |
| 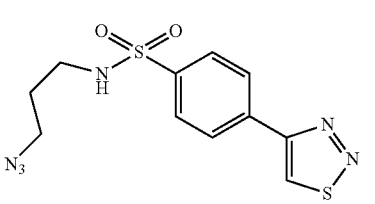 [SMILES: [N-]=[N+]=NCCCNS(=O)(=O)c1ccc(-c2csnn2)cc1] | 14fa |
| 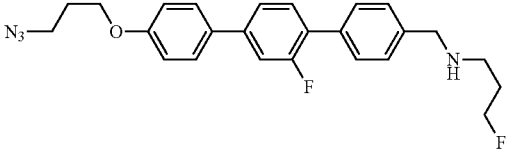 [SMILES: [N-]=[N+]=NCCCOc1ccc(-c2ccc(-c3ccc(CNCCCF)cc3)c(F)c2)cc1] | 14fb |
| 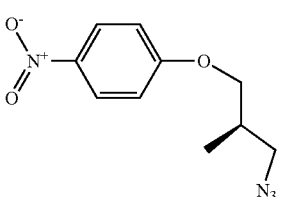 | 14fc |
| 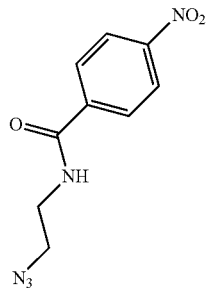 [SMILES: [N-]=[N+]=NCCNC(=O)c1ccc([N+](=O)[O-])cc1] | 14fd |
| 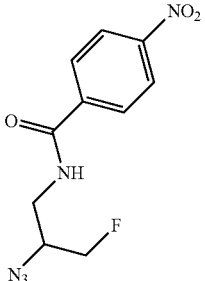 | 14fe |
| 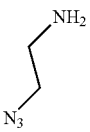 | 14ff |
| 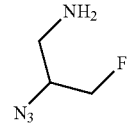 | 14fg |
| 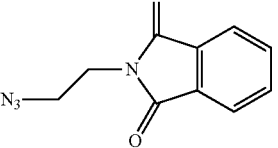 | 14fh |
| 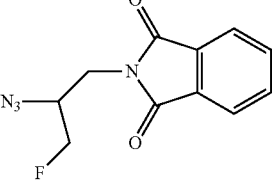 | 14fi |
| 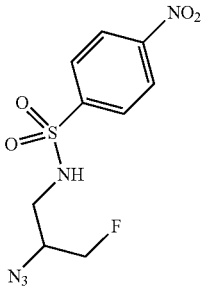 [SMILES: [N-]=[N+]=NC(CF)CNS(=O)(=O)c1ccc([N+](=O)[O-])cc1] | 14fj |
| 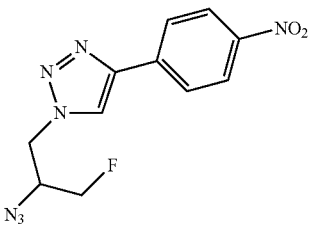 [SMILES: [N-]=[N+]=NC(CF)Cn1cc(-c2ccc([N+](=O)[O-])cc2)nn1] | 14fk |

TABLE 11-continued
| Structure | Compound |
|---|---|
| 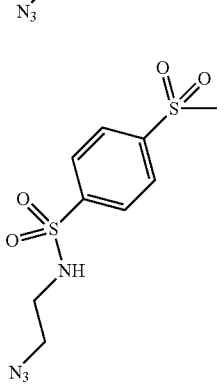 | 14fl |
| 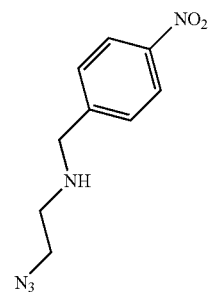 [SMILES: [N-]=[N+]=NCCNCc1ccc([N+](=O)[O-])cc1] | 14fm |
| 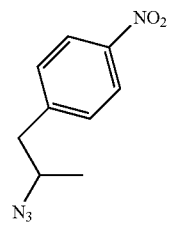 | 14fn |
| 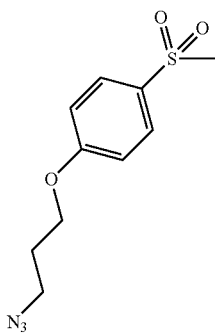 | 14fo |
| 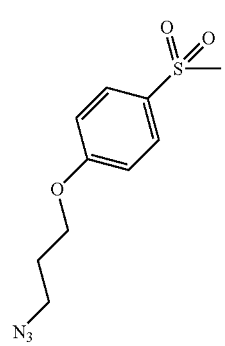 [SMILES: CS(=O)(=O)c1ccc(OCCCN=[N+]=[N-])cc1] | 14fp |
TABLE 11-continued
| Structure | Compound |
|---|---|
| 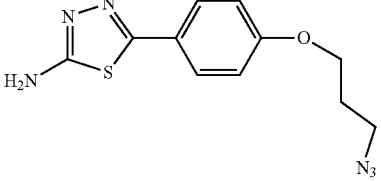 | 14fq |
| 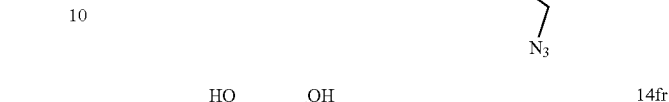 | 14fr |
| 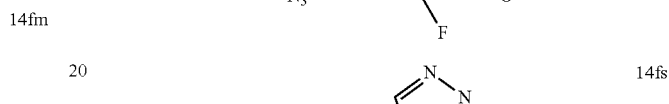 | 14fs |
| 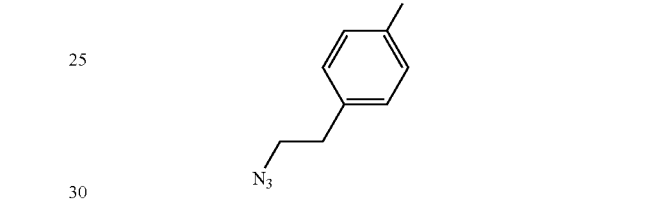 | 14ft |
| 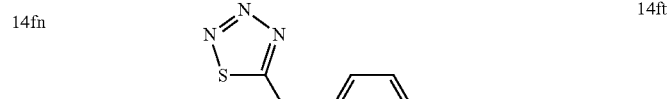 | 14fu |
| 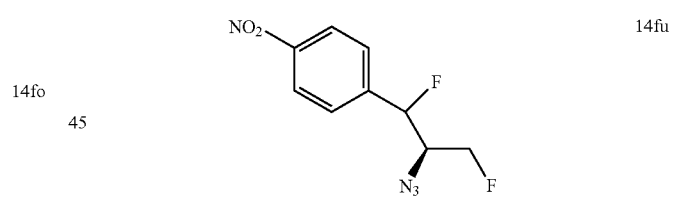 | 14fv |
| 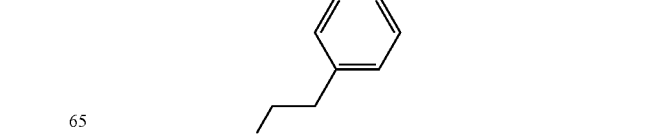 | 14fw |

TABLE 11-continued

| Structure | Compound |
|---|---|
| (4-sulfamoylphenyl)-CH2-CH(N3)-C(=O)NH2 | 14fx |
| BnO-CH2-CH(N3)-CH2-O-(4-phenyl)-thiadiazole | 14fy |
| 4-O2N-C6H4-S-CH2CH2CH2-N3 | 14fz |
| 4-O2N-C6H4-S(=O)2-CH2CH2CH2-N3 | 14ga |
| 4-O2N-C6H4-CH2-N(CH3)-CH2CH2-N3 | 14gb |
| 4-(MeSO2)-C6H4-CH2-NH-CH2CH2CH2-N3 | 14gc |
| 4-O2N-C6H4-O-CH2-CH(OH)-CH2-N3 (R) | 14gd |
| 4-O2N-C6H4-O-CH2-CH(OH)-CH2-N3 (S) | 14ge |
| 4-(MeSO2)-C6H4-O-CH2-CH(OH)-CH2-N3 | 14gf |
| 4-(MeSO2)-C6H4-O-CH2-CH(F)-CH2-N3 | 14gg |
| 4-(thiadiazol-4-yl)-C6H4-O-CH2-CH(OH)-CH2-N3 | 14gh |

TABLE 11-continued

| Structure | Compound |
|---|---|
| 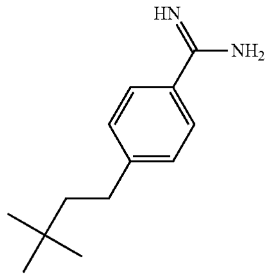 | 14gi |
| 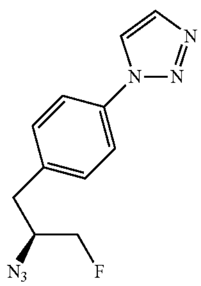 [SMILES: [N-]=[N+]=N[C@H](CF)Cc1ccc(-n2ccnn2)cc1] | 14gj |
| 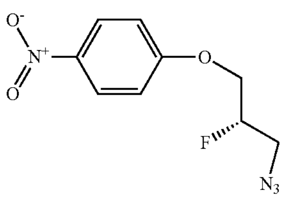 [SMILES: [N-]=[N+]=NC[C@H](F)COc1ccc([N+](=O)[O-])cc1] | 14gk |
| 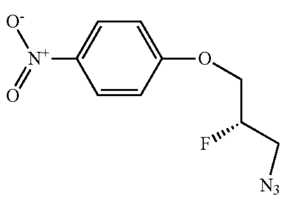 | 14gl |
| 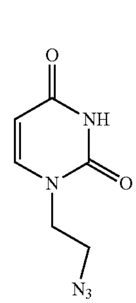 [SMILES: [N-]=[N+]=NCCn1ccc(=O)[nH]c1=O] | 14gm |

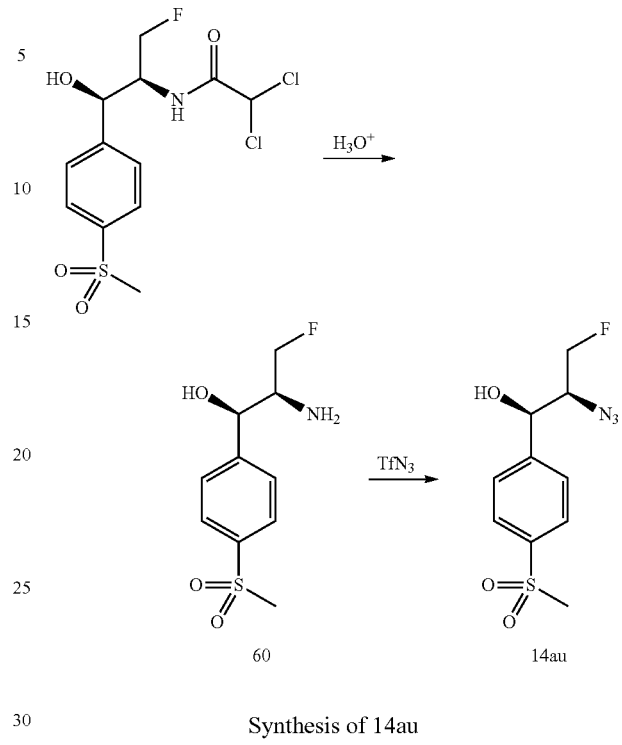

Scheme 127. Synthesis of azide 14au

Synthesis of 14au

A solution of florfenicol (0.090 g, 0.25 mmol) in acetic acid (3.0 mL) was treated with sulfuric acid (10%, 15 mL) and heated to 110° C. for 12 h. The reaction mixture was cooled to room temperature, treated with 10 M aqueous sodium hydroxide to adjust the pH to 14, extracted with dichloromethane (3×30 mL), dried ($Na_2SO_4$), and evaporated to provide florfenicol amine 60 (65 mg, 0.25 mmol) as a yellow oil.

A solution of florfenicol amine 60 (0.90 g, 3.6 mmol) in $H_2O$ (10 mL) and methanol (30 mL) was treated with triethylamine (1.5 mL, 10.8 mmol) and trifluoromethanesulfonyl azide (13.4 mmol dissolved in 20 mL of dichloromethane; solution prepared according to method described in *J. Am. Chem. Soc.* 2002, 124, 10773), and stirred at 0° C. 3 h and then warmed to 23° C. for 1 h. The reaction mixture was diluted with $H_2O$ (30 mL), extracted with dichloromethane (30 mL) and evaporated. Flash chromatography ($SiO_2$, 50-100% ethyl acetate/hexanes) provided azide 14au (0.65 g, 2.4 mmol) as a yellow solid.

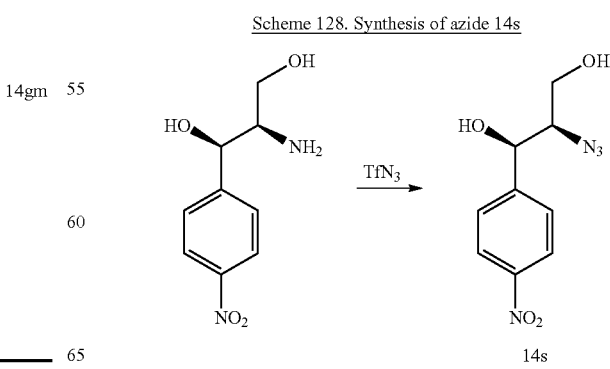

Scheme 128. Synthesis of azide 14s

Synthesis of Azide 14s

A solution of D-(−)-threo-2-amino-1-(4-nitrophenyl)-1,3-propanediol (0.42 g, 2.0 mmol) in H$_2$O (5 mL) and methanol (17 mL) was treated with triethylamine (0.84 mL, 6.0 mmol) and trifluoromethanesulfonyl azide (3.0 mmol dissolved in 5 mL of dichloromethane; solution prepared according to method described in *J. Am. Chem. Soc.* 2002, 124, 10773), and stirred at 23° C. for 3 h. The reaction mixture was diluted with H$_2$O (30 mL), extracted with dichloromethane (30 mL) and evaporated. Flash chromatography (SiO$_2$, 50-100% ethyl acetate/hexanes) provided azide 14s (0.28 g, 1.2 mmol) as a yellow solid.

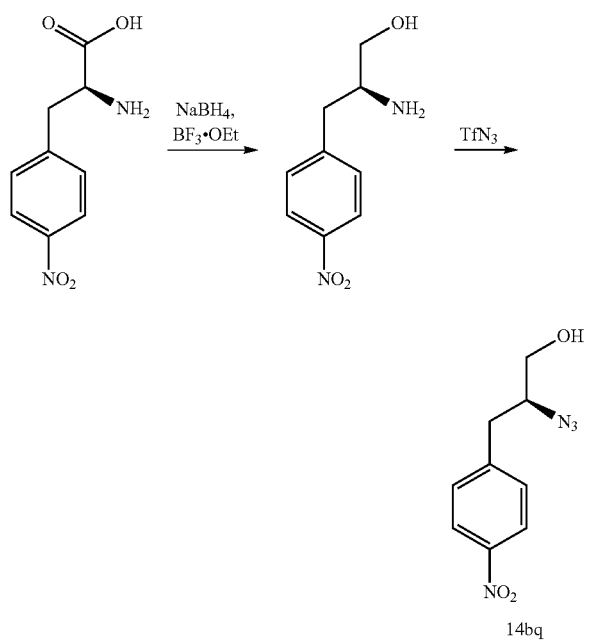

Synthesis of Azide 14bq

To a stirred 0° C. solution of 4-nitrophenylalanine (4.6 g, 20 mmol) and NaBH$_4$ (3.2 g, 84 mmol) in THF (50 mL) was added BF$_3$·OEt (14.8 mL, 106 mmol). The reaction was warmed to rt and stirred for 24 h. The mixture was cooled to 0° C. and quenched with methanol. The reaction mixture was filtered and the filtrate concentrated to give a solid residue. 10% of this residue was dissolved in water (5 mL), methanol (20 mL) and triethyl amine (0.9 mL). Triflic azide solution (3.5 mmol dissolved in 7 mL of dichloromethane; solution prepared according to method described in *J. Am. Chem. Soc.* 2002, 124, 10773) was added and the mixture was stirred at rt for 14 h. The reaction mixture was diluted with dichloromethane (30 mL) washed with saturated NaHCO3, and with brine. The organic extract was dried, filtered and concentrated to give 14bq as a white solid (150 mg)

Synthesis of Azide 14ed

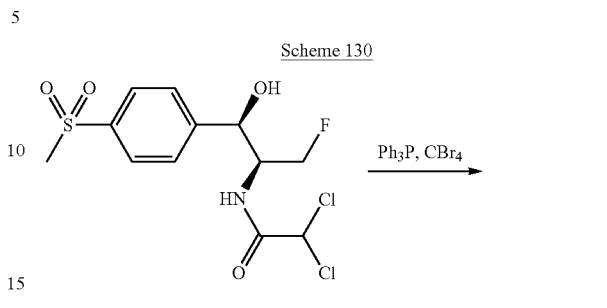

A solution of florfenicol (0.494 g, 1.38 mmol) in acetonitrile (15.0 mL) was treated with carbontetrabromide (0.594 g, 1.66 mmol) and triphenylphosphine (0.434 g, 1.66 mmol), and stirred at 23° C. for 12 h. The reaction mixture evaporated to a yellow residue and purified by flash chromatography (SiO$_2$, 10% ethyl acetate/dichloromethane) to provide 61 (0.28 g, 0.67 mmol) as a white powder.

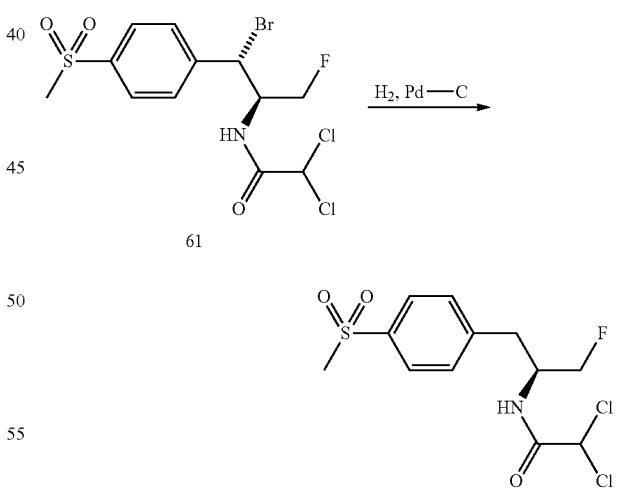

A solution of 61 (0.20 g, 0.41 mmol) in methanol (5.0 mL) was treated with 10% palladium on charcoal (20 mg) and stirred at 23° C. for 2 h under a balloon of hydrogen. The reaction mixture was filtered, evaporated and purified by preparative thin-layer chromatography (SiO$_2$, 10% ethyl acetate/dichloromethane) to afford 62 (90 mg, 0.26 mmol) as a white film.

Scheme 132

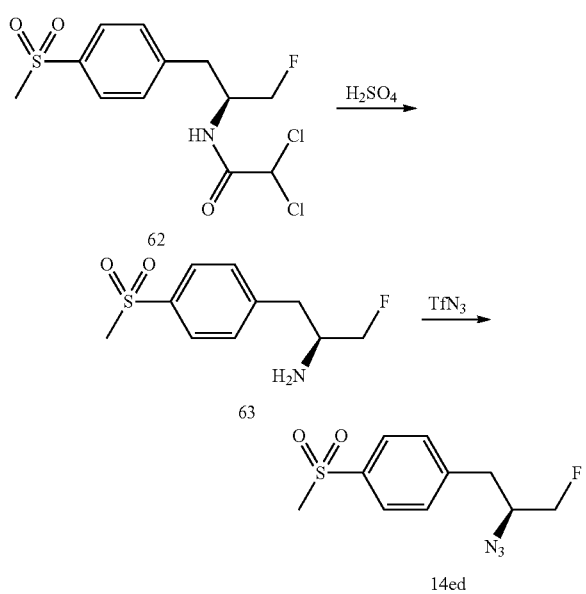

A solution of 62 (90 mg, 0.26 mmol) in acetic acid (3.0 mmol) was treated with 10% sulfuric acid (15 mL) and heated to 110° C. for 12 h. The reaction mixture was cooled to room temperature, treated with 10 M aqueous sodium hydroxide to adjust the pH to 14, extracted with dichloromethane (3×30 mL), dried (Na$_2$SO$_4$), and evaporated to provide crude 63 as a yellow oil. A solution of this crude amine (83 mg) in methanol (3.6 mL) and dichloromethane (3.0 mL) was cooled to 0° C. and treated with triethylamine (0.14 mL, 1 mmol) and triflic azide (1.2 mL of a 0.3 M solution in dichloromethane) and allowed to warm to 23 0° C. After 2 h, the reaction mixture was evaporated and purified by preparative thin-layer chromatography (SiO$_2$, 10% ethyl acetate/dichloromethane) to afford the 63 (60 mg, 0.23 mmol) as a colorless oil.

Synthesis of Azide 14ag

Azide 14ag was synthesized from 1S, 2S 2-Amino-1-(4-methylsulfanyl-phenyl)-propane-1,3-diol using the procedure described for the synthesis of azide 14bq.

Azides 14a, 14t, 14u, 14at, 14aw, 14ax, 14ay, 14df, 14ds, 14dv, 14dw, and 14dz, were readily synthesized using the Mitsunobu approach shown in Scheme 133 and exemplified below for azide 14dw.

Scheme 133. Synthesis of azide 14dw

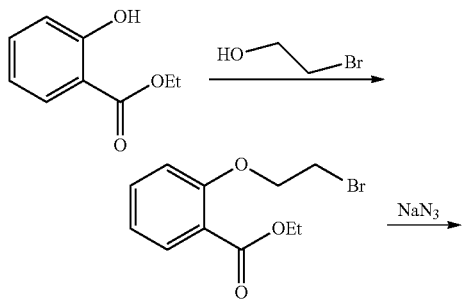

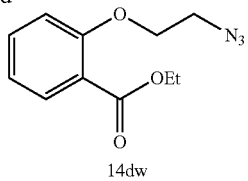
14dw

Synthesis of Azide 14dw

To a mixture of ethyl salicylate (1.0 g, 6.0 mmol), 2-bromoethanol (0.445 mL, 6.06 mmol), and triphenylphosphene (1.8 g, 6.9 mmol) in THF (10 mL) was added diisopropyl azodicarboxylate (DIAD, 1.40 mL, 6.60 mmol) at 0° C. The mixture was slowly warmed up to RT and stirred for 2 h. The reaction mixture was concentrated and redissolved in ethyl ether (50 mL). It was washed with brine (3×50 mL), dried (Na$_2$SO$_4$), concentrated and purified by flash chromatography (silica gel, 5% ethyl acetate in hexane) to yield 0.8 g of the intermediate bromoethyl ether. The bromoethyl ether (0.678 g, 2.4 mmol) was dissolved in DMF (5 mL) and sodium azide (0.473 g, 7.2 mmol) was added. The mixture was heated in an oil bath at 70° C. for 2-3 h. The reaction mixture was diluted with ether (50 mL), washed with water (4×50 mL), dried (anhydrous Na$_2$SO$_4$), and concentrated under reduced pressure. The crude product was purified by flash chromatography (silica gel, 10% ethyl acetate in hexane) to yield 0.52 g (89%) of pure azide 14dw.

Synthesis of Azides 14a, 14t, 14u, 14at, 14aw, 14ax, 14ay, 14df, 14ds, and 14dz These compounds were prepared from the starting phenols using the same procedure as that described for azide 14dw.

Synthesis of Azide 14dv

This azide was prepared from ethyl salicylate using the same procedure as described for azide 14dw except that 3-bromopropanol was substituted for 2-bromoethanol.

Synthesis of Azides 14dg, 14dh, 14di, 14dj, and 14dn

These azides were synthesized from the corresponding anilines by the diazotization as shown in scheme 134 and exemplified below for compound 14dg.

Scheme 134: Synthesis of Azide 14dg.

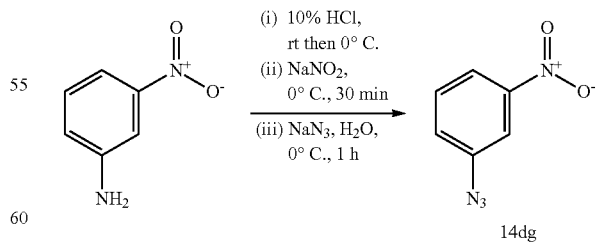

Synthesis of Azide 14dg

3-Nitroaniline 4 (2.00 g, 14.20 mmol) was vigorously stirred in 10% HCl (80 mL) at room temperature until completely dissolved. The solution was cooled to 0° C. in an ice-water bath followed by addition of NaNO₂ (1.13 g, 16.33 mmol) stirred for 30 min. A solution of NaN₃ (1.39 g, 21.30 mmol) in H₂O (20 mL) was added drop-wise and stirring continued for another 1 h. EtOAc (120 mL) was added to the resulting suspension and the two layers were separated. The organic layer was extracted once with 10% HCl (100 mL), saturated NaHCO₃ (100 mL), saturated brine (100 mL) and dried over Na₂SO₄. The solvent was evaporated to give 14dg as a white solid (2.27 g, 97%).

Synthesis of Azides 14dh, 14di, 14dj and 14dn

These azides were synthesized from the corresponding anilines using the conditions described for compound 14dg.

Azide 14z was synthesized from azide 14v by the sequence shown in Scheme 135.

Scheme 135: Synthesis of Azide 14z.

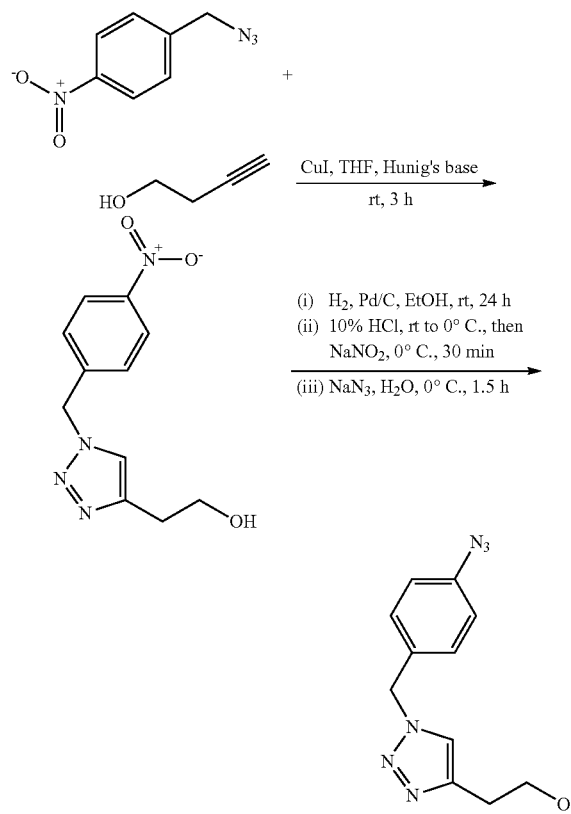

Synthesis of Azide 14z

Cycloaddition reaction between azide 14v (0.66 g, 3.43 mmol) and 1-butyn-4-ol (0.32 mL, 4.12 mmol) in the presence of CuI (0.668 g, 3.43 mmol) in THF (20 mL) and Hunig's base (10 mL) at room temperature within 3 h resulted in compound 15. Crude 15 was reduced with Pd/C (0.10 g, 10% wt, Degussa) in EtOH (15 mL) under hydrogen atmosphere (balloon) followed by diazotization with NaNO₂ (0.14 g, 2.0 mmol) in 10% HCl (20 mL) and azidation with NaN₃ (0.17 g, 2.6 mmol) in H₂O (1.0 mL) as described for the synthesis of azide 14dg gave crude azide 14z.

Azide 14aa was synthesized according to the methodology illustrated in Scheme 136.

Scheme 136: Synthesis of Azide 14aa.

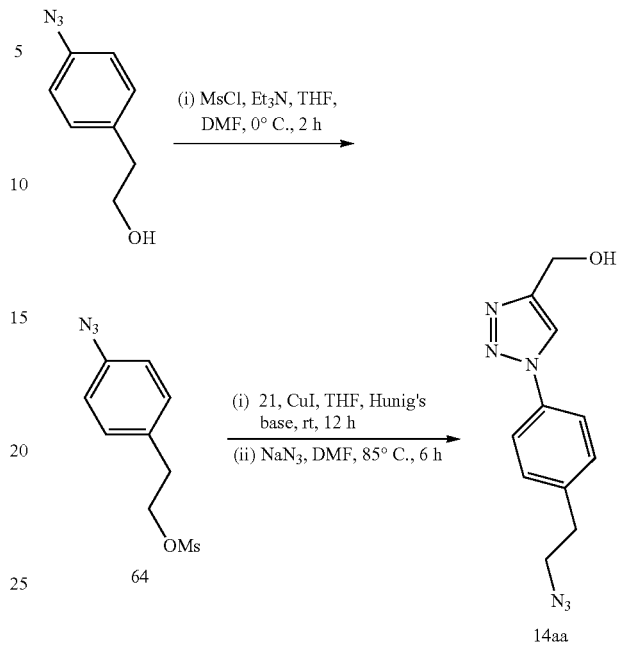

Synthesis of Azide 14aa 4-azidophenethyl alcohol (0.6 g, 3.68 mmol) was dissolved in anhydrous THF (15 mL), DMF (5 mL) and triethylamine (Et₃N) (0.54 mL, 3.7 mmol). The solution was cooled to 0° C. in ice-water bath, MsCl (0.30 mL, 3.7 mmol) was added and stirring was continued at 0° C. for 2 h. The reaction was quenched with H₂O (1 mL) and concentrated in-vacuo. EtOAc (60 mL) and saturated NaHCO₃ (40 mL) were added and the two layers were separated. The aqueous layer was washed with EtOAc (2×40 mL), the combined organic layer was dried over Na₂SO₄ and solvent evaporated off to give mesylated derivative as a brown solid. The crude mesylate was reacted with propargyl alcohol (0.40 mL, 6.83 mmol) in the presence of CuI (0.54 g, 2.84 mmol) in THF (10 mL) and Hunig's base (1 mL) at room temperature for 12 h. The reaction was worked-up as described for the synthesis of 14v. To the solution of the crude product in DMF (10 mL) was added NaN₃ (0.96 g, 14.7 mmol) and the mixture was heated at 85° C. for 6 h. The reaction was filtered and solvent evaporated off. The residue was partitioned between H₂O (30 mL) and 5% MeOH in EtOAc (40 mL). The aqueous layer was extracted with 5% MeOH in EtOAc (5×20 mL), the combined organic layer was dried over Na₂SO₄ and the solvent evaporated. The crude was purified on silica gel, eluting with CH₂Cl₂/MeOH 17:1 to furnish azide 14aa as a solid (0.51 g, 57%).

Scheme 137: Synthesis of Azide 14af.

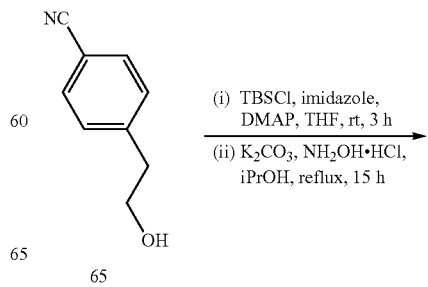

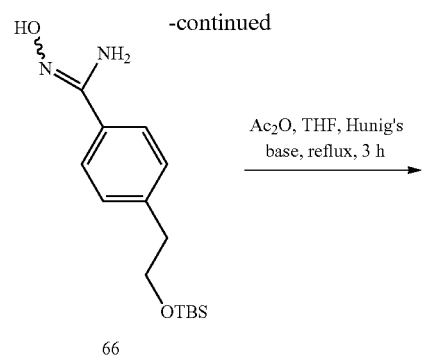

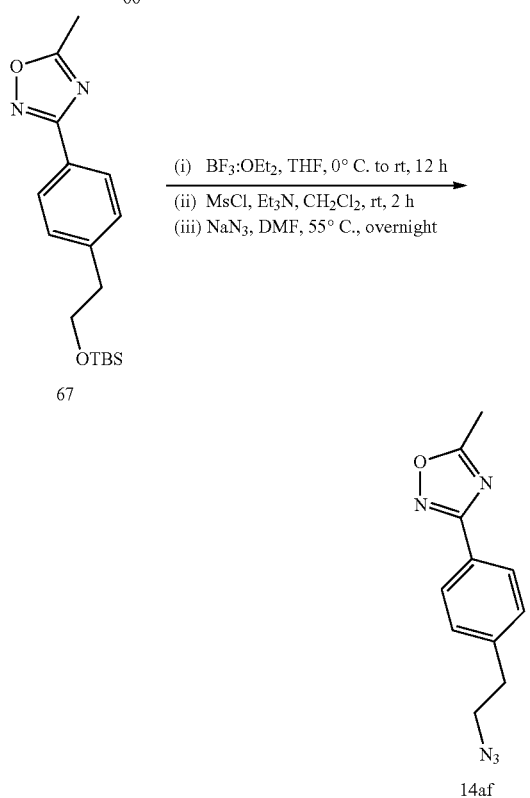

Synthesis of Azide 14af

Cyano-alcohol 65 (0.65 g, 4.42 mmol), imidazole (0.67 g, 9.73 mmol) and DMAP (0.05 g, 0.44 mmol) were dissolved in anhydrous THF (20 mL). To this solution was added TBSCl (0.70 g, 4.65 mmol) and stirring continued for 3 h during which TLC indicated a quantitative consumption of 65. CH$_2$Cl$_2$ (60 mL) was added and the mixture was extracted with saturated NaHCO$_3$ (1×30 mL), saturated brine (1×30 mL) and dried over Na$_2$SO$_4$. Solvent was evaporated off to give colorless oil.

To the solution of the crude product in isopropanol (15 mL) was added potassium carbonate (0.28 g, 2.04 mmol) and hydroxylamine hydrochloride (0.29 g, 4.08 mmol) and the resulting mixture was heated at gentle reflux (about 100° C.) for 24 h. A substantial formation of a baseline product in addition to a new product (Rf=0.31, CH$_2$Cl$_2$/MeOH 30:1) was noticed by TLC. The reaction was filtered and solvent was evaporated off to give white solid. MS (ESI) analysis confirmed the presence of the desired carboxami-doxime 66 (M+H$^+$=295.1) and the corresponding TBS-deprotected product (M+H$^+$=181.0) in about 1:1 ratio.

Half of the crude 66 (about 2.2 mmol based on 65) was dissolved in THF (10 mL) and Hunig's base (5 mL). To this solution was added acetic anhydride (1.05 mL, 11.0 mmol) and the mixture was heated under reflux for 3 h. Solvent was evaporated off and the residue was partitioned between CH$_2$Cl$_2$ (40 mL) and saturated NaHCO$_3$ (30 mL). The two layers were separated, the organic layer was extracted with saturated NaHCO$_3$ (2×30 mL), saturated brine (1×30 mL) and dried over Na$_2$SO$_4$. Solvent was evaporated off and the crude was purified on silica gel, eluting with EtOAc/Hexanes 1:8 to 1:6 to 1:4 to 1:3 to give oxidiazole 67 (0.040 g, 6%). To a solution of oxidiazole 67 (0.039 g, 0.12 mmol) in THF (3 mL) was added BF$_3$:OEt$_2$ (0.16 mL, 1.26 mmol) with stirring at 0° C. The reaction was allowed to warm up to room temperature and stirring continued overnight. Ethanol was added to destroy excess BF$_3$:OEt$_2$ and solvent was evaporated off. The residue was taken up into CH$_2$Cl$_2$ (40 mL), extracted with saturated NaHCO$_3$ (2×25 mL) and dried over Na$_2$SO$_4$. Solvent was evaporated off and the crude was used without further purification. The crude was dissolved in CH$_2$Cl$_2$ (2 mL) and Et$_3$N (0.05 mL, 0.36 mmol). To this solution was added MsCl (0.04 mL, 0.48 mmol) at room temperature with stirring. Stirring continued at room temperature for 2 h, and the reaction was partitioned between CH$_2$Cl$_2$ (40 mL) and saturated NaHCO$_3$ (30 mL). The two layers were separated, the organic layer was extracted with saturated NaHCO$_3$ (2×30 mL), saturated brine (1×20 mL), dried over Na$_2$SO$_4$, and solvent was evaporated off. The crude was dissolved in DMF (3 mL), NaN$_3$ (0.10 g, 1.5 mmol) was added and the mixture was heated at 55° C. overnight. Diethyl ether (50 mL) was added, the solution was extracted with saturated NaHCO$_3$ (3×30 mL), saturated brine (1×30 mL), dried over Na$_2$SO$_4$, and solvent was evaporated off. The crude was purified on silica gel, eluting with CH$_2$Cl$_2$/MeOH 120:1 to give azide 14af as colorless thick oil (0.018 g, 66%).

yield).

Scheme 138 Synthesis of Azide 14x

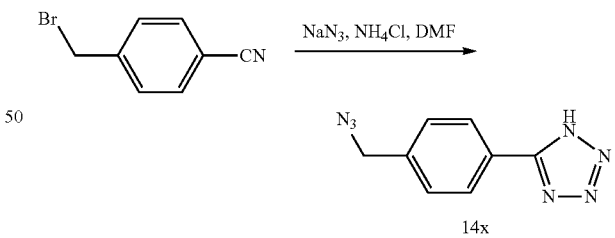

Synthesis of Azide 14x

A mixture of α-bromo-p-tolunitrile (196 mg, 1 mmol), NH$_4$Cl (107 mg, 2 mmol) and NaN$_3$ (260 mg, 4 mmol) in DMF (2 mL) was heated at 120° C. for 8 h. The reaction was then diluted with CH$_2$Cl$_2$. The inorganic salt was removed by filtration, the resulted solution was concentrated and purified by flash column (10:1:0.1/CH$_2$Cl$_2$:MeOH:NH$_3$.H$_2$O) to provide azide 20 (180 g, 90% yield).

Scheme 139 Synthesis of Azide 14dp

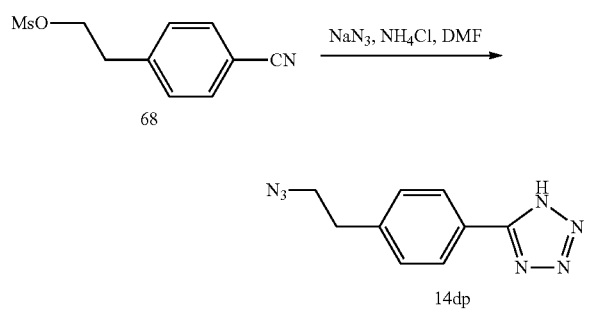

Synthesis of Azide 14dp

A mixture of mesylate 68 (700 mg, 3.1 mmol), NH$_4$Cl (332 mg, 6.2 mmol) and NaN$_3$ (808 mg, 12.4 mmol) in DMF (5 mL) was heated at 120° C. for 4 h. The reaction was then diluted with CH$_2$Cl$_2$. The inorganic salt was removed by filtration, the resulting solution was concentrated and the product purified by flash column chromatography (10:1:0.1/ CH$_2$Cl$_2$:MeOH:NH$_3$.H$_2$O) to provide azide 14dp (600 mg, 90% yield).

Scheme 140 Synthesis of Azide 14bd

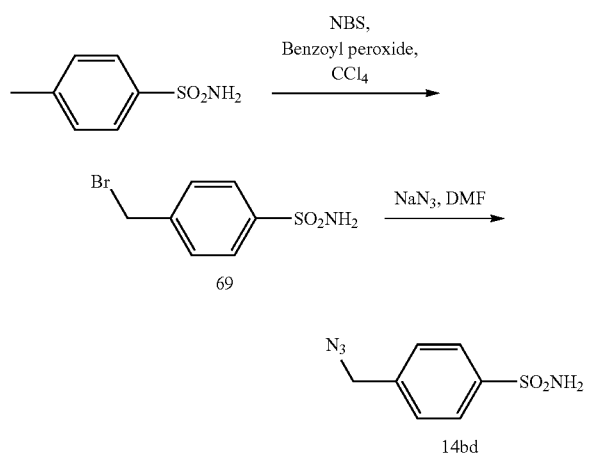

Synthesis of Azide 14bd

A mixture of p-toluenesulfonamide (6.84 g, 40 mmol), N-bromosuccinimide (7.12 g, 40 mmol) and benzoyl peroxide (0.29 g, 1.2 mmol) in carbontetrachloride (CCl$_4$) (100 mL) was refluxed for 3 h. The reaction mixture was concentrated and the residue was extracted with EtOAc. The resulting crude product was crystallized in CH$_2$Cl$_2$ to provide 69 (2.60 g, 26% yield). A mixture of 69 (150 mg, 0.6 mmol) and NaN$_3$ (156 mg, 2.4 mmol) in DMF (2 mL) was heated at 80° C. for 6 h. The reaction was then diluted with ethyl acetate, washed with brine, dried (MgSO$_4$) and evaporated to provide azide 14bd (110 mg, 86%

Scheme 141 Synthesis of Azide 14bz

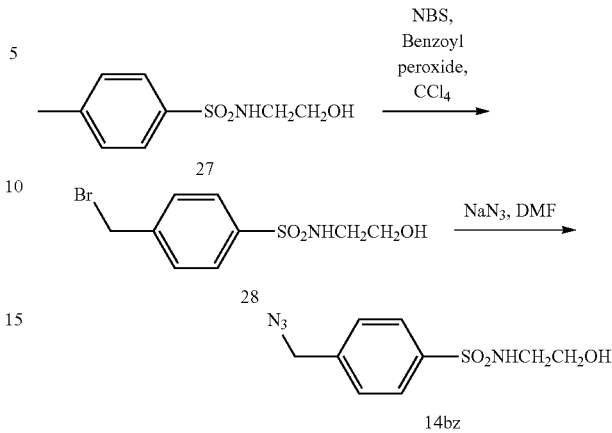

Synthesis of Azide 14bz

Azide 14bz was prepared from the reaction of bromide 28 and sodium azide following the procedure for the synthesis of 14bd. Yield, 90%. Bromide 28 was prepared from the reaction of N-(2-hydroxyethyl)-p-toluenesulfonamide and N-bromosuccinimide following the procedure for the synthesis of 17. Yield, 23%.

Synthesis of Azide 14bm

Azide 14bm was prepared from 2-fluoro-4-sulfonamido toluene according to the procedure described above for azide 14bd.

Synthesis of Azide 14bh

Azide 14bh was prepared from 3-fluoro-4-sulfonamido toluene according to the procedure described above for azide 14bd.

Synthesis of Azide 14bo

Azide 14bo was prepared from 1-p-tolyl-ethanone according to the procedure described above for azide 14bd.

Synthesis of Azide 14cm

Azide 14cm was prepared from 4-dimethylaminosulfonyl toluene according to the procedure described above for azide 14bd.

Synthesis of Azide 14cn

Azide 14cn was prepared from 4-methylaminosulfonyl toluene according to the procedure described above for azide 14bd.

Synthesis of Azide 14cr

Azide 14cr was synthesized from 3-(2-Fluoro-4-methylphenyl)-5-hydroxymethyl -oxazolidin-2-one as described above for azide 14bd.

Synthesis of Azide 14cp

Azide 14cp was synthesized from N-[3-(2-Fluoro-4-methyl-phenyl)-2-oxo-oxazolidin-5-ylmethyl]-acetamide as described above for azide 14bd.

Synthesis of Azide 14bl

Azide 14bl was prepared from 3-methoxy-4-sulfonamido toluene according to the procedure described above for azide 14bd.

Synthesis of Azide 14ca

Azide 14ca was prepared from the reaction of p-toluamide and N-bromosuccinimide followed by reaction with sodium azide following the procedure for the synthesis of 14bz. Yield, 40%.

and Et$_3$N (2.5 g, 25 mmol) in CH$_2$Cl$_2$ (20 mL) at 0° C. The mixture was kept stirring at 0° C. for 2 h. The reaction mixture was washed with brine, dried over MgSO$_4$ and concentrated to provide 69b (2.6 g, 89% yield).

Azide 14cb was prepared from the reaction of bis-mesylate 69b and sodium azide following the procedure for the synthesis of 14bd. Yield, 90%.

Synthesis of Azide 14cq

Azide 14cq was synthesized from acetic acid 3-[2-fluoro-4-(2-hydroxy-ethyl)-phenyl]-2-oxo-oxazolidin-5-ylmethyl ester according to the procedure described for azide 14cb.

Azide 14cs was synthesized from 4-bromomethylphenyl acetic acid by the route shown in Scheme 143.

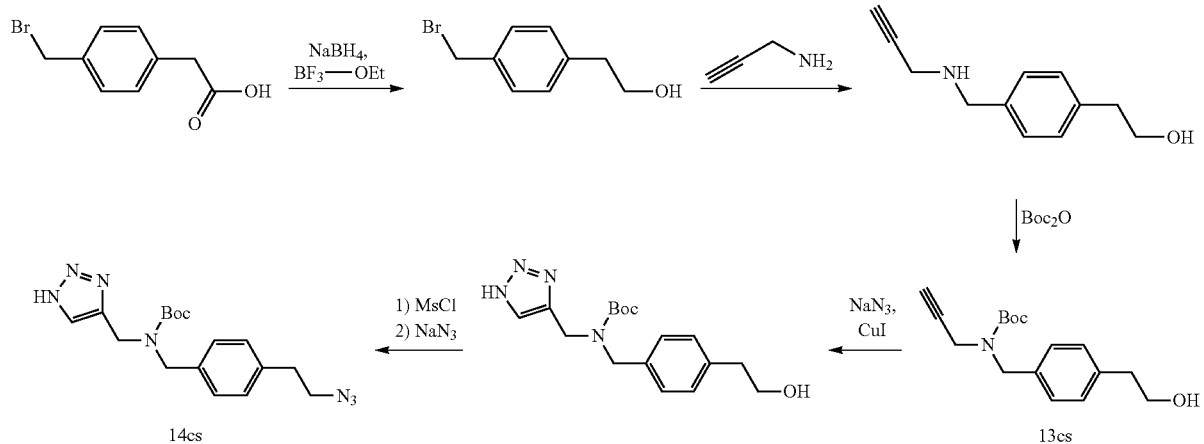

Scheme 143 Synthesis of Azide 14cs

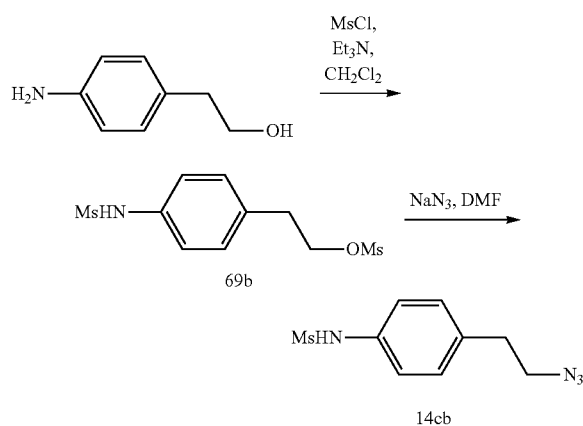

Scheme 142 Synthesis of azide 14cb

Synthesis of Azide 14o

Methanesulfonyl chloride (1.7 mL, 22 mmol) was added to a solution of 4-aminophenylethyl alcohol (1.37 g, 10 mmol)

Synthesis of Azide 14cs

4-Bromomethylphenyl acetic acid (1.15 g, 5 mmol) was treated with NaBH$_4$, BF3-OEt according to the conditions described below in the synthesis of azide 14b. The crude p-bromomethyl phenethyl alcohol was treated with propargyl amine hydrochloride (0.85 g, 9.3 mmol) in Hunig's base at rt for 2 h. The reaction mixture was concentrated and the crude residue dissolved in a 2:1 THF water mixture (30 mL) and treated with t-butoxycarbonyl (Boc) anhydride (1.1 g) and K$_2$CO$_3$ (0.83 g) for 12 h. The reaction mixture was partitioned between water and EtOAc, the organic layer was dried, filtered and concentrated to give a residue which was purified by preparative TLC (elution with 15:1:0.1 CH$_2$Cl$_2$:MeOH:NH$_4$OH to give 0.89 g of the intermediate 13cs. Alkyne 13cs (0.62 g, 2.15 mmol was converted to the corresponding triazole by reaction with sodium azide and NHCl as described above in the synthesis of 14dp. The triazole product was treated with mesyl chloride and azide as described below for the synthesis of azide 14dx to afford the azide 14cs as a colorless oil.

, Azides 14o-14r were synthesized from the corresponding phenylisocyanates by reaction with 2-bromoethanol followed by displacement with azide ion. The procedure given below for azide 14o is typical.

Scheme 144

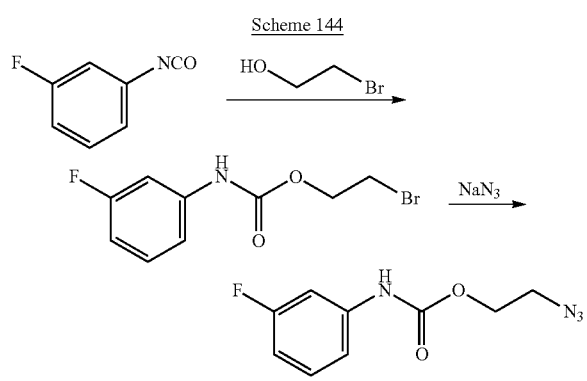

Synthesis of Azide 14o

To a stirred solution of 3-fluorophenylisocyanate (2 g, 14.6 mmol) in toluene was added bromoethanol (2 mL, 29.2 mmol). The reaction mixture was refluxed for 7 h. The reaction mixture was diluted with ether. (100 mL) and washed with water (3×100 mL). The organic extract was dried, filtered and concentrated and the residue dissolved in DMF (30 mL). NaN$_3$ (2.5 g, 30.5 mmol) was added and the reaction mixture was stirred at 70° C. for 4 h. The reaction mixture was partitioned between ether and water. The organic layer was separated and washed with water (3×100 mL) then dried and concentrated. The crude product was purified by silica gel chromatography (elution with 9:1 Hexane EtOAc) to give 14o as a white solid (2.4 g).

Azides 14p, 14q, and 14r were synthesized from the corresponding isocyanates under the same condition described for azide 14o.

Azide 14ar was synthesized from 4-(2-bromoethyl)benzoic acid by the sequence illustrated in Scheme 145 below.

Scheme 145 Synthesis of azide 14ar

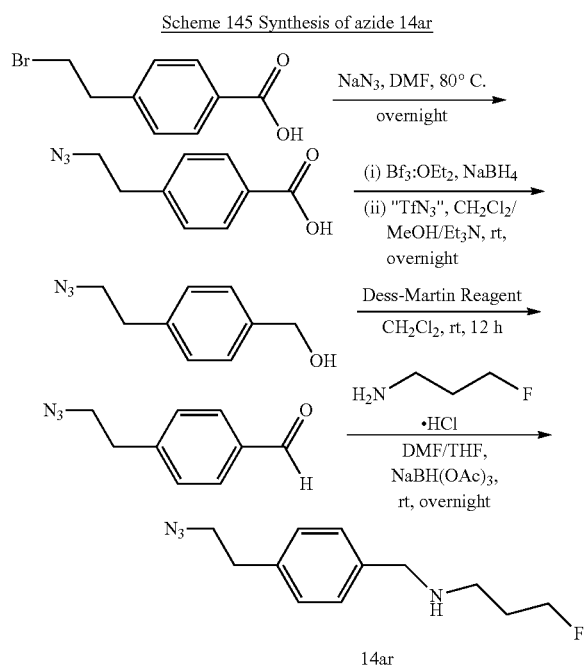

Synthesis of Azide 14ar

A mixture of 4-(2-Bromoethyl)benzoic acid (1.0 g, 4.40 mmol) and sodium azide (0.72 g, 11.0 mmol) in DMF (10 mL) was heated at 80° C. for about 12 h. The solvent was evaporated and the residue was suspended in cold water (40 mL) acidified with few drops of glacial acetic acid. The suspension was filtered, the residue was washed with cold water (40 mL) acidified with few drops of glacial acetic acid and dried in vacuo at 40° C. to give carboxylic acid as white solid (0.8 g, 95%) (Rf=0.51, EtOAc/Hexanes/MeOH 4:1:0.02).

To a solution of this carboxylic acid (0.70 g, 3.87 mmol) in anhydrous THF (8 mL) was added 1M BH$_3$:THF (12 mL, 12.0 mmol) at 0° C. Stirring was continued at 0° C. for 1 h and the reaction was warmed up to room temperature. The mixture was stirred at room temperature for 14 h. TLC (visualization with ninhydrin stain) showed azide reduction took place. NaBH$_4$ (0.46 g, 12 mmol) and BF$_3$:OEt$_2$ (1.6 mL, 12 mmol) were added and stirring continued for about 18 h to ensure a complete azide reduction. Excess boron trifluoride etherate was destroyed with ethanol, and the mixture filtered. The filtrate was evaporated to afford a semi solid. The crude was treated with freshly prepared triflic azide (12 mmol) as described for the synthesis of azide 14s. The crude was purified on silica gel eluting with EtOAc/Hexanes 2:3 to afford 4-(2-azidoethyl)-benzyl alcohol as clear oil (0.56 g, 82%) (Rf=0.53, EtOAc/Hexanes 2:3).

A mixture of azido-alcohol this (0.40 g, 2.26 mmol) and Dess-Martin reagent (1.25 g, 2.93 mmol) in CH$_2$Cl$_2$ (15 mL) was stirred at room temperature overnight. The reaction was quenched with 10% Na$_2$S$_2$O$_3$: saturated NaHCO$_3$ (1:1) (30 mL), CH$_2$Cl$_2$ (30 mL) was added and the two layers separated. The organic layer was washed with 10% Na$_2$S$_2$O$_3$: NaHCO$_3$ (1:1) (2×30 mL), saturated NaHCO$_3$ (2×30 mL) and dried over Na$_2$SO$_4$. Solvent was evaporated off and the residue was purified on silica gel, eluting with EtOAc/Hexanes 1:6 to give 4-(2-azidoethyl)-benzaldehyde as clear oil (0.23 g, 58%) (Rf=0.46, EtOAc/Hexanes 1:4).

A mixture of this azido-aldehyde (0.23 g, 1.31 mmol) and 3-fluoropropyl amine hydrochloride (0.25 g, 2.20 mmol) in DMF (4 ml) and THF (10 mL) was stirred at room temperature for 30 min. NaBH(OAc)$_3$ (0.51 g, 2.40 mmol) was added and stirring was continued at room temperature for about 18 h. MeOH (20 mL) was added, the suspension was filtered and the filtrate evaporated off to give oily residue. The residue was partitioned between 10% MeOH in CH$_2$Cl$_2$ (40 mL) and water (25 mL), the two layers were separated and the organic layer was dried over Na$_2$SO$_4$. Solvent was evaporated off and the residue was purified by preparative TLC (2000 micron plate) eluting with CH$_2$Cl$_2$/MeOH (2 N NH$_3$) 18:1 to give azide 14ar as light yellow oil (0.077 g, 25%) (Rf=0.34, CH$_2$Cl$_2$/MeOH (2 N NH$_3$) 18:1). MS (ESI) M/E; M+H$^+$ 237.0.

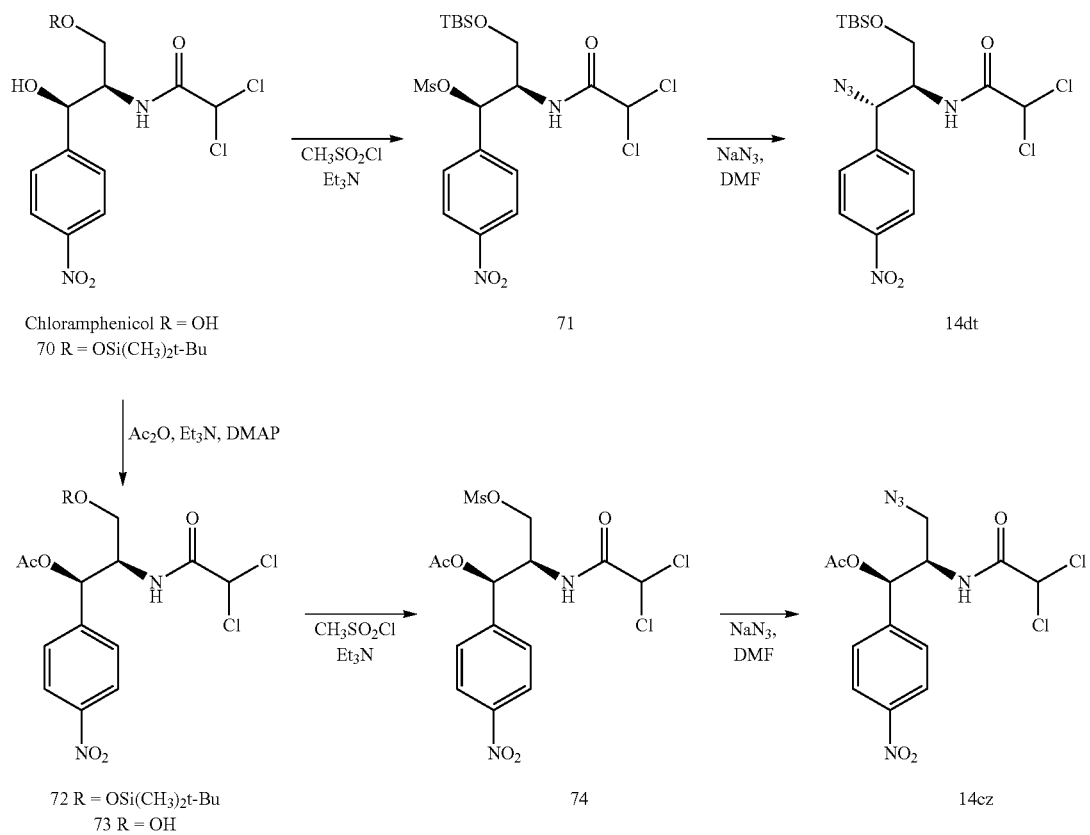

Scheme 146 Synthesis of azides 14dt and 14cz

Synthesis of Alcohol 70

To a mixture of chloramphenicol (6.26 g, 20 mmol) and tert-butyldimethylsilyl chloride (3.32 g, 22 mmol) in $CH_2Cl_2$ (40 mL) was added imidazole (1.70 g, 25 mmol). After stirring at room temperature for 4 h, the solution was quenched with saturated $NaHCO_3$ solution. The organic phase was washed with brine, dried over anhydrous $MgSO_4$ and concentrated under reduced pressure. After purification by flash chromatography (silica gel, hexane:ethyl acetate/6:1), 8.85 g of white crystalline 70 was obtained in a yield of 96%.

Synthesis of Mesylate 71

Methanesulfonyl chloride (0.32 g, 2.75 mmol) was added drop wise to a solution of 70 (1.09 g, 2.5 mmol) and $Et_3N$ (0.51 g, 5.0 mmol) in $CH_2Cl_2$ (5 mL) at 0° C. The mixture was kept stirring at 0° C. for 2 h and at room temperature for 12 h. The solvent was removed under reduced pressure and the residue was dissolved in EtOAc. The EtOAc solution was washed with brine, dried over anhydrous $MgSO_4$ and concentrated under reduced pressure to afford 1.22 g of 71 as light yellow oil. Yield: 95%.

Synthesis of Azide 14dt

A mixture of mesylate 71 (1.32 g, 2.5 mmol) and sodium azide (0.65 g, 10 mmol) in DMF (5 ml) was stirred at 50-60° C. for 5 h. The reaction was quenched with water. The solution was extracted with EtOAc, washed with brine, dried over anhydrous $MgSO_4$ and concentrated in vacuum. The crude product was purified by chromatography (silica gel, hexane: ethyl acetate/15:1) to afford 0.75 g of light yellow oil 53. Yield: 65%. MS (ESI) m/e 460 $(M-H)^+$.

Synthesis of Acetate 72

Triethylamine (2.5 mL, 17.9 mmol) was added to a solution of 70 (3.3 g, 7.6 mmol), acetic anhydride (2.4 g, 23.3 mmol) and 4-dimethylaminopyridine (60 mg, 0.49 mmol) in $CH_2Cl_2$ (30 mL) at 0° C. After stirring at same temperature for 2 h, the reaction was diluted with $CH_2Cl_2$, washed with saturated $NaHCO_3$, dried over anhydrous $MgSO_4$ and concentrated. Flash chromatography (silica gel, hexane:ethyl acetate/6:1) of crude product afforded 3.4 g of white crystalline 72. Yield: 94%.

Synthesis of Alcohol 73

To a solution of 72 (3.59 g, 7.5 mmol) in THF (50 mL) was added a solution of 1.0 M TBAF in THF (7.5 mL, 7.5 mmol). The reaction mixture was stirred at room temperature under argon atmosphere for 2 h. The solvent was removed under reduced pressure, and the residue was dissolved with EtOAc and washed with brine. The organic phase was dried ($MgSO_4$), concentrated and purified by chromatography (silica gel, hexane:ethyl acetate/4:1) to afford 2.40 g of light yellow oil 73. Yield: 88%.

Synthesis of Mesylate 74

Triethylamine (1.8 mL, 12.7 mmol) was added to a solution of 73 (2.32 g, 6.36 mmol) and methanesulfonyl chloride (0.80 g, 7.0 mmol) in CH$_2$Cl$_2$ (20 mL) at 0° C. After stirring at 0° C. for 2 h, the solvent was removed under reduced pressure, the residue was dissolved in EtOAc and washed with brine. The organic phase was dried (MgSO$_4$) and concentrated under reduced pressure to afford 2.8 g of 74 as light yellow oil. Yield: 99%.

Synthesis of Azide 14cz

The mixture of mesylate 74 (3.0 g, 6.8 mmol) and sodium azide (1.76 g, 27.1 mmol) in DMF (15 ml) was stirred at 60° C. under argon atmosphere for 2 h. The reaction was quenched with water and diluted with EtOAc. The organic layer was washed with brine, dried (MgSO$_4$), concentrated and purified by chromatography (silica gel, hexane:ethyl acetate/4:1) to afford 1.65 g light yellow solid 57. Yield: 63%. MS (ESI) m/e 388 (M−H)$^+$.

Synthesis of Azide 14cx

The synthesis of this azide is described in the patent application WO2004029066A3.

The majority of the azides in Table 11 including all those for which synthetic details are not provided in the preceding paragraphs were synthesized according to known procedures using the reactions shown in the schemes above. The specific route used for each azide was determined by the available commercial starting materials. When possible azides were produced from the corresponding substituted alkyl bromides by direct displacement with azide ion, this method is exemplified in the synthesis of azide 14c described below. When the required alkyl bromides were not readily available, the compounds were derived from substituted alkanols: to accomplish this the alcohols were first activated as their sulfonyl ester derivatives and then substituted with azide ion. This procedure is exemplified below for the synthesis of azide 14dx. If neither the required bromides or alkanols were commercially available, the azides were synthesized from the corresponding carboxylic acids by reduction with borohydride to the corresponding alcohols The resulting alkanols were then treated as above to yield the azides. The chemistry employed to convert a carboxylic acid to an azide is exemplified below for compound 14b. Finally, some azides of Table 11 were synthesized from the corresponding substituted alkyl amines by reaction with triflic azide. An example of this procedure is provided for the synthesis of azide 14w below.

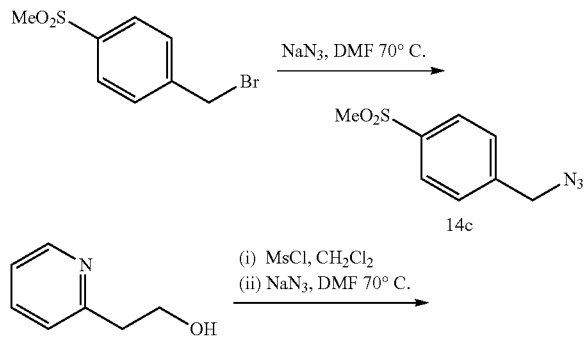

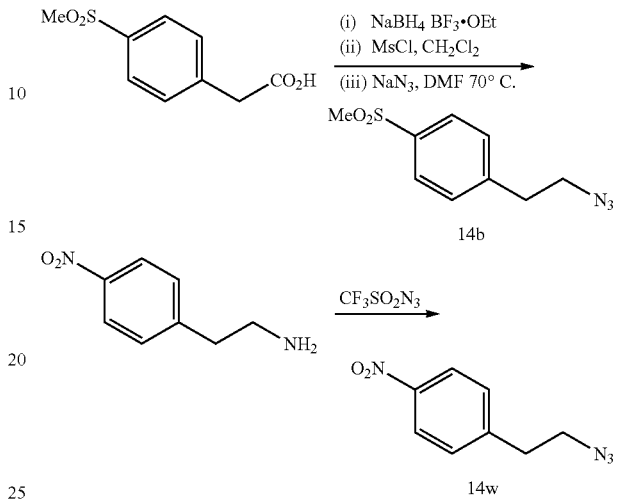

Synthesis of Azide 14c

To a solution of 4-methylsulfonyl benzyl bromide (1 g, 4.0 mmol) in DMF (20 mL) was added NaN$_3$ (0.52 g, 8.0 mmol). The mixture was stirred at rt for 1 h, then poured into 200 mL of a 1:1 water-ether mixture. The aqueous layer was separated and extracted with ether (2×50 mL) and the combined organic extracts dried (Na$_2$SO$_4$), and concentrated under reduced pressure to yield a crude product. Purification by silica gel chromatography (elution with 30% EtOAc in hexanes) afforded the pure azide as a white solid (0.52 g, 2.5 mmol)

Synthesis of Azides 14dx

To a solution of 2-(2-hydroxyethyl)pyridine (2 g, 16.2 mmol) and diisopropylethylamine (5.6 mL, 32.4 mmol) in CH$_2$Cl$_2$ (40 mL) was added methanesulfonyl chloride (1.4 mL, 17.8 mmol) at 0° C. The mixture was warmed to rt, stirred for 3 h, then quenched with water and diluted with CH$_2$Cl$_2$ (30 mL). The organic layer was washed with NaHCO$_3$ (2×50 mL), dried (Na$_2$SO$_4$), and concentrated under reduced pressure to yield 3.2 g of the crude mesylate which was of suitable purity to be used in subsequent reactions without purification. The above mesylate was converted to azide 14dx using the same procedure used to synthesize azide 14dw from the bromoethyl ether of ethyl salicylate.

Synthesis of Azide 14d

To a solution of 4-methylsulfonyl phenyl acetic acid (1 g, 4.7 mmol) in THF (25 mL) was added NaBH$_4$ (0.54 g, 14.1 mmol) after 5 minutes BF$_3$.OEt (2.4 mL, 18.8 mmol) was added and the reaction mixture allowed to stir 16 h at rt. The reaction was quenched with MeOH, filtered and concentrated in vacuo, then suspended in CH$_2$Cl$_2$. The solid was filtered, dried, and re-suspended in CH$_2$Cl$_2$ (10 mL). Triethylamine (1.3 mL, 9.4 mmol) was added followed by MsCl (0.6 mL, 7.0 mmol) After 4 h additional triethylamine (1.3 mL, 9.4 mmol) and MsCl (0.6 mL, 7.0 mmol) were added and stirring was continued for 16 h. The reaction mixture was diluted with 50 mL CH$_2$Cl$_2$, washed with saturated NaHCO$_3$ and with brine, then dried (Na$_2$SO$_4$), filtered and concentrated.

The crude mesylate was dissolved in DMF (10 mL), 0.61 g NaN$_3$ was added and the reaction stirred at 80° C. for 2 h. The reaction mixture was partitioned between ether and water and the aqueous layer further extracted with ether (3×30 mL). The combined organic extracts were washed with brine (100 mL), dried (Na$_2$SO$_4$), filtered, and concentrated to give a crude product which was purified by silica gel chromatography (elution with 40% EtOAc in hexanes) to afford 14d as a white solid (0.70 g, 12 mmol).

In a few cases the azides of Table 11 were synthesized by modification of other azides that had been synthesized according to the methodologies above:

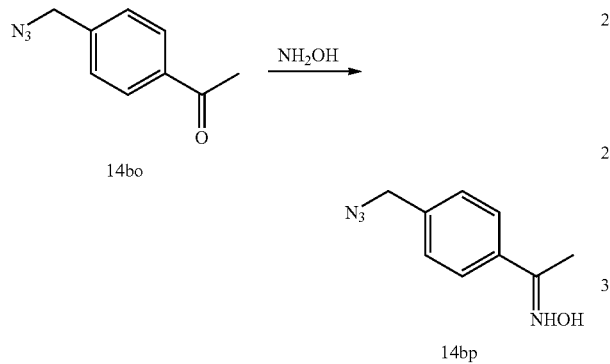

Synthesis of Azide 14bp from azide 14bo

To a solution of azide 14bo (0.18 g, 1 mmol) in MeOH (5 mL) was added HONH$_2$.HCl (0.35 g, 5 mmol) and triethylamine (0.35 mL, 2.5 mmol). The mixture was refluxed for 8 h, then diluted with EtOAc, washed with water and brine. The organic extracts were dried (Na$_2$SO$_4$), filtered and concentrated to afford 14 bp as a white solid (180 mg).

Synthesis of Azide 14bn from azide 14bk

Azide 14bn was prepared from 14bk according to the procedure described for the synthesis of azide 14bp

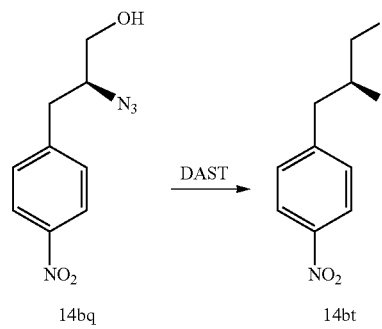

Synthesis of Azide 14bt from Azide 14bq

To a stirred −78° C. solution of azide 14bt (111 mg, 0.5 mmol) in CH$_2$Cl$_2$ was added (diethylamino)sulfur trifluoride (DAST) (0.1 mL,. 0.82 mmol). The reaction was stirred at −78° C. for 2 h, then allowed to warm to rt and stirred for 14 h. The reaction mixture was poured into water and extracted with CH$_2$Cl$_2$. The organic extracts were dried, filtered, and concentrated to give 14bq as a solid (36 mg, 0.16 mmol).

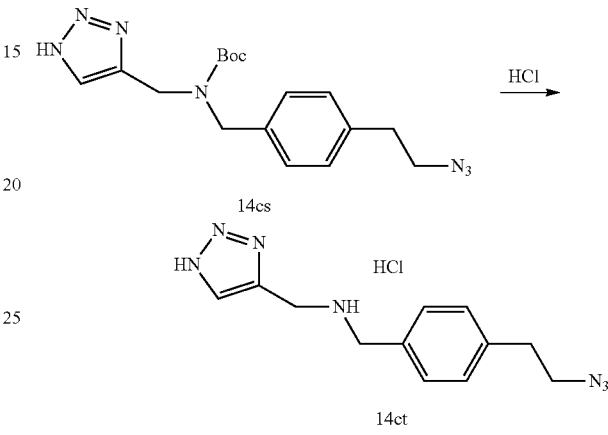

Synthesis of Azide 14ct from azide 14cs

To a stirred solution of 14ct (0.21 g) in CH$_2$Cl$_2$ (10 mL) was added 4M HCl in 1,4-dioxane (2 mL) the mixture was stirred at rt for 10 h, then concentrated under reduced pressure to afford the HCL salt of azide 14cz as a white solid (0.15 g).

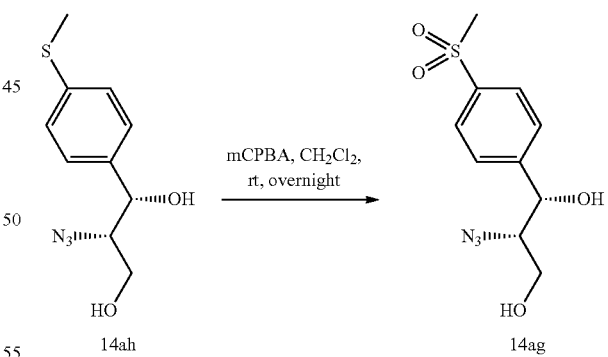

Synthesis of Azide 14ah from 14ag

To a solution of azide 14ah (0.27 g, 1.1 mmol) in CH$_2$Cl$_2$ (15 mL) was added mCPBA (1.10 g, 4.5 mmol) and the mixture was stirred at room temperature overnight. Solvent was evaporated and the crude was purified on silica gel eluting with CH$_2$Cl$_2$/MeOH 20:1 to 15:1 to 12:1 to give azide 14ag as colorless paste that solidified on standing (0.26 g, 87%).

Example 11

Synthesis of Compounds 601-630

TABLE 12

| Structure | cpd number | LCMS M/Z |
|---|---|---|
| 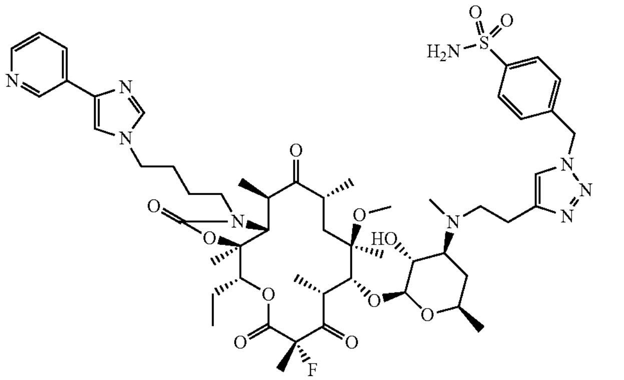 [SMILES: CC[C@H]1OC(=O)[C@@](C)(F)C(=O)[C@H](C)[C@@H](O[C@@H]2O[C@H](C)C[C@H](N(C)CCc3cn(Cc4ccc(S(N)(=O)=O)cc4)nn3)[C@H]2O)[C@](C)(OC)C[C@@H](C)C(=O)[C@H](C)[C@H]2N(CCCCn3cnc(-c4cccnc4)c3)C(=O)O[C@]12C] | 601 | 541.1 (M + 2H)$^{2+}$ |
| 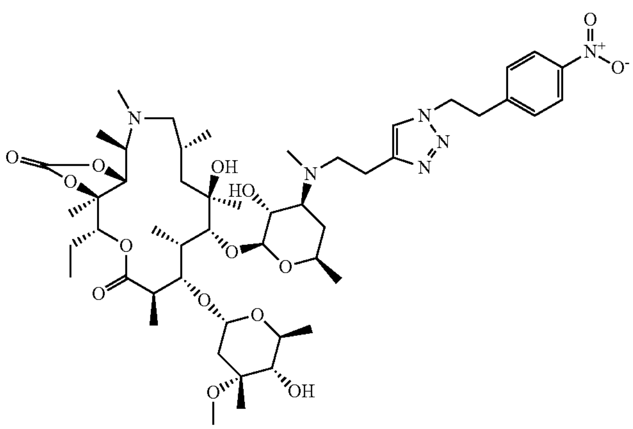 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc([N+](=O)[O-])cc4)nn3)[C@H]2O)[C@](C)(O)C[C@@H](C)CN(C)[C@H](C)[C@H]2OC(=O)O[C@@]21C] | 602 | 513.2 (M + 2H)$^{2+}$ |
| 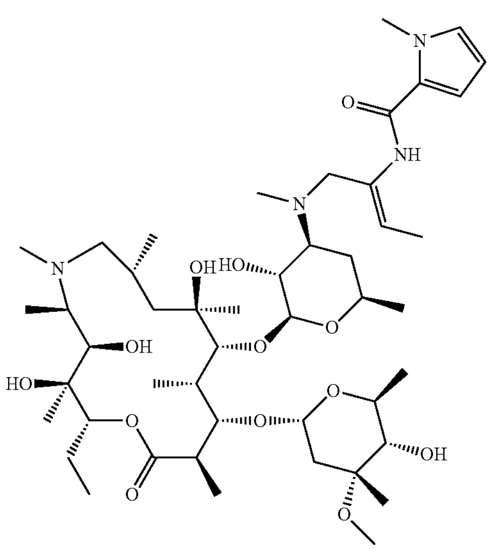 [SMILES: C/C=C(/CN(C)[C@H]1C[C@@H](C)O[C@@H](O[C@@H]2[C@@H](C)[C@H](O[C@H]3C[C@@](C)(OC)[C@@H](O)[C@H](C)O3)[C@@H](C)C(=O)O[C@H](CC)[C@@](C)(O)[C@H](O)[C@@H](C)N(C)C[C@H](C)C[C@@]2(C)O)[C@@H]1O)NC(=O)c1cccn1C] | 603 | 456.5 (M + 2H)$^{2+}$ |

TABLE 12-continued
| Structure | cpd number | LCMS M/Z |
|---|---|---|
| 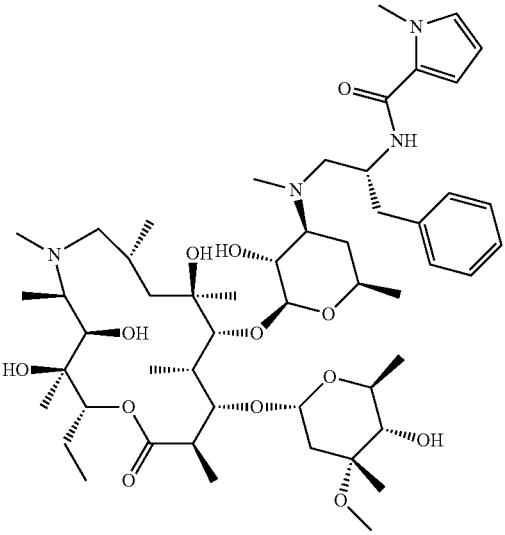 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)C[C@@H](Cc3ccccc3)NC(=O)c3cccn3C)[C@H]2O)[C@](C)(O)C[C@@H](C)CN(C)[C@H](C)[C@@H](O)[C@]1(C)O] | 604 | 488.6 (M + 2H)²⁺ |
| 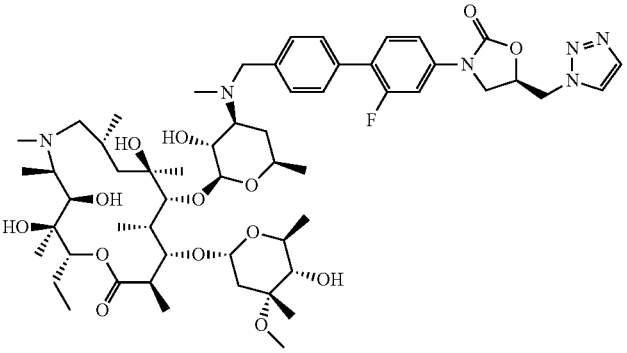 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)Cc3ccc(-c4ccc(N5C[C@H](Cn6ccnn6)OC5=O)cc4F)cc3)[C@H]2O)[C@](C)(O)C[C@@H](C)CN(C)[C@H](C)[C@@H](O)[C@]1(C)O] | 609 | 1086 (M + H)⁺<br>544 (M + 2H)²⁺ |
| 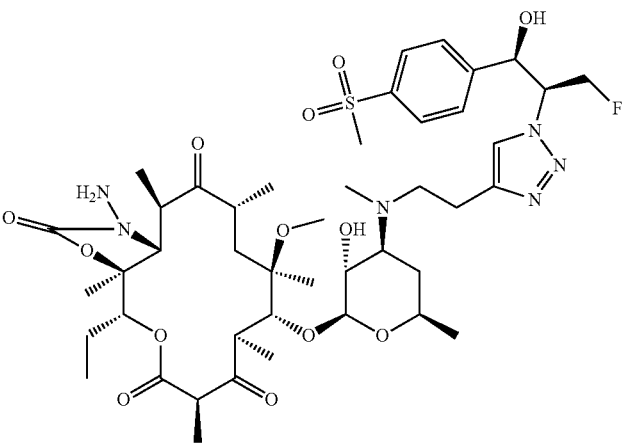 [SMILES: CC[C@H]1OC(=O)[C@H](C)C(=O)[C@H](C)[C@@H](O[C@@H]2O[C@H](C)C[C@H](N(C)CCc3cn([C@H](CF)[C@H](O)c4ccc(S(C)(=O)=O)cc4)nn3)[C@H]2O)[C@](C)(OC)C[C@@H](C)C(=O)[C@H](C)[C@H]2N(N)C(=O)O[C@]12C] | 610 | 940 (M + H)⁺ |

TABLE 12-continued
| Structure | cpd number | LCMS M/Z |
|---|---|---|
| 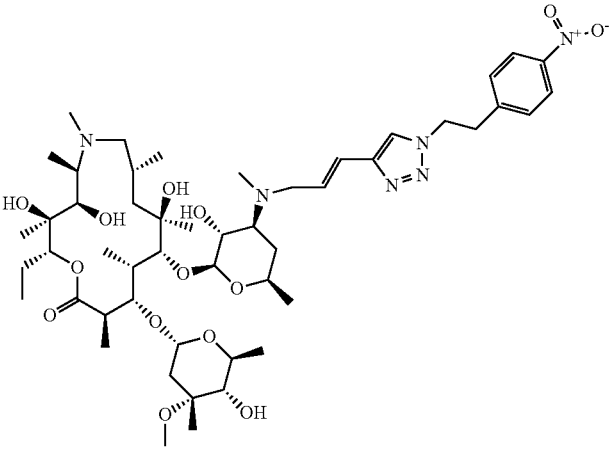 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)C/C=C/c3cn(CCc4ccc([N+](=O)[O-])cc4)nn3)[C@H]2O)[C@](C)(O)C[C@@H](C)CN(C)[C@H](C)[C@@H](O)[C@]1(C)O] | 611 | 497.1 (M + 2H)²⁺ |
| 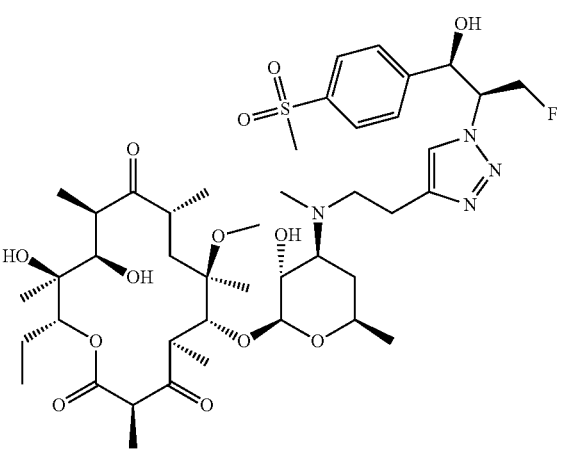 [SMILES: CC[C@H]1OC(=O)[C@H](C)C(=O)[C@H](C)[C@@H](O[C@@H]2O[C@H](C)C[C@H](N(C)CCc3cn([C@H](CF)[C@H](O)c4ccc(S(C)(=O)=O)cc4)nn3)[C@H]2O)[C@](C)(OC)C[C@@H](C)C(=O)[C@H](C)[C@@H](O)[C@]1(C)O] | 612 | 899 (M + H)⁺ |
| 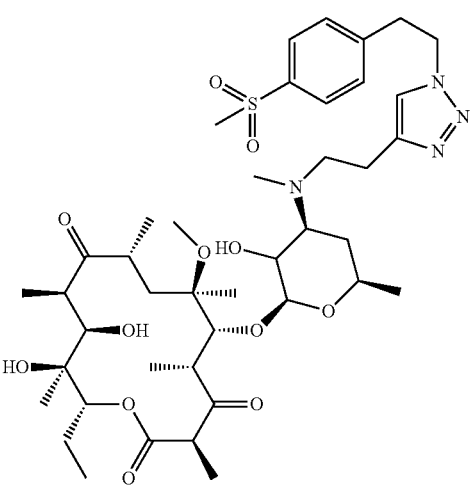 [SMILES: CC[C@H]1OC(=O)[C@H](C)C(=O)[C@H](C)[C@@H](O[C@@H]2O[C@H](C)C[C@H](N(C)CCc3cn(CCc4ccc(S(C)(=O)=O)cc4)nn3)C2O)[C@](C)(OC)C[C@@H](C)C(=O)[C@H](C)[C@@H](O)[C@]1(C)O] | 613 | 851 (M + H)⁺ |

TABLE 12-continued

| Structure | cpd number | LCMS M/Z |
|---|---|---|
| 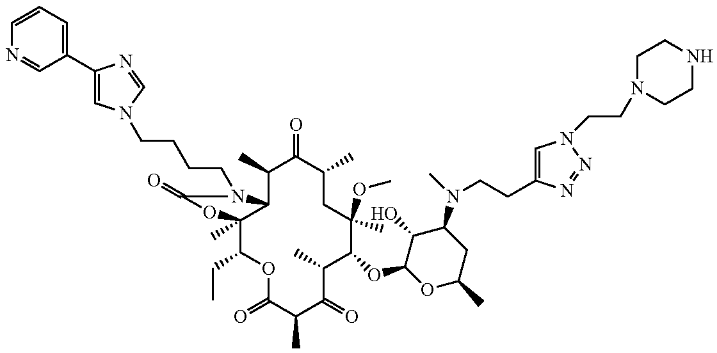 [SMILES: CC[C@H]1OC(=O)[C@H](C)C(=O)[C@H](C)[C@@H](O[C@@H]2O[C@H](C)C[C@H](N(C)CCc3cn(CCN4CCNCC4)nn3)[C@H]2O)[C@](C)(OC)C[C@@H](C)C(=O)[C@H](C)[C@H]2N(CCCCn3cnc(-c4cccnc4)c3)C(=O)O[C@]12C] | 614 | 503.4 (M + 2H)$^{2+}$ |
| 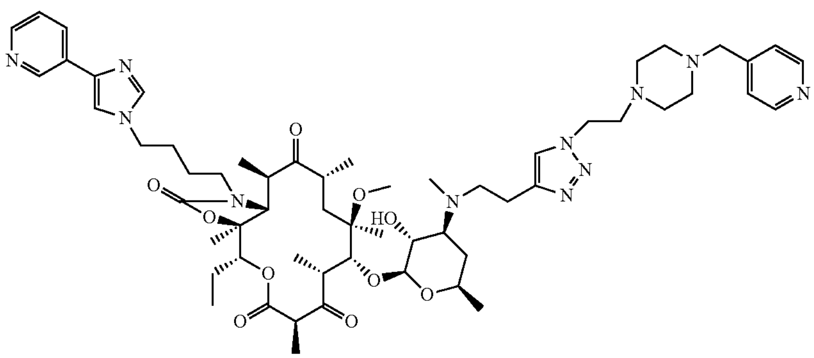 [SMILES: CC[C@H]1OC(=O)[C@H](C)C(=O)[C@H](C)[C@@H](O[C@@H]2O[C@H](C)C[C@H](N(C)CCc3cn(CCN4CCN(Cc5ccncc5)CC4)nn3)[C@H]2O)[C@](C)(OC)C[C@@H](C)C(=O)[C@H](C)[C@H]2N(CCCCn3cnc(-c4cccnc4)c3)C(=O)O[C@]12C] | 615 | 1097 (M + H)$^+$ |
| 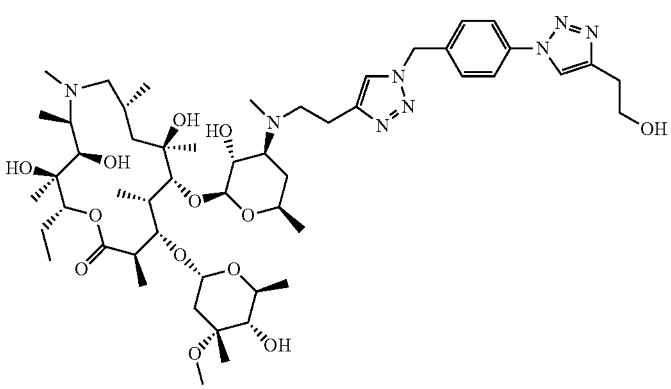 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc(-n5cc(CCO)nn5)cc4)nn3)[C@H]2O)[C@](C)(O)C[C@@H](C)CN(C)[C@H](C)[C@@H](O)[C@]1(C)O] | 616 | 1031.5 (M + H)$^+$ |
| 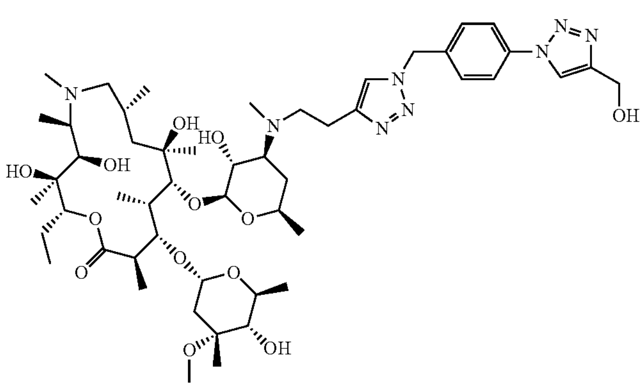 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(Cc4ccc(-n5cc(CO)nn5)cc4)nn3)[C@H]2O)[C@](C)(O)C[C@@H](C)CN(C)[C@H](C)[C@@H](O)[C@]1(C)O] | 617 | 1017.4 (M + H)$^+$ |

TABLE 12-continued

| Structure | cpd number | LCMS M/Z |
|---|---|---|
| 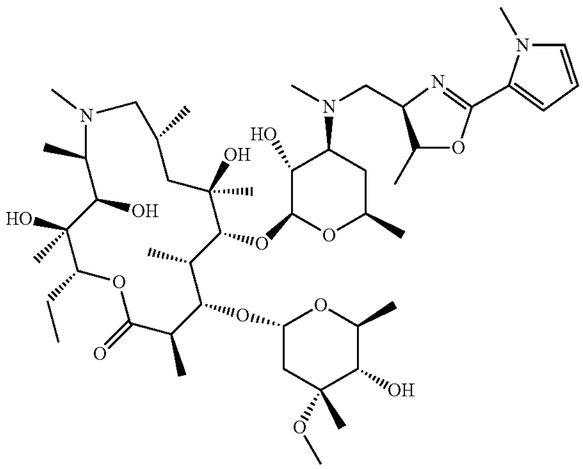 | 618 | 456.1 (M + 2H)$^{2+}$ |
| 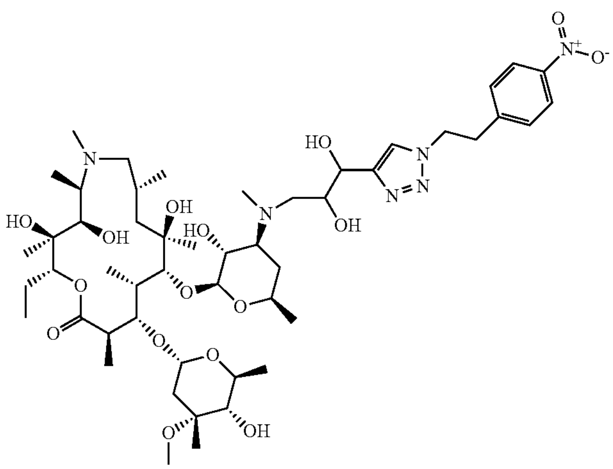 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CC(O)C(O)c3cn(CCc4ccc([N+](=O)[O-])cc4)nn3)[C@H]2O)[C@](C)(O)C[C@@H](C)CN(C)[C@H](C)[C@@H](O)[C@]1(C)O] | 619 | 513.5 (M + 2H)$^{2+}$ |
| 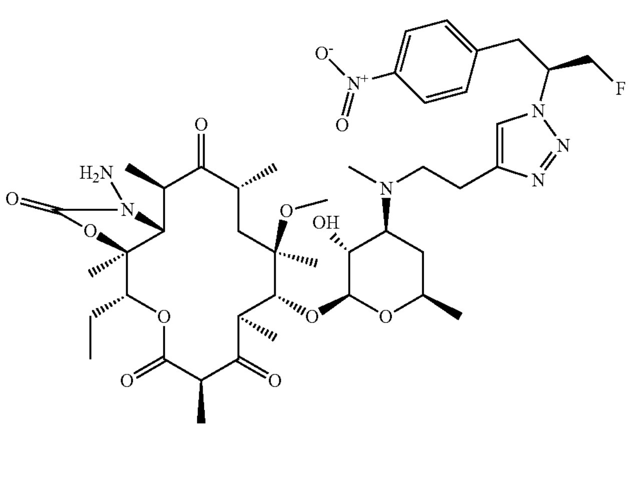 [SMILES: CC[C@H]1OC(=O)[C@H](C)C(=O)[C@H](C)[C@@H](O[C@@H]2O[C@H](C)C[C@H](N(C)CCc3cn([C@H](CF)Cc4ccc([N+](=O)[O-])cc4)nn3)[C@H]2O)[C@](C)(OC)C[C@@H](C)C(=O)[C@H](C)[C@H]2N(N)C(=O)O[C@]12C] | 620 | 890 (M + H)$^+$ |

TABLE 12-continued

| Structure | cpd number | LCMS M/Z |
|---|---|---|
| 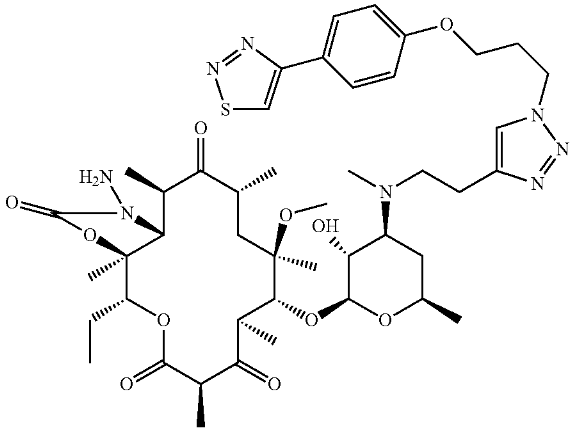 [SMILES: CC[C@H]1OC(=O)[C@H](C)C(=O)[C@H](C)[C@@H](O[C@@H]2O[C@H](C)C[C@H](N(C)CCc3cn(CCCOc4ccc(-c5csnn5)cc4)nn3)[C@H]2O)[C@](C)(OC)C[C@@H](C)C(=O)[C@H](C)[C@H]2N(N)C(=O)O[C@]12C] | 621 | 927 (M + H)+ |
| 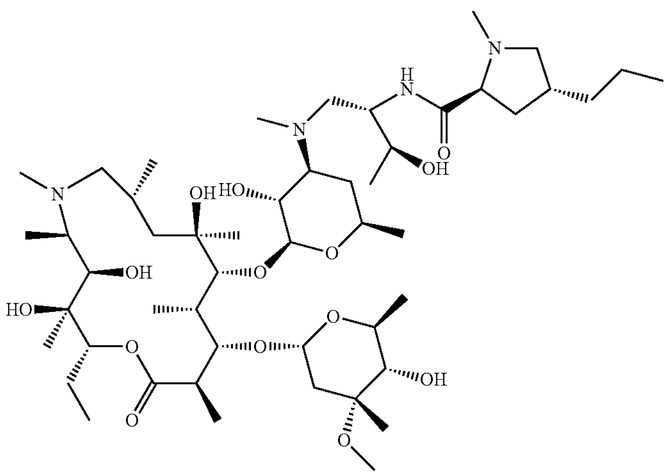 [SMILES: CCC[C@@H]1C[C@@H](C(=O)N[C@@H](CN(C)[C@H]2C[C@@H](C)O[C@@H](O[C@@H]3[C@@H](C)[C@H](O[C@H]4C[C@@](C)(OC)[C@@H](O)[C@H](C)O4)[C@@H](C)C(=O)O[C@H](CC)[C@@](C)(O)[C@H](O)[C@@H](C)N(C)C[C@H](C)C[C@@]3(C)O)[C@@H]2O)[C@H](C)O)N(C)C1] | 622 | 975.8 (M + H)+<br>447.8 (M + 2H)2+ |
| 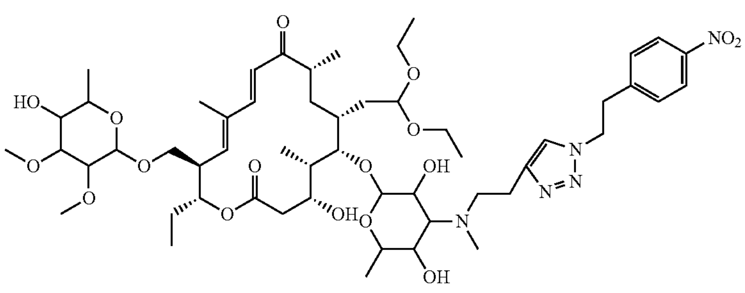 [SMILES: CCOC(C[C@H]1C[C@@H](C)C(=O)/C=C/C(C)=C/[C@H](COC2OC(C)C(O)C(OC)C2OC)[C@@H](CC)OC(=O)C[C@@H](O)[C@H](C)[C@H]1OC1OC(C)C(O)C(N(C)CCc2cn(CCc3ccc([N+](=O)[O-])cc3)nn2)C1O)OCC] | 623 | 1076 (M + H)+ |
| 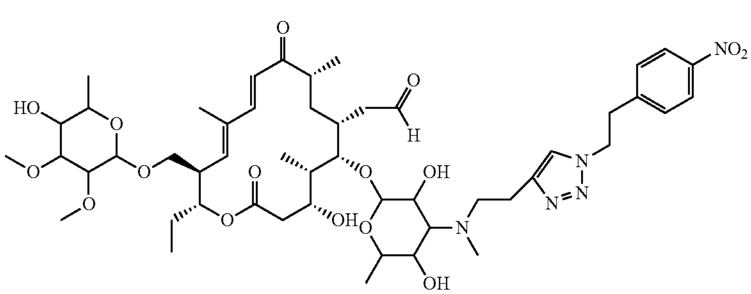 [SMILES: CC[C@H]1OC(=O)C[C@@H](O)[C@H](C)[C@@H](OC2OC(C)C(O)C(N(C)CCc3cn(CCc4ccc([N+](=O)[O-])cc4)nn3)C2O)[C@@H](CC=O)C[C@@H](C)C(=O)/C=C/C(C)=C/[C@@H]1COC1OC(C)C(O)C(OC)C1OC] | 624 | 1003 (M + H)+ |

TABLE 12-continued

| Structure | cpd number | LCMS M/Z |
|---|---|---|
| 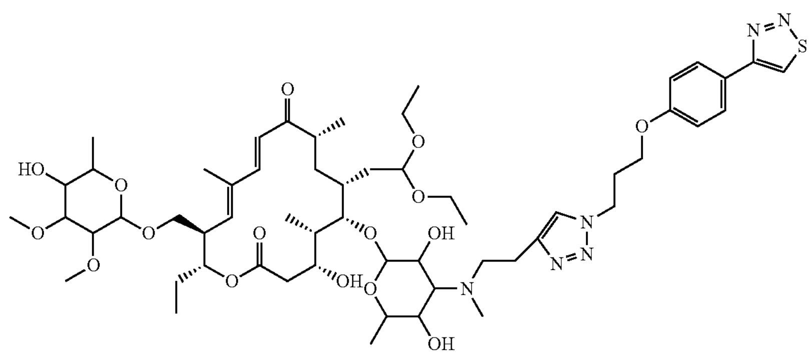 [SMILES: CCOC(C[C@H]1C[C@@H](C)C(=O)/C=C/C(C)=C/[C@H](COC2OC(C)C(O)C(OC)C2OC)[C@@H](CC)OC(=O)C[C@@H](O)[C@H](C)[C@H]1OC1OC(C)C(O)C(N(C)CCc2cn(CCCOc3ccc(-c4csnn4)cc3)nn2)C1O)OCC] | 625 | 1145 (M + H)+ |
| 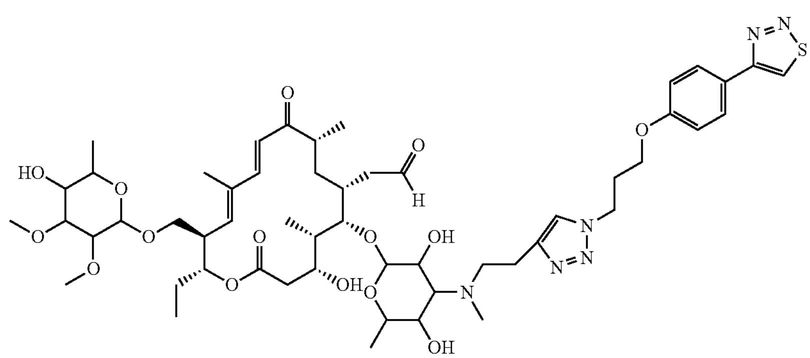 [SMILES: CC[C@H]1OC(=O)C[C@@H](O)[C@H](C)[C@@H](OC2OC(C)C(O)C(N(C)CCc3cn(CCCOc4ccc(-c5csnn5)cc4)nn3)C2O)[C@@H](CC=O)C[C@@H](C)C(=O)/C=C/C(C)=C/[C@@H]1COC1OC(C)C(O)C(OC)C1OC] | 626 | 1072 (M + H)+ |
| 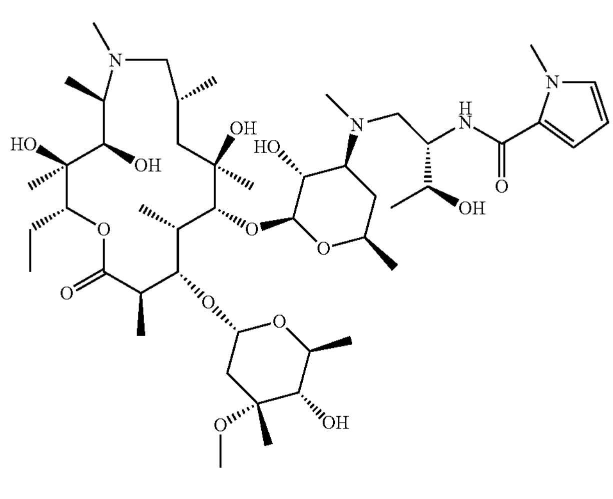 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)C[C@H](NC(=O)c3cccn3C)[C@H](C)O)[C@H]2O)[C@](C)(O)C[C@@H](C)CN(C)[C@H](C)[C@@H](O)[C@]1(C)O] | 627 | 929.8 (M + H)+<br>465.5 (M + 2H)2+ |

TABLE 12-continued
| Structure | cpd number | LCMS M/Z |
|---|---|---|
| 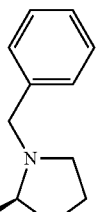 | 628 | 506.6 (M + 2H)$^{2+}$ |
| 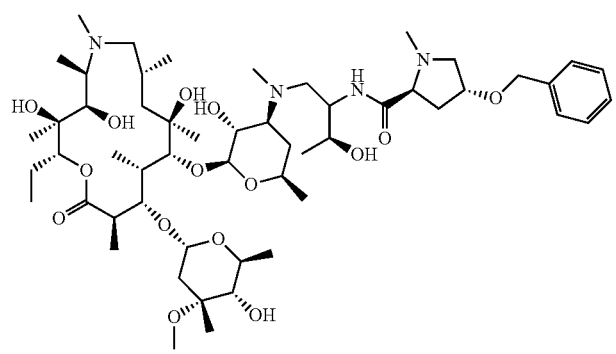 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CC(NC(=O)[C@@H]3C[C@@H](OCc4ccccc4)CN3C)[C@H](C)O)[C@H]2O)[C@](C)(O)C[C@@H](C)CN(C)[C@H](C)[C@@H](O)[C@]1(C)O] | 629 | 1040 (M + H)$^+$<br>520.4 (M + 2H)$^{2+}$ |
| 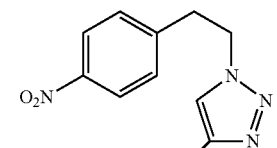 | 630 | 1031 (M + H)$^+$ |

Synthesis of Compound 601
Compound 601 was synthesized as shown in Scheme 152. Amine 30 of Example 3 was treated according to the procedures of U.S. Pat. No. 6,124,269 to afford the 2-fluoro amine 30a. This was then alkylated with tosylate 11 under the conditions of Example 3 to afford fluoroalkyne 31a. This compound was treated with azide 14bd using the procedures of Example 1 to yield compound 601.
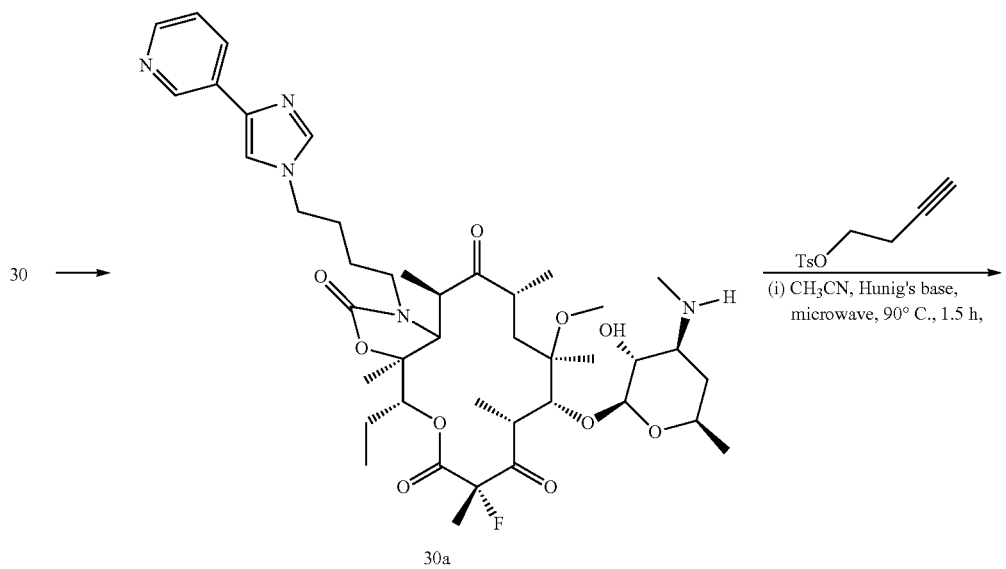
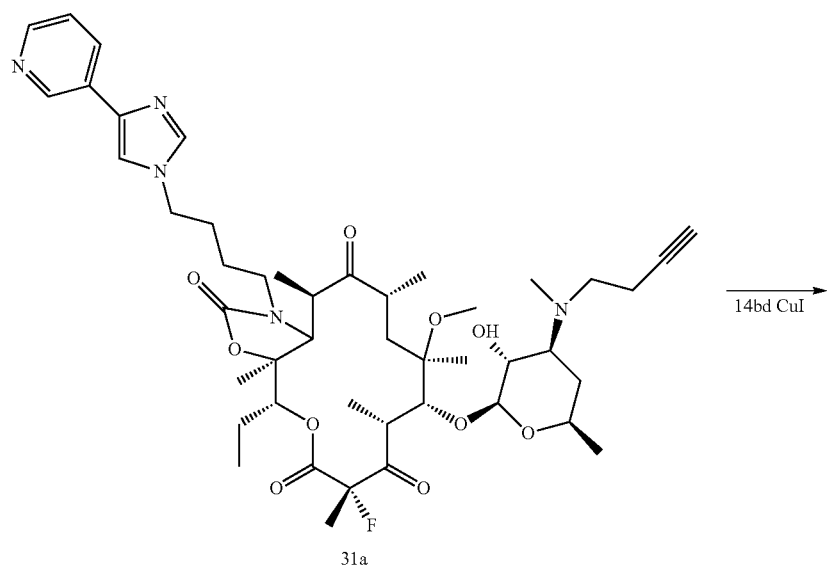

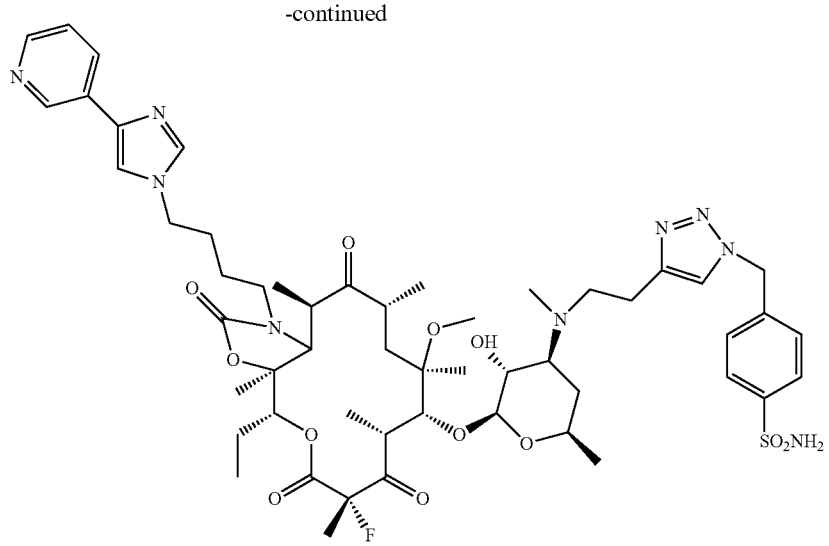
601
Compound 602 was synthesized from compound 122 of Eexample 1 and ethylene carbonate as shown in Scheme 153.
Scheme 153
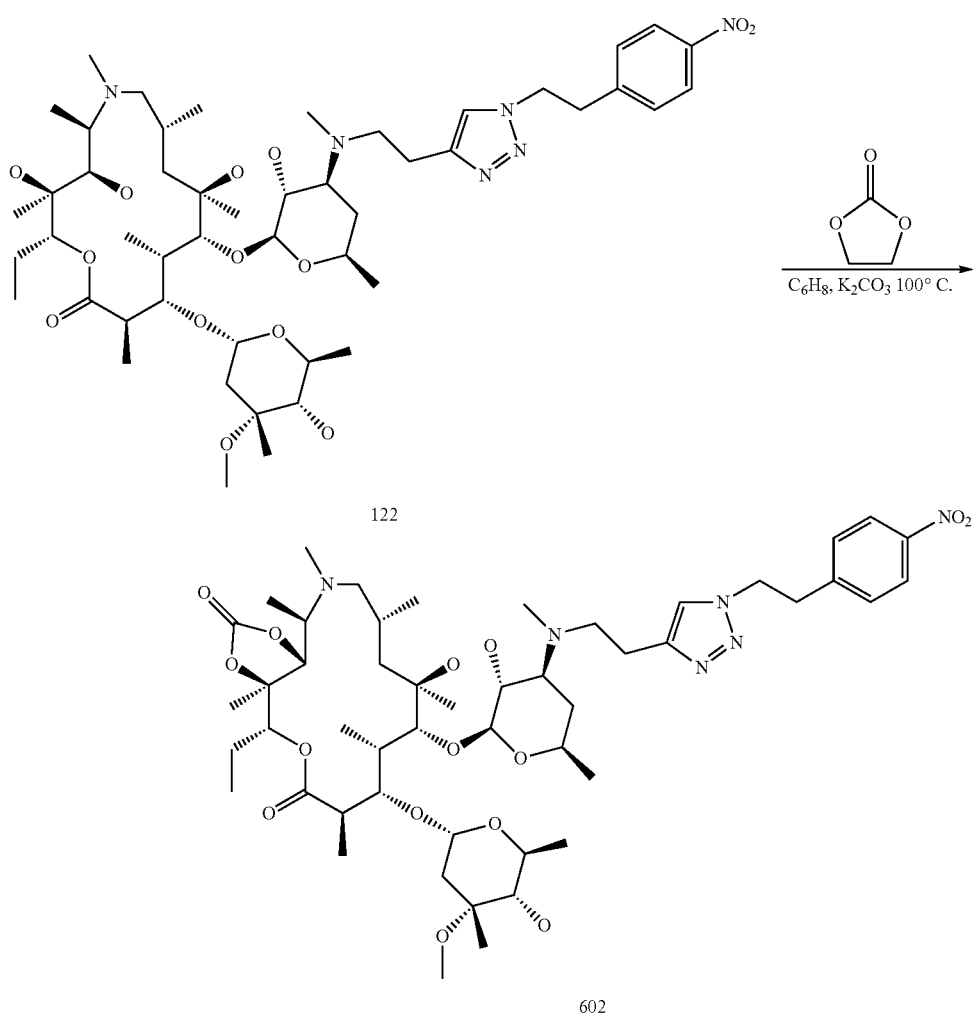

Synthesis of Compound 602

To a solution of 122 (0.1 g, 0.1 mmol) in benzene (5 mL) was added $K_2CO_3$ (0.2 g) and ethylene carbonate. The mixture was heated to reflux for 16 h then partitioned between water and ether. The ether layer was dried ($K_2CO_3$), filtered and concentrated to give 0.28 g of an oily residue which was purified by silica gel chromatography (elution with 2% methanolic ammonia (2M $NH_3$) in $CH_2Cl_2$ to give 0.1 g of 601 as a white solid. MS (ESI) m/e 513.2 $(M+2H)^{2+}$.

Synthesis of Compound 609

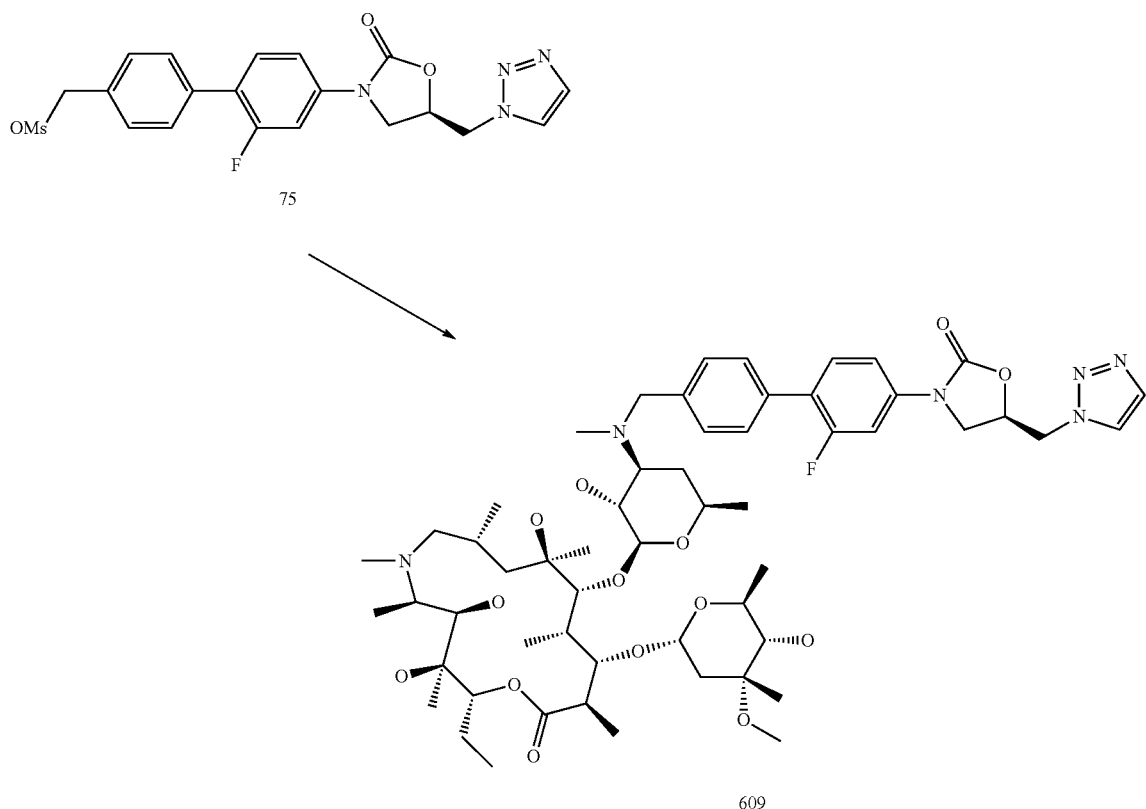

A solution N-desmethylazithromycin 2 (0.1 g, 0.136 mmol), mesylate 75 (0.067 g, 0.15 mmol) and Hunig's base (1 mL) in DMF (1 mL) was heated to 70° C. for 12 h. The reaction mixture was concentrated and purified by flash chromatography over silica gel ($CH_2Cl_2$-MeOH—$NH_4OH$=20:1:0.05) to gave 0.055 g (38%) of 609. MS (ESI) m/z 1086 $(M+H)^+$, 544 $(M+2H)^+$.

Synthesis of Compound 610

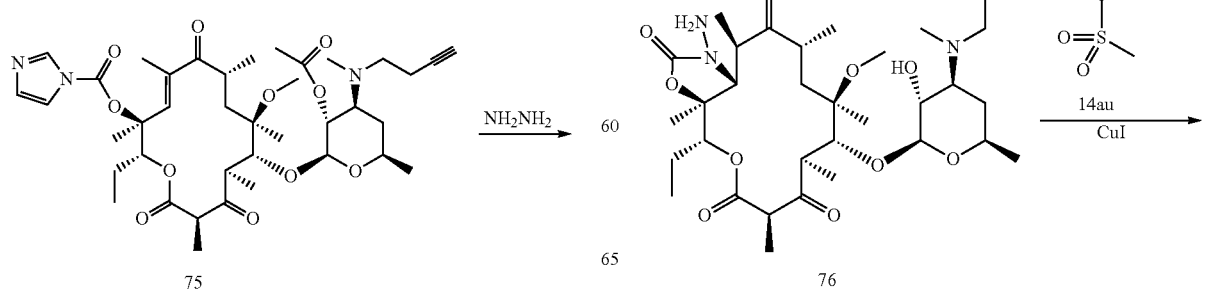

-continued

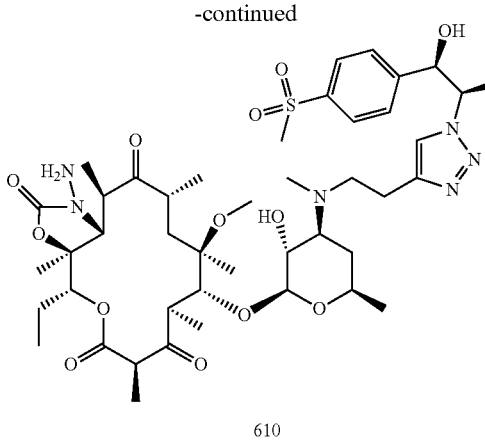

610

A solution of acylimidazole 75 (0.74 g, 1.0 mmol) in acetonitrile (20 mL) and H₂O (3 mL) was treated with hydrazine monohydrate (0.50 mL, 10 mmol) and stirred at 50° C. for 1 h. The reaction mixture was evaporated to yellow foam and redissolved in methanol (50 mL) and heated to reflux for 20 h. Solvent was evaporated purification by flash chromatography (SiO₂, 50-100% ethyl acetate/hexanes) provide the alkyne carbazate 76 (0.50 g, 0.75 mmol) as a white powder.

A solution of 76 (0.10 g, 0.15 mmol) in tetrahydrofuran (3.0 mL) was treated with azide 14au (62 mg, 0.22 mmol), diisopropylethylamine (0.080 mL, 0.46 mmol), and copper (I) iodide (8.0 mg, 0.042 mmol) and stirred at 23° C. for 24 h. The reaction mixture was diluted with ammonium hydroxide (30 mL) and extracted with dichloromethane (3×30 mL), dried (Na₂SO₄), and evaporated. Preparative thin-layer chromatography (SiO₂, 10% methanol/dichloromethane, then ethyl acetate) provided 610 (98 mg, 0.10 mmol) as a white solid: LCMS (ESI) m/e 940 (M+H)⁺.

Synthesis of Compound 611

Scheme 156 illustrates the synthesis of triazole 611. 2-Penten-4-yn-1-ol was converted to tosylate 77 which was used to alkylate amine 2 to yield enyne 78. The cycloaddition of alkyne 78 with azide 14w gave the triazole product 611.

Scheme 156

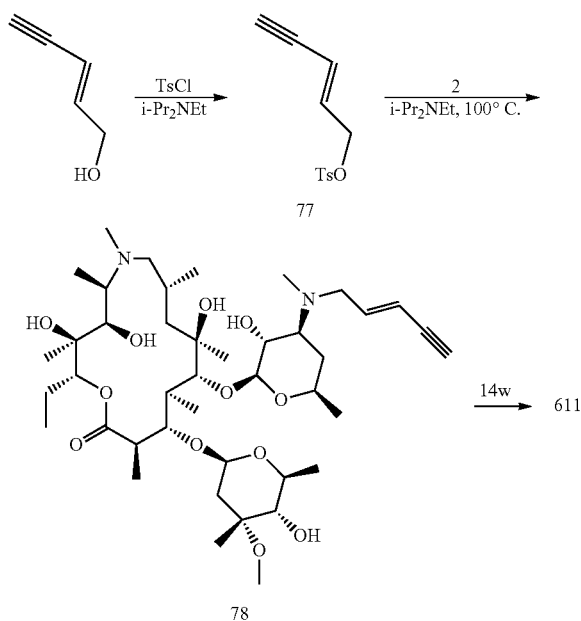

Synthesis of Tosylate 77

To a stirred ice-cold solution of 2-penten-4-yn-1-ol (0.821 g, 10 mmol) in ether (25 mL) was added p-toluenesulfonyl chloride (2.0 g, 10.5 mmol). Powdered KOH (1.0 g, 17.8 mmol) was then added portionwise over 5 minutes. The slurry was stirred at 0° C. for 45 minutes. The reaction mixture was poured into 100 mL water, and extracted with ether (2×50 mL). The combined organic extracts were washed with brine, dried over MgSO₄, filtered, and concentrated to afford 77 as a yellow oil (2.1 g, 89% yield). Data for 77: ¹HNMR (300 MHz, CDCl₃): δ 7.80 (d, J=8 Hz, 2H), 7.35 (d, J=8 Hz, 2H), 6.12 (dt, J=16, 6 Hz, 1H), 5.70 (ddd, J=16, 2, 2 Hz, 1H), 4.60-4.50 (m, 2H), 2.95 (d, J=2, Hz 1H), 2.45 (s, 3H); ¹³C NMR (75 MHz, CDCl₃): δ 145.1, 135.9, 132.9, 130.0, 127.9, 113.9, 80.3, 79.8, 69.0, 21.66.

Synthesis of Enyne 78

A 20 mL vial was charged with tosylate 77 (0.20 g, 0.85 mmol), N-desmethyl azithromycin 2 (0.5 g, 0.68 mmol), and Hunig's base (10 mL) then purged with argon gas and sealed. The solution was stirred in a 100° C. oil bath for 1 h. After cooling to room temperature, the reaction mixture was poured into saturated aqueous NaHCO₃ (50 mL) and extracted with CH₂Cl₂ (3×50 mL). The combined organic extracts were washed with brine, dried over K₂CO₃, filtered, and concentrated to afford 0.72 g of a viscous yellow oil. Purification by silica gel flash chromatography (25 mm×6" column eluted with 50:1 CH₂Cl₂/2N NH₃ in MeOH) gave 78 as a yellow solid (0.48 g, 88% yield). Data for 78: MS (ESI) m/e 400.2 (M+2H)²⁺, 799.3 (M+H)⁺, 821.2 (M+Na)⁺; ¹HNMR (300 MHz, CDCl₃, partial): δ 8.00 (bs, 1H), 6.20 (dt, J=16, 7, Hz, 1H), 5.70-5.60 (m, 1H), 5.00 (d, J=4 Hz, 1H), 4.65 (m, 1H), 4.48 (d, J=7 Hz, 1H), 4.28 (dd, J=6, 2 Hz, 1H), 4.15-3.99 (m, 1H), 3.82 (d, J=6 Hz, 1H), 3.65 (d, J=7 Hz, 1H), 3.60-3.40 (m, 1H), 3.32 (s, 3H), 3.32-3.20 (m, 2H), 2.32 (s, 3H), 2.26 (s, 3H), 0.86 (m, 6H); ¹³C NMR (75 MHz, CDCl₃): δ 179.3, 144.4, 111.8, 103.8, 96.2, 85.1, 82.6, 79.7, 79.0, 78.5, 77.5, 75.7, 75.3, 74.4, 73.8, 71.9, 71.0, 69.4, 66.5, 65.4, 62.9, 57.0, 50.39, 45.9, 43.4, 42.0, 37.6, 37.5, 35.9, 31.8, 31.2, 28.2, 27.7, 22.8, 22.5, 22.2, 22.0, 19.3, 17.1, 16.3, 12.1, 10.3, 8.6.

Synthesis of Triazole 611

To a stirred solution of 78 (20 mg, 25 μmol) in THF (100 μL) was added Hunig's base (20 μL), azide 14au (16 mg, 50 μmol), and cuprous iodide (2.4 mg, 13 μmol). The resulting mixture was degassed by alternately applying vacuum and purging with argon gas. The slurry was stirred under argon at ambient temperature for 4 h. The entire reaction mixture was then placed atop a silica gel flash chromatography column and eluted with 50:1 CH₂Cl₂/2N NH₃ in MeOH to afford triazole 611 as a white solid (14 mg, 50% yield). Data for 611: MS (ESI) m/e 496.8 (M+2H)²⁺, 992.3 (M+H)⁺.

Synthesis of Compound 612

Compound 612 was synthesized from alkyne 27d of Example 4 and azide 14au of Table 11 using the copper catalyzed cycloaddition conditions of Example 1.

Synthesis of Compound 613

Compound 612 was synthesized from alkyne 27d of Example 4 and azide 14b of Table 11 using the copper catalyzed cycloaddition conditions of Example 1.

Synthesis of 619

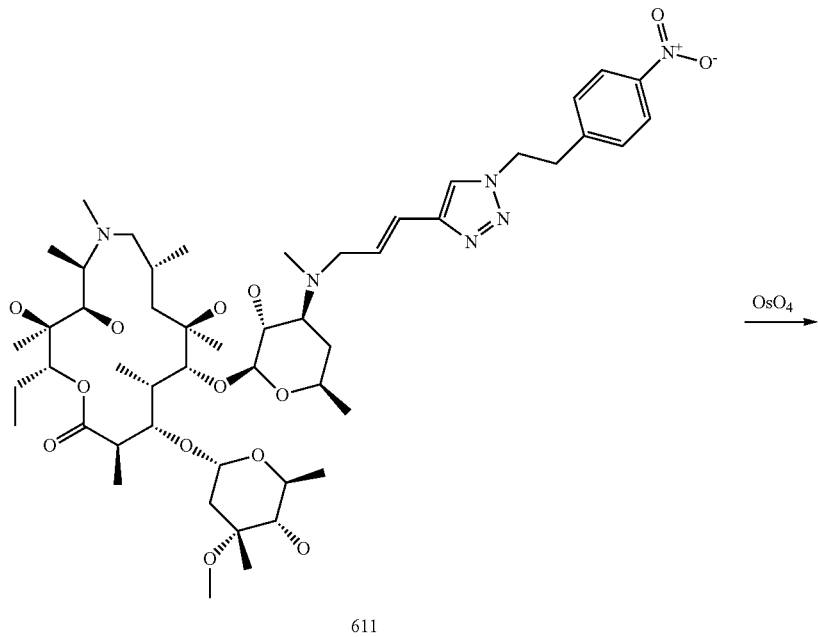

611

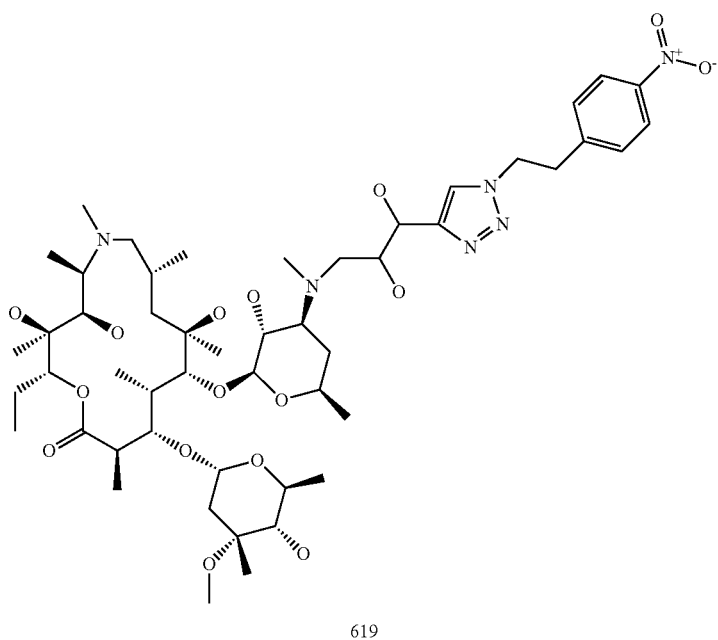

619

To a solution of alkene 611 (0.05 g, 0.0504 mmol) in acetone (1.5 mL)—H$_2$O (0.2 mL) was added a solution of N-Methylmorpholine N-oxide in water (0.013 mL, 50% in H$_2$O) followed by solution of OsO$_4$ in tertiary-butanol (0.005 mmol, 0.1 M in Bu$^t$OH). The resulting solution was stirred at ambient temperature overnight and diluted with CH$_2$Cl$_2$ (50 mL) and brine (50 mL). The organic layer was separated and washed with brine (2×50 mL), dried (anhydrous Na$_2$SO$_4$), concentrated and purified by preparative TLC (CH$_2$Cl$_2$: 2% NH$_3$-MeOH=13:1). Yield: 20 mg (40%). MS (ESI) m/z 1026 (M+H)$^+$, 513.5 (M+2H)$^+$.

Synthesis of Compounds 614 and 615

Compound 614 was synthesized from compound 411 of Example 3 by treatment with hydrochloric acid. Compound 615 was synthesized from 614 by reductive alkylation with pyridine-4-carboxaldehyde as shown in Scheme 158.

Scheme 158

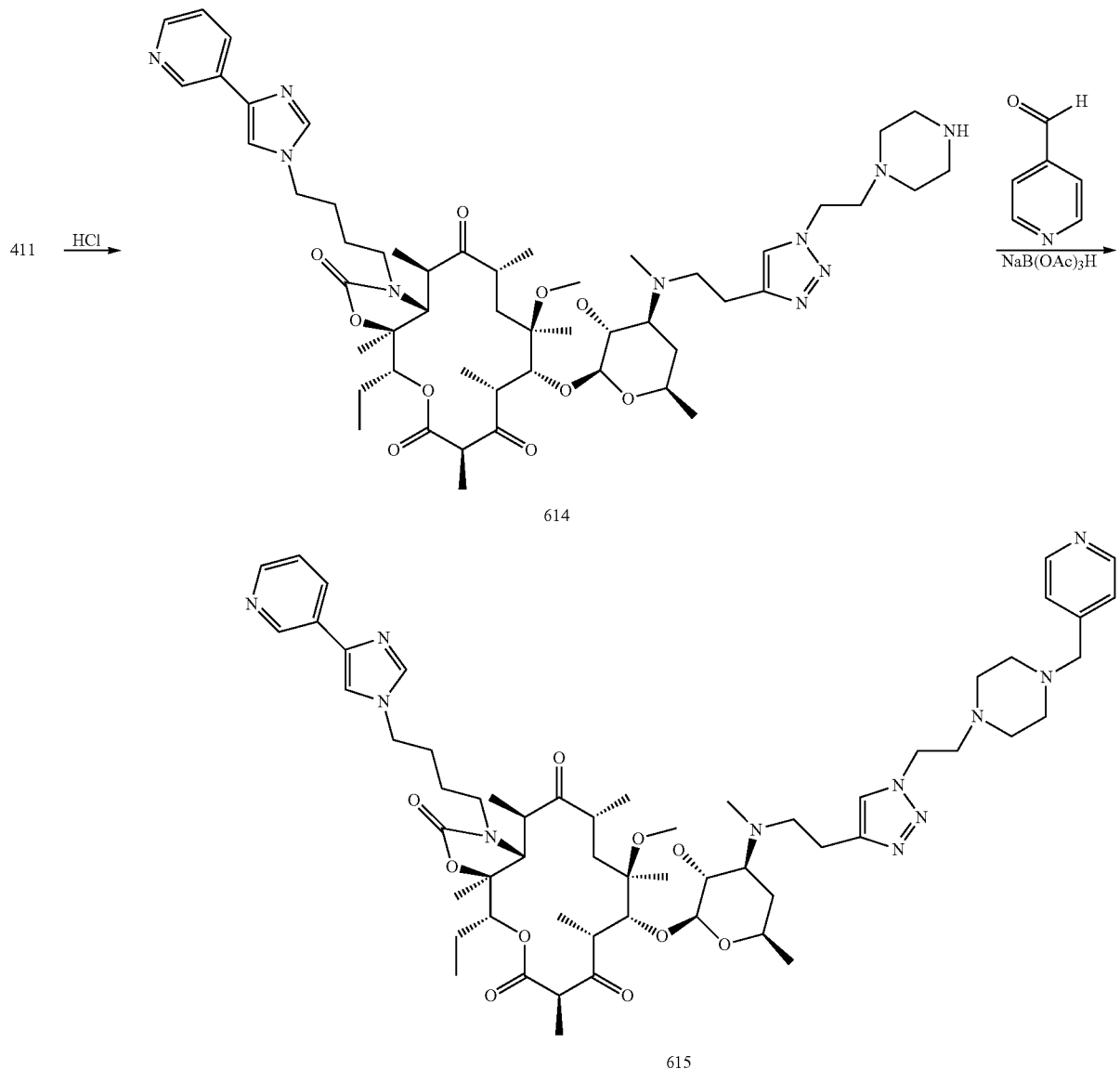

To a solution of 0.015 g (0.015 mmol) of 614, 0.006 g (0.060 mmol) of pyridine 4-carboxaldehyde in 1.0 ml of DMF was added 0.007 g (0.030 mmol) of NaBH(OAc)$_3$. The reaction mixture was allowed to stir at 25° C. for 4 h, DMF was removed by rotary evaporation, and the residue was purified through preparative TLC to give 0.003 g of compound 615. MS (M+1): 1097.

Synthesis of Compound 616

This compound was synthesized by heating a mixture of mesylate 82 (0.18 g, 0.46 mmol) and amine 2 (0.43 g, 0.55 mmol) in DMF (6 mL) and Hunig's was heated under reflux for 20 h. Solvent was evaporated off. The crude residue after solvent evaporation was suspended in CH$_2$Cl$_2$ (50 mL) and extracted with saturated NaHCO$_3$ (2×30 mL) and saturated brine (1×30 mL). The organic layer was decolorized with decolorizing charcoal and dried over Na$_2$SO$_4$. Solvent was evaporated off and the crude was purified on silica gel column, eluting with CH$_2$Cl$_2$/MeOH/H$_2$O 14:1:0.05 to 12:1: 0.05 to 10:1:0.05 to give 616 (0.048 g, 10%) as a white solid. LC-MS; M+H$^+$ 1031.5

Synthesis of Compound 82

Alcohol 80 was converted to the mesylate derivative 81 (LC-MS; M+H$^+$ 322.9). Compound 81 (0.39 g, 1.21 mmol) was reacted with alkyne 82a (0.13 mL, 2.22 mmol) in the presence of CuI (0.183 g, 0.96 mmol) in THF (10 mL) and Hunig's base (1 mL) mixture at room temperature within 12 h. The reaction was partitioned between saturated ammonium chloride (30 mL) and EtOAc (40 mL). The aqueous layer was extracted with EtOAc (4×20 mL) and the combine organic layer was dried over Na$_2$SO$_4$. Solvent was evaporated and the crude was purified on silica gel, eluting with CH$_2$Cl$_2$/MeOH 19:1 to 17:1 to furnish alcohol 82 as a white solid (0.171 g, 37%). LC-MS; M+H$^+$ 378.8

Synthesis of Compound 83
This compound was synthesized from compound 80 and alkyne 83a as described for the synthesis of 82 except that the crude 83 was used without further purification (90% yield, whitish-yellow solid). LC-MS; M+H$^+$ 392.9.
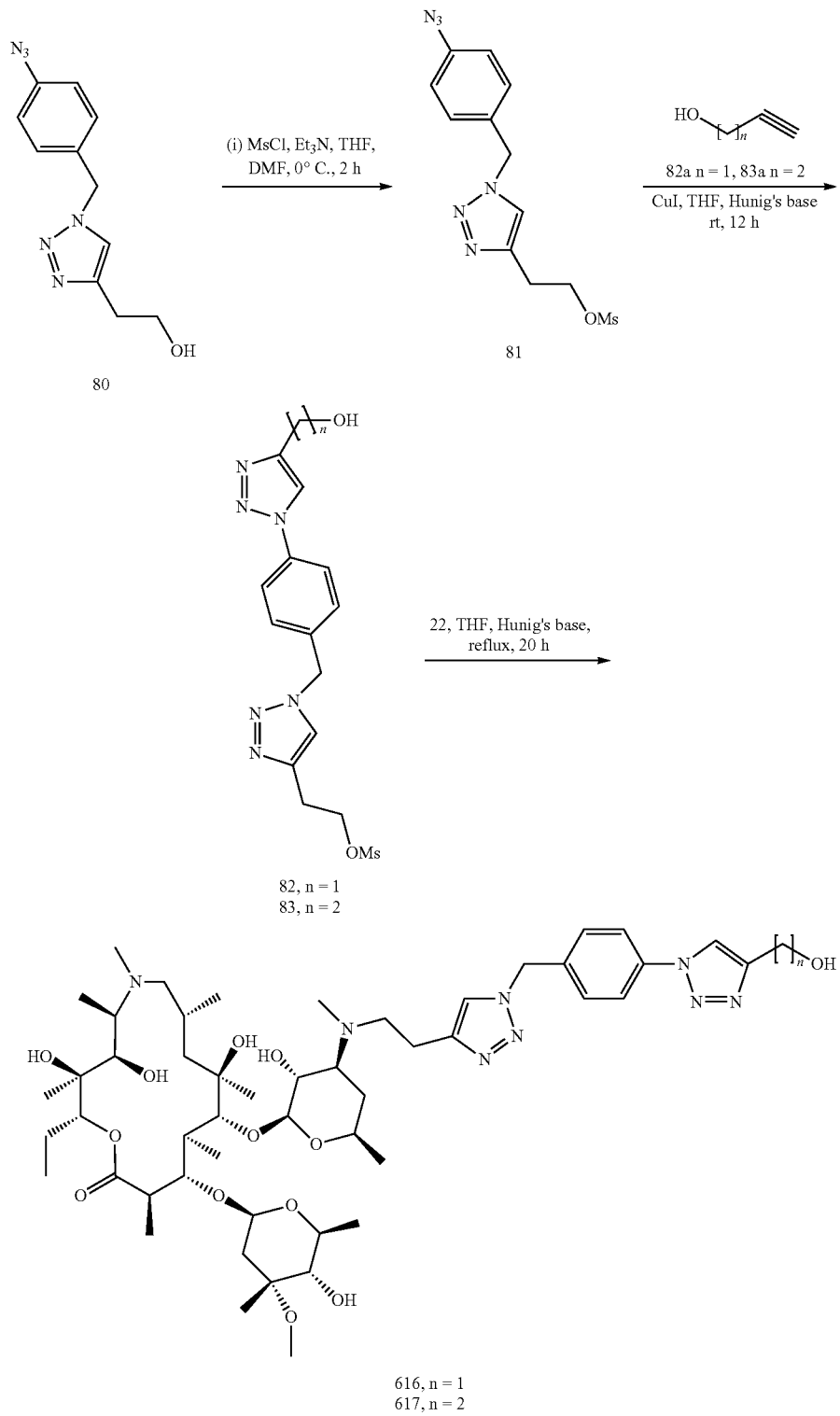
Scheme 159

Synthesis of Compound 617

This compound was synthesized by heating a mixture of alcohol 83 (0.14 g, 0.37 mmol) and amine 2 (0.346 g, 0.44 mmol) in DMF (4 mL) and Hunig's base (2 mL) at 110° C. for 24 h. Solvent was evaporated off and the crude was purified on silica gel column, eluting with CH$_2$Cl$_2$/MeOH/NH$_4$OH 20:1:0.05 to 18:1:0.05 to 15:1:0.05 to give 617 (0.173 g, 46%) as a white solid. LC-MS; M+H$^+$ 1017.4.

Synthesis of Compound 629

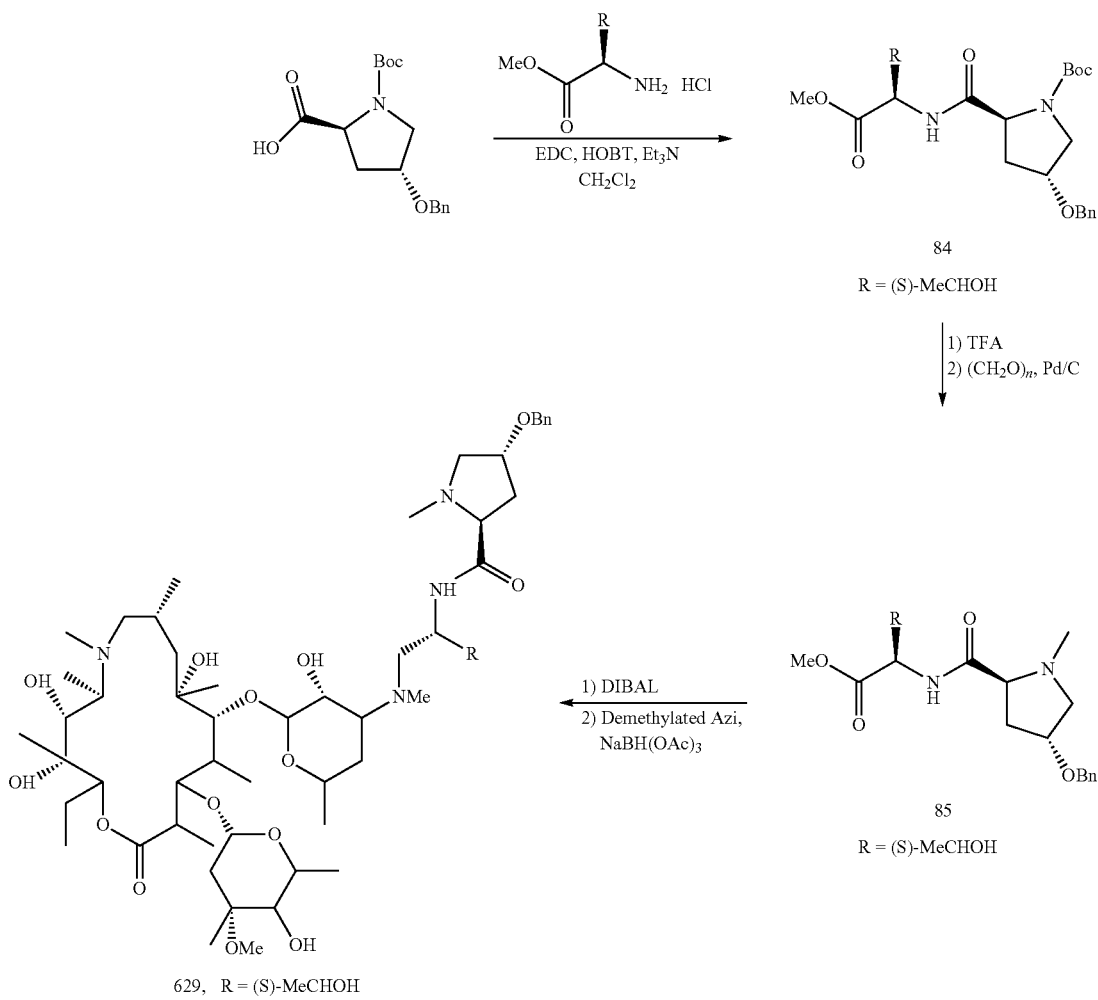

Synthesis of 84

To a stirred solution of Boc-Hyp(Bz)-OH (321.4 mg, 1.0 mmol), Thr-OMe hydrochloride (155.6 mg, 1.0 mmol), EDC (249.2 mg, 1.3 mmol), and HOBT (202.7 mg, 1.5 mmol) in CH$_2$Cl$_2$ was added Et$_3$N (0.42 mL) at rt. The resulting mixture was stirred at this temperature for 3 hr. Water (10 mL) was added, and the aqueous phase was extracted with CH$_2$Cl$_2$ (20 mL×3). The combined organic phase was washed with brine, and dried over MgSO$_4$. The concentrated residue was purified on silica gel with gradient elution from 1:9 to 7:3 of EtOAc:Hexanes to provide the dipeptide 84 as a clear oil (374.6 mg, 95%)

Synthesis of 85

The dipeptide 84 (775.0 mg) prepared above was dissolved in CH$_2$Cl$_2$/TFA (5 mL/5 mL). The mixture was stirred at room temperature for 1.5 hr and concentrated to dryness. The solid residue obtained was dissolved in EtOH (70 mL), treated with (CH$_2$O)$_n$ (514.5 mg, 17.15 mmol), Pd/C (77.5 mg) under hydrogen atmosphere (balloon) overnight. The mixture was filtered. The concentrated filtrate was purified on silica gel with gradient elution from 1:1 to 1:0 of EtOAc:Hexanes to give the N-methylated dipeptide 85 as a white solid (320.2 mg, 53%).

Synthesis of 629

DIBAL (1.0 M in toluene, 2.61 mL) was added in 10 min. to a stirred solution of the dipeptide 85 (320.2 mg, 1.05 mmol) in toluene at −78° C. After 2 hr at this temperature, the mixture was quenched by addition of methanol (0.6 mL). The mixture was diluted with EtOAc and then stirred with saturated Rochelle salt (5.2 mL) at 0° C. for 1.5 hr. The aqueous phase was extracted with EtOAc (20 mL×3). The combined organic phase was washed with brine, and dried over MgSO$_4$.

The concentrated residue obtained above was dissolved in 1,2-dichloroethane (10 mL), and treated with demethylated azith 2 (308.7 mg, 0.42 mmol), and NaBH(OAc)₃ (133.5 mg, 0.63 mmol). The mixture was stirred at room temperature for 16 hr. and quenched with saturated NaHCO₃. The organic phase was separated, washed with brine, and dried over MgSO₄. The concentrated residue was purified on silica gel with gradient elution from 0:1 to 15:85 of MeOH: CH₂Cl₂ to provide 629 as a white solid (105.8 mg, 25%).

Synthesis of Compounds 603, 604, 622, 627, and 628

Similar procedures to those described for compound 629 were employed to synthesize compounds 603, 604, 622, 627, and 628, all of which contain related dipeptide substituents. Compound 618 was synthesized as shown in scheme 161 below.

Synthesis of Intermediate 87

Dipeptide 86 (495.9 mg, 2.07 mmol) and Burgess reagent (738.6 mg, 3.10 mmol) were dissolved in THF (15 mL). The resulting mixture was refluxed for 3 hr. After the mixture was cooled down, water (10 mL) was added, and the mixture was extracted by EtOAc (30 mL×3). The combined organic phase was washed with brine and dried over MgSO₄. The concentrated residue was purified on silica gel with gradient elution from 0:1 to 3:7 of EtOAc: Hexanes to provide the dehydrated dipeptide as a light yellow oil (348.1 mg, 76%).

Synthesis of Compound 618

This compound was synthesized from intermediate 87 and amine 2 using the conditions described above for the synthesis of compound 629 from intermediate 85

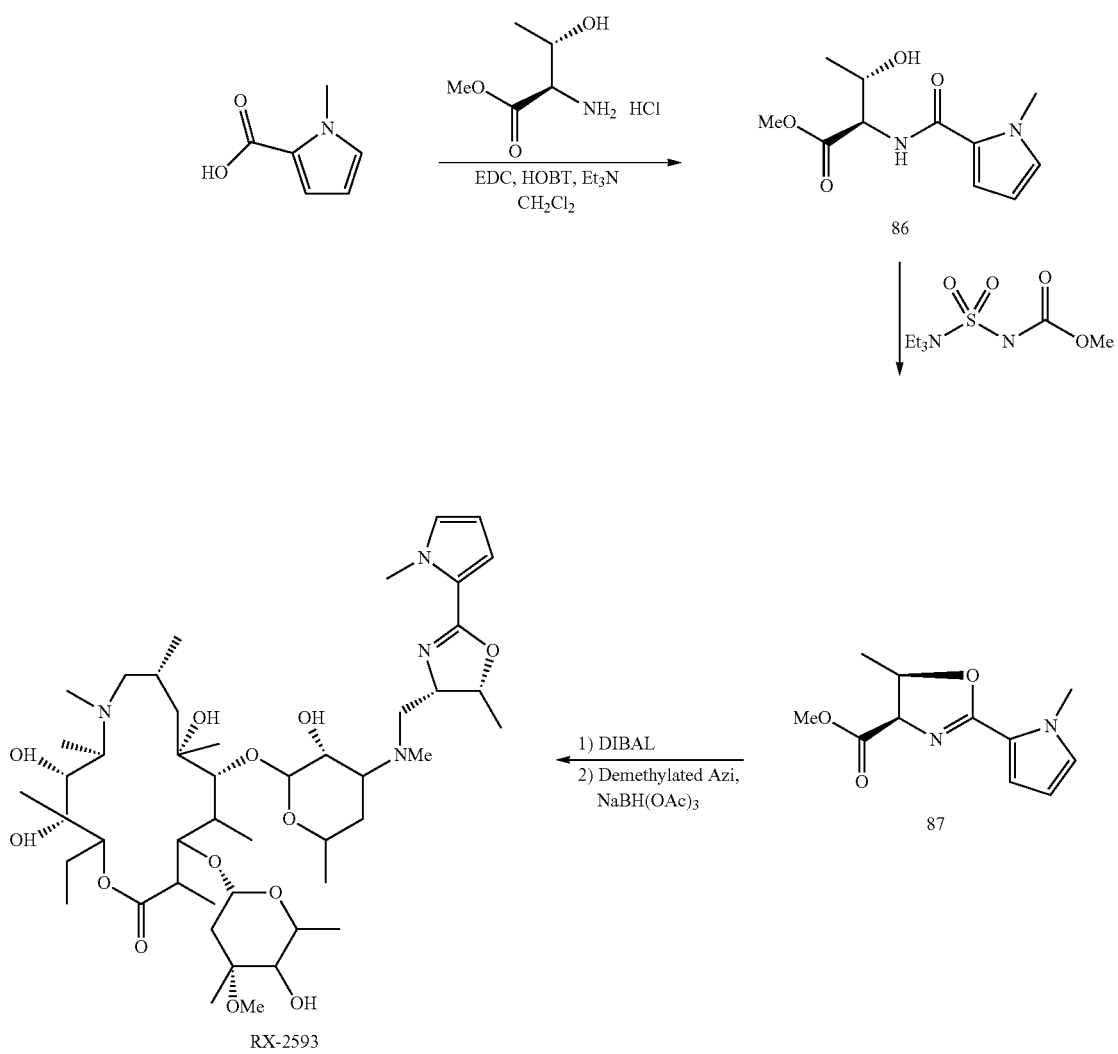

Synthesis of Compound 630

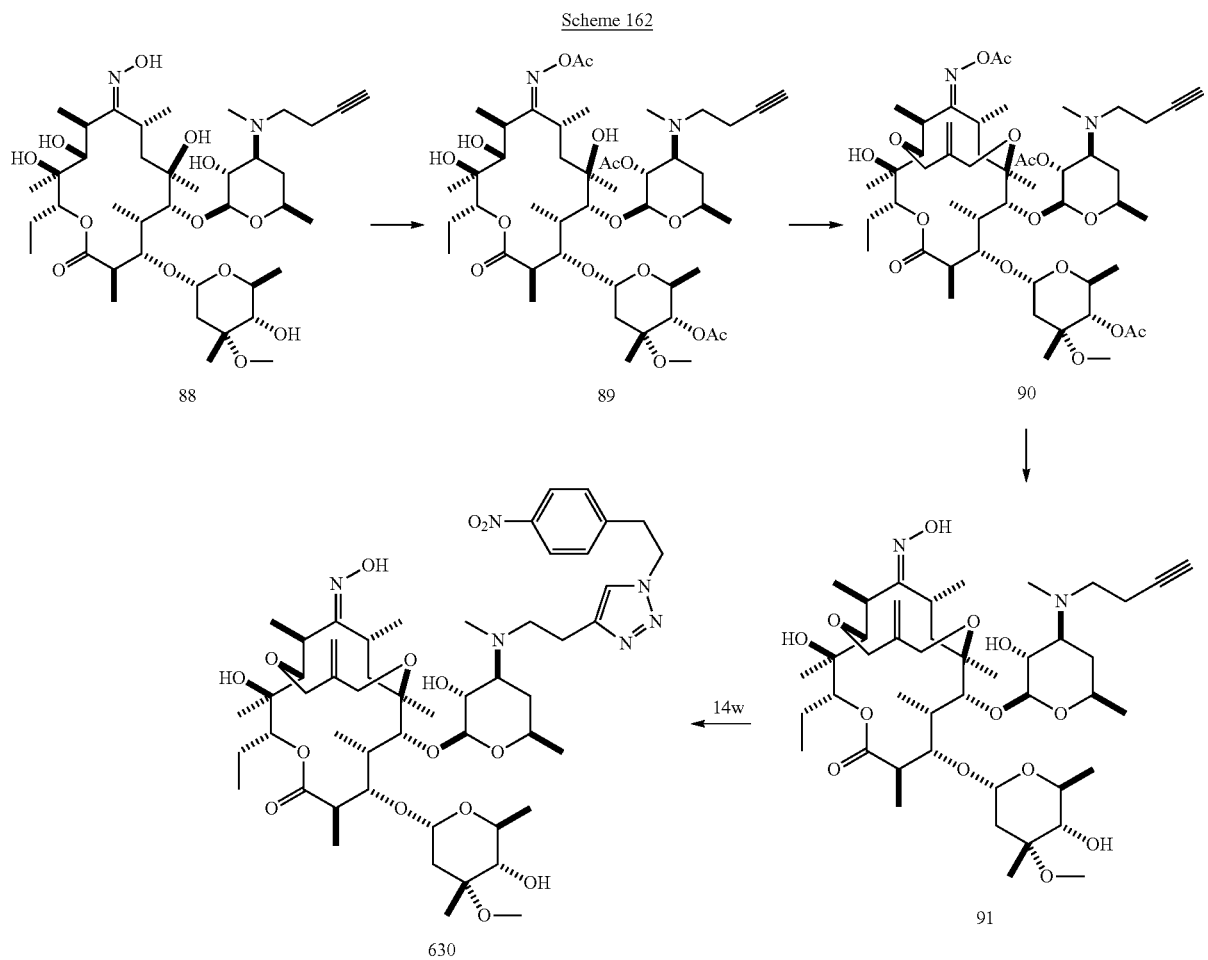

Scheme 162

Synthesis of compound 89

To a solution of compound 88 (2.00 g, 2.54 mmol) in THF (17 mL) at 0° C. was added Et$_3$N (1.50 mL, 10.67 mmol), followed by addition of acetic anhydride (946 μL, 9.91 mmol), then, DMAP (34 mg, 0.25 mmol). The mixture was stirred at 0° C. for 3 h, then, Et$_3$N (150 μL, 1.07 mmol) and acetic anhydride (95 μL, 0.99 mmol) were added. The mixture was stirred for 3 h, then, MeOH (2.0 ml) was added. The reaction mixture was concentrated and EtOAc (100 mL) was added, washed with saturated NaHCO$_3$ (30.0 mL), then, brine (30.0 mL), dried with Na$_2$SO$_4$, gave 2.28 g 89. The residue was used for the next step without further purification. MS (ESI) m/e 913 (M+H)$^+$.

Synthesis of Compound 90

To a solution of triacetate compound 89 (913 mg, 1.00 mmol, crude), 2-methylene-1,3-propane-[bis-(tert-butyl)carbonate] (865 mg, 3.00 mmol) and 1,4-bis(diphenylphosphino)-butane (dppb) (305 mg, 0.70 mmol) in THF (10 mL, degassed) was added Pd$_2$(dba)$_3$ (92 mg, 0.10 mmol) at room temperature. The mixture was refluxed for 12 h, then, the reaction mixture was concentrated and EtOAc (100 mL) was added. Washed with saturated NaHCO$_3$ (30 mL), brine (30 mL), dried with Na$_2$SO$_4$, The residue was isolated by silica gel chromatography (CH$_2$Cl$_2$ to 2% MeOH in CH$_2$Cl$_2$ containing 0.2% NH$_4$OH), gave 340 mg of 90 in 35% yield for two steps.MS (ESI) m/e 966 (M+H)$^+$.

Synthesis of Compound 91

A compound 90 (330 mg, 0.34 mmol) in MeOH (6 mL), was refluxed for 5 days. The residue was isolated by FC(CH$_2$Cl$_2$ to 2% MeOH in CH$_2$Cl$_2$ containing 0.2% NH$_4$OH), gave 143 mg of 91 in 50% yield.

MS (ESI) m/e 839 (M+H)$^+$.

Synthesis of Compound 630

A mixture of compound 91 (58 mg, 0.07 mmol) and azide 14w (40 mg, 0.21 mmol), CuI (2 mg) and Hunig's base (3 drops) in THF (0.3 mL) was stirred at room temperature for 10 hours. The reaction was quenched by addition of NH$_4$OH (3drops), saturated NH$_4$Cl (1 drop), water (2 mL) and CH$_2$Cl$_2$ (3 mL). After stirring for 20 min, the organic layer was separated and the aqueous phase was extracted with CH$_2$Cl$_2$ (10 mL×3), and dried with Na$_2$SO$_4$, The residue was isolated by FC (2/100/0.2 MeOH/CH$_2$Cl$_2$/NH$_4$OH), to give 62 mg of 630 in 86% yield. MS (ESI) m/e 1031 (M+H)$^+$.

Synthesis of Compounds 625 and 626
Scheme 163
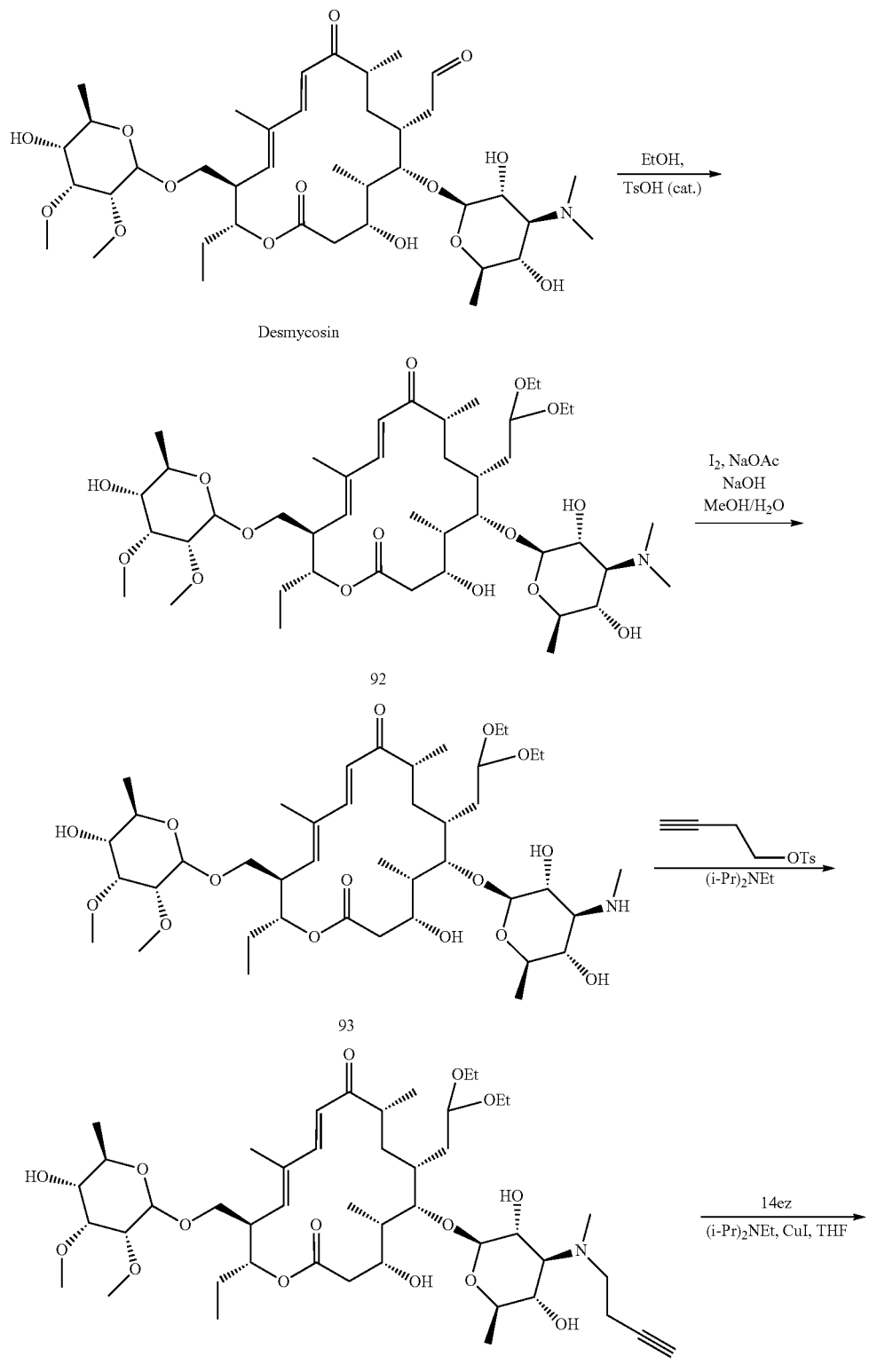

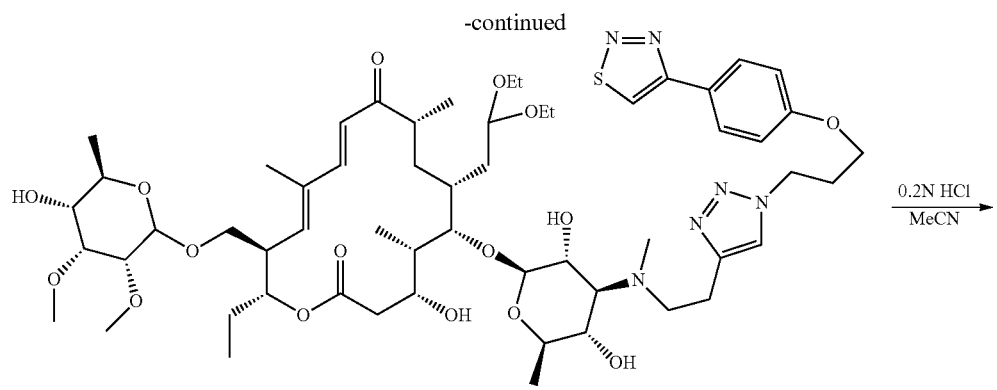

625

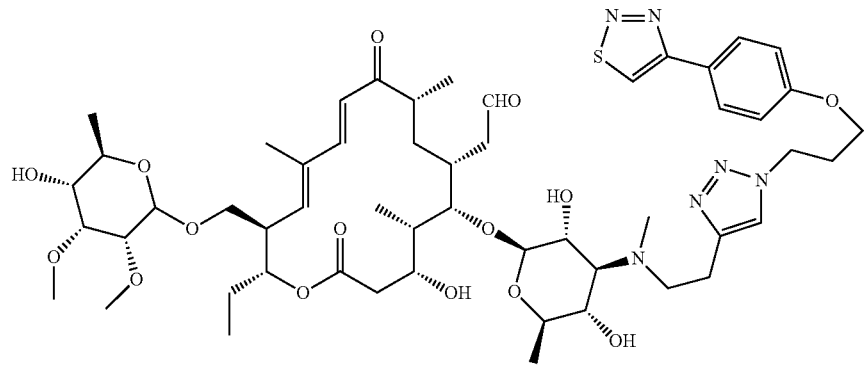

626

Synthesis of compound 92

To a solution of 1.00 g (1.30 mmol) of desmycocin in 10 ml of ethyl alcohol was added 0.260 g (1.36 mmol) of p-toluenesulfonic acid at ambient temperature. The reaction mixture was allowed to stir for 3 h, then diluted with 30 mL of saturated aqueous NaHCO$_3$, and extracted with EtOAc. The combined ethyl acetate extracts were washed with brine, dried over MgSO$_4$, and concentrated to give 1.220 g of 92 which was used without further purification.

Synthesis of Compound 93

To a mixture of 0.250 g (0.29 mmol) of 92 and 0.486 g (5.92 mmol) of NaOAc in 10 mL of MeOH/H$_2$O (80% MeOH) at 55° C. was added 0.075 g (0.29 mmol) of solid iodine. The pH value of the reaction mixture was maintained at 9 by addition of 1 N NaOH at time intervals of 10, 30, and 60 minutes after the addition of iodine. The reaction mixture was stirred at 55° C. for 1 h following the last addition of NaOH solution, then diluted with 25 mL of saturated NaHCO$_3$ and extracted with EtOAc (50 ml×2). The combined EtOAc extracts were washed sequentially with 15 ml of 5% NaS$_2$O$_4$ and brine, dried over MgSO$_4$, filtered and concentrated to give 0.221 g of 93.

Synthesis of Alkyne 94

A mixture of 0.200 g (0.24 mmol) of 93, 0.270 g (1.20 mmol) of tosylate 11, 0.311 g (2.41 mmol) of di-isopropylethylamine and 10 mg of dimethylaminopyridine in 5 ml of THF was allowed to stir at 55° C. for 48 h. The mixture was diluted with 20 ml of saturated NaHCO$_3$, extracted with EtOAc (30 ml×3). The combined organic layers were washed with brine (20 ml), dried over MgSO$_4$, filtered and concentrated to give 0.065 g of desired product 94 and 0.063 g of recovered starting material 93 after purification through flash column chromatography on silica gel.

Synthesis of Compound 625

A solution of 0.300 g (0.03 mmol) of alkyne 94, 0.018 g (0.06 mmol) of azide 14ez and 0.006 g (0.03 mmol) of CuI in 3.0 ml of THF was degassed, then put under argon. To the mixture was added 4 drops of Hunig's base. The reaction was stirred at 25° C. for 6 h. To it was added 20 mL of 10% NH$_4$OH, stirred for 10 min, extracted with CH$_2$Cl$_2$ (30 mL×3), combined organic layers were washed with brine, dried, concentrated, purified through preparative TLC to give 0.020 g of the final product. MS (ESI) m/e 1145 (M+H)$^+$.

Synthesis of Compound 626

A solution of 0.015 g (0.013 mmol) of compound 625 in 1.0 ml of 0.2 N HCl and 1.0 mL of acetonitrile was stirred at 25° C. for 4 h. To it was added 15 mL of saturated aqueous NaHCO$_3$ solution, the aqueous layer was then extracted with CH$_2$Cl$_2$ (40 mL×3), combined organic layers were washed with brine, dried, and concentrated to give 0.003 g of pure 626. MS (ESI) m/e 1172 (M+H)$^+$.

Synthesis of Compounds 623 and 624

These compounds were synthesized from intermediate 94 and azide 14w using the procedures described above for compounds 625 and 626.

Example 12
Compounds 701-756
Additional compounds of the invention are shown in Table 13 below. These compounds are made in accordance with the procedures presented in Examples 1-11 above.
TABLE 13
| Compound Number | Structure |
| --- | --- |
| 701 | 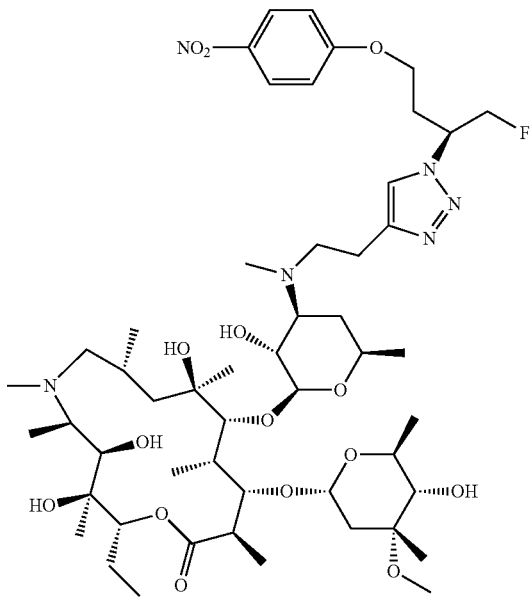 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CF)CCOc4ccc([N+](=O)[O-])cc4)nn3)[C@H]2O)[C@](C)(O)CC[C@@H](C)CN(C)[C@H](C)[C@@H](O)C[C@]1(C)O] |
| 702 | 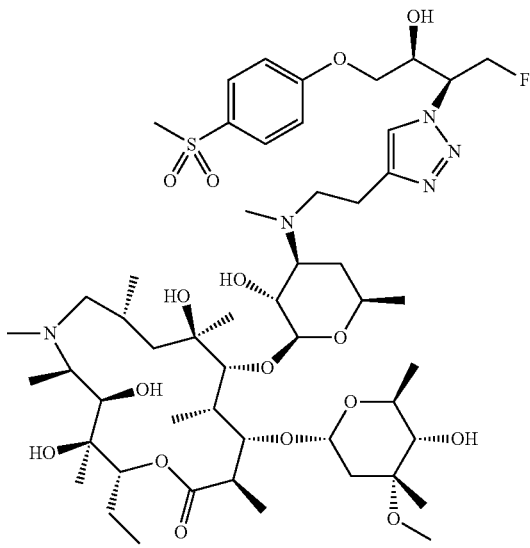 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CF)[C@H](O)COc4ccc(S(C)(=O)=O)cc4)nn3)[C@H]2O)[C@](C)(O)CC[C@@H](C)CN(C)[C@H](C)[C@@H](O)C[C@]1(C)O] |

TABLE 13-continued
| Compound Number | Structure |
|---|---|
| 703 | 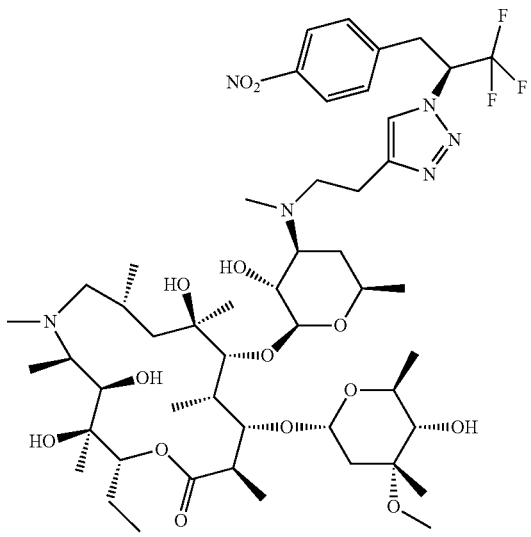 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@@H](Cc4ccc([N+](=O)[O-])cc4)C(F)(F)F)nn3)[C@H]2O)[C@](C)(O)CC[C@@H](C)CN(C)[C@H](C)[C@@H](O)C[C@]1(C)O] |
| 704 | 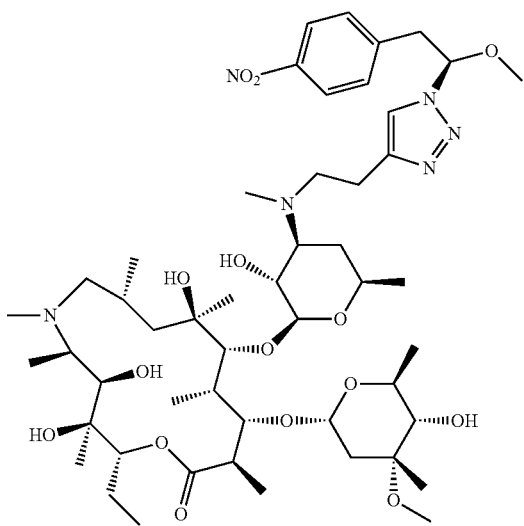 |
| 705 | 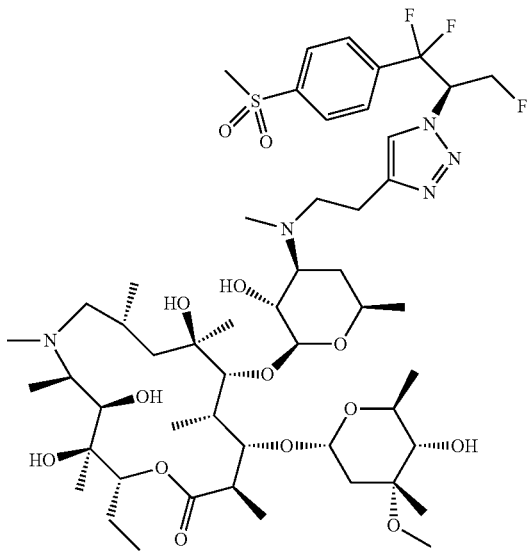 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CF)C(F)(F)c4ccc(S(C)(=O)=O)cc4)nn3)[C@H]2O)[C@](C)(O)CC[C@@H](C)CN(C)[C@H](C)[C@@H](O)C[C@]1(C)O] |

TABLE 13-continued

| Compound Number | Structure |
|---|---|
| 706 | 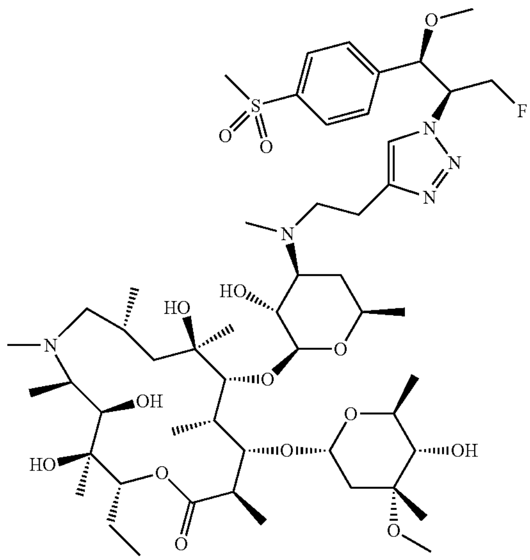 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CF)[C@H](OC)c4ccc(S(C)(=O)=O)cc4)nn3)[C@H]2O)[C@](C)(O)CC[C@@H](C)CN(C)[C@H](C)[C@@H](O)C[C@]1(C)O] |
| 707 | 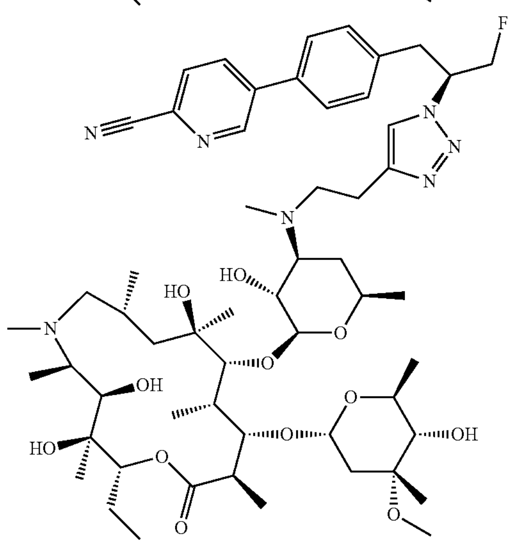 |
| 708 | 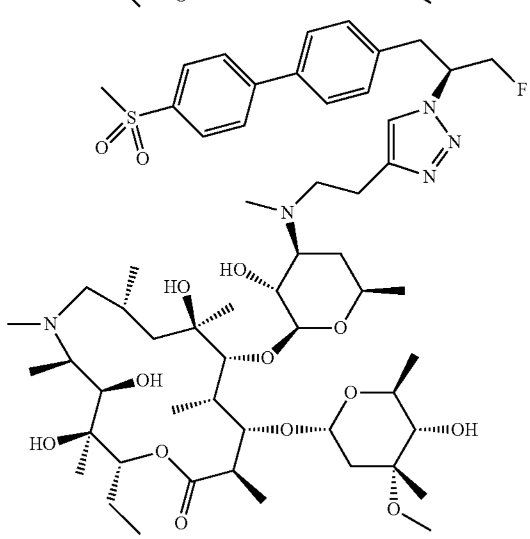 |

TABLE 13-continued

| Compound Number | Structure |
|---|---|
| 709 | 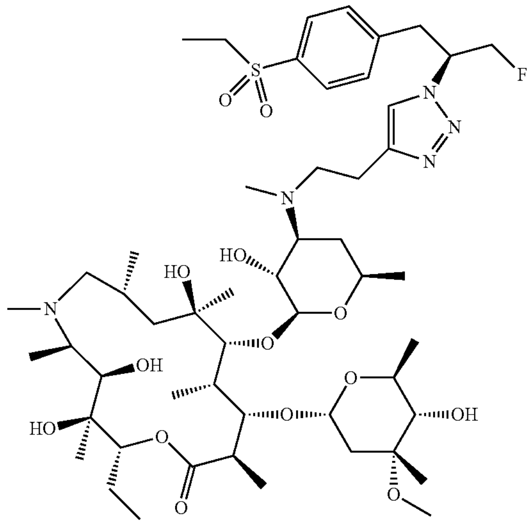 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CF)Cc4ccc(S(=O)(=O)CC)cc4)nn3)[C@H]2O)[C@](C)(O)CC[C@@H](C)CN(C)[C@H](C)[C@@H](O)C[C@]1(C)O] |
| 710 | 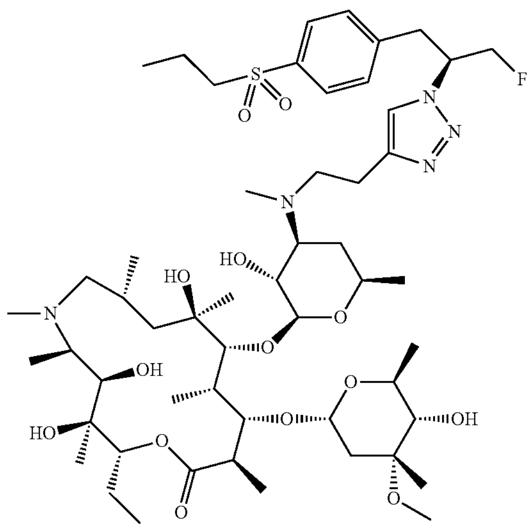 [SMILES: CCCS(=O)(=O)c1ccc(C[C@@H](CF)n2cc(CCN(C)[C@H]3C[C@@H](C)O[C@@H](O[C@@H]4[C@@H](C)[C@H](O[C@H]5C[C@@](C)(OC)[C@@H](O)[C@H](C)O5)[C@@H](C)C(=O)O[C@H](CC)[C@@](C)(O)C[C@H](O)[C@@H](C)N(C)C[C@H](C)CC[C@@]4(C)O)[C@@H]3O)nn2)cc1] |
| 711 | 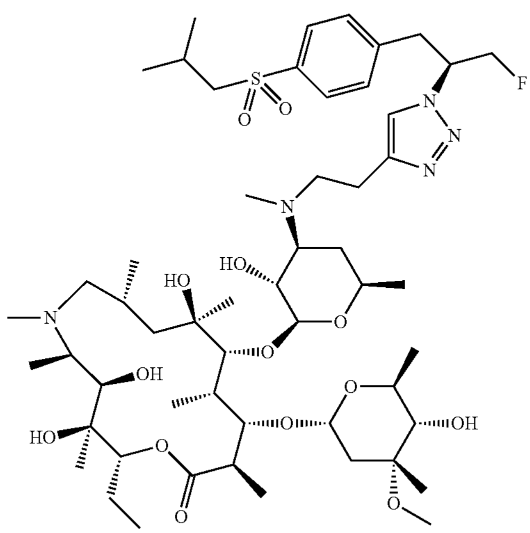 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CF)Cc4ccc(S(=O)(=O)CC(C)C)cc4)nn3)[C@H]2O)[C@](C)(O)CC[C@@H](C)CN(C)[C@H](C)[C@@H](O)C[C@]1(C)O] |

TABLE 13-continued
| Compound Number | Structure |
|---|---|
| 712 | 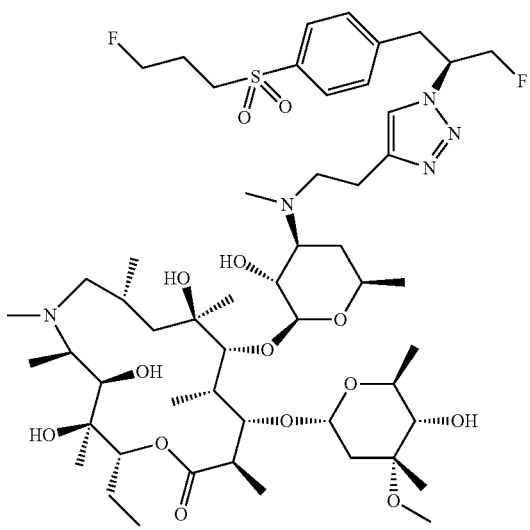 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CF)Cc4ccc(S(=O)(=O)CCCF)cc4)nn3)[C@H]2O)[C@](C)(O)CC[C@@H](C)CN(C)[C@H](C)[C@@H](O)C[C@]1(C)O] |
| 713 | 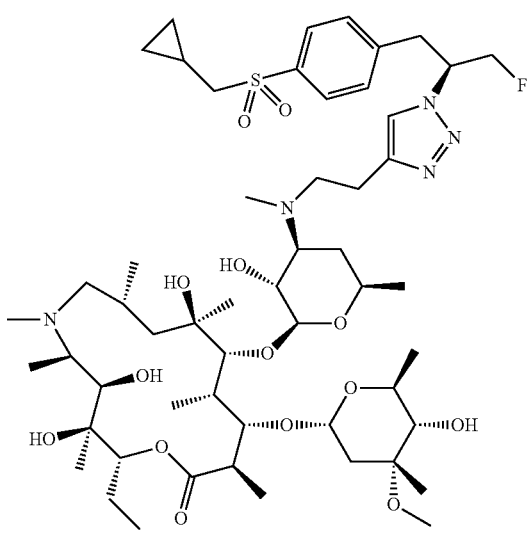 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CF)Cc4ccc(S(=O)(=O)CC5CC5)cc4)nn3)[C@H]2O)[C@](C)(O)CC[C@@H](C)CN(C)[C@H](C)[C@@H](O)C[C@]1(C)O] |
| 714 | 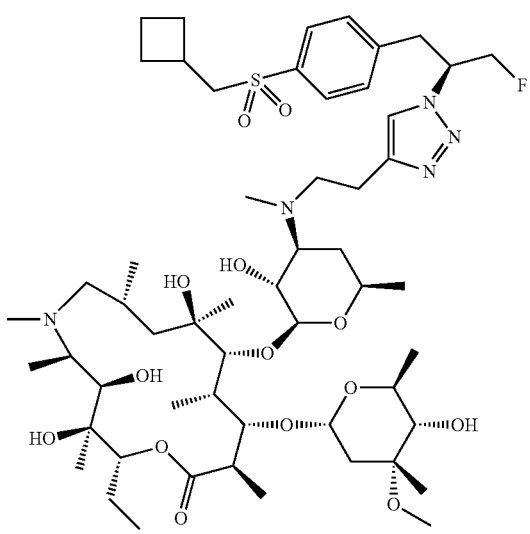 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CF)Cc4ccc(S(=O)(=O)CC5CCC5)cc4)nn3)[C@H]2O)[C@](C)(O)CC[C@@H](C)CN(C)[C@H](C)[C@@H](O)C[C@]1(C)O] |

TABLE 13-continued

| Compound Number | Structure |
| --- | --- |
| 715 | 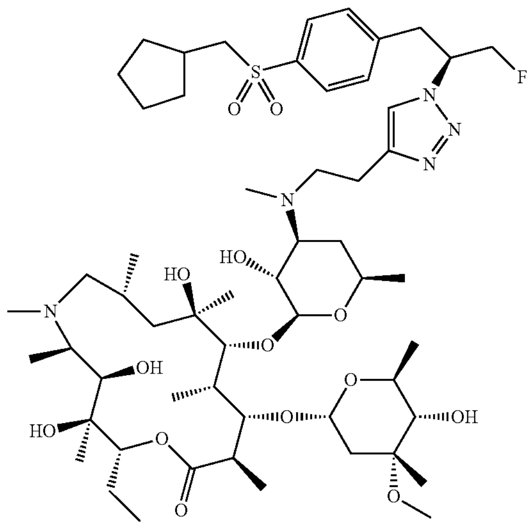 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CF)Cc4ccc(S(=O)(=O)CC5CCCC5)cc4)nn3)[C@H]2O)[C@](C)(O)CC[C@@H](C)CN(C)[C@H](C)[C@@H](O)C[C@]1(C)O] |
| 716 | 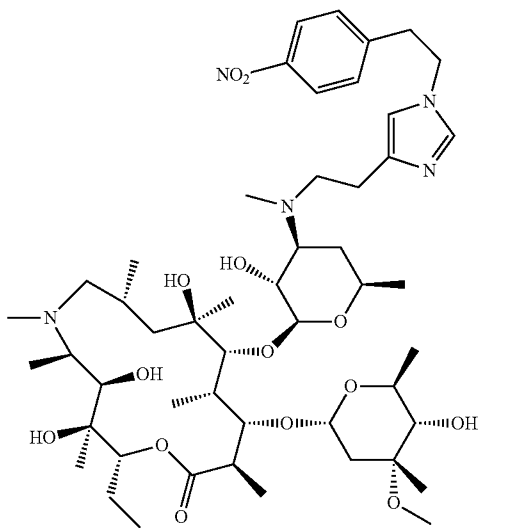 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc([N+](=O)[O-])cc4)cn3)[C@H]2O)[C@](C)(O)CC[C@@H](C)CN(C)[C@H](C)[C@@H](O)C[C@]1(C)O] |
| 717 | 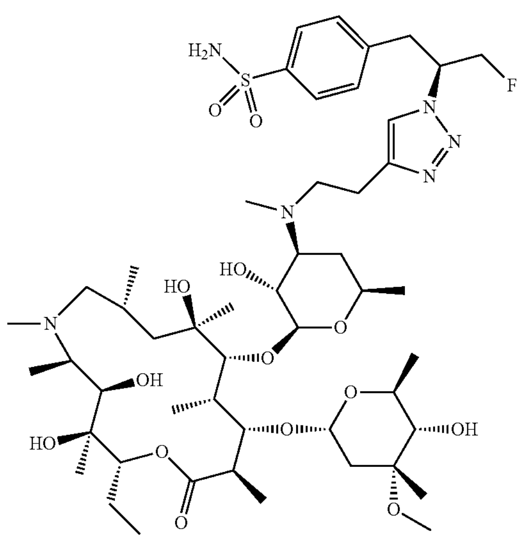 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CF)Cc4ccc(S(N)(=O)=O)cc4)nn3)[C@H]2O)[C@](C)(O)CC[C@@H](C)CN(C)[C@H](C)[C@@H](O)C[C@]1(C)O] |

TABLE 13-continued
| Compound Number | Structure |
|---|---|
| 718 | 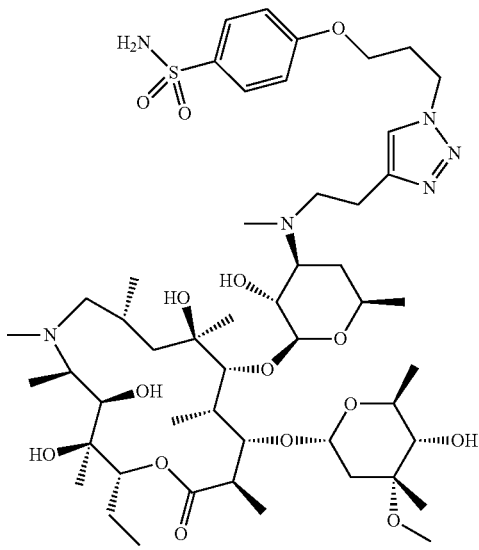 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(S(N)(=O)=O)cc4)nn3)[C@H]2O)[C@](C)(O)CC[C@@H](C)CN(C)[C@H](C)[C@@H](O)C[C@]1(C)O] |
| 719 | 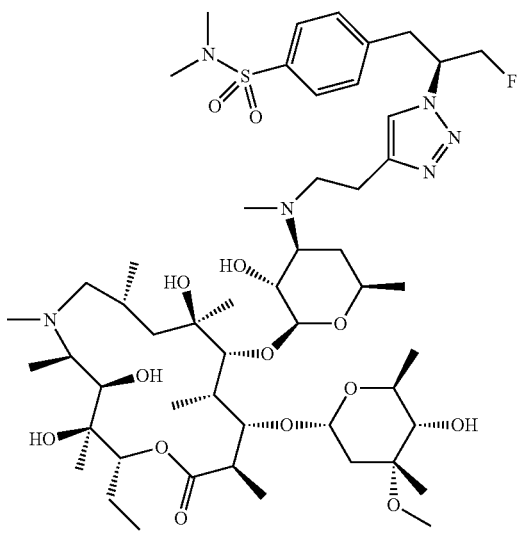 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CF)Cc4ccc(S(=O)(=O)N(C)C)cc4)nn3)[C@H]2O)[C@](C)(O)CC[C@@H](C)CN(C)[C@H](C)[C@@H](O)C[C@]1(C)O] |
| 720 | 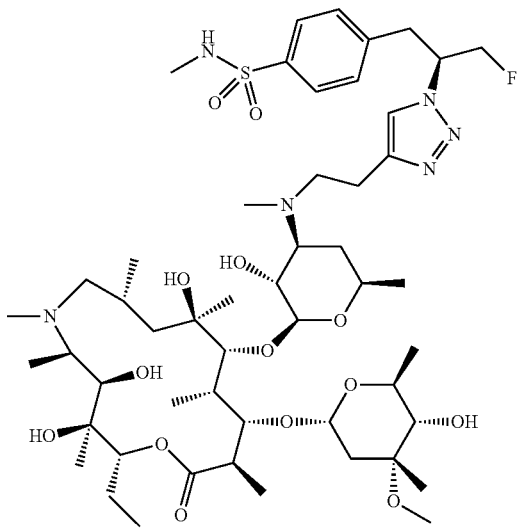 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CF)Cc4ccc(S(=O)(=O)NC)cc4)nn3)[C@H]2O)[C@](C)(O)CC[C@@H](C)CN(C)[C@H](C)[C@@H](O)C[C@]1(C)O] |

TABLE 13-continued

| Compound Number | Structure |
|---|---|
| 721 | 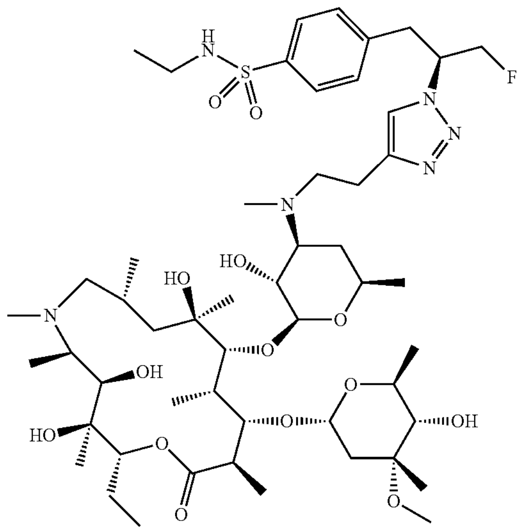 [SMILES: CCNS(=O)(=O)c1ccc(C[C@@H](CF)n2cc(CCN(C)[C@H]3C[C@@H](C)O[C@@H](O[C@@H]4[C@@H](C)[C@H](O[C@H]5C[C@@](C)(OC)[C@@H](O)[C@H](C)O5)[C@@H](C)C(=O)O[C@H](CC)[C@@](C)(O)C[C@H](O)[C@@H](C)N(C)C[C@H](C)CC[C@@]4(C)O)[C@@H]3O)nn2)cc1] |
| 722 | 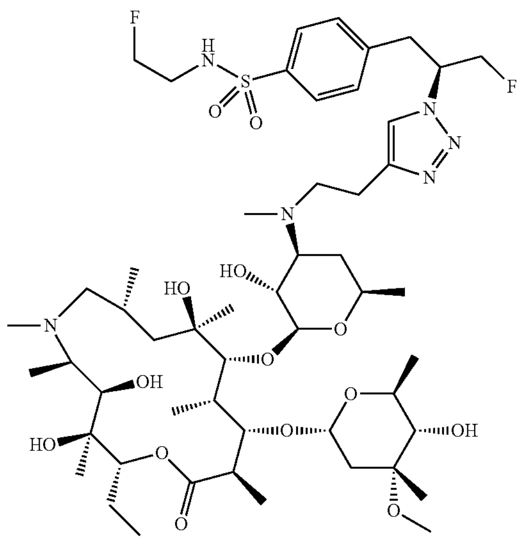 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CF)Cc4ccc(S(=O)(=O)NCCF)cc4)nn3)[C@H]2O)[C@](C)(O)CC[C@@H](C)CN(C)[C@H](C)[C@@H](O)C[C@]1(C)O] |
| 723 | 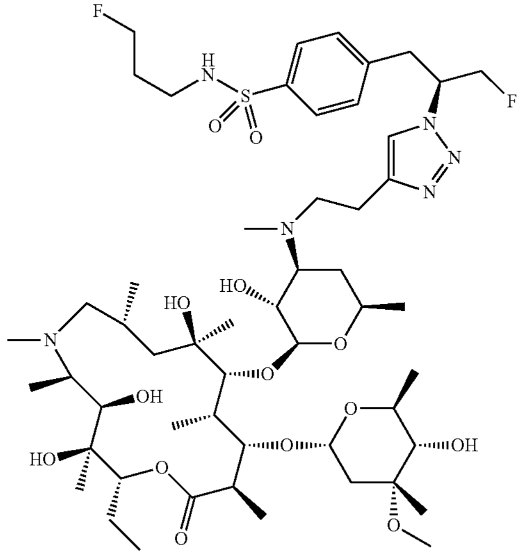 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CF)Cc4ccc(S(=O)(=O)NCCCF)cc4)nn3)[C@H]2O)[C@](C)(O)CC[C@@H](C)CN(C)[C@H](C)[C@@H](O)C[C@]1(C)O] |

TABLE 13-continued
| Compound Number | Structure |
|---|---|
| 724 | 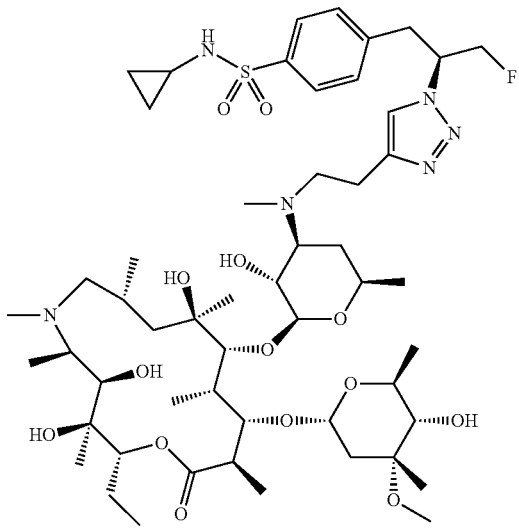 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CF)Cc4ccc(S(=O)(=O)NC5CC5)cc4)nn3)[C@H]2O)[C@](C)(O)CC[C@@H](C)CN(C)[C@H](C)[C@@H](O)C[C@]1(C)O] |
| 725 | 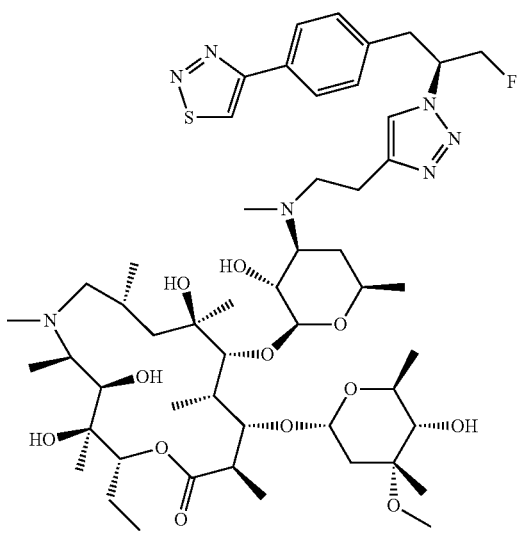 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CF)Cc4ccc(-c5csnn5)cc4)nn3)[C@H]2O)[C@](C)(O)CC[C@@H](C)CN(C)[C@H](C)[C@@H](O)C[C@]1(C)O] |
| 726 | 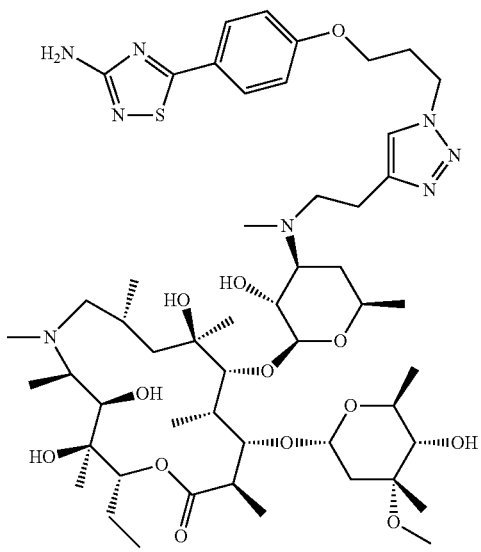 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCCOc4ccc(-c5nc(N)ns5)cc4)nn3)[C@H]2O)[C@](C)(O)CC[C@@H](C)CN(C)[C@H](C)[C@@H](O)C[C@]1(C)O] |

TABLE 13-continued
| Compound Number | Structure |
|---|---|
| 727 | 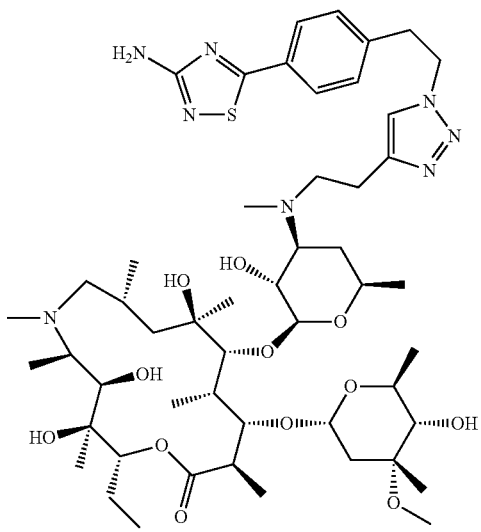 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc(-c5nc(N)ns5)cc4)nn3)[C@H]2O)[C@](C)(O)CC[C@@H](C)CN(C)[C@H](C)[C@@H](O)C[C@]1(C)O] |
| 728 | 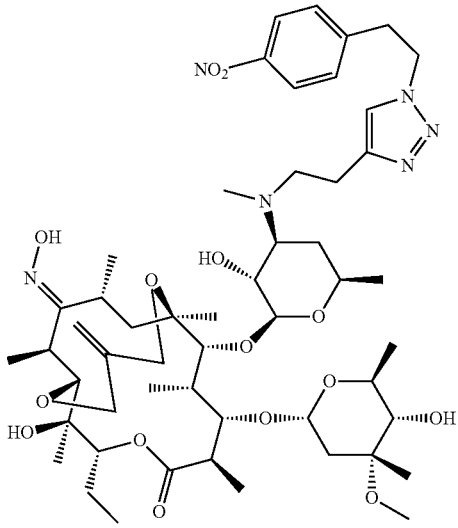 [SMILES: C=C1CO[C@@H]2[C@@H](C)/C(=N/O)[C@H](C)C[C@@](C)(OC1)[C@H](O[C@@H]1O[C@H](C)C[C@H](N(C)CCc3cn(CCc4ccc([N+](=O)[O-])cc4)nn3)[C@H]1O)[C@@H](C)[C@H](O[C@H]1C[C@@](C)(OC)[C@@H](O)[C@H](C)O1)[C@@H](C)C(=O)O[C@H](CC)[C@@]2(C)O] |
| 729 | 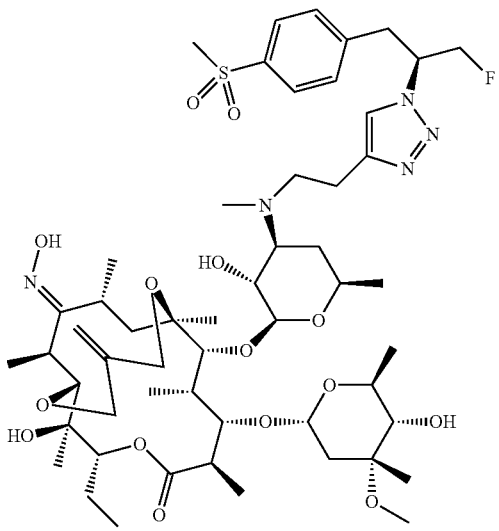 [SMILES: C=C1CO[C@@H]2[C@@H](C)/C(=N/O)[C@H](C)C[C@@](C)(OC1)[C@H](O[C@@H]1O[C@H](C)C[C@H](N(C)CCc3cn([C@H](CF)Cc4ccc(S(C)(=O)=O)cc4)nn3)[C@H]1O)[C@@H](C)[C@H](O[C@H]1C[C@@](C)(OC)[C@@H](O)[C@H](C)O1)[C@@H](C)C(=O)O[C@H](CC)[C@@]2(C)O] |

TABLE 13-continued
| Compound Number | Structure |
| --- | --- |
| 730 | 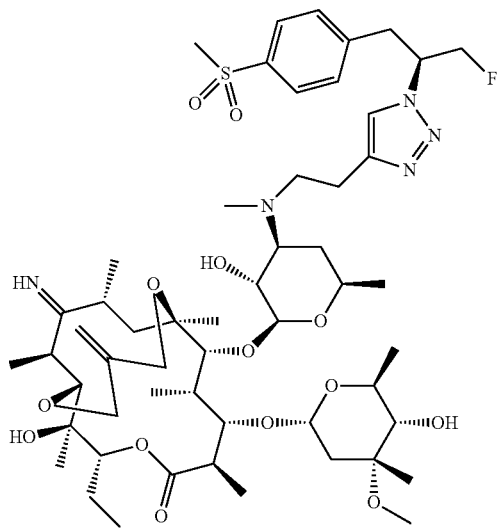 [SMILES: C=C1CO[C@@H]2[C@@H](C)C(=N)[C@H](C)C[C@@](C)(OC1)[C@H](O[C@@H]1O[C@H](C)C[C@H](N(C)CCc3cn([C@H](CF)Cc4ccc(S(C)(=O)=O)cc4)nn3)[C@H]1O)[C@@H](C)[C@H](O[C@H]1C[C@@](C)(OC)[C@@H](O)[C@H](C)O1)[C@@H](C)C(=O)O[C@H](CC)[C@@]2(C)O] |
| 731 | 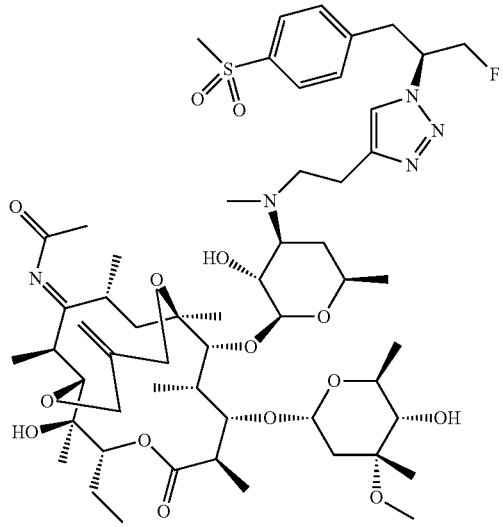 [SMILES: C=C1CO[C@@H]2[C@@H](C)/C(=N/C(C)=O)[C@H](C)C[C@@](C)(OC1)[C@H](O[C@@H]1O[C@H](C)C[C@H](N(C)CCc3cn([C@H](CF)Cc4ccc(S(C)(=O)=O)cc4)nn3)[C@H]1O)[C@@H](C)[C@H](O[C@H]1C[C@@](C)(OC)[C@@H](O)[C@H](C)O1)[C@@H](C)C(=O)O[C@H](CC)[C@@]2(C)O] |
| 732 | 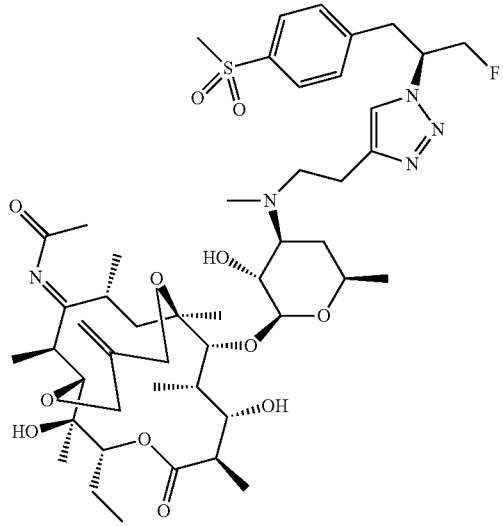 |

TABLE 13-continued
| Compound Number | Structure |
|---|---|
| 733 | 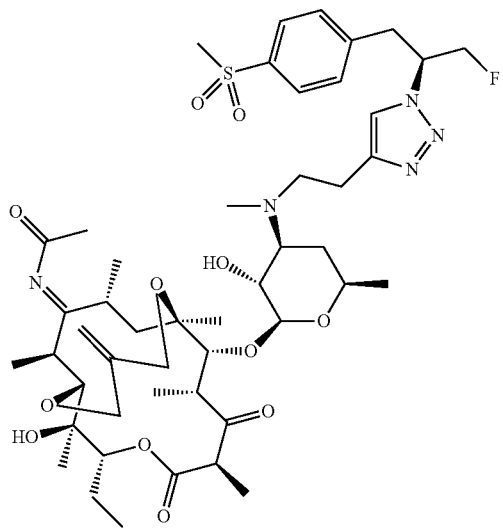 [SMILES: C=C1CO[C@@H]2[C@@H](C)/C(=N/C(C)=O)[C@H](C)C[C@@](C)(OC1)[C@H](O[C@@H]1O[C@H](C)C[C@H](N(C)CCc3cn([C@H](CF)Cc4ccc(S(C)(=O)=O)cc4)nn3)[C@H]1O)[C@@H](C)C(=O)[C@@H](C)C(=O)O[C@H](CC)[C@@]2(C)O] |
| 734 | 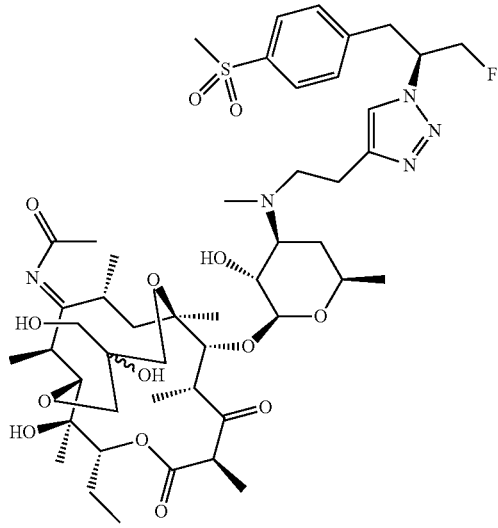 [SMILES: CC[C@H]1OC(=O)[C@H](C)C(=O)[C@H](C)[C@@H](O[C@@H]2O[C@H](C)C[C@H](N(C)CCc3cn([C@H](CF)Cc4ccc(S(C)(=O)=O)cc4)nn3)[C@H]2O)[C@@]2(C)C[C@@H](C)/C(=N\C(C)=O)[C@H](C)[C@@H](OCC(O)(CO)CO2)[C@]1(C)O] |
| 735 | 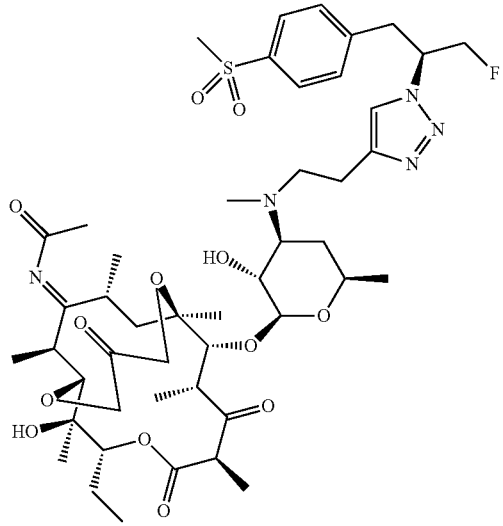 [SMILES: CC[C@H]1OC(=O)[C@H](C)C(=O)[C@H](C)[C@@H](O[C@@H]2O[C@H](C)C[C@H](N(C)CCc3cn([C@H](CF)Cc4ccc(S(C)(=O)=O)cc4)nn3)[C@H]2O)[C@@]2(C)C[C@@H](C)/C(=N\C(C)=O)[C@H](C)[C@@H](OCC(=O)CO2)[C@]1(C)O] |

TABLE 13-continued

| Compound Number | Structure |
|---|---|
| 736 | 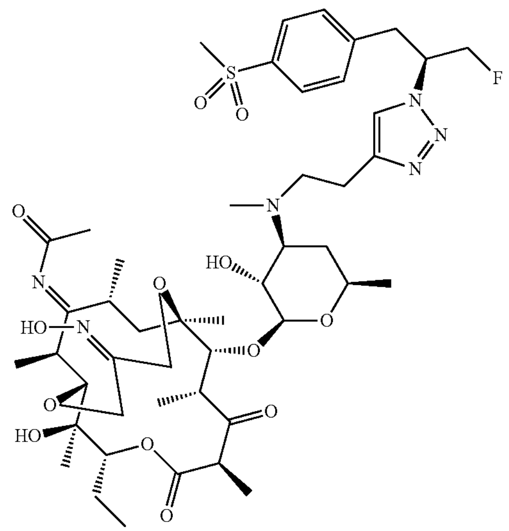 [SMILES: CC[C@H]1OC(=O)[C@H](C)C(=O)[C@H](C)[C@@H](O[C@@H]2O[C@H](C)C[C@H](N(C)CCc3cn([C@H](CF)Cc4ccc(S(C)(=O)=O)cc4)nn3)[C@H]2O)[C@@]2(C)C[C@@H](C)/C(=N\C(C)=O)[C@H](C)[C@@H](OC/C(=N\O)CO2)[C@]1(C)O] |
| 737 | 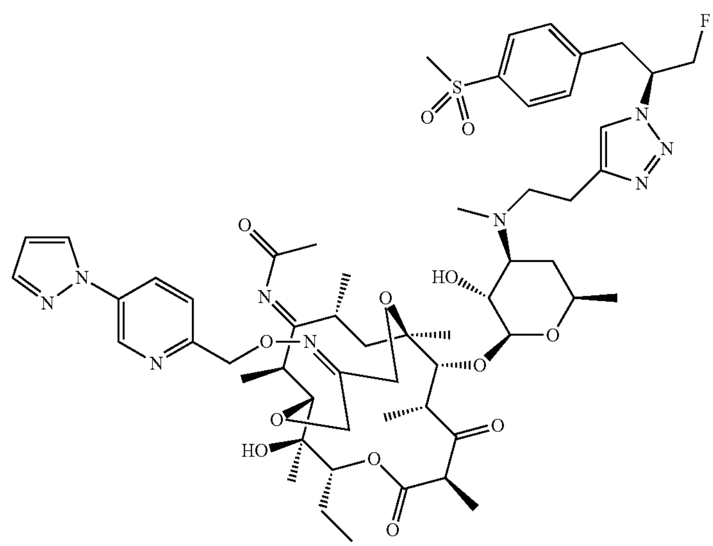 [SMILES: CC[C@H]1OC(=O)[C@H](C)C(=O)[C@H](C)[C@@H](O[C@@H]2O[C@H](C)C[C@H](N(C)CCc3cn([C@H](CF)Cc4ccc(S(C)(=O)=O)cc4)nn3)[C@H]2O)[C@@]2(C)C[C@@H](C)/C(=N\C(C)=O)[C@H](C)[C@@H](OC/C(=N\OCc3ccc(-n4cccn4)cn3)CO2)[C@]1(C)O] |
| 738 | 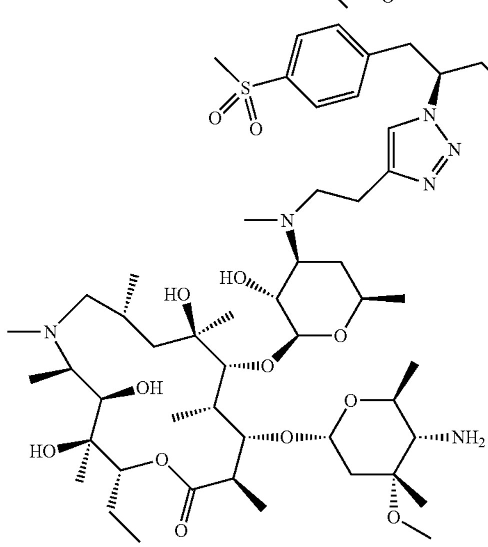 |

TABLE 13-continued
| Compound Number | Structure |
|---|---|
| 739 | 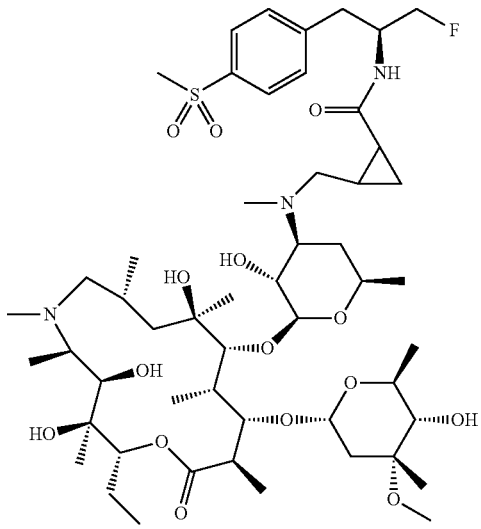 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CC3CC3C(=O)N[C@H](CF)Cc3ccc(S(C)(=O)=O)cc3)[C@H]2O)[C@](C)(O)CC[C@@H](C)CN(C)[C@H](C)[C@@H](O)C[C@]1(C)O] |
| 740 | 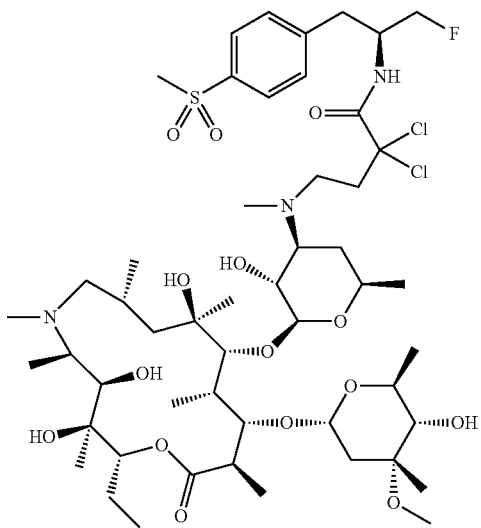 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCC(Cl)(Cl)C(=O)N[C@H](CF)Cc3ccc(S(C)(=O)=O)cc3)[C@H]2O)[C@](C)(O)CC[C@@H](C)CN(C)[C@H](C)[C@@H](O)C[C@]1(C)O] |
| 741 | 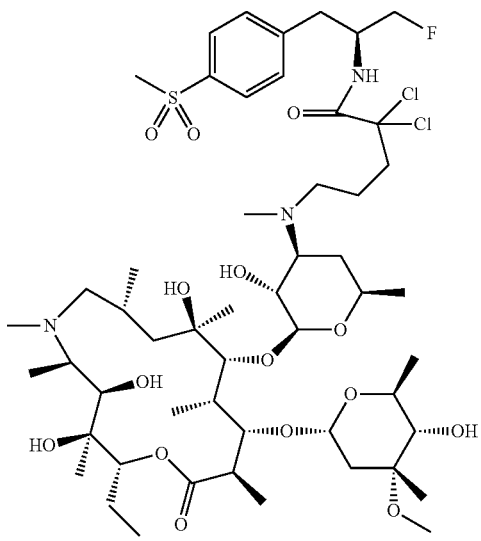 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCC(Cl)(Cl)C(=O)N[C@H](CF)Cc3ccc(S(C)(=O)=O)cc3)[C@H]2O)[C@](C)(O)CC[C@@H](C)CN(C)[C@H](C)[C@@H](O)C[C@]1(C)O] |

TABLE 13-continued

| Compound Number | Structure |
| --- | --- |
| 742 | 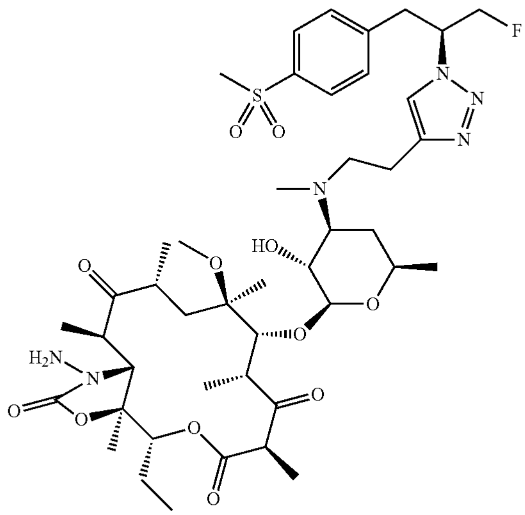 [SMILES: CC[C@H]1OC(=O)[C@H](C)C(=O)[C@H](C)[C@@H](O[C@@H]2O[C@H](C)C[C@H](N(C)CCc3cn([C@H](CF)Cc4ccc(S(C)(=O)=O)cc4)nn3)[C@H]2O)[C@](C)(OC)CC[C@@H](C)C(=O)[C@H](C)[C@@H]2C[C@]1(C)OC(=O)N2N] |
| 743 | 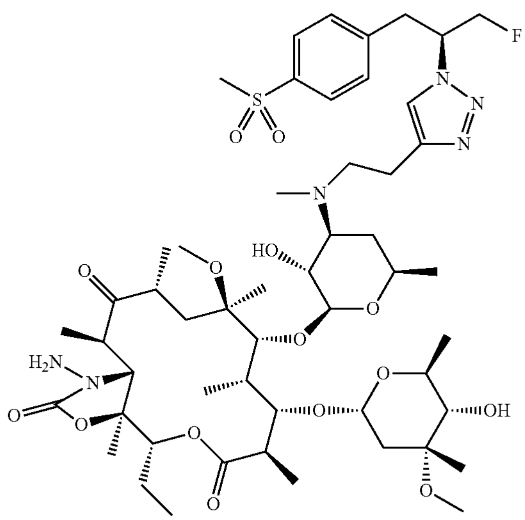 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CF)Cc4ccc(S(C)(=O)=O)cc4)nn3)[C@H]2O)[C@](C)(OC)CC[C@@H](C)C(=O)[C@H](C)[C@@H]2C[C@]1(C)OC(=O)N2N] |
| 744 | 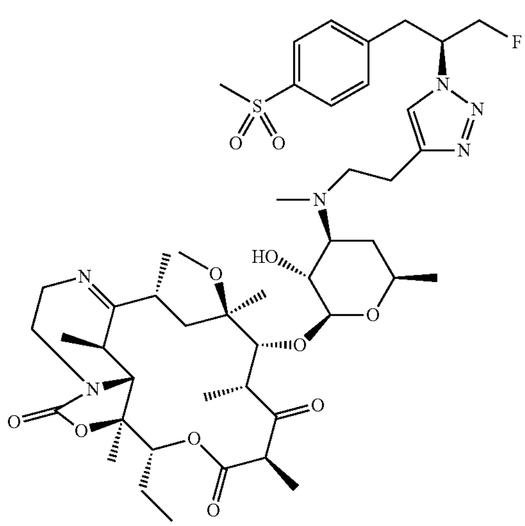 [SMILES: CC[C@H]1OC(=O)[C@H](C)C(=O)[C@H](C)[C@@H](O[C@@H]2O[C@H](C)C[C@H](N(C)CCc3cn([C@H](CF)Cc4ccc(S(C)(=O)=O)cc4)nn3)[C@H]2O)[C@](C)(OC)CC[C@@H](C)C2=NCCN3C(=O)O[C@@]1(C)C[C@H]3[C@H]2C] |

TABLE 13-continued
| Compound Number | Structure |
|---|---|
| 745 | 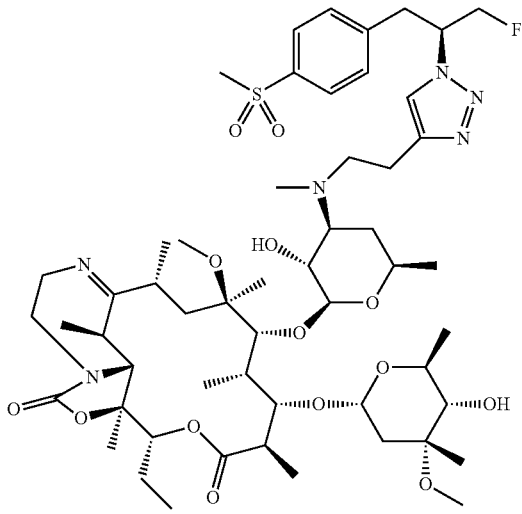 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CF)Cc4ccc(S(C)(=O)=O)cc4)nn3)[C@H]2O)[C@](C)(OC)CC[C@@H](C)C2=NCCN3C(=O)O[C@@]1(C)C[C@H]3[C@H]2C] |
| 746 | 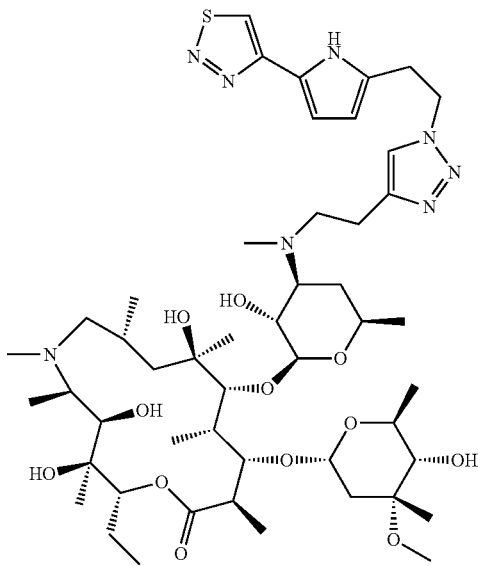 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc(-c5csnn5)[nH]4)nn3)[C@H]2O)[C@](C)(O)CC[C@@H](C)CN(C)[C@H](C)[C@@H](O)C[C@]1(C)O] |
| 747 | 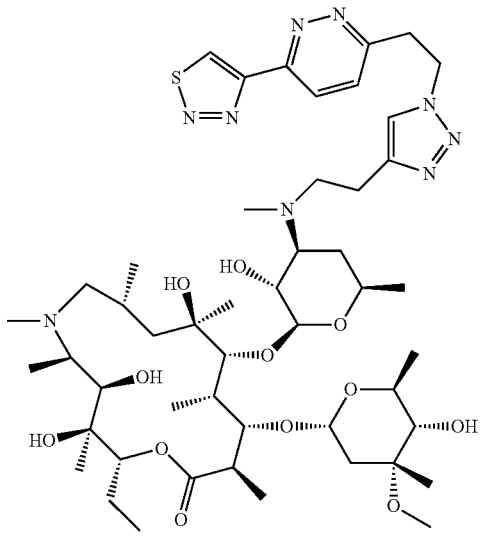 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc(-c5csnn5)nn4)nn3)[C@H]2O)[C@](C)(O)CC[C@@H](C)CN(C)[C@H](C)[C@@H](O)C[C@]1(C)O] |

TABLE 13-continued
| Compound Number | Structure |
|---|---|
| 748 | 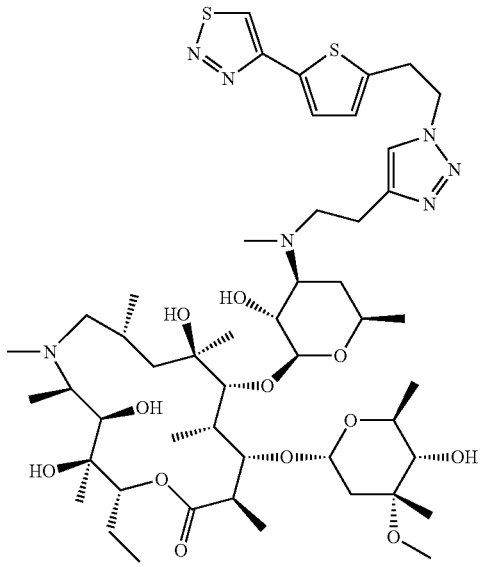 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCc4ccc(-c5csnn5)s4)nn3)[C@H]2O)[C@](C)(O)CC[C@@H](C)CN(C)[C@H](C)[C@@H](O)C[C@]1(C)O] |
| 749 | 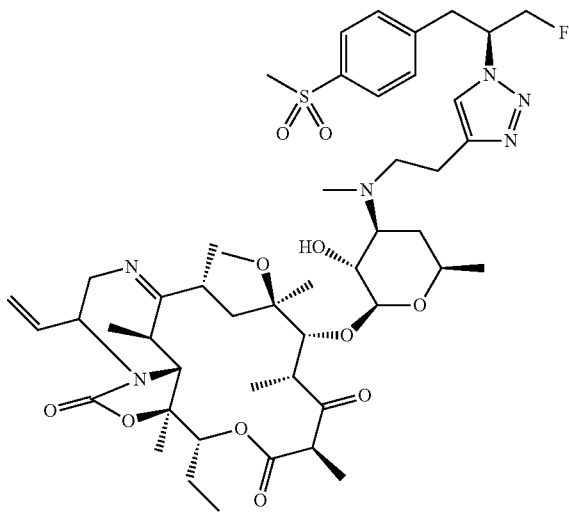 [SMILES: C=CC1CN=C2[C@H](C)CC[C@@](C)(OC)[C@H](O[C@@H]3O[C@H](C)C[C@H](N(C)CCc4cn([C@H](CF)Cc5ccc(S(C)(=O)=O)cc5)nn4)[C@H]3O)[C@@H](C)C(=O)[C@@H](C)C(=O)O[C@H](CC)[C@]3(C)C[C@@H]([C@H]2C)N1C(=O)O3] |
| 750 | 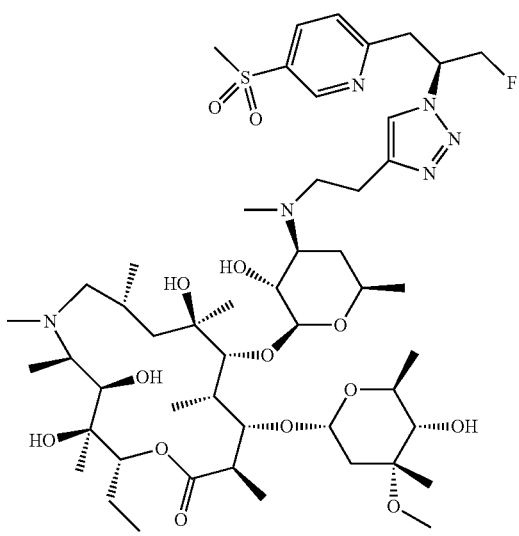 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CF)Cc4ccc(S(C)(=O)=O)cn4)nn3)[C@H]2O)[C@](C)(O)CC[C@@H](C)CN(C)[C@H](C)[C@@H](O)C[C@]1(C)O] |

TABLE 13-continued

| Compound Number | Structure |
|---|---|
| 751 | 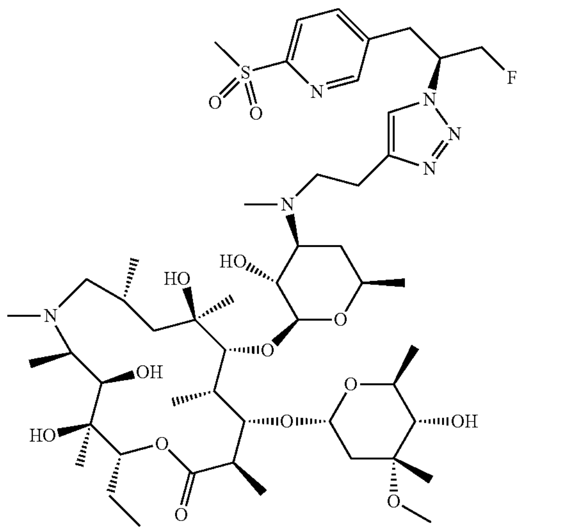 |
| 752 | 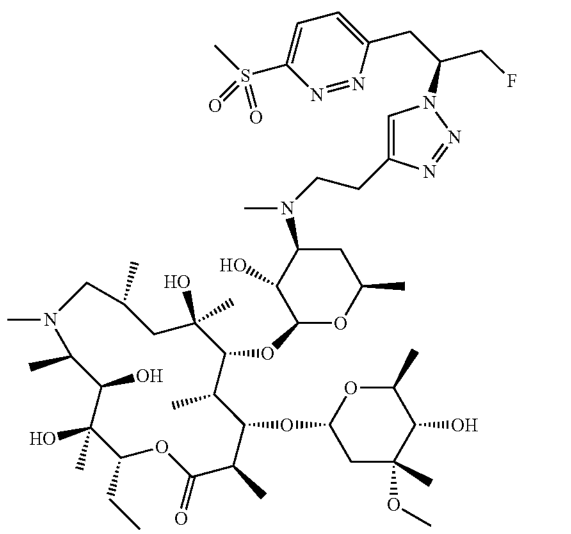 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn([C@H](CF)Cc4ccc(S(C)(=O)=O)nn4)nn3)[C@H]2O)[C@](C)(O)CC[C@@H](C)CN(C)[C@H](C)[C@@H](O)C[C@]1(C)O] |
| 753 | 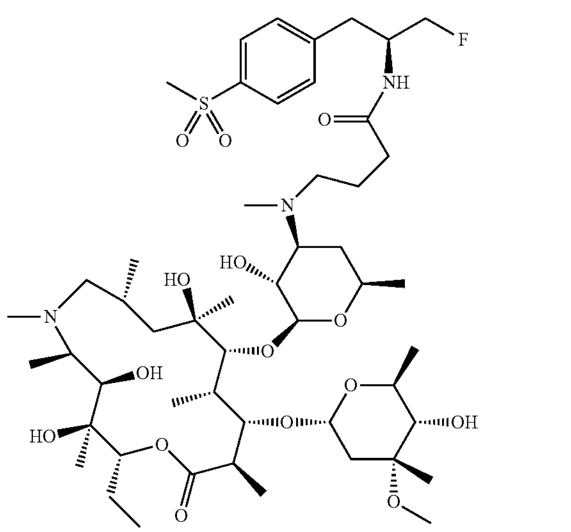 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCC(=O)N[C@H](CF)Cc3ccc(S(C)(=O)=O)cc3)[C@H]2O)[C@](C)(O)CC[C@@H](C)CN(C)[C@H](C)[C@@H](O)C[C@]1(C)O] |

TABLE 13-continued

| Compound Number | Structure |
|---|---|
| 754 | 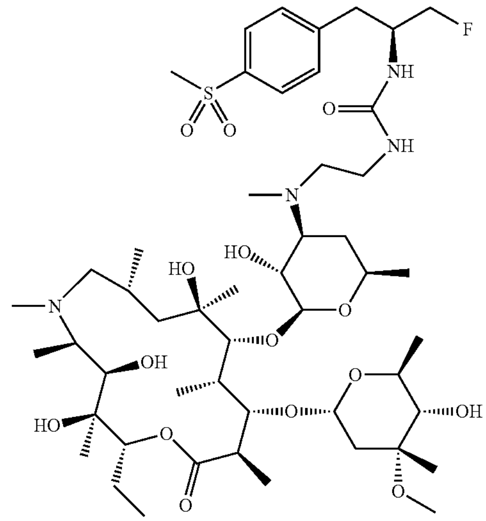 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCNC(=O)N[C@H](CF)Cc3ccc(S(C)(=O)=O)cc3)[C@H]2O)[C@](C)(O)CC[C@@H](C)CN(C)[C@H](C)[C@@H](O)C[C@]1(C)O] |
| 755 | 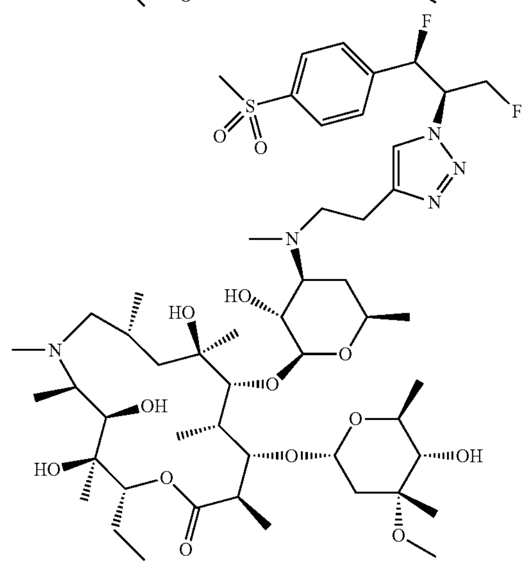 |
| 756 | 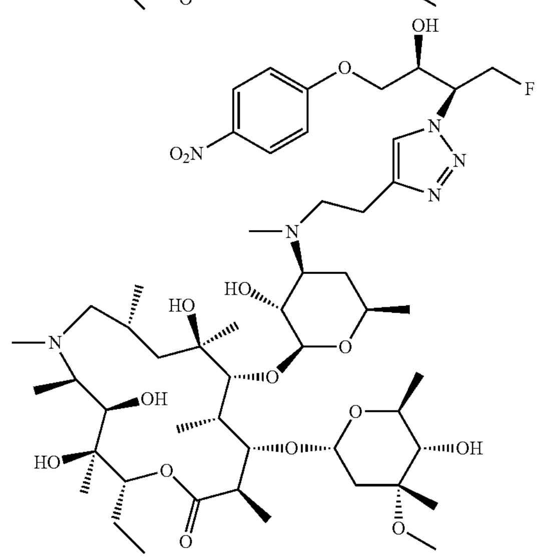 |

Incorporation by Reference

The entire disclosure of each of the patent documents and scientific articles referred to herein is incorporated by reference for all purposes.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A compound having the structure:

| Compound Number | Structure |
|---|---|
| 220 | 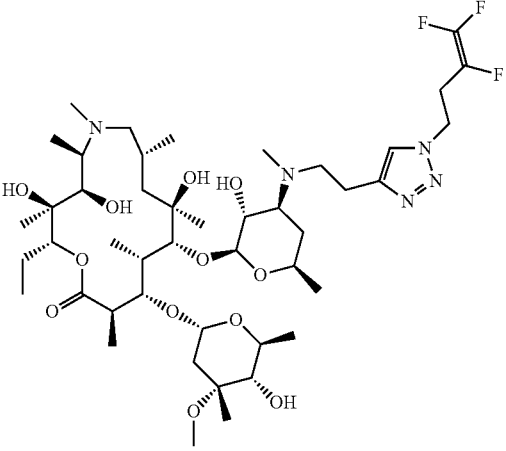 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCC(F)=C(F)F)nn3)[C@H]2O)[C@](C)(O)C[C@@H](C)CN(C)[C@H](C)[C@@H](O)[C@]1(C)O] |
| 242 | 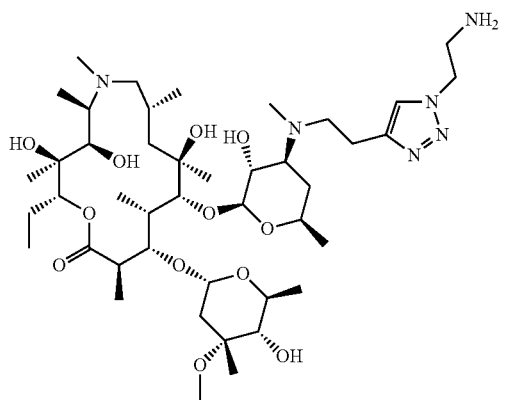 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(CCN)nn3)[C@H]2O)[C@](C)(O)C[C@@H](C)CN(C)[C@H](C)[C@@H](O)[C@]1(C)O] |
| 243 | 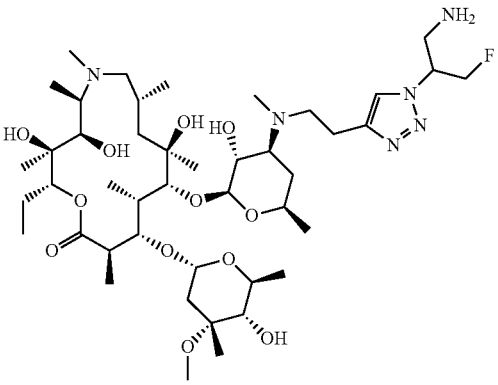 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCc3cn(C(CN)CF)nn3)[C@H]2O)[C@](C)(O)C[C@@H](C)CN(C)[C@H](C)[C@@H](O)[C@]1(C)O] |
| 475 | 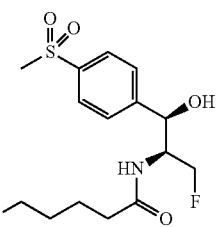 |
| 476 | 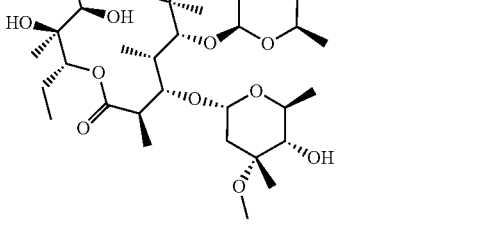 |

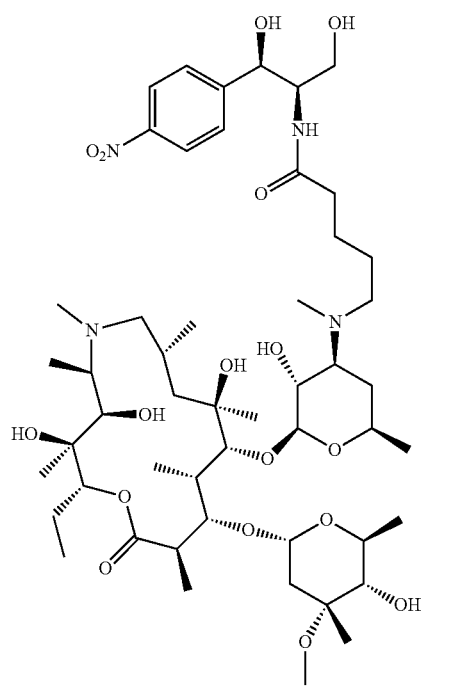 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCCC(=O)N[C@H](CO)[C@H](O)c3ccc([N+](=O)[O-])cc3)[C@H]2O)[C@](C)(O)C[C@@H](C)CN(C)[C@H](C)[C@@H](O)[C@]1(C)O]

659
-continued
| Compound Number | Structure |
|---|---|
| 477 | 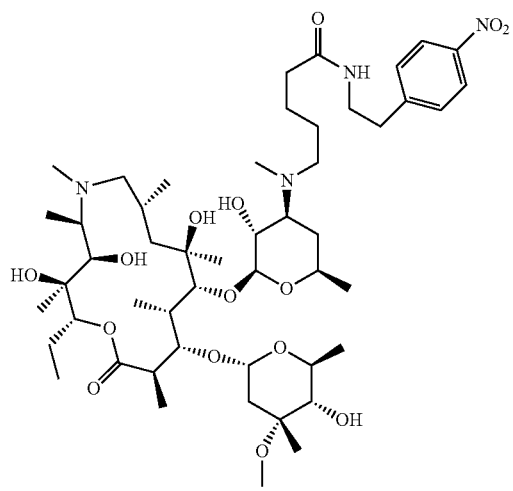 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCCC(=O)NCCc3ccc([N+](=O)[O-])cc3)[C@H]2O)[C@](C)(O)C[C@@H](C)CN(C)[C@H](C)[C@@H](O)[C@]1(C)O] |
| 478 | 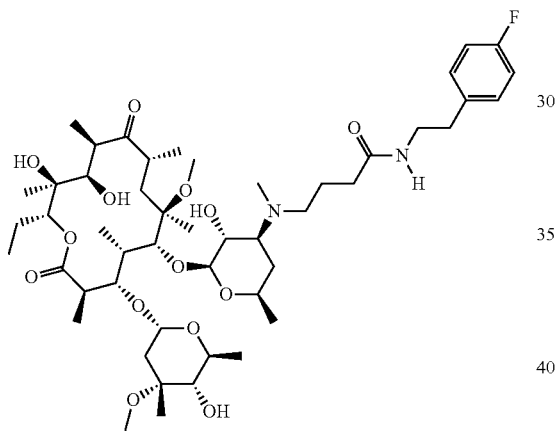 |
| 479 | 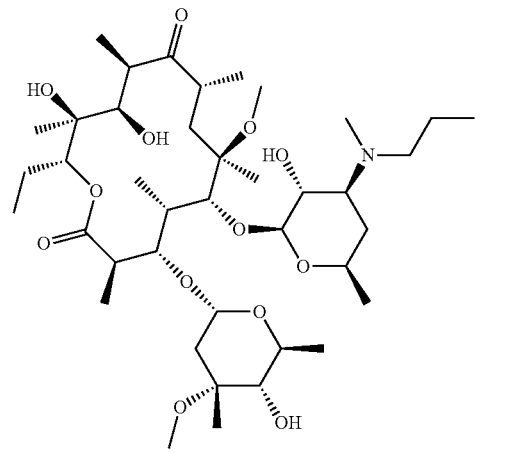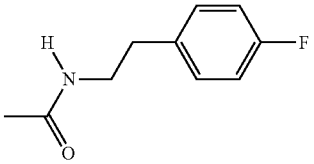 |
660
-continued
| Compound Number | Structure |
|---|---|
| 480 | 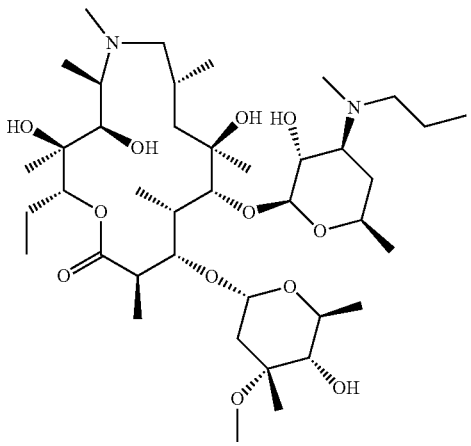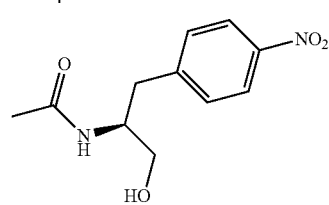 |
| 501 | 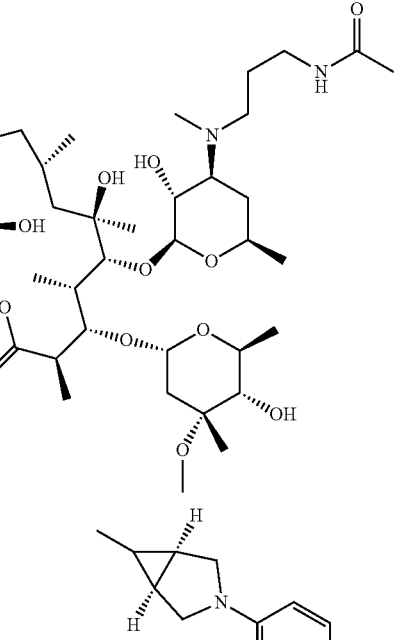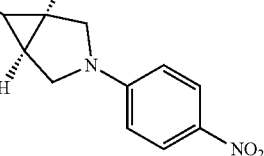 |

| Compound Number | Structure |
|---|---|
| 502 | 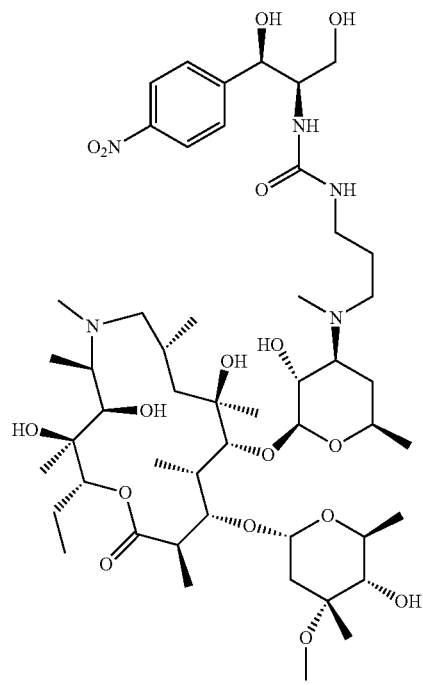 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCNC(=O)N[C@H](CO)[C@H](O)c3ccc([N+](=O)[O-])cc3)[C@H]2O)[C@](C)(O)C[C@@H](C)CN(C)[C@H](C)[C@@H](O)[C@]1(C)O] |
| 503 | 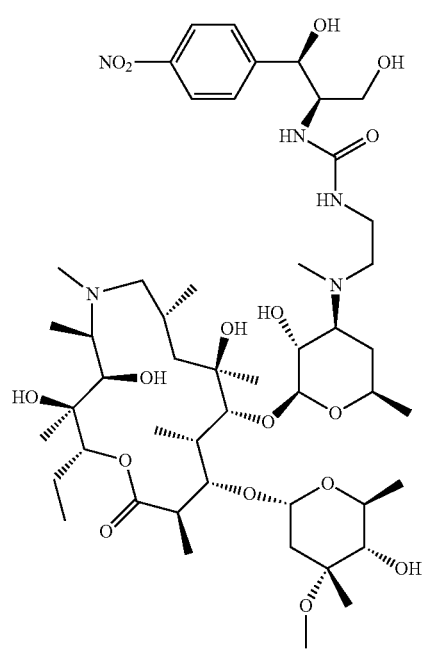 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCNC(=O)N[C@H](CO)[C@H](O)c3ccc([N+](=O)[O-])cc3)[C@H]2O)[C@](C)(O)C[C@@H](C)CN(C)[C@H](C)[C@@H](O)[C@]1(C)O] |
| Compound Number | Structure |
|---|---|
| 504 | 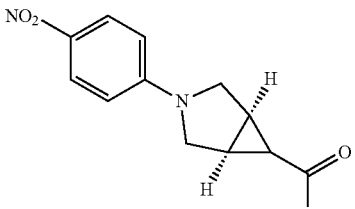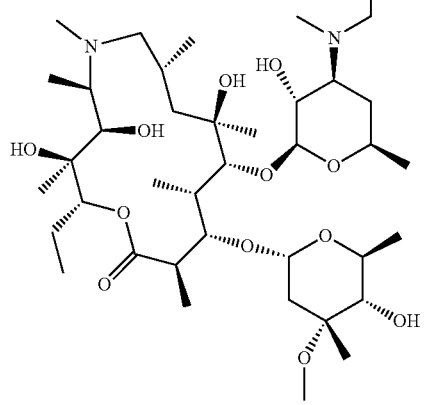 |
| 505 | 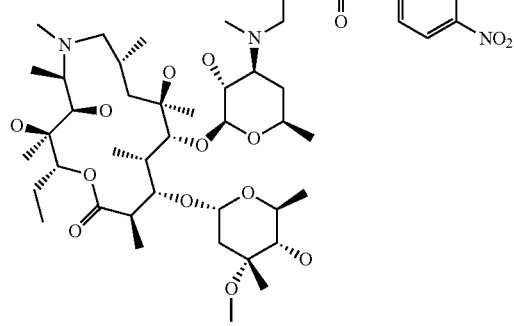 |
| 506 | 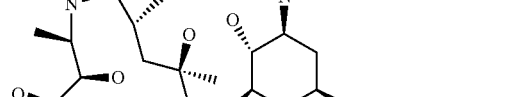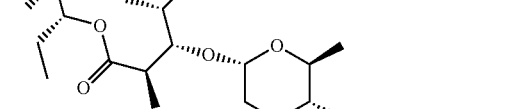 |

| Compound Number | Structure |
|---|---|
| 507 | 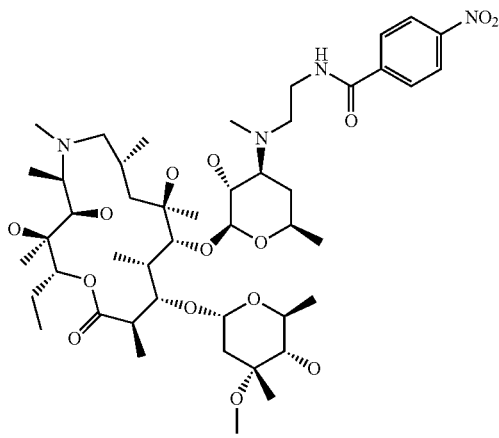 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCNC(=O)c3ccc([N+](=O)[O-])cc3)[C@H]2O)[C@](C)(O)C[C@@H](C)CN(C)[C@H](C)[C@@H](O)[C@]1(C)O] |
| 508 | 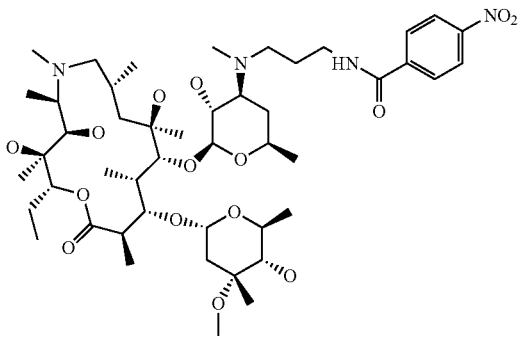 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCNC(=O)c3ccc([N+](=O)[O-])cc3)[C@H]2O)[C@](C)(O)C[C@@H](C)CN(C)[C@H](C)[C@@H](O)[C@]1(C)O] |
| 509 | 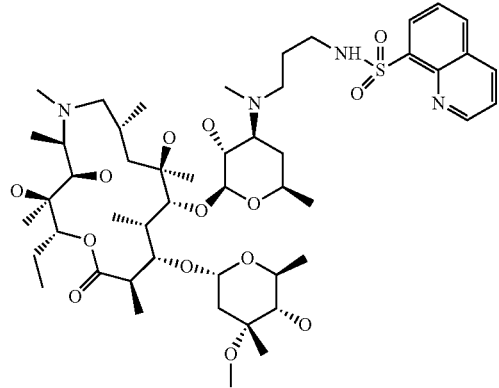 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCNS(=O)(=O)c3cccc4cccnc34)[C@H]2O)[C@](C)(O)C[C@@H](C)CN(C)[C@H](C)[C@@H](O)[C@]1(C)O] |
| Compound Number | Structure |
|---|---|
| 510 | 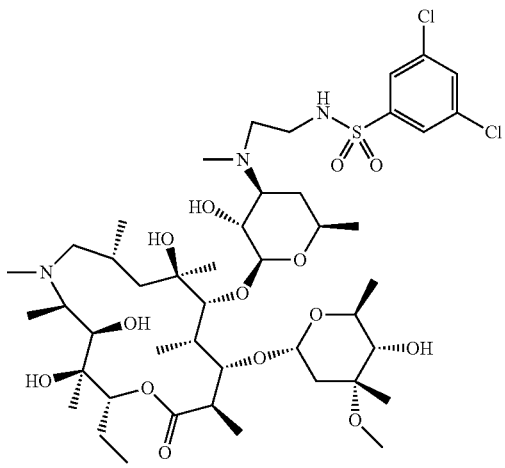 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCNS(=O)(=O)c3cc(Cl)cc(Cl)c3)[C@H]2O)[C@](C)(O)C[C@@H](C)CN(C)[C@H](C)[C@@H](O)[C@]1(C)O] |
| 511 | 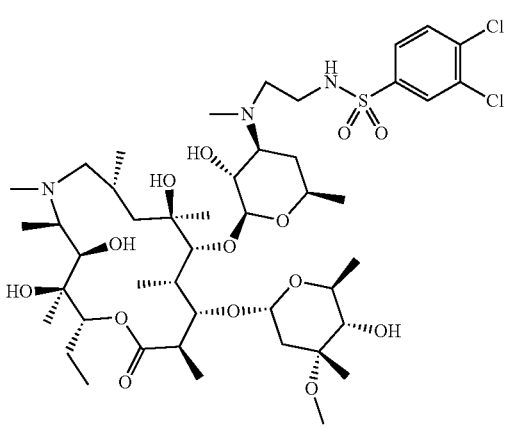 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCNS(=O)(=O)c3ccc(Cl)c(Cl)c3)[C@H]2O)[C@](C)(O)C[C@@H](C)CN(C)[C@H](C)[C@@H](O)[C@]1(C)O] |
| 512 | 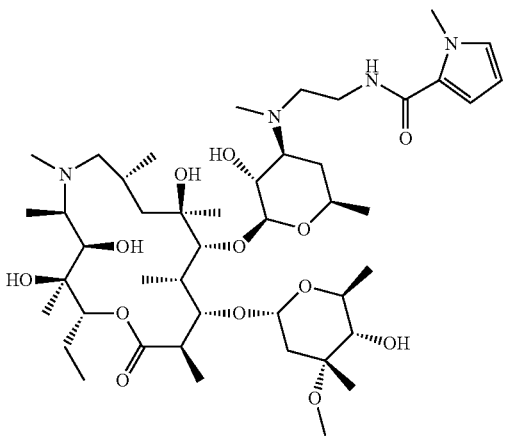 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCNC(=O)c3cccn3C)[C@H]2O)[C@](C)(O)C[C@@H](C)CN(C)[C@H](C)[C@@H](O)[C@]1(C)O] |

| Compound Number | Structure |
|---|---|
| 513 | 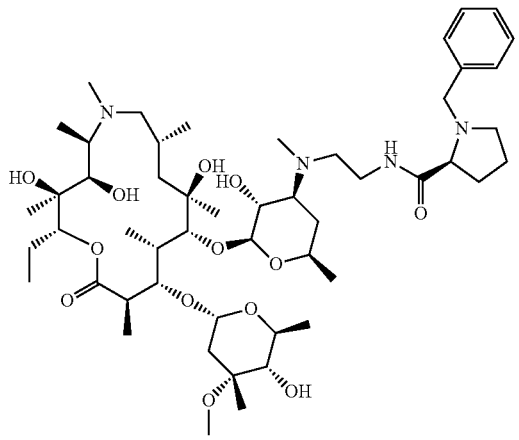 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCNC(=O)[C@@H]3CCCN3Cc3ccccc3)[C@H]2O)[C@](C)(O)C[C@@H](C)CN(C)[C@H](C)[C@@H](O)[C@]1(C)O] |
| 514 | 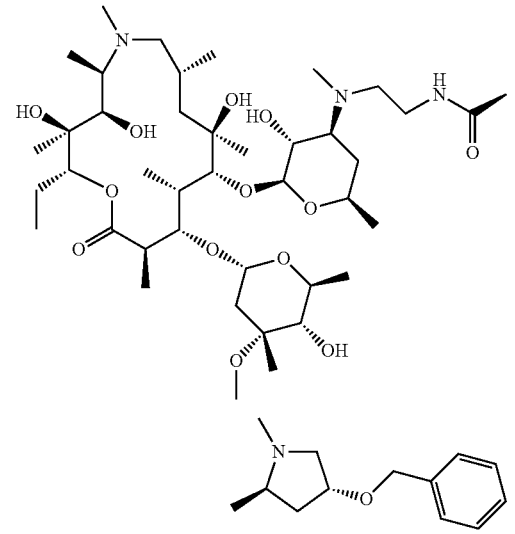 |
| 515 | 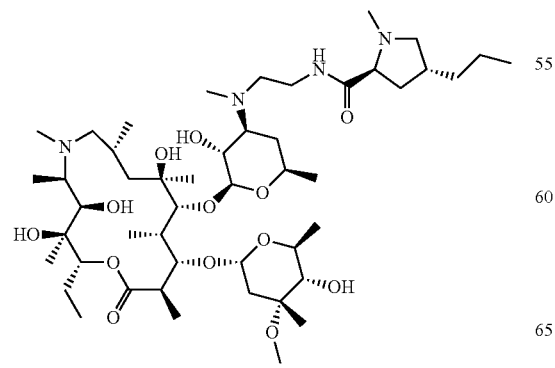 |
| Compound Number | Structure |
|---|---|
| 525 | 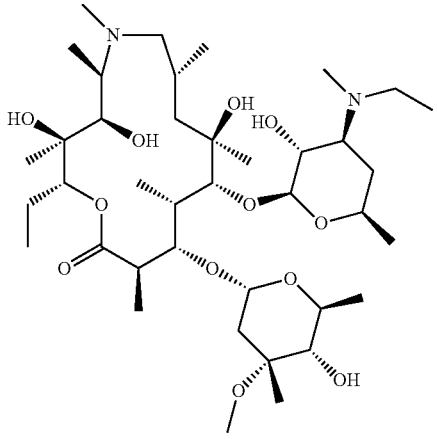 |
| | 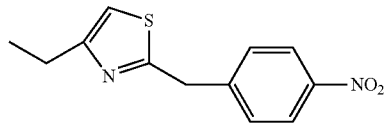 |
| 526 | 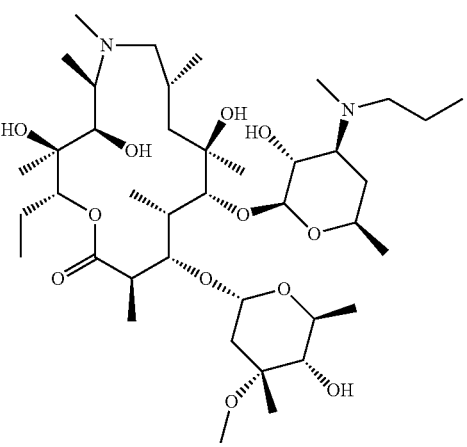 |
| | 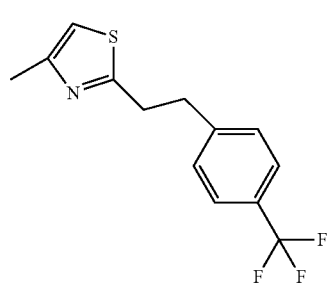 |

| Compound Number | Structure |
|---|---|
| 527 | 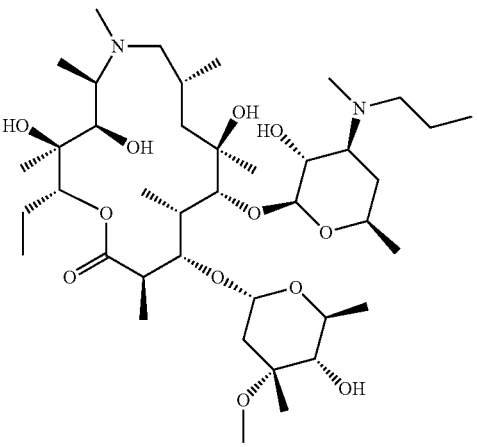 |
| 528 | 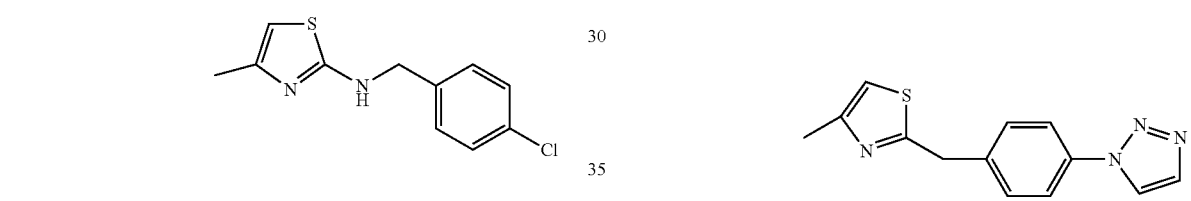 |
| Compound Number | Structure |
|---|---|
| 529 | 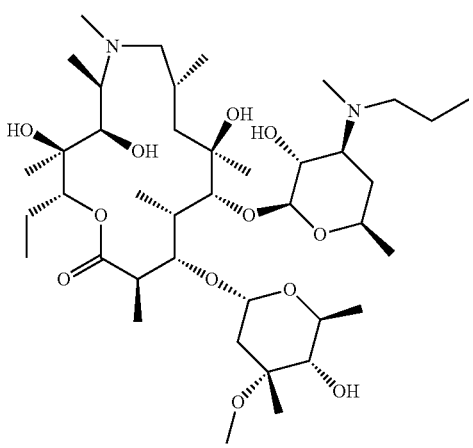 |
| 603 | 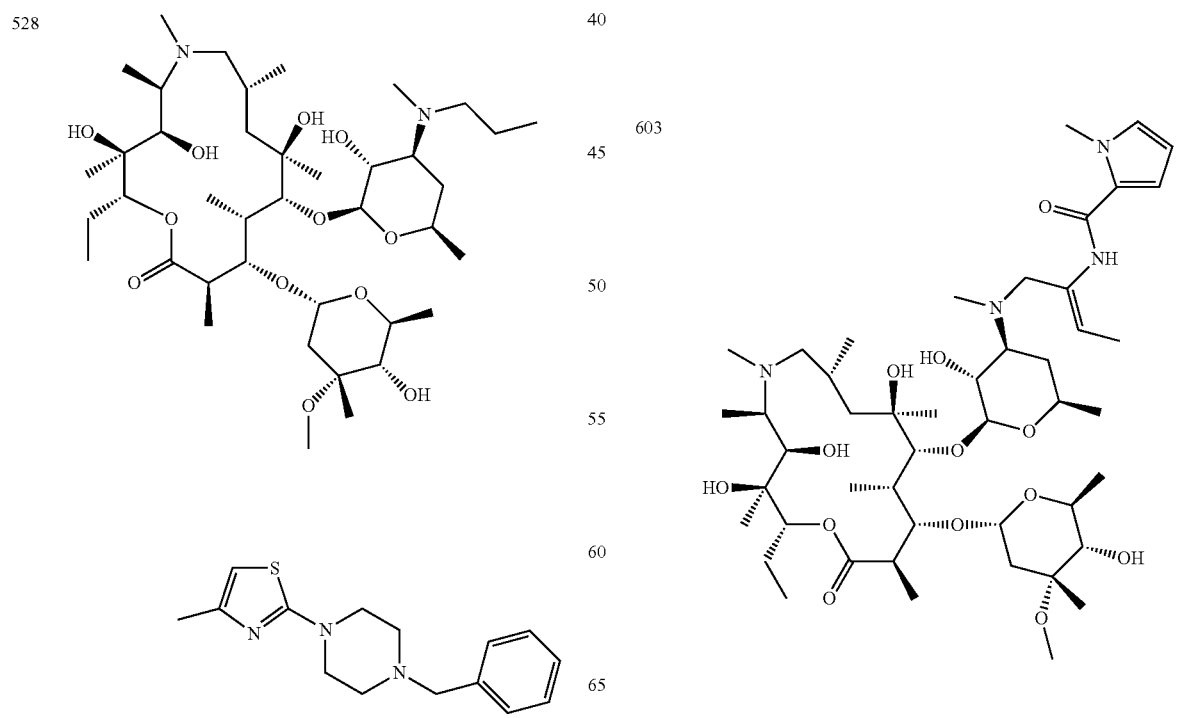 |

| Compound Number | Structure |
|---|---|
| 604 | 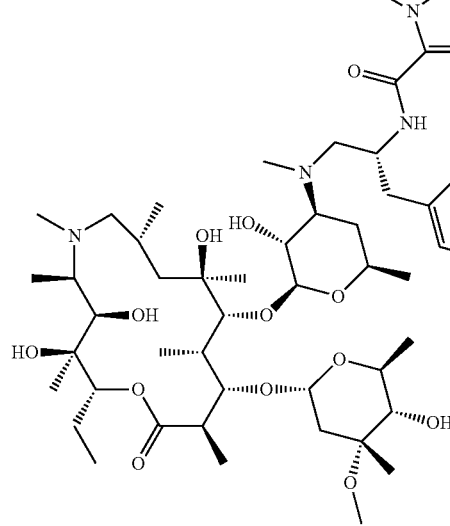 |
| 605 | 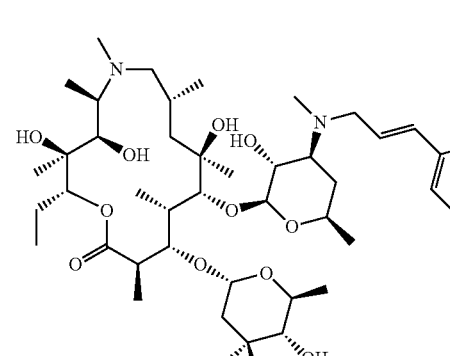 |
| 606 | 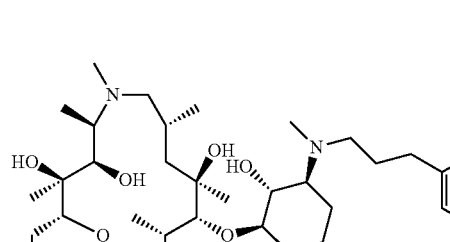 |
| 607 | 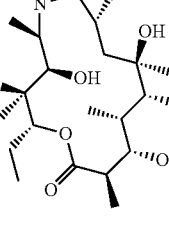 |
| 609 | 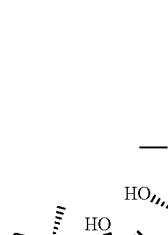 |
| 611 | 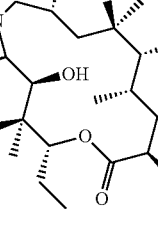 |

| Compound Number | Structure |
|---|---|
| 618 | 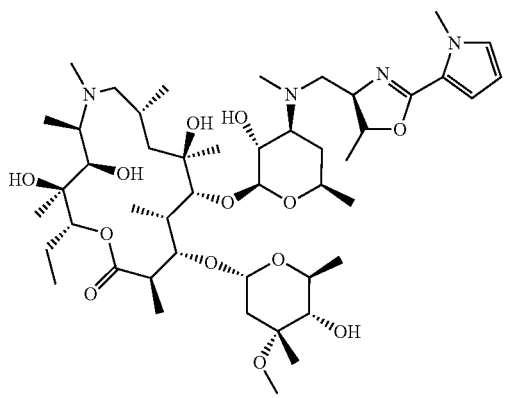 |
| 619 | 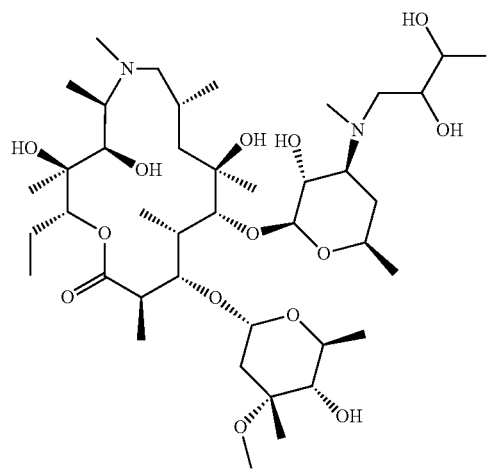 |
| 622 | 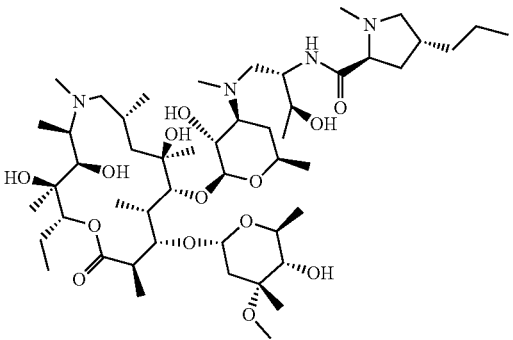 [SMILES: CCC[C@@H]1C[C@@H](C(=O)N[C@@H](CN(C)[C@H]2C[C@@H](C)O[C@@H](O[C@@H]3[C@@H](C)[C@H](O[C@H]4C[C@@](C)(OC)[C@@H](O)[C@H](C)O4)[C@@H](C)C(=O)O[C@H](CC)[C@@](C)(O)[C@H](O)[C@@H](C)N(C)C[C@H](C)C[C@@]3(C)O)[C@@H]2O)[C@H](C)O)N(C)C1] |
| Compound Number | Structure |
|---|---|
| 623 | 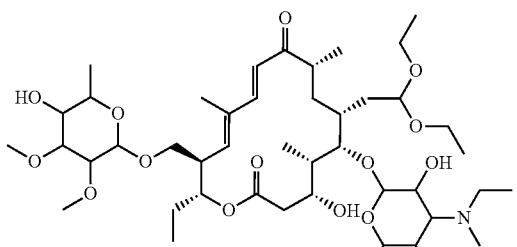 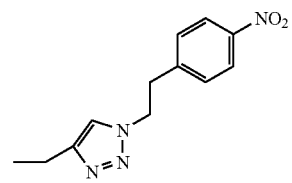 |
| 624 | 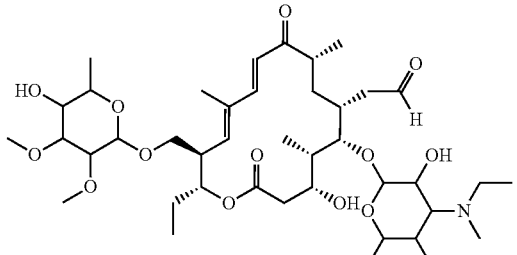 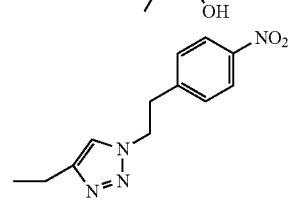 |
| 625 | 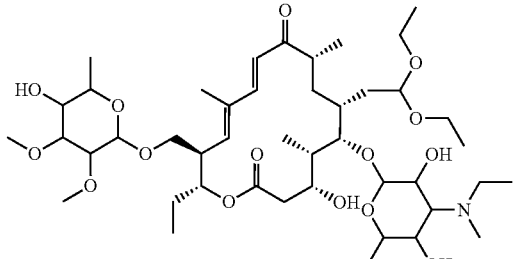 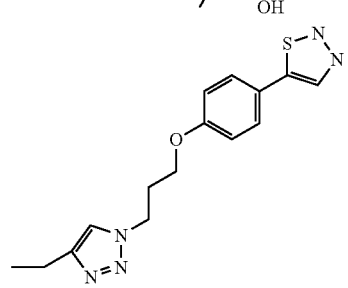 |

-continued
| Compound Number | Structure |
|---|---|
| 626 | 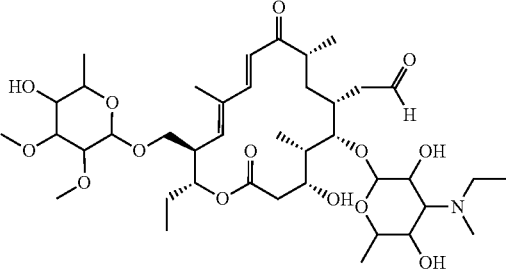 |
| 627 | 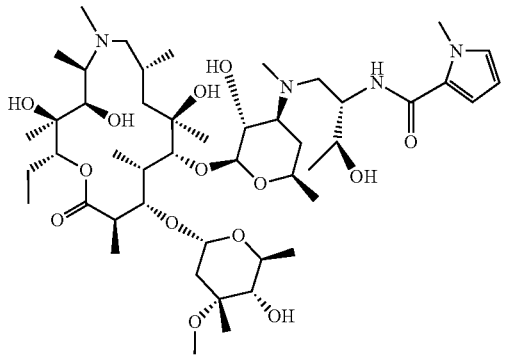 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)C[C@H](NC(=O)c3cccn3C)[C@H](C)O)[C@H]2O)[C@](C)(O)C[C@@H](C)CN(C)[C@H](C)[C@@H](O)[C@]1(C)O] |
| 628 | 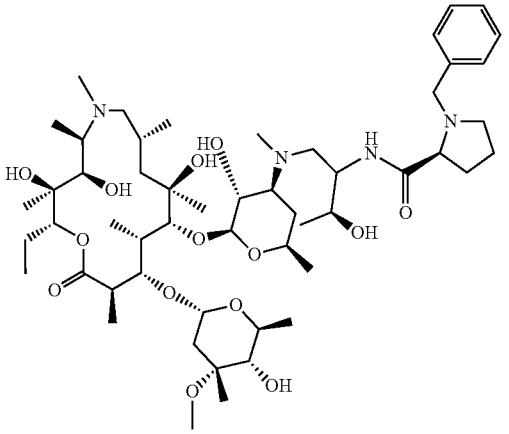 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CC(NC(=O)[C@@H]3CCCN3Cc3ccccc3)[C@H](C)O)[C@H]2O)[C@](C)(O)C[C@@H](C)CN(C)[C@H](C)[C@@H](O)[C@]1(C)O] |
-continued
| Compound Number | Structure |
|---|---|
| 629 | 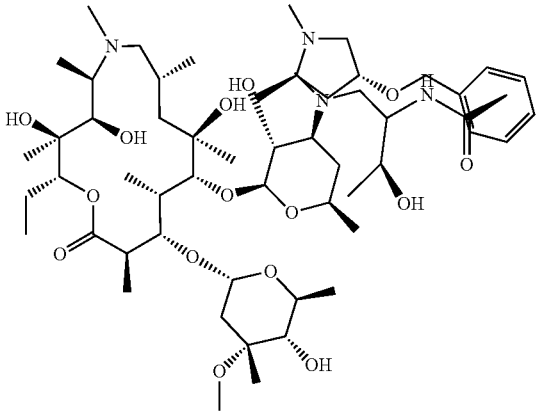 |
| 739 | 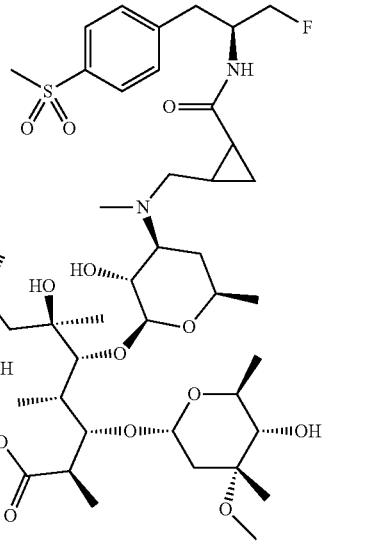 |
| 740 | 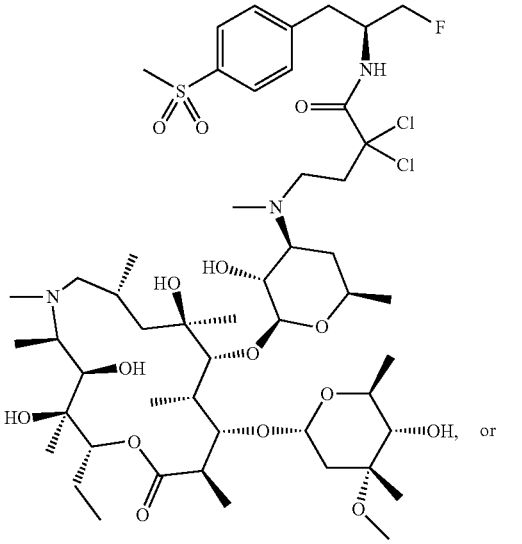 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCC(Cl)(Cl)C(=O)N[C@H](CF)Cc3ccc(S(C)(=O)=O)cc3)[C@H]2O)[C@](C)(O)C[C@@H](C)CN(C)[C@H](C)[C@@H](O)[C@]1(C)O], or |

| Compound Number | Structure |
|---|---|
| 741 | 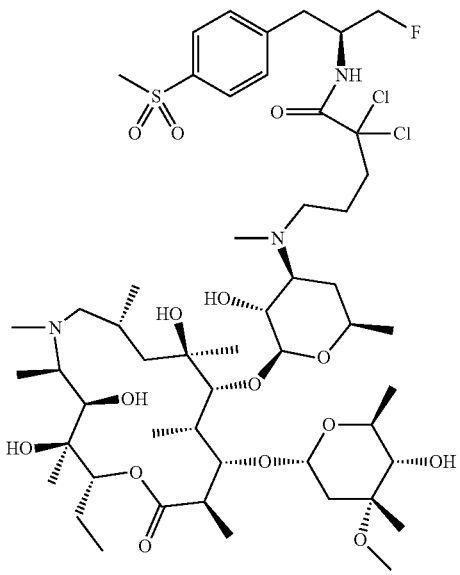 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CCCC(Cl)(Cl)C(=O)N[C@H](CF)Cc3ccc(S(C)(=O)=O)cc3)[C@H]2O)[C@](C)(O)C[C@@H](C)CN(C)[C@H](C)[C@@H](O)[C@]1(C)O] | or a pharmaceutically acceptable salt, ester, or N-oxide thereof.

2. A pharmaceutical composition comprising a compound according to claim 1 or a pharmaceutically acceptable salt, ester, or N-oxide thereof and a pharmaceutically acceptable carrier.

3. A method for treating bacterial infection in a mammal comprising administering to a mammal in need thereof an effective amount of a compound according to claim 1 or a pharmaceutically acceptable salt, ester, or N-oxide thereof.

* * * * *

UNITED STATES PATENT AND TRADEMARK OFFICE
CERTIFICATE OF CORRECTION

PATENT NO. : 8,841,263 B2
APPLICATION NO. : 13/525900
DATED : September 23, 2014
INVENTOR(S) : Jay J. Farmer et al.

It is certified that error appears in the above-identified patent and that said Letters Patent is hereby corrected as shown below:

In the Claims

Claim 1, Column 659, lines 44-65:
    Please replace the structure shown for compound 479 as indicated below.

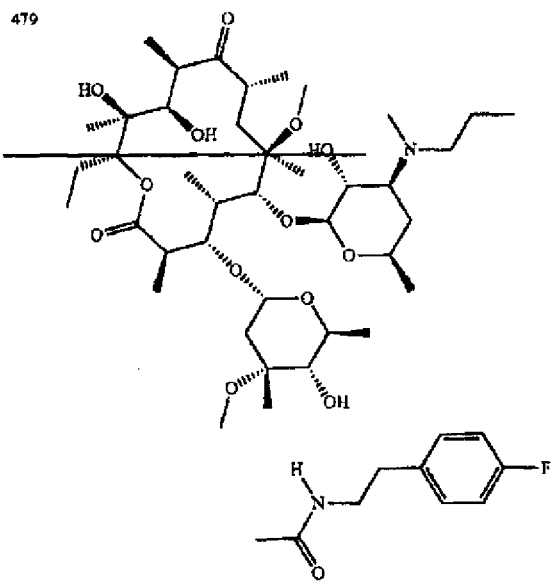

Signed and Sealed this
Twenty-first Day of July, 2015

Michelle K. Lee
*Director of the United States Patent and Trademark Office*

CERTIFICATE OF CORRECTION (continued)
U.S. Pat. No. 8,841,263 B2

479 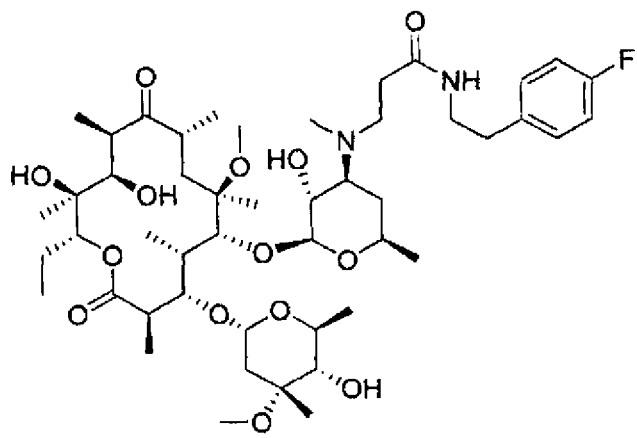

-- --

Claim 1, Column 660, lines 10-35
Please replace the structure shown for compound 480 as indicated below.

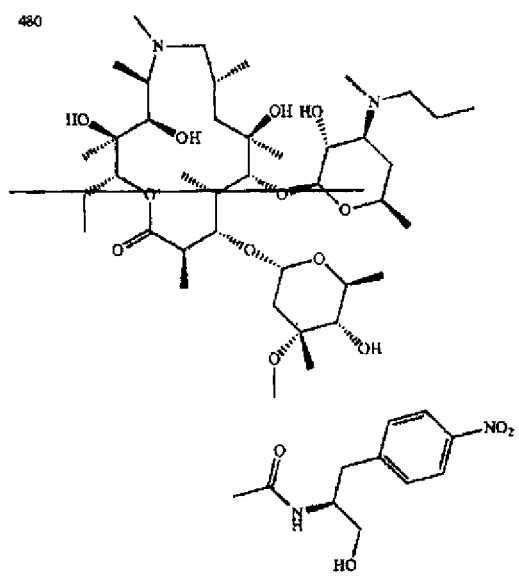

480 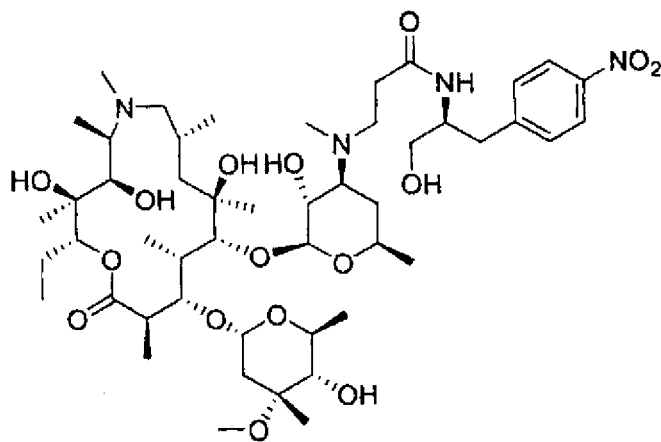

-- --

Claim 1, Column 660, lines 38-65:
　　　Please replace the structure shown for compound 501 as indicated below.
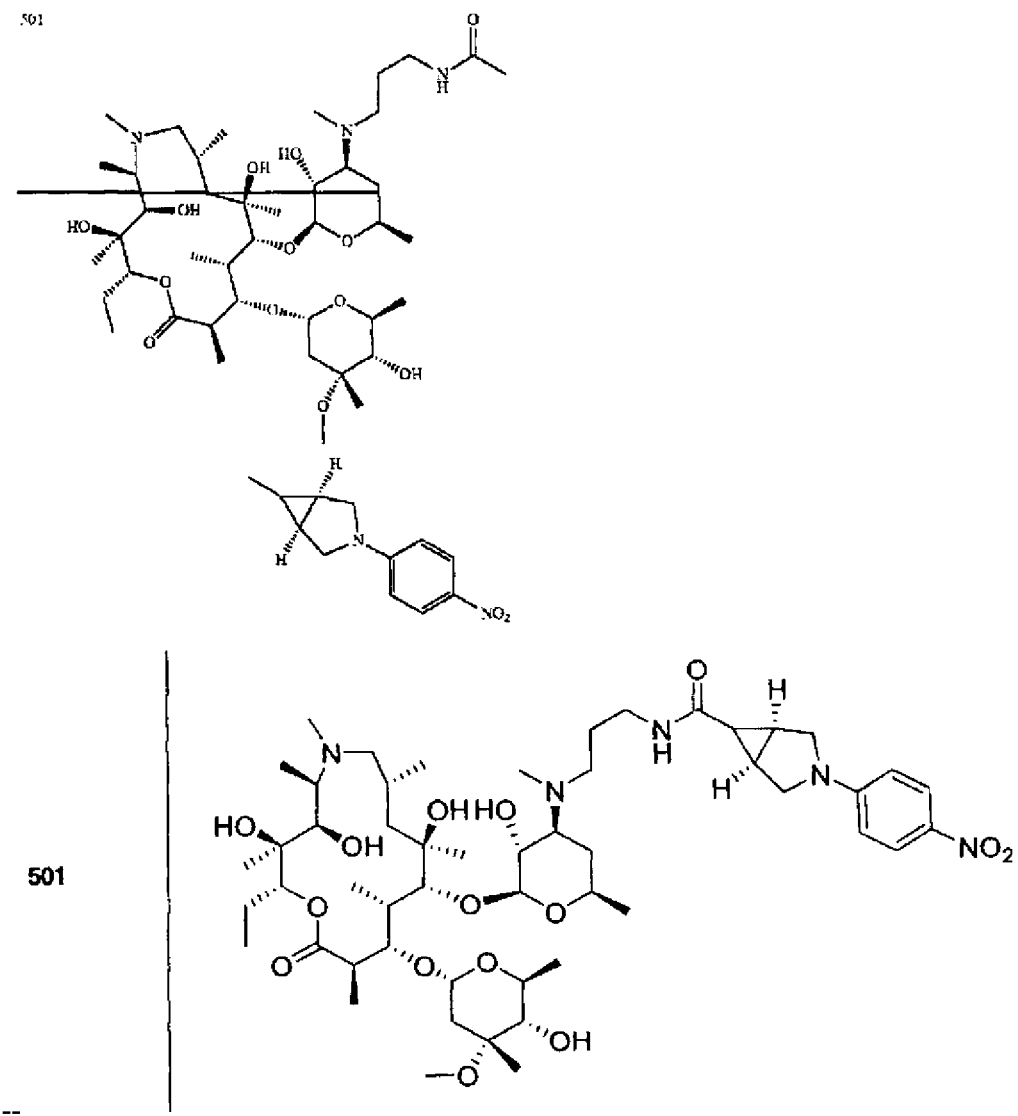

CERTIFICATE OF CORRECTION (continued)
U.S. Pat. No. 8,841,263 B2

Claim 1, Column 665, lines 28-50:
Please replace the structure shown for compound 514 as indicated below.

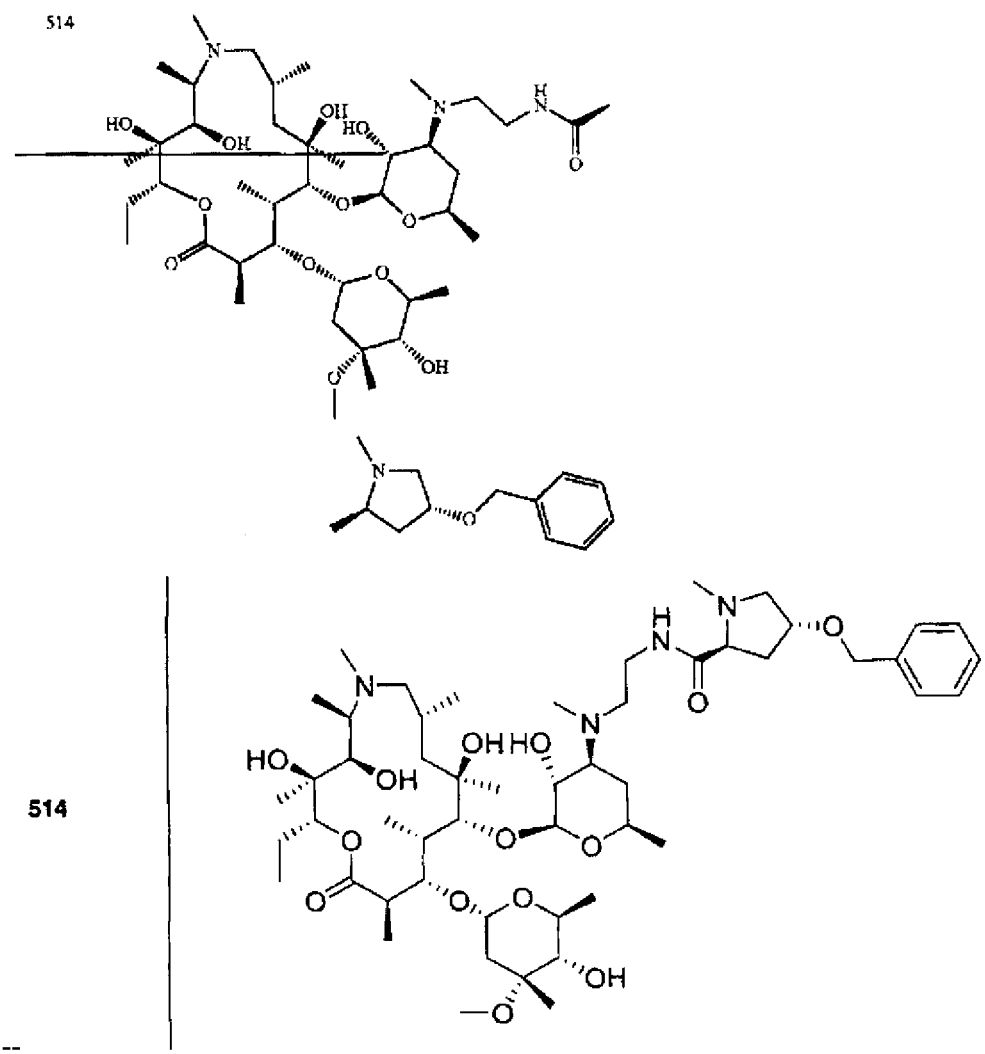

CERTIFICATE OF CORRECTION (continued)
U.S. Pat. No. 8,841,263 B2

Claim 1, Column 666, lines 8-32:
    Please replace the structure shown for compound 525 as indicated below.

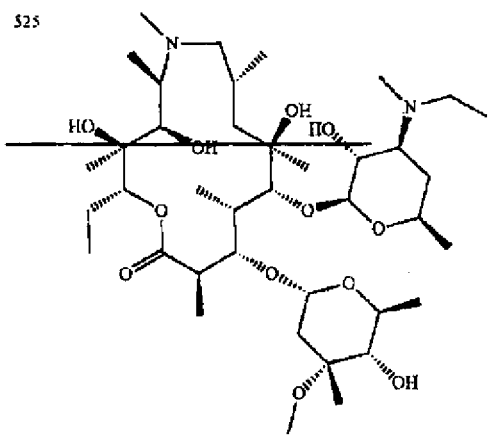

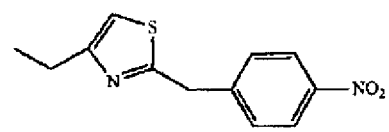

525

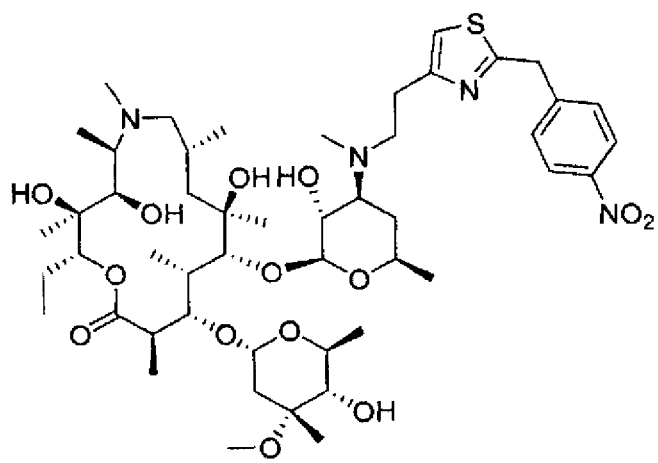

CERTIFICATE OF CORRECTION (continued)
U.S. Pat. No. 8,841,263 B2

Claim 1, Column 666, lines 36-65:
  Please replace the structure shown for compound 526 as indicated below.

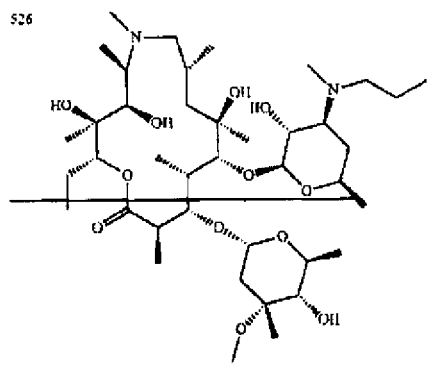

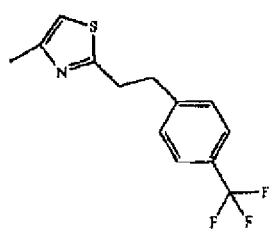

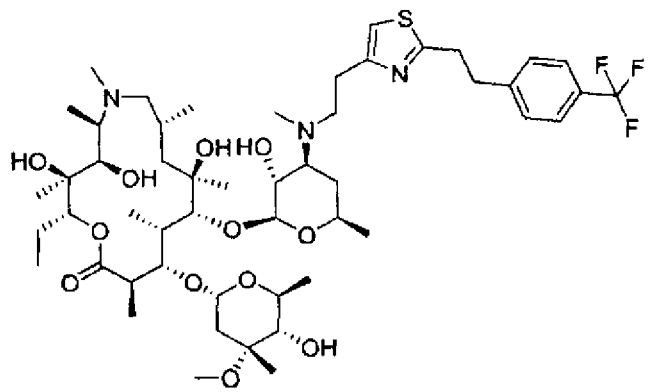

Claim 1, Column 667, lines 8-35:
Please replace the structure shown for compound 527 as indicated below.
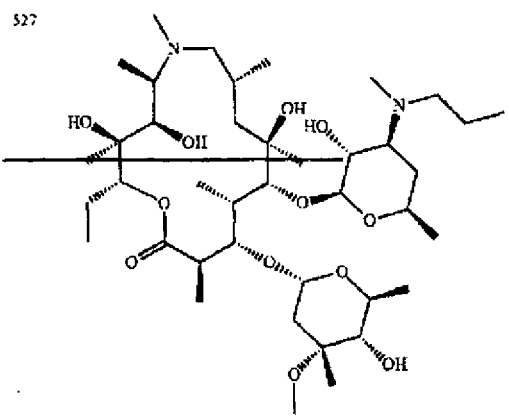
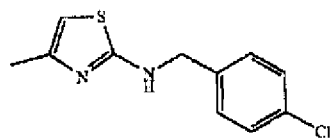
527
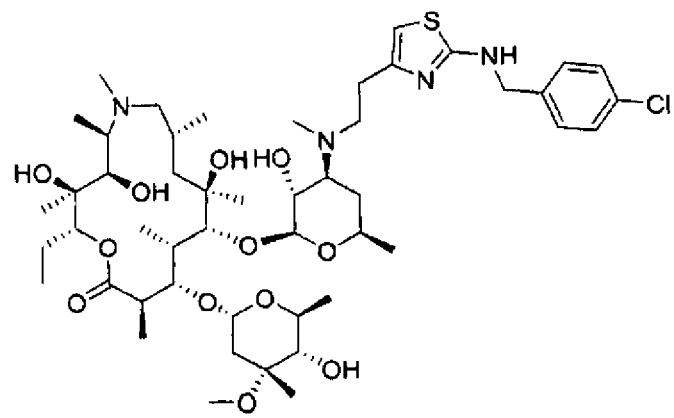

CERTIFICATE OF CORRECTION (continued)
U.S. Pat. No. 8,841,263 B2

Claim 1, Column 667, lines 40-65:
Please replace the structure shown for compound 528 as indicated below.

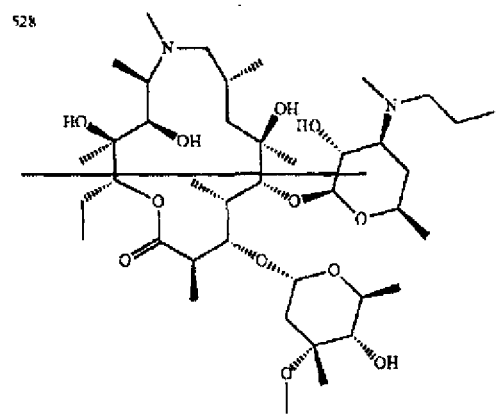

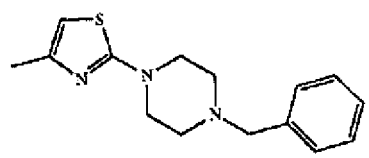

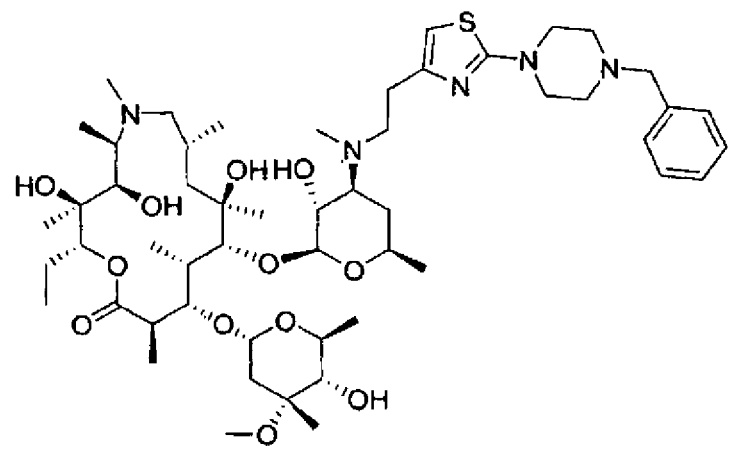

CERTIFICATE OF CORRECTION (continued)
U.S. Pat. No. 8,841,263 B2

Claim 1, Column 668, lines 8-35:
    Please replace the structure shown for compound 529 as indicated below.

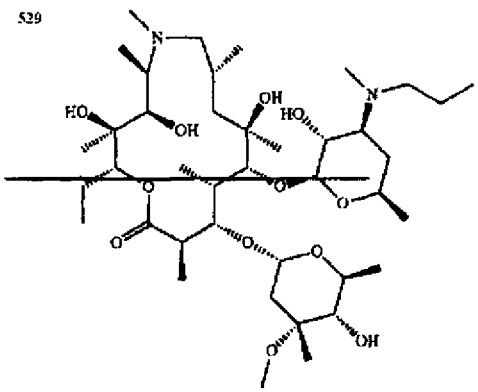

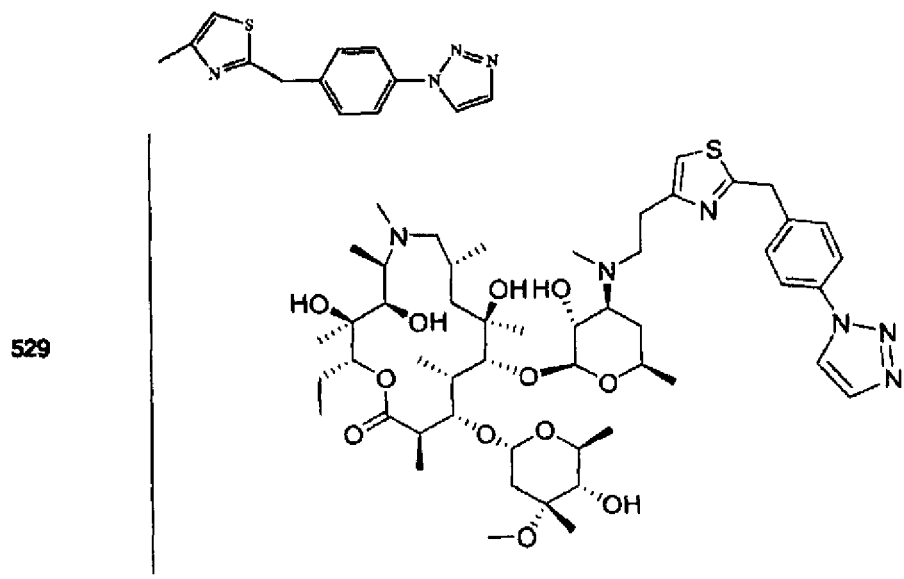

Claim 1, Column 670, lines 20-39:
  Please replace the structure shown for compound 609 as indicated below.
609
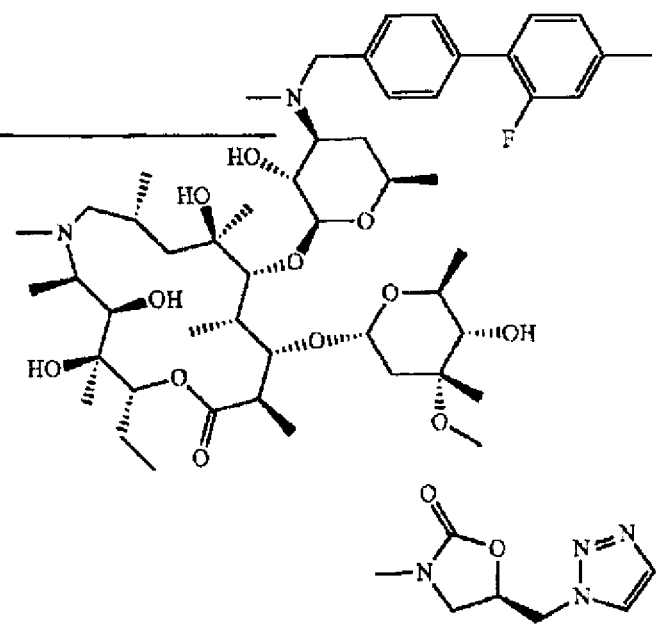
609
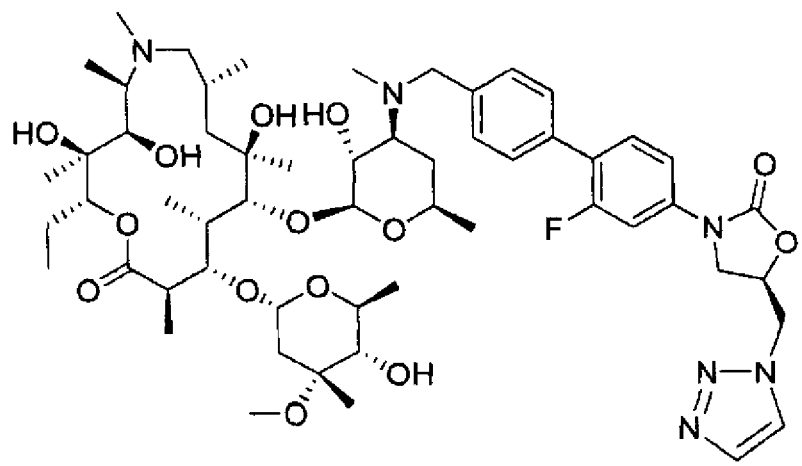

CERTIFICATE OF CORRECTION (continued)
U.S. Pat. No. 8,841,263 B2

Claim 1, Column 670, lines 40-65:
   Please replace the structure shown for compound 611 as indicated below.

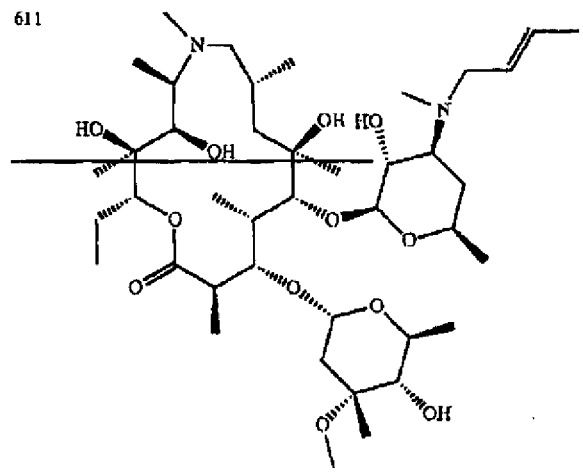
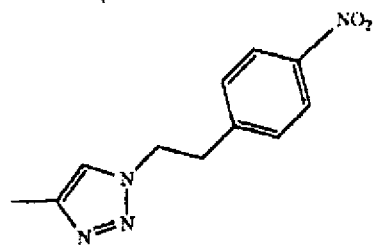
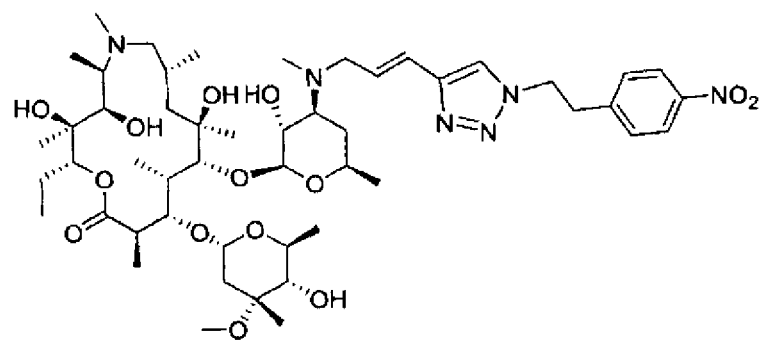

Claim 1, Column 671, lines 24-51:
    Please replace the structure shown for compound 619 as indicated below.
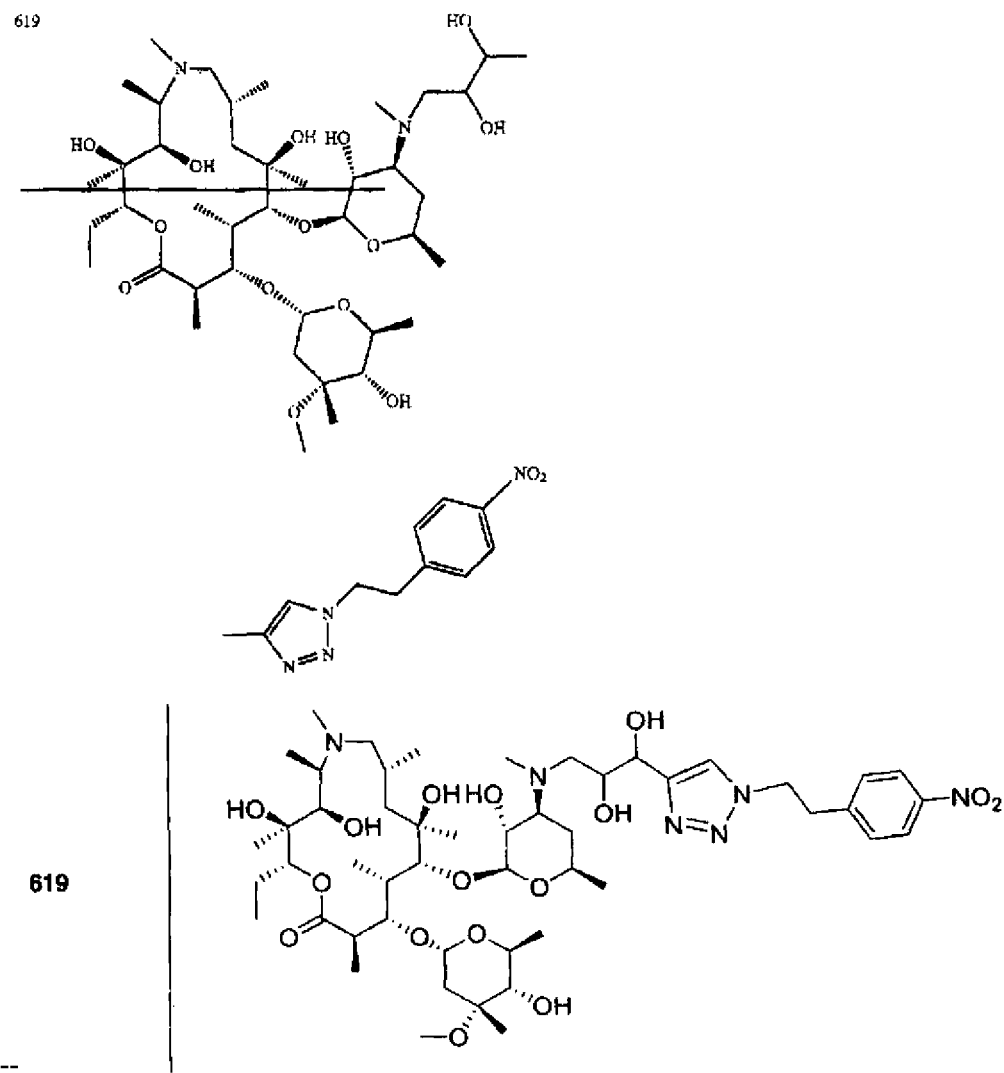

Claim 1, Column 672, lines 8-25:
Please replace the structure shown for compound 623 as indicated below.
623
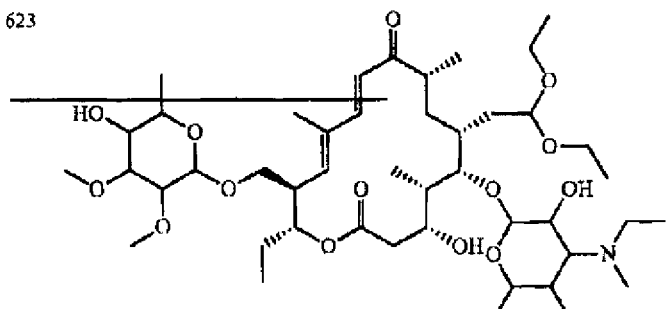
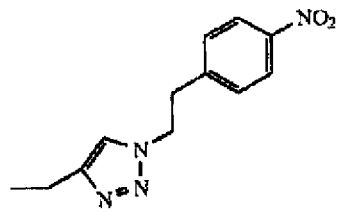
623
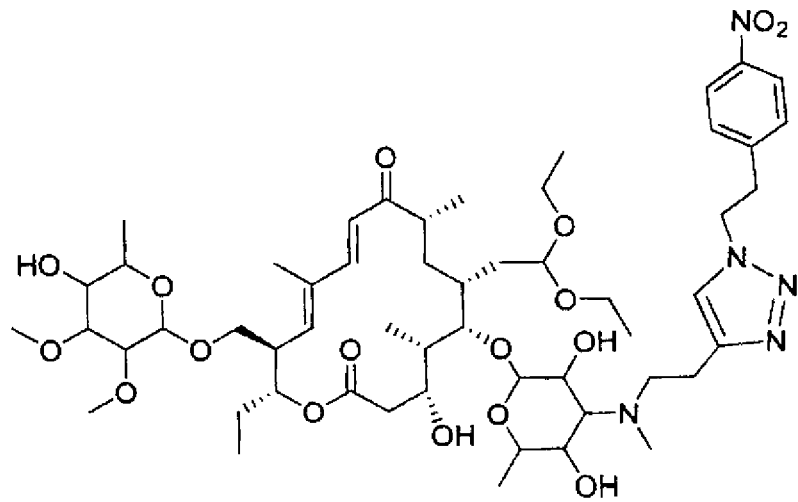
--    --

CERTIFICATE OF CORRECTION (continued)
U.S. Pat. No. 8,841,263 B2

Claim 1, Column 672, lines 26-44:
    Please replace the structure shown for compound 624 as indicated below.

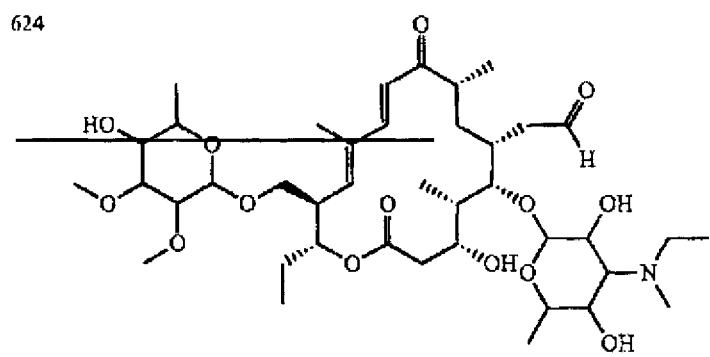

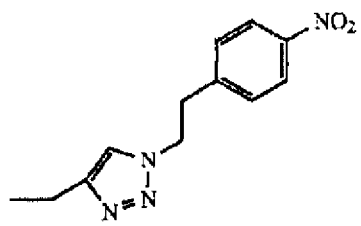

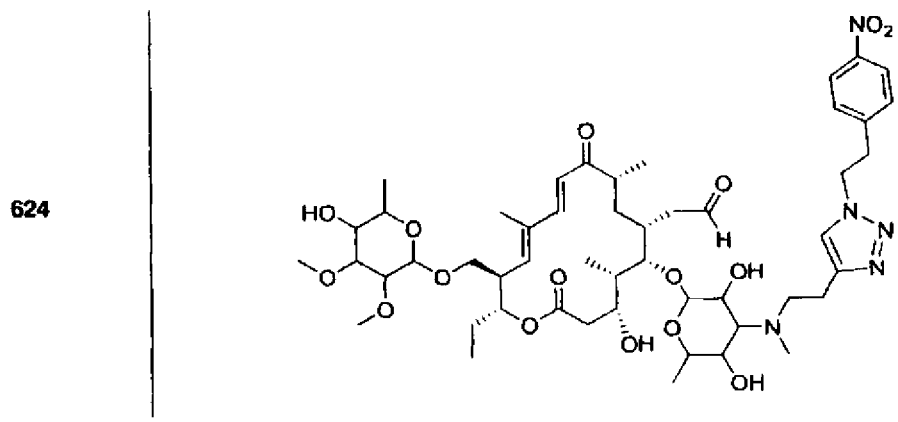

CERTIFICATE OF CORRECTION (continued)
U.S. Pat. No. 8,841,263 B2

Claim 1, Column 672, lines 45-65:
   Please replace the structure shown for compound 625 as indicated below.

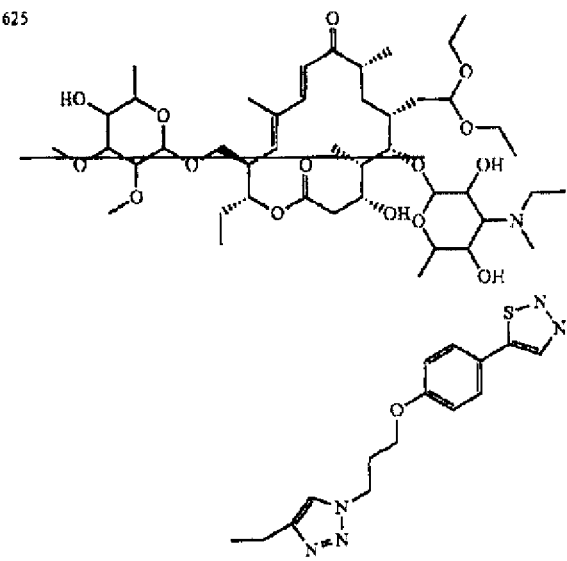

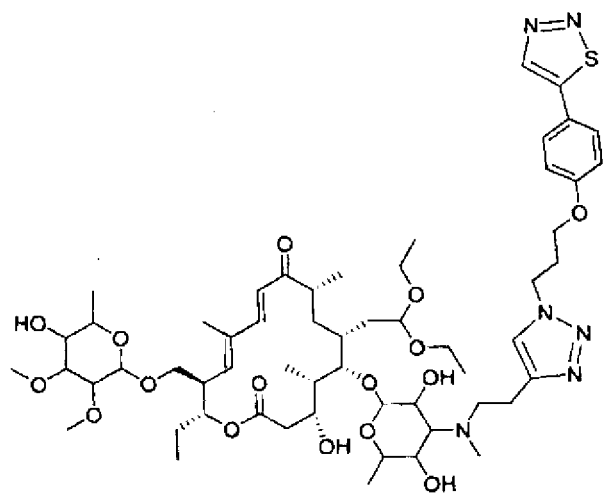

CERTIFICATE OF CORRECTION (continued)
U.S. Pat. No. 8,841,263 B2

Claim 1, Column 673, lines 8-30:
    Please replace the structure shown for compound 626 as indicated below.

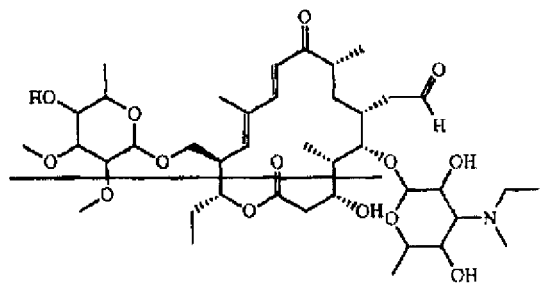

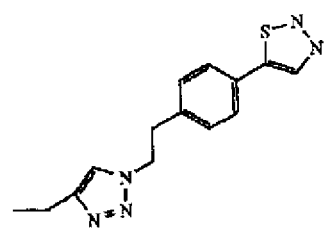

626

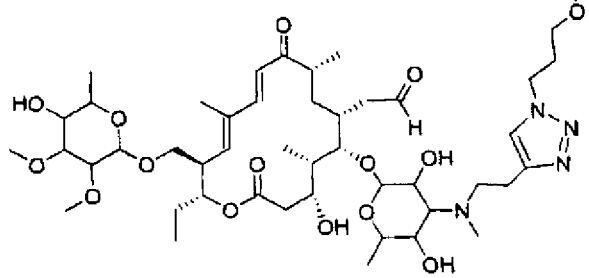

--                                                                                                --

Claim 1, Column 674, lines 8-24:
    Please replace the structure shown for compound 629 as indicated below.
629
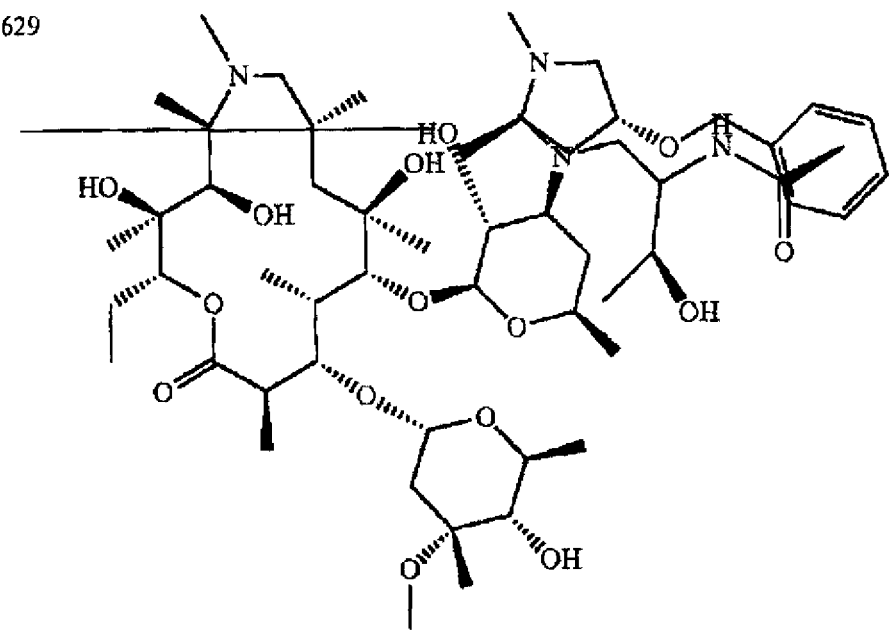
629
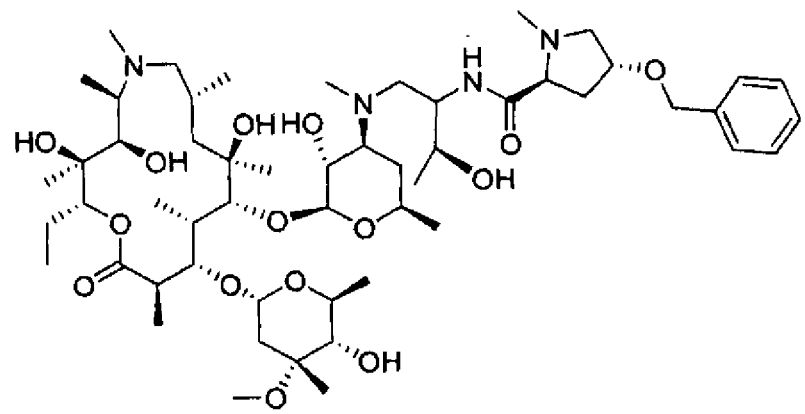
-- --